US012357661B2

(12) United States Patent
Thanos et al.

(10) Patent No.: US 12,357,661 B2
(45) Date of Patent: *Jul. 15, 2025

(54) ENGINEERED IMMUNOSTIMULATORY BACTERIAL STRAINS AND USES THEREOF

(71) Applicant: Actym Therapeutics, Inc., Berkeley, CA (US)

(72) Inventors: Christopher D. Thanos, Tiburon, CA (US); Laura Hix Glickman, Oakland, CA (US); Justin Skoble, Berkeley, CA (US); Alexandre Charles Michel Iannello, San Diego, CA (US)

(73) Assignee: Actym Therapeutics, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/037,455

(22) Filed: Sep. 29, 2020

(65) Prior Publication Data

US 2021/0030813 A1 Feb. 4, 2021

Related U.S. Application Data

(63) Continuation of application No. 16/520,155, filed on Jul. 23, 2019, now Pat. No. 11,779,612, and a continuation of application No. PCT/US2019/041489, filed on Jul. 11, 2019, said application No. 16/520,155 is a continuation of (Continued)

(51) Int. Cl.

| | |
|---|---|
| ***A61K 35/74*** | (2015.01) |
| ***A61K 39/112*** | (2006.01) |
| ***A61K 40/11*** | (2025.01) |
| ***A61K 40/17*** | (2025.01) |
| ***A61K 40/24*** | (2025.01) |
| ***A61K 40/42*** | (2025.01) |
| ***A61K 40/45*** | (2025.01) |
| ***A61K 45/06*** | (2006.01) |
| ***A61P 35/00*** | (2006.01) |
| ***C07K 14/52*** | (2006.01) |
| ***C07K 16/24*** | (2006.01) |
| ***C07K 16/28*** | (2006.01) |
| ***C12N 1/20*** | (2006.01) |

(Continued)

(52) U.S. Cl.

CPC .......... *A61K 35/74* (2013.01); *A61K 39/0275* (2013.01); *A61K 40/11* (2025.01); *A61K 40/17* (2025.01); *A61K 40/24* (2025.01); *A61K 40/42* (2025.01); *A61K 40/4562* (2025.01); *A61P 35/00* (2018.01); *C07K 14/521* (2013.01); *C07K 16/248* (2013.01); *C07K 16/2818* (2013.01); *C07K 16/2827* (2013.01); *C12N 1/205* (2021.05); *C12N 15/74* (2013.01); *A61K 45/06* (2013.01); *A61K 2239/50* (2023.05); *C12R 2001/42* (2021.05)

(58) Field of Classification Search

CPC .... A61K 35/74; A61K 39/0275; A61K 40/42; A61P 35/00

See application file for complete search history.

(56) References Cited

U.S. PATENT DOCUMENTS

| | | | |
|---|---|---|---|
| 3,536,809 A | 10/1970 | Applezweig | 424/28 |
| 3,598,123 A | 8/1971 | Zaffaroni | 128/268 |

(Continued)

FOREIGN PATENT DOCUMENTS

| | | |
|---|---|---|
| AU | 2005316458 | 6/2006 |
| CA | 2591565 | 6/2006 |

(Continued)

OTHER PUBLICATIONS

Bereta et al. 2007 (Improving tumor targeting and therapeutic potential of *Salmonella* VNP20009 by displaying cell surface CEA-specific antibodies; Vaccine 25: 4183-4192). (Year: 2007).*

(Continued)

*Primary Examiner* — Brian Gangle
*Assistant Examiner* — Lakia J Jackson-Tongue
(74) *Attorney, Agent, or Firm* — Womble Bond Dickinson (US) LLP; Stephanie Seidman

(57) ABSTRACT

Provided are delivery immunostimulatory bacteria that have enhanced colonization of tumors, the tumor microenvironment and/or tumor-resident immune cells, and enhanced anti-tumor activity. The immunostimulatory bacteria are modified by deletion of genes encoding the flagella, or by modification of the genes so that functional flagella are not produced, and/or are modified by deletion of pagP or modification of pagP to produce inactive PagP product. As a result, the immunostimulatory bacteria are flagellin$^-$ and/or pagP$^-$. The immunostimulatory bacteria optionally have additional genomic modifications so that the bacteria are adenosine or purine auxotrophs. The bacteria optionally are one or more of asd$^-$, purI$^-$, and msbB$^-$. The immunostimulatory bacteria, such as *Salmonella* species, are modified to encode immunostimulatory proteins that confer anti-tumor activity in the tumor microenvironment, and/or are modified so that the bacteria preferentially infect immune cells in the tumor microenvironment, or tumor-resident immune cells, and/or are modified to induce less cell death in immune cells than in other cells. Also provided are methods of inhibiting the growth or reducing the volume of a solid tumor by administering the immunostimulatory bacteria.

37 Claims, 25 Drawing Sheets

Specification includes a Sequence Listing.

Related U.S. Application Data application No. PCT/US2019/041489, filed on Jul. 11, 2019, which is a continuation-in-part of application No. PCT/US2018/041713, filed on Jul. 11, 2018, and a continuation-in-part of application No. 16/033,187, filed on Jul. 11, 2018, now Pat. No. 11,168,326.

(60) Provisional application No. 62/828,990, filed on Apr. 3, 2019, provisional application No. 62/789,983, filed on Jan. 8, 2019.

(51) Int. Cl.
*C12N 15/74* (2006.01)
*C12R 1/42* (2006.01)

(56) References Cited

U.S. PATENT DOCUMENTS 3,630,200 A 12/1971 Higuchi ........................ 128/260
3,710,795 A 1/1973 Higuchi et al. ............... 128/260
3,845,770 A 11/1974 Theeuwes et al. ........... 128/260
3,847,770 A 11/1974 Radlowe et al. ........ 204/159.23
3,916,899 A 11/1975 Theeuwes et al. ........... 128/260
3,936,354 A 2/1976 LaPointe et al. ............... 195/79
4,008,719 A 2/1977 Theeuwes et al. ........... 128/260
4,044,126 A 8/1977 Cook et al. ................... 424/243
4,364,923 A 12/1982 Cook et al. ..................... 424/46
4,414,209 A 11/1983 Cook et al. ................... 424/243
4,687,660 A 8/1987 Baker et al. .................. 424/465
4,769,027 A 9/1988 Baker et al. .................. 424/493
5,033,252 A 7/1991 Carter ............................ 53/425
5,052,558 A 10/1991 Carter .......................... 206/439
5,059,595 A 10/1991 Le Grazie ..................... 424/468
5,073,543 A 12/1991 Marshall et al. ............... 514/21
5,120,548 A 6/1992 McClelland et al. ......... 424/473
5,323,907 A 6/1994 Kalvelage ..................... 206/531
5,354,556 A 10/1994 Sparks et al. ................. 424/419
5,591,767 A 1/1997 Mohr et al. ................... 514/413
5,639,476 A 6/1997 Oshlack et al. .............. 424/468
5,674,533 A 10/1997 Santus et al. ................. 424/493
5,733,566 A 3/1998 Lewis ........................... 424/426
5,759,808 A 6/1998 Casterman et al. ......... 435/69.1
5,997,881 A 12/1999 Powell et al. ............. 424/234.1
6,024,961 A 2/2000 Curtiss, III et al. ....... 424/200.1
6,080,849 A 6/2000 Bermudes et al. .......... 536/23.7
6,190,657 B1 2/2001 Pawelek et al. ............. 424/93.1
6,383,496 B1 5/2002 Curtiss, III et al. ....... 424/200.1
6,447,784 B1 9/2002 Bermudes et al. ........ 424/235.1
6,475,482 B1 11/2002 Bermudes et al. .......... 424/93.4
6,548,287 B1 4/2003 Powell et al. .............. 435/69.1
6,682,736 B1 1/2004 Hanson et al. ............ 424/144.1
6,863,894 B2 3/2005 Bermudes et al. ........... 424/235
6,962,696 B1 11/2005 Bermudes et al. .......... 424/93.4
6,984,720 B1 1/2006 Korman et al. ......... 530/388.22
7,083,794 B2 8/2006 Curtiss, III et al. ....... 424/200.1
7,115,269 B2 10/2006 Darji et al. ................ 424/200.1
7,195,757 B2 3/2007 Curtiss, III et al. ....... 424/93.48
7,344,710 B2 3/2008 Dang et al. .................. 424/93.1
7,354,592 B2 4/2008 Bermudes et al. .......... 424/93.2
7,390,646 B2 6/2008 Andino-Pavlovsky et al. ............ 435/252.33
7,452,531 B2 11/2008 Bermudes et al. .......... 424/93.4
7,514,089 B2 4/2009 Bermudes et al. ........ 369/30.31
7,732,417 B2 6/2010 Beach et al. .................... 514/44
7,892,740 B2 2/2011 Weichselbaum et al. ........ 435/6
7,943,743 B2 5/2011 Korman et al. ......... 530/388.15
7,998,461 B2 8/2011 Forbes et al. .................. 424/9.2
8,008,449 B2 8/2011 Korman et al. ......... 530/388.15
8,093,025 B2 1/2012 Loessner et al. ............ 435/69.5
8,202,846 B2 6/2012 Harmon et al. ................ 514/44
8,217,149 B2 7/2012 Irving et al. ............... 530/387.1
8,221,739 B2 7/2012 Leonard et al. ............. 424/93.2
8,232,259 B2 7/2012 Klinman et al. ................ 514/44
8,241,844 B2 8/2012 Bulla, Jr. et al. ................. 435/5
8,383,599 B2 2/2013 Harmon et al. ................ 514/44
8,426,375 B2 4/2013 Kandimalla et al. ........... 514/44
8,426,675 B2 4/2013 Dickins et al. ................. 800/14
8,440,207 B2 5/2013 Bermudes .................. 424/200.1
8,524,220 B1 9/2013 Bermudes .................... 424/93.2
8,580,757 B2 11/2013 Federov et al. ............ 514/44 A
8,647,618 B2 2/2014 Leonard et al. ........... 424/93.48
8,647,642 B2 2/2014 Bermudes .................. 424/258.1
8,679,473 B2 3/2014 Fensterle et al. ............ 424/93.1
8,679,767 B2 3/2014 Kaur et al. ..................... 435/7.1
8,735,553 B1 5/2014 Li et al. ................... 530/388.22
8,779,108 B2 7/2014 Queva et al. ............ 530/388.73
8,822,194 B2 9/2014 Zhao et al. ................ 435/252.3
8,829,254 B2 9/2014 Nair et al. .................... 570/155
9,068,187 B1 6/2015 Bermudes .................... 424/93.2
9,181,546 B2 11/2015 Li et al. ........................ 424/93.1
9,242,000 B2 1/2016 Cheresh et al. ............ 514/44 R
9,265,804 B2 2/2016 Newman .................... 424/93.48
9,315,817 B2 4/2016 Bermudes .................. 435/252.3
9,320,787 B2 4/2016 Gunn ......................... 424/257.1
9,415,098 B2 8/2016 Lubenau .................... 424/258.1
9,421,252 B2 8/2016 Bermudes .................. 424/258.1
9,453,227 B2 9/2016 Diamond et al. .......... 424/258.1
9,511,129 B2 12/2016 Hanson et al. ............... 435/821
9,560,621 B2 * 1/2017 Li .......................... H04L 67/52
9,616,114 B1 4/2017 Bermudes .................. 424/258.1
9,624,494 B2 4/2017 Hannon et al. ............. 514/44 A
9,731,011 B2 8/2017 Brahmbhatt et al. .... 424/197.11
9,790,504 B2 10/2017 Khodarev et al. .......... 514/44 A
9,878,023 B1 1/2018 Bermudes .................... 424/93.2
10,052,371 B2 8/2018 Newman .................... 424/93.48
10,087,451 B2 10/2018 Bermudes .................. 424/258.1
10,100,314 B2 10/2018 Diamond et al. .......... 424/258.1
10,131,712 B2 11/2018 Rossi et al. .................. 424/1.11
10,188,722 B2 1/2019 Bermudes .................. 424/258.1
10,190,145 B2 * 1/2019 Yam ........................ C12P 21/02
10,195,259 B2 2/2019 Newman .................... 530/388.4
10,286,051 B1 5/2019 Bermudes .................. 424/258.1
10,293,037 B2 5/2019 Lubenau .................... 424/185.1
10,421,971 B2 9/2019 Deng et al. ................. 514/44 R
10,449,237 B1 10/2019 Bermudes .................. 424/258.1
10,450,353 B2 * 10/2019 Thanos .................. C07K 16/00
10,487,140 B2 * 11/2019 Aman ...................... C12N 9/52
10,493,113 B2 12/2019 Goodman et al. ........... 424/85.2
10,500,277 B2 12/2019 Brahmbhatt et al. .... 424/197.11
10,525,082 B2 1/2020 Crane et al. ............... 424/130.1
10,584,339 B2 3/2020 Diamond et al. ............ 424/93.2
10,626,403 B2 4/2020 Bermudes .................. 424/258.1
10,653,774 B2 5/2020 Dubensky, Jr. et al. ... 424/184.1
10,702,561 B2 7/2020 Goodman et al. ........... 424/85.2
10,729,731 B1 8/2020 Bermudes .................. 424/200.1
10,774,354 B2 * 9/2020 Yam ......................... C12N 9/90
10,821,163 B2 11/2020 Lubenau .................... 424/186.1
10,828,356 B1 11/2020 Bennudes .................. 424/200.1
10,961,538 B2 3/2021 Diamond et al. .......... 424/258.1
11,028,153 B2 * 6/2021 Aman ..................... A61P 31/04
11,045,504 B2 6/2021 Newman .................... 530/388.4
11,103,538 B2 8/2021 Forbes et al. ................ 424/93.2
11,141,492 B2 10/2021 Diamond et al. .......... 424/93.48
11,168,326 B2 * 11/2021 Thanos ................... A61P 35/00
11,174,486 B2 11/2021 Hasty et al. ............... 424/184.1
11,242,528 B2 * 2/2022 Thanos .............. A61K 47/6873
11,261,219 B2 * 3/2022 Thanos ................ C07K 14/245
11,471,494 B2 10/2022 Falb et al. ................... 424/93.4
11,590,215 B2 2/2023 Lubenau .................... 424/186.1
11,613,758 B2 3/2023 Hasty et al. ............... 424/184.1
11,723,932 B2 8/2023 Falb et al. ................... 424/93.2
11,779,612 B2 10/2023 Thanos et al. ............... 424/93.4
2002/0026655 A1 2/2002 Bermudes et al. ........ 424/235.1
2002/0086014 A1 7/2002 Korman et al. ........... 424/144.1
2003/0031683 A1 2/2003 Curtiss, III et al. ....... 424/200.1
2003/0109026 A1 6/2003 Bermudes et al. ........ 435/252.3
2003/0170276 A1 9/2003 Bermudes et al. ........ 424/258.1
2003/0175297 A1 9/2003 Urashima .................. 424/200.1
2003/0180320 A1 9/2003 Darji et al. ................ 424/200.1
2004/0120962 A1 6/2004 Curtiss, III et al. ....... 424/184.1
2004/0229338 A1 11/2004 King ......................... 435/252.3
2005/0118193 A1 6/2005 Andino-Pavlovsky et al. ............ 435/252.33
2005/0180969 A1 8/2005 Hardy et al. ............... 424/141.1

(56) References Cited

U.S. PATENT DOCUMENTS

2005/0244375 A1 11/2005 Leonard et al. ............ 424/93.2
2005/0249706 A1 11/2005 Bermudes et al. .......... 424/93.4
2005/0255088 A1 11/2005 Bermudes et al. .......... 424/93.2
2006/0051380 A1 3/2006 Schulick et al. ........... 424/277.1
2007/0009489 A1 1/2007 Bermudes et al. ........ 369/30.31
2007/0166281 A1 7/2007 Kosak .......................... 424/85.1
2007/0207171 A1 9/2007 Dubensky et al. .......... 536/23.1
2007/0298012 A1 12/2007 King et al. ................... 424/93.2
2008/0091375 A1 4/2008 Brunell ......................... 702/107
2008/0112928 A1 5/2008 Loessner et al. ............ 435/69.5
2008/0124355 A1 5/2008 Bermudes .................. 424/200.1
2009/0074787 A1 3/2009 Gomez-Navarro et al. ................ 424/142.1
2009/0111762 A1 4/2009 Roth et al. ...................... 514/44
2009/0123426 A1 5/2009 Li et al. ....................... 424/93.1
2009/0169517 A1 7/2009 Bermudes et al. .......... 424/93.4
2009/0175829 A1 7/2009 Forbes et al. ............... 424/93.2
2009/0208534 A1 8/2009 Xu et al. .................... 424/258.1
2009/0220459 A1 9/2009 Fensterle et al. ............ 424/93.2
2010/0098665 A1 4/2010 Leonard et al. ............ 424/93.2
2010/0135961 A1 6/2010 Bermudes .................. 424/258.1
2012/0009153 A1 1/2012 Guo et al. .................... 424/93.2
2012/0142080 A1 6/2012 Bermudes .................. 424/200.1
2012/0171159 A1 7/2012 Fensterle et al. ............ 424/93.1
2012/0294929 A1 11/2012 Roth et al. .................... 424/450
2013/0034559 A1 2/2013 Queva et al. .............. 424/139.1
2013/0045202 A1 2/2013 Irving et al. ............... 424/133.1
2013/0045525 A1 2/2013 Leonard et al. ........... 424/93.48
2013/0142786 A1 6/2013 Liu et al. ................... 424/133.1
2013/0150258 A1 6/2013 Weichselbaum et al. ........ 435/6
2014/0127284 A1 5/2014 Cheresh et al. .............. 424/450
2014/0127816 A1 5/2014 Hanson et al. ............... 435/821
2014/0178341 A1 6/2014 Zhao et al. .................. 424/93.2
2014/0186401 A1 7/2014 Diamond et al. .......... 424/258.1
2014/0212396 A1 7/2014 Newman ................... 424/93.48
2014/0220661 A1 8/2014 Bermudes .................. 435/252.3
2014/0242095 A1 8/2014 Wang et al. ............... 424/174.1
2015/0017204 A1 1/2015 Bermudes .................. 424/258.1
2015/0071873 A1 3/2015 Biot et al. .................... 424/85.1
2015/0098897 A1 4/2015 Brahmbhatt et al. .... 424/197.11
2015/0147315 A1 5/2015 Wei ............................. 435/7.32
2015/0165011 A1 6/2015 Lubenau .................... 424/258.1
2015/0224151 A1 8/2015 Julian Gomez et al. .... 424/93.4
2015/0232880 A1 8/2015 Hemminki et al. ......... 424/93.1
2016/0184456 A1 6/2016 Diamond et al. .......... 424/93.48
2016/0199422 A1 7/2016 Newman .................... 424/93.48
2016/0222387 A1 8/2016 Khodarev et al. .......... 514/44 A
2016/0222393 A1 8/2016 Bermudes .................. 424/258.1
2016/0228523 A1 8/2016 Newman .................... 530/388.4
2016/0250311 A1 9/2016 Lubenau .................... 424/258.1
2016/0333355 A1 11/2016 Deng et al. ................. 514/44 R
2016/0369282 A1 12/2016 Li et al. ....................... 424/93.1
2017/0020931 A1 1/2017 Zhou et al. ................ 424/144.1
2017/0081671 A1 3/2017 Diamond et al. .......... 424/258.1
2017/0081673 A1 3/2017 Hanson et al. ............... 435/821
2017/0157239 A1 6/2017 Bennudes .................. 424/258.1
2017/0275375 A1 9/2017 Rossi et al. .................. 424/1.11
2017/0298362 A1 10/2017 Khodarev et al. .......... 514/44 A
2017/0326235 A1 11/2017 Brahmhatt et al. ...... 424/197.11
2017/0333490 A1 11/2017 Forbes et al. ................ 424/93.2
2018/0104320 A1 4/2018 Gravekamp ............... 424/236.1
2018/0148729 A1 5/2018 Hasty et al. ............... 424/184.1
2018/0311343 A1 11/2018 Huang et al. ............... 514/44 R
2019/0008936 A1 1/2019 Lubenau .................... 424/185.1
2019/0017050 A1 1/2019 Thanos et al. ............ 424/258.1
2019/0017057 A1 1/2019 Bermudes .................. 424/258.1
2019/0071679 A1 3/2019 Khodarev et al. .......... 514/44 A
2019/0153452 A1 5/2019 Diamond et al. .......... 424/258.1
2019/0307869 A1 10/2019 Newman .................... 530/388.4
2019/0336544 A1 11/2019 Falb et al. ................... 424/93.4
2020/0023053 A1 1/2020 Bermudes .................. 424/200.1
2020/0055904 A1 2/2020 Erhardt et al. ............ 424/258.1
2020/0071702 A1 3/2020 Thanos et al. .............. 514/44 A
2020/0157549 A1 5/2020 Diamond et al. .......... 484/258.1
2020/0215123 A1* 7/2020 Thanos ............. C07K 16/2818
2020/0261572 A1 8/2020 Huang et al. ............... 514/44 R
2020/0270613 A1 8/2020 Thanos et al. ............... 424/94.1
2021/0030813 A1 2/2021 Thanos et al. ............... 424/93.4
2021/0113628 A1 4/2021 Loughhead et al. ....... 424/133.1
2022/0017904 A1* 1/2022 Thanos ............. C12N 15/1135
2022/0047649 A1 2/2022 Newman .................... 424/277.1
2022/0072112 A1 3/2022 Lubenau .................... 424/186.1
2022/0112501 A1* 4/2022 Thanos ................ A61K 35/768
2022/0119824 A1* 4/2022 Glickman .......... C07K 14/4705
2022/0135980 A1* 5/2022 Thanos ............... C07K 14/461 514/44 A
2022/0241432 A1 8/2022 Diamond et al. .......... 424/93.48
2022/0251579 A1 8/2022 Hasty et al. ............... 424/184.1
2023/0226122 A1 7/2023 Falb et al. ................... 424/93.4
2024/0180974 A1 6/2024 Falb et al. ................... 424/93.2

FOREIGN PATENT DOCUMENTS

CA 3069523 1/2019
CN 103468626 B 5/2016
EP 1 262 193 12/2002
EP 1 655 370 5/2006
EP 2 270 136 1/2011
EP 3820992 5/2021
JP 2002-513287 5/2002
WO WO 98/48026 10/1998
WO WO 1998/048026 10/1998
WO WO 1999/013053 3/1999
WO WO 1999/025387 5/1999
WO WO 2000/037504 6/2000
WO WO 2001/025399 4/2001
WO WO-02059292 A2 * 8/2002 ............. A61K 39/00
WO WO 2003/096812 11/2003
WO WO 2005/116233 12/2005
WO WO 2006/066048 6/2006
WO WO 2007/112518 10/2007
WO WO 2007/130604 11/2007
WO WO 2008/091375 7/2008
WO WO 2008/156712 12/2008
WO WO 2009/006450 1/2009
WO WO 2009/095436 8/2009
WO WO-2010010983 A1 * 1/2010 ............. C12N 15/70
WO WO 2010/045620 4/2010
WO WO 2010/057009 5/2010
WO WO 2010/077634 7/2010
WO WO 2011/100489 8/2011
WO WO 2011/150421 12/2011
WO WO 2012/149364 11/2012
WO WO 2013/019906 2/2013
WO WO 2013/163893 11/2013
WO WO 2014/189996 11/2014
WO WO 2015/002969 1/2015
WO WO 2015/032165 3/2015
WO WO 2015/059303 4/2015
WO WO 2015/108595 7/2015
WO WO 2015/134722 9/2015
WO WO 2015/142875 9/2015
WO WO 2015/191861 12/2015
WO WO 2016/025582 2/2016
WO WO 2017/005773 1/2017
WO WO 2017/043815 3/2017
WO WO 2017/044487 3/2017
WO WO 2017/123675 7/2017
WO WO 2017/156349 9/2017
WO WO 2018/006005 1/2018
WO WO 2018/011289 1/2018
WO WO 2018/045058 3/2018
WO WO 2018/106754 6/2018
WO WO 2018/129404 7/2018
WO WO 2018/191619 10/2018
WO WO 2018/191654 10/2018
WO WO 2018/197621 11/2018
WO WO 2019/014398 1/2019
WO WO 2019/183117 9/2019
WO WO 2020/014543 1/2020

(56) References Cited

FOREIGN PATENT DOCUMENTS

WO WO 2020/176809 9/2020
WO WO 2021/097144 5/2021

OTHER PUBLICATIONS

Leschner et al. 2010 (*Salmonella*—allies in the fight against cancer; J Mol Med 88:763-773) (Year: 2010).*
Wu 2014 (IL-15 Agonists: The Cancer Cure Cytokine; J Mol Genet Med 7; doi:10.4172/1747-0862.1000085). (Year: 2014).*
McFarland et al. 1987 (Effect of different purine auxotrophic mutations on mouse-virulence of a Vi-positive strain of *Salmonella dublin* and of two strains of *Salmonella typhimurium*; Microbial Pathogenesis 3:129-141). (Year: 1987).*
Gahan et al. 2007 (Impact of plasmid stability on oral DNA delivery by *Salmonella enterica* serovar Typhimurium; Vaccine 25: 1476-1483). (Year: 2007).*
Felgner et al. 2016 (Review Article: Bacteria in Cancer Therapy: Renaissance of an Old Concept; International Journal of Microbiology, 2016, ID 8451728; 1-14) (Year: 2016).*
Low et al. 1999 (Lipid A mutant Salmonella with suppressed virulence and TNFa induction retain tumor-targeting in vivo (Nature Biotechnology 17:37-41) (Year: 1999).*
Olsen et al. 2013 (The role of flagella and chemotaxis genes in host pathogen interaction of the host pathogen interaction of the host adapted *Salmonella enterica* serovar Dublin compared to the broad host range serovar *S. Typhimurium*; BMC Microbiology 13: 67). (Year: 2013).*
Low et al. 2004 A Novel, Genetically Stable Antibiotic Sensitive Strain of Tumor Targeting Salmonella for Parenteral Administration in Humans; CH3 Construction of VNP20009; Methods in Molecular Medicine 90: Suicide Gene Therapy Methods and Reviews; Eds C.J. Springer; Humanna Press Inc, Totowa NJ; p. 47 (Year: 2004).*
Schmitt et al. 2001 (Absence of All Components of the Flagellar Export and Synthesis Machinery Differentially Alters Virulence of Salmonella enterica Serovar Typhimurium in Models of Typhoid Fever, Survival in Macrophages, Tissue Culture Invasiveness, and Calf Enterocolitis; Infect & Imm 69(9): 5619 (Year: 2001).*
Felgner et al. 2016 (aroA-Deficient *Salmonella enterica* Serovar Typhimurium is more than a metabolically attenuated mutant; mBio 7(5):e01220-16.doi:10.1128/mBio.01220-16) (Year: 2016).*
Letter/Written Disclosure of the Information Disclosure Statement for the above-referenced application, filed herewith on Jan. 7, 2021, 2 pages.
Ablasser et al., "Cell intrinsic immunity spreads to bystander cells via the intercellular transfer of cGAMP," Nature 503(7477):530-534 (2013).
Ablasser et al., "TREX1 Deficiency Triggers Cell-Autonomous Immunity in a cGAS-Dependent Manner," J. Immunol. 192:5993-5997 (2014).
Agbor, T. A. and McCormick, B. A., "*Salmonella* Effectors: Important players modulating host cell function during infection," Cell Microbiol. 13(12):1858-1869 (2011).
Ahn et al., "Intrinsic Self-DNA Triggers Inflammatory Disease Dependent on STING," J. Immunol. 193(9):4634-4642 (2014).
Ahn et al., "Extrinsic Phagocyte-Dependent STING Signaling Dictates the Immunogenicity of Dying Cells," Cancer Cell 33(5):862-873 (2018).
Akira et al., "Toll-like receptors: critical proteins linking innate and acquired immunity," Nat. Immunol. 2(8):675-680 (2001).
Aleksic et al., "Different affinity windows for virus and cancer-specific T-cell receptors—implications for therapeutic strategies," Eur. J. Immunol. 42(12):3174-3179 (2012).
Allen et al., "CCL3 augments tumor rejection and enhances CD8+ T cell infiltration through NK and CD103+ dendritic cell recruitment via IFNγ," Oncoimmunology 7(3):e1393598 (2018), 12 pages.
Alshangiti et al., "Antiangiogenic therapies in non-small-cell lung cancer," Curr. Oncol. 25(Suppl 1):S45-S58 (2018).
Anassi, E. and Ndefo, U. A., "Sipuleucel-T (Provenge) Injection The First Immunotherapy Agent (Vaccine) For Hormone-Refractory Prostate Cancer," P&T 36(4):197-202 (2011).
Angelakopoulos, H. and Hohmann, E. L., "Pilot Study of phoP/phoQ-Deleted *Salmonella enterica* Serovar Typhimurium Expressing *Helicobacter pylori* Urease in Adult Volunteers," Infection and Immunity 68(4):2135-2141 (2000).
Ansel HC, "Introduction to Pharmaceutical Dosage Forms," Fourth Edition, 1985, p. 126.
Antonioli et al., "Immunity, inflammation and cancer: a leading role for adenosine," Nat. Rev. Cancer 13(12):842-857 (2013).
Anwar et al., "Modulation of Biofilm-Formation in *Salmonella enterica* Serovar Typhimurium by the Periplasmic DsbA/DsbB Oxidoreductase System Requires the GGDEF-EAL Domain Protein STM3615," PLoS ONE 9(8):e106095 (2014), 12 pages.
Argyle D. and T. Kitamura, "Targeting Macrophage-Recruiting Chemokines as a Novel Therapeutic Strategy to Prevent the Progression of Solid Tumors," Front. Immunol. 9:2629 (2018), 15 pages.
Arpaia et al., "TLR signaling is required for virulence of an intracellular pathogen," Cell 144(5):675-688 (2011).
Auyeung et al., "Beyond secondary structure: primary-sequence determinants license pri-miRNA hairpins for processing," Cell 152(4):844-858 (2013).
Baban et al., "Bacteria as vectors for gene therapy of cancer," Bioengineered Bugs 1(6):385-394 (2010).
Barber, G. N., "Cytoplasmic DNA innate immune pathways," Immunol. Rev. 243(1):99-108 (2011).
Barber, G. N., "STING: infection, inflammation and cancer," Nat. Rev. Immunol. 15(12):760-770 (2015).
Bastin et al., "Capitalizing on Cancer Specific Replication: Oncolytic Viruses as a Versatile Platform for the Enhancement of Cancer Immunotherapy Strategies," Biomedicines 4(3), 21 (2016), 19 pages.
Bermudes et al., "Tumour-Selective *Salmonella*-Based Cancer Therapy," Biotechnology and Genetic Engineering Reviews 18(1):219-233 (2001).
Bermudes et al., "Tumor-Targeted *Salmonella* Highly Selective Delivery Vectors," Cancer Gene Therapy: Past Achievements and Future Challenges, ed. Habib, Kluwer Academic/Plenum Publishers, New York, Chp. 6, pp. 57-63 (2000).
Bermudes et al., "Live bacteria as anticancer agents and tumor-selective protein delivery vectors," Curr. Opin. Drug Discov. Devel. 5(2):194-199 (2002).
Bian et al., "Cd47-Sirpα interaction and IL-10 constrain inflammation-induced macrophage phagocytosis of healthy self-cells," Proc. Natl. Acad. Sci. U.S.A. 113(37):E5434-E5443 (2016).
Binder et al., "Antigen-Specific Bacterial Vaccine Combined with Anti-PD-L1 Rescues Dysfunctional Endogenous T Cells to Reject Long-Established Cancer," Cancer Immunol. Res. 1(2):123-133 (2013).
Blache et al., "Systemic Delivery of *Salmonella typhimurium* Transformed with IDO shRNA Enhances Intratumoral Vector Colonization and Suppresses Tumor Growth," Cancer Res. 72(24):6447-6456 (2012).
Boden et al., "Enhanced gene silencing of HIV-1 specific siRNA using microRNA designed hairpins," Nucleic Acids Research 32(3):1154-1158 (2004).
Broadway et al., "Complete genome sequence of *Salmonella enterica* serovar Typhimurium VNP20009, a strain engineered for tumor targeting," Journal of Biotechnology 192:177-178 (2014).
Broadway et al., "Rescuing chemotaxis of the anticancer agent *Salmonella enterica* serovar Typhimurium VNP20009," Journal of Biotechnology 211:117-120 (2015).
Broz, P. and Monack, D. M., "Molecular Mechanisms of Inflammasome Activation during Microbial Infections," Immunol. Rev. 243(1):174-190 (2011).
Bucarey et al., "The *Salmonella enterica* Serovar Typhi tsx Gene, Encoding a Nucleoside-Specific Porin, Is Essential for Prototrophic Growth in the Absence of Nucleosides," Infection and Immunity 73(10):6210-6219 (2005).
Buchbinder, E. and Hodi, F. S., "Cytotoxic T lymphocyte antigen-4 and immune checkpoint blockade," J. Clin. Invest. 125(9):3377-3383 (2015).

(56) References Cited

OTHER PUBLICATIONS

Burdette et al., "STING is a direct innate immune sensor of cyclic-di-GMP," Nature 478(7370):515-518 (2011).
Carrillo, H. and Lipman, D., "The multiple sequence alignment problem in biology," SIAM J. Applied Math 48(5):1073-1082 (1988).
Carroll, VA. and Ashcroft, M., "Targeting the molecular basis for tumour hypoxia," Expert Rev. Mol. Med. 7(6):1-16 (2005).
Caskey et al., "Synthetic double-stranded RNA induces innate immune responses similar to a live viral vaccine in humans," J. Exp. Med. 208(12):2357-2366 (2011).
Chang et al., "Creating an miR30-Based shRNA Vector," Cold Spring Harb. Protoc., doi:10.1101/pdb.prot075853, pp. 631-635 (2013).
Chatfield et al., "Use of the nirB promoter to direct the stable expression of heterologous antigens in *Salmonella* oral vaccine strains: development of a single-dose oral tetanus vaccine," Biotechnology 10(8):888-892 (1992).
Chen et al., "The Neutrophil NLRC4 Inflammasome Selectively Promotes IL-1β Maturation without Pyroptosis during Acute *Salmonella* Challenge," Cell Reports 8:570-582 (2014).
Chen, L. and Han, X., "Anti-PD-1/PD-L1 therapy of human cancer: past, present and future," J. Clin. Invest. 125(9):3384-3391 (2015).
Chi et al., "Anti-tumor Activity of Toll-Like Receptor 7 Agonists," Frontiers in Pharmacology 8:304 (2017), 10 pages.
Chiocca, E.A. and Rabkin, S.D., "Oncolytic Viruses and Their Application to Cancer Immunotherapy," Cancer Immunol. Res. 2(4):295-300 (2014).
Chiu et al., "RNA polymerase III detects cytosolic DNA and induces type-I interferons through the RIG-I pathway," Cell 138(3):576-591 (2009).
Chorobik et al., "*Salmonella* and cancer: from pathogens to therapeutics," Acta Biochimica Polonica 60(3):285-297 (2013).
Chowdhury et al., "Programmable bacteria induce durable tumor regression and systemic antitumor immunity," Nature Medicine 25(7):1057-1063 (2019).
Chung et al., "Polycistronic RNA polymerase II expression vectors for RNA interference based on BIC/miR-155," Nucleic Acids Res. 34(7):e53 (2006), 14 pages.
Civril et al., "Structural mechanism of cytosolic DNA sensing by cGAS," Nature 498(7454):332-337 (2013).
Clairmont et al., "Biodistribution and Genetic Stability of the Novel Antitumor Agent VNP20009, a Genetically Modified Strain of *Salmonella typhimurium*," Journal of Infectious Diseases 181:1996-2002 (2000).
Clevers H. and Nusse R., "Wnt/β-Catenin Signaling and Disease," Cell 149:1192-1205 (2012).
Cobum et al., "Type III Secretion Systems and Disease," Clinical Microbiology Reviews 20(4):535-549 (2007).
Copier, J. and Dalgleish, A.,"Whole-cell vaccines: A failure or a success waiting to happen?" Curr. Opin. Mol. Ther. 12(1):14-20 (2010) [abstract].
Corrales et al., "Direct activation of STING in the tumor microenvironment leads to potent and systemic tumor regression and immunity," Cell Rep. 11(7):1018-1030 (2015).
Crull et al., "Biofilm formation by *Salmonella enterica* serovar Typhimurium colonizing solid tumours," Cellular Microbiology 13(8):1223-1233 (2011).
Dang et al., "Combination bacteriolytic therapy for the treatment of experimental tumors," Proc. Natl. Acad. Sci. U.S.A. 98(26):15155-15160 (2001).
Datsenko, K. A. and Wanner, B. L., "One-step inactivation of chromosomal genes in *Escherichia coli* K-12 using PCR products," Proc. Natl. Acad. Sci. U.S.A. 97(12):6640-6645 (2000).
Dean et al., "Sequence requirements for plasmid nuclear import," Exp. Cell Res. 253(2):713-722 (1999).
Del Solar et al., "Replication and Control of Circular Bacterial Plasmids," Microbiology and Molecular Biology Reviews 62(2):434-464 (1998).
Deng et al., "A New VISTA on combination therapy for negative checkpoint regulator blockade," Journal for ImmunoTherapy of Cancer 4:86 (2016), 7 pages.
Diamond et al., "Type I interferon is selectively required by dendritic cells for immune rejection of tumors," J. Exp. Med. 208(10):1989-2003 (2011).
Dinarello, C.A., "Proinflammatory and Anti-inflammatory Cytokines as Mediators in the Pathogenesis of Septic Shock," Chest 112(6 Suppl):321S-329S (1997).
Diner et al., "The innate immune DNA sensor cGAS produces a non-canonical cyclic-di-nucleotide that activates human STING," Cell Rep. 3(5):1355-1361 (2013).
DiPetrillo et al., "Safety and immunogenicity of phoP/phoQ-deleted *Salmonella typhi* expressing *Helicobacter pylori* urease in adult volunteers," Vaccine 18(5-6):449-459 (2000).
Di Domenico et al., "Biofilm Producing *Salmonella* Typhi: Chronic Colonization and Development of Gallbladder Cancer," Int. J. Mol. Sci. 18:1887 (2017), 14 pages.
Dotti et al., "Transgenic expression of CD40 ligand produces an in vivo antitumor immune response against both CD40+ and CD40+ plasmacytoma cells," Blood 100(1):200-207 (2002).
Dreher et al., "Genetic background of attenuated *Salmonella typhimurium* has profound influence on infection and cytokine patterns in human dendritic cells," J. Leukoc. Biol. 69:583-589 (2001).
Dubinett et al., "Chemokines: Can Effector Cells be Re-directed to the Site of Tumor?" Cancer J. 16(4):325-335 (2010).
Durfee et al., "The complete genome sequence of *Escherichia coli* DH10B: insights into the biology of a laboratory workhorse," J. Bacteriol. 190(7):2597-2606 (2008).
Edwards et al., "DNA Damage Repair Genes Controlling Human Papillomavirus (HPV) Episome Levels under Conditions of Stability and Extreme Instability," PLoS One 8(10):e75406 (2013), 16 pages.
Eisenstark et al., "Development of *Salmonella* Strains as Cancer Therapy Agents and Testing in Tumor Cell Lines," Methods in Molecular Biology 394:323-354 (2007).
Esebanmen, G.E. and Langridge, W.H.R., "The role of TGF-beta signaling in dendritic cell tolerance," Immunol. Res. 65(5):987-994 (2017).
Fabbi et al., "Context-dependent role of IL-18 in cancer biology and counter-regulation by IL-18BP," J. Leukoc. Biol. 97:665-675 (2015).
Faulds-Pain et al., "Flagellin Redundancy in *Caulobacter crescentus* and its Implications for Flagellar Filament Assembly," Journal of Bacteriology 193(11):2695-2707 (2011).
Feigner et al., "aroA-Deficient *Salmonella enterica* Serovar Typhimurium Is More Than a Metabolically Attenuated Mutant," mBio 7(5):e01220-16 (2016), 12 pages.
Feigner et al., "Optimizing *Salmonella enterica* serovar Typhimurium for bacteria-mediated tumor therapy," Gut Microbes 7(2):171-177 (2016).
Feigner et al., "Engineered *Salmonella enterica* serovar Typhimurium overcomes limitations of anti-bacterial immunity in bacteria-mediated tumor therapy," Oncoimmunology 7(2):e1382791 (2018), 12 pages.
Feigner et al., "Tumor-targeting bacteria-based cancer therapies for increased specificity and improved outcome," Microbial Biotechnology 10(5):1074-1078 (2017).
Fellmann et al., "An optimized microRNA backbone for effective single-copy RNAi," Cell Rep. 5(6):1704-1713 (2013).
Fields et al., "Mutants of *Salmonella typhimurium* that cannot survive within the macrophage are avirulent," Proc. Natl. Acad. Sci. U.S.A. 83:5189-5193 (1986).
Figueira, R. and Holden, D.W., "Functions of the *Salmonella* pathogenicity island 2 (SPI-2) type III secretion system effectors," Microbiology 158:1147-1161 (2012).
Fink, S.L. and Cookson, B.T., "Pyroptosis and host cell death responses during *Salmonella* infection," Cellular Microbiology 9(11):2562-2570 (2007).
Frahm et al., "Efficiency of Conditionally Attenuated *Salmonella enterica* Serovar Typhimurium in Bacterium-Mediated Tumor Therapy," mBio 6(2):e00254-15 (2015), 11 pages.

(56) References Cited

OTHER PUBLICATIONS

Fuertes et al., "Host type I IFN signals are required for antitumor CD8+ T cell responses through CD8α+ dendritic cells," J. Exp. Med. 208(10):2005-2016 (2011).
Fujita et al., "The Clinical Relevance of the miR-197/CKSIB/STAT3-mediated PD-L1 Network in Chemoresistant Non-small-cell Lung Cancer," Mol. Ther. 23(4):717-727 (2015).
Gajewski et al., "Molecular profiling to identify relevant immune resistance mechanisms in the tumor microenvironment," Curr. Opin. Immunol. 23(2):286-292 (2011).
Galan, J. E. and Curtiss, R. III., "Virulence and vaccine potential of phoP mutants of *Salmonella typhimurium*," Microb. Pathog. 6(6):433-443 (1989).
Galan, J. E. and Wolf-Watz, H., "Protein delivery into eukaryotic cells by type III secretion machines," Nature 444:567-573 (2006).
Galan et al., "Cloning and characterization of the asd gene of *Salmonella typhimurium*: use in stable maintenance of recombinant plasmids in *Salmonella* vaccine strains," Gene 94(1):29-35 (1990).
Gao et al., "Overexpression of PD-L1 Significantly Associates with Tumor Aggressiveness and Postoperative Recurrence in Human Hepatocellular Carcinoma," Clin. Cancer Res. 15(3):971-979 (2009).
Gao et al., "Integrative Analysis of Complex Cancer Genomics and Clinical Profiles Using the cBioPortal," Sci. Signal. 6(269):pl1 (2013), 34 pages.
Gao et al., "VISTA is an inhibitory immune checkpoint that is increased after ipilimumab therapy inpatients with prostate cancer," Nat. Med. 23(5):551-555 (2017).
Gardlik et al., "Gene therapy for cancer: bacteria-mediated anti-angiogenesis therapy," Gene Therapy 18:425-431 (2011).
Goodman et al., "Tumor Mutational Burden as an Independent Predictor of Response to Immunotherapy in Diverse Cancers," Mol. Cancer Ther. 16(11):2598-2608 (2017).
Gray et al., "Cutting Edge: cGAS Is Required for Lethal Autoimmune Disease in the Trex1-Deficient Mouse Model of Aicardi-Goutieres Syndrome," J. Immunol. 195(5):1939-1943 (2015).
Grenga et al., "PD-L1 and MHC-I expression in 19 human tumor cell lines and modulation by interferon-gamma treatment," J. ImmunoTherapy of Cancer 2(Suppl 3):P102 (2014).
Gribskov, M. and Burgess, R.R., "Sigma factors from *E. coli, B. subtilis*, phage SP01, and phage T4 are homologous proteins," Nucl. Acids Res. 14(16):6745-6763 (1986).
Groisman et al., "*Salmonella typhimurium* phoP virulence gene is a transcriptional regulator," Proc. Natl. Acad. Sci. U.S.A. 86:7077-7081 (1989).
Guo et al., "Targeting tumor gene by shRNA-expressing *Salmonella*-mediated RNAi," Gene Therapy 18:95-105 (2011).
Hagar et al., "WildCARDs: Inflammatory caspases directly detect LPS," Cell Research 25:149-150 (2015).
Halama et al., "Tumoral Immune Cell Exploitation in Colorectal Cancer Metastases Can Be Targeted Effectively by Anti-CCR5 Therapy in Cancer Patients," Cancer Cell 29(4):587-601 (2016).
Han et al., "IL-15:IL-15 receptor alpha superagonist complex: High-level co-expression in recombinant mammalian cells, purification and characterization," Cytokine 56(3):804-810 (2011).
Haque, S. and Morris, J.C., "Transforming growth factor-β: A therapeutic target for cancer," Human Vaccines & Immunotherapeutics 13(8):1741-1750 (2017).
Hasan, M. and Yan, N., "Safeguard against DNA sensing: the role of TREX1 in HIV-1 infection and autoimmune diseases," Front. Microbiol. 5:193 (2014), 6 pages.
Heimann, D.M. and Rosenberg, S.A., "Continuous Intravenous Administration of Live Genetically Modified *Salmonella typhimurium* in Patients With Metastatic Melanoma," J. Immunother. 26(2):179-180 (2003).
Hervas-Stubbs et al., "Conventional but not plasmacytoid dendritic cells foster the systemic virus-induced type I IFN response needed for efficient CD8 T cell priming," J. Immunol. 193(3):1151-1161 (2014).
Hodi et al., "Improved Survival with Ipilimumab in Patients with Metastatic Melanoma," N. Engl. J. Med. 363(8):711-723 (2010).
Hohmann et al., "phoP/phoQ-Deleted *Salmonella typhi* (Ty800) Is a Safe and Immunogenic Single-Dose Typhoid Fever Vaccine in Volunteers," J. Infect. Dis. 173:1408-1414 (1996).
Hossain et al., "Leukemia cell-targeted STAT3 silencing and TLR9 triggering generate systemic antitumor immunity," Blood 123(1):15-25 (2014).
Hu et al., "Differential outcome of TRIF-mediated signaling in TLR4 and TLR3 induced DC maturation," Proc. Natl. Acad. Sci. U.S.A. 112(45):13994-13999 (2015).
Huang, X., "A Time-Efficient, Linear-Space Local Similarity Algorithm," Adv. Appl. Math. 12:337-357 (1991).
Huang et al., "Targeting CD47: the achievements and concerns of current studies on cancer immunotherapy," J. Thorac. Dis. 9(2):E168-E174 (2017).
Husseiny, M.I. and Hensel, M., "Rapid method for the construction of *Salmonella enterica* Serovar Typhimurium vaccine carrier strains," Infect. Immun. 73(3):1598-1605 (2005).
Ireton, R. C. and Gale, M. Jr., "RIG-I Like Receptors in Antiviral Immunity and Therapeutic Applications," Viruses 3:906-919 (2011).
IUPAC-IUB Commission on Biochemical Nomenclature, "A One-Letter Notation for Amino Acid Sequences: Tentative Rules," The Journal of Biological Chemistry 243(13):3557-3559 (1968).
IUPAC-IUB Commission on Biochemical Nomenclature, "Symbols for Amino-Acid Derivatives and Peptides: Recommendations (1971)," Biochem. 11(9):1726-1732 (1972).
Jackson et al., "Driving CAR T-cells forward," Nat. Rev. Clin. Oncol. 13(6):370-383 (2016).
Kahn, M., "Can we safely target the WNT pathway?" Nat. Rev. Drug Discov. 13(7):513-532 (2014).
Kakarla, S. and Gottschalk, S., "CAR T cells for solid tumors: armed and ready to go?" Cancer J. 20(2):151-155 (2014).
Kalinski et al., "Prostaglandin $E_2$ is a selective inducer of interleukin-12 p40 (IL-12p40) production and an inhibitor of bioactive IL-12p70 heterodimer," Blood 97:3466-3469 (2001).
Kang et al., "Preventative and therapeutic effects of auxotrophic *Edwardsiella tarda* mutant harboring CpG 1668 motif-enriched plasmids against scuticociliatosis in olive flounder (*Paralichthys olivaceus*)," Experimental Parasitology 144:34-38 (2014).
Kasinkas, R.W. and Forbes, N.S., "*Salmonella typhimurium* lacking ribose chemoreceptors localize in tumor quiescence and induce apoptosis," Cancer Res. 67(7):3201-3209 (2007).
Kawaguchi et al., "High-efficacy targeting of colon-cancer liver metastasis with *Salmonella typhimurium* A1-R via intra-portal-vein injection in orthotopic nude-mouse models," Oncotarget 8(12):19065-19073 (2017).
Kawai, T. and Akira, S., "Pathogen recognition with Toll-like receptors," Curr. Opin. Immunol. 17(4):338-344 (2005).
Khan et al., "A lethal role for lipid A in *Salmonella* infections," Mol. Microbiol. 29(2):571-579 (1998).
Kim et al., "Inhibition of vascular endothelial growth factor-induced angiogenesis suppresses tumour growth in vivo," Nature 362(6423):841-844 (1993).
Kimbrough, T.G. and Miller, S.I., "Assembly of the type III secretion needle complex of *Salmonella typhimurium*," Microbes Infect. 4(1):75-82 (2002).
Kimura et al., "Selective Localization and Growth of *Bifidobacterium bifidum* in Mouse Tumors following Intravenous Administration," Cancer Res. 40:2061-2068 (1980).
Kistner et al., "Interferon-inducible CXC-chemokines are crucial immune modulators and survival predictors in colorectal cancer," Oncotarget 8(52):89998-90012 (2017).
Kocijancic et al., "Local application of bacteria improves safety of *Salmonella*-mediated tumor therapy and retains advantages of systemic infection," Oncotarget 8(30):49988-50001 (2017).
Kong et al., "Turning self-destructing *Salmonella* into a universal DNA vaccine delivery platform," Proc. Natl. Acad. Sci. U.S.A. 109(47):19414-19419 (2012).
Kong et al., "Palmitoylation State Impacts Induction of Innate and Acquired Immunity by the *Salmonella enterica* Serovar Typhimurium msbB Mutant," Infection and Immunity 79(12):5027-5038 (2011).
Koopman et al., "Inhibition of *Salmonella enterica* Biofilm Formation Using Small-Molecule Adenosine Mimetics," Antimicrobial Agents and Chemotherapy 59(1):76-84 (2015).

(56) References Cited

OTHER PUBLICATIONS

Kortmann et al., "Cutting Edge: Inflammasome Activation in Primary Human Macrophages is Dependent on Flagellin," J. Immunol. 195:815-819 (2015).
Kuo et al., "The Role of CXCR3 and Its Chemokine Ligands in Skin Disease and Cancer," Front. Med. (Lausanne) 5:271 (2018), 10 pages.
Kzhyshkowska et al., "Stabilin-1, a homeostatic scavenger receptor with multiple functions," J. Cell. Mol. Med. 10(3):635-649 (2006).
Lan et al., "Dnase2a deficiency uncovers lysosomal clearance of damaged nuclear DNA via autophagy," Cell Rep. 9(1):180-192 (2014).
Larocca, C. and Schlom, J., "Viral Vector-based Therapeutic Cancer Vaccines," Cancer J. 17(5):359-371 (2011).
Le et al., "A Live-attenuated Listeria Vaccine (ANZ-100) and a Live-attenuated Listeria Vaccine Expressing Mesothelin (CRS-207) for Advanced Cancers: Phase 1 Studies of Safety and Immune Induction," Clin. Cancer Res. 18(3):858-868 (2012).
Le et al., "Safety and Survival With GVAx Pancreas Prime and Listeria Monocytogenes-Expressing Mesothelin (CRS-207) Boost Vaccines for Metastatic Pancreatic Cancer," J. Clin. Oncol. 33(12):1325-1333 (2015).
Lechner et al., "Chemokines, costimulatory molecules and fusion proteins for the immunotherapy of solid tumors," Immunotherapy 3(11):1317-1340 (2011).
Lee et al., "B7-H1 (Programmed Cell Death Ligand 1) Is Required for the Development of Multifunctional Th1 Cells and Immunity to Primary, but Not Secondary, *Salmonella* Infection," J. Immunol. 185:2442-2449 (2010).
Lee et al., "Comparative Evaluation of the Acute Toxic Effects in Monkeys, Pigs and Mice of a Genetically Engineered *Salmonella* Strain (VNP20009) Being Developed as an Antitumor Agent," Int. J. Toxicol. 19:19-25 (2000).
Lee, S. and Margolin, K., "Cytokines in Cancer Immunotherapy," Cancers 3:3856-3893 (2011).
Lee et al., "MHC class-I-restricted CD8 T cells play a protective role during primary *Salmonella* infection," Immunol. Lett. 148(2):138-143 (2012).
Lee et al., "The *C. elegans* heterochronic gene lin-4 encodes small RNAs with antisense complementarity to lin-14," Cell 75(5):843-854 (1993).
LeMercier et al., "VISTA regulates the development of protective anti-tumor immunity," Cancer Res. 74(7):1933-1944 (2014).
Leschner et al., "Tumor Invasion of *Salmonella enterica* Serovar Typhimurium Is Accompanied by Strong Hemorrhage Promoted by TNF-α," PLoS ONE 4(8):e6692 (2009), 11 pages.
Leventhal et al., "LB-131/28—Activation of innate and adaptive immunity via combinatorial immunotherapy using Synthetic Biotic™ Medicines," Abstract presented at the American Association for Cancer Research (AACR) meeting from Apr. 14-18, 2018, Chicago, IL, 2 pages.
Li et al., "Murine Dendritic Cells Modified with CXCL10 Gene and Tumour Cell Lysate Mediate Potent Antitumour Immune Responses in Mice," Scand. J. Immunol. 65(1):8-13 (2007).
Li et al., "Optimal promoter usage for lentiviral vector-mediated transduction of cultured central nervous system cells," J. Neurosci. Methods 189(1):56-64 (2010).
Li et al., "Pyroptosis of *Salmonella typhimurium*-infected macrophages was supressed and elimination of intracellular bacteria from macrophages was promoted by blocking QseC," Scientific Reports 6:37447 (2016), 12 pages.
Li, Y. and Kowdley, K. V., "MicroRNAs in Common Human Diseases," Genomics Proteomics Bioinformatics 10:246-253 (2012).
Lightfield et al., "Critical role of Naip5 in inflammasome activation by a conserved C-terminal domain of flagellin," Nat. Immunol. 9(10):1171-1178 (2008).
Lin et al., "The role of IL-7 in Immunity and Cancer," Anticancer Research 37:963-968 (2017).
Lindahl et al., "Biochemical properties of mammalian TREX1 and its association with DNA replication and inherited inflammatory disease," Biochem. Soc. Trans. 37(Pt 3):535-538 (2009).
Liu et al., "Blockage of autophagy pathway enhances *Salmonella* tumor-targeting," Oncotarget 7(16):22873-22882 (2016).
Liu et al., "NF-κB signaling in inflammation," Signal Transduction and Targeted Therapy 2:e17023 (2017), 9 pages.
Liu et al., "Inhibition of HIV-1 by multiple siRNAs expressed from a single microRNA polycistron," Nucleic Acids Res. 36(9):2811-2824 (2008).
Liu et al., "Immune-checkpoint proteins VISTA and PD-1 nonredundantly regulate murine T-cell responses," Proc. Natl. Acad. Sci. U.S.A. 112(21):6682-6687 (2015).
Liu et al., "Pre-Clinical Development of a Humanized Anti-CD47 Antibody with Anti-Cancer Therapeutic Potential," PLoS ONE 10(9):e0137345 (2015), 23 pages.
Liu et al., "CD47 Blockade Triggers T cell-mediated Destruction of Immunogenic Tumors," Nat. Med. 21(10):1209-1215 (2015).
Liu et al., "Outer membrane vesicles from flagellin-deficient *Salmonella enterica* serovar Typhimurium induce cross-reactive immunity and provide cross-protection against heterologous *Salmonella* challenge," Scientific Reports 6:34776 (2016), 13 pages.
Lo et al., "T cell responses to Gram-negative intracellular bacterial pathogens: a role for CD8+ T cells in immunity to *Salmonella* infection and the involvement of MHC class Ib molecules," J. Immunol. 162(9):5398-5406 (1999).
Loeffler et al., "Attenuated *Salmonella* engineered to produce human cytokine LIGHT inhibit tumor growth," Proc. Natl. Acad. Sci. U.S.A. 104(31):12879-12883 (2007).
Loeffler et al., "IL-18-producing *Salmonella* inhibit tumor growth," Cancer Gene Ther. 15(12):787-794 (2008).
Loeffler et al., "Inhibition of Tumor Growth Using *Salmonella* Expressing Fas Ligand," J. Natl. Cancer. Inst. 100:1113-1116 (2008).
Low et al., "Construction of VNP20009: A Novel, Genetically Stable Antibiotic-Sensitive Strain of Tumor-Targeting *Salmonella* for Parenteral Administration in Humans," Methods in Molecular Medicine, vol. 90, Suicide Gene Therapy: Methods and Reviews (Chp 3), pp. 47-59 (2003).
Low et al., "Lipid A mutant *Salmonella* with suppressed virulence and TNFα induction retain tumor-targeting in vivo," Nature Biotechnology 17:37-41 (1999).
Lundberg et al., "Growth phase-regulated induction of *Salmonella*-induced macrophage apoptosis correlates with transient expression of SPI-1 genes," J. Bacteriol. 181(11):3433-3437 (1999).
Luo et al., "Antitumor Effect of VNP20009, an Attenuated *Salmonella*, in Murine Tumor Models," Oncology Research 12:501-508 (2002).
Machine-generated English language translation of Chinese Patent No. CN 103468626 B, 35 pages.
Mackenzie et al., "Ribonuclease H2 mutations induce a cGAS/STING-dependent innate immune response," EMBO J. 35(8):831-844 (2016).
Mahoney et al., "Combination cancer immunotherapy and new immunomodulatory targets," Nat. Rev. DrugDiscov. 14(8):561-584 (2015).
Makinen et al., "Stable RNA interference: comparison of U6 and H1 promoters in endothelial cells and in mouse brain," J. Gene. Med. 8:433-441 (2006).
Manon et al., "Chapter 17: The Different Strategies Used by *Salmonella* to Invade Host Cells," In: *Salmonella*—Distribution, Adaptation, Control Measures and Molecular Technologies, eds. Annous and Gurtler, Rijeka, pp. 339-364 (2012).
Manuel et al., "*Salmonella*-Based Therapy Targeting Indoleamine 2,3-Dioxygenase Coupled with Enzymatic Depletion of Tumor Hyaluronan Induces Complete Regression of Aggressive Pancreatic Tumors," Cancer Immunol. Res. 3(9):1096-1107 (2015).
Manuel et al., "Enhancement of Cancer Vaccine Therapy by Systemic Delivery of a Tumor-Targeting *Salmonella*-Based STAT3 shRNA Suppresses the Growth of Established Melanoma Tumors," Cancer Res. 71(12):4183-4191 (2011).
Marin-Acevedo et al., "Next generation of immune checkpoint therapy in cancer: new developments and challenges," Journal of Hematology & Oncology 11:39 (2018), 20 pages.

(56) References Cited

OTHER PUBLICATIONS

Maroun et al., "Designing and building oncolytic viruses," Future Virol. 12(4):193-213 (2017).
Mazur, D.J. and Perrino, F.W., "Excision of 3' Termini by the Trexl and TREX2 3' -> 5' Exonucleases," J. Biol. Chem. 276(20):17022-17029 (2001).
McBride et al., "Artificial miRNAs mitigate shRNA-mediated toxicity in the brain: Implications for the therapeutic development of RNAi," Proc. Natl. Acad. Sci. U.S.A. 105(15):5868-5873 (2008).
McCracken et al., "Molecular Pathways: Activating T Cells After Cancer Cell Phagocytosis from Blockade of CD47 "Don't Eat Me" Signals," Clin. Cancer Res. 21(16):3597-3601 (2015).
McKelvey et al., "Cell-specific expression of TLR9 isoforms in inflammation," J. Autoimmun. 36(1):76-86 (2011).
Methner et al., "*Salmonella* Enteritidis with double deletion in phoP fliC- A potential live *Salmonella* vaccine candidate with novel characteristics for use in chickens," Vaccine 29:3248-3253 (2011).
Miao et al., "Innate immune detection of the type III secretion apparatus through the NLRC4 inflammosome," Proc. Natl. Acad. Sci. U.S.A. 107(7):3076-3080 (2010).
Miao, E.A. and Rajan, J.V., "*Salmonella* and Caspase-1: a complex interplay of detection and evasion," Frontiers in Microbiology 2:85 (2011), 6 pages.
Miller et al., "A two-component regulatory system (phoP phoQ) controls *Salmonella typhimurium* virulence," Proc. Natl. Acad. Sci. U.S.A. 86:5054-5058 (1989).
Moore et al., "Short Hairpin RNA (shRNA): Design, Delivery and Assessment of Gene Knockdown," Methods Mol. Biol. 629:141-158 (2010).
Morita et al., "Gene-Targeted Mice Lacking the Trexl (DNase III) 3'—→5' DNA Exonuclease Develop Inflammatory Myocarditis," Mol. Cell. Biol. 24(15):6719-6727 (2004).
Muenchmeier et al., "A Novel CXCL 10-Based GPI-Anchored Fusion Protein as Adjuvant in NK-Based Tumor Therapy," PLoS One 8(8):e72749 (2013), 12 pages.
Murakami et al., "Tumor-targeting *Salmonella typhimurium* A1-R regresses an osteosarcoma in a patient-derived xenograft model resistant to a molecular-targeting drug," Oncotarget 8(5):8035-8042 (2017).
Murata et al., "The CD47-SIRPα signalling system: its physiological roles and therapeutic application," J. Biochem. 155(6):335-344 (2014).
Murugaiyan et al., "Differential CD40/CD40L Expression Results in Counteracting Antitumor Immune Responses," J. Immunol. 178:2047-2055 (2007).
Needleman, S.B., and Wunsch, C.D., "A General Method Applicable to the Search for Similarities in the Amino Acid Sequence of Two Proteins," J. Mol. Biol. 48:443-453 (1970).
Nemunaitis et al., "Pilot trial of genetically modified, attenuated *Salmonella* expressing the *E. coli* cytosine deaminase gene in refractory cancer patients," Cancer Gene Therapy 10:737-744 (2003).
Nie et al., "Regulation of U6 Promoter Activity by Transcriptional Interference in Viral Vector-Based RNAi," Genomics Proteomics Bioinformatics 8(3):170-179 (2010).
Ohlson et al., "Structure and function of SifA indicate that interactions with SKIP, SseJ, and RhoA family GTPases induce endosomal tabulation," Cell Host Microbe 4(5):434-446 (2008).
Olsen et al., "The role of flagella and chemotaxis genes in host pathogen interaction of the host adapted *Salmonella enterica* serovar Dublin compared to the broad host range serovar S. Typhimurium," BMC Microbiology 13:67 (2013), 11 pages.
O'Rourke et al., "A single dose of peripherally infused EGFRvIII-directed CAR T cells mediates antigen loss and induces adaptive resistance in patients with recurrent glioblastoma," Sci. Transl. Med. 9(399):eaaa0984 (2017), 30 pages.
Osterberg et al., "Decrease of VEGF-A in myeloid cells attenuates glioma progression and prolongs survival in an experimental glioma model," Neuro-Oncology 18(7):939-949 (2016).
Owen et al., "*Salmonella* Suppresses the TRIF-Dependent Type I Interferon Response in Macrophages," mBio 7(1):e02051-15 (2016), 15 pages.
Palani et al., "Monocyte Stabilin-1 Suppresses the Activation of Th1 Lymphocytes," J. Immunol. 196(1):115-123 (2016).
Pandey et al., "Microbial Sensing by Toll-Like Receptors and Intracellular Nucleic Acid Sensors," Cold Spring Harb. Perspect. Biol. 7:a016246 (2015), 18 pages.
Park et al., "Analysis of virulence and growth of a purine auxotrophic mutant of *Xanthomonas oryzae* pathovar *oryzae*," FEMS Microbiol. Lett. 276(1):55-59 (2007).
Pasquinelli et al., "Conservation of the sequence and temporal expression of let-7 heterochronic regulatory RNA," Nature 408(6808):86-89 (2000).
Patyar et al., "Bacteria in cancer therapy: a novel experimental strategy," J. Biomed. Sci. 17:21 (2010), 9 pages.
Pawelek et al., "Bacteria as tumour-targeting vectors," Lancet Oncol. 4:548-556 (2003).
Pawelek et al., "Tumor-targeted *Salmonella* as a Novel Anticancer Vector," Cancer Research 57:4537-4544 (1997).
Pebernard, S. and Iggo, R. D., "Determinants of interferon-stimulated gene induction by RNAi vectors," Differentiation 72(2-3):103-111 (2004).
Peggs et al., "Cancer immunotherapy: co-stimulatory agonists and co-inhibitory antagonists," Clinical and Experimental Immunology 157:9-19 (2009).
Pereira-Lopes et al., "The exonuclease Trex1 restrains macrophage proinflammatory activation," J. Immunol. 191:6128-6135 (2013).
Peschke et al., "Loss of Trex1 in Dendritic Cells Is Sufficient To Trigger Systemic Autoimmunity," J. Immunol. 197(6):2157-2166 (2016).
Phan et al., "Cancer regression and autoimmunity induced by cytotoxic T lymphocyte-associated antigen 4 blockade in patients with metastatic melanoma," Proc. Natl. Acad. Sci. U.S.A. 100(14):8372-8377 (2003).
Prati et al., "Three Prime Repair Exonuclease 1 (TREX1) Expression Correlates with Cervical Cancer Cells Growth in vitro and Disease Progression in vivo," Scientific Reports 9:351 (2019), 14 pages.
Pulliero et al., "Inhibition of neuroblastoma cell growth by TREX1-mutated human lymphocytes," Oncology Reports 27:1689-1694 (2012).
Rabe, B., "Aicardi-Goutieres syndrome: clues from the RNase H2 knock-out mouse," J. Mol. Med. (Berl.) 91(11):1235-1240 (2013).
Raetz, C.R.H. and Whitfield, C., "Lipopolysaccharide endotoxins," Annu. Rev. Biochem. 71:635-700 (2002).
Rantakari et al., "Stabilin-1 expression defines a subset of macrophages that mediate tissue homeostasis and prevent fibrosis in chronic liver injury," Proc. Natl. Acad. Sci. U.S.A. 113(33):9298-9303 (2016).
Ribas, A., "Releasing the Brakes on Cancer Immunotherapy," N. Engl. J. Med. 373(16):1490-1492 (2015).
Rosenberg et al., "Antitumor Effects in Mice of the Intravenous Injection of Attenuated *Salmonella Typhimurium*," Journal of Immunotherapy 25(3):218-225 (2002).
Rosenberg et al., "Cancer immunotherapy: moving beyond current vaccines," Nat. Med. 10(9):909-915 (2004).
Re: Rosenberg et al. (2004) Nat Med 10(9):909-915, Correspondence to the Editor by Mocellin et al., p. 1278, Correspondence to the Editor by Timmerman et al., p. 1279, and Reply by Rosenberg et al., in Nat. Med. 10(12): 1278-1280 (2004).
Ruehlmann et al., "Mig (CXCL9) Chemokine Gene Therapy Combines with Antibody-Cytokine Fusion Protein to Suppress Growth and Dissemination of Murine Colon Carcinoma," Cancer Res. 61(23):8498-8503 (2001).
Ruella, M. and Maus, M.V., "Catch me if you can: Leukemia Escape after CD19-Directed T Cell Immunotherapies," Comput. Struct. Biotechnol. J. 14:357-362 (2016).
Sadelain, M., "CAR therapy: the CD19 paradigm," J. Clin. Invest. 125(9):3392-3400 (2015).
Schadendorf et al., "Pooled Analysis of Long-Term Survival Data From Phase II and Phase III Trials of Ipilimumab in Unresectable or Metastatic Melanoma," J. Clin. Oncol. 33(17):1889-1894 (2015).

(56) References Cited

OTHER PUBLICATIONS

Schaller et al., "Chemokines as adjuvants for immunotherapy: Implications for immune activation with CCL3," Expert Rev. Clin. Immunol. 13(11):1049-1060 (2017).
Scheiermann, J. and Klinman, D.M., "Clinical evaluation of CpG oligonucleotides as adjuvants for vaccines targeting infectious diseases and cancer," Vaccine 32(48):6377-6389 (2014).
Schmitt et al., "Absence of All Components of the Flagellar Export and Synthesis Machinery Differentially Alters Virulence of *Salmonella enterica* Serovar Typhimurium in Models of Typhoid Fever, Survival in Macrophages, Tissue Culture Invasiveness, and Calf Enterocolitis," Infection and Immunity 69(9):5619-5625 (2001).
Schwartz, R.M. and Dayhoff, M.O., "Matrices for detecting distant relationships," in Atlas of Protein Sequence and Structure, National Biomedical Research Foundation, pp. 353-358 (1978).
Sharma et al., "Novel cancer immunotherapy agents with survival benefit: recent successes and next steps," Nat. Rev. Cancer 11(11):805-812 (2011).
Sharma et al., "Primary, Adaptive, and Acquired Resistance to Cancer Immunotherapy," Cell 168:707-723 (2017).
Sheikhi et al., "Whole Tumor Cell Vaccine Adjuvants: Comparing IL-12 to IL-2 and IL-15," Iran J. Immunol. 13(3):148-166 (2016).
Shi et al., "Combined prokaryotic-eukaryotic delivery and expression of therapeutic factors through a primed autocatalytic positive-feedback loop," Journal of Controlled Release 222:130-140 (2016).
Sirard et al., "Live attenuated *Salmonella*: a paradigm of mucosal vaccines," Immunol. Rev. 171:5-26 (1999).
Smith, T.F. and Waterman, M.S., "Comparison of Biosequences," Adv. Appl. Math. 2:482-489 (1981).
Sockolosky et al, "Durable antitumor responses to CD47 blockade require adaptive immune stimulation," Proc. Natl. Acad. Sci. U.S.A. 113:E2646-E2654 (2016).
Sorenson et al., "Safety and immunogenicity of *Salmonella* typhimurium expressing C-terminal truncated human IL-2 in a murine model," Biologies: Targets & Therapy 4:61-73 (2010).
Spranger et al., "Melanoma-intrinsic β-catenin signalling prevents anti-tumour immunity," Nature 523(7559):231-235 (2015).
Stagg, J. and Smyth, M.J., "Extracellular adenosine triphosphate and adenosine in cancer," Oncogene 29:5346-5358 (2010).
Starks et al., "*Listeria monocytogenes* as a Vaccine Vector: Virulence Attenuation or Existing Antivector Immunity Does Not Diminish Therapeutic Efficacy," J. Immunol. 173:420-427 (2004).
Stetson et al., "Trex1 prevents cell-intrinsic initiation of autoimmunity," Cell 134(4):587-598 (2008).
Stijlemans et al., "Efficient Targeting of Conserved Cryptic Epitopes of Infectious Agents by Single Domain Antibodies," J. Biol. Chem. 279(2):1256-1261 (2004).
Stritzker et al., "Enterobacterial tumor colonization in mice depends on bacterial metabolism and macrophages but is independent of chemotaxis and motility," Int. J. Med. Microbiol. 300:449-456 (2010).
Sun et al., "Cyclic GMP-AMP Synthase is a Cytosolic DNA Sensor that Activates the Type-I Interferon Pathway," Science 339(6121):786-791 (2013).
Tai et al., "Targeting the WNT Signaling Pathway in Cancer Therapeutics," The Oncologist 20:1189-1198 (2015).
Tjuvajev et al., "*Salmonella*-based tumor-targeted cancer therapy: tumor amplified protein expression therapy (TAPET™) for diagnostic imaging," J. Control Release 74(1-3):313-315 (2001).
Tome et al., "Primer Dosing of *S. typhimuium* A1-R Potentiates Tumor-Targeting and Efficacy in Immunocompetent Mice," Anticancer Research 33:97-102 (2013).
Toley, B. J. and Forbes, N. S., "Motility is Critical for Effective Distribution and Accumulation of Bacteria in Tumor Tissue," Integr. Biol. (Camb.) 4(2):165-176 (2012).
Tomicic et al., "Human three prime exonuclease TREX1 is induced by genotoxic stress and involved in protection of glioma and melanoma cells to anticancer drugs," Biochimica et Biophysica Acta 1833:1832-1843 (2013).
Topalian et al., "Safety, Activity, and Immune Correlates of Anti-PD-1 Antibody in Cancer," N. Engl. J. Med. 366(26):2443-2454 (2012).
Torres et al., "Bacteria in cancer therapy: beyond immunostimulation," J. Cancer Metastasis Treat. 4:4 (2018), 25 pages.
Toso et al., "Phase I Study of the Intravenous Administration of Attenuated *Salmonella typhimurium* to Patients With Metastatic Melanoma," Journal of Clinical Oncology 20(1):142-152 (2002).
Travis, M.A. and Sheppard, D., "TGF-β activation and function in immunity," Annu. Rev. Immunol. 32:51-82 (2014).
Tukel et al., "CsgA is a pathogen-associated molecular pattern of *Salmonella enterica* serotype Typhimurium that is recognized by Toll-like receptor 2," Mol. Microbiol. 58(1):289-304 (2005).
Tyle, P., "Iontophoretic Devices for Drug Delivery," Pharmaceutical Research 3(6):318-326 (1986).
Vanpouille-Box et al., "DNA exonuclease Trex1 regulates radiotherapy-induced tumor immunogenicity," Nat. Comm. 8:15618 (2017), 15 pages.
Vaupel, P. and Mayer, A., "Hypoxia-Driven Adenosine Accumulation: A Crucial Microenvironmental Factor Promoting Tumor Progression," in: Oxygen Transport to Tissue XXXVII, Advances in Experimental Medicine and Biology 876, C. E. Elwell et al. (eds.), Springer Science + Business Media, New York, Chp 22, pp. 177-183 (2016).
Wang et al., "TREX1 acts in degrading damaged DNA from drug-treated tumor cells," DNA Repair (Amst.) 8(10):1179-1189 (2009).
Wang, R.F. and Kushner, S.R., "Construction of versatile low-copy-number vectors for cloning, sequencing and gene expression in *Escherichia coli*" Gene 100:195-199 (1991).
Wang et al., "VISTA, a novel mouse Ig superfamily ligand that negatively regulates T cell responses," J. Exp. Med. 208(3):577-592 (2011).
Wang et al., "New technologies in developing recombinant attenuated *Salmonella* vaccine vectors," Microbial Pathogenesis 58:17-28 (2013).
Watanabe et al., "Quantitative evaluation of first, second, and third generation hairpin systems reveals the limit of mammalian vector-based RNAi," RNA Biology 13(1):25-33 (2016).
Watson et al., "Molecular Biology of the Gene," 4th Edition, The Benjamin/Cummings Publ. Co., Inc, p. 224 (1987), 25 pages.
Weiskopf et al., "CD47-blocking immunotherapies stimulate macrophage-mediated destruction of small-cell lung cancer," J. Clin. Invest. 126(7):2610-2620 (2016).
Wheeler et al., "TREX1 Knockdown Induces an Interferon Response to HIV that Delays Viral Infection in Humanized Mice," Cell Reports 15:1715-1727 (2016).
Wilson et al., "MicroRNA regulation of endothelial TREX1 reprograms the tumour microenvironment," Nat. Comm. 7:13597 (2016), 10 pages.
Winter et al., "The Flagellar Regulator TviA Reduces Pyroptosis by *Salmonella enterica* Serovar Typhi," Infect. Immun. 83(4):1546-1555 (2015).
Wu et al., "Cyclic-GMP-AMP Is An Endogenous Second Messenger in Innate Immune Signaling by Cytosolic DNA," Science 339(6121):826-830 (2013).
Xia et al., "An enhanced U6 promoter for synthesis of short hairpin RNA," Nucleic Acids Res. 31(17):e100 (2003), 5 pages.
Xie et al., "MiR-140 Expression Regulates Cell Proliferation and Targets PD-L1 in NSCLC," Cell Physiol. Biochem. 46(2):654-663 (2018).
Xu et al., "Effective Cancer Vaccine Platform Based on Attenuated *Salmonella* and a Type III Secretion System," Cancer Res. 74(21):6260-6270 (2014).
Yan et al., "The cytosolic exonuclease TREX1 inhibits the innate immune response to HIV-1," Nat. Immunol. 11(11):1005-1013 (2010).
Yanagita et al., "Anti-SIRPα antibodies as a potential new tool for cancer immunotherapy," JCI Insight 2(1):e89140 (2017), 15 pages.
Yang et al., "Trex1 Exonuclease Degrades ssDNA to Prevent Chronic Checkpoint Activation and Autoimmune Disease," Cell 131:873-886 (2007).

(56) References Cited

OTHER PUBLICATIONS

Yasutake et al., "Comparison of antitumor activity of *Lactobacillus casei* with other bacterial immunopotentiators," Med. Microbiol. Immunol. 173(3):113-125 (1984).
Yee, C., "Adoptive T Cell Therapy for Cancer: Boutique Therapy or Treatment Modality?" Clin. Cancer Res. 19(17):4550-4552 (2013).
Yee et al., "MicroRNA-155 induction via TNF-α and IFN-γ suppresses expression of programmed death ligand-1 (PD-L1) in human primary cells," J. Biol. Chem. 292(50):20683-20693 (2017).
Yoon et al., "Application of genetically engineered *Salmonella typhimurium* for interferon-gamma-induced therapy against melanoma," European Journal of Cancer 70:48-61 (2017).
Yoon et al., "Suppression of Inflammation by Recombinant *Salmonella typhimurium* Harboring CCL22 MicroRNA," DNA and Cell Biology 31(3):289-296 (2012).
Yu et al., "Explicit hypoxia targeting with tumor suppression by creating an "obligate" anaerobic *Salmonella typhimurium* strain," Scientific Reports 2:436 (2012), 10 pages.
Zakikhany et al., "Unphosphorylated CsgD controls biofilm formation in *Salmonella enterica* serovar Typhimurium," Molecular Microbiology 77(3):771-786 (2010).
Zeng et al., "Flagellin is the Major Proinflammatory Determinant of Enteropathogenic *Salmonella*" J. Immunol. 171:3668-3674 (2003).
Zhang et al., "Intratumoral Delivery and Suppression of Prostate Tumor Growth by Attenuated *Salmonella enterica* serovar *typhimurium* Carrying Plasmid-Based Small Interfering RNAs," Cancer Res. 67(12):5859-5864 (2007).
Zhang et al., "The genes slyA, STM3120 and htrA are required for the anticancer ability of VNP20009," Oncotarget 7(49):81187-81196 (2016).
Zhang et al., "shRNA-armed conditionally replicative adenoviruses: a promising approach for cancer therapy," Oncotarget 7(20):29824-29834 (2016).
Zhao et al., "Efficacy against lung metastasis with a tumor-targeting mutant of *Salmonella typhimurium* in immunocompetent mice," Cell Cycle 11(1):187-193 (2012).
Zhao et al., "Targeted Therapy with a *Salmonella typhimurium* Leucine-Arginine Auxotroph Cures Orthotopic Human Breast Tumors in Nude Mice," Cancer Res. 66(15):7647-7652 (2006).
Zhao et al., "Tumor-targeting bacterial therapy with amino acid auxotrophs of GFP-expressing *Salmonella typhimurium*," Proc. Natl. Acad. Sci. U.S.A. 102(3):755-760 (2005).
Zheng et al., "Two-step enhanced cancer immunotherapy with engineered *Salmonella typhimurium* secreting heterologous flagellin," Sci. Transl. Med. 9:eaak9537 (2017), 34 pages.
Zheng et al., "Targeted Cancer Therapy Using Engineered *Salmonella typhimurium*," Chonnam Med. J. 52:173-184 (2016).
Zheng et al., "Tumor Amplified Protein Expression Therapy: *Salmonella* as a Tumor-Selective Protein Delivery Vector," Oncol. Res. 12:127-135 (2000).
Zielinski et al., "Dissecting the human immunologic memory for pathogens," Immunol. Rev. 240:40-51 (2011).
Zitvogel et al., "Type I interferons in anticancer immunity" Nature Reviews Immunology 15:405-414 (2015).
Zu, C. and Wang, J., "Tumor-colonizing bacteria: A potential tumor targeting therapy," Crit. Rev. Microbiol. 40(3):225-235 (2014).
Glickman et al., Actym Therapeutics Poster Presentation, entitled "STACT-TREX1: A Novel Tumor-Targeting Systemically-Delivered STING Pathway Agonist Demonstrates Robust Anti-Tumor Efficacy in Multiple Murine Cancer Models." Abstract #P235. Presented at the Society for Immunotherapy of Cancer (SITC) Annual Meeting, in Washington, D.C., on Nov. 9, 2018, 1 page.
Makarova et al., Actym Therapeutics Poster Presentation, entitled "STACT-TREX1: A Systemically-Administered STING Pathway Agonist Targets Tumor-Resident Myeloid Cells and Induces Adaptive Anti-Tumor Immunity in Multiple Preclinical Models," Abstract #5016. Presented at the American Association for Cancer Research (AACR) Annual Meeting, in Atlanta, GA, on Apr. 3, 2019, 1 page.
Rae et al., Actym Therapeutics Poster Presentation, entitled "STACT: A novel Tumor-Targeting, Systemically-Administered Delivery Platform Capable of Targeting Intractable Pathways and Precise Immuno-Modulation of the Tumor Microenvironment." Abstract #4782. Presented at the American Association for Cancer Research (AACR) Annual Meeting, in Atlanta, GA, on Apr. 3, 2019, 1 page.
Christopher D. Thanos, Ph.D., Actym Therapeutics Presentation, entitled "A Novel Systemically Delivered STING Pathway Agonist Therapy Demonstrates Robust Anti-Tumor Efficacy in Multiple Murine Cancer Models." Presented at the 15th Annual PEGS Conference in Boston, MA, on Apr. 12, 2019, 35 pages.
Glickman et al., Actym Therapeutics Poster Presentation, entitled "STACT: A Novel Therapeutic Platform that Delivers Immunomodulatory Payloads to Tumor-Resident Myeloid Cells After IV Dosing and Demonstrates Potent Anti-Tumor Efficacy in Preclinical Studies." Poster #P482. Presented at the Society for Immunotherapy of Cancer (SITC) Annual Meeting, in National Harbor, MD, on Nov. 9, 2019, 1 page.
Actym Therapeutics, Inc., "The next frontier in immuno-oncology," BioPharma Dealmakers, B22, Mar. 2019, 1 page.
Actym Therapeutics Press Release, entitled "Actym Therapeutics Raises $34 Million Series A. Financing will fund Actym's cancer immunotherapy pipeline into clinical development." Published Apr. 27, 2020 [online]; retrieved on Nov. 23, 2020, from: <URL:prnewswire.com/news-releases/actym-therapeutics-raises-34-million-series-a-301047161.html, 3 pages.
Invitation to Pay Additional Fees and Partial International Search, dated Oct. 17, 2018, in connection with International Patent Application No. PCT/US2018/041713, 25 pages.
Response to Invitation to Pay Additional Fees, submitted Nov. 15, 2018, in connection with International Patent Application No. PCT/US2018/041713, 13 pages.
International Search Report and Written Opinion, dated Jan. 3, 2019, in connection with International Patent Application No. PCT/US2018/041713, 34 pages.
Response, filed May 13, 2019, to International Search Report and Written Opinion, dated Jan. 3, 2019, in connection with International Patent Application No. PCT/US2018/041713, 55 pages.
Invitation to Restrict or Pay Additional Examination Fees, dated Jun. 7, 2019, in connection with International Patent Application No. PCT/US2018/041713, 9 pages.
Response, filed Jul. 5, 2019, to Invitation to Restrict or Pay Additional Examination Fees, dated Jun. 7, 2019, in connection with International Patent Application No. PCT/US2018/041713, 4 pages.
Written Opinion of the International Preliminary Examining Authority, dated Aug. 6, 2019, in connection with International Patent Application No. PCT/US2018/041713, 13 pages.
Replacement Claim Sets, filed Sep. 6, 2019, and Response, filed Sep. 5, 2019, to the Written Opinion of the International Preliminary Examining Authority, dated Aug. 6, 2019, in connection with International Patent Application No. PCT/US2018/041713, 61 pages.
International Preliminary Report on Patentability (Chapter II of the PCT), dated Oct. 14, 2019, in connection with International Patent Application No. PCT/US2018/041713, 17 pages.
Office Action, dated Mar. 11, 2020, in connection with U.S. Appl. No. 16/033,187, 16 pages.
Response, filed Apr. 10, 2020, to Office Action, dated Mar. 11, 2020, in connection with U.S. Appl. No. 16/033,187, 19 pages.
Final Office Action, dated Jul. 14, 2020, in connection with U.S. Appl. No. 16/033,187, 9 pages.
Request for Continued Examination (RCE) and Preliminary Amendment, filed Aug. 12, 2020, in response to the Final Office Action, dated Jul. 14, 2020, in connection with U.S. Appl. No. 16/033,187, 11 pages.
Office Action, dated Nov. 3, 2020, in connection with U.S. Appl. No. 16/033,187, 8 pages.
Response, filed Nov. 24, 2020, to Office Action, dated Nov. 3, 2020, in connection with U.S. Appl. No. 16/033,187, 11 pages.
Invitation to Pay Additional Fees and Partial International Search, dated Nov. 22, 2019, in connection with International Patent Application No. PCT/US2019/048659, 20 pages.

(56) References Cited

OTHER PUBLICATIONS

Response, filed Dec. 20, 2019, to Invitation to Pay Additional Fees and Partial International Search, dated Nov. 220, 2019, in connection with International Patent Application No. PCT/US2019/048659, 11 pages.
Written Opinion of the International Preliminary Examining Authority, dated Nov. 13, 2020, in connection with International Patent Application No. PCT/US2019/048659, 15 pages.
Response, filed Dec. 14, 2020, to the Written Opinion of the International Preliminary Examining Authority, dated Nov. 13, 2020, in connection with International Patent Application No. PCT/US2019/048659, 51 pages.
Invitation to Pay Additional Fees and Partial International Search, dated Oct. 18, 2019, in connection with corresponding International Patent Application No. PCT/US2019/041489, 22 pages.
Response, filed Nov. 15, 2019, to Invitation to Pay Additional Fees and Partial International Search, dated Oct. 18, 2019, in connection with corresponding International Patent Application No. PCT/US2019/041489, 17 pages.
International Search Report and Written Opinion, dated Jan. 16, 2020, in connection with corresponding International Patent Application No. PCT/US2019/041489, 30 pages.
Demand for International Preliminary Examination (Chapter II) and Response under Article 34(2)(b) PCT, filed May 11, 2020, in response to the International Search Report and Written Opinion, dated Jan. 16, 2020, in connection with corresponding International Patent Application No. PCT/US2019/041489, 54 pages.
Written Opinion of the International Preliminary Examining Authority, dated May 27, 2020, in connection with corresponding International Patent Application No. PCT/US2019/041489, 11 pages.
Response, filed Jun. 29, 2020, to the Written Opinion of the International Preliminary Examining Authority, dated May 27, 2020, in connection with corresponding International Patent Application No. PCT/US2019/041489, 63 pages.
International Preliminary Report on Patentability (Chapter II of the PCT), dated Oct. 21, 2020, in connection with corresponding International Patent Application No. PCT/US2019/041489, 13 pages.
PCT Demand for International Preliminary Examination (Chapter II), and Response and Amendment under Article 34 PCT, filed Dec. 24, 2020, in response to the International Search Report and Written Opinion, dated Nov. 11, 2020, in connection with International Patent Application No. PCT/US/2020/020240, 86 pages.
Supplementary Response, filed Dec. 31, 2020, to the Written Opinion of the International Preliminary Examining Authority, dated Nov. 13, 2020, and to the Notification Concerning Informal Communications with the Applicant, dated Dec. 22, 2020, in connection with International Patent Application No. PCT/US2019/048659, 16 pages.
Response, filed Dec. 31, 2020, to the International Preliminary Report on Patentability (Chapter II of the PCT), dated Oct. 21, 2020, in connection with corresponding International Patent Application No. PCT/US2019/041489, 28 pages.
Letter/Written Disclosure of the Supplemental Information Disclosure Statement for the above-referenced application, filed herewith on Nov. 9, 2021, 2 pages.
Tominaga, A. and Kutsukake, K., "Expressed and cryptic flagellin genes in the H44 and H55 type strains of *Escherichia coli*," Genes Genet. Syst. 82:1-8 (2007).
Glickman et al.. Actym Therapeutics Abstract, entitled "STACT-TREX1: A Novel Tumor-Targeting Systemically-Delivered STING Pathway Agonist Demonstrates Robust Anti-Tumor Efficacy in Multiple Murine Cancer Models," Journal for ImmunoTherapv of Cancer 6(Suppl 1):Abstract #P235, 2 pages.
Rae et al., Actvm Therapeutics Abstract, entitled "STACT: A novel Tumor-Targeting, Systemically-Administered Delivery Platform Capable of Targeting Intractable Pathways and Precise Immuno-Modulation of the Tumor Microenvironment," Cancer Res. 79(Suppl 13): Abstract #4782, 4 pages.
Illumina Ventures Portfolio Company Spotlight, entitled, "Acvtm Therapeutics: A New Path to Immunology." Published Aug. 2021 [online]; retrieved on Nov. 8, 2021. from: <URL:illuminaventurcs.com/spotlight-actym-2021, 2 pages.
Office Action, dated Mar. 11, 2021, in connection with U.S. Appl. No. 16/033,187, 10 pages.
Response, filed Apr. 7, 2021, to Office Action, dated Mar. 11, 2021, in connection with U.S. Appl. No. 16/033,187, 9 pages.
Final Office Action, dated Jul. 15, 2021. in connection with U.S. Appl. No. 16/033,187, 6 pages.
Amendment After Final, filed Jul. 16, 2021, in response to the Final Office Action, dated Jul. 15, 2021, in connection with U.S. Appl. No. 16/033,187, 7 pages.
Notice of Allowance, dated Aug. 11. 2021, and Examiner-Initiated Interview Summary, dated Aug. 5, 2021, in connection with U.S. Appl. No. 16/033,187, 10 pages.
Office Action, dated Oct. 12, 2021, in connection with Japanese Patent Application No. 2020-523685 [English summary of Office Action; English translation of Office Action; and original document as issued in Japanese], 5 pages.
International Preliminary Report on Patentability (Chapter II of the PCT), dated Jan. 22, 2021, in connection with International Patent Application No. PCT/US2019/048659, 14 pages.
Office Action, dated Jan. 15, 2021, in connection with U.S. Appl. No. 16/554,478, 15 pages.
Response, filed Jul. 14, 2021, to Office Action, dated Jan. 15, 2021. in connection with U.S. Appl. No. 16/554,478, 51 pages.
International Preliminary Report on Patentability (Chapter II of the PCT), dated Jan. 28, 2021, in connection with International Patent Application No. PCT/US2019/041489, 12 pages.
Office Action, dated Sep. 30, 2021, in connection with U.S. Appl. No. 16/520,155, 7 pages.
Response, filed Oct. 25, 2021, to Office Action, dated Sep. 30, 2021, in connection with U.S. Appl. No. 16/520,155, 47 pages.
U.S. Appl. No. 16/033,187, filed Jul. 11, 2018, 2019/0017050, Jan. 17, 2019.
U.S. Appl. No. 16/554,478, filed Aug. 28, 2019, 2020/0071702, Mar. 5, 2020.
U.S. Appl. No. 16/520,155, filed Jul. 23, 2019, 2020/014543, Jan. 15, 2020.
U.S. Appl. No. 16/824,500, filed Mar. 19, 2020, 2020/0270613, Aug. 27, 2020.
U.S. Appl. No. 17/483,523, filed Sep. 23, 2021.
U.S. Appl. No. 17/560,080, filed Dec. 22, 2021.
U.S. Appl. No. 17/573,569, filed Jan. 11, 2022.
U.S. Appl. No. 17/320,200, filed May 13, 2021.
U.S. Appl. No. 17/569,290, filed Jan. 5, 2022.
Letter/Written Disclosure of the Supplemental Information Disclosure Statement for the above-referenced application, filed herewith on Jan. 13, 2022, 2 pages.
Pinero-Lambea et al.. "Engineered bacteria as therapeutic agents," *Curr. Opin. Biotechnol.* 35:94-102 (2015).
Vassaux et al., "Bacterial gene therapy strategies," *J. Pathol.* 208(2):290-298 (2006).
Examiner's Report, dated Dec. 24, 2021, in connection with corresponding Canadian Patent Application No. 3,106,143, 4 pages.
Letter/Written Disclosure of the Supplemental Information Disclosure Statement for the above-referenced application, filed herewith on Jun. 1, 2022, 2 pages.
Glickman et al., Actym Therapeutics Abstract, entitled "STACT: A Novel Therapeutic Platform that Delivers Immunomodulatory Payloads to Tumor-Resident Myeloid Cells After IV Dosing and Demonstrates Potent Anti-Tumor Efficacy in Preclinical Studies." Abstract #P482. Journal for ImmunoTherapy of Cancer 7(Suppl 1):263, Published on Nov. 6, 2019.
Examiner's Report, dated Dec. 30, 2021, issued in connection with Canadian Patent Application No. 3,069,523, 5 pages.
Response, filed Apr. 29, 2022, to the Examiner's Report, dated Dec. 30, 2021, issued in connection with Canadian Patent Application No. 3,069,523 [Response as filed, and listing of pending claims], 16 pages.
Response, filed Mar. 25, 2022, to the Communication under Rule 164(2)(b) EPC and Article 94(3) EPC, dated Jun. 10, 2021, issued in connection with European Patent Application No. 18 752 908.6, 11 pages.

(56) References Cited

OTHER PUBLICATIONS

Response, filed Jan. 7, 2022, to Office Action, dated Oct. 12, 2021, in connection with Japanese Patent Application No. 2020-523685 [English instructions; original document as filed in Japanese; and English translation of the pending claims], 17 pages.
Decision of Rejection, dated Jan. 25, 2022, in connection with Japanese Patent Application No. 2020-523685 [English summary of Office Action; English translation of Office Action; and original document as issued in Japanese], 5 pages.
Response, filed Apr. 6, 2022, to Decision of Rejection, dated Jan. 25, 2022, in connection with Japanese Patent Application No. 2020-523685 [English instructions; original document as filed in Japanese; and English translation of the pending claims], 21 pages.
Notice of Allowance, dated Mar. 11, 2022, in connection with U.S. Appl. No. 16/520,115, 8 pages.
Response, filed Apr. 22, 2022, to Examiner's Report, dated Dec. 24, 2021, in connection with Canadian Patent Application No. 3,106,143, 57 pages.
Decision to Grant, dated May 31, 2022, in connection with Japanese Patent Application No. 2020-523685 [English reporting letter, and original document as issued in Japanese], 5 pages.
U.S. Appl. No. 17/747,689, filed May 18, 2022.
U.S. Appl. No. 17/590,700, filed Feb. 1, 2022, 2022/0154136, May 19, 2022.
Allen et al., "Linear doggybone DNA vaccine induces similar immunological responses to conventional plasmid DNA independently of immune recognition by TLR9 in a pre-clinical model," Cancer Immunology, Immunotherapy 67:627-638 (2018).
Crull et al., "Influence of infection route and virulence factors on colonization of solid tumors by *Salmonella enterica* scrovar Typhimurim," FEMS Immunol. Med. Microbiol. 62:75-83 (2011).
Miller et al., "Genetic diversity and population structure of the endangered marsupial *Sarcophilus harrisii* (Tasmanian devil)," Proc. Natl. Acad. Sci. U.S.A. 108(30):12348-12353 (2011).
Office Action, issued Jun. 29, 2022, in connection with U.S. Appl. No. 16/824,500, 25 pages.
Letter/Written Disclosure of the Supplemental Information Disclosure Statement for the above-referenced application, filed herewith on Jul. 12, 2022, 4 pages.
Notification of Reopening Prosecution Due to Consideration of an Information Disclosure Statement Filed After Mailing of a Notice of Allowance, mailed Sep. 12, 2022, in connection with U.S. Appl. No. 16/520,155, 3 pages.
Office Action, dated Oct. 7, 2022, in connection with U.S. Appl. No. 16/520,155, 14 pages.
Office Action, issued Aug. 29, 2022, in connection with corresponding Chinese Patent Application No. 201980059088.5 [English translation of office action; and original document as issued in Chinese], 10 pages.
Communication pursuant to Rule 164(2)(b) and Article 94(3) EPC (Examination Report), dated Sep. 15, 2022, in connection with corresponding European Patent Application No. 19 745 021.6, 11 pages.
Search Report and Written Opinion, dated Sep. 2, 2022, in connection with corresponding Singapore Patent Application No. 11202100023X, 12 pages.
Letter/Written Disclosure of the Supplemental Information Disclosure Statement for the above-referenced application, filed herewith on Oct. 11, 2022, 5 pages.
Letter/Written Disclosure of the Supplemental Information Disclosure Statement for the above-referenced application, filed herewith on Aug. 7, 2023, 2 pages.
Avogadri et al., "Cancer Immunotherapy Based on Killing of Salmonella-Infected Tumor Cells," Cancer Res. 65(9): 3920-3927 (2005).
Examiner's Report, dated Dec. 14, 2022, issued in connection with Canadian Patent Application No. 3,069,523, 4 pages.
Response, filed Apr. 13, 2023, to Examiner's Report, dated Dec. 14, 2022, issued in connection with Canadian Patent Application No. 3,069,523, 15 pages.
Office Action, dated May 16, 2023, in connection with Japanese Patent Application No. 2022-063218 [English summary of Office Action, English translation of Office Action, and original document as issued in Japanese], 11 pages.
Response, filed Mar. 7, 2023, to Office Action, dated Oct. 7, 2022, in connection with U.S. Appl. No. 16/520,155 [Response as filed with Statement of Prior Art Exception Under 35 U.S.C. § 102(B)(2)(C)], 16 pages.
Notice of Allowance, mailed Jul. 17, 2023, in connection with U.S. Appl. No. 16/520,155, 7 pages.
Response, filed Jun. 22, 2023, to Examination Report, dated Oct. 8, 2022, in connection with Australian Patent Application No. 2019301699, 131 pages.
Examination Report, dated Jul. 8, 2023, in connection with Australian Patent Application No. 2019301699, 5 pages.
Examiner's Report, dated Dec. 23, 2022, in connection with Canadian Patent Application No. 3,106,143, 5 pages.
Responsc, filed Apr. 21, 2023, to Examiner's Report, dated Dcc. 23, 2022, in connection with Canadian Patent Application No. 3,106,143, 39 pages.
Examiner's Report, dated Jul. 25, 2023, in connection with Canadian Patent Application No. 3,106,143, 4 pages.
Examiner's Report, dated Dec. 9, 2022, in connection with Canadian Patent Application No. 3,176,812, 4 pages.
Response, filed Mar. 13, 2023, to Office Action, issued Aug. 29, 2022, in connection with Chinese Patent Application No. 201980059088.5 [English instructions for response; document as filed in Chinese; and English translation of the claims], 55 pages.
Response, filed Jun. 29, 2023, to Communication pursuant to Rule 164(2)(b) and Article 94(3) EPC (Examination Report), dated Sep. 15, 2022, issued in connection with European Patent Application No. 19 745 021.6, 39 pages.
Office Action, issued Dec. 20, 2022, in connection with Japanese Patent Application No. 2021-500579 [English summary of Office Action; English translation of Office Action; and Document as issued in Japanese], 8 pages.
Response, filed May 19, 2023, to Office Action, issued Dec. 20, 2022, in connection with Japanese Patent Application No. 2021-500579 [English instructions for responsc; Response as-filed in Japanese; and English translation of pending claims], 66 pages.
Office Action, mailed Jun. 20, 2023, in connection with Japanese Patent Application No. 2021-500579 [English translation of Office Action, and Document as issued in Japanese], 5 pages.
Response, filed Jul. 11, 2023, to Office Action, mailed Jun. 20, 2023, in connection with Japanese Patent Application No. 2021-500579 [English instructions for response; documents as filed in Japanese; and English translation of claims as filed], 27 pages.
Decision to Grant, issued Aug. 1, 2023, in connection with Japanese Patent Application No. 2021-500579 [English reporting letter, and original document as issued in Japanese], 6 pages.
Office Action, issued May 2, 2023, in connection with Korean Patent Application No. 10-2021-7004205 [English translation of Office Action; and document as issued in Korean], 14 pages.
Response, filed Feb. 3, 2023, to Search Report and Written Opinion, dated Sep. 2, 2022, in connection with Singapore Patent Application No. 11202100023X, 22 pages.
Response, filed Dec. 29, 2022, to Office Action, issued Jun. 29, 2022, in connection with U.S. Appl. No. 16/824,500, 66 pages.
Office Action, issued Mar. 14, 2023, in connection with U.S. Appl. No. 16/824,500, 21 pages.
Letter/Written Disclosure of the Supplemental Information Disclosure Statement for the above-referenced application, filed herewith on Nov. 18, 2024, 2 pages.
Response, filed Sep. 18, 2024, to Office Action, dated Jun. 21, 2024, in connection with U.S. Appl. No. 17/747,689, 18 pages.
Notice of Allowance, mailed Nov. 12, 2024, in connection with U.S. Appl. No. 17/747,689, 7 pages.
Notice of Allowance, mailed Nov. 7, 2024, in connection with U.S. Appl. No. 17/934,166, 7 pages.
Response, filed Sep. 24, 2024, to Office Action, dated Jun. 24, 2024, in connection with Korean Patent Application No. 10-2021-7004205 [English instructions; Response as filed in Korean; copies

(56) References Cited

OTHER PUBLICATIONS of 3 references as provided with the response; and English translation of marked up and clean claims], 182 pages.
Response, filed Nov. 7, 2024, to Office Action, dated Aug. 27, 2024, in connection with Korean Patent Application No. 10-2024-7014462 [English instructions; Response as filed in Korean, including references cited; and English translation of marked up and clean claims], 466 pages.
Response, filed Oct. 16, 2024, to Examination Report, dated Mar. 20, 2024, in connection with New Zealand Patent Application No. 771198 [Response as filed, copy of clean and marked up claims, and copies of 4 references cited in response], 131 pages.
Notice of Acceptance, dated Nov. 8, 2024, in connection with New Zealand Patent Application No. 771198, 2 pages.
Letter/Written Disclosure of the Supplemental Information Disclosure Statement for the above-referenced application, filed herewith on Sep. 13, 2024, 2 pages.
Creative Biolabs, "Bacterial Vector Vaccines: *Salmonella* as Vaccine-vectors," [online]; Accessed from <URL:creative-biolabs.com/vaccine/salmonella-as-vaccine-vectors.htm on Mar. 29, 2024, 4 pages.
Liang et al., "Genetically engineered *Salmonella Typhimurium*: Recent advances in cancer therapy," Cancer Letters 448:168-181 (2019).
Paglia et al., "Gene Transfer in Dendritic Cells, Induced by Oral DNA Vaccination with Salmonella typhimurium, Results in Protective Immunity Against a Murine Fibrosarcoma," Blood 92(9):3172-3176 (1998).
Examiner's Report, dated Jun. 4, 2024, issued in connection with Canadian Patent Application No. 3,069,523, 5 pages.
Office Action, mailed Jan. 16, 2024, in connection with Japanese Patent Application No. 2023- 194108 [English summary of Office Action, English translation of Office Action, and original document as issued in Japanese], 9 pages.
Office Action, dated Jun. 21, 2024, in connection with U.S. Appl. No. 17/747,689, 9 pages.
Office Action, dated Mar. 28, 2024, in connection with U.S. Appl. No. 17/934,166, 11 pages.
Response, filed Jun. 27, 2024, to Office Action, dated Mar. 28, 2024, in connection with U.S. Appl. No. 17/934,166 [Response as filed with two references], 51 pages.
Response, filed Sep. 29, 2023, to Examination Report, dated Jul. 8, 2023, in connection with Australian Patent Application No. 2019301699 [document as filed with cited reference], 58 pages.
Notice of Acceptance, issued Oct. 20, 2023, in connection with Australian Patent Application No. 2019301699, 3 pages.
Response, filed Nov. 24, 2023, to Examiner's Report, dated Jul. 25, 2023, in connection with Canadian Patent Application No. 3,106,143, 88 pages.
Response, filed Jun. 7, 2024, to Examiner's Report, dated Dec. 9, 2022, in connection with Canadian Patent Application No. 3,176,812, 71 pages.
Office Action, dated Aug. 5, 2023, in connection with Chinese Patent Application No. 201980059088.5 [English translation of Office Action; and original document as issued in Chinese], 14 pages.
Response, to Office Action dated Aug. 5, 2023, in connection with Chinese Patent Application No. 201980059088.5 [English instructions for response; documents as filed in Chinese; and English translation of claims as filed], received on Dec. 22, 2023, 68 pages.
Notification of Granting a Patent Right, issued Jan. 5, 2024, in connection with Chinese Patent Application No. 201980059088.5 [English translation of notification; and original document as issued in Chinese], 4 pages.
Office Action, dated Nov. 15, 2023, and received Feb. 13, 2024, issued in connection with Eurasian Patent Application No. 202100009 [English translation of Office Action, and original document as issued in Russian], 7 pages.
Office Action, mailed Sep. 3, 2024, in connection with Japanese Patent Application No. 2023- 137908 [English translation of Office Action, and Document as issued in Japanese], 5 pages.
Response, filed Aug. 11, 2023, to Office Action, issued May 2, 2023, in connection with Korean Patent Application No. 10-2021-7004205 [English instructions for response; Document as filed in Korean, with cited references; and English translation of marked-up and clean claims as amended], 441 pages.
Notice of Final Rejection, issued Jan. 29, 2024, in connection with Korean Patent Application No. 10-2021-7004205 [English translation of Office Action; and Document as issued in Korean], 6 pages.
Response, filed Apr. 30, 2024, to Notice of Final Rejection, issued Jan. 29, 2024, in connection with Korean Patent Application No. 10-2021-7004205 [English instructions for response; Document as filed in Korean; and English translation of marked-up and clean claims as amended], 79 pages.
Office Action, dated Jun. 24, 2024, in connection with Korean Patent Application No. 10-2021-7004205 [English translation of Office Action; and Document as issued in Korean], 9 pages.
Office Action, dated Aug. 27, 2024, in connection with Korean Patent Application No. 10-2024-7014462 [English translation of Office Action; and Document as issued in Korean], 9 pages.
Examination Report, dated Mar. 20, 2024, in connection with New Zealand Patent Application No. 771198, 5 pages.
Written Opinion, dated Feb. 26, 2024, in connection with Singapore Patent Application No. 11202100023X, 8 pages.
Response, filed Jul. 24, 2024, to Written Opinion, dated Feb. 26, 2024, in connection with Singapore Patent Application No. 11202100023X [Response as filed, and three references as provided with Response], 109 pages.
Response, filed Sep. 14, 2023, to Office Action, issued Mar. 14, 2023, in connection with U.S. Appl. No. 16/824,500, 53 pages.
Letter/Written Disclosure of the Supplemental Information Disclosure Statement for the above-referenced application, filed herewith on Feb. 18, 2025, 3 pages.
Notice of Allowance, dated Feb. 6, 2025, in connection with Canadian Patent Application No. 3,106,143, 1 page.
Office Action, dated Jan. 30, 2025, in connection with Korcan Patent Application No. 10-2021-7004205 [Machine-generated English translation of Office Action; and Document as issued in Korean], 8 pages.
Letter/Written Disclosure of the Supplemental Information Disclosure Statement for the above-referenced application, filed herewith on Nov. 7, 2022, 3 pages.
Examination Report, dated Oct. 8, 2022, in connection with corresponding Australian Patent Application No. 2019301699, 3 pages.

* cited by examiner

Adapted from Kimbrough and Miller (2002)
*Microbes Infect.* 4(1):75-82.

Miao and Rajan (2011) Front. Microbiol. 2:85

ENGINEERED IMMUNOSTIMULATORY BACTERIAL STRAINS AND USES THEREOF

RELATED APPLICATIONS

This application is a continuation of International Patent Application No. PCT/US2019/041489, filed on Jul. 11, 2019, and published as WO 2020/014543, on Jan. 16, 2020, to Applicant Actym Therapeutics, Inc., inventors Christopher D. Thanos, Laura Hix Glickman, Justin Skoble, and Alexandre Charles Michel Iannello, and entitled "ENGINEERED IMMUNOSTIMULATORY BACTERIAL STRAINS AND USES THEREOF." International Patent Application No. PCT/US2019/041489 claims priority, as does this application, to International Patent Application No. PCT/US2018/041713, filed on Jul. 11, 2018, and published as WO 2019/014398 on Jan. 17, 2019, and to U.S. patent application Ser. No. 16/033,187, filed on Jul. 11, 2018, and published as U.S. Publication No. U.S. 2019/0017050 A1 on Jan. 17, 2019, each to Applicant Actym Therapeutics, Inc., inventors Christopher D. Thanos, Laura Hix Glickman, and Justin Skoble, and each entitled "ENGINEERED IMMUNOSTIMULATORY BACTERIAL STRAINS AND USES THEREOF." International Patent Application No. PCT/US2019/041489 also claims priority to U.S. Provisional Application Ser. No. 62/789,983, filed on Jan. 8, 2019, to Applicant Actym Therapeutics, Inc., inventors Christopher D. Thanos, Laura Hix Glickman, Justin Skoble, and Alexandre Charles Michel Iannello, and entitled "ENGINEERED IMMUNOSTIMULATORY BACTERIAL STRAINS AND USES THEREOF;" and to U.S. Provisional Application Ser. No. 62/828,990, filed on Apr. 3, 2019, to Applicant Actym Therapeutics, Inc., inventors Christopher D. Thanos, Laura Hix Glickman, Justin Skoble, and Alexandre Charles Michel Iannello, and entitled "*SALMONELLA* STRAINS ENGINEERED TO COLONIZE TUMORS AND THE TUMOR MICROENVIRONMENT."

This application also is a continuation of U.S. patent application Ser. No. 16/520,155, filed on Jul. 23, 2019, and published as U.S. Publication No. U.S. 2020/0215123 A1 on Jul. 9, 2020, to Applicant Actym Therapeutics, Inc., inventors Christopher D. Thanos, Laura Hix Glickman, Justin Skoble, and Alexandre Charles Michel Iannello, and entitled "ENGINEERED IMMUNOSTIMULATORY BACTERIAL STRAINS AND USES THEREOF." U.S. patent application Ser. No. 16/520,155 is a continuation of International Patent Application No. PCT/US2019/041489, filed on Jul. 11, 2019, and published as WO 2020/014543, on Jan. 16, 2020, and claims benefit of priority to U.S. Provisional Application Ser. No. 62/789,983, filed on Jan. 8, 2019, and to U.S. Provisional Application Ser. No. 62/828,990, filed on Apr. 3, 2019.

Benefit of priority also is claimed to International Patent Application No. PCT/US2018/041713, filed on Jul. 11, 2018, and published as WO 2019/014398 on Jan. 17, 2019, and to U.S. patent application Ser. No. 16/033,187, filed on Jul. 11, 2018, and published as U.S. Publication No. U.S. 2019/0017050 A1 on Jan. 17, 2019, each to Applicant Actym Therapeutics, Inc., inventors Christopher D. Thanos, Laura Hix Glickman, and Justin Skoble, and each entitled "ENGINEERED IMMUNOSTIMULATORY BACTERIAL STRAINS AND USES THEREOF".

Benefit of priority also is claimed to U.S. Provisional Application Ser. No. 62/789,983, filed Jan. 8, 2019, to Applicant Actym Therapeutics, Inc., inventors Christopher D. Thanos, Laura Hix Glickman, Justin Skoble, and Alexandre Charles Michel Iannello, and entitled "ENGINEERED IMMUNOSTIMULATORY BACTERIAL STRAINS AND USES THEREOF;" and to U.S. Provisional Application Ser. No. 62/828,990, filed Apr. 3, 2019, to Applicant Actym Therapeutics, Inc., inventors Christopher D. Thanos, Laura Hix Glickman, Justin Skoble, and Alexandre Charles Michel Iannello, and entitled "*SALMONELLA* STRAINS ENGINEERED TO COLONIZE TUMORS AND THE TUMOR MICROENVIRONMENT."

The immunostimulatory bacteria provided in each of these applications can be modified as described in this application, and such bacteria are incorporated by reference herein. Where permitted, the subject matter of each of these applications is incorporated by reference in its entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Sep. 21, 2020, is 457 kilobytes in size, and is entitled 1704BSEQ001.txt.

BACKGROUND

The field of cancer immunotherapy has made great strides, as evidenced by the clinical successes of anti-CTLA4, anti-PD-1, and anti-PD-L1 immune checkpoint antibodies (see, e.g., Buchbinder et al. (2015) *J. Clin. Invest.* 125:3377-3383; Hodi et al. (2010) *N. Engl. J. Med.* 363(8): 711-723; and Chen et al. (2015) *J. Clin. Invest.* 125:3384-3391). Tumors have evolved a profoundly immunosuppressive environment. They initiate multiple mechanisms to evade immune surveillance, reprogram anti-tumor immune cells to suppress immunity, and continually mutate resistance to the latest cancer therapies (see, e.g., Mahoney et al. (2015) *Nat. Rev. Drug Discov.* 14(8):561-584). Designing immunotherapies that overcome immune tolerance and escape, while limiting the autoimmune-related toxicities of current immunotherapies, challenges the field of immuno-oncology. Hence, additional and innovative immunotherapies and other therapies are needed.

SUMMARY

Provided are bacteria modified to be immunostimulatory for anti-cancer therapy. Immunostimulatory bacteria, as provided herein, provide a multi-faceted approach to anti-tumor therapy. Bacteria provide a platform in which there are numerous avenues for eliciting anti-tumor immunostimulatory activity. As provided herein, bacteria, such as species of *Salmonella*, are fine-tuned to have potent anti-tumor activity by increasing their ability to accumulate in, or target tumors, tumor-resident-immune cells, and/or the tumor microenvironment (TME). This is achieved by modifications that, for example, alter the type of cells that they can infect (tropism), their toxicity, their ability to escape the immune system, such as complement, and/or the environments in which they can replicate. The immunostimulatory bacteria also can encode, for example, products that enhance or invoke an immune response, and therapeutic products. The immunostimulatory bacteria provided herein, by virtue of their improved colonization of tumors, the tumor microenvironment, and/or tumor-resident immune cells, and their resistance to complement and other anti-bacterial immune responses, can be administered systemically.

The genomes of the bacteria provided herein are modified to increase accumulation in tumors and in tumor-resident immune cells, and also in the tumor microenvironment. This is effected herein by deleting or disabling genes responsible for infection or invasion of non-tumor cells, such as epithelial cells, and/or decreasing the cytopathogenicity of the bacteria, particularly to immune cells and tumor-resident immune cells.

Bacteria by their nature stimulate the immune system; bacterial infection induces immune and inflammatory pathways and responses, some of which are desirable for anti-tumor treatment, and others, are undesirable. Modification of the bacteria by deleting or modifying genes and products that result in undesirable inflammatory responses, and adding or modifying genes and products that induce desirable immunostimulatory anti-tumor responses, improves the anti-tumor activity of the bacteria.

Bacteria accumulate in tumor cells and tissues, and by replicating therein, can lyse cells. Bacteria migrate from the sites of administration and can accumulate in other tumors and tumor cells to provide an abscopal effect. The bacteria provided herein are modified so that they preferentially infect and accumulate in tumor-resident immune cells, tumors, and the tumor microenvironment.

Herein, all of these properties of bacteria are exploited to produce demonstrably immunostimulatory bacteria with a plurality of anti-tumor activities and properties that can act individually and synergistically.

Provided are compositions, uses thereof, and methods that modulate immune responses for the treatment of diseases, including for the treatment of cancer. The compositions contain immunostimulatory bacteria provided herein. Methods of treatment and uses of the bacteria for treatment also are provided. The subjects for treatment include humans and other primates, pets, such as dogs and cats, and other animals, such as horses.

Provided are pharmaceutical compositions containing the immunostimulatory bacteria, and methods and uses thereof for treatment of diseases and disorders, particularly proliferative disorders, such as tumors, including solid tumors and hematologic malignancies.

Also provided are methods of inhibiting the growth or reducing the volume of a solid tumor by administering the immunostimulatory bacteria or pharmaceutical compositions, or using the compositions for treatment. For example, provided are methods of administering or using a composition that contains, for a single dosage, an effective amount of an attenuated *Salmonella* species to a subject, such as a human patient, having a solid tumor cancer. It is understood that all modifications to the genome of the bacteria, such as anti-tumor therapeutics, and other modifications of the bacterial genome and the plasmids described, can be combined in any desired combination.

Provided are immunostimulatory bacteria that have enhanced colonization of tumors, the tumor microenvironment and/or tumor-resident immune cells, and enhanced anti-tumor activity. The immunostimulatory bacteria are modified by deletion of genes encoding the flagella, or by modification of the genes so that functional flagella are not produced, and/or by deletion of pagP or modification of pagP to produce inactive PagP product. As a result, the immunostimulatory bacteria are flagellin$^-$ (fliC$^-$/fljB$^-$) and/or pagP$^-$. Alternatively, or additionally, the immunostimulatory bacteria can be pagP$^-$/msbB$^-$.

The immunostimulatory bacteria can be flagellin deficient, such as by deletion of, or disruption in, a gene(s) encoding the flagella. For example, provided are immunostimulatory bacteria that contain deletions in the genes encoding one or both of flagellin subunits fliC and fljB, whereby the bacterium is flagella deficient, and wherein the wild-type bacterium expresses flagella. The immunostimulatory bacteria also can have a deletion or modification in the gene encoding endonuclease I (endA), whereby endA activity is inhibited or eliminated.

The immunostimulatory bacteria optionally have additional genomic modifications so that the bacteria are adenosine or purine auxotrophs. The bacteria optionally are one or more of asd$^-$, purI$^-$, and msbB$^-$. The immunostimulatory bacteria, such as *Salmonella* species, are modified to encode immunostimulatory proteins that confer anti-tumor activity in the tumor microenvironment, and/or are modified so that the bacteria preferentially infect immune cells in the tumor microenvironment or tumor-resident immune cells, and/or induce less cell death in immune cells than in other cells. Also provided are methods of inhibiting the growth or reducing the volume of a solid tumor by administering the immunostimulatory bacteria.

Provided are methods of increasing tumor colonization of an immunostimulatory bacterium, such as a *Salmonella* species, by modifying the genome of the immunostimulatory bacterium to be flagellin$^-$ (fliC$^-$/fljB$^-$) and/or pagP$^-$.

The bacteria also contain plasmids that encode therapeutic products, such as anti-tumor agents, proteins that increase the immune response of a subject, and inhibitory RNA (RNAi) that target immune checkpoints. For example, the plasmids can encode immunostimulatory proteins, such as cytokines, chemokines, and co-stimulatory molecules, that increase the anti-tumor response in the subject. The bacteria contain plasmids that encode anti-cancer therapeutics, such as RNA, including microRNA, shRNA, and siRNA, and antibodies and antigen-binding fragments thereof that are designed to suppress, inhibit, disrupt or otherwise silence immune checkpoint genes and products, and other targets that play a role in pathways that are immunosuppressive. The bacteria also can encode tumor antigens and tumor neoantigens on the plasmids to stimulate the immune response against the tumors. The encoded proteins are expressed under the control of promoters recognized by eukaryotic, such as mammalian and animal, or viral, transcription machinery.

Provided are immunostimulatory bacteria that contain a plasmid encoding a therapeutic product, such as an anti-cancer therapeutic; the genome of the immunostimulatory bacterium is modified so that it preferentially infects tumor-resident immune cells, and/or so that it induces less cell death in tumor-resident immune cells.

Provided are immunostimulatory bacteria containing a plasmid encoding a product, generally a therapeutic product, such as an anti-cancer therapeutic product, under control of a eukaryotic promoter, where the genome of the immunostimulatory bacterium is modified whereby the bacterium is flagellin$^-$ (fliC$^-$/fljB$^-$) and/or pagP$^-$, and whereby the wild-type bacteria have flagella. The bacteria can be one or both of flagellin$^-$ (fliC$^-$/fljB$^-$) and pagP$^-$. These immunostimulatory bacteria exhibit increased colonization of tumors, the tumor microenvironment and/or tumor-resident immune cells, and have increased anti-tumor activity.

Among these immunostimulatory bacteria are those that are flagellin$^-$ (fliC$^-$/fljB$^-$), and whereby the therapeutic product is an anti-cancer product. In some embodiments, the bacteria are flagellin$^-$ (fliC$^-$/fljB$^-$), and the product is an anti-cancer therapeutic protein or nucleic acid.

Among these immunostimulatory bacteria are those in which the therapeutic product is a TGF-beta antagonist polypeptide, where the genome of the immunostimulatory bacterium is modified so that the bacterium preferentially infects tumor-resident immune cells, and/or the genome of the immunostimulatory bacterium is modified so that it induces less cell death in tumor-resident immune cells (decreases pyroptosis), whereby the immunostimulatory bacterium accumulates in tumors or in the tumor microenvironment or in tumor-resident immune cells to thereby deliver the TGF-beta antagonist polypeptide to the tumor microenvironment. The TGF-beta antagonist can be selected from among an anti-TGF-beta antibody, an anti-TGF-beta receptor antibody, and a soluble TGF-beta antagonist polypeptide. The nucleic acid encoding the TGF-beta antagonist polypeptide can include nucleic acid encoding a signal sequence for secretion of the encoded polypeptide, so that it is released into the tumor cells, tumor-resident immune cells, and/or the tumor microenvironment.

In other embodiments of any of the immunostimulatory bacteria provided herein, the plasmid encodes an immunostimulatory protein that confers, enhances, or contributes to an anti-tumor immune response in the tumor microenvironment. Exemplary of immunostimulatory proteins that confer or contribute to anti-tumor immunity in the tumor microenvironment is/are one or more of: IL-2, IL-7, IL-12p70 (IL-12p40+IL-12p35), IL-15, IL-36 gamma, IL-2 that has attenuated binding to IL-2Ra, IL-15/IL-15R alpha chain complex, IL-18, IL-21, IL-23, IL-36γ, IL-2 modified so that it does not bind to IL-2Ra, CXCL9, CXCL10, CXCL11, interferon-α, interferon-β, interferon-γ, CCL3, CCL4, CCL5, proteins that are involved in or that effect or potentiate the recruitment or persistence of T cells, CD40, CD40 ligand (CD40L), CD28, OX40, OX40 ligand (OX40L), 4-1BB, 4-1BB ligand (4-1BBL), members of the B7-CD28 family, CD47 antagonists, TGF-beta polypeptide antagonists, and members of the tumor necrosis factor receptor (TNFR) superfamily.

In other embodiments of the immunostimulatory bacteria provided herein, the therapeutic product is an antibody or antigen-binding fragment thereof. Exemplary of such is a Fab, Fab', F(ab')2, single-chain Fv (scFv), Fv, disulfide-stabilized Fv (dsFv), nanobody, diabody fragment, or a single-chain antibody. The antibody or antigen-binding fragment thereof can be humanized or human. Exemplary of an antibody or antigen-binding fragment thereof is an antagonist of PD-1, PD-L1, CTLA-4, VEGF, VEGFR2, or IL-6.

The immunostimulatory bacteria provided herein, including those described above, can contain a plasmid encoding a therapeutic product under control of a eukaryotic promoter; the genome of the immunostimulatory bacterium is modified whereby the bacterium is $pagP^-/msbB^-$, and optionally $flagellin^-$ ($fliC^-/fljB^-$).

Exemplary of immunostimulatory bacteria are those that contain a plasmid encoding an immunostimulatory protein, where: an immunostimulatory protein, when expressed in a mammalian subject, confers or contributes to anti-tumor immunity in the tumor microenvironment; the immunostimulatory protein is encoded on a plasmid in the bacterium under control of a eukaryotic promoter; and the genome of the immunostimulatory bacterium is modified so that it preferentially infects tumor-resident immune cells. In other embodiments, the immunostimulatory bacteria contain a sequence of nucleotides encoding an immunostimulatory protein, where the immunostimulatory protein, when expressed in a mammalian subject, confers or contributes to anti-tumor immunity in the tumor microenvironment; the immunostimulatory protein is encoded on a plasmid in the bacterium under control of a eukaryotic promoter; and the genome of the immunostimulatory bacterium is modified so that it induces less cell death in tumor-resident immune cells. Exemplary immunostimulatory proteins include cytokines and chemokines, and other immune stimulatory proteins, such as, for example one or more of: IL-2, IL-7, IL-12p70 (IL-12p40+IL-12p35), IL-15, IL-36 gamma, IL-2 that has attenuated binding to IL-2Ra, IL-15/IL-15R alpha chain complex, IL-18, IL-21, IL-23, IL-36γ, IL-2 modified so that it does not bind to IL-2Ra, CXCL9, CXCL10, CXCL11, interferon-α, interferon-β, interferon-γ, CCL3, CCL4, CCL5, proteins that are involved in or that effect or potentiate the recruitment/persistence of T cells, CD40, CD40 ligand, CD28, OX40, OX40 ligand, 4-1BB, 4-1BB ligand, members of the B7-CD28 family, CD47 antagonists, TGF-beta polypeptide antagonists, and members of the tumor necrosis factor receptor (TNFR) superfamily.

These immunostimulatory bacteria can include modification(s) in the genomes of the immunostimulatory bacteria so that the bacteria exhibit one or both of preferentially infecting tumor-resident immune cells, and inducing less cell death in tumor-resident immune cells. The immunostimulatory bacteria can also include a mutation in the genome that reduces toxicity or infectivity of non-immune cells in a host.

Modifications of the bacterial genome include $pagP^-$, or $pagP^-$ and $flagellin^-$ ($fliC^-/fljB^-$). In other embodiments, the immunostimulatory bacteria are one or more of $purI^-$ ($purM^-$), $msbB^-$, $purD^-$, $flagellin^-$ ($fliC^-/fljB^-$), $pagP^-$, $adrA^-$, $csgD^-$, $qseC^-$, and $hilA^-$, such as $flagellin^-$ (fliC/$fljB^-$)/$pagP^-/msbB^-/purI^-$, or $flagellin^-$ ($fliC^-/fljB^-$)/$pagP^-/msbB^-/purI^-/hilA^-$. In other embodiments, the immunostimulatory bacteria are $hilA^-$ and/or $flagellin^-$ ($fliC^-/fljB^-$) or $pagP^-$ or $pagP^-$, or the immunostimulatory bacteria are $hilA^-$, or the immunostimulatory bacteria are $flagellin^-$ ($fliC^-/fljB^-$) and $pagP^-$. The genome modifications, among other properties, can increase targeting to or colonization of the tumor microenvironment and/or tumor-resident immune cells, and/or render the bacteria substantially or completely resistant to inactivation by complement. These properties improve the use of the bacteria as therapeutics, and permit systemic administration.

In the immunostimulatory bacteria provided herein, the nucleic acid encoding the therapeutic product is operatively linked for expression to a nucleic acid encoding a secretory signal, whereby, upon expression in a host, the immunostimulatory protein is secreted. The therapeutic product can be a protein, such as an immunostimulatory protein, or a nucleic acid, such as a CRISPR cassette or an RNAi.

In all embodiments, the immunostimulatory bacteria can be auxotrophic for adenosine, or for adenosine and adenine. The immunostimulatory bacteria provided herein can include modifications in the genome whereby the bacterium preferentially infects tumor-resident immune cells, and/or the genome of the immunostimulatory bacterium is modified so that it induces less cell death in tumor-resident immune cells (decreases pyroptosis), whereby the immunostimulatory bacterium accumulates in tumors or in the tumor microenvironment or in tumor-resident immune cells to thereby deliver an encoded therapeutic product.

In the immunostimulatory bacteria, the plasmid encodes the therapeutic product under control of a eukaryotic promoter so that it is expressed in a eukaryotic host, such as a human or other mammal. The therapeutic product generally is an anti-cancer therapeutic, such as an anti-cancer therapeutic protein that stimulates the immune system of the host. Other therapeutic products include antibodies and antigen-binding fragments thereof, and nucleic acids, such as RNAi. These products can be designed to inhibit, suppress, or disrupt a target, such as an immune checkpoint, and other such targets that impair the ability of the immune system of a subject to recognize the tumor cells.

The unmodified immunostimulatory bacteria can be a wild-type strain or an attenuated strain. The genome modifications provided and described herein attenuate the bacteria outside of the tumor microenvironment or tumors; the modifications, among other properties, alter the infectivity of the bacteria. Exemplary of bacteria that can be modified as described herein are *Salmonella*, such as a *Salmonella typhimurium* strain. Exemplary of *Salmonella typhimurium* strains are attenuated and wild-type strains, such as, for example, *Salmonella typhimurium* strains derived from strains designated as AST-100, VNP20009, YS1646 (ATCC #202165), RE88, SL7207, $\chi$8429, $\chi$8431, $\chi$8468, or a wild-type strain with ATCC accession no. 14028.

As discussed above, provided are immunostimulatory bacteria containing a plasmid encoding a product under control of a eukaryotic promoter, where the genome of the immunostimulatory bacterium is modified whereby the bacterium is $pagP^-/msbB^-$. Deletion of msbB alters the acyl composition of the lipid A domain of lipopolysaccharide (LPS), the major component of the outer membranes of Gram-negative bacteria, such that the bacteria predominantly produce penta-acylated LPS instead of the more toxic and pro-inflammatory hexa-acylated LPS. In wild type *S. typhimurium*, expression of pagP results in hepta-acylated lipid A, while in an $msbB^-$ mutant, the induction of pagP results in hexa-acylated LPS. Thus, a $pagP^-/msbB^-$ mutant produces only penta-acylated LPS, resulting in lower induction of pro-inflammatory cytokines, and enhanced tolerability, which allows for higher dosing in humans. Higher dosing leads to increased colonization of tumors, tumor-resident immune cells, and the tumor microenvironment. Because of the resulting change in bacterial membranes and structure, the host immune response, such as complement activity, is altered so that the bacteria are not eliminated upon systemic administration. For example, it is shown herein that $pagP^-/msbB^-$ mutant strains have increased resistance to complement inactivation and enhanced stability in human serum. These bacteria also can be flagellin$^-$ ($fliC^-/fljB^-$), which further enhances tolerability, resistance to complement inactivation, and tumor/TME/tumor-resident immune cell colonization. The bacteria also can comprise other modifications as described herein, including modifications that alter the cells that they can infect, resulting in accumulation in the tumor microenvironment, tumors and tumor-resident immune cells. Hence, the immunostimulatory bacteria provided herein can be systemically administered and exhibit a high level of tumor, tumor microenvironment and/or tumor-resident immune cell colonization. The immunostimulatory bacteria can be $purI^-$ ($purM^-$), and one or more of $asd^-$, $msbB^-$, and one or both of flagellin$^-$ ($fliC^-/fljB^-$) and $pagP^-$.

The immunostimulatory bacteria can be aspartate-semialdehyde dehydrogenase$^-$ ($asd^-$), such as by virtue of disruption or deletion of all or a portion of the endogenous gene encoding aspartate-semialdehyde dehydrogenase (asd), whereby endogenous asd is not expressed. These immunostimulatory bacteria can be modified to encode aspartate-semialdehyde dehydrogenase (asd) on a plasmid under control of a bacterial promoter so that the bacteria can be produced in vitro.

The immunostimulatory bacteria can be rendered auxotrophic for particular nutrients that are rich or that accumulate in the tumor microenvironment, such as adenosine and adenine. Also, they can be modified to be auxotrophic for such nutrients to reduce or eliminate their ability to replicate. The inactivated/deleted bacterial genome genes can be complemented by providing them on a plasmid under the control of promoters recognized by the host.

The products encoded on the plasmids for expression in a eukaryotic, such as a human, host, are under control of eukaryotic regulatory sequences, including eukaryotic promoters, such as promoters recognized by RNA polymerase II or III. These include mammalian RNA polymerase II promoters. Viral promoters also can be used. Exemplary viral promoters, include, but are not limited to, a cytomegalovirus (CMV) promoter, an SV40 promoter, an Epstein Barr virus (EBV) promoter, a herpes virus promoter, and an adenovirus promoter. Other RNA polymerase II promoters include, but are not limited to, an elongation factor-1 (EF1) alpha promoter, a UbC promoter (lentivirus), a PGK (3-phosphoglycerate kinase) promoter, and a synthetic promoter such as a CAGG (or CAG) promoter. The synthetic CAG promoter contains the cytomegalovirus (CMV) early enhancer element (C); the promoter, the first exon and the first intron of chicken beta-actin gene (A); and the splice acceptor of the rabbit beta-globin gene (G). Other strong regulatable or constitutive promoters can be used. The regulatory sequences also include terminators, enhancers, and secretory and other trafficking signals.

The plasmids included in the immunostimulatory bacteria can be present in low copy number or medium copy number, such as by selection of an origin of replication that results in medium-to-low copy number, such as a low copy number origin of replication. It is shown herein that the anti-tumor activity and other properties of the bacteria are improved when the plasmid is present in low to medium copy number, where medium copy number is less than 150 or less than about 150 and more than 20 or about 20 or is between 20 or 25 and 150 copies, and low copy number is less than 25 or less than 20 or less than about 25 or less than about 20 copies.

These immunostimulatory bacteria can be modified so that the bacteria preferentially infect tumor-resident immune cells, and/or the genome of the immunostimulatory bacteria can be modified so that they induces less cell death in tumor-resident immune cells (decrease pyroptosis), whereby the immunostimulatory bacteria accumulate in tumors, or in the tumor microenvironment, or in tumor-resident immune cells.

As discussed above, the genome of the immunostimulatory bacteria also is modified so that the bacteria preferentially infect immune cells, such as tumor-resident immune cells, such as myeloid cells, such as cells that are $CD45^+$, and/or the genome is modified so that the bacteria induce less cell death in tumor-resident immune cells (decreased pyroptosis) than the unmodified bacteria. As a result, the immunostimulatory bacteria accumulate, or accumulate to a greater extent than those without the modifications, in tumors or in the tumor microenvironment or in tumor-resident immune cells, to thereby deliver the therapeutic product or products encoded on the plasmid. The bacteria can be one or more of flagellin$^-$ ($fliC^-/fljB^-$), $pagP^-$, and $msbB^-$, and can include other such modifications as described herein. The bacteria can be auxotrophic for adenosine, and/or $purI^-$ ($purM^-$) and/or $asd^-$.

The immunostimulatory bacteria provided herein can include a modification of the bacterial genome, whereby the bacteria induce less cell death in tumor-resident immune cells; and/or a modification of the bacterial genome, whereby the bacteria accumulate more effectively in tumors, the tumor microenvironment, or tumor-resident immune cells, such as tumor-resident $CD45^+$ cells, and myeloid cells.

For example, the immunostimulatory bacteria can include deletions or modifications of one or more genes or operons involved in SPI-1 invasion (and/or SPI-2), whereby the immunostimulatory bacteria do not invade or infect epithelial cells. Exemplary of genes that can be deleted or inactivated are one or more of avrA, hilA, hilD, invA, invB, invC, invE, invF, invG, invH, invI, invJ, iacP, iagB, spaO, spaP, spaQ, spaR, spaS, orgA, orgB, orgC, prgH, prgI, prgJ, prgK, sicA, sicP, sipA, sipB, sipC, sipD, sirC, sopB, sopD, sopE, sopE2, sprB, and sptP. Elimination of the ability to infect epithelial cells also can be achieved by engineering the immunostimulatory bacteria herein to contain knockouts or deletions of genes encoding proteins involved in SPI-1-independent invasion, such as one or more of the genes selected from among rck, pagN, hlyE, pefI, srgD, srgA, srgB, and srgC. Similarly, the immunostimulatory bacteria can include deletions in genes and/or operons in SPI-2, for example, to engineer the bacteria to escape the *Salmonella*-containing vacuole (SCV). These genes include, for example, sifA, sseJ, sseL, sopD2, pipB2, sseF, sseG, spvB, and steA.

The immunostimulatory bacteria provided herein also can contain a sequence of nucleotides encoding an immunostimulatory protein that, when expressed in a mammalian subject, confers or contributes to anti-tumor immunity in the tumor microenvironment; the immunostimulatory protein is encoded on a plasmid in the bacterium under control of a eukaryotic promoter. Exemplary promoters include, but are not limited to, an elongation factor-1 (EF1) alpha promoter, or a UbC promoter, or a PGK promoter, or a CAGG promoter, or a CAG promoter.

Additionally, the genome of the immunostimulatory bacterium is modified so that it preferentially infects tumor-resident immune cells. This is achieved by deleting or disrupting bacterial genes that play a role in invasiveness or infectivity of the bacteria, and/or that play a role in inducing cell death. The bacteria are modified to preferentially infect tumor-resident immune cells, and/or induce less cell death in tumor-resident immune cells than in other cells that the bacteria can infect, than unmodified bacteria.

The immunostimulatory bacteria also can encode a therapeutic product, such as inhibitory RNA (RNAi), immunostimulatory proteins such as cytokines, chemokines, and co-stimulatory molecules, other proteins that increase the immune response in a subject, and other anti-tumor agents, that, when expressed in a mammalian subject, confer or contribute to anti-tumor immunity. The therapeutic product is encoded on a plasmid in the bacterium under control of a eukaryotic promoter. The genome of the immunostimulatory bacterium is modified so that it induces less cell death in tumor-resident immune cells. The plasmid generally is present in low or medium copy number.

Also provided are immunostimulatory bacteria that encode an immunostimulatory protein on a plasmid in the bacterium under control of a eukaryotic promoter, that, when expressed in a mammalian subject, confers or contributes to anti-tumor immunity in the tumor microenvironment. The immunostimulatory bacteria can be modified to have reduced pathogenicity, whereby infection of epithelial and/or other non-immune cells is reduced, relative to the bacterium without the modification. These include modification of the type 3 secretion system (T3SS) or type 4 secretion system (T4SS), such as modification of the SPI-1 pathway of *Salmonella* as described and exemplified herein. The bacteria further can be modified to induce less cell death, such as by deletion or disruption of nucleic acid encoding lipid A palmitoyltransferase (pagP), which reduces virulence of the bacteria.

The genome of the immunostimulatory bacteria provided herein can be modified to increase or promote infection of immune cells, particularly immune cells in the tumor microenvironment, such as phagocytic cells. This includes reducing infection of non-immune cells, such as epithelial cells, or increasing infection of immune cells. The bacteria also can be modified to decrease pyroptosis in immune cells. Numerous modifications of the bacterial genome can do one or both of increasing infection of immune cells and decreasing pyroptosis. The immunostimulatory bacteria provided herein include such modifications, for example, deletions and/or disruptions of genes involved in the SPI-1 T3SS pathway, such as disruption or deletion of hilA, and/or disruption/deletion of genes encoding flagellin, rod protein (PrgJ), needle protein (PrgI), and QseC.

The immunostimulatory bacteria can be one or more of $purI^-$ ($purM^-$), $msbB^-$, $purD^-$, $flagellin^-$ ($fliC^-/fljB^-$), $pagP^-$, $adrA^-$, $csgD^-$, $qseC^-$, and $hilA^-$, and particularly $flagellin^-$ ($fliC^-/fljB^-$) and/or $pagP^-$, and/or $msbB^-/pagP^-$. For example, the immunostimulatory bacteria can include mutations in the genome, such as gene deletions or disruptions that reduce toxicity or infectivity of non-immune cells in a host. For example, the immunostimulatory bacteria can be $pagP^-$. As another example, the immunostimulatory bacteria can be $hilA^-$ and/or $flagellin^-$ ($fliC^-/fljB^-$), and also can be $pagP^-$. Thus, for example, the immunostimulatory bacteria can encode an immunostimulatory protein, such as a cytokine, and the bacteria can be modified so that they accumulate and express the cytokine in the tumor microenvironment (TME), thereby delivering an immunotherapeutic anti-tumor product into the environment in which it has beneficial activity, and avoiding adverse or toxic side effects from expression in other cells/environments. The nucleic acid encoding the immunostimulatory protein can be operatively linked for expression to nucleic acid encoding a secretory signal, whereby, upon expression in a host, the immunostimulatory protein is secreted into the tumor microenvironment.

The immunostimulatory bacteria provided herein include any of the strains and bacteria described in U.S. application Ser. No. 16/033,187, or in published International Application No. PCT/US2018/041713 (published as WO 2019/014398), further modified to express an immunostimulatory protein and/or to preferentially infect and/or to be less toxic in immune cells in the tumor microenvironment, or in tumor-resident immune cells, as described and exemplified herein.

The immunostimulatory bacteria can be aspartate-semialdehyde $dehydrogenase^-$ ($asd^-$), such as by virtue of disruption or deletion of all or a portion of the endogenous gene encoding aspartate-semialdehyde dehydrogenase (asd), whereby the endogenous asd is not expressed. The immunostimulatory bacteria can be modified to encode aspartate-semialdehyde dehydrogenase (asd) on a plasmid under control of a bacterial promoter for growing the bacteria in vitro, so that bacteria will have limited replication in vivo.

The immunostimulatory bacteria provided herein can encode, on a plasmid, an immunostimulatory protein as a therapeutic product. The immunostimulatory protein can be a cytokine, such as a chemokine, or a co-stimulatory molecule. Exemplary of immunostimulatory proteins are IL-2, IL-7, IL-12p70 (IL-12p40+IL-12p35), IL-15, IL-15/IL-15R alpha chain complex, IL-36 gamma, IL-18, CXCL9, CXCL10, CXCL11, CCL3, CCL4, CCL5, proteins that are involved in or that effect or potentiate the recruitment/persistence of T cells, CD40, CD40 Ligand (CD40L), OX40, OX40 Ligand (OX40L), 4-1BB, 4-1BB Ligand (4-1BBL), members of the B7-CD28 family, and members of the tumor necrosis factor receptor (TNFR) superfamily.

The immunostimulatory bacteria optionally can include a sequence of nucleotides encoding inhibitory RNA (RNAi) that inhibits, suppresses or disrupts expression of an immune checkpoint. The RNAi can be encoded on a plasmid in the bacterium. The nucleotides encoding the immunostimulatory protein, and optionally an RNAi, can be on a plasmid present in low to medium copy number.

The immunostimulatory bacteria also can encode therapeutic products, such as RNAi or a CRISPR cassette that inhibits, suppresses or disrupts expression of an immune checkpoint or other target whose inhibition, suppression or disruption increases the anti-tumor immune response in a subject; the RNAi or CRISPR cassette is encoded on a plasmid in the bacterium. Other therapeutic products include, for example, antibodies that bind to immune checkpoints to inhibit their activities.

RNAi includes all forms of double-stranded RNA that can be used to silence the expression of targeted nucleic acids. RNAi includes shRNA, siRNA and microRNA (miRNA). Any of these forms can be interchanged in the embodiments disclosed and described herein. In general, the RNAi is encoded on a plasmid in the bacterium. The plasmids can include other heterologous nucleic acids that encode products of interest that modulate or add activities or products to the bacterium, or other such products that can modulate the immune system of a subject to be treated with the bacterium. Bacterial genes also can be added, deleted or disrupted. These genes can encode products for growth and replication of the bacteria, or products that also modulate the immune response of the host to the bacteria.

The immunostimulatory bacteria provided herein also can be auxotrophic for adenosine, or for adenosine and adenine.

Bacterial species for modification as described herein, carrying plasmids as described herein, include, but are not limited to, for example, strains of *Salmonella, Shigella, Listeria, E. coli*, and Bifidobacteriae. For example, species include *Shigella sonnei, Shigella flexneri, Shigella dysenteriae, Listeria monocytogenes, Salmonella typhi, Salmonella typhimurium, Salmonella gallinarum*, and *Salmonella enteritidis*.

Species include, for example, strains of *Salmonella, Shigella, E. coli*, Bifidobacteriae, *Rickettsia, Vibrio, Listeria, Klebsiella, Bordetella, Neisseria, Aeromonas, Francisella, Cholera, Corynebacterium, Citrobacter, Chlamydia, Haemophilus, Brucella, Mycobacterium, Mycoplasma, Legionella, Rhodococcus, Pseudomonas, Helicobacter, Bacillus*, and *Erysipelothrix*, or an attenuated strain thereof, or a modified strain thereof, of any of the preceding list of bacterial strains.

Other suitable bacterial species include *Rickettsia, Klebsiella, Bordetella, Neisseria, Aeromonas, Francisella, Corynebacterium, Citrobacter, Chlamydia, Haemophilus, Brucella, Mycobacterium, Mycoplasma, Legionella, Rhodococcus, Pseudomonas, Helicobacter, Vibrio, Bacillus*, and *Erysipelothrix*. For example, *Rickettsia rickettsii, Rickettsia prowazekii, Rickettsia tsutsugamushi, Rickettsia mooseri, Rickettsia sibirica, Bordetella bronchiseptica, Neisseria meningitidis, Neisseria gonorrhoeae, Aeromonas eucrenophila, Aeromonas salmonicida, Francisella tularensis, Corynebacterium pseudotuberculosis, Citrobacter freundii, Chlamydia pneumoniae, Haemophilus somnus, Brucella abortus, Mycobacterium intracellulare, Legionella pneumophila, Rhodococcus equi, Pseudomonas aeruginosa, Helicobacter mustelae, Vibrio cholerae, Bacillus subtilis, Erysipelothrix rhusiopathiae, Yersinia enterocolitica, Rochalimaea quintana*, and *Agrobacterium tumefaciens*.

*Salmonella* is exemplified herein, and particularly, *Salmonella typhimurium* strains. The *Salmonella* can be a wild-type species or an attenuated species. Exemplary of some attenuated species are the strains designated YS1646 (ATCC #202165), or VNP20009. Other strains include, RE88, SL7207, $\chi$8429, $\chi$8431, and $\chi$ 8468. Exemplary of wild-type or unattenuated species include, for example, the wild-type strain deposited as ATCC 14028, or a strain having all of the identifying characteristics of ATCC 14028. The modifications herein attenuate any strain by constraining the cells that the bacteria can infect, or in which they can replicate.

These strains can be further modified to encode immunostimulatory proteins and/or immune modulatory proteins. For example, the immunostimulatory bacteria can encode immunostimulatory proteins, such as cytokines, that increase the immune response in the tumor microenvironment. The immunostimulatory bacteria also can be modified to preferentially infect immune cells in the tumor microenvironment, or to infect tumor-resident immune cells, and/or to induce less cell death in such immune cells, as described herein. Sequences thereof and descriptions are provided in the detailed description, examples and sequence listing. The immunostimulatory bacteria can be derived from attenuated strains of bacteria, or they become attenuated by virtue of the modifications described herein, such as deletion of asd, whereby replication is limited in vivo.

It is understood that instances in which bacterial genes are modified and referenced herein, they are referenced with respect to their designation (name) in *Salmonella* species, which is exemplary of bacteria from which immunostimulatory bacteria can be produced. The skilled person recognizes that other species have corresponding proteins, but that their designations or names can be different from the names in *Salmonella*. The generic disclosure herein, however, can be applied to other bacterial species. For example, as shown herein, deletion or inactivation of flagellin ($fliC^-$/$fljB^-$) in *Salmonella* and/or pagP results in increased colonization of tumors. Similar genes encoding flagella, or similar functions for infection, can be modified in other bacterial species to achieve increased tumor colonization. Similarly, inactivation/deletion of bacterial products, such as the products of pagP and/or msbB, as described herein, can reduce complement activation and/or other inflammatory responses, thereby increasing targeting to tumors, tumor-resident immune cells, and the tumor microenvironment. Corresponding genes in other species that are involved in activating the complement pathway or other inflammatory pathway, can be deleted, as exemplified herein for *Salmonella*.

The immunostimulatory bacteria provided herein encode inhibitors of various genes that reduce anti-tumor immune responses, and/or express genes and/or gene products that contribute to anti-tumor immune responses, and/or products that stimulate the immune system, such as immunostimulatory proteins, such as cytokines, chemokines, and co-stimulatory molecules, and thereby are immunostimulatory. Adenosine auxotrophy is immunostimulatory. Other therapeutic products that can be encoded on the plasmids are nucleic acids, such as inhibitory RNA (RNAi), such as shRNA or microRNA or siRNA, targeted for disruption or inhibition of expression of TREX1, PD-L1, VISTA (the gene encoding V-domain Ig suppressor of T-cell activation), TGF-beta, and CTNNB1 (the gene that encodes β-catenin), among others, combinations thereof, and combinations thereof with any RNAi's that inhibit, suppress or disrupt expression of other immune suppressive genes whose expression is activated or enhanced by tumors or the tumor microenvironment (TME). Expression of these RNAs exploits two independent immunostimulatory pathways, and leads to enhanced tumor colonization in a single therapy. The effects of this combination are enhanced by the strains provided herein that are auxotrophic for adenosine, which provides preferential accumulation in, or recruitment into, adenosine-rich immunosuppressive tumor microenvironments. Reducing adenosine in such TMEs further enhances the immunostimulatory effects. Such combinations of traits in any of the bacterial strains known, or that can be engineered for therapeutic administration, provide similar immunostimulatory effects.

Among the targets is TGF-beta, which has three isoforms: 1, 2 and 3. Among the targets is TGF-beta, particularly isoform 1, and not isoforms 2 and 3. Toxicities are associated with inhibition of isoforms 2 and 3. For example, cardiac valve toxicity is associated with inhibition of isoform 2. Isoform 1 is present in most cancers (see, e.g., TCGA database). It is advantageous to inhibit only isoform 1. RNAi can be advantageously employed for this purpose, since it can be designed to very specifically recognize a target. For TGF-beta, specific inhibition of isoform 1 can be effected by targeting a sequence unique to isoform 1 that is not present in isoforms 2 or 3, or to select a sequence to target isoforms 1 and 3, and not 2. Also provided are immunostimulatory bacteria in which the plasmid encodes an shRNA or microRNA that specifically inhibits, suppresses or disrupts expression of TGF-beta isoform 1, but not TGF-beta isoform 2 or TGF-beta isoform 3; or the plasmid encodes an shRNA or microRNA that specifically inhibits, suppresses or disrupts expression of TGF-beta isoforms 1 and 3, but not isoform 2.

RNAi, such a miRNA- or shRNA-mediated gene disruption of PD-L1 by the immunostimulatory bacteria provided herein, also improves colonization of tumors, the TME, and/or tumor-resident immune cells. It has been shown that knockout of PD-L1 enhances *S. typhimurium* infection. For example, an at least 10-fold higher bacterial load in PD-L1 knockout mice than in wild-type mice has been observed, indicating that PD-L1 is protective against *S. typhimurium* infection (see, e.g., Lee et al. (2010) *J. Immunol.* 185:2442-2449).

Engineered immunostimulatory bacteria, such as the *S. typhimurium* immunostimulatory bacteria provided herein, contain multiple synergistic modalities to induce immune re-activation of cold tumors, to promote tumor antigen-specific immune responses, while inhibiting immune checkpoint pathways that the tumor utilizes to subvert and evade durable anti-tumor immunity. Included in embodiments is adenosine auxotrophy and enhanced vascular disruption. This improvement in tumor targeting through adenosine auxotrophy and enhanced vascular disruption increases potency, while localizing the inflammation to limit systemic cytokine exposure and the autoimmune toxicities observed with other immunotherapy modalities.

The heterologous therapeutic proteins and other products, such as the immunostimulatory proteins, antibodies, and RNAs, are expressed on plasmids under the control of promoters that are recognized by the eukaryotic host cell transcription machinery, such as RNA polymerase II (RNAP II) and RNA polymerase III (RNAP III) promoters. RNAP III promoters generally are constitutively expressed in a eukaryotic host; RNAP II promoters can be regulated. The therapeutic products are encoded on plasmids stably expressed by the bacteria. Exemplary of such bacteria are *Salmonella* strains, generally attenuated strains, either attenuated by passage or other methods, or by virtue of modifications described herein, such as adenosine auxotrophy. Exemplary of *Salmonella* strains are modified *S. typhimurium* strains that have a defective asd gene. These bacteria can be modified to include carrying a functional asd gene on the introduced plasmid; this maintains selection for the plasmid so that an antibiotic-based plasmid maintenance/selection system is not needed. The asd defective strains, that do not contain a functional asd gene on a plasmid, are autolytic in the host.

The promoters can be selected for the environment of the tumor cell, such as a promoter expressed in a tumor microenvironment (TME), a promoter expressed in hypoxic conditions, or a promoter expressed in conditions where the pH is less than 7.

Plasmids can be present in many copies or fewer. This can be controlled by selection of elements, such as the origin of replication. Low, medium, and high copy number plasmids and origins of replication are well-known to those of skill in the art and can be selected. In embodiments of the immunostimulatory bacteria herein, the plasmid can be present in low to medium copy number, such as about 150 or 150 and fewer copies, to low copy number, which is less than about 25 or about 20 or 25 copies. Exemplary origins of replication are those derived from pBR322, p15A, pSC101, pMB1, colE1, colE2, pPS10, R6K, R1, RK2, and pUC.

The plasmids can include RNAi such that the RNA inhibits, suppresses, or disrupts expression of an immune checkpoint or other target, and, additionally, their products. The plasmids also can include sequences of nucleic acids encoding a listeriolysin O (LLO) protein lacking the signal sequence (cytoLLO), a CpG motif, a DNA nuclear targeting sequence (DTS), and a retinoic acid-inducible gene-I (RIG-I) binding element. The immunostimulatory bacterium that comprises nucleic acid can include a CpG motif recognized by toll-like receptor 9 (TLR9). The CpG motif can be encoded on the plasmid. The CpG motif can be included in, or is part of, a bacterial gene that is encoded on the plasmid. For example, the gene that comprises CpGs can be asd, encoded on the plasmid. The immunostimulatory bacteria provided herein can include one or more of a CpG motif, an asd gene selectable marker for plasmid maintenance, and a DNA nuclear targeting sequence.

The immunostimulatory bacteria provided herein can encode two or more different RNA molecules that inhibit, suppress, or disrupt expression of an immune checkpoint, and/or an RNA molecule that encodes an inhibitor of a metabolite that is immunosuppressive, or is in an immunosuppressive pathway.

The immunostimulatory bacteria provided herein can be aspartate-semialdehyde dehydrogenase$^-$ (asd$^-$), which permits growth in diaminopimelic acid (DAP) supplemented medium, but limits replication in vivo when administered to subjects for treatment. Such bacteria will be self-limiting, which can be advantageous for treatment. The bacterium can be asd$^-$ by virtue of disruption or deletion of all or a portion of the endogenous gene encoding aspartate-semialdehyde dehydrogenase (asd), whereby the endogenous asd is not expressed. In other embodiments, the gene encoding aspartate-semialdehyde dehydrogenase can be included on the plasmid for expression in vivo.

Any of the immunostimulatory bacteria provided herein can include nucleic acid, generally on the plasmid, that includes a CpG motif or a CpG island, wherein the CpG motif is recognized by toll-like receptor 9 (TLR9). Nucleic acid encoding CpG motifs or islands are plentiful in prokaryotes, and, thus, the CpG motif can be included in, or can be a part of, a bacterial gene that is encoded on the plasmid. For example, the bacterial gene asd contains immunostimulatory CpGs.

The immunostimulatory bacteria provided herein can be auxotrophic for adenosine, or adenosine and adenine. Any of the bacteria herein can be rendered auxotrophic for adenosine, which advantageously can increase the anti-tumor activity, since adenosine accumulates in many tumors, and is immunosuppressive.

The immunostimulatory bacteria provided herein can be flagellin deficient, where the wild-type bacterium comprises flagella. They can be rendered flagellin deficient by disrupting or deleting all or a part of the gene or genes that encode the flagella. For example, provided are immunostimulatory bacteria that have deletions in the genes encoding one or both of flagellin subunits fliC and fljB, whereby the bacteria is flagella deficient.

The immunostimulatory bacteria provided herein can include nucleic acid encoding cytoLLO, which is a listeriolysin O (LLO) protein lacking the periplasmic secretion signal sequence, so that it accumulates in the cytoplasm. This mutation is advantageously combined with asd$^-$ bacteria. LLO is a cholesterol-dependent pore forming hemolysin from *Listeria monocytogenes* that mediates phagosomal escape of bacteria. When the autolytic strain is introduced into tumor-bearing hosts, such as humans, the bacteria are taken up by phagocytic immune cells and enter the vacuole. In this environment, the lack of DAP prevents bacterial replication, and results in autolysis of the bacteria in the vacuole. Lysis then releases the plasmid, and the accumulated LLO forms pores in the cholesterol-containing vacuole membrane and allows for delivery of the plasmid into the cytosol of the host cell.

The immunostimulatory bacteria can include a DNA nuclear targeting sequence (DTS), such as an SV40 DTS, encoded on the plasmid.

The immunostimulatory bacteria can have a deletion or modification in the gene encoding endonuclease-1 (endA), whereby endA activity is inhibited or eliminated. Exemplary of these are immunostimulatory bacteria that contain one or more of a CpG motif, an asd gene selectable marker for plasmid maintenance, and a DNA nuclear targeting sequence.

The immunostimulatory bacteria can contain nucleic acids on the plasmid encoding two or more different RNA molecules that inhibit, suppress, or disrupt expression of an immune checkpoint, or an RNA molecule that encodes an inhibitor of a metabolite that is immunosuppressive or that is in an immunosuppressive pathway.

The nucleic acids encoding the RNAi, such as shRNA or miRNA or siRNA, can include a transcriptional terminator following the RNA-encoding nucleic acid. In all embodiments, the RNAi encoded on the plasmid in the immunostimulatory bacteria can be short hairpin RNAs (shRNAs), or micro-RNAs (miRNAs).

The immunostimulatory bacteria can additionally encode a therapeutic product, such as RNAi that inhibits, suppresses, disrupts, or silences expression of immune checkpoints and other targets whose inhibition, suppression, disruption, or silencing is immunostimulatory, or an antibody or other binding protein that inhibits expression of these targets. These targets include, but are not limited to, one or more of three prime repair exonuclease 1 (TREX1), PD-1, PD-L1 (B7-H1), VEGF, TGF-beta isoform 1, beta-catenin, CTLA-4, PD-L2, PD-2, IDOL IDO2, SIRPα, CD47, VISTA (B7-H5), LIGHT, HVEM, CD28, LAG3, TIM3, TIGIT, Galectin-9, CEACAM1, CD155, CD112, CD226, CD244 (2B4), B7-H2, B7-H3, ICOS, GITR, B7-H4, B7-H6, CD27, CD40, CD40L, CD48, CD70, CD80, CD86, CD137 (4-1BB), CD200, CD272 (BTLA), CD160, CD39, CD73, A2a receptor, A2b receptor, HHLA2, ILT-2, ILT-4, gp49B, PIR-B, HLA-G, ILT-2/4, OX40, OX-40L, KIR, TIM1, TIM4, STAT3, Stabilin-1 (CLEVER-1), DNase II, and RNase H2. For example, any of the immunostimulatory bacteria can contain RNA that inhibits, suppresses, or disrupts expression of one or a combination of TREX1, PD-L1, VISTA, TGF-beta, such as TGF-beta isoform 1 or isoforms 1 and 3, beta-catenin, SIRP-alpha, VEGF, RNase H2, DNase II, and CLEVER-1/Stabilin-1. Cluster of Differentiation 47 (CD47), also known as integrin associated protein (IAP), is a transmembrane receptor belonging to the immunoglobulin superfamily of proteins. CD47 is ubiquitously expressed on cells and serves as a marker for self-recognition, preventing phagocytosis. CD47 mediates its effects through interactions with several other proteins, including thrombospondin (TSP) and signal regulatory protein-alpha (SIRPα). The interaction between SIRPα on phagocytic cells and CD47 on target cells helps ensure that target cells do not become engulfed by the phagocytic cells. Certain cancers co-opt the CD47-based immune evasion mechanism of a cell by increasing expression of CD47 on the cell surface of the cancer cell, thus avoiding clearance by the immune system. Targeting CD47-expressing cells in a subject results in toxicities. Encoding a CD47 inhibitory molecule, such as an antibody or antibody fragment, such as a nanobody (see, e.g., Sockolosky et al. (2016) *Proc. Natl. Acad. Sci. U.S.A.* 113:E2646-E2654) on plasmids in the immunostimulatory bacteria provided herein results in expression of the anti-CD47 product in the tumor microenvironment or tumor. Anti-CD47 antibody fragments have been encoded in bacteria, such as *E. coli*, that are administered intratumorally (see, e.g., Chowdhury et al. (2019) *Nature Medicine* 25:1057-1063). The bacteria herein have improved targeting and colonization of the tumor microenvironment, tumors, and/or tumor-resident immune cells, and, thus, can more effectively deliver the anti-CD47 antibody or antibody fragment. The immunostimulatory bacteria provided herein can be systemically administered to colonize tumors and the tumor microenvironment.

Provided are immunostimulatory bacteria where the plasmid comprises a sequence of nucleotides that encode a therapeutic product that inhibits an immune checkpoint or other immune suppressing target. Targets include, but are not limited to, TREX1, PD-L1, VISTA, TGF-beta isoform 1, beta-catenin, SIRP-alpha, VEGF, RNase H2, DNase II, CLEVER-1/Stabilin-1, and CD47. Other targets to be inhibited, suppressed or disrupted, are selected from among any of CTLA-4, PD-L2, PD-1, PD-2, IDO1, IDO2, LIGHT, HVEM, CD28, LAG3, TIM3, TIGIT, Galectin-9, CEACAM1, CD155, CD112, CD226, CD244 (2B4), B7-H2, B7-H3, ICOS, GITR, B7-H4, B7-H6, CD27, CD40, CD40L, CD48, CD70, CD80, CD86, CD137 (4-1BB), CD200, CD272 (BTLA), CD160, CD39, CD73, A2a receptor, A2b receptor, HHLA2, ILT-2, ILT-4, gp49B, PIR-B, HLA-G, ILT-2/4, OX40, OX-40L, KIR, TIM1, TIM4, and STAT3. Exemplary thereof are among human PD-L1 (SEQ ID NO:31), human beta-catenin (SEQ ID NO:32), human SIRPα (SEQ ID NO:33), human TREX1 (SEQ ID NO:34), human VISTA (SEQ ID NO:35), human TGF-beta isoform 1 (SEQ ID NO:193), and human VEGF (SEQ ID NO:194). RNA can target or contain a sequence in the immune checkpoint nucleic acids set forth in any of SEQ ID NOs: 1-30, 36-40, and 195-217. The plasmids in any of the immunostimulatory bacteria also can encode a sequence of nucleotides that is an agonist of retinoic acid-inducible gene I (RIG-I), or a RIG-I binding element.

The immunostimulatory bacteria can include one or more of deletions in genes, for example, the bacteria can be one or more of purI$^-$ (purM$^-$), msbB$^-$, purD$^-$, flagellin$^-$ (fliC$^-$/fljB$^-$), pagP$^-$, adrA$^-$, csgD$^-$ and hilA$^-$. The immunostimulatory bacteria can be msbB$^-$. For example, the immunostimulatory bacteria can contain a purI deletion, an msbB deletion, an asd deletion, an adrA deletion, and optionally, a csgD deletion. Exemplary of bacterial gene deletions/modifications are any of the following:

one or more of a mutation in a gene that alters the biosynthesis of lipopolysaccharide, selected from among one or more of rfaL, rfaG, rfaH, rfaD, rfaP, rFb, rfa, msbB, htrB, firA, pagL, pagP, lpxR, arnT, eptA, and lpxT; and/or one or more of a mutation that introduces a suicide gene and is selected from one or more of sacB, nuk, hok, gef, kil, or phlA; and/or one or more of a mutation that introduces a bacterial lysis gene and is selected from one or both of hly and cly; and/or a mutation in one or more virulence factor(s), selected from among IsyA, pag, prg, iscA, virG, plc, and act; and/or one or more of a mutation in a gene that modifies the stress response, selected from among recA, htrA, htpR, hsp, and groEL; and/or a mutation in min that disrupts the cell cycle; and/or one or more mutations in genes that disrupt or inactivate regulatory functions, selected from among cya, crp, phoP/phoQ, and ompR.

The immunostimulatory bacterium can be a strain of *Salmonella, Shigella, E. coli*, Bifidobacteriae, *Rickettsia, Vibrio, Listeria, Klebsiella, Bordetella, Neisseria, Aeromonas, Francisella, Cholera, Corynebacterium, Citrobacter, Chlamydia, Haemophilus, Brucella, Mycobacterium, Mycoplasma, Legionella, Rhodococcus, Pseudomonas, Helicobacter, Bacillus*, or *Erysipelothrix*, or an attenuated strain thereof, or a modified strain thereof, of any of the preceding list of bacterial strains.

Exemplary of the immunostimulatory bacteria are those where the plasmid contains one or more of a sequence of nucleic acids encoding a listeriolysin O (LLO) protein lacking the signal sequence (cytoLLO), a CpG motif, a DNA nuclear targeting sequence (DTS), and a retinoic acid-inducible gene-I (RIG-I) binding element.

Other exemplary immunostimulatory bacteria include those that are auxotrophic for adenosine, and comprise: a deletion in the gene(s) encoding the flagella; a deletion in endA; a plasmid that encodes CytoLLO; a nuclear localization sequence; and an asd plasmid complementation system; and that encode RNA that inhibits, suppresses, or disrupts expression of an immune checkpoint or other target whose inhibition, suppression, or disruption increases the anti-tumor immune response in a subject.

Such immunostimulatory bacteria include strains of *Salmonella*, such as a wild type *Salmonella typhimurium* strain, such as the strain deposited under ATCC accession no. 14028, or a strain having all of the identifying characteristics of the strain deposited under ATCC accession #14028. Other strains include, for example, an attenuated *Salmonella typhimurium* strain selected from among strains designated as AST-100, VNP20009, or strains YS1646 (ATCC #202165), RE88, SL7207, $\chi$ 8429, $\chi$8431, and $\chi$ 8468.

The immunostimulatory bacteria can contain one or more of a purI deletion, an msbB deletion, an asd deletion, and an adrA deletion, in addition to the modifications that increase accumulation in tumor cells, the TME, and/or tumor-resident immune cells, and/or modifications that reduce immune cell death, and can encode an immunostimulatory protein or other therapeutic product as described herein. The immunostimulatory bacteria also can include:

one or more of a mutation in a gene that alters the biosynthesis of lipopolysaccharide, selected from among one or more of rfaL, rfaG, rfaH, rfaD, rfaP, rFb, rfa, msbB, htrB, firA, pagL, pagP, lpxR, arnT, eptA, and lpxT; and/or one or more of a mutation that introduces a suicide gene and is selected from among one or more of sacB, nuk, hok, gef, kil, and phlA; and/or one or more of a mutation that introduces a bacterial lysis gene and is selected from among one or both of hly and cly; and/or a mutation in one or more virulence factor(s), selected from among IsyA, pag, prg, iscA, virG, plc, and act; and/or one or more mutations in a gene or genes that modify the stress response, selected from among recA, htrA, htpR, hsp, and groEL; and/or a mutation in min that disrupts the cell cycle; and/or one or more mutations that disrupt or inactivate regulatory functions, selected from among cya, crp, phoP/phoQ, and ompR.

The strains can be one or more of msbB$^-$, asd$^-$, hilA$^-$ and/or flagellin$^-$ (fliC$^-$/fljB$^-$), and/or pagP$^-$. In particular, the strains are flagellin$^-$ (fliC$^-$/fljB$^-$), such as flagellin$^-$ (fliC$^-$/fljB$^-$), msbB$^-$, purI$^-$/purM$^-$, and optionally, asd$^-$ and/or hilA$^-$. The bacteria can be auxotrophic for adenosine, or for adenosine and adenine. The therapeutic product, such as RNAi, and/or an immunostimulatory protein, and/or an antibody or fragment thereof, are expressed under control of a promoter recognized by the host, such as an RNAP III promoter, or an RNAP II promoter, as described herein. The immunostimulatory bacterium can be a strain of *Salmonella, Shigella, E. coli*, Bifidobacteriae, *Rickettsia, Vibrio, Listeria, Klebsiella, Bordetella, Neisseria, Aeromonas, Francisella, Cholera, Corynebacterium, Citrobacter, Chlamydia, Haemophilus, Brucella, Mycobacterium, Mycoplasma, Legionella, Rhodococcus, Pseudomonas, Helicobacter, Bacillus*, or *Erysipelothrix*, or an attenuated strain thereof, or a modified strain thereof, of any of the preceding list of bacterial strains. Generally, the strain is one that is attenuated in the host. *Salmonella* strains, such as *S. typhimurium*, are exemplary of the bacteria. Exemplary strains include *Salmonella typhimurium* strains derived from strains designated as AST-100, VNP20009, or strains YS1646 (ATCC #202165), RE88, SL7207, $\chi$8429, $\chi$8431, $\chi$8468, and the wild-type strain ATCC #14028.

Compositions containing the immunostimulatory bacteria are provided. Such compositions contain the bacteria, and a pharmaceutically acceptable excipient or vehicle. The immunostimulatory bacteria include any described herein, or in patents/applications incorporated herein, or known to those of skill in the art. The bacteria encode a therapeutic product, generally an anti-cancer product, such as an inhibitor of an immune checkpoint, or an immunostimulatory protein that increases anti-tumor activity in the tumor microenvironment or in the tumor, such as a cytokine, or chemokine, or co-stimulatory molecule. The genomes of the bacteria can be modified to have increased infectivity of immune cells, and or reduced infectivity of non-immune cells, and/or reduced ability to induce cell death of immune cells. Hence, the bacteria are modified as described herein to accumulate in tumors, or in the tumor microenvironment, or in tumor-resident immune cells, and/or to deliver immunostimulatory proteins and other therapeutic products that promote anti-tumor activity. The immunostimulatory bacteria can additionally contain a plasmid encoding a therapeutic anti-cancer product, such as RNAi, such as miRNA or shRNA, or a CRISPR cassette, that target an immune checkpoint, or otherwise enhance the anti-tumor activity of the bacteria.

A single dose is therapeutically effective for treating a disease or disorder in which immune stimulation effects treatment. Exemplary of such stimulation is an immune response, that includes, but is not limited to, one or both of a specific immune response and non-specific immune response, both specific and non-specific immune responses, an innate response, a primary immune response, adaptive immunity, a secondary immune response, a memory immune response, immune cell activation, immune cell proliferation, immune cell differentiation, and cytokine expression.

Pharmaceutical compositions containing any of the immunostimulatory bacteria are provided. As are uses thereof for treatment of cancers, and methods of treatment of cancer. Methods and uses include treating a subject who has cancer, comprising administering an immunostimulatory bacterium or the pharmaceutical composition to a subject, such as a human. A method of treating a subject who has cancer, comprising administering an immunostimulatory bacterium, is provided.

Methods and uses include combination therapy, in which a second anti-cancer agent or treatment is administered. The second anti-cancer agent is a chemotherapeutic agent that results in cytosolic DNA, or radiotherapy, or an anti-immune checkpoint inhibitor, such as an anti-PD-1, or anti-PD-L1, or anti-CTLA4 antibody, or CAR-T cells, or other therapeutic cells, such as stem cells, TIL cells and modified cells for cancer therapy. The combination therapy also can include anti-VEGF or anti-VEGFR, or anti-VEGFR2 antibodies, or fragments thereof, or an anti-IL-6 antibody or fragment thereof, or oncolytic virus therapy, or a cancer vaccine.

Administration can be by any suitable route, such as parenteral, and can include additional agents that can facilitate or enhance delivery. Administration can be oral, or rectal, or by aerosol into the lung, or can be intratumorally, intravenously, intramuscularly, or subcutaneously.

Cancers include solid tumors and hematologic malignancies, such as, but not limited to, lymphoma, leukemia, gastric cancer, and cancer of the breast, heart, lung, small intestine, colon, spleen, kidney, bladder, head and neck, colorectum, ovary, prostate, brain, pancreas, skin, bone, bone marrow, blood, thymus, uterus, testicles, cervix, and liver.

The immunostimulatory bacteria can be formulated into compositions for administration, such as suspensions. They can be dried and stored as powders. Combinations of the immunostimulatory bacteria with other anti-cancer agents also are provided.

Combination therapies for treatment of cancers and malignancies are provided. The immunostimulatory bacteria can be administered before, or concurrently with, other cancer therapies, including radiotherapy, chemotherapies, particularly genotoxic chemotherapies that result in cytosolic DNA, and immunotherapies, such as anti-checkpoint inhibitor antibodies, including anti-PD-1 antibodies, anti-PD-L1 antibodies, and anti-CTLA4 antibodies, and other such immunotherapies. Other cancer therapies also include anti-VEGF, anti-VEGFR, anti-VEGFR2, or anti-IL-6 antibodies, or fragments thereof, cancer vaccines, and oncolytic viruses.

Administration can be by any suitable route, including systemic, or local, or topical, such as parenteral, including, for example, oral, or rectal, or by aerosol into the lung, or intratumorally, intravenously, intramuscularly, or subcutaneously.

Also provided are methods for increasing the colonization of tumors, tumor-resident immune cells, and/or the tumor microenvironment by an immunostimulatory bacterium. The methods include, for example, modifying the genome of a bacterium to render the bacterium flagellin$^-$ (fliC$^-$/fljB$^-$) and/or pagP$^-$. It is shown herein that such modification(s) strikingly enhance tumor/tumor microenvironment/tumor-resident immune cell colonization.

The terms and expressions that are employed are used as terms of description and not of limitation, and there is no intention in the use of such terms and expressions to exclude any equivalents of the features shown and described or portions thereof, but it is recognized that various modifications are contemplated.

BRIEF DESCRIPTION OF THE DRAWINGS

FIG. 18A depicts the mean CFUs per gram of tumor tissue, ±SD. FIG. 18B depicts the tumor to spleen colonization ratios.

DETAILED DESCRIPTION

OUTLINE

Figure 1:
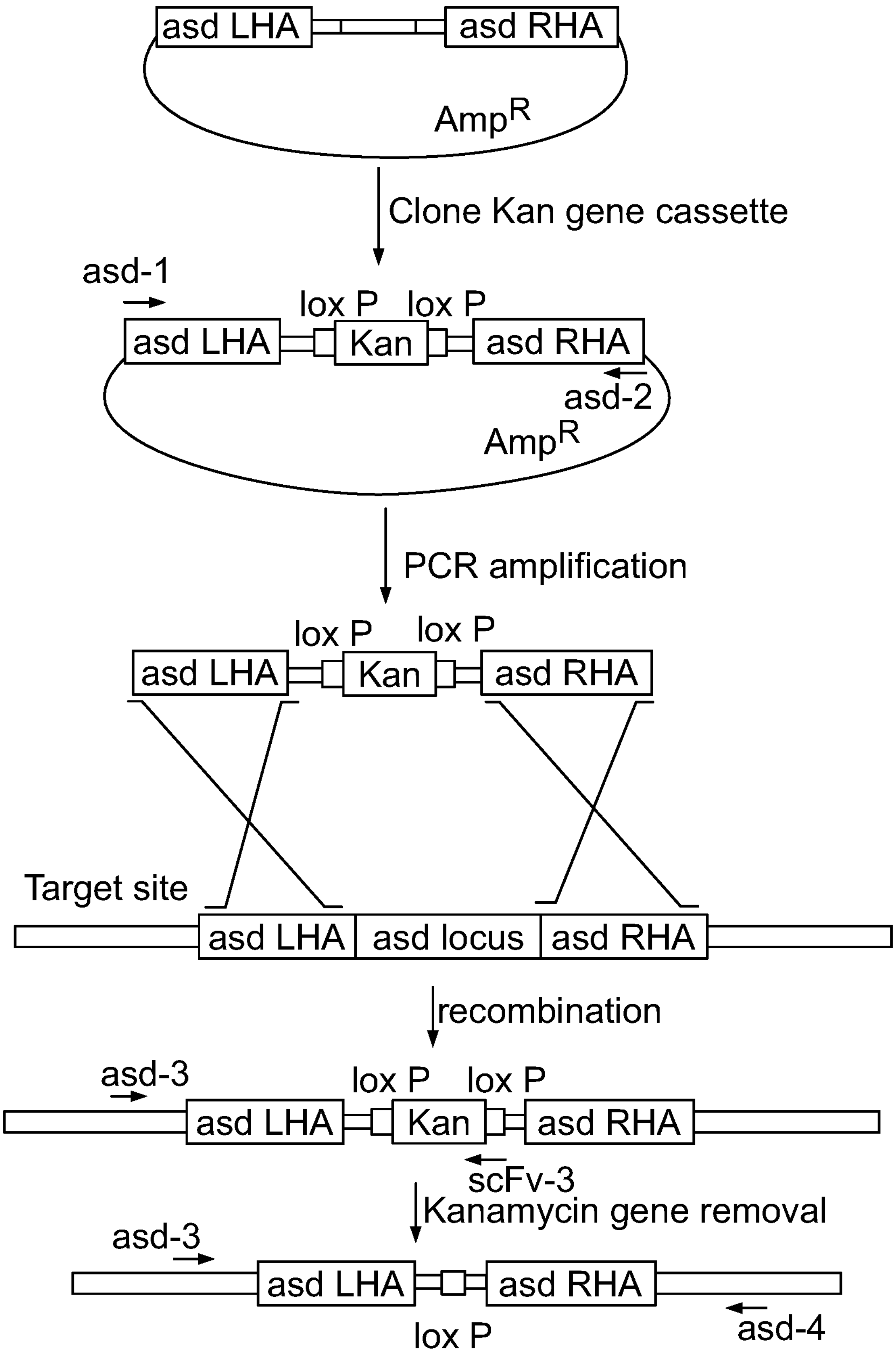
FIG. 1 depicts a schematic of the process used to delete the asd gene from strain YS1646. The asd gene from *S. typhimurium* strain YS1646 was deleted using lambda-derived Red recombination system, as described in Datsenko and Wanner (*Proc. Natl. Acad. Sci. U.S.A.* 97:6640-6645 (2000)).

A. DEFINITIONS
B. OVERVIEW OF THE IMMUNOSTIMULATORY BACTERIA
C. CANCER IMMUNOTHERAPEUTICS
  1. Immunotherapies
  2. Adoptive Immunotherapies
  3. Cancer Vaccines and Oncolytic Viruses
D. BACTERIAL CANCER IMMUNOTHERAPY
  1. Bacterial Therapies
  2. Comparison of the Immune Responses to Bacteria and Viruses
  3. *Salmonella* Therapy
    a. Tumor-Tropic Bacteria
    b. *Salmonella enterica* Serovar Typhimurium
    c. Bacterial Attenuation
      i. $msbB^-$ Mutants
      ii. $purI^-$ Mutants
      iii. Combinations of Attenuating Mutations
      iv. VNP20009 and Other Attenuated and Wild-type *S. typhimurium* Strains
      v. *S. typhimurium* Engineered to Deliver Macromolecules
  4. Enhancements of Immunostimulatory Bacteria to Increase Therapeutic Index
    a. asd Gene Deletion
    b. Adenosine Auxotrophy
    c. Flagellin Deficient Strains
    d. *Salmonella* Engineered to Escape the *Salmonella*-Containing Vacuole (SCV)
    e. Deletions in *Salmonella* Genes Required for Biofilm Formation
    f. Deletions in Genes in the LPS Biosynthetic Pathway
    g. Deletions of SPI-1 and SPI-2 Genes
    h. Endonuclease (endA) Mutations to Increase Plasmid Delivery
    i. RIG-I Inhibition
    j. DNase II Inhibition
    k. RNase H2 Inhibition
    l. Stabilin-1/CLEVER-1 Inhibition -continued 5. Immunostimulatory Proteins
6. Modifications that Increase Uptake of Gram-Negative Bacteria, such as *Salmonella*, by Immune Cells and Reduce Immune Cell Death
7. Bacterial Culture Conditions
E. BACTERIAL ATTENUATION AND COLONIZATION
1. Deletion of Flagellin (fliC/fljB)
2. Deletion of Genes in the LPS Biosynthetic Pathway
3. Colonization
F. CONSTRUCTING EXEMPLARY PLASMIDS ENCODING THERAPEUTIC PROTEINS
1. Immunostimulatory Proteins
2. Antibodies and Antibody Fragments
3. Interfering RNAs (RNAi)
a. shRNA
b. MicroRNA
4. Origin of Replication and Plasmid Copy Number
5. CpG Motifs and CpG Islands
6. Plasmid Maintenance/Selection Components
7. RNA Polymerase Promoters
8. DNA Nuclear Targeting Sequences
9. CRISPR
G. TUMOR-TARGETING IMMUNOSTIMULATORY BACTERIA CONTAIN RNAI AGAINST EXEMPLARY IMMUNE TARGET GENES TO STIMULATE ANTI-TUMOR IMMUNITY
1. TREX1
2. PD-L1
3. VISTA
4. SIRPα
5. β-catenin
6. TGF-β
7. VEGF
8. Additional Exemplary Checkpoint Targets
H. PHARMACEUTICAL PRODUCTION, COMPOSITIONS, AND FORMULATIONS
1. Manufacturing
a. Cell Bank Manufacturing
b. Drug Substance Manufacturing
c. Drug Product Manufacturing
2. Compositions
3. Formulations
a. Liquids, Injectables, Emulsions
b. Dried Thermostable Formulations
4. Compositions for Other Routes of Administration
5. Dosages and Administration
6. Packaging and Articles of Manufacture
I. METHODS OF TREATMENT AND USES
1. Tumors
2. Administration
3. Monitoring
J. EXAMPLES

A. Definitions

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, therapeutic bacteria are bacteria that effect therapy, such as cancer or anti-tumor therapy, when administered to a subject, such as a human.

As used herein, immunostimulatory bacteria are therapeutic bacteria that, when introduced into a subject, accumulate in immunoprivileged tissues and cells, such as tumors, and replicate and/or express products that are immunostimulatory or that result in immunostimulation. For example, the immunostimulatory bacteria are attenuated in the host by virtue of reduced toxicity or pathogenicity and/or by virtue of encoded products that reduce toxicity or pathogenicity, as the immunostimulatory bacteria cannot replicate and/or express products (or have reduced replication/product expression), except primarily in immunoprivileged environments. Immunostimulatory bacteria provided herein are modified to encode a product or products or exhibit a trait or property that renders them immunostimulatory. Such products, properties and traits include, but are not limited to, for example, at least one of: an immunostimulatory protein, such as a cytokine, chemokine or co-stimulatory molecule; RNAi, such as siRNA (shRNA and microRNA), or CRISPR, that targets, disrupts or inhibits an immune checkpoint gene such as TREX1 and/or PD-L1; or an inhibitor of an immune checkpoint such as an anti-immune checkpoint antibody. Immunostimulatory bacteria also can include a modification that renders the bacterium auxotrophic for a metabolite that is immunosuppressive or that is in an immunosuppressive pathway, such as adenosine.

As used herein, the strain designations VNP20009 (see, e.g., International PCT Application Publication No. WO 99/13053, see, also U.S. Pat. No. 6,863,894) and YS1646 and 41.2.9 are used interchangeably and each refer to the strain deposited with the American Type Culture Collection (ATCC) and assigned Accession No. 202165. VNP20009 is a modified attenuated strain of *Salmonella typhimurium*, which contains deletions in msbB and purI, and was generated from wild type strain ATCC #14028.

As used herein, the strain designations YS1456 and 8.7 are used interchangeably and each refer to the strain deposited with the American Type Culture Collection (ATCC) and assigned Accession No. 202164 (see, U.S. Pat. No. 6,863,894).

As used herein, an origin of replication is a sequence of DNA at which replication is initiated on a chromosome, plasmid or virus. For small DNA, including bacterial plasmids and small viruses, a single origin is sufficient.

The origin of replication determines the vector copy number, which depends upon the selected origin of replication. For example, if the expression vector is derived from the low-copy-number plasmid pBR322, it is between about 25-50 copies/cell, and if derived from the high-copy-number plasmid pUC, it can be 150-200 copies/cell.

As used herein, medium copy number of a plasmid in cells is about or is 150 or less than 150, low copy number is 15-30, such as 20 or less than 20. Low to medium copy number is less than 150. High copy number is greater than 150 copies/cell.

As used herein, a CpG motif is a pattern of bases that include an unmethylated central CpG ("p" refers to the phosphodiester link between consecutive C and G nucleotides) surrounded by at least one base flanking (on the 3' and the 5' side of) the central CpG. A CpG oligodeoxynucleotide is an oligodeoxynucleotide that is at least about ten nucleotides in length and includes an unmethylated CpG. At least the C of the 5' CG 3' is unmethylated.

As used herein, a RIG-I binding sequence refers to a 5'triphosphate (5'ppp) structure directly, or that which is synthesized by RNA pol III from a poly(dA-dT) sequence, which by virtue of interaction with RIG-I can activate type I IFN via the RIG-I pathway. The RNA includes at least four A ribonucleotides (A-A-A-A); it can contain 4, 5, 6, 7, 8, 9, 10 or more. The RIG-I binding sequence is introduced into a plasmid in the bacterium for transcription into the polyA.

As used herein, an immunostimulatory protein is one that confers, promotes, enhance or increases immune responses, particularly in the tumor microenvironment, such as in tumors and/or in tumor-resident immune cells. Immunostimulatory proteins include, but are not limited to, cytokines, chemokines, co-stimulatory molecules, and other immune regulatory proteins and products. Thus, as used herein, an "immunostimulatory protein" is a protein that confers, exhibits or promotes an anti-tumor immune response in the tumor microenvironment. Exemplary of such proteins are cytokines, chemokines, and co-stimulatory molecules, such as, but not limited to, GM-CSF, IL-2, IL-7, IL-12, IL-15, IL-18, IL-21, IL-12p70 (IL-12p40+IL-12p35), IL-15/IL-15R alpha chain complex, CXCL9, CXCL10, CXCL11, CCL3, CCL4, CCL5, molecules involved in the potential recruitment/persistence of T cells, CD40, CD40 ligand (CD40L), OX40, OX40 ligand (OX40L), 4-1BB, 4-1BB ligand (4-1BBL), members of the B7-CD28 family, CD47 antagonists, TGF-beta polypeptide antagonists, and members of the TNFR superfamily.

As used herein, "cytokines" are a broad and loose category of small proteins (~5-20 kDa) that are important in cell signaling. Cytokines include chemokines, interferons, interleukins, lymphokines, and tumor necrosis factors. Cytokines are cell signaling molecules that aid cell to cell communication in immune responses, and stimulate the movement of cells towards sites of inflammation, infection and trauma.

As used herein, "chemokines" refer to chemoattractant (chemotactic) cytokines that bind to chemokine receptors and include proteins isolated from natural sources as well as those made synthetically, as by recombinant means or by chemical synthesis. Exemplary chemokines include, but are not limited to, IL-8, IL-10, GCP-2, GRO-α, GRO-β, GRO-γ, ENA-78, PBP, CTAP III, NAP-2, LAPF-4, MIG (CXCL9), CXCL10, CXCL11, PF4, IP-10, SDF-1α, SDF-1β, SDF-2, MCP-1, MCP-2, MCP-3, MCP-4, MCP-5, MIP-1α (CCL3), MIP-1β (CCL4), MIP-1γ, MIP-2, MIP-2α, MIP-3α, MIP-3β, MIP-4, MIP-5, MDC, HCC-1, ALP, lungkine, Tim-1, eotaxin-1, eotaxin-2, I-309, SCYA17, TRAC, RANTES (CCL5), DC-CK-1, lymphotactin, ALP, lungkine and fractalkine, and others known to those of skill in the art. Chemokines are involved in the migration of immune cells to sites of inflammation, as well as in the maturation of immune cells and in the generation of adaptive immune responses.

As used herein, a bacterium that is modified so that it "induces less cell death in tumor-resident immune cells" or "induces less cell death in immune cells" is one that is less toxic than the bacterium without the modification, or one that has reduced virulence compared to the bacterium without the modification. Exemplary of such modifications are those that decrease/eliminate pyroptosis and that alter lipopolysaccharide (LPS) profiles on the bacterium. These modifications include one or more of disruption of or deletion of flagellin genes, pagP, or one or more components of the SPI-1 pathway, such as hilA, rod protein, needle protein, and QseC.

As used herein, a bacterium that is "modified so that it preferentially infects tumor-resident immune cells" or "modified so that it preferentially infects immune cells" has a modification in its genome that reduces its ability to infect cells other than immune cells. Exemplary of such modifications are modifications that disrupt the type 3 secretion system or type 4 secretion system or other genes or systems that affect the ability of a bacterium to invade a non-immune cell. For example, disruption/deletion of an SPI-1 component, which is needed for infection of cells, such as epithelial cells, but does not affect infection of immune cells, such as phagocytic cells, by *Salmonella.*

As used herein, a "modification" is in reference to modification of a sequence of amino acids of a polypeptide or a sequence of nucleotides in a nucleic acid molecule and includes deletions, insertions, and replacements of amino acids or nucleotides, respectively. Methods of modifying a polypeptide are routine to those of skill in the art, such as by using recombinant DNA methodologies.

As used herein, a modification to a bacterial genome or to a plasmid or gene includes deletions, replacements and insertions of nucleic acid.

As used herein, RNA interference (RNAi) is a biological process in which RNA molecules inhibit gene expression or translation, by neutralizing targeted mRNA molecules to inhibit translation and thereby expression of a targeted gene.

As used herein, RNA molecules that act via RNAi are referred to as inhibitory by virtue of their silencing of expression of a targeted gene. Silencing expression means that expression of the targeted gene is reduced or suppressed or inhibited.

As used herein, gene silencing via RNAi is said to inhibit, suppress, disrupt or silence expression of a targeted gene. A targeted gene contains sequences of nucleotides that correspond to the sequences in the inhibitory RNA, whereby the inhibitory RNA silences expression of mRNA.

As used herein, inhibiting, suppressing, disrupting or silencing a targeted gene refers to processes that alter expression, such as translation, of the targeted gene, whereby activity or expression of the product encoded by the targeted gene is reduced. Reduction, includes a complete knock-out or a partial knockout, whereby with reference to the immunostimulatory bacterium provided herein and administration herein, treatment is effected.

As used herein, small interfering RNAs (siRNAs) are small pieces of double-stranded (ds) RNA, usually about 21 nucleotides long, with 3' overhangs (2 nucleotides) at each end that can be used to "interfere" with the translation of proteins by binding to and promoting the degradation of messenger RNA (mRNA) at specific sequences. In doing so, siRNAs prevent the production of specific proteins based on the nucleotide sequences of their corresponding mRNAs. The process is called RNA interference (RNAi), and also is referred to as siRNA silencing or siRNA knockdown.

As used herein, a short-hairpin RNA or small-hairpin RNA (shRNA) is an artificial RNA molecule with a tight hairpin turn that can be used to silence target gene expression via RNA interference (RNAi). Expression of shRNA in cells is typically accomplished by delivery of plasmids or through viral or bacterial vectors.

As used herein, a tumor microenvironment (TME) is the cellular environment in which the tumor exists, including surrounding blood vessels, immune cells, fibroblasts, bone marrow-derived inflammatory cells, lymphocytes, signaling molecules and the extracellular matrix (ECM). Conditions that exist include, but are not limited to, increased vascularization, hypoxia, low pH, increased lactate concentration, increased pyruvate concentration, increased interstitial fluid pressure and altered metabolites or metabolism, such as higher levels of adenosine, indicative of a tumor.

As used herein, human type I interferons (IFNs) are a subgroup of interferon proteins that regulate the activity of the immune system. All type I IFNs bind to a specific cell surface receptor complex, such as the IFN-α receptor. Type I interferons include IFN-α and IFN-β, among others. IFN-β proteins are produced by fibroblasts, and have antiviral activity that is involved mainly in innate immune response. Two types of IFN-β are IFN-β1 (IFNB1) and IFN-β3 (IFNB3).

As used herein, recitation that a nucleic acid or encoded RNA targets a gene means that it inhibits or suppresses or silences expression of the gene by any mechanism. Generally, such nucleic acid includes at least a portion complementary to the targeted gene, where the portion is sufficient to form a hybrid with the complementary portion.

As used herein, "deletion," when referring to a nucleic acid or polypeptide sequence, refers to the deletion of one or more nucleotides or amino acids compared to a sequence, such as a target polynucleotide or polypeptide or a native or wild-type sequence.

As used herein, "insertion," when referring to a nucleic acid or amino acid sequence, describes the inclusion of one or more additional nucleotides or amino acids, within a target, native, wild-type or other related sequence. Thus, a nucleic acid molecule that contains one or more insertions compared to a wild-type sequence, contains one or more additional nucleotides within the linear length of the sequence.

As used herein, "additions" to nucleic acid and amino acid sequences describe addition of nucleotides or amino acids onto either termini compared to another sequence.

As used herein, "substitution" or "replacement" refers to the replacing of one or more nucleotides or amino acids in a native, target, wild-type or other nucleic acid or polypeptide sequence with an alternative nucleotide or amino acid, without changing the length (as described in numbers of residues) of the molecule. Thus, one or more substitutions in a molecule does not change the number of amino acid residues or nucleotides of the molecule. Amino acid replacements compared to a particular polypeptide can be expressed in terms of the number of the amino acid residue along the length of the polypeptide sequence.

As used herein, "at a position corresponding to," or recitation that nucleotides or amino acid positions "correspond to" nucleotides or amino acid positions in a disclosed sequence, such as set forth in the Sequence Listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g., *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M Stockton Press, New York, 1991; and Carrillo et al. (1988) *SIAM J. Applied Math* 48:1073).

As used herein, alignment of a sequence refers to the use of homology to align two or more sequences of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence. Related or variant polypeptides or nucleic acid molecules can be aligned by any method known to those of skill in the art. Such methods typically maximize matches, and include methods, such as using manual alignments and by using the numerous alignment programs available (e.g., BLASTP) and others known to those of skill in the art. By aligning the sequences of polypeptides or nucleic acids, one skilled in the art can identify analogous portions or positions, using conserved and identical amino acid residues as guides. Further, one skilled in the art also can employ conserved amino acid or nucleotide residues as guides to find corresponding amino acid or nucleotide residues between and among human and non-human sequences. Corresponding positions also can be based on structural alignments, for example by using computer simulated alignments of protein structure. In other instances, corresponding regions can be identified. One skilled in the art also can employ conserved amino acid residues as guides to find corresponding amino acid residues between and among human and non-human sequences.

As used herein, a "property" of a polypeptide, such as an antibody, refers to any property exhibited by a polypeptide, including, but not limited to, binding specificity, structural configuration or conformation, protein stability, resistance to proteolysis, conformational stability, thermal tolerance, and tolerance to pH conditions. Changes in properties can alter an "activity" of the polypeptide. For example, a change in the binding specificity of the antibody polypeptide can alter the ability to bind an antigen, and/or various binding activities, such as affinity or avidity, or in vivo activities of the polypeptide.

As used herein, an "activity" or a "functional activity" of a polypeptide, such as an antibody, refers to any activity exhibited by the polypeptide. Such activities can be empirically determined. Exemplary activities include, but are not limited to, ability to interact with a biomolecule, for example, through antigen-binding, DNA binding, ligand binding, or dimerization, or enzymatic activity, for example, kinase activity or proteolytic activity. For an antibody (including antibody fragments), activities include, but are not limited to, the ability to specifically bind a particular antigen, affinity of antigen-binding (e.g., high or low affinity), avidity of antigen-binding (e.g., high or low avidity), on-rate, off-rate, effector functions, such as the ability to promote antigen neutralization or clearance, virus neutralization, and in vivo activities, such as the ability to prevent infection or invasion of a pathogen, or to promote clearance, or to penetrate a particular tissue or fluid or cell in the body. Activity can be assessed in vitro or in vivo using recognized assays, such as ELISA, flow cytometry, surface plasmon resonance or equivalent assays to measure on- or off-rate, immunohistochemistry and immunofluorescence histology and microscopy, cell-based assays, flow cytometry and binding assays (e.g., panning assays).

As used herein, "bind," "bound" or grammatical variations thereof refers to the participation of a molecule in any attractive interaction with another molecule, resulting in a stable association in which the two molecules are in close proximity to one another. Binding includes, but is not limited to, non-covalent bonds, covalent bonds (such as reversible and irreversible covalent bonds), and includes interactions between molecules such as, but not limited to, proteins, nucleic acids, carbohydrates, lipids, and small molecules, such as chemical compounds including drugs.

As used herein, "antibody" refers to immunoglobulins and immunoglobulin fragments, whether natural or partially or wholly synthetic, such as recombinantly produced, including any fragment thereof containing at least a portion of the variable heavy chain and light region of the immunoglobulin molecule that is sufficient to form an antigen-binding site and, when assembled, to specifically bind an antigen. Hence, an antibody includes any protein having a binding domain that is homologous or substantially homologous to an immunoglobulin antigen-binding domain (antibody combining site). For example, an antibody refers to an antibody that contains two heavy chains (which can be denoted H and H') and two light chains (which can be denoted L and L'), where each heavy chain can be a full-length immunoglobulin heavy chain or a portion thereof sufficient to form an antigen binding site (e.g., heavy chains include, but are not limited to, $V_H$ chains, $V_H$-$C_H1$ chains and $V_H$-$C_H1$-$C_H2$-$C_H3$ chains), and each light chain can be a full-length light chain or a portion thereof sufficient to form an antigen binding site (e.g., light chains include, but are not limited to, $V_L$ chains and $V_L$-$C_L$ chains). Each heavy chain (H and H') pairs with one light chain (L and L', respectively). Typically, antibodies minimally include all or at least a portion of the variable heavy ($V_H$) chain and/or the variable light ($V_L$) chain. The antibody also can include all or a portion of the constant region.

For purposes herein, the term antibody includes full-length antibodies and portions thereof, including antibody fragments, such as anti-EGFR antibody fragments. Antibody fragments, include, but are not limited to, Fab fragments, Fab' fragments, $F(ab')_2$ fragments, a nanobody (such as a camelid antibody), fragments, disulfide-linked Fvs (dsFv), Fd fragments, Fd' fragments, single-chain Fvs (scFv), single-chain Fabs (scFab), diabodies, anti-idiotypic (anti-Id) antibodies, or antigen-binding fragments of any of the above. Antibody also includes synthetic antibodies, recombinantly produced antibodies, multi-specific antibodies (e.g., bispecific antibodies), human antibodies, non-human antibodies, humanized antibodies, chimeric antibodies, and intrabodies. Antibodies provided herein include members of any immunoglobulin class (e.g., IgG, IgM, IgD, IgE, IgA and IgY), any subclass (e.g., IgG1, IgG2, IgG3, IgG4, IgA1 and IgA2) or sub-subclass (e.g., IgG2a and IgG2b). Antibodies for human therapy generally are human antibodies or are humanized.

As used herein, "antibody fragment(s)" refers to (i) monovalent and monospecific antibody derivatives that contain the variable heavy and/or light chains or functional fragments of an antibody and lack an Fc part; and (ii) BiTE® (tandem scFv), DARTs, diabodies and single-chain diabodies (scDB). Thus, an antibody fragment includes a/an: Fab, Fab', scFab, scFv, Fv fragment, nanobody (see, e.g., antibodies derived from *Camelus bactriamus, Calelus dromedarius*, or *Lama paccos*) (see, e.g., U.S. Pat. No. 5,759,808; and Stijlemans et al. (2004) *J. Biol. Chem.* 279:1256-1261), $V_{HH}$, dAb, minimal recognition unit, single-chain diabody (scDb), BiTE® and DART. The recited antibody fragments have a molecular weight below 60 kDa.

As used herein, "nucleic acid" refers to at least two linked nucleotides or nucleotide derivatives, including a deoxyribonucleic acid (DNA) and a ribonucleic acid (RNA), joined together, typically by phosphodiester linkages. Also included in the term "nucleic acid" are analogs of nucleic acids such as peptide nucleic acid (PNA), phosphorothioate DNA, and other such analogs and derivatives or combinations thereof. Nucleic acids also include DNA and RNA derivatives containing, for example, a nucleotide analog or a "backbone" bond other than a phosphodiester bond, for example, a phosphotriester bond, a phosphoramidate bond, a phosphorothioate bond, a thioester bond, or a peptide bond (peptide nucleic acid). The term also includes, as equivalents, derivatives, variants and analogs of either RNA or DNA made from nucleotide analogs, single (sense or antisense) and double-stranded nucleic acids. Deoxyribonucleotides include deoxyadenosine, deoxycytidine, deoxyguanosine and deoxythymidine. For RNA, the uracil base is uridine.

As used herein, an isolated nucleic acid molecule is one which is separated from other nucleic acid molecules which are present in the natural source of the nucleic acid molecule. An "isolated" nucleic acid molecule, such as a cDNA molecule, can be substantially free of other cellular material, or culture medium when produced by recombinant techniques, or substantially free of chemical precursors or other chemicals when chemically synthesized. Exemplary isolated nucleic acid molecules provided herein include isolated nucleic acid molecules encoding an antibody or antigen-binding fragments provided.

As used herein, "operably linked" with reference to nucleic acid sequences, regions, elements or domains means that the nucleic acid regions are functionally related to each other. For example, a nucleic acid encoding a leader peptide can be operably linked to a nucleic acid encoding a polypeptide, whereby the nucleic acids can be transcribed and translated to express a functional fusion protein, wherein the leader peptide effects secretion of the fusion polypeptide. In some instances, the nucleic acid encoding a first polypeptide (e.g., a leader peptide) is operably linked to a nucleic acid encoding a second polypeptide and the nucleic acids are transcribed as a single mRNA transcript, but translation of the mRNA transcript can result in one of two polypeptides being expressed. For example, an amber stop codon can be located between the nucleic acid encoding the first polypeptide and the nucleic acid encoding the second polypeptide, such that, when introduced into a partial amber suppressor cell, the resulting single mRNA transcript can be translated to produce either a fusion protein containing the first and second polypeptides, or can be translated to produce only the first polypeptide. In another example, a promoter can be operably linked to nucleic acid encoding a polypeptide, whereby the promoter regulates or mediates the transcription of the nucleic acid.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, the residues of naturally occurring α-amino acids are the residues of those 20 α-amino acids found in nature which are incorporated into protein by the specific recognition of the charged tRNA molecule with its cognate mRNA codon in humans.

As used herein, "polypeptide" refers to two or more amino acids covalently joined. The terms "polypeptide" and "protein" are used interchangeably herein.

As used herein, a "peptide" refers to a polypeptide that is from 2 to about or 40 amino acids in length.

As used herein, an "amino acid" is an organic compound containing an amino group and a carboxylic acid group. A polypeptide contains two or more amino acids. For purposes herein, amino acids contained in the antibodies provided include the twenty naturally-occurring amino acids (see Table below), non-natural amino acids, and amino acid analogs (e.g., amino acids wherein the α-carbon has a side chain). As used herein, the amino acids, which occur in the various amino acid sequences of polypeptides appearing herein, are identified according to their well-known, three-letter or one-letter abbreviations (see Table below). The nucleotides, which occur in the various nucleic acid molecules and fragments, are designated with the standard single-letter designations used routinely in the art.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.,* 243:3557-59 (1968) and adopted at 37 C.F.R. §§ 1.821-1.822, abbreviations for amino acid residues are shown in the following Table:

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glutamic Acid and/or Glutamine |
| W | Trp | Tryptophan |
| R | Arg | Arginine |
| D | Asp | Aspartic acid |
| N | Asn | Asparagine |
| B | Asx | Aspartic Acid and/or Asparagine |
| C | Cys | Cysteine |
| X | Xaa | Unknown or other |

All sequences of amino acid residues represented herein by a formula have a left to right orientation in the conventional direction of amino-terminus to carboxyl-terminus. The phrase "amino acid residue" is defined to include the amino acids listed in the above Table of Correspondence, modified, non-natural and unusual amino acids. A dash at the beginning or end of an amino acid residue sequence indicates a peptide bond to a further sequence of one or more amino acid residues or to an amino-terminal group such as $NH_2$ or to a carboxyl-terminal group such as COOH.

In a peptide or protein, suitable conservative substitutions of amino acids are known to those of skill in the art and generally can be made without altering a biological activity of a resulting molecule. Those of skill in the art recognize that, in general, single amino acid substitutions in non-essential regions of a polypeptide do not substantially alter biological activity (see, e.g., Watson et al., *Molecular Biology of the Gene,* 4th Edition, 1987, The Benjamin/Cummings Pub. Co., p. 224).

Such substitutions can be made in accordance with the exemplary substitutions set forth in the following Table:

Exemplary Conservative Amino Acid Substitutions

| Original Residue | Exemplary Conservative Sub stitution(s) |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative or non-conservative substitutions.

As used herein, "naturally occurring amino acids" refer to the 20 L-amino acids that occur in polypeptides.

As used herein, the term "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally occurring amino acids and include, but are not limited to, the D-stereoisomers of amino acids. Exemplary non-natural amino acids are known to those of skill in the art, and include, but are not limited to, 2-Aminoadipic acid (Aad), 3-Aminoadipic acid (bAad), β-alanine/β-Amino-propionic acid (Bala), 2-Aminobutyric acid (Abu), 4-Aminobutyric acid/piperidinic acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethyl asparagine (EtAsn), Hydroxylysine (Hyl), allo-Hydroxylysine (Ahyl), 3-Hydroxyproline (3Hyp), 4-Hydroxyproline (4Hyp), Isodesmosine (Ide), allo-Isoleucine (Aile), N-Methylglycine, sarcosine (MeGly), N-Methylisoleucine (MeIle), 6-N-Methyllysine (MeLys), N-Methylvaline (MeVal), Norvaline (Nva), Norleucine (Nle), and Ornithine (Orn).

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, production by recombinant methods refers means the use of the well-known methods of molecular biology for expressing proteins encoded by cloned DNA.

As used herein, "heterologous nucleic acid" is nucleic acid that encodes products (i.e., RNA and/or proteins) that are not normally produced in vivo by the cell in which it is expressed, or nucleic acid that is in a locus in which it does not normally occur, or that mediates or encodes mediators that alter expression of endogenous nucleic acid, such as DNA, by affecting transcription, translation, or other regulatable biochemical processes. Heterologous nucleic acid, such as DNA, also is referred to as foreign nucleic acid. Any nucleic acid, such as DNA, that one of skill in the art would recognize or consider as heterologous or foreign to the cell in which it is expressed, is herein encompassed by heterologous nucleic acid; heterologous nucleic acid includes exogenously added nucleic acid that is also expressed endogenously. Heterologous nucleic acid is generally not endogenous to the cell into which it is introduced, but has been obtained from another cell or prepared synthetically or is introduced into a genomic locus in which it does not occur naturally, or its expression is under the control of regulatory sequences or a sequence that differs from the natural regulatory sequence or sequences.

Examples of heterologous nucleic acid herein include, but are not limited to, nucleic acid that encodes RNAi, or an immunostimulatory protein, such as a cytokine, that confers or contributes to anti-tumor immunity in the tumor microenvironment, or that encodes an antibody, antibody fragment or other therapeutic product or therapeutic protein. In the immunostimulatory bacteria, the heterologous nucleic acid generally is encoded on the introduced plasmid, but it can be introduced into the genome of the bacterium, such as a promoter that alters expression of a bacterial product. Heterologous nucleic acid, such as DNA, includes nucleic acid that can, in some manner, mediate expression of DNA that encodes a therapeutic product, or it can encode a product, such as a peptide or RNA, that in some manner mediates, directly or indirectly, expression of a therapeutic product.

As used herein, cell therapy involves the delivery of cells to a subject to treat a disease or condition. The cells, which can be allogeneic or autologous, are modified ex vivo, such as by infection of cells with immunostimulatory bacteria provided herein, so that they deliver or express products when introduced to a subject.

As used herein, genetic therapy involves the transfer of heterologous nucleic acid, such as DNA, into certain cells, such as target cells, of a mammal, particularly a human, with a disorder or condition for which such therapy is sought. The nucleic acid, such as DNA, is introduced into the selected target cells in a manner such that the heterologous nucleic acid, such as DNA, is expressed and a therapeutic product(s) encoded thereby is produced. Genetic therapy can also be used to deliver nucleic acid encoding a gene product that replaces a defective gene or supplements a gene product produced by the mammal or the cell in which it is introduced. The introduced nucleic acid can encode a therapeutic compound, such as a growth factor or inhibitor thereof, or a tumor necrosis factor or inhibitor thereof, such as a receptor thereof, that is not normally produced in the mammalian host or that is not produced in therapeutically effective amounts or at a therapeutically useful time. The heterologous nucleic acid, such as DNA, encoding the therapeutic product, can be modified prior to introduction into the cells of the afflicted host in order to enhance or otherwise alter the product or expression thereof. Genetic therapy can also involve delivery of an inhibitor or repressor or other modulator of gene expression.

As used herein, "expression" refers to the process by which polypeptides are produced by transcription and translation of polynucleotides. The level of expression of a polypeptide can be assessed using any method known in art, including, for example, methods of determining the amount of the polypeptide produced from the host cell. Such methods can include, but are not limited to, quantitation of the polypeptide in the cell lysate by ELISA, Coomassie blue staining following gel electrophoresis, Lowry protein assay and Bradford protein assay.

As used herein, a "host cell" is a cell that is used to receive, maintain, reproduce and/or amplify a vector. A host cell also can be used to express the polypeptide encoded by the vector. The nucleic acid contained in the vector is replicated when the host cell divides, thereby amplifying the nucleic acids.

As used herein, a "vector" is a replicable nucleic acid from which one or more heterologous proteins can be expressed when the vector is transformed into an appropriate host cell. Reference to a vector includes those vectors into which a nucleic acid encoding a polypeptide or fragment thereof can be introduced, typically by restriction digest and ligation. Reference to a vector also includes those vectors that contain nucleic acid encoding a polypeptide, such as a modified anti-EGFR antibody. The vector is used to introduce the nucleic acid encoding the polypeptide into the host cell for amplification of the nucleic acid or for expression/display of the polypeptide encoded by the nucleic acid. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well-known to those of skill in the art. A vector also includes "virus vectors" or "viral vectors." Viral vectors are engineered viruses that are operatively linked to exogenous genes to transfer (as vehicles or shuttles) the exogenous genes into cells.

As used herein, an "expression vector" includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well-known to those of skill in the art and include those that are replicable in eukaryotic cells and/or prokaryotic cells and those that remain episomal or those which integrate into the host cell genome.

As used herein, "primary sequence" refers to the sequence of amino acid residues in a polypeptide or the sequence of nucleotides in a nucleic acid molecule.

As used herein, "sequence identity" refers to the number of identical or similar amino acids or nucleotide bases in a comparison between a test and a reference polypeptide or polynucleotide. Sequence identity can be determined by sequence alignment of nucleic acid or protein sequences to identify regions of similarity or identity. For purposes herein, sequence identity is generally determined by alignment to identify identical residues. The alignment can be local or global. Matches, mismatches and gaps can be identified between compared sequences. Gaps are null amino acids or nucleotides inserted between the residues of aligned sequences so that identical or similar characters are aligned. Generally, there can be internal and terminal gaps. When using gap penalties, sequence identity can be determined with no penalty for end gaps (e.g., terminal gaps are not penalized). Alternatively, sequence identity can be determined without taking into account gaps as the number of identical positions/length of the total aligned sequence×100.

As used herein, a "global alignment" is an alignment that aligns two sequences from beginning to end, aligning each letter in each sequence only once. An alignment is produced, regardless of whether or not there is similarity or identity between the sequences. For example, 50% sequence identity based on "global alignment" means that in an alignment of the full sequence of two compared sequences each of 100 nucleotides in length, 50% of the residues are the same. It is understood that global alignment also can be used in determining sequence identity even when the length of the aligned sequences is not the same. The differences in the terminal ends of the sequences will be taken into account in determining sequence identity, unless the "no penalty for end gaps" is selected. Generally, a global alignment is used on sequences that share significant similarity over most of their length. Exemplary algorithms for performing global alignment include the Needleman-Wunsch algorithm (Needleman et al. (1970) *J. Mol. Biol.* 48: 443). Exemplary programs for performing global alignment are publicly available and include the Global Sequence Alignment Tool available at the National Center for Biotechnology Information (NCBI) website (ncbi.nlm.nih.gov/), and the program available at deepc2.psi.iastate.edu/aat/align/align.html.

As used herein, a "local alignment" is an alignment that aligns two sequences, but only aligns those portions of the sequences that share similarity or identity. Hence, a local alignment determines if sub-segments of one sequence are present in another sequence. If there is no similarity, no alignment will be returned. Local alignment algorithms include BLAST or Smith-Waterman algorithm (*Adv. Appl. Math.* 2:482 (1981)). For example, 50% sequence identity based on "local alignment" means that in an alignment of the full sequence of two compared sequences of any length, a region of similarity or identity of 100 nucleotides in length has 50% of the residues that are the same in the region of similarity or identity.

For purposes herein, sequence identity can be determined by standard alignment algorithm programs used with default gap penalties established by each supplier. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps. Whether any two nucleic acid molecules have nucleotide sequences or any two polypeptides have amino acid sequences that are at least 80%, 85%, 90%, 95%, 96%, 97%, 98% or 99% "identical," or other similar variations reciting a percent identity, can be determined using known computer algorithms based on local or global alignment (see e.g., wikipedia.org/wiki/Sequence_alignment_software, providing links to dozens of known and publicly available alignment databases and programs). Generally, for purposes herein sequence identity is determined using computer algorithms based on global alignment, such as the Needleman-Wunsch Global Sequence Alignment tool available from NCBI/BLAST (blast.ncbi.nlm.nih.gov/Blast.cgi?CMD=Web&Page TYPE=BlastHome); LAlign (William Pearson implementing the Huang and Miller algorithm (*Adv. Appl. Math.* (1991) 12:337-357)); and program from Xiaoqui Huang available at deepc2.psi.iastate.edu/aat/align/align.html. Typically, the full-length sequence of each of the compared polypeptides or nucleotides is aligned across the full-length of each sequence in a global alignment. Local alignment also can be used when the sequences being compared are substantially the same length.

Therefore, as used herein, the term "identity" represents a comparison or alignment between a test and a reference polypeptide or polynucleotide. In one non-limiting example, "at least 90% identical to" refers to percent identities from 90 to 100% relative to the reference polypeptide or polynucleotide. Identity at a level of 90% or more is indicative of the fact that, assuming for exemplification purposes a test and reference polypeptide or polynucleotide length of 100 amino acids or nucleotides are compared, no more than 10% (i.e., 10 out of 100) of amino acids or nucleotides in the test polypeptide or polynucleotide differ from those of the reference polypeptide or polynucleotide. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid differences (approximately 90% identity). Differences also can be due to deletions or truncations of amino acid residues. Differences are defined as nucleic acid or amino acid substitutions, insertions or deletions. Depending on the length of the compared sequences, at the level of homologies or identities above about 85-90%, the result can be independent of the program and gap parameters set; such high levels of identity can be assessed readily, often without relying on software.

As used herein, "disease or disorder" refers to a pathological condition in an organism resulting from a cause or condition including, but not limited to, infections, acquired conditions, and genetic conditions, and that is characterized by identifiable symptoms.

As used herein, "treating" a subject with a disease or condition means that the subject's symptoms are partially or totally alleviated, or remain static following treatment.

As used herein, treatment refers to any effects that ameliorate symptoms of a disease or disorder. Treatment encompasses prophylaxis, therapy and/or cure. Treatment also encompasses any pharmaceutical use of any immunostimulatory bacterium or composition provided herein.

As used herein, prophylaxis refers to prevention of a potential disease and/or a prevention of worsening of symptoms or progression of a disease.

As used herein, "prevention" or prophylaxis, and grammatically equivalent forms thereof, refers to methods in which the risk or probability of developing a disease or condition is reduced.

As used herein, a "pharmaceutically effective agent" includes any therapeutic agent or bioactive agent, including, but not limited to, for example, anesthetics, vasoconstrictors, dispersing agents, and conventional therapeutic drugs, including small molecule drugs and therapeutic proteins.

As used herein, a "therapeutic effect" means an effect resulting from treatment of a subject that alters, typically improves or ameliorates, the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect following administration to a subject. Hence, it is the quantity necessary for preventing, curing, ameliorating, arresting or partially arresting a symptom of a disease or disorder.

As used herein, "therapeutic efficacy" refers to the ability of an agent, compound, material, or composition containing a compound to produce a therapeutic effect in a subject to whom the agent, compound, material, or composition containing a compound has been administered.

As used herein, a "prophylactically effective amount" or a "prophylactically effective dose" refers to the quantity of an agent, compound, material, or composition containing a compound that when administered to a subject, will have the intended prophylactic effect, e.g., preventing or delaying the onset, or reoccurrence, of disease or symptoms, reducing the likelihood of the onset, or reoccurrence, of disease or symptoms, or reducing the incidence of viral infection. The full prophylactic effect does not necessarily occur by administration of one dose, and can occur only after administration of a series of doses. Thus, a prophylactically effective amount can be administered in one or more administrations.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, an "anti-cancer agent" refers to any agent that is destructive or toxic to malignant cells and tissues. For example, anti-cancer agents include agents that kill cancer cells or otherwise inhibit or impair the growth of tumors or cancer cells. Exemplary anti-cancer agents are chemotherapeutic agents.

As used herein "therapeutic activity" refers to the in vivo activity of a therapeutic polypeptide. Generally, the therapeutic activity is the activity that is associated with treatment of a disease or condition.

As used herein, the term "subject" refers to an animal, including a mammal, such as a human being.

As used herein, a patient refers to a human subject.

As used herein, animal includes any animal, such as, but not limited to, primates including humans, gorillas and monkeys; rodents, such as mice and rats; fowl, such as chickens; ruminants, such as goats, cows, deer, and sheep; and pigs and other animals. Non-human animals exclude humans as the contemplated animal. The polypeptides provided herein are from any source, animal, plant, prokaryotic and fungal. Most polypeptides are of animal origin, including mammalian origin.

As used herein, a "composition" refers to any mixture. It can be a solution, suspension, liquid, powder, paste, aqueous, non-aqueous or any combination thereof.

As used herein, a "combination" refers to any association between or among two or more items. The combination can be two or more separate items, such as two compositions or two collections, a mixture thereof, such as a single mixture of the two or more items, or any variation thereof. The elements of a combination are generally functionally associated or related.

As used herein, combination therapy refers to administration of two or more different therapeutics. The different therapeutics or therapeutic agents can be provided and administered separately, sequentially, intermittently, or can be provided in a single composition.

As used herein, a kit is a packaged combination that optionally includes other elements, such as additional reagents and instructions for use of the combination or elements thereof, for a purpose including, but not limited to, activation, administration, diagnosis, and assessment of a biological activity or property.

As used herein, a "unit dose form" refers to physically discrete units suitable for human and animal subjects and packaged individually as is known in the art.

As used herein, a "single dosage formulation" refers to a formulation for direct administration.

As used herein, a multi-dose formulation refers to a formulation that contains multiple doses of a therapeutic agent and that can be directly administered to provide several single doses of the therapeutic agent. The doses can be administered over the course of minutes, hours, weeks, days or months. Multi-dose formulations can allow dose adjustment, dose-pooling and/or dose-splitting. Because multi-dose formulations are used over time, they generally contain one or more preservatives to prevent microbial growth.

As used herein, an "article of manufacture" is a product that is made and sold. As used throughout this application, the term is intended to encompass any of the compositions provided herein contained in articles of packaging.

As used herein, a "fluid" refers to any composition that can flow. Fluids, thus, encompass compositions that are in the form of semi-solids, pastes, solutions, aqueous mixtures, gels, lotions, creams and other such compositions.

As used herein, an isolated or purified polypeptide or protein (e.g., an isolated antibody or antigen-binding fragment thereof) or biologically-active portion thereof (e.g., an isolated antigen-binding fragment) is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification does not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound. As used herein, a "cellular extract" or "lysate" refers to a preparation or fraction which is made from a lysed or disrupted cell.

As used herein, a "control" refers to a sample that is substantially identical to the test sample, except that it is not treated with a test parameter, or, if it is a plasma sample, it can be from a normal volunteer not affected with the condition of interest. A control also can be an internal control.

As used herein, the singular forms "a," "an" and "the" include plural referents unless the context clearly dictates otherwise. Thus, for example, reference to a polypeptide, comprising "an immunoglobulin domain" includes polypeptides with one or a plurality of immunoglobulin domains.

As used herein, the term "or" is used to mean "and/or" unless explicitly indicated to refer to alternatives only or the alternatives are mutually exclusive.

As used herein, ranges and amounts can be expressed as "about" a particular value or range. About also includes the exact amount. Hence, "about 5 amino acids" means "about 5 amino acids" and also "5 amino acids."

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* (1972) 11(9): 1726-1732).

For clarity of disclosure, and not by way of limitation, the detailed description is divided into the subsections that follow.

B. Overview of the Immunostimulatory Bacteria

Provided are modified bacteria, called immunostimulatory bacteria herein that accumulate and/or replicate in (i.e., colonize) tumors, tumor-resident immune cells and/or the tumor microenvironment (TME); and/or induce less cell death in tumor-resident immune cells; and/or encode therapeutic products, such as anti-tumor agents, immunostimulatory proteins, and inhibitory RNAs (RNAi), such as shRNAs and microRNAs (miRNAs), that target genes whose inhibition, suppression or silencing effects tumor therapy. Strains of bacteria for modification are any suitable for therapeutic use. The modified immunostimulatory bacteria provided herein are for uses and for methods for treating cancer. The bacteria are modified for such uses and methods.

The immunostimulatory bacteria provided herein are modified by deletion or modification of bacterial genes to attenuate their inflammatory responses, increase their tolerability, increase their resistance to complement, increase their infectivity of, accumulation in or colonization of tumors, tumor-resident immune cells and/or the TME, decrease their induction of immune cell death (e.g., decrease pyroptosis), and to enhance the anti-tumor immune responses in hosts treated with the bacteria. The modifications also can be in genes encoded on a plasmid in the bacteria. For example, the bacteria can be auxotrophic for adenosine, or adenosine and adenine, and plasmids encoding therapeutic products, such as immunostimulatory proteins, antibodies, or RNAi that inhibit immune checkpoint genes in the host are included in the bacteria. Attenuation of the inflammatory responses to the bacteria can be effected by deletion of the msbB gene, which decreases TNF-alpha in the host, and/or knocking out flagellin genes and/or deletion/mutation of pagP. The bacteria are modified to stimulate host anti-tumor activity, for example, by adding plasmids encoding immunostimulatory proteins such as cytokines, chemokines and co-stimulatory molecules, or RNAi that target host immune checkpoints, and by adding nucleic acid with CpGs/CpG motifs.

Bacterial strains can be attenuated strains, or strains that are attenuated by standard methods, or that, by virtue of the modifications provided herein, are attenuated in that their ability to colonize is limited primarily to immunoprivileged tissues and organs, particularly immune and tumor cells, including solid tumors. Bacteria include, but are not limited to, for example, strains of *Salmonella, Shigella, Listeria, E. coli*, and Bifidobacteriae. For example, species include *Shigella sonnei, Shigella flexneri, Shigella dysenteriae, Listeria monocytogenes, Salmonella typhi, Salmonella typhimurium, Salmonella gallinarum*, and *Salmonella enteritidis*. Other suitable bacterial species include *Rickettsia, Klebsiella, Bordetella, Neisseria, Aeromonas, Francisella, Corynebacterium, Citrobacter, Chlamydia, Haemophilus, Brucella, Mycobacterium, Mycoplasma, Legionella, Rhodococcus, Pseudomonas, Helicobacter, Vibrio, Bacillus*, and *Erysipelothrix*. For example, *Rickettsia rickettsii, Rickettsia prowazekii, Rickettsia tsutsugamushi, Rickettsia mooseri, Rickettsia sibirica, Bordetella bronchiseptica, Neisseria meningitidis, Neisseria gonorrhoeae, Aeromonas eucrenophila, Aeromonas salmonicida, Francisella tularensis, Corynebacterium pseudotuberculosis, Citrobacter freundii, Chlamydia pneumoniae, Haemophilus somnus, Brucella abortus, Mycobacterium intracellulare, Legionella pneumophila, Rhodococcus equi, Pseudomonas aeruginosa, Helicobacter mustelae, Vibrio cholerae, Bacillus subtilis, Erysipelothrix rhusiopathiae, Yersinia enterocolitica, Rochalimaea quintana*, and *Agrobacterium tumefaciens*.

The bacteria accumulate by virtue of one or more properties, including, diffusion, migration and chemotaxis to immunoprivileged tissues or organs or environments, environments that provide nutrients or other molecules for which they are auxotrophic, and/or environments that contain replicating cells that provide environments suitable for entry and replication of the bacteria. The immunostimulatory bacteria provided herein and species that effect such therapy include species of *Salmonella, Listeria*, and *E. coli*.

The bacteria contain plasmids that encode a therapeutic protein, such as an immunostimulatory protein or an immune checkpoint inhibitor or other immune stimulating or immune-suppression blocking product. Products include antibodies, such as antibody fragments, and nanobodies, RNAi, such as one or more short hairpin (sh) RNA construct(s), microRNAs, or other RNAi modalities, whose expression inhibits or disrupts or suppresses the expression of targeted genes, or otherwise increases immune responses or decreases immune suppression. The therapeutic products are expressed under control of a eukaryotic promoter, such as an RNA polymerase (RNAP) II or III promoter. Typically, RNAPIII (also referred to as POLIII) promoters are constitutive, and RNAPII (also referred to as POLII) can be regulated. In some examples, the shRNAs target the gene TREX1, to inhibit its expression.

In some embodiments, the plasmids can encode a plurality of therapeutic products, including immunostimulatory proteins, such as cytokines, and RNAi molecules, such as shRNAs, and antibodies, including nanobodies, that inhibit two or more immune checkpoint genes, such as TREX1, PD-L1, VISTA, SIRPα, CTNNB1, TGF-beta, CD47, and/or VEGF and any others known to those of skill in the art. Where a plurality of therapeutic products are encoded, expression of each generally is under control of a different promoter.

Among the bacteria provided herein, are bacteria that are modified so that they are auxotrophic for adenosine. This can be achieved by modification or deletion of genes involved in purine synthesis, metabolism, or transport. For example, disruption of the tsx gene in *Salmonella* species, such as *Salmonella typhi*, results in adenosine auxotrophy. Adenosine is immunosuppressive and accumulates to high concentrations in tumors; auxotrophy for adenosine improves the anti-tumor activity of the bacteria because the bacteria selectively replicate in tissues rich in adenosine.

Also provided are bacteria that are modified so that they have a defective asd gene. These bacteria for use in vivo are modified to include carrying a functional asd gene on the introduced plasmid; this maintains selection for the plasmid so that an antibiotic-based plasmid maintenance/selection system is not needed. Also provided is the use of asd defective strains that do not contain a functional asd gene on a plasmid, and are thus engineered to be autolytic in the host.

Also provided are bacteria that are modified so that they are incapable of producing flagella. This can be achieved by modifying the bacteria by deleting the genes that encode the flagellin subunits. The modified bacteria lacking flagellin are less inflammatory and therefore better tolerated, and induce a more potent anti-tumor response.

Also provided are bacteria that are modified to produce listeriolysin O (LLO), which improves plasmid delivery in phagocytic cells.

Also provided are bacteria modified to carry a low copy, CpG-containing plasmid. The plasmid further can include other modifications, and can encode therapeutic products, such as immunostimulatory proteins, antibodies and fragments thereof, and RNAi.

The bacteria also can be modified to grow in a manner such that the bacteria, if a *Salmonella* species, expresses less of the toxic SPI-1 (*Salmonella* pathogenicity island-1) genes. In *Salmonella*, genes responsible for virulence, invasion, survival, and extra intestinal spread are located in *Salmonella* pathogenicity islands (SPIs).

The bacteria include plasmids that encode RNAi, such as shRNA or microRNA, that inhibits checkpoints, such as PD-L1 or TREX1 only, or TREX1 and one or more of a second immune checkpoint. The bacteria can be further modified for other desirable traits, including for selection of plasmid maintenance, particularly for selection without antibiotics, for preparation of the strains. The immunostimulatory bacteria optionally can encode therapeutic polypeptides, including anti-tumor therapeutic polypeptides and agents.

Exemplary of the immunostimulatory bacteria provided herein are species of *Salmonella*. Exemplary of bacteria for modification as described herein are engineered strains of *Salmonella typhimurium*, such as strain YS1646 (ATCC Catalog #202165; also referred to as VNP20009, see, International PCT Application Publication No. WO 99/13053), that are engineered with plasmids to complement an asd gene knockout and antibiotic-free plasmid maintenance.

Modified immunostimulatory bacterial strains that are rendered auxotrophic for adenosine are provided herein, as are pharmaceutical compositions containing such strains, formulated for administration to a subject, such as a human, for use in methods of treating tumors and cancers.

Also provided are methods or uses of the immunostimulatory bacteria or pharmaceutical compositions containing the bacteria, wherein the treatment comprises combination therapy, in which a second anti-cancer agent or treatment is administered. The second anti-cancer agent or treatment can be administered before, concomitantly with, after, or intermittently with, the immunostimulatory bacteria or pharmaceutical composition, and includes immunotherapy, such as an antibody or antibody fragment; oncolytic virus therapy; radiation/radiotherapy; and chemotherapy. The immunotherapy can comprise, for example, administration of an anti-PD-1, or anti-PD-L1 or anti-CTLA4, or anti-IL6, or anti-VEGF, or anti-VEGFR, or anti-VEGFR2 antibody, or a fragment thereof. Combination therapy also can include surgery.

The engineered immunostimulatory bacteria provided herein contain multiple synergistic modalities to induce immune re-activation of cold tumors and to promote tumor antigen-specific immune responses, while inhibiting immune checkpoint pathways that the tumor utilizes to subvert and evade durable anti-tumor immunity. Improved tumor targeting through adenosine auxotrophy and enhanced vascular disruption have improved potency, while localizing the inflammation to limit systemic cytokine exposure and the autoimmune toxicities observed with other immunotherapy modalities. Exemplary of the bacteria so-modified are *S. typhimurium* strains, including such modifications of the strain YS1646, particularly $asd^-$ strains.

For example, as provided herein, are immunostimulatory bacteria that provide for shRNA-mediated gene disruption of PD-L1. It has been shown in mice that gene disruption of PD-L1 can improve tumor colonization. It has been shown, for example, that *S. typhimurium* infection in PD-L1 knockout mice, results in a 10-fold higher bacterial load than in wild-type mice (see, Lee et al. (2010) *J. Immunol.* 185:2442-2449). Hence, PD-L1 is protective against *S. typhimurium* infection. Provided herein are immunostimulatory bacteria, such as *S. typhimurium*, carrying plasmids capable of RNAi-mediated gene knockdown of TREX1, PD-L1, or of PD-L1 and TREX1. Such bacteria provide anti-tumor effects due to the combination of two independent pathways that lead to enhanced and sustained anti-tumor immune responses in a single therapy.

C. Cancer Immunotherapeutics

The immunosuppressive milieu found within the tumor microenvironment (TME) is a driver of tumor initiation and progression. Cancers emerge after the immune system fails to control and contain tumors. Multiple tumor-specific mechanisms create tumor environments wherein the immune system is forced to tolerate tumors and their cells instead of eliminating them. The goal of cancer immunotherapy is to rescue the immune system's natural ability to eliminate tumors. Acute inflammation associated with microbial infection has been observationally linked with the spontaneous elimination of tumors for centuries.

1. Immunotherapies

Several clinical cancer immunotherapies have sought to perturb the balance of immune suppression towards anti-tumor immunity. Strategies to stimulate immunity through directly administering cytokines such as IL-2 and IFN-α have seen modest clinical responses in a minority of patients, while inducing serious systemic inflammation-related toxicities (Sharma et al. (2011) *Nat. Rev. Cancer*

11:805-812). The immune system has evolved several checks and balances to limit autoimmunity, such as upregulation of programmed cell death protein 1 (PD-1) on T cells and its binding to its cognate ligand, programmed death-ligand 1 (PD-L1), which is expressed on both antigen presenting cells (APCs) and tumor cells. The binding of PD-L1 to PD-1 interferes with $CD8^+$ T cell signaling pathways, impairing the proliferation and effector function of $CD8^+$ T cells, and inducing T cell tolerance. PD-1 and PD-L1 are two examples of numerous inhibitory "immune checkpoints," which function by downregulating immune responses. Other inhibitory immune checkpoints include cytotoxic T-lymphocyte-associated protein 4 (CTLA-4), signal regulatory protein α (SIRPα), V-domain Ig suppressor of T cell activation (VISTA), programmed death-ligand 2 (PD-L2), indoleamine 2,3-dioxygenase (IDO) 1 and 2, lymphocyte-activation gene 3 (LAG3), Galectin-9, T cell immunoreceptor with Ig and ITIM domains (TIGIT), T cell immunoglobulin and mucin-domain containing-3 (TIM-3, also known as hepatitis A virus cellular receptor 2 (HAVCR2)), herpesvirus entry mediator (HVEM), CD39, CD73, B7-H3 (also known as CD276), B7-H4, CD47, CD48, CD80 (B7-1), CD86 (B7-2), CD155, CD160, CD244 (2B4), B- and T-lymphocyte attenuator (BTLA, or CD272) and carcinoembryonic antigen-related cell adhesion molecule 1 (CEACAM1, or CD66a).

Antibodies designed to block immune checkpoints, such as anti-PD-1 (for example, pembrolizumab, nivolumab) and anti-PD-L1 (for example, atezolizumab, avelumab, durvalumab), have had durable success in preventing T cell anergy and breaking immune tolerance. Only a fraction of treated patients demonstrate clinical benefit, and those that do often present with autoimmune-related toxicities (see, e.g., Ribas (2015) *N. Engl. J. Med.* 373:1490-1492; Topalian et al. (2012) *N. Engl. J. Med.* 366:2443-2454). This is further evidence for the need for therapies, provided herein, that are more effective and less toxic.

Another checkpoint blockade strategy inhibits the induction of CTLA-4 on T cells, which binds to and inhibits co-stimulatory receptors on APCs, such as CD80 or CD86, out-competing the co-stimulatory cluster differentiation 28 (CD28), which binds the same receptors, but with a lower affinity. This blocks the stimulatory signal from CD28, while the inhibitory signal from CTLA-4 is transmitted, preventing T cell activation (see, Phan et al. (2003) *Proc. Natl. Acad. Sci. U.S.A.* 100:8372-8377). Anti-CTLA-4 therapy (for example, ipilimumab) have clinical success and durability in some patients, whilst exhibiting an even greater incidence of severe immune-related adverse events (see, e.g., Hodi et al. (2010) *N. Engl. J. Med.* 363:711-723; Schadendorf et al. (2015) *J. Clin. Oncol.* 33:1889-1894). It also has been shown that tumors develop resistance to anti-immune checkpoint antibodies, highlighting the need for more durable anticancer therapies, and provided herein.

2. Adoptive Immunotherapies

In seeking to reactivate a cold tumor to become more immunogenic, a class of immunotherapies known as adoptive cell therapy (ACT) encompasses a variety of strategies to harness immune cells and reprogram them to have anti-tumor activity (Zielinski et al. (2011) *Immunol. Rev.* 240:40-51). Dendritic cell-based therapies introduce genetically engineered dendritic cells (DCs) with more immune-stimulatory properties. These therapies have not been successful because they fail to break immune tolerance to cancer (see, e.g., Rosenberg et al. (2004) *Nat. Med.* 10(12):1279). A method using whole irradiated tumor cells containing endogenous tumor antigens and granulocyte macrophage colony-stimulating factor (GM-CSF) to stimulate DC recruitment, known as GVAX, similarly failed in the clinic due to the lack of ability to break tumor tolerance (Copier et al. (2010) *Curr. Opin. Mol. Ther.* 12:14-20). A separate autologous cell-based therapy, Sipuleucel-T (Provenge), was FDA approved in 2010 for castration-resistant prostate cancer. It utilizes APCs retrieved from the patient and re-armed to express prostatic acid phosphatase (PAP) antigen to stimulate a T cell response, then re-introduced following lymphablation. Unfortunately, its broader adoption has been limited by low observed objective response rates and high costs, and its use is limited to only the early stages of prostate cancer (Anassi et al. (2011) *P T.* 36(4):197-202). Similarly, autologous T cell therapies (ATCs) harvest a patient's own T cells and reactivate them ex vivo to overcome tumor tolerance, then reintroduce them to the patient following lymphablation. ATCs have had limited clinical success, and only in melanoma, while generating serious safety and feasibility issues that limit their utility (Yee 94 (2013) *Clin. Cancer Res.* 19:4550-4552).

Chimeric antigen receptor T cell (CAR-T) therapies are T cells harvested from patients that have been re-engineered to express a fusion protein between the T cell receptor and an antibody Ig variable extracellular domain. This confers upon them the antigen-recognition properties of antibodies with the cytolytic properties of activated T cells (Sadelain (2015) *J. Clin. Invest.* 125:3392-3400). Success has been limited to B cell and hematopoietic malignancies, at the cost of deadly immune-related adverse events (Jackson et al. (2016) *Nat. Rev. Clin. Oncol.* 13:370-383). Tumors can also mutate to escape recognition by a target antigen, including CD19 (Ruella et al., (2016) *Comput. Struct. Biotechnol. J.* 14:357-362) and EGFRvIII (O'Rourke et al. (2017) *Sci. Transl. Med.* (399):eaaa0984), thereby fostering immune escape. In addition, while CAR-T therapies are approved and are approved in the context of hematological malignancies, they face a significant hurdle for feasibility to treat solid tumors: overcoming the highly immunosuppressive nature of the solid tumor microenvironment. A number of additional modifications to existing CAR-T therapies will be required to potentially provide feasibility against solid tumors (Kakarla et al. (2014) *Cancer J.* 20(2):151-155). When the safety of CAR-Ts is significantly improved and their efficacy expanded to solid tumors, the feasibility and costs associated with these labor-intensive therapies will continue to limit their broader adoption.

3. Cancer Vaccines and Oncolytic Viruses

Cold tumors lack T cell and dendritic cell (DC) infiltration, and are non-T-cell-inflamed (Sharma et al. (2017) *Cell* 9; 168(4):707-723). In seeking to reactivate a cold tumor to become more immunogenic, another class of immunotherapies harness microorganisms that can accumulate in tumors, either naturally or by virtue of engineering. These include viruses designed to stimulate the immune system to express tumor antigens, thereby activating and reprogramming the immune system to reject the tumor. Virally-based cancer vaccines have largely failed clinically for a number of factors, including pre-existing or acquired immunity to the viral vector itself, as well as a lack of sufficient immunogenicity to the expressed tumor antigens (Larocca et al. (2011) *Cancer J.* 17(5):359-371). Lack of proper adjuvant activation of APCs has also hampered other non-viral vector cancer vaccines, such as DNA vaccines. Oncolytic viruses, in contrast, seek to preferentially replicate in dividing tumor cells over healthy tissue, whereupon subsequent tumor cell lysis leads to immunogenic tumor cell death and further viral dissemination. The oncolytic virus Talimogene laherparepvec (T-VEC), which uses a modified herpes simplex virus in combination with the DC-recruiting cytokine GM-CSF, is FDA approved for metastatic melanoma (Bastin et al. (2016) *Biomedicines* 4(3):21). While demonstrating clinical benefit in some melanoma patients, and with fewer immune toxicities than with other immunotherapies, the intratumoral route of administration and manufacturing conditions have been limiting, as well as its lack of distal tumor efficacy and broader application to other tumor types. Other oncolytic virus (OV)-based vaccines, such as those utilizing paramyxovirus, reovirus and picornavirus, among others, have met with similar limitations in inducing systemic anti-tumor immunity (Chiocca et al. (2014) *Cancer Immunol. Res.* 2(4):295-300). Systemic administration of oncolytic viruses presents unique challenges. Upon I.V. administration, the virus is rapidly diluted, thus requiring high titers that can lead to hepatotoxicity. Further, if pre-existing immunity exists, the virus is rapidly neutralized in the blood, and acquired immunity then restricts repeat dosing (Maroun et al. (2017) *Future Virol.* 12(4):193-213).

Of the limitations of virally-based vaccine vectors and oncolytic viruses, the greatest limitations can be the virus itself. Viral antigens have strikingly higher affinities to human T cell receptors (TCRs) compared to tumor antigens (Aleksic et al. (2012) *Eur. J. Immunol.* 42(12):3174-3179). Tumor antigens, presented alongside of viral vector antigens by MHC-1 on the surface of even highly activated APCs, will be outcompeted for binding to TCRs, resulting in very poor antigen-specific anti-tumor immunity. A tumor-targeting immunostimulatory vector, as provided herein, that does not itself provide high affinity T cell epitopes can circumvent these limitations.

D. Bacterial Cancer Immunotherapy

1. Bacterial Therapies

The recognition that bacteria have anticancer activity goes back to the 1800s, when several physicians observed regression of tumors in patients infected with *Streptococcus pyogenes*. William Coley began the first study utilizing bacteria for the treatment of end stage cancers, and developed a vaccine composed of *S. pyogenes* and *Serratia marcescens*, which was successfully used to treat a variety of cancers, including sarcomas, carcinomas, lymphomas and melanomas. Since then, a number of bacteria, including species of *Clostridium, Mycobacterium, Bifidobacterium, Listeria*, such as, *L. monocytogenes*, and *Escherichia* species, have been studied as sources of anti-cancer vaccines (see, e.g., International PCT Application Publication No. WO 1999/013053; International PCT Application Publication No. WO 2001/025399; Bermudes et al. (2002) *Curr. Opin. Drug Discov. Devel.* 5:194-199; Patyar et al. (2010) *Journal of Biomedical Science* 17:21; Pawelek et al. (2003) *Lancet Oncol.* 4:548-556).

Bacteria can infect animal and human cells, and some possess the innate ability to deliver DNA into the cytosol of cells, and these are candidate vectors for gene therapy. Bacteria also are suitable for therapy because they can be administered orally, they propagate readily in vitro and in vivo, and they can be stored and transported in a lyophilized state. Bacterial genetics are readily manipulated, and the complete genomes for many strains have been fully characterized (Felgner et al. (2016) *mbio* 7(5):e01220-16). As a result, bacteria have been used to deliver and express a wide variety of genes, including those that encode cytokines, angiogenesis inhibitors, toxins and prodrug-converting enzymes. *Salmonella*, for example, has been used to express immune-stimulating molecules like IL-18 (Loeffler et al. (2008) *Cancer Gene Ther.* 15(12):787-794), LIGHT (Loeffler et al. (2007) *Proc. Natl. Acad. Sci. U.S.A.* 104(31): 12879-12883), and Fas ligand (Loeffler et al. (2008) *J. Natl. Cancer Inst.* 100:1113-1116) in tumors. Bacterial vectors also are cheaper and easier to produce than viral vectors, and bacterial delivery is favorable over viral delivery because it can be quickly eliminated by antibiotics if necessary, rendering it a safer alternative.

To be used, however, the strains themselves must not be pathogenic or are not pathogenic after modification for use as a therapeutic. For example, in the treatment of cancer, the therapeutic bacterial strains must be attenuated or rendered sufficiently non-toxic so as to not cause systemic disease and/or septic shock, but still maintain some level of infectivity to effectively colonize tumors. Genetically modified bacteria have been described that are to be used as antitumor agents to elicit direct tumoricidal effects and/or to deliver tumoricidal molecules (Clairmont et al. (2000) *J. Infect. Dis.* 181:1996-2002; Bermudes, D. et al. (2002) *Curr. Opin. Drug Discov. Devel.* 5:194-199; Zhao, M. et al. (2005) *Proc. Natl. Acad. Sci. U.S.A.* 102:755-760; Zhao, M. et al. (2006) *Cancer Res.* 66:7647-7652). Among these are bioengineered strains of *Salmonella enterica* serovar *Typhimurium* (*S. typhimurium*). These bacteria accumulate preferentially >1,000-fold greater in tumors than in normal tissues and disperse homogeneously in tumor tissues (Pawelek, J. et al. (1997) *Cancer Res.* 57:4537-4544; Low, K. B. et al. (1999) *Nat. Biotechnol.* 17:37-41). Preferential replication allows the bacteria to produce and deliver a variety of anticancer therapeutic agents at high concentrations directly within the tumor, while minimizing toxicity to normal tissues. These attenuated bacteria are safe in mice, pigs, and monkeys when administered intravenously (Zhao, M. et al. (2005) *Proc. Natl. Acad. Sci. U.S.A.* 102:755-760; Zhao, M. et al. (2006) *Cancer Res* 66:7647-7652; Tjuvajev J. et al. (2001) *J. Control Release* 74:313-315; Zheng, L. et al. (2000) *Oncol. Res.* 12:127-135), and certain live attenuated *Salmonella* strains have been shown to be well tolerated after oral administration in human clinical trials (Chatfield, S. N. et al. (1992) *Biotechnology* 10:888-892; DiPetrillo, M. D. et al. (1999) *Vaccine* 18:449-459; Hohmann, E. L. et al. (1996) *J. Infect. Dis.* 173:1408-1414; Sirard, J. C. et al. (1999) *Immunol. Rev.* 171:5-26). The *S. typhimurium* phoP/phoQ operon is a typical bacterial two-component regulatory system composed of a membrane-associated sensor kinase (PhoQ) and a cytoplasmic transcriptional regulator (PhoP: Miller, S. I. et al. (1989) *Proc. Natl. Acad. Sci. U.S.A.* 86:5054-5058; Groisman, E. A. et al. (1989) *Proc. Natl. Acad. Sci. U.S.A.* 86: 7077-7081). PhoP/phoQ is required for virulence, and its deletion results in poor survival of this bacterium in macrophages and a marked attenuation in mice and humans (Miller, S. I. et al. (1989) *Proc. Natl. Acad. Sci. U.S.A.* 86:5054-5058; Groisman, E. A. et al. (1989) *Proc. Natl. Acad. Sci.* U.S.A. 86: 7077-7081; Galan, J. E. and Curtiss, R. III. (1989) *Microb. Pathog.* 6:433-443; Fields, P. I. et al. (1986) *Proc. Natl. Acad. Sci. U.S.A* 83:5189-5193). PhoP/phoQ deletion strains have been employed as effective vaccine delivery vehicles (Galan, J. E. and Curtiss, R. III. (1989) *Microb. Pathog.* 6:433-443; Fields, P. I. et al. (1986) *Proc. Natl. Acad. Sci. U.S.A* 83:5189-5193; Angelakopoulos, H. and Hohmann, E. L. (2000) *Infect. Immun.* 68:2135-2141). Attenuated Salmonellae have been used for targeted delivery of tumoricidal proteins (Bermudes, D. et al. (2002) *Curr. Opin. Drug Discov. Devel.* 5:194-199; Tjuvajev J. et al. (2001) *J. Control. Release* 74:313-315).

Bacterially-based cancer therapies have demonstrated limited clinical benefit. A variety of bacterial species, including *Clostridium novyi* (Dang et al. (2001) *Proc. Natl. Acad. Sci. U.S.A.* 98(26):15155-15160; U.S. Patent Publication Nos. 2017/0020931, and 2015/0147315; U.S. Pat. Nos. 7,344,710, and 3,936,354), *Mycobacterium bovis* (U.S. Patent Publication Nos. 2015/0224151 and 2015/0071873), *Bifidobacterium bifidum* (Kimura et al. (1980) *Cancer Res.* 40:2061-2068), *Lactobacillus casei* (Yasutake et al. (1984) *Med Microbiol Immunol.* 173(3):113-125), *Listeria monocytogenes* (Le et al. (2012) *Clin. Cancer Res.* 18(3):858-868; Starks et al. (2004) *J. Immunol.* 173:420-427; U.S. Patent Publication No. 2006/0051380) and *Escherichia coli* (U.S. Pat. No. 9,320,787) have been studied as possible agents for anticancer therapy.

The *Bacillus* Calmette-Guerin (BCG) strain, for example, is approved for the treatment of bladder cancer in humans, and is more effective than intravesical chemotherapy, often being used as a first-line treatment (Gardlik et al. (2011) *Gene Therapy* 18:425-431). Another approach utilizes *Listeria monocytogenes*, a live attenuated intracellular bacterium capable of inducing potent $CD8^+$ T cell priming to expressed tumor antigens in mice (Le et al. (2012) *Clin. Cancer Res.* 18(3):858-868). In a clinical trial of the *Listeria*-based vaccine incorporating the tumor antigen mesothelin, together with an allogeneic pancreatic cancer-based GVAX vaccine in a prime-boost approach, a median survival of 6.1 months was noted in patients with advanced pancreatic cancer, versus a median survival of 3.9 months for patients treated with the GVAX vaccine alone (Le et al. (2015) *J. Clin. Oncol.* 33(12):1325-1333). These results were not replicated in a larger phase 2b study, possibly pointing to the difficulties in attempting to induce immunity to a low affinity self-antigen such as mesothelin.

Bacterial strains can be modified as described and exemplified herein to express inhibitory RNA (RNAi), such as shRNAs and microRNAs, that inhibit or disrupt TREX1 and/or PD-L1 and optionally one or more additional immune checkpoint genes. The strains can be attenuated by standard methods and/or by deletion or modification of genes, and by alteration or introduction of genes that render the bacteria able to grow in vivo primarily in immunoprivileged environments, such as the TME, in tumor cells and solid tumors. Strains for modification as described herein can be selected from among, for example, *Shigella, Listeria, E. coli*, Bifidobacteriae and *Salmonella*. For example, *Shigella sonnei, Shigella flexneri, Shigella dysenteriae, Listeria monocytogenes, Salmonella typhi, Salmonella typhimurium, Salmonella gallinarum*, and *Salmonella enteritidis*. Other suitable bacterial species include *Rickettsia, Klebsiella, Bordetella, Neisseria, Aeromonas, Francisella, Corynebacterium, Citrobacter, Chlamydia, Haemophilus, Brucella, Mycobacterium, Mycoplasma, Legionella, Rhodococcus, Pseudomonas, Helicobacter, Vibrio, Bacillus*, and *Erysipelothrix*. For example, *Rickettsia rickettsii, Rickettsia prowazekii, Rickettsia tsutsugamushi, Rickettsia mooseri, Rickettsia sibirica, Bordetella bronchiseptica, Neisseria meningitidis, Neisseria gonorrhoeae, Aeromonas eucrenophila, Aeromonas salmonicida, Francisella tularensis, Corynebacterium pseudotuberculosis, Citrobacter freundii, Chlamydia pneumoniae, Haemophilus somnus, Brucella abortus, Mycobacterium intracellulare, Legionella pneumophila, Rhodococcus equi, Pseudomonas aeruginosa, Helicobacter mustelae, Vibrio cholerae, Bacillus subtilis, Erysipelothrix rhusiopathiae, Yersinia enterocolitica, Rochalimaea quintana*, and *Agrobacterium tumefaciens*. Any known therapeutic, including immunostimulatory, bacteria can be modified as described herein.

2. Comparison of the Immune Responses to Bacteria and Viruses

Bacteria, like viruses, have the advantage of being naturally immunostimulatory. Bacteria and viruses are known to contain conserved structures known as Pathogen-Associated Molecular Patterns (PAMPs), which are sensed by host cell Pattern Recognition Receptors (PRRs). Recognition of PAMPs by PRRs triggers downstream signaling cascades that result in the induction of cytokines and chemokines, and initiation of immune responses that lead to pathogen clearance (Iwasaki and Medzhitov (2010) *Science* 327(5963): 291-295). The manner in which the innate immune system is engaged by PAMPs, and from what type of infectious agent, determines the appropriate adaptive immune response to combat the invading pathogen.

A class of PRRs known as Toll Like Receptors (TLRs) recognize PAMPs derived from bacterial and viral origins, and are located in various compartments within the cell. TLRs bind a range of ligands, including lipopolysaccharide (TLR4), lipoproteins (TLR2), flagellin (TLR5), unmethylated CpG motifs in DNA (TLR9), double-stranded RNA (TLR3), and single-stranded RNA (TLR7 and TLR8) (Akira et al. (2001) *Nat. Immunol.* 2(8):675-680; Kawai and Akira (2005) *Curr. Opin. Immunol.* 17(4):338-344). Host surveillance of *S. typhimurium* for example, is largely mediated through TLR2, TLR4 and TLR5 (Arpaia et al. (2011) *Cell* 144(5):675-688). These TLRs signal through MyD88 and TRIF adaptor molecules to mediate induction of NF-kB dependent pro-inflammatory cytokines such as TNF-α, IL-6 and IFN-γ (Pandey et al. (2015) *Cold Spring Harb. Perspect. Biol.* 7(1):a016246).

Another category of PRRs are the nod-like receptor (NLR) family. These receptors reside in the cytosol of host cells and recognize intracellular PAMPS. For example, *S. typhimurium* flagellin was shown to activate the NLRC4/NAIP5 inflammasome pathway, resulting in the cleavage of caspase-1 and induction of the pro-inflammatory cytokines IL-1β and IL-18, leading to pyroptotic cell death of infected macrophages (Fink et al. (2007) *Cell Microbiol.* 9(11):2562-2570).

While engagement of TLR2, TLR4, TLR5 and the inflammasome induces pro-inflammatory cytokines that mediate bacterial clearance, they activate a predominantly NF-κB-driven signaling cascade that leads to recruitment and activation of neutrophils, macrophages and $CD4^+$ T cells, but not the DCs and $CD8^+$ T cells that are required for anti-tumor immunity (Liu et al. (2017) *Signal Transduct. Target Ther.* 2:e17023). In order to activate $CD8^+$ T cell-mediated anti-tumor immunity, IRF3/IRF7-dependent type I interferon signaling is critical for DC activation and cross-presentation of tumor antigens to promote $CD8^+$ T cell priming (Diamond et al. (2011) *J. Exp. Med.* 208(10):1989-2003; Fuertes et al. (2011) *J Exp. Med.* 208(10):2005-2016). Type I interferons (IFN-α, IFN-β) are the signature cytokines induced by two distinct TLR-dependent and TLR-independent signaling pathways. The TLR-dependent pathway for inducing IFN-β occurs following endocytosis of pathogens, whereby TLR3, 7, 8 and 9 detect pathogen-derived DNA and RNA elements within the endosomes. TLRs 7 and 8 recognize viral nucleosides and nucleotides, and synthetic agonists of these, such as resiquimod and imiquimod have been clinically validated (Chi et al. (2017) *Frontiers in Pharmacology* 8:304). Synthetic dsRNA, such as polyinosinic:polycytidylic acid (poly (I:C)) and poly ICLC, an analog that is formulated with poly-L-lysine to resist RNase digestion, is an agonist for TLR3 and MDA5 pathways and a powerful inducer of IFN-β (Caskey et al. (2011) *J. Exp. Med.* 208(12):2357-66). TLR9 detection of endosomal CpG motifs present in viral and bacterial DNA can also induce IFN-β via IRF3. Additionally, TLR4 has been shown to induce IFN-β via MyD88-independent TRIF activation of IRF3 (Owen et al. (2016) *mBio.* (1):e02051-15). It subsequently was shown that TLR4 activation of DCs was independent of type I IFN, so the ability of TLR4 to activate DCs via type I IFN is not likely biologically relevant (Hu et al. (2015) *Proc. Natl. Acad. Sci. U.S.A.* 112(45): 13994-13999). Further, TLR4 signaling has not been shown to directly recruit or activate $CD8^+$ T cells.

Of the TLR-independent type I IFN pathways, one is mediated by host recognition of single-stranded (ss) and double-stranded (ds) RNA in the cytosol. These are sensed by RNA helicases, including retinoic acid-inducible gene I (RIG-I), melanoma differentiation-associated gene 5 (MDA-5), and through the IFN-β promoter stimulator 1 (IPS-1; also known as mitochondrial antiviral-signaling protein or MAVS) adaptor protein-mediated phosphorylation of the IRF-3 transcription factor, leading to induction of IFN-β (Ireton and Gale (2011) Viruses 3(6):906-919). Synthetic RIG-I-binding elements have also been discovered unintentionally in common lentiviral shRNA vectors, in the form of an AA dinucleotide sequence at the U6 promoter transcription start site. Its subsequent deletion in the plasmid prevented confounding off-target type I IFN activation (Pebernard et al. (2004) *Differentiation* 72:103-111).

The second type of TLR-independent type I interferon induction pathway is mediated through Stimulator of Interferon Genes (STING), a cytosolic ER-resident adaptor protein that is now recognized as the central mediator for sensing cytosolic dsDNA from infectious pathogens or aberrant host cell damage (Barber (2011) *Immunol. Rev.* 243(1): 99-108). STING signaling activates the TANK binding kinase (TBK1)/IRF3 axis and the NF-κB signaling axis, resulting in the induction of IFN-β and other pro-inflammatory cytokines and chemokines that strongly activate innate and adaptive immunity (Burdette et al. (2011) *Nature* 478 (7370):515-518). Sensing of cytosolic dsDNA through STING requires cyclic GMP-AMP synthase (cGAS), a host cell nucleotidyl transferase that directly binds dsDNA, and in response, synthesizes a cyclic dinucleotide (CDN) second messenger, cyclic GMP-AMP (cGAMP), which binds and activates STING (Sun et al. (2013) *Science* 339(6121):786-791; Wu et al. (2013) *Science* 339(6121):826-830). CDNs derived from bacteria such as c-di-AMP produced from intracellular *Listeria monocytogenes* can also directly bind murine STING, but only 3 of the 5 human STING alleles. Unlike the CDNs produced by bacteria, in which the two purine nucleosides are joined by a phosphate bridge with 3'-3' linkages, the internucleotide phosphate bridge in the cGAMP synthesized by mammalian cGAS is joined by a non-canonical 2'-3' linkage. These 2'-3' molecules bind to STING with 300-fold better affinity than bacterial 3'-3' CDNs, and thus are more potent physiological ligands of human STING (see, e.g., Civril et al. (2013) *Nature* 498 (7454):332-337; Diner et al. (2013) *Cell Rep.* 3(5):1355-1361; Gao et al. (2013) *Sci. Signal* 6(269):p11; Ablasser et al. (2013) *Nature* 503(7477):530-534).

The cGAS/STING signaling pathway in humans may have evolved over time to preferentially respond to viral pathogens over bacterial pathogens, and this can explain why bacterial vaccines harboring host tumor antigens have made for poor $CD8^+$ T cell priming vectors in humans. TLR-independent activation of $CD8^+$ T cells by STING-dependent type I IFN signaling from conventional DCs is the primary mechanism by which viruses are detected, with TLR-dependent type I IFN production by plasmacytoid DCs operating only when the STING pathway has been virally-inactivated (Hervas-Stubbs et al. (2014)*J. Immunol.* 193: 1151-1161). Further, for bacteria such as *S. typhimurium*, while capable of inducing IFN-β via TLR4, $CD8^+$ T cells are neither induced nor required for clearance or protective immunity (Lee et al. (2012) *Immunol. Lett.* 148(2): 138-143). The lack of physiologically relevant $CD8^+$ T epitopes for many strains of bacteria, including *S. typhimurium*, has impeded both bacterial vaccine development and protective immunity to subsequent infections, even from the same genetic strains (Lo et al. (1999) *J. Immunol.* 162:5398-5406). Thus, bacterially-based cancer immunotherapies are biologically limited in their ability to induce type I IFN to recruit and activate $CD8^+$ T cells, necessary to promote tumor antigen cross-presentation and durable anti-tumor immunity. Hence, engineering a bacterial immunotherapy provided herein to induce viral-like TLR-independent type I IFN signaling, rather than TLR-dependent bacterial immune signaling, will preferentially induce $CD8^+$ T cell mediated anti-tumor immunity.

STING activates innate immunity in response to sensing nucleic acids in the cytosol. Downstream signaling is activated through binding of CDNs, which are synthesized by bacteria or by the host enzyme cGAS in response to binding to cytosolic dsDNA. Bacterial and host-produced CDNs have distinct phosphate bridge structures, which differentiates their capacity to activate STING. IFN-β is the signature cytokine of activated STING, and virally-induce type I IFN, rather than bacterially-induced IFN, is required for effective $CD8^+$ T cell mediated anti-tumor immunity. Immunostimulatory bacteria provided herein include those that are STING agonists.

3. *Salmonella* Therapy

*Salmonella* is exemplary of a bacterial genus that can be used as a cancer therapeutic. The *Salmonella* exemplified herein is an attenuated species or one that, by virtue of the modifications for use as a cancer therapeutic, has reduced toxicity.

a. Tumor-Tropic Bacteria

A number of bacterial species have demonstrated preferential replication within solid tumors when injected from a distal site. These include, but are not limited to, species of *Salmonella, Bifidobacterium, Clostridium*, and *Escherichia*. The natural tumor-homing properties of the bacteria combined with the host's innate immune response to the bacterial infection is thought to mediate the anti-tumor response. This tumor tissue tropism has been shown to reduce the size of tumors to varying degrees. One contributing factor to the tumor tropism of these bacterial species is the ability to replicate in anoxic or hypoxic environments. A number of these naturally tumor-tropic bacteria have been further engineered to increase the potency of the antitumor response (reviewed in Zu et al. (2014) *Crit. Rev. Microbiol.* 40(3): 225-235; and Felgner et al. (2017) *Microbial Biotechnology* 10(5):1074-1078).

b. *Salmonella enterica* Serovar *Typhimurium*

*Salmonella enterica* serovar *Typhimurium* (*S. typhimurium*) is exemplary of a bacterial species for use as an anti-cancer therapeutic. One approach to using bacteria to stimulate host immunity to cancer has been through the Gram-negative facultative anaerobe *S. typhimurium*, which preferentially accumulates in hypoxic and necrotic areas in the body, including tumor microenvironments. *S. typhimu-*

*rium* accumulates in these environments due to the availability of nutrients from tissue necrosis, the leaky tumor vasculature and their increased likelihood to survive in the immune system-evading tumor microenvironment (Baban et al. (2010) *Bioengineered Bugs* 1(6):385-394). *S. typhimurium* is able to grow under both aerobic and anaerobic conditions; therefore it is able to colonize small tumors that are less hypoxic and large tumors that are more hypoxic.

*S. typhimurium* is a Gram-negative, facultative pathogen that is transmitted via the fecal-oral route. It causes localized gastrointestinal infections, but also enters the bloodstream and lymphatic system after oral ingestion, infecting systemic tissues such as the liver, spleen and lungs. Systemic administration of wild-type *S. typhimurium* overstimulates TNF-α induction, leading to a cytokine cascade and septic shock, which, if left untreated, can be fatal. As a result, pathogenic bacterial strains, such as *S. typhimurium*, must be attenuated to prevent systemic infection, without completely suppressing their ability to effectively colonize tumor tissues. Attenuation is often achieved by mutating a cellular structure that can elicit an immune response, such as the bacterial outer membrane or limiting its ability to replicate in the absence of supplemental nutrients.

*S. typhimurium* is an intracellular pathogen that is rapidly taken up by myeloid cells such as macrophages or it can induce its own uptake in in non-phagocytic cells such as epithelial cells. Once inside cells, it can replicate within a *Salmonella* containing vacuole (SCV) and can also escape into the cytosol of some epithelial cells. Many of the molecular determinants of *S. typhimurium* pathogenicity have been identified and the genes are clustered in *Salmonella* pathogenicity islands (SPIs). The two best characterized pathogenicity islands are SPI-1 which is responsible for mediating bacterial invasion of non-phagocytic cells, and SPI-2 which is required for replication within the SCV (Agbor and McCormick (2011) *Cell Microbiol.* 13(12):1858-1869). Both of these pathogenicity islands encode macromolecular structures called type three secretion systems (T3SS) that can translocate effector proteins across the host membrane (Galan and Wolf-Watz (2006) *Nature* 444:567-573).

c. Bacterial Attenuation

Therapeutic bacteria for administration as a cancer treatment should be attenuated. Various methods for attenuation of bacterial pathogens are known in the art. Auxotrophic mutations, for example, render bacteria incapable of synthesizing an essential nutrient, and deletions/mutations in genes such as aro, pur, gua, thy, nad and asd (U.S. Patent Publication No. 2012/0009153) are widely used. Nutrients produced by the biosynthesis pathways involving these genes are often unavailable in host cells, and as such, bacterial survival is challenging. For example, attenuation of *Salmonella* and other species can be achieved by deletion of the aroA gene, which is part of the shikimate pathway, connecting glycolysis to aromatic amino acid biosynthesis (Felgner et al. (2016) *mBio* 7(5):e01220-16). Deletion of aroA therefore results in bacterial auxotrophy for aromatic amino acids and subsequent attenuation (see, e.g., U.S. Patent Publication Nos. 2003/0170276, 2003/0175297, 2012/0009153, and 2016/0369282; International Application Publication Nos. WO 2015/032165 and WO 2016/025582). Similarly, other enzymes involved in the biosynthesis pathway for aromatic amino acids, including aroC and aroD have been deleted to achieve attenuation (see, e.g., U.S. Patent Publication No. 2016/0369282; International Patent Application Publication No. WO 2016/025582). For example, *S. typhimurium* strain SL7207 is an aromatic amino acid auxotroph (aroA$^-$ mutant); strains A1 and A1-R are leucine-arginine auxotrophs. VNP20009 is a purine auxotroph (purI$^-$ mutant). As shown herein, it is also auxotrophic for the immunosuppressive nucleoside adenosine.

Mutations that attenuate bacteria also include, but are not limited to, mutations in genes that alter the biosynthesis of lipopolysaccharide, such as rfaL, rfaG, rfaH, rfaD, rfaP, rFb, rfa, msbB, htrB, firA, pagL, pagP, lpxR, arnT, eptA, and lpxT; mutations that introduce a suicide gene such as sacB, nuk, hok, gef, kil or phlA; mutations that introduce a bacterial lysis gene such as hly and cly; mutations in virulence factors such as IsyA, pag, prg, iscA, virG, plc and act; mutations that modify the stress response such as recA, htrA, htpR, hsp and groEL; mutations that disrupt the cell cycle such as min; and mutations that disrupt or inactivate regulatory functions, such as cya, crp, phoP/phoQ, and ompR (see, e.g., U.S. Patent Publication Nos. 2012/0009153, 2003/0170276, and 2007/0298012; U.S. Pat. No. 6,190,657; International Application Publication No. WO 2015/032165; Felgner et al. (2016) *Gut Microbes* 7(2):171-177; Broadway et al. (2014) *J. Biotechnology* 192:177-178; Frahm et al. (2015) mBio 6(2):e00254-15; Kong et al. (2011) *Infection and Immunity* 79(12):5027-5038; Kong et al. (2012) *Proc. Natl. Acad. Sci. U.S.A.* 109(47):19414-19419). Ideally, the genetic attenuations comprise gene deletions rather than point mutations to prevent spontaneous compensatory mutations that might result in reversion to a virulent phenotype.

i. msbB$^-$ Mutants

The enzyme lipid A biosynthesis myristoyltransferase, encoded by the msbB gene in *S. typhimurium*, catalyzes the addition of a terminal myristyl group to the lipid A domain of lipopolysaccharide (LPS) (Low et al. (1999) *Nat. Biotechnol.* 17(1):37-41). Deletion of msbB thus alters the acyl composition of the lipid A domain of LPS, the major component of the outer membranes of Gram-negative bacteria. This modification significantly reduces the ability of the LPS to induce septic shock, attenuating the bacterial strain and reducing the potentially harmful production of TNFα, thus lowering systemic toxicity. *S. typhimurium* msbB mutants maintain their ability to preferentially colonize tumors over other tissues in mice and retain anti-tumor activity, thus increasing the therapeutic index of *Salmonella* based immunotherapeutics (see, e.g., U.S. Patent Publication Nos. 2003/0170276, 2003/0109026, 2004/0229338, 2005/0255088, and 2007/0298012).

For example, deletion of msbB in the *S. typhimurium* strain VNP20009 results in production of a predominantly penta-acylated LPS, which is less toxic than native hexa-acylated LPS and allows for systemic delivery without the induction of toxic shock (Lee et al. (2000) *International Journal of Toxicology* 19:19-25). Other LPS mutations can be introduced into the bacterial strains provided herein, including the *Salmonella* strains, that dramatically reduce virulence, and thereby provide for lower toxicity, and permit administration of higher doses.

ii. purI$^-$ Mutants

Immunostimulatory bacteria that can be attenuated by rendering them auxotrophic for one or more essential nutrients, such as purines (for example, adenine), nucleosides (for example, adenosine) or amino acids (for example, arginine and leucine), are employed. In particular, in embodiments of the immunostimulatory bacteria provided herein, such as *S. typhimurium*, the bacteria are rendered auxotrophic for adenosine, which preferentially accumulates in tumor microenvironments. Hence, strains of immunostimulatory bacteria described herein are attenuated because they require adenosine for growth, and they preferentially colonize TMEs, which, as discussed below, have an abundance of adenosine.

Phosphoribosylaminoimidazole synthetase, an enzyme encoded by the purI gene (synonymous with the purM gene), is involved in the biosynthesis pathway of purines. Disruption of the purI gene thus renders the bacteria auxotrophic for purines. In addition to being attenuated, purI$^-$ mutants are enriched in the tumor environment and have significant anti-tumor activity (Pawelek et al. (1997) *Cancer Research* 57:4537-4544). It was previously described that this colonization results from the high concentration of purines present in the interstitial fluid of tumors as a result of their rapid cellular turnover. Since the pulI$^-$ bacteria are unable to synthesize purines, they require an external source of adenine, and it was thought that this would lead to their restricted growth in the purine-enriched tumor microenvironment (Rosenberg et al. (2002) *J. Immunotherapy* 25(3): 218-225). While the VNP20009 strain was initially reported to contain a deletion of the purI gene (Low et al. (2003) *Methods in Molecular Medicine Vol.* 90, *Suicide Gene Therapy:* 47-59), subsequent analysis of the entire genome of VNP20009 demonstrated that the purI gene is not deleted, but is disrupted by a chromosomal inversion (Broadway et al. (2014) *Journal of Biotechnology* 192:177-178). The entire gene is contained within two parts of the VNP20009 chromosome that is flanked by insertion sequences (one of which has an active transposase).

It is shown herein, that, purI mutant *S. typhimurium* strains are auxotrophic for the nucleoside adenosine, which is highly enriched in tumor microenvironments. Hence, when using VNP20009, it is not necessary to introduce any further modification to achieve adenosine auxotrophy. For other strains and bacteria, the purI gene can be disrupted as it has been in VNP20009, or it can contain a deletion of all or a portion of the purI gene to prevent reversion to a wild-type gene.

iii. Combinations of Attenuating Mutations

A bacterium with multiple genetic attenuations by means of gene deletions on disparate regions of the chromosome is desirable for bacterial immunotherapies because the attenuation can be increased, while decreasing the possibility of reversion to a virulent phenotype by acquisition of genes by homologous recombination with a wild-type genetic material. Restoration of virulence by homologous recombination would require two separate recombination events to occur within the same organism. Ideally the combinations of attenuating mutations selected for use in an immunotherapeutic agent increases the tolerability without decreasing the potency, thereby increasing the therapeutic index. For example, disruption of the msbB and purI genes in *S. typhimurium* strain VNP20009, has been used for tumor-targeting and growth suppression, and elicits low toxicity in animal models (Clairmont et al. (2000) *J. Infect. Dis.* 181:1996-2002; Bermudes et al. (2000) *Cancer Gene Therapy: Past Achievements and Future Challenges*, edited by Habib Kluwer Academic/Plenum Publishers, New York, pp. 57-63; Low et al. (2003) *Methods in Molecular Medicine*, Vol. 90, *Suicide Gene Therapy:* 47-59; Lee et al. (2000) *International Journal of Toxicology* 19:19-25; Rosenberg et al. (2002) *J. Immunotherapy* 25(3):218-225; Broadway et al. (2014) *J. Biotechnology* 192:177-178; Loeffler et al. (2007) *Proc. Natl. Acad. Sci. U.S.A.* 104(31): 12879-12883; Luo et al. (2002) *Oncology Research* 12:501-508). When VNP20009 (msbB$^-$/purI$^-$) was administered to mice bearing syngeneic or human xenograft tumors, the bacteria accumulated preferentially within the extracellular components of tumors at ratios exceeding 300-1000 to 1, reduced TNFα induction, and demonstrated tumor regression and prolonged survival compared to control mice (Clairmont et al. (2000) *J. Infect. Dis.* 181:1996-2002). Results from the Phase 1 clinical trial in humans, however, revealed that while VNP20009 was relatively safe and well tolerated, poor accumulation was observed in human melanoma tumors, and very little anti-tumor activity was demonstrated (Toso et al. (2002) *J. Clin. Oncol.* 20(1):142-152). Higher doses, which are required to manifest any anti-tumor activity, were not possible due to toxicity.

Thus, further improvements are needed. The immunostimulatory bacteria provided herein address this problem.

iv. VNP20009 and Other Attenuated and Wild-Type *S. typhimurium* Strains

The starting strain can be a wild-type non-attenuated strain, such as a strain having all of the identifying characteristics of ATCC 14028. The strain is then modified to increase its specificity or targeting to the tumor microenvironment or to tumor cells and/or to tumor resident immune cells. It also can be modified to be auxotrophic for adenosine. The strain can be rendered flagellin$^-$ (fliC$^-$/fljB$^-$), and optionally one or more of msbB$^-$, purI$^-$/purM$^-$, and pagP$^-$. The strains also can be asd$^-$. The modified strains encode a therapeutic product on a plasmid, generally present in low to medium copy number, under control of a promoter recognized by a mammalian host, such as RNA polymerase II or III. Additional regulatory sequences to control expression in the tumor microenvironment and trafficking in the cells also can be included.

Exemplary of a therapeutic bacterium that can be modified as described herein is the strain designated as VNP20009 (ATCC #202165, YS1646), which is derived from the strain ATCC accession no. 14028. The strain designated VNP20009 (ATCC #202165, YS1646), was a clinical candidate, and at least 50,000-fold attenuated for safety by deletion of the msbB and purI genes (Clairmont et al. (2000) *J. Infect. Dis.* 181:1996-2002; Low et al. (2003) *Methods in Molecular Medicine*, Vol. 90, *Suicide Gene Therapy:* 47-59; Lee et al. (2000) *International Journal of Toxicology* 19:19-25). Similar strains of *Salmonella* that are attenuated also are contemplated. As described above, deletion of msbB alters the composition of the lipid A domain of lipopolysaccharide, the major component of Gram-negative bacterial outer membranes (Low et al. (1999) *Nat. Biotechnol.* 17(1):37-41). This prevents lipopolysaccharide-induced septic shock, attenuating the bacterial strain and lowering systemic toxicity, while reducing the potentially harmful production of TNFα (Dinarello, C. A. (1997) *Chest* 112(6 Suppl): 321S-329S; Low et al. (1999) *Nat. Biotechnol.* 17(1):37-41). Deletion of the purI gene renders the bacteria auxotrophic for purines, which further attenuates the bacteria and enriches it in the tumor microenvironment (Pawelek et al. (1997) *Cancer Res.* 57:4537-4544; Broadway et al. (2014) *J. Biotechnology* 192:177-178).

Accumulation of VNP20009 in tumors results from a combination of factors including: the inherent invasiveness of the parental strain, ATCC accession number 14028, its ability to replicate in hypoxic environments, and its requirement for high concentrations of purines that are present in the interstitial fluid of tumors. It is shown herein that VNP20009 also is auxotrophic for the nucleoside adenosine, which can accumulate to pathologically high levels in the tumor microenvironment and contribute to an immunosuppressive tumor microenvironment (Peter Vaupel and Arnulf Mayer Oxygen Transport to Tissue XXXVII, Advances in Experimental Medicine and Biology 876 chapter 22, pp.

177-183). VNP20009 was administered into mice bearing syngeneic or human xenograft tumors, the bacteria accumulated preferentially within the extracellular components of tumors at ratios exceeding 300-1000 to 1 and demonstrated tumor growth inhibition as well as prolonged survival compared to control mice (Clairmont et al. (2000) *J. Infect. Dis.* 181:1996-2002). Results from the Phase 1 clinical trial revealed that while VNP20009 was relatively safe and well tolerated, poor accumulation was observed in human melanoma tumors, and very little anti-tumor activity was demonstrated (Toso et al. (2002) *J. Clin. Oncol.* 20(1):142-152). Higher doses, which would be required to affect any anti-tumor activity, were not possible due to toxicity that correlated with high levels of pro-inflammatory cytokines. The modifications provided herein, including the flagellin deletion ($fliC^-/fljB^-$), and optional $pagP^-$ and/or WA" modifications, significantly increase accumulation of the immunostimulatory bacteria in tumors, in the tumor microenvironment and/or in tumor-resident immune cells, such as myeloid cells. Other modifications that increase targeting to immune cells, and eliminate infection of other cells, such as epithelial cells, increase the accumulation of the bacteria in the tumors and in the tumor microenvironment. Additional modifications to render the wild-type bacteria auxotrophic for adenosine further increases accumulation in the tumor microenvironment.

Other strains of *S. typhimurium* can be used for tumor-targeted delivery of therapeutic proteins and therapy, such as, for example, leucine-arginine auxotroph A-1 (see, e.g., Zhao et al. (2005) *Proc. Natl. Acad. Sci. U.S.A.* 102(3):755-760; Yu et al. (2012) *Scientific Reports* 2:436; U.S. Pat. No. 8,822,194; U.S. Patent Publication No. 2014/0178341) and its derivative AR-1 (see, e.g., Yu et al. (2012) *Scientific Reports* 2:436; Kawaguchi et al. (2017) *Oncotarget* 8(12): 19065-19073; Zhao et al. (2006) *Cancer Res.* 66(15):7647-7652; Zhao et al. (2012) *Cell Cycle* 11(1):187-193; Tome et al. (2013) *Anticancer Research* 33:97-102; Murakami et al. (2017) *Oncotarget* 8(5):8035-8042; Liu et al. (2016) *Oncotarget* 7(16):22873-22882; Binder et al. (2013) *Cancer Immunol. Res.* 1(2):123-133); $aroA^-$ mutant *S. typhimurium* strain SL7207 (see, e.g., Guo et al. (2011) *Gene Therapy* 18:95-105; U.S. Patent Publication Nos. 2012/0009153, 2016/0369282, and 2016/0184456), and its obligate anaerobe derivative YB1 (see, e.g., International Application Publication No. WO 2015/032165; Yu et al. (2012) *Scientific Reports* 2:436; Leschner et al. (2009) *PLoS ONE* 4(8): e6692); $aroA^-/aroD^-$ mutant *S. typhimurium* strain BRD509, a derivative of the SL1344 (WT) strain (see, e.g., Yoon et al. (2017) *European J. of Cancer* 70:48-61); $asd^-/cya^-/crp^-$ mutant *S. typhimurium* strain $\chi$4550 (see, e.g., Sorenson et al. (2010) *Biologics: Targets & Therapy* 4:61-73) and $phoP^-/phoQ^-$ *S. typhimurium* strain LH430 (see, e.g., International Application Publication No. WO 2008/091375).

The strain VNP20009 failed to show a clinical benefit in a study involving patients with advanced melanoma, but the treatment was safely administered to advanced cancer patients. A maximum tolerated dose (MTD) was established. Hence, this strain, as well as other similarly engineered bacterial strains, can be used as a starting material for tumor-targeting, therapeutic delivery vehicles. Modifications provided herein provide a strategy to increase efficacy, by increasing the anti-tumor efficiency and/or the safety and tolerability of the therapeutic agent.

v. *S. typhimurium* Engineered to Deliver Macromolecules

*S. typhimurium* also has been modified to deliver the tumor-associated antigen (TAA) survivin (SVN) to APCs to prime adaptive immunity (U.S. Patent Publication No. 2014/0186401; Xu et al. (2014) *Cancer Res.* 74(21):6260-6270). SVN is an inhibitor of apoptosis protein (IAP) which prolongs cell survival and provides cell cycle control, and is overexpressed in all solid tumors and poorly expressed in normal tissues. This technology utilizes *Salmonella* Pathogenicity Island 2 (SPI-2) and its type III secretion system (T3SS) to deliver the TAAs into the cytosol of APCs, which then are activated to induce TAA-specific $CD8^+$ T cells and anti-tumor immunity (Xu et al. (2014) *Cancer Res.* 74(21): 6260-6270). Similar to the *Listeria*-based TAA vaccines, this approach has shown promise in mouse models, but has yet to demonstrate effective tumor antigen-specific T cell priming in humans.

In addition to gene delivery, *S. typhimurium* also has been used for the delivery of small interfering RNAs (siRNAs) and short hairpin RNAs (shRNAs) for cancer therapy. For example, attenuated *S. typhimurium* have been modified to express certain shRNAs, such as those that target STAT3 and IDO1 (PCT/US2007/074272, and U.S. Pat. No. 9,453,227). VNP20009 transformed with an shRNA plasmid against the immunosuppressive gene indolamine dioxygenase (IDO), successfully silenced IDO expression in a murine melanoma model, resulting in tumor cell death and significant tumor infiltration by neutrophils (Blache et al. (2012) *Cancer Res.* 72(24):6447-6456). Combining this vector with the co-administration of a hyaluronidase, such as PEGylated soluble PH20 (PEGPH20; an enzyme that depletes extracellular hyaluronan), shows positive results in the treatment of pancreatic ductal adenocarcinoma tumors (see, e.g., Manuel et al. (2015) *Cancer Immunol. Res.* 3(9):1096-1107; U.S. Patent Publication No. 2016/0184456). In another study, an *S. typhimurium* strain attenuated by a phoP/phoQ deletion and expressing a signal transducer and activator of transcription 3 (STAT3)-specific shRNA, was found to inhibit tumor growth and reduce the number of metastatic organs, extending the life of C57BL6 mice (Zhang et al. (2007) *Cancer Res.* 67(12):5859-5864). In another example, *S. typhimurium* strain SL7207 has been used for the delivery of shRNA targeting CTNNB1, the gene that encodes β-catenin (see, e.g., Guo et al. (2011) *Gene Therapy* 18:95-105; U.S. Patent Publication Nos. 2009/0123426, and 2016/0369282), while *S. typhimurium* strain VNP20009 has been used in the delivery of shRNA targeting STAT3 (see, e.g., Manuel et al. (2011) *Cancer Res.* 71(12):4183-4191; U.S. Patent Publication Nos. 2009/0208534, 2014/0186401, and 2016/0184456; International Application Publication Nos. WO 2008/091375, and WO 2012/149364). siRNAs targeting the autophagy genes Atg5 and BeclinI have been delivered to tumor cells using *S. typhimurium* strains A1-R and VNP20009 (Liu et al. (2016) *Oncotarget* 7(16):22873-22882). Improvement of such strains is needed so that they more effectively colonize tumors, the TME, and/or tumor-resident immune cells, and also stimulate the immune response, and have other advantageous properties, such as the immunostimulatory bacteria provided herein. Modifications of various bacteria have been described in International PCT Application Publication No. WO 2019/014398 and U.S. Publication No. 2019/0017050 A1. The bacteria described in each of these publications, also described herein, can be modified as described herein to further improve the immunostimulatory and tumor-targeting properties.

The bacteria can be modified as described herein to have reduced inflammatory effects, and thus, to be less toxic. As a result, for example, higher dosages can be administered. Any of these strains of *Salmonella*, as well as other species of bacteria, known to those of skill in the art and/or listed above and herein, can be modified as described herein, such as by introducing adenosine auxotrophy, a plasmid encoding a therapeutic product, such as an immunostimulatory protein and/or RNAi, such as miRNA or shRNA, or an antibody or fragment thereof, for inhibiting an immune checkpoint, and other modifications as described herein. Exemplary are the *S. typhimurium* species described herein.

The bacterial strains provided herein are engineered to deliver therapeutic molecules. The strains herein deliver immunostimulatory proteins, such as cytokines, that promote an anti-tumor immune response in the tumor microenvironment. The strains also can include genomic modifications that reduce pyroptosis of phagocytic cells, thereby providing for a more robust immune response, and/or reduce or eliminate the ability to infect/invade epithelial cells, but retain the ability to infect/invade phagocytic cells, so that they accumulate more effectively in tumors and in tumor-resident immune cells. The bacterial strains also can be modified to encode therapeutic products, including, for example, RNAi targeted and inhibitory to immune checkpoints, and also to other such targets.

4. Enhancements of Immunostimulatory Bacteria to Increase Therapeutic Index

Provided herein are enhancements to immunostimulatory bacteria that reduce toxicity and improve the anti-tumor activity. Exemplary of such enhancements are the following. They are described with respect to *Salmonella*, particularly *S. typhimurium*; it is understood that the skilled person can effect similar enhancements in other bacterial species and other *Salmonella* strains.

a. asd Gene Deletion

The asd gene in bacteria encodes an aspartate-semialdehyde dehydrogenase. asd-mutants of *S. typhimurium* have an obligate requirement for diaminopimelic acid (DAP) which is required for cell wall synthesis and will undergo lysis in environments deprived of DAP. This DAP auxotrophy can be used for plasmid selection and maintenance of plasmid stability in vivo without the use of antibiotics when the asd gene is complemented in trans on a plasmid. Non-antibiotic-based plasmid selection systems are advantageous and allow for 1) use of administered antibiotics as rapid clearance mechanism in the event of adverse symptoms, and 2) for antibiotic-free scale up of production, where such use is commonly avoided. The asd gene complementation system provides for such selection (Galan et al. (1990) *Gene* 94(1): 29-35). The use of the asd gene complementation system to maintain plasmids in the tumor microenvironment is expected to increase the potency of *S. typhimurium* engineered to deliver plasmids encoding genes or interfering RNAs.

An alternative use for an asd mutant of *S. typhimurium* is to exploit the DAP auxotrophy to produce an autolytic (or suicidal) strain for delivery of macromolecules to infected cells without the ability to persistently colonize host tumors. Deletion of the asd gene makes the bacteria auxotrophic for DAP when grown in vitro or in vivo. An example described herein, provides an asd deletion strain that is auxotrophic for DAP and contains a plasmid suitable for delivery of RNAi, such as shRNA or miRNA, that does not contain an asd complementing gene, resulting in a strain that is defective for replication in vivo. This strain is propagated in vitro in the presence of DAP and grows normally, and then is administered as an immunotherapeutic agent to a mammalian host where DAP is not present. The suicidal strain is able to invade host cells but is not be able to replicate due to the absence of DAP in mammalian tissues, lysing automatically and delivering its cytosolic contents (e.g., plasmids or proteins). In examples provided herein, an asd gene deleted strain of VNP20009 was further modified to express an LLO protein lacking its endogenous periplasmic secretion signal sequence, causing it to accumulate in the cytoplasm of the *Salmonella*. LLO is a cholesterol-dependent pore forming hemolysin from *Listeria monocytogenes* that mediates phagosomal escape of bacteria. When the autolytic strain is introduced into tumor bearing mice, the bacteria are taken up by phagocytic immune cells and enter the *Salmonella*-containing vacuole (SCV). In this environment, the lack of DAP will prevent bacterial replication, and result in autolysis of the bacteria in the SCV. Lysis of the suicidal strain will then allow for release of the plasmid and the accumulated LLO that will form pores in the cholesterol-containing SVC membrane, and allow for delivery of the plasmid into the cytosol of the host cell.

b. Adenosine Auxotrophy

Metabolites derived from the tryptophan and ATP/adenosine pathways are major drivers in forming an immunosuppressive environment within the tumor. Adenosine, which exists in the free form inside and outside of cells, is an effector of immune function. Adenosine decreases T-cell receptor induced activation of NF-κB, and inhibits IL-2, IL-4, and IFN-γ. Adenosine decreases T-cell cytotoxicity, increases T-cell anergy, and increases T-cell differentiation to $Foxp3^+$ or $Lag\text{-}3^+$ regulatory (T-reg) T-cells. On NK cells, adenosine decreases IFN-γ production, and suppresses NK cell cytotoxicity. Adenosine blocks neutrophil adhesion and extravasation, decreases phagocytosis, and attenuates levels of superoxide and nitric oxide. Adenosine also decreases the expression of TNF-α, IL-12, and MIP-1α on macrophages, attenuates MHC Class II expression, and increases levels of IL-10 and IL-6. Adenosine immunomodulation activity occurs after its release into the extracellular space of the tumor and activation of adenosine receptors (ADRs) on the surface of target immune cells, cancer cells or endothelial cells. The high adenosine levels in the tumor microenvironment result in local immunosuppression, which limits the capacity of the immune system to eliminate cancer cells.

Extracellular adenosine is produced by the sequential activities of membrane associated ectoenzymes, CD39 and CD73, which are expressed on tumor stromal cells, together producing adenosine by phosphohydrolysis of ATP or ADP produced from dead or dying cells. CD39 converts extracellular ATP (or ADP) to 5'AMP, which is converted to adenosine by 5'AMP. Expression of CD39 and CD73 on endothelial cells is increased under the hypoxic conditions of the tumor microenvironment, thereby increasing levels of adenosine. Tumor hypoxia can result from inadequate blood supply and disorganized tumor vasculature, impairing delivery of oxygen (Carroll and Ashcroft (2005) *Expert. Rev. Mol. Med.* 7(6):1-16). Hypoxia, which occurs in the tumor microenvironment, also inhibits adenylate kinase (AK), which converts adenosine to AMP, leading to very high extracellular adenosine concentrations. The extracellular concentration of adenosine in the hypoxic tumor microenvironment has been measured at 10-100 which is up to about 100-1000 fold higher than the typical extracellular adenosine concentration of approximately 0.1 μM (Vaupel et al. (2016) *Adv. Exp. Med. Biol.* 876:177-183; Antonioli et al. (2013) *Nat. Rev. Can.* 13:842-857). Since hypoxic regions in tumors are distal from microvessels, the local concentration of adenosine in some regions of the tumor can be higher than others.

To direct effects to inhibit the immune system, adenosine also can control cancer cell growth and dissemination by effects on cancer cell proliferation, apoptosis and angiogenesis. For example, adenosine can promote angiogenesis, primarily through the stimulation of $A_{2A}$ and $A_{2B}$ receptors. Stimulation of the receptors on endothelial cells can regulate the expression of intercellular adhesion molecule 1 (ICAM-1) and E-selectin on endothelial cells, maintain vascular integrity, and promote vessel growth (Antonioli et al. (2013) *Nat. Rev. Can.* 13:842-857). Activation of one or more of $A_{2A}$, $A_{2B}$ or $A_3$ on various cells by adenosine can stimulate the production of the pro-angiogenic factors, such as vascular endothelial growth factor (VEGF), interleukin-8 (IL-8) or angiopoietin 2 (Antonioli et al. (2013) *Nat. Rev. Can.* 13:842-857).

Adenosine also can directly regulate tumor cell proliferation, apoptosis and metastasis through interaction with receptors on cancer cells. For example, studies have shown that the activation of $A_1$ and $A_{2A}$ receptors promote tumor cell proliferation in some breast cancer cell lines, and activation of $A_{2B}$ receptors have cancer growth-promoting properties in colon carcinoma cells (Antonioli et al. (2013) *Nat. Rev. Can.* 13:842-857). Adenosine also can trigger apoptosis of cancer cells, and various studies have correlated this activity to activation of the extrinsic apoptotic pathway through $A_3$ or the intrinsic apoptotic pathway through $A_{2A}$ and $A_{2B}$ (Antonioli et al. (2013)). Adenosine can promote tumor cell migration and metastasis, by increasing cell motility, adhesion to the extracellular matrix, and expression of cell attachment proteins and receptors to promote cell movement and motility.

The extracellular release of adenosine triphosphate (ATP) occurs from stimulated immune cells and damaged, dying or stressed cells. The NLR family pyrin domain-containing 3 (NLRP3) inflammasome, when stimulated by this extracellular release of ATP, activates caspase-1 and results in the secretion of the cytokines IL-1β and IL-18, which in turn activate innate and adaptive immune responses (Stagg and Smyth (2010) *Oncogene* 29:5346-5358). ATP is catabolized into adenosine by the enzymes CD39 and CD73. Activated adenosine acts as a highly immunosuppressive metabolite via a negative-feedback mechanism and has a pleiotropic effect against multiple immune cell types in the hypoxic tumor microenvironment (Stagg and Smyth (2010) *Oncogene* 29:5346-5358). Adenosine receptors $A_{2A}$ and $A_{2B}$ are expressed on a variety of immune cells and are stimulated by adenosine to promote cAMP-mediated signaling changes, resulting in immunosuppressive phenotypes of T-cells, B-cells, NK cells, dendritic cells, mast cells, macrophages, neutrophils, and NKT cells. As a result of this, adenosine levels can accumulate to over one hundred times their normal concentration in pathological tissues, such as solid tumors, which have been shown to overexpress ecto-nucleotidases, such as CD73. Adenosine has also been shown to promote tumor angiogenesis and development. An engineered bacterium that is auxotrophic for adenosine would thus exhibit enhanced tumor-targeting and colonization.

Immunostimulatory bacteria, such as *Salmonella typhi*, can be made auxotrophic for adenosine by deletion of the tsx gene (Bucarey et al. (2005) *Infection and Immunity* 73(10): 6210-6219), or by deletion of purD (Husseiny (2005) *Infection and Immunity* 73(3):1598-1605). In the Gram negative bacteria *Xanthomonas oryzae*, a purD gene knockout was shown to be auxotrophic for adenosine (Park et al. (2007) *FEMS Microbiol. Lett.* 276:55-59). As exemplified herein, *S. typhimurium* strain VNP20009, is auxotrophic for adenosine due to its purI deletion, hence, further modification to render it auxotrophic for adenosine is not required. Hence, embodiments of the immunostimulatory bacterial strains, as provided herein, are auxotrophic for adenosine. Such auxotrophic bacteria selectively replicate in the tumor microenvironment, further increasing accumulation and replication of the administered bacteria in tumors and decreasing the levels of adenosine in and around tumors, thereby reducing or eliminating the immunosuppression caused by accumulation of adenosine. Exemplary of such bacteria, provided herein is a modified strain of *S. typhimurium* containing $purI^-/msbB^-$ mutations to provide adenosine auxotrophy.

c. Flagellin Deficient Strains

Flagella are organelles on the surface of bacteria that are composed of a long filament attached via a hook to a rotary motor that can rotate in a clockwise or counterclockwise manner to provide a means for locomotion. Flagella in *S. typhimurium* are important for chemotaxis and for establishing an infection via the oral route, due to the ability to mediate motility across the mucous layer in the gastrointestinal tract. While flagella have been demonstrated to be required for chemotaxis to and colonization of tumor cylindroids in vitro (Kasinskas and Forbes (2007) *Cancer Res.* 67(7):3201-3209), and motility has been shown to be important for tumor penetration (Toley and Forbes (2012) *Integr. Biol.* (Camb). 4(2):165-176), flagella are not required for tumor colonization in animals when the bacteria are administered intravenously (Stritzker et al. (2010) *International Journal of Medical Microbiology* 300:449-456). Each flagellar filament is composed of tens of thousands of flagellin subunits. The *S. typhimurium* chromosome contains two genes, fliC and fljB, that encode antigenically distinct flagellin monomers. Mutants defective for both fliC and fljB are nonmotile and avirulent when administered via the oral route of infection, but maintain virulence when administered parenterally.

Flagellin is a major pro-inflammatory determinant of *Salmonella* (Zeng et al. (2003) *J. Immunol.* 171:3668-3674), and is directly recognized by TLR5 on the surface of cells, and by NLCR4 in the cytosol (Lightfield et al. (2008) *Nat. Immunol.* 9(10):1171-1178). Both pathways lead to pro-inflammatory responses resulting in the secretion of cytokines, including IL-1β, IL-18, TNF-α and IL-6. Attempts have been made to make *Salmonella*-based cancer immunotherapy more potent by increasing the pro-inflammatory response to flagellin by engineering the bacteria to secrete *Vibrio vulnificus* flagellin B, which induces greater inflammation than flagellin encoded by fliC and fljB (Zheng et al. (2017) *Sci. Transl. Med.* 9(376):eaak9537).

Herein, *Salmonella* bacteria, *S. typhimurium*, are engineered to lack both flagellin subunits fliC and fljB, to reduce pro-inflammatory signaling. For example, as shown herein, a *Salmonella* strain lacking msbB, which results in reduced TNF-alpha induction, is combined with fliC and fljB knockouts. This results in a *Salmonella* strain that has a combined reduction in TNF-alpha induction and reduction in TLR5 recognition. These modifications can be combined with $msbB^-$, $fliC^-$ and $fljB^-$, and transformed with an immunostimulatory plasmid, optionally containing CpGs, and a therapeutic molecule, such as an antibody or RNAi molecule(s) targeting an immune checkpoint, such as TREX1, PD-L1, VISTA, SIRP-alpha, TGF-beta, beta-catenin, CD47, VEGF, and combinations thereof. The resulting bacteria have reduced pro-inflammatory signaling, but robust anti-tumor activity.

For example, as provided herein, a fliC and fljB double mutant was constructed in the asd deleted strain of *S. typhimurium* VNP20009. VNP20009, which is attenuated for virulence by disruption of purI/purM, was also engineered to contain an msbB deletion that results in production of a lipid A subunit that is less toxigenic than wild-type lipid A. This results in reduced TNF-α production in the mouse model after intravenous administration, compared to strains with wild-type lipid A. The resulting strain is exemplary of strains that are attenuated for bacterial inflammation by modification of lipid A to reduce TLR2/4 signaling, and deletion of the flagellin subunits to reduce TLR5 recognition and inflammasome induction. Deletion of the flagellin subunits combined with modification of the LPS allows for greater tolerability in the host, and directs the immunostimulatory response towards delivery of RNA interference against desired targets in the TME which elicit an anti-tumor response and promote an adaptive immune response to the tumor.

d. *Salmonella* Engineered to Escape the *Salmonella*-Containing Vacuole (SCV)

*Salmonella*, such as *S. typhimurium*, are intracellular pathogens that replicate primarily in a membrane bound compartment called a *Salmonella*-containing vacuole (SCV). In some epithelial cell lines and at a low frequency, *S. typhimurium* have been shown to escape into the cytosol where they can replicate. *Salmonella* engineered to escape the SCV with higher efficiency will be more efficient at delivering macromolecules, such as plasmids, as the lipid bilayer of the SCV is a potential barrier. Provided herein are *Salmonella* and methods that have enhanced frequency of SCV escape. This is achieved by deletion of genes required for *Salmonella* induced filament (SIF) formation. These mutants have an increased frequency of SCV escape and can replicate in the cytosol.

For example, enhanced plasmid delivery using a sifA mutant of *S. typhimurium* has been demonstrated. The sifA gene encodes SPI-2, T3SS-2 secreted effector protein that mimics or activates a RhoA family of host GTPases (Ohlson et al. (2008) *Cell Host & Microbe* 4:434-446). Other genes encoding secreted effectors involved in SIF formation can be targeted. These include, for example, sseJ, sseL, sopD2, pipB2, sseF, sseG, spvB, and steA. Enhancing the escape of *S. typhimurium* by prevention of SIF formation releases live bacteria into the cytosol, where they can replicate.

Another method to enhance *S. typhimurium* escape from the SCV and increase the delivery of macromolecules such as plasmids, is the expression of a heterologous hemolysin that results in pore formation in, or rupture of, the SCV membrane. One such hemolysin is the Listeriolysin O protein (LLO) from *Listeria monocytogenes*, which is encoded by the hlyA gene. LLO is a cholesterol-dependent pore-forming cytolysin that is secreted from *L. monocytogenes* and is primarily responsible for phagosomal escape and entry into the cytosol of host cells. Secretion of LLO from *S. typhimurium* can result in bacterial escape and lead to replication in the cytosol. To prevent intact *S. typhimurium* from escaping the SCV and replicating in the cytosol, the nucleotides encoding the signal sequence can be removed from the gene. In this manner, the active LLO is contained within the cytoplasm of the *S. typhimurium* and LLO is only released when the bacteria undergo lysis. As provided herein, VNP20009 engineered to express cytoLLO to enhance delivery of plasmids for expression of interfering RNAs to targets, such as TREX1, can increase the therapeutic potency of the immunostimulatory bacteria.

e. Deletions in *Salmonella* Genes Required for Biofilm Formation

Bacteria and fungi are capable of forming multicellular structures called biofilms. Bacterial biofilms are encased within a mixture of secreted and cell wall-associated polysaccharides, glycoproteins, and glycolipids, as well as extracellular DNA, known collectively as extracellular polymeric substances. These extracellular polymeric substances protect the bacteria from multiple insults, such as cleaning agents, antibiotics, and antimicrobial peptides. Bacterial biofilms allow for colonization of surfaces, and are a cause of significant infection of prosthetics, such as injection ports and catheters. Biofilms can also form in tissues during the course of an infection, which leads to increases in the duration of bacterial persistence and shedding, and limits the effectiveness of antibiotic therapies. Chronic persistence of bacteria in biofilms is associated with increased tumorigenesis, for example in *S. typhi* infection of the gall bladder (Di Domenico et al. (2017) Int. J. Mol. Sci. 18:1887).

*S. typhimurium* biofilm formation is regulated by CsgD. CsgD activates the csgBAC operon, which results in increased production of the curli fimbrial subunits CsgA and CsgB (Zakikhany et al. (2010) *Molecular Microbiology* 77(3):771-786). CsgA is recognized as a PAMP by TLR2 and induces production of IL-8 from human macrophages (Tukel et al. (2005) *Molecular Microbiology* 58(1):289-304). Further, CsgD indirectly increases cellulose production by activating the adrA gene that encodes for di-guanylate cyclase. The small molecule cyclic di-guanosine monophosphate (c-di-GMP) generated by AdrA is a ubiquitous secondary messenger found in almost all bacterial species. The AdrA-mediated increase in c-di-GMP enhances expression of the cellulose synthase gene bcsA, which in turn increases cellulose production via stimulation of the bcsABZC and bcsEFG operons. Reduction in the capability of immunostimulatory bacteria such as *S. typhimurium* to form biofilms can be achieved through deletion of genes involved in biofilm formation such as, for example, csgD, csgA, csgB, adrA, bcsA, bcsB, bcsZ, bcsE, bcsF, bcsG, dsbA or dsbB (Anwar et al. (2014) *PLoS ONE* 9(8): e106095).

*S. typhimurium* can form biofilms in solid tumors as protection against phagocytosis by host immune cells. *Salmonella* mutants that cannot form biofilms are taken up more rapidly by host phagocytic cells and are cleared from infected tumors (Crull et al. (2011) *Cellular Microbiology* 13(8):1223-1233). This increase in intracellular localization within phagocytic cells can reduce the persistence of extracellular bacteria, and enhance the effectiveness of plasmid delivery and gene knockdown by RNA interference as described herein. Immunostimulatory bacteria engineered to reduce biofilm formation, will increase clearance rate from tumors/tissues and therefore increase the tolerability of the therapy, and will prevent colonization of prosthetics in patients, thereby increasing the therapeutic benefit of these strains. Adenosine mimetics can inhibit *S. typhimurium* biofilm formation, indicating that the high adenosine concentration in the tumor microenvironment can contribute to tumor-associated biofilm formation (Koopman et al. (2015) *Antimicrob. Agents Chemother.* 59:76-84). As provided herein, live attenuated strains of bacteria, such as *S. typhimurium*, that contain a purI disruption (and therefore, colonize adenosine-rich tumors), and are also prevented from forming biofilms, by deletion of one or more genes required for biofilm formation, are engineered to deliver plasmids encoding interfering RNA to stimulate a robust anti-tumor immune response.

The adrA gene encodes a di-guanylate cyclase that produces c-di-GMP, which is required for *S. typhimurium* biofilm formation. c-di-GMP binds to and is an agonist for the host cytosolic protein STING. As described above, STING agonists are pursued as anti-cancer treatments, vaccine adjuvants, and bacteria engineered to secrete cyclic di-nucleotides for use in immunotherapies (Libanova 2012, Synlogic 2018 AACR poster). Immunostimulatory bacteria that are reduced in c-di-GMP production via the deletion of adrA is counterintuitive, but bacterial mutants, such as *S. typhimurium* mutants, that are unable to form biofilms (including an adrA mutant), have demonstrated reduced therapeutic potential in mouse tumor models (Crull et al. (2011) *Cellular Microbiology* 13(8):1223-1233). Several human alleles of STING are refractory to binding bacterially-produced 3'3' CDNs (Corrales et al. (2015) *Cell Reports* 11:1018-1030).

As described herein, bacterial strains, such as *S. typhimurium* strains, that are engineered to be adenosine auxotrophic, and are reduced in their ability to induce pro-inflammatory cytokines by modification of the LPS and/or deletion of flagellin, and/or deletion of genes required for biofilm formation, and further modified to deliver interfering RNAs, promote robust anti-tumor immune responses.

f. Deletions in Genes in the LPS Biosynthetic Pathway

The LPS of Gram-negative bacteria is the major component of the outer leaflet of the bacterial membrane. It is composed of three major parts, lipid A, a non-repeating core oligosaccharide, and the O antigen (or O polysaccharide). O antigen is the outermost portion on LPS and serves as a protective layer against bacterial permeability, however, the sugar composition of O antigen varies widely between strains. The lipid A and core oligosaccharide vary less, and are more typically conserved within strains of the same species. Lipid A is the portion of LPS that contains endotoxin activity. It is typically a disaccharide decorated with multiple fatty acids. These hydrophobic fatty acid chains anchor the LPS into the bacterial membrane, and the rest of the LPS projects from the cell surface. The lipid A domain is responsible for much of the toxicity of Gram-negative bacteria. Typically, LPS in the blood is recognized as a significant pathogen associated molecular pattern (PAMP) and induces a profound pro-inflammatory response. LPS is the ligand for a membrane-bound receptor complex comprising CD14, MD2 and TLR4. TLR4 is a transmembrane protein that can signal through the MyD88 and TRIF pathways to stimulate the NF-κB pathway and result in the production of pro-inflammatory cytokines such as TNF-α and IL-1β, the result of which can be endotoxic shock, which can be fatal. LPS in the cytosol of mammalian cells can bind directly to the CARD domains of caspases 4, 5, and 11, leading to autoactivation and pyroptotic cell death (Hagar et al. (2015) *Cell Research* 25:149-150). The composition of lipid A and the toxigenicity of lipid A variants is well documented. For example, a monophosphorylated lipid A is much less inflammatory than lipid A with multiple phosphate groups. The number and length of the acyl chains on lipid A can also have a profound impact on the degree of toxicity. Canonical lipid A from *E. coli* has six acyl chains, and this hexa-acylation is potently toxic. *S. typhimurium* lipid A is similar to that of *E. coli*; it is a glucosamine disaccharide that carries four primary and two secondary hydroxyacyl chains (Raetz and Whitfield (2002) *Annu. Rev. Biochem.* 71:635-700).

As described above, msbB mutants of *S. typhimurium* cannot undergo the terminal myristoylation of its LPS and produce predominantly penta-acylated LPS that is significantly less toxic than hexa-acylated lipid A. The modification of lipid A with palmitate is catalyzed by palmitoyl transferase (PagP). Transcription of the pagP gene is under control of the PhoP/PhoQ system which is activated by low concentrations of magnesium, e.g., inside the SCV. Thus, the acyl content of *S. typhimurium* is variable, and with wild-type bacteria it can be hexa- or penta-acylated. The ability of *S. typhimurium* to palmitate its lipid A increases resistance to antimicrobial peptides that are secreted into phagolysosomes.

In wild type *S. typhimurium*, expression of pagP results in a lipid A that is hepta-acylated. In an msbB mutant (in which the terminal acyl chain of the lipid A cannot be added), the induction of pagP results in a hexa-acylated LPS (Kong et al. (2011) *Infection and Immunity* 79(12):5027-5038). Hexa-acylated LPS has been shown to be the most pro-inflammatory. While other groups have sought to exploit this pro-inflammatory signal, for example, by deletion of pagP to allow only hexa-acylated LPS to be produced (Felgner et al. (2016) *Gut Microbes* 7(2):171-177; Felgner et al. (2018) *Oncoimmunology* 7(2): e1382791), this can lead to poor tolerability, due to the TNF-α-mediated pro-inflammatory nature of the LPS and paradoxically less adaptive immunity (Kocijancic et al. (2017) *Oncotarget* 8(30):49988-50001).

LPS is a potent TLR-4 agonist that induces TNF-α and IL-6. The dose-limiting toxicities in the I.V. VNP20009 clinical trial (Toso et al. (2002) *J. Clin. Oncol.* 20(1):142-152) at 1E9 CFU/$m^2$ were cytokine mediated (fever, hypotension), with TNF-α levels >100,000 pg/ml and IL-6 levels >10,000 pg/ml in serum at 2 hr. Despite the msbB deletion in VNP20009 and its reduced pyrogenicity, the LPS still can be toxic at high doses, possibly due to the presence of hexa-acylated LPS. Thus, a $pagP^-/msbB^-$ strain is better tolerated at higher doses, as it cannot produce hexa-acylated LPS, and will allow for dosing in humans at or above 1E9 CFU/$m^2$. Higher dosing can lead to increased tumor colonization, enhancing the therapeutic efficacy of the immunostimulatory bacteria.

Provided herein, are live attenuated *Salmonella* strains, such as the exemplary strain of *S. typhimurium*, that only can produce penta-acylated LPS, that contain a deletion of the msbB gene (that prevents the terminal myristoylation of lipid A, as described above), and that further are modified by deletion of pagP (preventing palmitoylation). A strain modified to produce penta-acylated LPS allows for lower levels of pro-inflammatory cytokines, increased sensitivity to antimicrobial peptides, enhanced tolerability, and increased anti-tumor immunity when further modified to express interfering RNAs against immune checkpoints such as TREX1.

g. Deletions of SPI-1 and SPI-2 Genes

Figure 22:
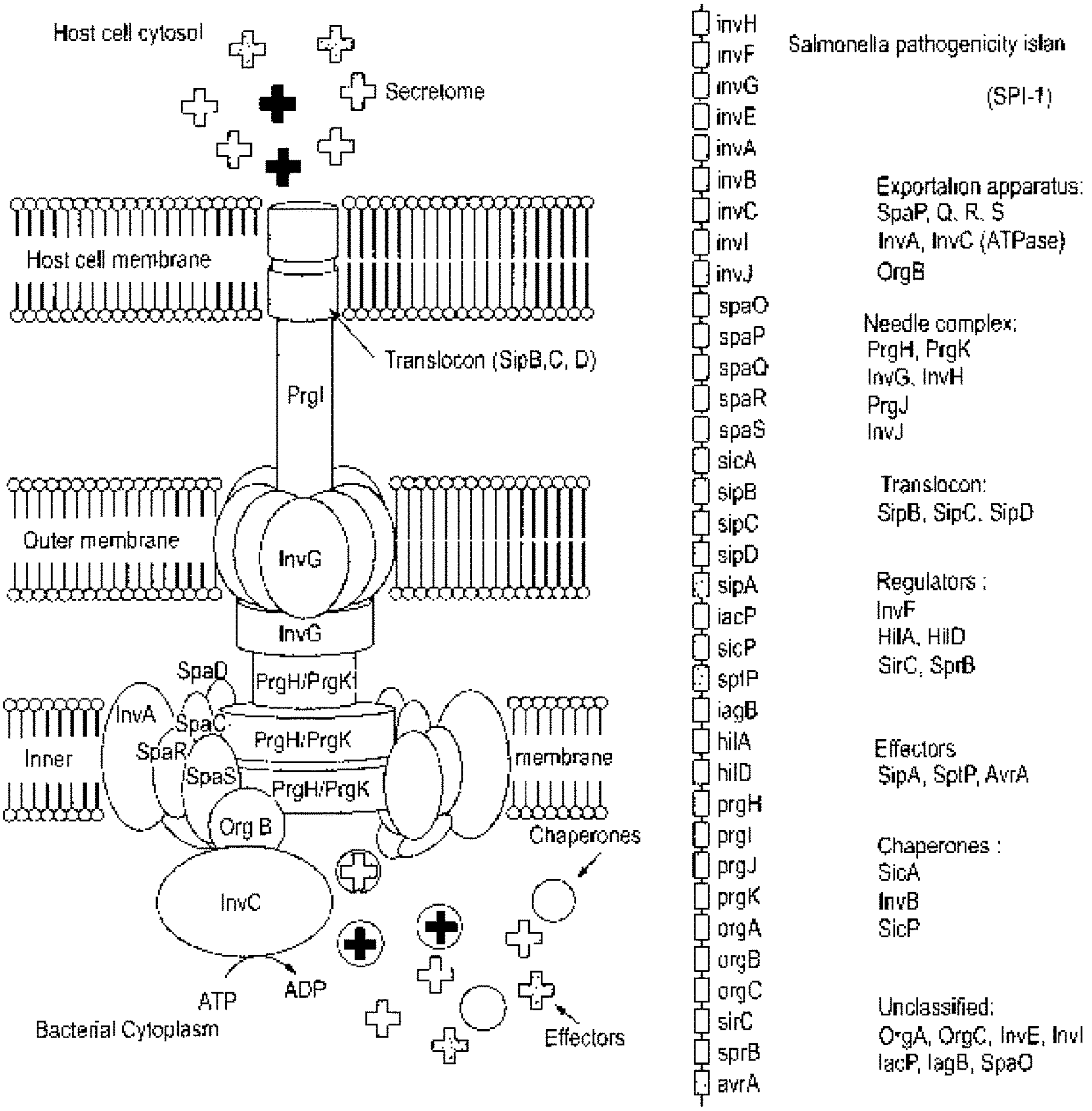
FIG. 22 depicts the SPI-1 T3SS, and the functional classification of SPI-1 encoded proteins (adapted from Kimbrough and Miller (2002) *Microbes Infect.* 4(1):75-82).
Figure 23:
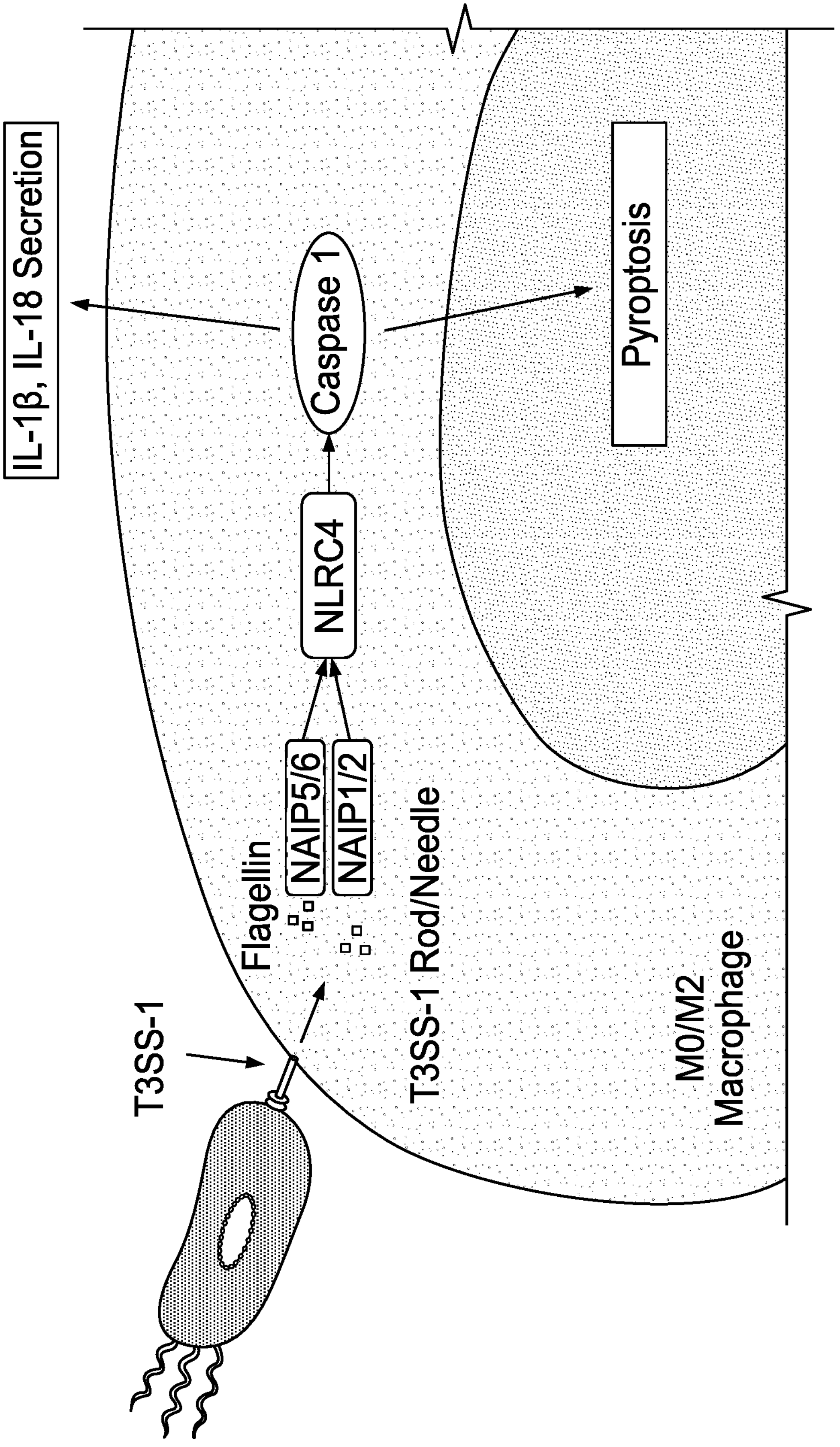
FIG. 23 depicts the effects of the SPI-1 T3SS on macrophages. Flagellin is detected by NAIP5/6, and the rod and needle proteins are detected by NAIP1/2, which leads to activation of the NLRC4 inflammasome and caspase-1, resulting in the release of IL-1β and IL-18, and pyroptosis.
Figure 24:
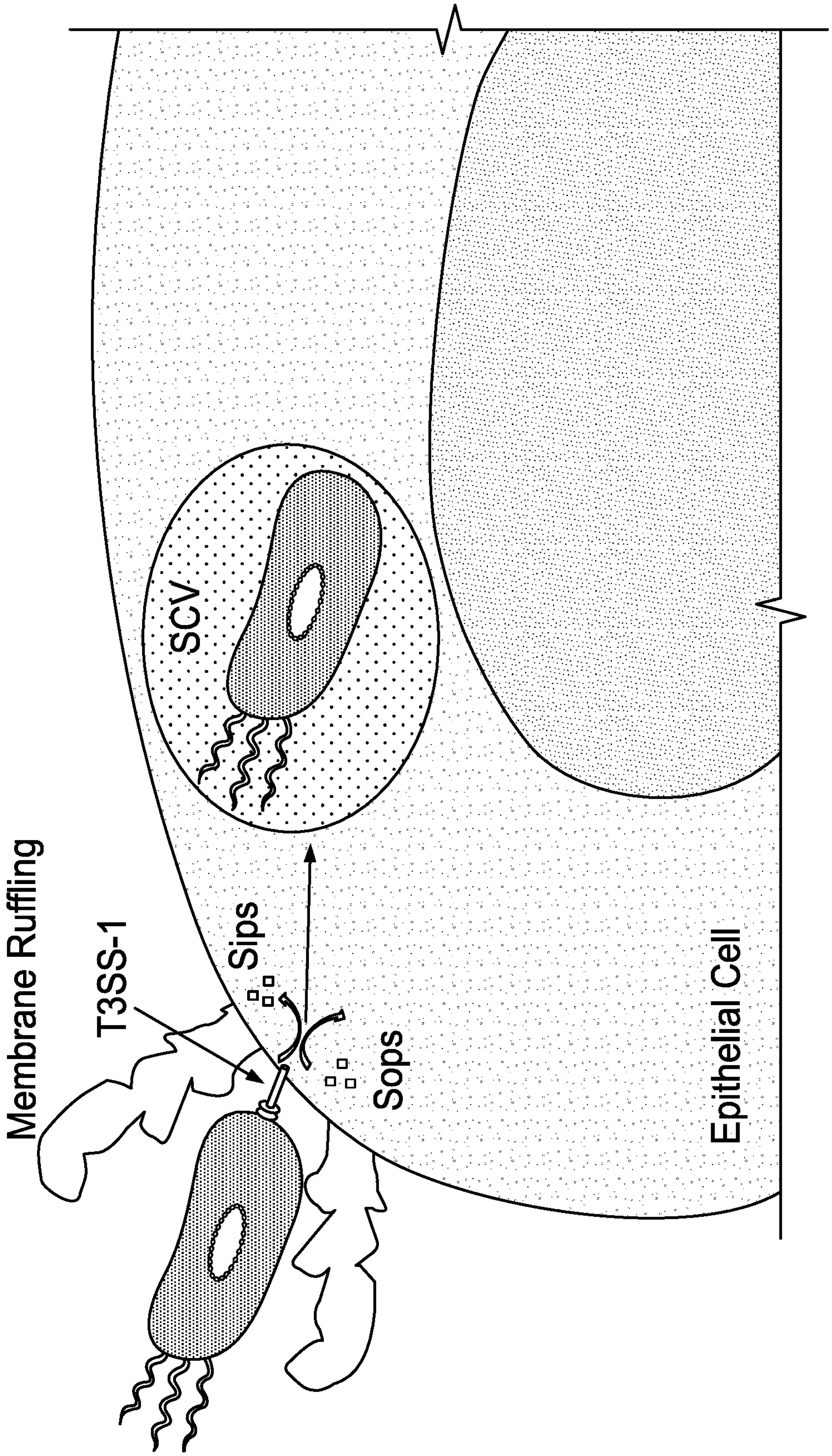
FIG. 24 depicts T3SS-1-mediated entry of the bacterium into the epithelial cell and the SCV.
Figure 25:
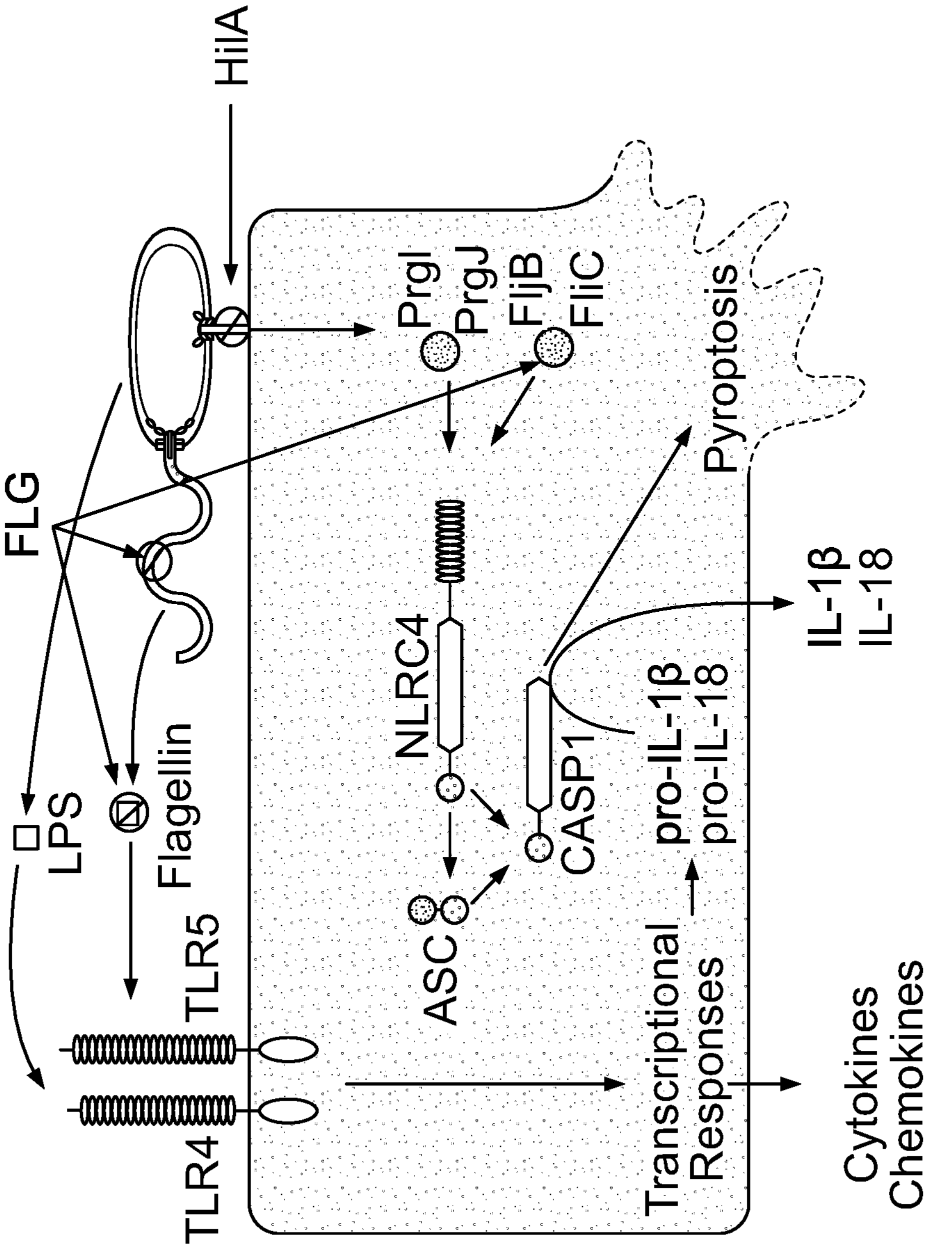
FIG. 25 depicts recognition of bacterial flagellin by TLR5, and recognition of bacterial LPS by TLR4, and the roles that flagellin (FLG), LPS, HilA, PrgI and PrgJ play in host cell infection, cytokine release, inflammasome activation, and pyroptosis.

As described above, pathogenesis, in certain bacterial species, including *Salmonella* species, such as *S. typhimurium*, involves a cluster of genes referred to as *Salmonella* pathogenicity islands (SPIs; see FIG. 22) The SPI designated SPI-1 mediates invasion of epithelial cells. The operons and genes and their functions are depicted in FIG. 22. SPI-1 genes include, but are not limited to: avrA, hilA, hilD, invA, invB, invC, invE, invF, invG, invH, invI, invJ, iacP, iagB, spaO, spaP, spaQ, spaR, spaS, orgA, orgB, orgC, prgH, prgI, prgJ, prgK, sicA, sicP, sipA, sipB, sipC, sipD, sirC, sopB, sopD, sopE, sopE2, sprB, and sptP. Deletion of one or more of these genes reduces or eliminates the ability of the bacterium to infect epithelial cells, but does not affect their ability to infect or invade phagocytic cells, including phagocytic immune cells.

*Salmonella* invades non-phagocytic intestinal epithelial cells using a type 3 secretion system (T3SS) encoded by the *Salmonella* pathogenicity island 1, which forms a needle-like structure that injects effector proteins directly into the cytosol of host cells. These effector proteins lead to rearrangement of the eukaryotic cell cytoskeleton to facilitate invasion of the intestinal epithelium, and also induces proinflammatory cytokines. The SPI-1 locus includes 39 genes that encode components of this invasion system (see, FIG. 22, reproduced from Kimbrough and Miller (2002) *Microbes Infect.* 4(1):75-82).

SPI-1 encodes a type 3 secretion system (T3SS) that is responsible for translocation of effector proteins into the cytosol of host cells that can cause actin rearrangements that lead to uptake of *Salmonella*. The SPI-1 T3SS is essential for crossing the gut epithelial layer, but is dispensable for infection when bacteria are injected parenterally. The injection of some proteins and the needle complex itself can also induce inflammasome activation and pyroptosis of phagocytic cells. This pro-inflammatory cell death can limit the initiation of a robust adaptive immune response by directly inducing the death of antigen-presenting cells (APCs), as well as modifying the cytokine milieu to prevent the generation of memory T-cells. SPI-1 genes comprise a number of operons including: sitABCD, sprB, avrA, hilC, orgABC, prgKJIH, hilD, hilA, iagB, sptP, sicC, iacP, sipADCB, sicA, spaOPQRS, invFGEABCIJ, and invH.

T3SSs are complexes that play a large role in the infectivity of Gram-negative bacteria, by injecting bacterial protein effectors directly into host cells in an ATP-dependent manner. T3SS complexes cross the inner and outer bacterial membranes and create a pore in eukaryotic cell membranes upon contact with a host cell. They consist of an exportation apparatus, a needle complex and a translocon at the tip of the needle (FIG. 22). The needle complex includes the needle protein PrgI, a basal body, which anchors the complex in the bacterial membranes and consists of the proteins PrgH, PrgK and InvG, and other proteins, including InvH, PrgJ (rod protein) and InvJ. The translocon, which forms the pore in the host cell, is a complex of the proteins SipB, SipC and SipD. The exportation apparatus, which allows for the translocation of the effector proteins, is comprised of the proteins SpaP, SpaQ, SpaR, SpaS, InvA, InvC and OrgB. A cytoplasmic sorting platform, which establishes the specific order of protein secretion, is composed of the proteins SpaO, OrgA and OrgB (Manon et al. (2012), *Salmonella*, Chapter 17, eds. Annous and Gurtler, Rijeka, pp. 339-364).

The effectors translocated into the host cell by T3SS-1 include SipA, SipC, SopB, SopD, SopE, SopE2 and SptP, which are essential for cell invasion. For example, *S. typhimurium* sipA mutants exhibit 60-80% decreased invasion, sipC deletion results in a 95% decrease in invasion, and sopB deletion results in a 50% decrease in invasion (Manon et al. (2012), *Salmonella*, Chapter 17, eds. Annous and Gurtler, Rijeka, pp. 339-364). Other effectors include AvrA, which controls *Salmonella*-induced inflammation. Chaperones, which bind secreted proteins and maintain them in a conformation that is competent for secretion, include SicA, InvB and SicP. Transcriptional regulators include HilA, HilD, InvF, SirC and SprB. Unclassified T3SS SPI-1 proteins, which have various functions in type III secretion, include OrgC, InvE, InvI, IacP and IagB (see, FIG. 22, adapted from Kimbrough et al. (2002) *Microbes Infect.* 4(1):75-82).

Thus, the inactivation of SPI-1-dependent invasion, through the inactivation or knockout of one or more genes involved in the SPI-1 pathway, eliminates the ability of the bacteria to infect epithelial cells. These genes include, but are not limited to, one more of: avrA, hilA, hilD, invA, invB, invC, invE, invF, invG, invH, invI, iacP, iagB, spaO, spaP, spaQ, spaR, spaS, orgA, orgB, orgC, prgH, prgI, prgJ, prgK, sicA, sicP, sipA, sipB, sipC, sipD, sirC, sopB, sopD, sopE, sopE2, sprB, and sptP.

*Salmonella* mutants lacking the T3SS-1 have been shown to invade numerous cell lines/types, by a T3SS-1 independent invasion mechanism, involving several proteins, including the invasins Rck, PagN and HlyE. The rck operon contains 6 open reading frames: pefI, srgD, srgA, srgB, rck and srgC. pefI encodes a transcriptional regulator of the pef operon, which is involved in the biosynthesis of the Pef fimbriae. These fimbriae are involved in biofilm formation, adhesion to murine small intestine and fluid accumulation in the infant mouse. SrgA oxidizes the disulfide bond of PefA, the major structural subunit of the Pef fimbriae. srgD encodes a putative transcriptional regulator; SrgD together with PefI work to induce a synergistic negative regulation of flagellar gene expression. srgB encodes a putative outer membrane protein, and srgC encodes a putative transcriptional regulator (Manon et al. (2012), *Salmonella*, Chapter 17, eds. Annous and Gurtler, Rijeka, pp. 339-364).

Rck is a 17 kDa outer membrane protein encoded by the large virulence plasmid of *S. Enteritidis* and *S. Typhimurium*, that induces adhesion to and invasion of epithelial cells, and confers a high level of resistance to neutralization by complement, by preventing the formation of the membrane attack complex. An rck mutant exhibited a 2-3 fold decrease in epithelial cell invasion compared to the wild-type strain, while Rck overexpression leads to increased invasion. Rck induces cell entry by a receptor-mediated process, promoting local actin remodeling and weak and closely adherent membrane extensions. Thus, *Salmonella* can enter cells by two distinct mechanisms: the Trigger mechanism mediated by the T3SS-1 complex, and a Zipper mechanism induced by Rck (Manon et al. (2012), *Salmonella*, Chapter 17, eds. Annous and Gurtler, Rijeka, pp. 339-364).

The invasin PagN is an outer membrane protein that has also been shown to play a role in *Salmonella* invasion. pagN expression is regulated by phoP. Specific stimuli, for example, acidified macrophage phagosome environments or low $Mg^{2+}$ concentrations, are sensed by PhoQ, which then activates PhoP to regulate specific genes. It has been shown that the deletion of pagN in *S. typhimurium* results in a 3-fold decrease in the invasion of enterocytes, without altering cell adhesion. Although the PagN-mediated entry mechanism is not fully understood, it has been shown that actin polymerization is required for invasion. Studies have shown that PagN is required for *Salmonella* survival in BALB/c mice, and that a pagN mutant is less competitive for colonizing the spleen of mice than the parent strain. Because pagN is activated by PhoP, it is mostly expressed intracellularly, where the SPI-1 island encoding T3SS-1 is down-regulated. It is thus possible that bacteria exiting epithelial cells or macrophages have an optimal level of PagN expression, but have low T3SS-1 expression, which can mediate subsequent interactions with other cells encountered following host cell destruction, indicating a role for PagN in *Salmonella* pathogenesis (Manon et al. (2012), *Salmonella*, Chapter 17, eds. Annous and Gurtler, Rijeka, pp. 339-364).

hlyE shares more than 90% sequence identity with the *E. coli* HlyE (ClyA) hemolysin. The HlyE protein lyses epithelial cells when exported from bacterial cells via outer membrane vesicle release, and is involved in epithelial cell invasion. HlyE also is involved in the establishment of systemic *Salmonella* infection (Manon et al. (2012), *Salmonella*, Chapter 17, eds. Annous and Gurtler, Rijeka, pp. 339-364).

Elimination of the ability to infect epithelial cells also can be achieved by engineering the immunostimulatory bacteria herein to contain knockouts or deletions of genes encoding proteins involved in SPI-1-independent invasion, such as one or more of the genes rck, pagN, hlyE, pefI, srgD, srgA, srgB, and srgC.

As described herein, provided are immunostimulatory bacteria that are modified so that they do not infect epithelial cells, but retain the ability to infect phagocytic cells, including tumor-resident immune cells, thereby effectively targeting the immunostimulatory bacteria to the tumor microenvironment. This is achieved by deleting or knocking out any of the proteins in SPI-1, including, but are not limited to, deletions of one more of: avrA, hilA, hilD, invA, invB, invC, invE, invF, invG, invH, invI, invJ, iacP, iagB, spaO, spaP, spaQ, spaR, spaS, orgA, orgB, orgC, prgH, prgI, prgJ, prgK, sicA, sicP, sipA, sipB, sipC, sipD, sirC, sopB, sopD, sopE, sopE2, sprB, and sptP, as well as one or more of rck, pagN, hlyE, pefI, srgD, srgA, srgB, and srgC.

The immunostimulatory bacteria that do not infect epithelial cells can be further modified as described here to encode products that stimulate the immune system, including, for example, cytokines. The bacteria generally have an asd deletion to render them unable to replicate in a mammalian host.

For example, provided are strains of *S. typhimurium* modified by deletion of one or more SPI-1 genes, and also modified by one or more of a purI deletion, an msbB deletion, and an asd deletion, and by delivering plasmids encoding proteins that stimulate the immune system, such as genes encoding immunostimulatory cytokines. For example, bacteria with deletions of a regulatory gene (e.g., hilA or invF) required for expression of the SPI-1-associated type 3 secretion system (T3SS-1), a T3SS-1 structural gene (e.g., invG or prgH), and/or a T3SS-1 effector gene (e.g., sipA or avrA) are provided. As discussed above, this secretion system is responsible for injecting effector proteins into the cytosol of non-phagocytic host cells such as epithelial cells that cause the uptake of the bacteria; deletion of one or more of these genes eliminates infection/invasion of epithelial cells. Deletion of one or more of the genes, such as hilA, provides immunostimulatory bacteria that can be administered intravenously or intratumorally, resulting in infection of phagocytic cells, which do not require the SPI-1 T3SS for uptake, and also prolongs the longevity of these phagocytic cells. The hilA mutation also reduces the quantity of pro-inflammatory cytokines, increasing the tolerability of the therapy, as well as the quality of the adaptive immune response.

*Salmonella* also have a *Salmonella* pathogenicity island 2 (SPI-2), encoding another T3SS that is activated following entry of the bacterium into the host cell, and interferes with phagosome maturation, resulting in the formation of a specialized *Salmonella*-containing vacuole (SCV), where the *Salmonella* resides during intracellular survival and replication. SPI-2 T3SS effectors include SseB, SseC, SseD and SpiC, which are responsible for assembly of the F-actin coat around intracellular bacteria; this actin coat promotes fusion of the SCV with actin-containing or actin-propelled vesicles, and prevents it from fusing with unfavorable compartments. SifA is responsible for the formation of *Salmonella*-induced filaments (SIFs), which are tubules that connect the individual SCVs in the infected cell. sifA is essential to maintaining the integrity of the SCV, and sifA mutants are released into the cytosol of host cells. SseF and SseG are components of the SPI-2 T3SS that are involved in SCV positioning and cellular trafficking processes that direct materials required for the bacterium's survival and replication to the SCV. SseF and SseG also are involved in SIF formation. Other SPI-2 T3SS effectors include PipB2, SopD2, and SseJ, which are involved in SIF and SCV formation, and maintenance of vacuole integrity; SpvC, SseL, and SspH1, which are involved in host immune signaling; and SteC, SspH2, SrfH/SseI and SpvB, which are involved in the formation of the SCV F-actin meshwork, in the migration of infected phagocytes, in the inhibition of actin polymerization, and in P-body disassembly in infected cells (Coburn et al. (2007) *Clinical Microbiology Reviews* 20(4):535-549; Figueira and Holden (2012) *Microbiology* 158:1147-1161).

The immunostimulatory bacteria herein can include deletions or modifications in any of the SPI-2 T3SS genes that affect the formation or integrity of the SCV and associated structures, such as SIFs. These mutants have an increased frequency of SCV escape and can replicate in the cytosol. For example, immunostimulatory bacteria, such as *Salmonella* species, engineered to escape the SCV are more efficient at delivering macromolecules, such as plasmids, as the lipid bilayer of the SCV is a potential barrier. This is achieved by deletion or mutation of genes required for *Salmonella* induced filament (SIF) formation, including, for example, sifA, sseJ, sseL, sopD2, pipB2, sseF, sseG, spvB, and steA.

The immunostimulatory bacteria that can escape the SCV can be further modified as described here to encode products that stimulate the immune system, including, for example, cytokines. The bacteria generally have an asd deletion to render them unable to replicate in a mammalian host.

h. Endonuclease (endA) Mutations to Increase Plasmid Delivery

The endA gene (for example, SEQ ID NO:250) encodes an endonuclease (for example, SEQ ID NO:251) that mediates degradation of double stranded DNA in the periplasm of Gram negative bacteria. Most common strains of laboratory *E. coli* are endA−, as a mutation in the endA gene allows for higher yields of plasmid DNA. This gene is conserved among species. To facilitate intact plasmid DNA delivery, the endA gene of the engineered immunostimulatory bacteria is deleted or mutated to prevent its endonuclease activity. Exemplary of such mutations is an E208K amino acid substitution (Durfee, et al. (2008) *J. Bacteriol.* 190(7):2597-2606) or a corresponding mutation in the species of interest. endA, including E208, is conserved among bacterial species, including *Salmonella*. Thus, the E208K mutation can be used to eliminate endonuclease activity in other species, including *Salmonella* species. Those of skill in the art can introduce other mutations or deletions to eliminate endA activity. Effecting this mutation or deleting or disrupting the gene to eliminate activity of the endA in the immunostimulatory bacteria herein, such as in *Salmonella*, increases efficiency of intact plasmid DNA delivery, thereby increasing expression of the RNAs, such as the shRNA and/or miRNA, targeting any or two or more of the immune checkpoints, encoded in the plasmid, thereby increasing RNAi-mediated knockdown of checkpoint genes and enhancing anti-tumor efficacy.

i. RIG-I Inhibition

Of the TLR-independent type I IFN pathways, one is mediated by host recognition of single-stranded (ss) and double-stranded (ds) RNA in the cytosol. These are sensed by RNA helicases, including retinoic acid-inducible gene I (RIG-I), melanoma differentiation-associated gene 5 (MDA-5), and through the IFN-β promoter stimulator 1 (IPS-1) adaptor protein-mediated phosphorylation of the IRF-3 transcription factor, leading to induction of type I IFN (Ireton and Gale (2011) *Viruses* 3(6):906-919). RIG-I recognizes dsRNA and ssRNA bearing 5'-triphosphates. This moiety can directly bind RIG-I, or be synthesized from a poly(dA-dT) template by the poly DNA-dependent RNA polymerase III (Pol III) (Chiu, Y. H. et al. (2009) Cell 138(3):576-91). A poly(dA-dT) template containing two AA dinucleotide sequences occurs at the U6 promoter transcription start site in a common lentiviral shRNA cloning vector. Its subsequent deletion in the plasmid prevents type I IFN activation (Pebernard et al. (2004) *Differentiation* 72:103-111). A RIG-I binding sequence can be included in the plasmids provided herein; inclusion can increase immunostimulation that increases anti-tumoral activity of the immunostimulatory bacteria herein.

j. DNase II Inhibition

Another nuclease responsible for degrading foreign and self DNA is DNase II, an endonuclease, which resides in the endosomal compartment and degrades DNA following apoptosis. Lack of DNase II (Dnase2a in mice) results in the accumulation of endosomal DNA that escapes to the cytosol and activates cGAS/STING signaling (Lan, Y. Y. et al. (2014) *Cell Rep.* 9(1):180-192). Similar to TREX1, DNase II-deficiency in humans presents with autoimmune type I interferonopathies. In cancer, dying tumor cells that are engulfed by tumor-resident macrophages prevent cGAS/STING activation and potential autoimmunity through DNase II digestion of DNA within the endosomal compartment (Ahn et al. (2018) *Cancer Cell* 33:862-873). Hence, embodiments of the immunostimulatory bacterial strains, as provided herein, encode RNAi, such as shRNA or miRNA that inhibit, suppress or disrupt expression of DNase II, which can inhibit DNase II in the tumor microenvironment, thereby provoking accumulation of endocytosed apoptotic tumor DNA in the cytosol, where it can act as a potent cGAS/STING agonist.

k. RNase 112 Inhibition

While TREX1 and DNase II function to clear aberrant DNA accumulation, RNase H2 functions similarly to eliminate pathogenic accumulation of RNA:DNA hybrids in the cytosol. Similar to TREX1, deficiencies in RNase H2 also contribute to the autoimmune phenotype of Aicardi-Goutières syndrome (Rabe, B. (2013) *J Mol. Med.* 91:1235-1240). Specifically, loss of RNase H2 and subsequent accumulation of RNA:DNA hybrids or genome-embedded ribonucleotide substrates has been shown to activate cGAS/STING signaling (Mackenzie et al. (2016) *EMBO J* 35(8):831-44). Hence, embodiments of the immunostimulatory bacterial strains, as provided herein, encode RNAi, such as shRNA or miRNA that inhibit, suppress or disrupt expression of RNase H2, to thereby inhibit RNase H2, resulting in tumor-derived RNA:DNA hybrids and derivatives thereof, which activate cGAS/STING signaling and anti-tumor immunity.

1. Stabilin-1/CLEVER-1 Inhibition

Another molecule expressed primarily on monocytes and involved in regulating immunity is stabilin-1 (gene name STAB1, also known as CLEVER-1, FEEL-1). Stabilin-1 is a type I transmembrane protein that is upregulated on endothelial cells and macrophages following inflammation, and in particular, on tumor-associated macrophages (Kzhyshkowska et al. (2006) *J. Cell. Mol. Med.* 10(3):635-649). Upon inflammatory activation, stabilin-1 acts as a scavenger and aids in wound healing and apoptotic body clearance, and can prevent tissue injury, such as liver fibrosis (Rantakari et al. (2016) *Proc. Natl. Acad. Sci. U.S.A.* 113 (33):9298-9303). Upregulation of stabilin-1 directly inhibits antigen-specific T cell responses, and knockdown by siRNA in monocytes was shown to enhance their pro-inflammatory function (Palani, S. et al. (2016) *J. Immunol.* 196:115-123). Hence, embodiments of the immunostimulatory bacterial strains, as provided herein, encode RNAi, such as shRNA or miRNA that inhibit, suppress or disrupt expression of Stabilin-1/CLEVER-1 in the tumor microenvironment, thereby enhancing the pro-inflammatory functions of tumor-resident macrophages.

5. Immunostimulatory Proteins

The immunostimulatory bacteria herein can be modified to encode an immunostimulatory protein that promotes or induces or enhances an anti-tumor response. The immunostimulatory protein can be encoded on a plasmid in the bacterium, under the control of a eukaryotic promoter, such as a promoter recognized by RNA polymerase II, for expression in a eukaryotic subject, particularly the subject for whom the immunostimulatory bacterium is to be administered, such as a human. The nucleic acid encoding the immunostimulatory protein can include, in addition to the eukaryotic promoter, other regulatory signals for expression or trafficking in the cells, such as for secretion or expression on the surface of a cell.

Immunostimulatory proteins are those that, in the appropriate environment, such as a tumor microenvironment (TME), can promote or participate in or enhance an anti-tumor response by the subject to whom the immunostimulatory bacterium is administered. Immunostimulatory proteins include, but are not limited to, cytokines, chemokines and co-stimulatory molecules. These include cytokines, such as, but not limited to, IL-2, IL-7, IL-12, IL-15, and IL-18; chemokines, such as, but not limited to, CCL3, CCL4, CCL5, CXCL9, CXCL10, and CXCL11; and/or co-stimulatory molecules, such as, but not limited to, CD40, CD40L, OX40, OX40L, 4-1BB, 4-1BBL, members of the TNF/TNFR superfamily, and members of the B7-CD28 family. Other such immunostimulatory proteins that are used for treatment of tumors or that can promote, enhance or otherwise increase or evoke an anti-tumor response, known to those of skill in the art, are contemplated for encoding in the immunostimulatory bacteria provided herein.

The genome of the immunostimulatory bacteria provided herein also can be modified to increase or promote infection of immune cells, particularly immune cells in the tumor microenvironment, such as phagocytic cells. The bacteria also can be modified to decrease pyroptosis in immune cells. The immunostimulatory bacteria include those, for example, that have modifications that disrupt/inhibit the SPI-1 pathway, such as disruption or deletion of hilA, and/or disruption/deletion of flagellin genes, rod protein, needle protein, and/or pagP as detailed and exemplified elsewhere herein.

Immunostimulatory Bacteria Encoding Cytokines and Chemokines

In some embodiments, the immunostimulatory bacteria herein are engineered to express cytokines to stimulate the immune system, including, but not limited to, IL-2, IL-7, IL-12 (IL-12p70 (IL-12p40+IL-12p35)), IL-15 (and the IL-15:IL-15R alpha chain complex), and IL-18. Cytokines stimulate immune effector cells and stromal cells at the tumor site, and enhance tumor cell recognition by cytotoxic cells. In some embodiments, the immunostimulatory bacteria can be engineered to express chemokines, such as, for example, CCL3, CCL4, CCL5, CXCL9, CXCL10 and CXCL11.

IL-2

Interleukin-2 (IL-2), which was the first cytokine approved for the treatment of cancer, is implicated in the activation of the immune system by several mechanisms, including the activation and promotion of CTL growth, the generation of lymphokine-activated killer (LAK) cells, the promotion of Treg cell growth and proliferation, the stimulation of TILs, and the promotion of T cell, B cell and NK cell proliferation and differentiation. Recombinant IL-2 (rIL-2) is FDA-approved for the treatment of metastatic renal cell carcinoma (RCC) and metastatic melanoma (Sheikhi et al. (2016) *Iran J. Immunol.* 13(3):148-166).

IL-7

IL-7, which is a member of the IL-2 superfamily, is implicated in the survival, proliferation and homeostasis of T cells. Mutations in the IL-7 receptor have been shown to result in the loss of T cells, and the development of severe combined immunodeficiency (SCID), highlighting the critical role that IL-7 plays in T-cell development. IL-7 is a homeostatic cytokine that provides continuous signals to resting naïve and memory T cells, and which accumulates during conditions of lymphopenia, leading to an increase in both T cell proliferation and T-cell repertoire diversity. In comparison to IL-2, IL-7 is selective for expanding $CD8^+$ T cells over $CD4^+$ $FOXP3^+$ regulatory T cells. Recombinant IL-7 has been shown to augment antigen-specific T cell responses following vaccination and adoptive cell therapy in mice. IL-7 also can play a role in promoting T-cell recovery following chemotherapy of hematopoietic stem cell transplantation. Early phase clinical trials on patients with advanced malignancy have shown that recombinant IL-7 is well-tolerated and has limited toxicity at biologically active doses (i.e., in which the numbers of circulating $CD4^+$ and $CD8^+$ T cells increased by 3-4 fold) (Lee, S. and Margolin, K. (2011) *Cancers* 3:3856-3893). IL-7 has been shown to possess antitumor effects in tumors such as gliomas, melanomas, lymphomas, leukemia, prostate cancer and glioblastoma, and the in vivo administration of IL-7 in murine models resulted in decreased cancer cell growth. IL-7 also has been shown to enhance the antitumor effects of IFN-γ in rat glioma tumors, and to induce the production of IL-1α, IL-1β and TNF-α by monocytes, which results in the inhibition of melanoma growth. Additionally, administration of recombinant IL-7 following the treatment of pediatric sarcomas resulted in the promotion of immune recovery (Lin et al. (2017) *Anticancer Research* 37:963-968).

IL-12 (IL-12p70 (IL-12p40+IL-12p35))

Bioactive IL-12 (IL-12p70), which promotes cell-mediated immunity, is a heterodimer, composed of p35 and p40 subunits, whereas IL-12p40 monomers and homodimers act as IL-12 antagonists. IL-12, which is secreted by antigen-presenting cells, promotes the secretion of IFN-γ from NK and T cells, inhibits tumor angiogenesis, results in the activation and proliferation of NK cells, $CD8^+$ T cells and $CD4^+$ T cells, enhances the differentiation of $CD4^+$ Th0 cells into Th1 cells, and promotes antibody-dependent cell-mediated cytotoxicity (ADCC) against tumor cells. IL-12 has been shown to exhibit antitumor effects in murine models of melanoma, colon carcinoma, mammary carcinoma and sarcoma (Kalinski et al. (2001) *Blood* 97:3466-3469; Sheikhi et al. (2016) *Iran J. Immunol.* 13(3):148-166; Lee, S. and Margolin, K. (2011) *Cancers* 3:3856-3893).

IL-15 and IL-15:IL-15Rα

IL-15 is structurally similar to IL-2, and while both IL-2 and IL-15 provide early stimulation for the proliferation and activation of T cells, IL-15 blocks IL-2 induced apoptosis, which is a process that leads to the elimination of stimulated T cells and induction of T-cell tolerance, limiting memory T cell responses and potentially limiting the therapeutic efficacy of IL-2 alone. IL-15 also supports the persistence of memory $CD8^+$ T cells for maintaining long-term antitumor immunity, and has demonstrated significant antitumor activity in pre-clinical murine models via the direct activation of $CD8^+$ effector T cells in an antigen-independent manner. In addition to $CD8^+$ T cells, IL-15 is responsible for the development, proliferation and activation of effector natural killer (NK) cells (Lee, S. and Margolin, K. (2011) *Cancers* 3:3856-3893; Han et al. (2011) *Cytokine* 56(3):804-810).

IL-15 and IL-15 receptor alpha (IL-15Ra) are coordinately expressed by antigen-presenting cells such as monocytes and dendritic cells, and IL-15 is presented in trans by IL-15Rα to the IL-15$\beta\gamma_C$ receptor complex expressed on the surfaces of $CD8^+$ T cells and NK cells. Soluble 1L-15:IL15-Rα complexes have been shown to modulate immune responses via the IL-15$\beta\gamma_C$ complex, and the biological activity of IL-15 has been shown to be increased 50-fold by administering it in a preformed complex of IL-15 and soluble IL-15Ra, which has an increased half-life compared to IL-15 alone. This significant increase in the therapeutic efficacy of IL-15 by pre-association with IL-15Rα has been demonstrated in murine tumor models (Han et al. (2011) *Cytokine* 56(3):804-810).

IL-18

IL-18 induces the secretion of IFN-γ by NK and $CD8^+$ T cells, enhancing their toxicity. IL-18 also activates macrophages and stimulates the development of Th1 helper $CD4^+$ T cells. IL-18 has shown promising anti-tumor activity in several preclinical mouse models. For example, administration of recombinant IL-18 (rIL-18) resulted in the regression of melanoma or sarcoma in syngeneic mice through the activation of $CD4^+$ T cells and/or NK cell-mediated responses. Other studies showed that IL-18 anti-tumor effects were mediated by IFN-γ and involved antiangiogenic mechanisms. The combination of IL-18 with other cytokines, such as IL-12, or with co-stimulatory molecules, such as CD80, enhances the IL-18-mediated anti-tumor effects. Phase I clinical trials in patients with advanced solid tumors and lymphomas showed that IL-18 administration was safe, and that it resulted in immune modulatory activity and in the increase of serum IFN-γ and GM-CSF levels in patients, and modest clinical responses. Clinical trials showed that IL-18 can be combined with other anticancer therapeutic agents, such as monoclonal antibodies, cytotoxic drugs or vaccines (Fabbi et al. (2015) *J. Leukoc. Biol.* 97:665-675; Lee, S. and Margolin, K. (2011) *Cancers* 3:3856-3893).

It was found that an attenuated strain of *Salmonella typhimurium*, engineered to express IL-18, inhibited the growth of S.C. tumors or pulmonary metastases in syngeneic mice without any toxic effects following systemic administration. Treatment with this engineered bacterium induced the accumulation of T cells, NK cells and granulocytes in tumors, and resulted in the intratumoral production of cytokines (Fabbi et al. (2015) *J. Leukoc. Biol.* 97:665-675).

Chemokines

Chemokines are a family of small cytokines that mediate leukocyte migration to areas of injury or inflammation and are involved in mediating immune and inflammatory responses. Chemokines are classified into four subfamilies, based on the position of cysteine residues in their sequences, namely XC-, CC-, CXC- and CX3C-chemokine ligands, or XCL, CCL, CXCL and CX3CL. The chemokine ligands bind to their cognate receptors and regulate the circulation, homing and retention of immune cells, with each chemokine ligand-receptor pair selectively regulating a certain type of immune cell. Different chemokines attract different leukocyte populations, and form a concentration gradient in vivo, with attracted immune cells moving through the gradient towards the higher concentration of chemokine (Argyle D. and Kitamura, T. (2018) *Front. Immunol.* 9:2629; Dubinett et al. (2010) *Cancer J.* 16(4):325-335). Chemokines can improve the antitumor immune response by increasing the infiltration of immune cells into the tumor, and facilitating the movement of antigen-presenting cells (APCs) to tumor-draining lymph nodes, which primes naïve T cells and B cells (Lechner et al. (2011) *Immunotherapy* 3(11):1317-1340). The immunostimulatory bacteria herein can be engineered to encode chemokines, including, but not limited to, CCL3, CCL4, CCL5, CXCL9, CXCL10 and CXCL11.

CCL3, CCL4, CCL5

CCL3, CCL4 and CCL5 share a high degree of homology, and bind to CCR5 (CCL3, CCL4 and CCL5) and CCR1 (CCL3 and CCL5) on several cell types, including immature DCs and T cells, in both humans and mice. Therapeutic T cells have been shown to induce chemotaxis of innate immune cells to tumor sites, via the tumor-specific secretion of CCL3, CCL4 and CCL5 (Dubinett et al. (2010) *Cancer J.* 16(4):325-335).

The induction of the T helper cell type 1 (Th1) response releases CCL3. In vivo and in vitro studies of mice have indicated that CCL3 is chemotactic for both neutrophils and monocytes; specifically, CCL3 can mediate myeloid precursor cell (MPC) mobilization from the bone marrow, and has MPC regulatory and stimulatory effects. Human ovarian carcinoma cells transfected with CCL3 showed enhanced T cell infiltration and macrophages within the tumor, leading to an improved antitumor response, and indicated that CCL3-mediated chemotaxis of neutrophils suppressed tumor growth. DCs transfected with the tumor antigen human melanoma-associated gene (MAGE)-1 that were recruited by CCL3 exhibited superior anti-tumor effects, including increased lymphocyte proliferation, cytolytic capacity, survival, and decreased tumor growth in a mouse model of melanoma. A combinatorial use of CCL3 with an antigen-specific platform for MAGE-1 has also been used in the treatment of gastric cancer. CCL3 production by CT26, a highly immunogenic murine colon tumor, slowed in vivo tumor growth; this process was indicated to be driven by the CCL3-dependent accumulation of natural killer (NK) cells, and thus, IFNγ, resulting in the production of CXCL9 and CXLC10 (Allen et al. (2017) *Oncoimmunology* 7(3): e1393598; Schaller et al. (2017) *Expert Rev. Clin. Immunol.* 13(11):1049-1060).

CCL3 has been used as an adjuvant for the treatment of cancer. Administration of a CCL3 active variant, ECI301, after radiofrequency ablation in mouse hepatocellular carcinoma increased tumor-specific responses, and this mechanism was further shown to be dependent on the expression of CCR1. CCL3 has also shown success as an adjuvant in systemic cancers, whereby mice vaccinated with CCL3 and IL-2 or granulocyte-macrophage colony-stimulating factor (GM-CSF) in a model of leukemia/lymphoma exhibited increased survival (Schaller et al. (2017) *Expert Rev. Clin. Immunol.* 13(11): 1049-1060).

CCL3 and CCL4 play a role in directing $CD8^+$ T cell infiltration into primary tumor sites in melanoma and colon cancers. Tumor production of CCL4 leads to the accumulation of $CD103^+$ DCs; suppression of CCL4 through a WNT/β-catenin-dependent pathway prevented $CD103^+$ DC infiltration of melanoma tumors (Spranger et al. (2015) *Nature* 523(7559):231-235). CCL3 was also shown to enhance $CD4^+$ and $CD8^+$ T cell infiltration to the primary tumor site in a mouse model of colon cancer (Allen et al. (2017) *Oncoimmunology* 7(3):e1393598).

The binding of CCL3 or CCL5 to their receptors (CCR1 and CCR5, respectively), moves immature DCs, monocytes and memory and T effector cells from the circulation into sites of inflammation or infection. For example, CCL5 expression in colorectal tumors contributes to T lymphocyte chemoattraction and survival. CCL3 and CCL5 have been used alone or in combination therapy to induce tumor regression and immunity in several preclinical models. For example, studies have shown that the subcutaneous injection of Chinese hamster ovary cells genetically modified to express CCL3 resulted in tumor inhibition and neutrophilic infiltration. In another study, a recombinant oncolytic adenovirus expressing CCL5 (Ad-RANTES-E1A) resulted in primary tumor regression and blocked metastasis in a mammary carcinoma murine model (Lechner et al. (2011) *Immunotherapy* 3(11):1317-1340). In a translational study of colorectal cancer, CCL5 induced an "antiviral response pattern" in macrophages. As a result of CXCR3 mediated migration of lymphocytes at the invasive margin of liver metastases in colorectal cancer, CCL5 is produced. Blockade of CCR5, the CCL5 receptor, results in tumor death, driven by macrophages producing IFN and reactive oxygen species. While macrophages are present in the tumor microenvironment, CCR5 inhibition induces a phenotypic shift from an M2 to an M1 phenotype. CCR5 blockade also leads to clinical responses in colorectal cancer patients (Halama et al. (2016) *Cancer Cell* 29(4):587-601).

CCL3, CCL4 and CCL5 can be used for treating conditions including lymphatic tumors, bladder cancer, colorectal cancer, lung cancer, melanoma, pancreatic cancer, ovarian cancer, cervical cancer, or liver cancer (see, e.g., U.S. Patent Publication No. US 2015/0232880; International Application Publication Nos. WO 2015/059303, WO 2017/043815, WO 2017/156349 and WO 2018/191654).

CXCL9, CXCL10, CXCL11

CXCL9 (MIG), CXCL10 (IP10) and CXCL11 (ITAC) are induced by the production of IFN-γ. These chemokines bind CXCR3, preferentially expressed on activated T cells, and function both angiostatically and in the recruitment and activation of leukocytes. Prognosis in colorectal cancer is strongly correlated to tumor-infiltrating T cells, particularly Th1 and $CD8^+$ effector T cells; high intratumoral expression of CXCL9, CXCL10 and CXCL11 is indicative of good prognosis. For example, in a sample of 163 patients with colon cancer, those with high levels of CXCL9 or CXCL11 showed increased post-operative survival, and patients with high CXC expression had significantly higher numbers of $CD3^+$ T-cells, $CD4^+$ T-helper cells, and $CD8^+$ cytotoxic T-cells. In liver metastases of colorectal cancer patients, CXCL9 and CXCL10 levels were increased at the invasive margin and correlated with effector T cell density. The stimulation of lymphocyte migration via the action of CXCL9 and CXCL10 on CXCR3 leads to the production of CCL5 at the invasive margin (see, e.g., Halama et al. (2016) *Cancer Cell* 29(4):587-601; Kistner et al. (2017) *Oncotarget* 8(52):89998-90012).

In vivo, CXCL9 functions as a chemoattractant for tumor-infiltrating lymphocytes, activated peripheral blood lymphocytes, natural killer (NK) cells and Th1 lymphocytes. CXCL9 also is critical for T cell-mediated suppression of cutaneous tumors. For example, when combined with systemic IL-2, CXCL9 has been shown to inhibit tumor growth via the increased intratumoral infiltration of $CXCR3^+$ mononuclear cells. In a murine model of colon carcinoma, a combination of the huKS1/4-IL-2 fusion protein with CXCL9 gene therapy achieved a superior anti-tumor effect and prolonged lifespan through the chemoattraction and activation of $CD8^+$ and $CD4^+$ T lymphocytes (Dubinett et al. (2010) *Cancer J.* 16(4):325-335; Ruehlmann et al. (2001) *Cancer Res.* 61(23):8498-8503).

CXCL10, produced by activated monocytes, fibroblasts, endothelial cells and keratinocytes, is chemotactic for activated T cells and can act as an inhibitor of angiogenesis in vivo. Expression of CXCL10 in colorectal tumors has been shown to contribute to cytotoxic T lymphocyte chemoattraction and longer survival. The administration of immunostimulatory cytokines, such as IL-12, has been shown to enhance the antitumor effects generated by CXCL10. A DC vaccine primed with a tumor cell lysate and transfected with CXCL10 had increased immunological protection and effectiveness in mice; the animals showed a resistance to a tumor challenge, a slowing of tumor growth and longer survival time. In vivo and in vitro studies in mice using the CXCL10-mucin-GPI fusion protein resulted in tumors with higher levels of recruited NK cells compared to tumors not treated with the fusion protein. Interferons (which can be produced by plasmacytoid dendritic cells; these cells are associated with primary melanoma lesions and can be recruited to a tumor site by CCL20) can act on tumor DC subsets, for example, $CD103^+$ DCs, which have been shown to produce CXCL9/10 in a mouse melanoma model and were associated with CXCL9/10 in human disease. CXCL10 also has shown higher expression in human metastatic melanoma samples relative to primary melanoma samples. Therapeutically, adjuvant IFN-$\alpha$ melanoma therapy upregulates CXCL10 production, whereas the chemotherapy agent cisplatin induces CXCL9 and CXCL10 (see, e.g., Dubinett et al. (2010) *Cancer J.* 16(4):325-335; Kuo et al. (2018) *Front. Med.* (*Lausanne*) 5:271; Li et al. (2007) *Scand. J. Immunol.* 65(1):8-13; Muenchmeier et al. (2013) *PLoS One* 8(8): e72749).

CXCL10/11 and CXCR3 expression has been established in human keratinocytes derived from basal cell carcinomas (BCCs). CXCL11 also is capable of promoting immunosuppressive indoleamine 2,3-dioxygenase (IDO) expression in human basal cell carcinoma as well as enhancing keratinocyte proliferation, which could reduce the anti-tumor activity of any infiltrating $CXCR3^+$ effector T cells (Kuo et al. (2018) Front. Med. (*Lausanne*) 5:271).

CXCL9, CXCL10 and CXCL11 can be encoded in oncolytic viruses for treating cancer (U.S. Patent Publication No. US 2015/0232880; International Application Publication No. WO 2015/059303). Pseudotyped oncolytic viruses or a genetically engineered bacterium encoding the gene for CXCL10 also can be used to treat cancer (International Application Publication Nos. WO 2018/006005 and WO 2018/129404).

Co-Stimulatory Molecules

Co-stimulatory molecules enhance the immune response against tumor cells, and co-stimulatory pathways are inhibited by tumor cells to promote tumorigenesis. The immunostimulatory bacteria herein can be engineered to express co-stimulatory molecules, such as, for example, CD40, CD40L, 4-1BB, 4-1BBL, OX40 (CD134), OX40L (CD252), other members of the TNFR superfamily (e.g., CD27, GITR, CD30, Fas receptor, TRAIL-R, TNF-R, HVEM, RANK), B7 and CD28. The immunostimulatory bacteria herein also can be engineered to express agonistic antibodies against co-stimulatory molecules to enhance the anti-tumor immune response.

TNF Receptor Superfamily

The TNF superfamily of ligands (TNF SF) and their receptors (TNFRSF) are involved in the proliferation, differentiation, activation and survival of tumor and immune effector cells. Members of this family include CD30, Fas-L, TRAIL-R and TNF-R, which induce apoptosis, and CD27, OX40L, CD40L, GITR-L and 4-1BBL, which regulate B and T cell immune responses. Other members include herpesvirus entry mediator (HVEM) and CD27. The expression of TNFSF and TNFRSF by the immunostimulatory bacteria herein can enhance the antitumor immune response. It has been shown, for example, that the expression of 4-1BBL in murine tumors enhances immunogenicity, and intratumoral injection of dendritic cells (DCs) with increased expression of OX40L can result in tumor rejection in murine models. Studies have also shown that injection of an adenovirus expressing recombinant GITR into B16 melanoma cells promotes T cell infiltration and reduces tumor volume. Stimulatory antibodies against molecules such as 4-1BB, OX40 and GITR also can be encoded by the immunostimulatory bacteria to stimulate the immune system. For example, agonistic anti-4-1BB monoclonal antibodies have been shown to enhance anti-tumor CTL responses, and agonistic anti-OX40 antibodies have been shown to increase anti-tumor activity in transplantable tumor models. Additionally, agonistic anti-GITR antibodies have been shown to enhance anti-tumor responses and immunity (Lechner et al. (2011) *Immunotherapy* 3(11):1317-1340; Peggs et al. (2009) *Clinical and Experimental Immunology* 157:9-19).

CD40 and CD40L

CD40, which is a member of the TNF receptor superfamily, is expressed by APCs and B cells, while its ligand, CD40L (CD154), is expressed by activated T cells. Interaction between CD40 and CD40L stimulates B cells to produce cytokines, resulting in T cell activation and tumor cell death. Studies have shown that antitumor immune responses are impaired with reduced expression of CD40L on T cells or CD40 on dendritic cells. CD40 is expressed on the surface of several B-cell tumors, such as follicular lymphoma, Burkitt lymphoma, lymphoblastic leukemia, and chronic lymphocytic leukemia, and its interaction with CD40L has been shown to increase the expression of B7-1/CD80, B7-2/CD86 and HLA class II molecules in the $CD40^+$ tumor cells, as well as enhance their antigen-presenting abilities. Transgenic expression of CD40L in a murine model of multiple myeloma resulted in the induction of $CD4^+$ and $CD8^+$ T cells, local and systemic antitumor immune responses and reduced tumor growth. Anti-CD40 agonistic antibodies also induced anti-tumor T cell responses (Marin-Acevedo et al. (2018) *Journal of Hematology & Oncology* 11:39; Dotti et al. (2002) *Blood* 100(1):200-207; Murugaiyan et al. (2007) *J. Immunol.* 178:2047-2055).

4-1BB and 4-1BBL 4-1BB (CD137) is an inducible co-stimulatory receptor that is expressed by T cells, NK cells and APCs, including DCs, B cells and monocytes, which binds its ligand, 4-1BBL to trigger immune cell proliferation and activation. 4-1BB results in longer and more wide spread responses of activated T cells. Anti-4-1BB agonists and 4-1BBL fusion proteins have been shown to increase immune-mediated antitumor activity, for example, against sarcoma and mastocytoma tumors, mediated by $CD4^+$ and $CD^+$ T cells and tumor-specific CTL activity (Lechner et al. (2011) *Immunotherapy* 3(11):1317-1340; Marin-Acevedo et al. (2018) *Journal of Hematology & Oncology* 11:39).

OX40 and OX40L

OX40 (CD134) is a member of the TNF receptor superfamily that is expressed on activated effector T cells, while its ligand, OX40L is expressed on APCs, including DCs, B cells and macrophages, following activation by TLR agonists and CD40-CD40L signaling. OX40-OX40L signaling results in the activation, potentiation, proliferation and survival of T cells, as well as the modulation of NK cell function and inhibition of the suppressive activity of Tregs.

Signaling through OX40 also results in the secretion of cytokines (IL-2, IL-4, IL-5 and IFN-γ), boosting Th1 and Th2 cell responses. The recognition of tumor antigens by TILs results in increased expression of OX40 by the TILs, which has been correlated with improved prognosis. Studies have demonstrated that treatment with anti-OX40 agonist antibodies or Fc-OX40L fusion proteins results in enhanced tumor-specific $CD4^+$ T cell responses and increased survival in murine models of melanoma, sarcoma, colon carcinoma and breast cancer, while Fc-OX40L incorporated into tumor cell vaccines protected mice from subsequent challenge with breast carcinoma cells (Lechner et al. (2011) *Immunotherapy* 3(11):1317-1340; Marin-Acevedo et al. (2018) *Journal of Hematology* & *Oncology* 11:39).

B7-CD28 Family

CD28 is a costimulatory molecule expressed on the surface of T cells that acts as a receptor for B7-1 (CD80) and B7-2 (CD86), which are co-stimulatory molecules expressed on antigen-presenting cells. CD28-B7 signaling is required for T cell activation and survival, and prevention of T cell anergy, and results in the production of interleukins such as IL-6.

Optimal T-cell priming requires two signals: (1) T-cell receptor (TCR) recognition of WIC-presented antigens and (2) co-stimulatory signals resulting from the ligation of T-cell CD28 with B7-1 (CD80) or B7-2 (CD86) expressed on APCs. Following T cell activation, CTLA-4 receptors are induced, which then outcompete CD28 for binding to B7-1 and B7-2 ligands. Antigen presentation by tumor cells is poor due to their lack of expression of costimulatory molecules such as B7-1/CD80 and B7-2/CD86, resulting in a failure to activate the T-cell receptor complex. As a result, upregulation of these molecules on the surfaces of tumor cells can enhance their immunogenicity. Immunotherapy of solid tumors and hematologic malignancies has been successfully induced by B7, for example, via tumor cell expression of B7, or soluble B7-immunoglobulin fusion proteins. The viral-mediated tumor expression of B7, in combination with other co-stimulatory ligands such as ICAM-3 and LFA-3, has been successful in preclinical and clinical trials for the treatment of chronic lymphocytic leukemia and metastatic melanoma. Additionally, soluble B7 fusion proteins have demonstrated promising results in the immunotherapy of solid tumors as single agent immunotherapies (Lechner et al. (2011) *Immunotherapy* 3(11):1317-1340; Dotti et al. (2002) *Blood* 100(1):200-207).

6. Modifications that Increase Uptake of Gram-Negative Bacteria, Such as *Salmonella*, by Immune Cells and Reduce Immune Cell Death The genome of the immunostimulatory bacteria provided herein can be modified to increase or promote infection of immune cells, particularly immune cells in the tumor microenvironment, such as phagocytic cells. This includes reducing infection of non-immune cells, such as epithelial cells, or increasing infection of immune cells. The bacteria also can be modified to decrease pyroptosis in immune cells. Numerous modifications of the bacterial genome can do one or both of increasing infection of immune cells and decreasing pyroptosis. The immunostimulatory bacteria provided herein include such modifications, for example, deletions and/or disruptions of genes involved in the SPI-1 T3SS pathway, such as disruption or deletion of hilA, and/or disruption/deletion of genes encoding flagellin, rod protein and needle protein.

The invasive phenotype of Gram-negative bacteria, such as *Salmonella*, can result from the activity of genes encoded in pathways that promote the invasion of host cells. The invasion-associated *Salmonella* pathogenicity island-1 (SPI-1) of *Salmonella* is exemplary. SPI-1 includes the type 3 secretion system (T3SS), that is responsible for translocation of effector proteins into the cytosol of host cells. These proteins can cause actin rearrangements that lead to the uptake of *Salmonella*. T3SS effectors mediate the uptake of *S. typhimurium* into non-phagocytic host cells, such as epithelial cells. The SPI-1 T3SS has been shown to be essential for crossing the gut epithelial layer, but is dispensable for infection when bacteria are injected parenterally, for example. SPI-1 mutants have defects in epithelial cell invasion, dramatically reducing oral virulence, but are taken up normally by phagocytic cells, such as macrophages (Kong et al. (2012) *Proc. Natl. Acad. Sci. U.S.A.* 109(47):19414-19419). The immunostimulatory *S. typhimurium* strains provided herein can be engineered with mutations in SPI-1 T3SS genes, preventing their uptake by epithelial cells, and focusing them to immune cells such as macrophages, enhancing the anti-tumor immune response.

T3SS effectors also activate the NLRC4 inflammasome in macrophages, activating caspase-1 and leading to cell death via pyroptosis. Pyroptosis is a highly inflammatory form of programmed cell that occurs most frequently following infection with intracellular pathogens, and plays a role in the antimicrobial response. This pro-inflammatory cell death can limit the initiation of a robust adaptive immune response by directly inducing the death of antigen-presenting cells (APCs), as well as modifying the cytokine milieu to prevent the generation of memory T-cells. SPI-1 induces pyroptosis by injecting flagellin, needle and rod proteins (PrgI/J), while the extracellular flagellin stimulates TLR5 signaling. Thus, engineering the immunostimulatory bacteria herein to contain mutations in the genes involved in pyroptosis can enhance the anti-tumor immune effect by reducing cell death in immune cells such as macrophages.

Macrophage Pyroptosis

The macrophage NLRC4 inflammasome, which plays a role in the innate immune and antimicrobial responses, is a large multi-protein complex that recognizes cytosolic pathogens and provides for the autocatalytic activation of caspase-1. Activation of caspase-1 induces maturation and release of the pro-inflammatory cytokines IL-1β and IL-18, and triggers pyroptosis, a rapid inflammatory form of macrophage cell death. Infection by certain Gram-negative bacteria encoding type 3 or 4 secretion systems, such as *Salmonella typhimurium* and *Pseudomonas aeruginosa*, triggers the activation of the NLRC4 inflammasome upon recognition of bacterial ligands such as needle protein, rod protein and flagellin, following translocation into the host cell cytosol by the Stm pathogenicity island-1 type III secretion system (SPI-1 T3SS). Pyroptosis is not limited to macrophages; caspase-1-dependent death has been observed in dendritic cells following infection with *Salmonella* (Li et al. (2016) *Scientific Reports* 6:37447; Chen et al. (2014) *Cell Reports* 8:570-582; Fink and Cookson (2007) *Cellular Microbiology* 9(11):2562-2570). As shown herein, the knock-out of genes in the *Salmonella* genome involved in the induction of pyroptosis enhances the anti-tumor immune response. This prevents the loss of immune cells, including macrophages, following bacterial infection. For example, genes encoding hilA, rod protein (PrgJ), needle protein (PrgI), flagellin and/or QseC can be knocked out/disrupted in the immunostimulatory bacteria provided herein.

hilA

The invasion-associated *Salmonella* pathogenicity island-1 (SPI-1), including the type 3 secretion system (T3SS), is responsible for the translocation of effector proteins into the cytosol of host cells, causing actin rearrangements that lead to the uptake of *Salmonella*. hilA is a transcriptional activator for SPI-1 genes, and its expression is regulated by environmental signals such as, for example, oxygen, osmolarity, pH and growth phase. Suboptimal conditions repress the expression of hilA, thereby suppressing the invasive phenotype of the bacterium (Kong et al. (2012) *Proc. Natl. Acad. Sci. U.S.A.* 109(47):19414-19419). T3SS effectors mediate the uptake of *S. typhimurium* into non-phagocytic host cells, such as epithelial cells. The SPI-1 T3SS is essential for crossing the gut epithelial layer, but is dispensable for infection, such as when bacteria are injected parenterally. SPI-1 mutants have defects in epithelial cell invasion, reducing oral virulence, but are taken up normally by phagocytic cells, such as macrophages. The immunostimulatory bacteria provided herein include those with deletion or disruption of the hilA gene and/or other genes in the T3SS pathway. When these bacteria are administered, such as intravenously or intratumorally, infection is focused towards phagocytic cells, such as macrophages and dendritic cells, that do not require the SPI-1 T3SS for uptake. This enhances the safety profile of the immunostimulatory bacteria provided herein. It prevents off-target cell invasion and prevents fecal-oral transmission.

In addition to reducing the uptake of *Salmonella* by non-phagocytic cells, such as epithelial cells, deletion or disruption of hilA and/or other genes in this pathway also prolongs the longevity of the phagocytic cells, by preventing pyroptosis in macrophages, thus, inducing less cell death in human macrophages compared to bacteria that do not contain a deletion in hilA. For example, hilA deficient *Salmonella* strains prevent pyroptosis by preventing inflammasome activation, but maintain TLR5 signaling. hilA deletion/disruption also allows for the prolonged secretion of cytokines, such as those encoded by the immunostimulatory bacteria provided herein, and for macrophage trafficking to tumors, thus improving the efficacy of the immunostimulatory bacteria. For example, in comparison to *S. typhimurium* containing intact hilA, such as VNP20009, the hilA deletion mutants, exemplified herein, further reduce the quantity of pro-inflammatory cytokines, such as IL-6, increasing the tolerability of the therapy, as well as the quality of the adaptive immune response.

Flagellin

Bacterial, such as *Salmonella*, flagellin, in addition to SPI-1 T3SS, is necessary for triggering pyroptosis in macrophages, and can be detected by the macrophage NLRC4 inflammasome. Flagellin, which is the major component of flagellum, is recognized by TLR5. *Salmonella* encodes two flagellin genes, fliC and fljB; elimination of flagellin subunits decreases pyroptosis in macrophages. For example, *S. typhimurium* with deletions in fliC and fljB resulted in significantly reduced IL-1β secretion compared to the wild-type strain, whereas cellular uptake and intracellular replication of the bacterium remained unaffected. This demonstrates that flagellin plays a significant role in inflammasome activation. Additionally, *S. typhimurium* strains engineered to constitutively express FliC were found to induce macrophage pyroptosis (Li et al. (2016) *Scientific Reports* 6:37447; Fink and Cookson (2007) *Cellular Microbiology* 9(11):2562-2570; Winter et al. (2015) *Infect. Immun.* 83(4): 1546-1555). The genome of the immunostimulatory bacteria herein can be modified to delete or mutate the flagellin genes fliC and fljB in *S. typhimurium*, leading to decreased cell death of tumor resident immune cells, such as macrophages, and enhancing the antitumor immune response of the immunostimulatory bacteria.

Rod Protein (PrgJ)

NLRC4 also detects a flagellated *S. typhimurium*. The flagellin-independent response was discovered to be due to the detection of PrgJ, which is the SPI-1 T3SS rod protein in *S. typhimurium*. Delivery of purified PrgJ protein to the macrophage cytosol resulted in rapid NLRC4-dependent caspase-1 activation, as well as secretion of IL-1β, similar to the effects induced by flagellin (Miao et al. (2010) *Proc. Natl. Acad. Sci. U.S.A.* 107(7):3076-3080). Thus, the mutation or knockout of the gene encoding PrgJ in *S. typhimurium* can reduce macrophage pyroptosis, which enhances the antitumor immune effect of the immunostimulatory bacteria, by preserving immune cells that are susceptible to being killed by the bacteria.

Needle Protein (PrgI)

PrgI, which is the SPI-1 T3SS needle protein in *S. typhimurium*, also is recognized by, and activates, NLRC4. The delivery of *S. typhimurium* PrgI to the cytosol of human primary monocyte-derived macrophages resulted in IL-1β secretion and subsequent cell death, while a *Salmonella* mutant that expresses PrgI but not flagellin was shown to activate the inflammasome in primary monocyte-derived macrophages at later time points than strains expressing flagellin (Kortmann et al. (2015) *J. Immunol.* 195:815-819). The immunostimulatory bacteria provided herein can be modified to mutate or delete the gene encoding needle protein in *S. typhimurium*, preventing immune cell pyroptosis, and enhancing the antitumor immune effect.

QseC

QseC is a highly conserved membrane histidine sensor kinase that is found in many Gram-negative bacteria, responds to the environment and regulates the expression of several virulence factors, including the flhDC gene that encodes the master regulator of flagellum biosynthesis in *S. typhimurium*; the sopB gene, which encodes a protein that plays a role in the invasion of non-phagocytic cells, the early maturation and regulation of trafficking of the *Salmonella*-containing vacuole (SCV), and the inhibition of SCV-lysosome fusion; and the sifA gene, which is required for SCV maintenance and membrane integrity. It has been shown that selective inhibition of QseC by LED209 inhibits bacterial virulence without suppressing *S. typhimurium* growth, by inhibiting the QseC-mediated activation of virulence-related gene expression (e.g., flhDC, sifA, and sopB), and partially protects mice from death following infection with *S. typhimurium* or *Francisella tularensis*. QseC blockade was found to inhibit caspase-1 activation, IL-1β release, and *S. typhimurium*-induced pyroptosis of macrophages, by inhibiting excess inflammasome activation in the infected macrophages. Inhibition of QseC also suppressed flagellar gene expression and motility, and suppressed the invasion and replication capacities of *S. typhimurium* in epithelial cells (Li et al. (2016) *Scientific Reports* 6:37447). Thus, modification of the immunostimulatory bacteria herein, to mutate or knockout the gene encoding QseC, can enhance the antitumor immune response by focusing *S. typhimurium* infection to non-epithelial cells, and by reducing cell death in immune cells, such as by preventing pyroptosis in macrophages.

7. Bacterial Culture Conditions

Culture conditions for bacteria can influence their gene expression. It has been documented that *S. typhimurium* can induce rapid pro-inflammatory caspase-dependent cell death of macrophages, but not epithelial cells, within 30 to 60 min of infection by a mechanism involving the SPI-1 and its associated T3SS-1 (Lundberg et. al (1999) *Journal of Bacteriology* 181(11):3433-3437). It is now known that this cell death is mediated by activation of the inflammasome that subsequently activates caspase-1, which promotes the maturation and release of IL-1β and IL-18 and initiates a novel form of cell death called pyroptosis (Broz and Monack (2011) *Immunol. Rev.* 243(1):174-190). This pyroptotic activity can be induced by using log phase bacteria, whereas stationary phase bacteria do not induce this rapid cell death in macrophages. The SPI-1 genes are induced during log phase growth. Thus, by harvesting *S. typhimurium* to be used therapeutically at stationary phase, rapid pyroptosis of macrophages can be prevented. Macrophages are important mediators of the innate immune system and they can act to secrete cytokines that are critical for establishing appropriate anti-tumor responses. In addition, limiting pro-inflammatory cytokines such as IL-1β and IL-18 secretion will improve the tolerability of administered *S. typhimurium* therapy. As provided herein, immunostimulatory *S. typhimurium* harvested at stationary phase will be used to induce anti-tumor responses.

E. Bacterial Attenuation and Colonization

1. Deletion of Flagellin (fliC/fljB)

Provided are immunostimulatory bacteria, such as the *Salmonella* species *S. typhimurium*, engineered to lack both flagellin subunits fliC and fljB, to reduce pro-inflammatory signaling. For example, as shown herein, a *Salmonella* strain lacking msbB, which results in reduced TNF-alpha induction, is combined with fliC and fljB knockouts. The resulting *Salmonella* strain has a combined reduction in TNF-alpha induction and reduction in TLR5 recognition. These modifications, $msbB^-$, $fliC^-$ and $fljB^-$, can be combined with a bacterial plasmid, optionally containing CpGs, and also a cDNA expression cassette to provide expression of a therapeutic protein under the control of a eukaryotic promoter, such as for example, an immunostimulatory protein, such as a cytokine or chemokine, such as IL-2, and/or also inhibitory molecules, such as antibodies, including antibody fragments, such as nanobodies, and/or RNAi molecule(s), targeting an immune checkpoint, such as TREX1, PD-L1, VISTA, SIRP-alpha, TGF-beta, beta-catenin, CD47, VEGF, and combinations thereof. The resulting bacteria have reduced proinflammatory signaling, and robust anti-tumor activity.

For example, as exemplified herein, a $fliC^-$ and $fljB^-$ double mutant was constructed in the asd-deleted strain of *S. typhimurium* strain VNP20009 or in a wild-type *Salmonella typhimurium*, such as one having all of the identifying characteristics of the strain deposited under ATCC accession no. 14028. VNP20009, which is a derivative of ATCC 14028, was attenuated for virulence by disruption of purI/purM, and was also engineered to contain an msbB deletion that results in production of a lipid A subunit of LPS that is less toxigenic than wild-type lipid A. This results in reduced TNF-α production in the mouse model after intravenous administration, compared to strains with wild-type lipid A.

A $fliC^-$ and $fljB^-$ double mutant was constructed on a wild-type strain of *S. typhimurium* and also engineered to contain the asd, purI/purM and msbB deletions. The bacterium is optionally $pagP^-$. The resulting strains are exemplary of strains that are attenuated for bacterial inflammation by modification of lipid A to reduce TLR2/4 signaling, and deletion of the flagellin subunits to reduce TLR5 recognition and inflammasome induction. Deletion of the flagellin subunits combined with modification of the LPS allows for greater tolerability in the host, and directs the immunostimulatory response towards production of immunostimulatory proteins. The delivery of RNA interference by the modified bacteria against desired targets in the TME elicits an anti-tumor response and promotes an adaptive immune response to the tumor.

2. Deletion of Genes in the LPS Biosynthetic Pathway

The LPS of Gram-negative bacteria is the major component of the outer leaflet of the bacterial membrane. It is composed of three major parts, lipid A, a nonrepeating core oligosaccharide, and the O antigen (or O polysaccharide). O antigen is the outermost portion on LPS and serves as a protective layer against bacterial permeability, however, the sugar composition of O antigen varies widely between strains. The lipid A and core oligosaccharide vary less, and are more typically conserved within strains of the same species. Lipid A is the portion of LPS that contains endotoxin activity. It is typically a disaccharide decorated with multiple fatty acids. These hydrophobic fatty acid chains anchor the LPS into the bacterial membrane, and the rest of the LPS projects from the cell surface. The lipid A domain is responsible for much of the toxicity of Gram-negative bacteria. Typically, LPS in the blood is recognized as a significant pathogen associated molecular pattern (PAMP), and induces a profound pro-inflammatory response. LPS is the ligand for a membrane-bound receptor complex comprising CD14, MD2 and TLR4. TLR4 is a transmembrane protein that can signal through the MyD88 and TRIF pathways to stimulate the NF-κB pathway and result in the production of pro-inflammatory cytokines such as TNF-α and IL-1β, the result of which can be endotoxic shock, which can be fatal. LPS in the cytosol of mammalian cells can bind directly to the CARD domains of caspases 4, 5, and 11, leading to autoactivation and pyroptotic cell death (Hagar et al. (2015) *Cell Research* 25:149-150). The composition of lipid A and the toxigenicity of lipid A variants is well documented. For example, a monophosphorylated lipid A is much less inflammatory than lipid A with multiple phosphate groups. The number and length of the acyl chains on lipid A can also have a profound impact on the degree of toxicity. Canonical lipid A from *E. coli* has six acyl chains, and this hexa-acylation is potently toxic. *S. typhimurium* lipid A is similar to that of *E. coli*; it is a glucosamine disaccharide that carries four primary and two secondary hydroxyacyl chains (Raetz and Whitfield (2002) *Annu. Rev. Biochem.* 71:635-700). As described above, $msbB^-$ mutants of *S. typhimurium* cannot undergo the terminal myristoylation of its LPS and produce predominantly penta-acylated lipid A that is significantly less toxic than hexa-acylated lipid A. The modification of lipid A with palmitate is catalyzed by palmitoyl transferase (PagP). Transcription of the pagP gene is under control of the phoP/phoQ system, which is activated by low concentrations of magnesium, e.g., inside the SCV. Thus, the acyl content of *S. typhimurium* is variable, and with wild-type bacteria, it can be hexa- or penta-acylated. The ability of *S. typhimurium* to palmitate its lipid A increases resistance to antimicrobial peptides that are secreted into phagolysosomes.

In wild-type *S. typhimurium*, expression of pagP results in a lipid A that is hepta-acylated. In an $msbB^-$ mutant (in which the terminal acyl chain of the lipid A cannot be added), the induction of pagP results in a hexa-acylated LPS (Kong et al. (2011) *Infection and Immunity* 79(12):5027-5038). Hexa-acylated LPS has been shown to be the most pro-inflammatory. While other groups have sought to exploit this pro-inflammatory signal, for example, by deletion of pagP to allow only hexa-acylated LPS to be produced (Felgner et al. (2016) *Gut Microbes* 7(2):171-177; Felgner et al. (2018) *Oncoimmunology* 7(2): e1382791), this can lead to poor tolerability, due to the TNF-α-mediated pro-inflammatory nature of the LPS and paradoxically less adaptive immunity (Kocijancic et al. (2017) *Oncotarget* 8(30):49988-50001). Exemplified herein, is a live attenuated strain of *S. typhimurium* that can only produce penta-acylated LPS, that contains a deletion of the msbB gene (that prevents the terminal myristoylation of lipid A, as described above), and is further modified by deletion of pagP (preventing palmitoylation). A strain modified to produce penta-acylated LPS will allow for lower levels of pro-inflammatory cytokines, improved stability in the blood and resistance to complement fixation, increased sensitivity to antimicrobial peptides, enhanced tolerability, and increased anti-tumor immunity when further modified to express heterologous immune-stimulatory proteins and/or interfering RNAs against immune checkpoints.

As provided herein, a $pagP^-$ mutant was also constructed on an asd, msbB, purI/purM, and fliC/fljB deleted strain of *S. typhimurium* VNP20009 or wild-type *S. typhimurium*. The resulting strains are exemplary of strains that are attenuated for bacterial inflammation by modification of lipid A to reduce TLR2/4 signaling, and deletion of the flagellin subunits to reduce TLR5 recognition and inflammasome induction, and deletion of pagP to produce penta-acylated LPS. Deletion of the flagellin subunits combined with modification of the LPS allows for greater tolerability in the host, and greater stability in the blood and resistance to complement fixation, providing for improved trafficking to the tumor site, in order to direct the immuno-stimulatory response towards production of any gene product, such as immune-stimulatory proteins and/or delivery of RNA interference against desired targets in the TME to elicit an anti-tumor response and promote an adaptive immune response to the tumor.

3. Colonization

VNP20009 is an attenuated *S. typhimurium*-based microbial cancer therapy that was developed for the treatment of cancer. VNP20009 is attenuated through deletion of the genes msbB and purI (purM). The purI deletion renders the microbe auxotrophic for purines or adenosine. Deletion of the msbB gene reduced the toxicity associated with lipopolysaccharide (LPS) by preventing the addition of a terminal myristyl group to the lipid A domain (Khan et al., (1998) *Mol. Microbiol.* 29:571-579).

There is a difference between mouse and humans in the ability of VNP20009 to colonize tumors. Systemic administration of VNP20009 resulted in colonization of mouse tumors; whereas systemic administration of VNP20009 in human patients resulted in very little colonization. It was shown that in mice, VNP20009 showed a high degree of tumor colonization after systemic administration (Clairmont et al., (2000) *J. Infect. Dis.* 181:1996-2002; and Bermudes et al. (2001) *Biotechnol. Genet. Eng. Rev.* 18:219-33). In a Phase 1 Study in advanced melanoma patients, however, very little VNP20009 was detected in human tumors after a 30-minute intravenous infusion (see Toso et al., (2002) *J. Clin. Oncol.* 20:142-52). Patients that entered into a follow-up study evaluating a longer, four-hour infusion of VNP20009, also demonstrated a lack of detectable VNP20009 after tumor biopsy (Heimann et al. (2003) *J. Immunother.* 26:179-180). Following intratumoral administration, colonization of a derivative of VNP20009 was detected (Nemunaitis et al. (2003) *Cancer Gene Ther.* 10:737-44). Direct intratumoral administration of VNP20009 to human tumors resulted in tumor colonization, indicating that human tumors can be colonized at a high level, and that the difference in tumor colonization between mice and humans occurs only after systemic administration.

It is shown herein (see, e.g., Example 25) that VNP20009 is inactivated by human complement, which leads to low tumor colonization. Strains that provide improved resistance to complement are provided. These strains contain modifications in the bacterial genome and also can carry a plasmid, typically in low or medium copy number, to encode genes to provide for replication (asd under the control of a eukaryotic promoter), and nucleic acid(s) encoding a therapeutic product(s), such as, but not limited to, RNAi, immunostimulatory protein, such as cytokines, and other such therapeutic genes, as described elsewhere herein. The table below summarizes the bacterial genotypes/modifications, their functional effects, and the effects/benefits.

| Genotype/ Modification | Functional effect | Effect/Benefit |
|---|---|---|
| ΔpurI | Purine/adenosine auxotrophy | Tumor-specific enrichment<br>Limited replication in healthy tissue |
| ΔmsbB | LPS surface coat modification | Decreased TLR4 recognition<br>Reduced cytokine profile<br>Improved safety |
| ΔFLG | Flagella knockout | Removes major inflammatory and immune-suppressive element<br>Decreased TLR5 recognition<br>Reduced cytokine profile<br>Improved safety |
| ΔpagP | LPS surface coat modifications | Removes major inflammatory and immune-suppressive element<br>Decreased TLR4 recognition<br>Reduced IL-6 profile<br>Improved safety |
| Δasd (in genome) | Plasmid maintenance | Improved plasmid delivery<br>Plasmid maintenance |
| plasmid | Express gene products under control of host-recognized promoter | Eukaryotic promoter limits expression to cells containing the plasmid<br>Long term expression in the TME (i.e., asd encoded on plasmid under control of host-recognized promoter)<br>Expression of therapeutic product(s) |

Strains provided herein are ΔFLG and/or ΔpagP. Additionally, the strains are one or more of ΔpurI (ΔpurM), ΔmsbB, and Δasd (in the bacterial genome). The plasmid is modified to encode products under control of host-recognized promoters (e.g., eukaryotic promoters, such as RNA polymerase II promoters, including those from eukaryotes, and animal viruses). The plasmids can encode asd to permit replication in vivo, as well as nucleic acids with other beneficial functions and gene products as described elsewhere herein.

The immunostimulatory bacteria are derived from suitable bacterial strains. Bacterial strains can be attenuated strains, or strains that are attenuated by standard methods, or that, by virtue of the modifications provided herein, are attenuated in that their ability to colonize is limited primarily to immunoprivileged tissues and organs, particularly immune and tumor cells, including solid tumors. Bacteria include, but are not limited to, for example, strains of *Salmonella, Shigella, Listeria, E. coli*, and Bifidobacteriae. For example, species include *Shigella sonnei, Shigella flexneri, Shigella dysenteriae, Listeria monocytogenes, Salmonella typhi, Salmonella typhimurium, Salmonella gallinarum*, and *Salmonella enteritidis*. Other suitable bacterial species include *Rickettsia, Klebsiella, Bordetella, Neisseria, Aeromonas, Francisella, Corynebacterium, Citrobacter, Chlamydia, Haemophilus, Brucella, Mycobacterium, Mycoplasma, Legionella, Rhodococcus, Pseudomonas, Helico-*

*bacter, Vibrio, Bacillus*, and *Erysipelothrix*. For example, *Rickettsia rickettsii, Rickettsia prowazekii, Rickettsia tsutsugamushi, Rickettsia mooseri, Rickettsia sibirica, Bordetella bronchiseptica, Neisseria meningitidis, Neisseria gonorrhoeae, Aeromonas eucrenophila, Aeromonas salmonicida, Francisella tularensis, Corynebacterium pseudotuberculosis, Citrobacter freundii, Chlamydia pneumoniae, Haemophilus somnus, Brucella abortus, Mycobacterium intracellulare, Legionella pneumophila, Rhodococcus equi, Pseudomonas aeruginosa, Helicobacter mustelae, Vibrio cholerae, Bacillus subtilis, Erysipelothrix rhusiopathiae, Yersinia enterocolitica, Rochalimaea quintana*, and *Agrobacterium tumefaciens*.

Exemplary of the immunostimulatory bacteria provided herein are species of *Salmonella*. Exemplary of bacteria for modification as described herein are wild-type strains of *Salmonella*, such as the strain that has all of the identifying characteristics of the strain deposited in the ATCC as accession #14028. Engineered strains of *Salmonella typhimurium*, such as strain YS1646 (ATCC Catalog #202165; also referred to as VNP20009, see, International Application Publication No. WO 99/13053), are engineered with plasmids to complement an asd gene knockout and antibiotic-free plasmid maintenance. The strains then are modified to delete the flagellin genes and/or to delete pagP. The strains also are rendered auxotrophic for purines, particularly adenosine, and are $asd^-$ and $msbB^-$. The asd gene can be provided on a plasmid for replication in the eukaryotic host. These deletions and plasmids are described elsewhere herein. Any of the nucleic acid encoding therapeutic products and immunostimulatory proteins and products, described elsewhere herein and/or known to those of skill in the art, can be included on the plasmid. The plasmid generally is present in low to medium copy number as described elsewhere herein. Therapeutic products include immunostimulatory proteins, such as cytokines, that promote an anti-tumor immune response in the tumor microenvironment and other such products described herein.

F. Constructing Exemplary Plasmids Encoding Therapeutic Proteins

The immunostimulatory bacteria provided herein are modified. They include modifications to the bacterial genome and to bacterial expression and host cell invasion, as discussed below, such as to improve or increase targeting to or accumulation in tumors, tumor-resident immune cells, and the tumor microenvironment, and also, to include plasmids that encode products that are expressed in the bacteria by including a bacterial promoter, or in the host by including an appropriate eukaryotic promoter and other regulatory regions as appropriate. It is shown herein that the immunostimulatory bacteria that are $flagellin^-$ ($fliC^-/fljB^-$) and/or $pagP^-$, and optionally $hilA^-$, exhibit increased tumor colonization, and, thus, can overcome the previous problems encountered with VNP20009, which failed to adequately colonize tumors in humans. The clinical activity of VNP20009 was disappointing in part due to its poor ability to colonize human tumors (Nemunaitis et al. (2003) *Cancer Gene Ther.* 10(10):737-744; Toso et al. (2002) *J. Clin. Oncol.* 20(1):142-152; Heimann et al. (2003) *J. Immunother.* 26(2):179-180).

To introduce the plasmids, the bacteria are transformed using standard methods, such as electroporation, with purified DNA plasmids constructed with routine molecular biology tools and methods (DNA synthesis, PCR amplification, DNA restriction enzyme digestion and ligation of compatible cohesive end fragments with ligase). As discussed throughout, the plasmids encode one or more therapeutic products, including proteins, such as antibodies and fragments thereof, and immunostimulatory proteins, such as interleukins, under control of host-recognized promoters. The encoded immunostimulatory proteins stimulate the immune system, particularly in the tumor microenvironment. The antibodies, including antibody fragments and single chain antibodies, can inhibit immune checkpoints.

The plasmid can encode, for example, a therapeutic product or therapeutic protein that is one or more of GM-CSF, IL-2, IL-7, IL-12p70 (IL-12p40+IL-12p35), IL-15, IL-15/IL-15R alpha chain complex, IL-2 that has attenuated binding to IL-2Ra, IL-18, IL-36 gamma, CXCL9, CXCL10, CXCL11, CCL3, CCL4, CCL5, proteins that are involved in or that effect or potentiate recruitment/persistence of T cells, CD40, CD40 ligand, OX40, OX40 ligand, 4-1BB, 4-1BB ligand, members of the B7-CD28 family, a TGF-beta polypeptide antagonist, a CD47 antagonist, interferon-α, interferon-β, interferon-γ, or members of the tumor necrosis factor receptor (TNFR) superfamily.

The bacteria can encode other products on the plasmids, such as one or more short hairpin (sh) RNA construct(s), or other inhibitory RNA modalities, whose expression inhibits, suppresses or disrupts expression of targeted genes. The therapeutic products, such as the immunostimulatory proteins, antibodies, and RNAi, such as shRNA or microRNA constructs, are expressed under control of a eukaryotic promoter, such as an RNA polymerase (RNAP) II or III promoter. Typically, RNAPIII (also referred to as POLIII) promoters are constitutive, and RNAPII (also referred to as POLII) can be regulated. In some examples, the shRNAs target the gene TREX1, to inhibit its expression. In some embodiments the plasmids encode a plurality of therapeutic products. Where a plurality of products, such as RNAi's, are encoded, expression of each can be under control of different promoters, or the products can be encoded polycistronically.

The nucleic acids encoding the therapeutic products/proteins can be under the control of a eukaryotic promoter that is an RNA polymerase II promoter or an RNA polymerase III promoter. The RNA polymerase II promoter can be a viral promoter or a mammalian RNA polymerase II promoter. The viral promoter can be one selected from among well-known viral promoters. Exemplary of such are a cytomegalovirus (CMV) promoter, an SV40 promoter, an Epstein Barr virus (EBV) promoter, a herpes virus promoter, and an adenovirus promoter.

The therapeutic product can be under the control of a eukaryotic RNA polymerase II (RNAP II) promoter. Many such promoters are very well known. Exemplary of such promoters is an RNAPII promoter selected from among, for example, an elongation factor-1 (EF1) alpha promoter, a ubiquitin C (UBC) promoter, a phosphoglycerate kinase 1 promoter (PGK) promoter, a CAG promoter (which consists of: (C) the cytomegalovirus (CMV) early enhancer element, (A) the promoter, the first exon and the first intron of chicken beta-actin gene, and (G) the splice acceptor of the rabbit beta-globin gene), an EIF4a1 (eukaryotic initiation factor 4A) promoter, a CBA promoter (chicken beta actin), an MND promoter, a GAPDH promoter, and a CD68 promoter. MND is a synthetic promoter that contains the U3 region of a modified MoMuLV LTR with myeloproliferative sarcoma virus enhancer (murine leukemia virus-derived MND promoter (myeloproliferative sarcoma virus enhancer, negative control region deleted, d1587rev primer-binding site substituted; see, e.g., Li et al. (2010) *J. Neurosci. Methods* vol. 189:56-64)).

As provided herein, bacterial strains, such as strains of *Salmonella*, including *S. typhimurium*, are modified or identified to be auxotrophic for adenosine in the tumor microenvironment, and/or the genome of the immunostimulatory bacterium is modified so that it preferentially infects tumor-resident immune cells and/or so that it induces less cell death in tumor-resident immune cells, and the bacteria are modified to carry plasmids encoding a therapeutic product, such as an immunostimulatory protein, an antibody or antibody fragment, such as an anti-tumor antibody or fragment thereof or anti-checkpoint antibody, and other products, such as RNAi.

1. Immunostimulatory Proteins

As discussed below, and elsewhere herein, provided are immunostimulatory bacteria that contain sequences of nucleotides that encode gene products, such as immunostimulatory proteins, to confer, increase, or enhance immune responses in the tumor microenvironment. These immunostimulatory bacteria are modified to preferentially infect tumors, including tumor-resident immune cells, and/or the genome of the immunostimulatory bacteria is modified so that they induce less cell death in tumor-resident immune cells, whereby the immunostimulatory bacteria accumulate in tumor cells to thereby deliver the immunostimulatory proteins to the targeted cells to stimulate the immune response against the tumor. The immunostimulatory bacteria can further encode a tumor antigen to enhance the response against the particular tumor. Any of the immunostimulatory bacteria provided herein and described above and below can be modified to encode an immunostimulatory protein. Generally, the immunostimulatory protein is under the control of an RNA polymerase II (RNAPII) promoter, and also is encoded in the plasmid for secretion, upon expression, into the tumor microenvironment. Any of the bacteria described herein for modification, such as any of the strains of *Salmonella, Shigella, E. coli*, Bifidobacteriae, *Rickettsia, Vibrio, Listeria, Klebsiella, Bordetella, Neisseria, Aeromonas, Francisella, Cholera, Corynebacterium, Citrobacter, Chlamydia, Haemophilus, Brucella, Mycobacterium, Mycoplasma, Legionella, Rhodococcus, Pseudomonas, Helicobacter, Bacillus*, and *Erysipelothrix*, or an attenuated strain thereof or a modified strain thereof encode the immunostimulatory protein so that it is expressed in the infected subject's cells. The immunostimulatory bacteria include those that are modified, as described herein, to colonize, accumulate in, or to preferentially infect, tumors, tumor-resident immune cells and/or the TME.

As discussed in section D5, and elsewhere herein, the immunostimulatory bacteria can encode immunostimulatory proteins, such as cytokines, including chemokines, that enhance or stimulate or evoke an anti-tumor immune response, particularly when expressed in tumors, in the tumor microenvironment and/or in tumor-resident immune cells.

The immunostimulatory bacteria herein can be modified to encode an immunostimulatory protein that promotes or induces or enhances an anti-tumor response. The immunostimulatory protein can be encoded on a plasmid in the bacterium, under the control of a eukaryotic promoter, such as a promoter recognized by RNA polymerase II, for expression in a eukaryotic subject, particularly the subject for whom the immunostimulatory bacterium is to be administered, such as a human. The nucleic acid encoding the immunostimulatory protein can include, in addition to the eukaryotic promoter, other regulatory signals for expression or trafficking in the cells, such as for secretion or expression on the surface of a cell.

Immunostimulatory proteins are those that, in the appropriate environment, such as a tumor microenvironment (TME), can promote or participate in or enhance an anti-tumor response by the subject to whom the immunostimulatory bacterium is administered. Immunostimulatory proteins include, but are not limited to, cytokines, chemokines and co-stimulatory molecules. These include cytokines, such as, but not limited to, IL-2, IL-7, IL-12, IL-15, and IL-18; chemokines, such as, but not limited to, CCL3, CCL4, CCL5, CXCL9, CXCL10, and CXCL11; and/or co-stimulatory molecules, such as, but not limited to, CD40, CD40L, OX40, OX40L, 4-1BB, 4-1BBL, GM-CSF, members of the TNF/TNFR superfamily and members of the B7-CD28 family. Other such immunostimulatory proteins that are used for treatment of tumors or that can promote, enhance or otherwise increase or evoke an anti-tumor response, known to those of skill in the art, are contemplated for encoding in the immunostimulatory bacteria provided herein.

In some embodiments, the immunostimulatory bacteria herein are engineered to express cytokines to stimulate the immune system, including, but not limited to, IL-2, IL-7, IL-12 (IL-12p70 (IL-12p40+IL-12p35)), IL-15 (and the IL-15:IL-15R alpha chain complex), and IL-18. Cytokines stimulate immune effector cells and stromal cells at the tumor site, and enhance tumor cell recognition by cytotoxic cells. In some embodiments, the immunostimulatory bacteria can be engineered to express chemokines, such as, for example, CCL3, CCL4, CCL5, CXCL9, CXCL10, and CXCL11. These modifications and bacteria encoding them are discussed above, and exemplified below.

2. Antibodies and Antibody Fragments

Provided are immunostimulatory bacteria that contain sequences of nucleotides that encode gene products, such as antibodies and antibody fragments, to confer, increase, or enhance anti-tumor immune responses. These include antibodies and antibody fragments that target immune checkpoints, such as CTLA-4, PD-1, PD-L1, CD47, or that target tumor antigens and tumor neoantigens, including those identified from the tumor of a subject to be treated, amongst others, and, for example, anti-IL-6 antibodies that modulate, particularly inhibit, immune suppression. The antibodies or fragments thereof, such as scFv and other single chain antibodies, such as camelids and nanobodies, can be encoded on a plasmid in the bacterium, under the control of eukaryotic regulatory sequences and signals, including a eukaryotic promoter, such as a promoter recognized by RNA polymerase II, for expression in a eukaryotic subject, particularly the subject for whom the immunostimulatory bacterium is to be administered, such as a human. The nucleic acid encoding the antibodies and antibody fragments can include, in addition to the eukaryotic promoter, other regulatory signals for expression and/or trafficking in the cells, such as for secretion or expression on the surface of a cell.

These immunostimulatory bacteria are those provided herein whose genomes are modified to preferentially infect tumors, including tumor-resident immune cells, and/or to eliminate infection of cells that are not target cells, and/or so that they induce less cell death in tumor-resident immune cells, whereby the immunostimulatory bacteria accumulate in tumor cells to thereby deliver the antibody or antibody fragment to the targeted cells to stimulate the immune response against the tumor. The immunostimulatory bacteria also or alternatively can encode a tumor antigen or neoantigen to enhance the response against the particular tumor. Any of the immunostimulatory bacteria provided herein and described above and below can be modified to encode an antibody or fragment thereof. Generally, the antibody or fragment thereof is under the control of an RNA polymerase II (RNAPII) promoter, and also is encoded in the plasmid for secretion, upon expression, into the tumor microenvironment. Any of the bacteria described herein for modification, such as any of the strains of *Salmonella, Shigella, E. coli*, Bifidobacteriae, *Rickettsia, Vibrio, Listeria, Klebsiella, Bordetella, Neisseria, Aeromonas, Francisella, Cholera, Corynebacterium, Citrobacter, Chlamydia, Haemophilus, Brucella, Mycobacterium, Mycoplasma, Legionella, Rhodococcus, Pseudomonas, Helicobacter, Bacillus*, and *Erysipelothrix*, or an attenuated strain thereof or a modified strain thereof encode the antibody or fragment thereof so that it is expressed in the infected subject's cells. The immunostimulatory bacteria include those that are modified, as described herein, to colonize, accumulate in, or to preferentially infect, tumors, tumor-resident immune cells and/or the tumor microenvironment.

Therapeutic antibodies and fragments thereof are well known. For example, there are a plethora of anti-CTLA4, anti-PD-1, and anti-PD-L1 antibodies and antigen-binding fragments thereof, such as Fab, Fab', $F(ab')_2$, single-chain Fv (scFv), Fv, disulfide-stabilized Fv (dsFv), nanobodies and camelids, and diabody fragments, single-chain antibodies, and humanized and human antibodies that are known. For example, antibodies that bind to PD-1 or PD-L1 and inhibit PD-1-inhibitory activity, and that have been used in anti-tumor immunotherapy are known. Exemplary anti-PD-1 antibodies include, but are not limited to, any of those described in U.S. Pat. Nos. 7,943,743, 8,008,449, and 8,735,553; U.S. Publication Nos. 2005/0180969 and 2007/0166281; and International Patent Application Publication No. WO 2008/156712. Anti-PD-L1 antibodies include, but are not limited to, any of those described in U.S. Publ. Nos. 2013/0034559 and 2013/0045202; U.S. Pat. Nos. 7,943,743, 8,217,149, 8,679,767, and 8,779,108; and Intl. App. Publ. Nos. WO 2010/077634 and WO 2013/019906. Several antibodies, which bind to and inhibit CTLA-4 activity, have been described, and have been used in anti-tumor immunotherapy. Anti-CTLA4 antibodies include, but are not limited to, any of those described in U.S. Pat. Nos. 6,682,736 and 6,984,720; U.S. Publ. Nos. 2002/0086014 and 2009/0074787; European Patent No. EP 1262193; and International Patent Application Publication No. WO 2000/037504. Anti-CTLA4 antibodies include Ipilimumab (also called MDX-010 or 10D1) and Tremelimumab (also called Ticilimumab or CP-675,206). These anti-CTLA4 antibodies have been involved in numerous clinical trials for the treatment of cancers. Ipilimumab is FDA approved for the treatment of melanoma and has been in clinical trials for other cancers, such as prostate cancer, lung cancer, and renal cell carcinoma (RCC). Tremelimumab has been investigated in clinical trials for the treatment of colorectal cancer (CRC), gastric cancer, melanoma and non-small cell lung cancer (NSCLC). Exemplary checkpoint inhibitors include, but are not limited to, anti-CTLA4 agents, anti-PD-1 agents, anti-PD-L1 agents and others, exemplary of which are the following:

Exemplary Immune Checkpoint Target Proteins and Inhibitors

| Target | Target Function | Antibody/Fusion Protein | Synonyms and Code Names |
|---|---|---|---|
| CTLA-4 | Inhibitory receptor | Ipilimumab | (MDX-CTLA-4; BMS-734016; MDX-010) |
| | | Tremelimumab | (Ticilimumab; CP-675,206) |
| PD-1 | Inhibitory receptor | MK-3475 | (Pembrolizumab; Lambrolizumab; SCH 900475) |
| | | AMP-224 | (anti-PD-1 fusion protein AMP-224) |
| | | Nivolumab | (BMS-936558; MDX-1106; ONO-4538) |
| | | Pidilizumab | (CT-011) |
| PD-Ll | Ligand for PD-1 | MDX-1105 | (RG7446) |
| | | BMS-936559 | |
| | | MED14736 | |
| | | MPDL33280A | |

The immunostimulatory bacteria provided herein can be engineered to express any antibody/antigen-binding fragment thereof, including, but not limited to the anti-checkpoint antibodies (checkpoint antagonists/inhibitors) described herein, and known to those of skill in the art.

3. Interfering RNAs (RNAi)

The plasmids in the immunostimulatory bacterial strains herein encode the RNAi nucleic acids targeting the immune checkpoints and other targets of interest, as described above. RNAi includes shRNA, siRNA, and microRNA. RNA interference (RNAi) allows for the sequence-selective suppression of gene expression in eukaryotic cells using small interfering RNAs (siRNAs), which are short, synthetic, dsRNA molecules with a sequence homologous to the target gene. RNAi technology provides a powerful tool for the depletion of disease-related transcripts.

a. shRNA

The siRNAs, which are typically about 19-29 base pairs long, function by degrading specific host mRNA sequences, precluding translation into their respective protein products, effectively silencing the expression of the target gene. Short hairpin RNAs (shRNAs), containing a tight hairpin loop, are widely used in RNAi. shRNAs contain of two complementary RNA sequences, each 19-29 bps long, linked by a loop spacer of 4-15 nucleotides. The RNA sequence that is complementary to the target gene sequence (and is thus identical to the mRNA sequence), is known as the "sense" strand, while the strand which is complementary to the mRNA (and identical to the target gene sequence) is known as the "antisense" or "guide" strand. shRNA transcripts are processed by an RNase III enzyme known as Dicer into siRNA duplexes. The product is then loaded into the RNA-induced silencing complex (RISC) with Argonaute (Ago) proteins and other RNA-binding proteins. RISC then localizes the antisense, or "guide" strand to its complimentary mRNA sequence, which is subsequently cleaved by Ago (U.S. Pat. No. 9,624,494). The use of shRNA is preferred over siRNA, because it is more cost effective, high intracellular concentrations of siRNA are associated with off-target effects, and because the concentration of siRNA becomes diluted upon cell division. The use of shRNA, on the other hand, results in stable, long-term gene knockdown, without the need for multiple rounds of transfection (Moore et al. (2010) *Methods Mol. Bio.* 629:141-158).

Targets of interest for RNAi, such as micro-RNA and siRNA/shRNA-mediated silencing include, but are not limited to, developmental genes such as cytokines and their receptors, cyclin kinase inhibitors, neurotransmitters and their receptors, growth/differentiation factors and their receptors; oncogenes such as BCL2, ERBA, ERBB, JUN, KRAS, MYB, MYC; tumor suppressor genes such as BRCA1, BRCA2, MCC, p53; and enzymes such as ACC synthases and oxidases, ATPases, alcohol dehydrogenases, amylases, catalases, DNA polymerases, RNA polymerases, kinases, lactases and lipases (U.S. Pat. Nos. 7,732,417, 8,829,254, 8,383,599, 8,426,675, and 9,624,494; U.S. Patent Publication No. 2012/0009153). Of particular interest are immune checkpoint targets, such as PD-1, PD-2, PD-L1, PD-L2, CTLA-4, IDO 1 and 2, CTNNB1 (β-catenin), SIRPα, VISTA, RNase H2, DNase II, CLEVER-1/Stabilin-1, LIGHT, HVEM, LAG3, TIM3, TIGIT, Galectin-9, KIR, GITR, TIM1, TIM4, CEACAM1, CD27, CD47, CD40, CD40L, CD48, CD70, CD80, CD86, CD112, CD137 (4-1BB), CD155, CD160, CD200, CD226, CD244 (2B4), CD272 (BTLA), B7-H2, B7-H3, B7-H4, B7-H6, ICOS, A2aR, A2bR, HHLA2, ILT-2, ILT-4, gp49B, PIR-B, HLA-G, ILT-2/4, OX40 and OX-40L. Other targets include MDR1, Arginase1, iNOs, IL-10, TGF-β, pGE2, STAT3, VEGF, VEGFR, KSP, HER2, Ras, EZH2, NIPP1, PP1, TAK1, and PLK1 (U.S. Patent Publication Nos. 2008/091375, 2009/0208534, 2014/0186401, 2016/0184456, and 2016/0369282; International Application Publication Nos. WO 2012/149364, WO 2015/002969, WO 2015/032165, and WO 2016/025582).

Expressed RNAi, such as shRNAs, mediate long-term, stable knockdown of their target transcripts for as long as the shRNAs are transcribed. RNA Pol II and III promoters are used to drive expression of shRNA constructs, depending on the type of expression required. Consistent with their normal cellular roles in producing abundant, endogenous small RNAs, Pol III promoters (such as U6 or H1) drive high levels of constitutive shRNA expression, and their transcription initiation points and termination signals (4-6 thymidines) are well defined. Pol II promoter-driven shRNAs can be expressed tissue-specifically and are transcribed as longer precursors that mimic pri-miRNAs and have cap and polyA signals that must be processed. Such artificial miRNAs/shRNAs are efficiently incorporated into RISC, contributing to a more potent inhibition of target-gene expression; this allows lower levels of shRNA expression and might prevent saturation of components in the RNAi pathway. An additional advantage of Pol II promoters is that a single transcript can simultaneously express several miRNA and mimic shRNAs. This multiplexing strategy can be used to simultaneously knock down the expression of two or more therapeutic targets, or to target several sites in a single gene product (see, e.g., U.S. Publication No. 2009/0208534).

b. MicroRNA

MicroRNAs (miRNAs) are short, non-coding single-stranded RNA molecules that are about or are 20-24 nucleotides long. Naturally-occurring miRNAs are involved in the post-transcriptional regulation of gene expression; miRNAs do not encode genes. miRNAs have been shown to regulate cell proliferation and survival, as well as cellular differentiation. miRNAs inhibit translation or promote RNA degradation by binding to target mRNAs that share sequence complementarity. They affect the stability and translation of mRNAs; miRNAs inhibit translation, and/or promote RNA degradation, by binding to target mRNAs that share sequence complementarity. miRNAs, which occur in eukaryotes, are transcribed by RNA Pol II into capped and polyadenylated hairpin-containing primary transcripts, known as primary miRNAs, or pri-miRNAs. These pri-miRNAs are cleaved by the enzyme Drosha ribonuclease III and its cofactor Pasha/DGCR8 into ~70 nucleotide long precursor miRNA hairpins, known as precursor miRNAs, or pre-miRNAs, which are then transported from the nucleus into the cytoplasm, and cleaved by Dicer ribonuclease III into the miRNA: miRNA* duplex, with sense and antisense strand products that are approximately 22 nucleotides long. The mature miRNA is incorporated into the RNA-induced silencing complex (RISC), which recognizes and binds target mRNAs, usually at the 3'-untranslated region (UTR), through imperfect base pairing with the miRNA, resulting in the inhibition of translation, or destabilization/degradation of the target mRNA (see, e.g., Auyeung et al. (2013) *Cell* 152(4):844-85).

As described herein, regulating gene expression by RNA interference (RNAi), often uses short hairpin RNAs (shRNAs) to inhibit, disrupt or other interfere with expression of targeted genes. While advantageously used, and used herein, in some instances, shRNAs can be poor substrates for small RNA biogenesis factors, they can be processed into a heterogeneous mix of small RNAs, and their precursor transcripts can accumulate in cells, resulting in the induction of sequence-independent, non-specific effects and leading to in vivo toxicity. miRNAs are contemplated for use herein. miRNA-like scaffolds, or artificial miRNAs (amiRNAs) can be used to reduce sequence-independent non-specific effects (Watanabe et al. (2016) *RNA Biology* 13(1):25-33; Fellmann et al. (2013) *Cell Reports* 5:1704-1713). In addition to improved safety profiles, amiRNAs are more readily transcribed by Pol II than shRNAs, allowing for regulated and cell-specific expression. Artificial miRNAs (amiRNAs), in comparison to shRNAs, can effectively, and in some cases, more potently, silence gene expression without generating large amounts of inhibitory RNAs (McBride et al. (2008) *Proc. Natl. Acad. Sci. U.S.A.* 105(15):5868-5873). This effect was determined to be due to the more effective processing of siRNA from pre-miRNA precursors than from shRNA transcripts (Boden et al. (2004) *Nucl. Acid Res.* 32(3):1154-1158).

miRNAs have been shown to regulate several cellular processes, including cell proliferation and survival, intracellular signaling, cellular metabolism, and cellular differentiation. In 1993, the first miRNA was identified in *C. elegans* (Lee et al. (1993) *Cell* 75:843-854), and later, mammalian miRNAs were identified (Pasquinelli et al. (2000) *Nature* 408(6808):86-89). More than 17,000 miRNAs in 142 species have been identified, with more than 1900 miRNAs identified in humans, many of which have been associated with a variety of diseases, including cancer (e.g., miR-15 and miR-16 in B-CLL, miR-125b, miR-145, miR-21, miR-155 and miR-210 in breast cancer, miR-155 and let-7a in lung cancer, miR-145 in gastric cancer, miR-29b in liver cancer); viral infections (e.g., miR-122 and miR-155 in HCV infection, mir-28, miR-125b, miR-150, miR-223 and miR-382 in HIV-1 infection, miR-21 and miR-223 in influenza virus infection); immune-related diseases (e.g., miR-145, miR-34a, miR-155 and miR-326 in multiple sclerosis, miR-146a in systemic lupus erythematosus, miR-144, miR-146a, miR-150, miR-182, miR-103 and miR-107 in type II diabetes, miR-200a, miR-200b, miR-429, miR-122, miR-451 and miR-27 in nonalcoholic fatty liver disease, miR-29c, miR-34a, miR-155 and miR-200b in non-alcoholic steatohepatitis); and neurodegenerative diseases (e.g., miR- 30b, miR-30c, miR-26a, miR-133b, miR-184* and let-7 in Parkinson's disease, miR-29b-1, miR-29a and miR-9 in Alzheimer's disease) (Li and Kowdley (2012) *Genomics Proteomics Bioinformatics* 10:246-253).

Studies have shown that specific endogenous miRNAs are up-regulated or down-regulated in certain cancers. For example, miR-140 is down-regulated in non-small cell lung cancer (NSCLC) and its overexpression was found to suppress PD-L1 (Xie et al. (2018) *Cell Physiol. Biochem.* 46:654-663); miR-197 is downregulated in platinum-based chemotherapy resistant NSCLC, resulting in chemoresistance, tumorigenicity and metastasis (Fujita et al. (2015) *Mol. Ther.* 23(4):717-727); and several miRNAs have been found to be down-regulated in cancer cells to allow PD-L1 expression, including miR-200, miR-34a and miR-138 (Yee et al. (2017) *J. Biol. Chem.* 292(50):20683-20693). Several miRNAs also are upregulated, for example miR-21, miR-17 and miR-221 in lung cancer (Xie et al. (2018) *Cell Physiol. Biochem.* 46:654-663).

MicroRNA-103 (miR-103) was identified as the most upregulated microRNA in endothelial cells as a result of genotoxic stress and DNA damage following radiation. It was found that miR-103 led to the downregulation of the TREX1, TREX2 and FANCF genes, and the decrease in TREX1 expression was identified as the major mechanism by which miR-103 mediates cell death and suppresses angiogenesis (Wilson et al. (2016) *Nature Communications* 7:13597). Since the loss of TREX1 results in the accumulation of dsDNA and ssDNA, defective DNA repair, and release of cytokines, miR-103 expression significantly upregulates the pro-inflammatory chemokines IP-10, RANTES, MIG, and the cytokines IL-15, IL-12 and IFN-γ, and this upregulation was due to a miR-103 mediated decrease in TREX1 levels. Studies also revealed a significant increase in costimulatory receptors CD40 and CD160, and a decrease in the numbers of PD-L1$^+$ macrophages and neutrophils in the 4T1 tumors. miR-103 regulation of TREX1 is therefore a potent modulator of the immune TME. Other miRNAs that target TREX1 include miR-107 (U.S. Pat. No. 9,242,000), miR-27a and miR-148b (U.S. Pat. No. 8,580,757). miRNA-103 can be used in the plasmids herein to inhibit TREX1.

Artificial miRNAs (amiRNAs) can be delivered to cells and used to silence target genes by creating a microRNA-based siRNA or shRNA vector (shRNAmir). The miR-30a backbone is often used in mammals, and approximately 200-300 bases of the primary miRNA transcript are included in the vector, with the miRNA hairpin placed at the center of the fragment, and the natural miRNA stem sequence being replaced with the siRNA/shRNA-encoding sequence of interest. Viral promoters, such as CMV, MSCV and TLR promoters; cellular promoters, such as EIF-1a; inducible chimeric promoters, such as tet-CMV; and tissue-specific promoters, can be used (Chang et al. (2013) *Cold Spring Harb. Protoc.*; doi:10.1101/pdb.prot075853). Other miRNAs that can be used include mir-16-2 (Watanabe et al. (2016) *RNA Biology* 13(1):25-33), miR-155 (Chung et al. (2006) *Nuc. Acids Res.* 34:e53), miR17-92 (Liu et al. (2008) *Nuc. Acids Res.* 36(9):2811-2824), miR-15a, miR-16, miR-19b, miR-20, miR-23a, miR-27b, miR-29a, miR-30b, miR-30c, miR-104, miR-132s, miR-181, miR-191, miR-223 (U.S. Pat. No. 8,426,675), and Let-7 miRNA (International Application Publication Nos. WO 2009/006450, and WO 2015/032165).

shRNAmirs are limited by the low effectiveness of computationally-predicted shRNA sequences, particularly when expressed under low or single copy conditions. Third generation artificial miRNAs, such as miR-E (based on miR-30a) and miR-3G (based on miR-16-2) have been developed, and were found to exhibit stronger gene silencing in both Pol II- and Pol III-based expression vectors in comparison to shRNAmirs, due to the enhanced processing and accumulation of precisely-defined guide RNAs. miR-E, which was developed by the discovery of the conserved CNNC motif that enhances the processing of miRNA within the stem 3p flanking sequences, is different from endogenous miR-30a in three aspects: the stem of miR-E has no bulge and has the intended guide on the opposite strand; two conserved base pairs flanking the loop were mutated from CU/GG to UA/UA; and XhoI/EcoRI restriction sites were introduced into the flanking regions for shRNA cloning (Fellmann et al. (2013) *Cell Reports* 5:1704-1713). miR-E was found to be more potent than miR-30a, but symmetric processing of both the 3p and 5p strands of miR-30a does not favor guide strand delivery over passenger strand delivery, which is not optimal. Additionally, cloning into miR-E using oligos longer than 100 nt is costly and time consuming (Watanabe et al. (2016) *RNA Biology* 13(1):25-33).

The amiRNA designated miR-16-2 (see, e.g., Watanabe et al. (2016) *RNA Biology* 13(1):25-33, see FIG. 1) is a third generation (3G) amiRNA scaffold alternative; it is expressed in several tissues, is naturally asymmetric (the mature strand is derived exclusively from the 5p or 3p arm of the stem), and its stem and loop segments are small and rigid, simplifying vector cloning. miR-3G is generated by cloning the ~175 bp fragment containing the native miR-16-2 stem and loop, and the flanking 35 bps on either side of the stem, into the vector. miR-3G includes further modification of miR-16-2 by introducing cloning sites, such as MluI and EcoRI, into the 5p and 3p arm-flanking sequences, respectively, and fully base-pairing the guide (antisense) and passenger (sense) strand stem, with the exception of a mismatch at position 1 relative to the guide strand. The restriction sites allow for the generation of new targeting constructs via 88-mer duplexed DNA oligonucleotides without compromising the predicted secondary structure of the miR-16-2 hairpin and flanking elements. Additionally, one of the two CNNC motifs and the GHG motif (small RNA processing enhancers) are modified in the 3p flanking sequence of miR-16-2. siRNAs targeting the gene(s) of interest are then exchanged with the first 21 nucleotides of the mature 5p guide and 3p passenger sequences. Studies determined that miR-E and miR-3G were equally potent. miR-3G provides an attractive RNAi system, due to the smaller size of its expression cassette (~175 nts vs. ~375 for miR-E), and the simplified and cost effective single step cloning method for its production. As with shRNAs, bacteria can be used as vectors for the in vivo delivery of micro-RNAs. For example, it was shown that attenuated *S. typhimurium* can be used as a vector for the oral delivery of plasmids expressing miRNA against CCL22 in mice with inflammation. Down-regulation of CCL22 gene expression by this method was successful both in vitro and in vivo in mouse models of atopic dermatitis (Yoon et al. (2012) *DNA and Cell Biology* 31(3):289-296). For purposes herein a miRNA 16-2 can be used to produce miRNAs to be used in place of the shRNA. The sequences for the shRNA can be used for design of miRNAs.

DNA encoding RNAi for disrupting and/or inhibiting and/or targeting any of selected target genes, such as any immune checkpoint described herein or known to the skilled artisan, is inserted into a microRNA backbone, such as the microRNA backbone set forth in SEQ ID NO:249, and below. Any suitable microRNA backbone known to the skilled artisan can be used; generally such backbones are based on a naturally-occurring microRNA and are modified for expression of the RNAi. Exemplary of such backbones is one based on miR-16-2 (SEQ ID NO:248). The sequence of the modified microRNA backbone is:

```
                                    (SEQ ID NO: 249)
5'-CCGGATC AACGCCTAG GTTTATGTTT GGATGAACTG

ACATACGCGT ATCCGTC NNNNNNNNNNNNNNNNNNNNNN GTAG

TGAAATATAT ATTAAAC NNNNNNNNNNNNNNNNNNNNNN

TACGGTAACGCG GAATTCGCAA CTATTTTATC AATTTTTTGC

GTCGAC-3',
```

where the N's represent complementary, generally 18-26, such as 19-24, 19-22, 19-20, base pair long anti-sense and sense nucleotide sequences that target the gene to be silenced, and are inserted before and after the microRNA loop. RNAs, such as ARI-205 (SEQ ID NO:214) and ARI-206 (SEQ ID NO:215) are exemplary constructs based on the microRNA backbone of SEQ ID NO:249, that encode 21 and 22 base pair homology sequences, respectively. ARI-207 (SEQ ID NO:216) and ARI-208 (SEQ ID NO:217) are exemplary constructs based on the microRNA backbone of SEQ ID NO:249, that encode 19 base pair homology sequences. Another example, is the construct designated ARI-201, which is microRNA construct ARI-205, wherein the N's are replaced with a sequence of nucleotides targeting mouse PD-L1. The construct designated ARI-202 represents microRNA construct ARI-206, where the N's are replaced with sequences targeting mouse PD-L1. The skilled person readily can construct microRNAs for inclusion in plasmids as described and exemplified herein using the miR-16-2 backbone, or other suitable backbones known to the skilled artisan.

4. Origin of Replication and Plasmid Copy Number

Plasmids are autonomously-replicating extra-chromosomal circular double stranded DNA molecules that are maintained within bacteria by means of a replication origin. Copy number influences the plasmid stability. High copy number generally results in greater stability of the plasmid when the random partitioning occurs at cell division. A high number of plasmids generally decreases the growth rate, thus possibly allowing for cells with few plasmids to dominate the culture, since they grow faster. The origin of replication also determines the plasmid's compatibility: its ability to replicate in conjunction with another plasmid within the same bacterial cell. Plasmids that utilize the same replication system cannot co-exist in the same bacterial cell. They are said to belong to the same compatibility group. The introduction of a new origin, in the form of a second plasmid from the same compatibility group, mimics the result of replication of the resident plasmid. Thus, any further replication is prevented until after the two plasmids have been segregated to different cells to create the correct pre-replication copy number.

-continued

| Origin of Replication | Copy Number | SEQ ID NO. |
|---|---|---|
| pMB1 | 15-20 | 254 |
| p15A | 10-12 | 255 |
| pSC101 | ~5 | 256 |
| pBR322 | 15-20 | 243 |
| ColE1 | 15-20 | 257 |
| pPS10 | 15-20 | 258 |
| RK2 | ~5 | 259 |
| R6K (alpha origin) | 15-20 | 260 |
| R6K (beta origin) | 15-20 | 261 |
| R6K (gamma origin) | 15-20 | 262 |
| P1 (oriR) | Low | 263 |
| R1 | Low | 264 |
| pWSK | Low | 265 |
| ColE2 | 10-15 | 266 |
| pUC (pMB1) | 500-700 | 267 |
| F1 | 300-500 | 268 |

Numerous bacterial origins of replication are known to those of skill in the art. The origin can be selected to achieve a desired copy number. Origins of replication contain sequences that are recognized as initiation sites of plasmid replication via DNA dependent DNA polymerases (del Solar et al. (1998) *Microbiology And Molecular Biology Reviews* 62(2):434-464). Different origins of replication provide for varying plasmid copy levels within each cell and can range from 1 to hundreds of copies per cell. Commonly used bacterial plasmid origins of replication include, but are not limited to, pMB1 derived origins, which have very high copy derivatives, ColE1 origins, p15A, pSC101, pBR322, and others, which have low copy numbers. Such origins are well known to those of skill in the art. The pUC19 origin results in copy number of 500-700 copies per cell. The pBR322 origin has a known copy number of 15-20. These origins only vary by a single base pair. The ColE1 origin copy number is 15-20, and derivatives, such as pBluescript, have copy numbers ranging from 300-500. The p15A origin that is in pACYC184, for example, results in a copy number of approximately 10. The pSC101 origins confer a copy number of approximately 5. Other low copy number vectors from which origins can be obtained, include, for example, pWSK29, pWKS30, pWSK129 and pWKS130 (see, Wang et al. (1991) *Gene* 100:195-199). Medium to low copy number is less than 150, or less than 100. Low copy number is less than 20, 25, or 30. Those of skill in the art can identify plasmids with low or high copy number. For example, one way to determine experimentally if the copy number is high or low is to perform a miniprep. A high-copy plasmid should yield between 3-5 μg DNA per 1 ml LB culture; a low-copy plasmid will yield between 0.2-1 μg DNA per ml of LB culture.

Sequences of bacterial plasmids, including identification of and sequence of the origin of replication, are well known (see, e.g., snapgene.com/resources/plasmid files/basic cloning vectors/pBR322/).

High copy plasmids are selected for heterologous expression of proteins in vitro because the gene dosage is increased relative to chromosomal genes and higher specific yields of protein, and for therapeutic bacteria, higher therapeutic dosages of encoded therapeutics. It is shown, herein, however, that for delivery of plasmids encoding RNA interference (RNAi), such as by *S. typhimurium*, as described herein, while it would appear that a high copy plasmid would be ideally suited, therapeutically, a lower copy number is more effective.

The requirement for bacteria to maintain the high copy plasmids can be a problem if the expressed molecule is toxic to the organism. The metabolic requirements for maintaining these plasmids can come at a cost of replicative fitness in vivo. Optimal plasmid copy number for delivery of interfering RNAs can depend on the mechanism of attenuation of the strain engineered to deliver the plasmid. If needed, the skilled person, in view of the disclosure herein, can select an appropriate copy number for a particular immunostimulatory species and strain of bacteria. It is shown herein, that low copy number can be advantageous.

5. CpG Motifs and CpG Islands

Unmethylated cytidine-phosphate-guanosine (CpG) motifs are prevalent in bacterial, but not vertebrate, genomic DNA. Pathogenic DNA and synthetic oligodeoxynucleotides (ODNs) containing CpG motifs activate host defense mechanisms, leading to innate and acquired immune responses. The unmethylated CpG motifs contain a central unmethylated CG dinucleotide plus flanking regions. In humans, four distinct classes of CpG ODNs have been identified based on differences in structure and the nature of the immune response they induce. K-type ODNs (also referred to as B-type) contain from 1 to 5 CpG motifs typically on a phosphorothioate backbone. D-type ODNs (also referred to as A-type) have a mixed phosphodiester/phosphorothioate backbone and have a single CpG motif, flanked by palindromic sequences that permit the formation of a stem-loop structure, as well as poly G motifs at the 3' and 5' ends. C-type ODNs have a phosphorothioate backbone and contain multiple palindromic CpG motifs that can form stem loop structures or dimers. P-Class CpG ODNs have a phosphorothioate backbone and contain multiple CpG motifs with double palindromes that can form hairpins at their GC-rich 3' ends (Scheiermann and Klinman (2014) *Vaccine* 32(48):6377-6389). For purposes herein, the CpGs are encoded in the plasmid DNA; they can be introduced as a motif, or in a gene.

Toll-like receptors (TLRs) are key receptors for sensing pathogen-associated molecular patterns (PAMPs) and activating innate immunity against pathogens (Akira et al. (2001) *Nat. Immunol.* 2(8):675-680). TLR9 recognizes hypomethylated CpG motifs in DNA of prokaryotes that do not occur naturally in mammalian DNA (McKelvey et al. (2011) *J. Autoimmunity* 36:76-86). Recognition of CpG motifs upon phagocytosis of pathogens into endosomes in immune cell subsets induces IRF7-dependent type I interferon signaling and activates innate and adaptive immunity.

Immunostimulatory bacteria, such as *Salmonella* species, such as *S. typhimurium*, strains carrying plasmids containing CpG islands, are provided herein. These bacteria can activate TLR9 and induce type I IFN-mediated innate and adaptive immunity. As exemplified herein, bacterial plasmids that contain hypomethylated CpG islands can elicit innate and adaptive anti-tumor immune responses that, in combination with RNAi encoded in the plasmid, such as RNAi that targets immune checkpoints, such as the shRNA or miRNA that targets TREX1, and hence, TREX1-mediated STING pathway activation, can have synergistic or enhanced anti-tumor activity. For example, the asd gene (SEQ ID NO:48) encodes a high frequency of hypomethylated CpG islands. CpG motifs can be included in combination with any of the RNAi described or apparent from the description herein in the immunostimulatory bacteria, and thereby enhance or improve anti-tumor immune responses in a treated subject.

Immunostimulatory CpGs can be included in the plasmids, by including a nucleic acid, typically from a bacterial gene, that encodes a gene product, and also by adding a nucleic acid that encodes CpG motifs. The plasmids herein can include CpG motifs. Exemplary CpG motifs are known (see, e.g., U.S. Pat. Nos. 8,232,259, 8,426,375 and 8,241,844). These include, for example, synthetic immunostimulatory oligonucleotides, between 10 and 100, 10 and 20, 10 and 30, 10 and 40, 10 and 50, 10 and 75, base pairs long, with the general formula:

$(CpG)_n$, where n is the number of repeats.

Generally, at least one or two repeats are used; non-CG bases can be interspersed. Those of skill in the art are very familiar with the general use of CpG motifs for inducing an immune response by modulating TLRs, particularly TLR9.

6. Plasmid Maintenance/Selection Components

The maintenance of plasmids in laboratory settings is usually ensured by the inclusion of an antibiotic resistance gene on the plasmid and use of antibiotics in the growth media. As described above, the use of an asd deletion mutant complimented with a functional asd gene on the plasmid allows for plasmid selection in vitro without the use of antibiotics, and allows for plasmid maintenance in vivo. The asd gene complementation system provides for such selection/maintenance (Galán et al. (1990) *Gene* 94(1):29-35). The use of the asd gene complementation system to maintain plasmids in the tumor microenvironment increases the potency of *S. typhimurium* and other immunostimulatory bacterial strains, engineered to deliver plasmids encoding therapeutic products such as immunostimulatory proteins, antibodies, antibody fragments, or interfering RNAs.

7. RNA Polymerase Promoters

Plasmids provided herein are designed to encode interfering RNAs targeting immune checkpoints and other targets as described above. The RNA expression cassette contains a promoter for transcription in human cells such as an H1 promoter or a U6 promoter, or a CMV promoter. U6 and H1 are RNA polymerase III (RNAP III) promoters, which are for production and processing of small RNAs. The CMV promoter is recognized by RNA polymerase II, and is more amenable for expression of long RNA stretches than is RNAP III. The promoter precedes the interfering RNA, such as an shRNA, siRNA or miRNA, as described above.

In eukaryotic cells, DNA is transcribed by three types of RNA polymerases; RNA Pol I, II and III. RNA Pol I transcribes only ribosomal RNA (rRNA) genes, RNA Pol II transcribes DNA into mRNA and small nuclear RNAs (snRNAs), and RNA Pol III transcribes DNA into ribosomal 5S rRNA (type I), transfer RNA (tRNA) (type II) and other small RNAs such as U6 snRNAs (type III). shRNAs are typically transcribed in vivo under the control of eukaryotic type III RNA Pol III promoters, such as the human U6 promoter, which transcribes the U6 snRNA component of the spliceosome, and the H1 human promoter, which transcribes the RNA component of RNase P. U6 and H1 promoters are more suitable than other Pol III or Pol II promoters because they are structurally simple, with a well-defined transcription start-site, and naturally drive the transcription of small RNAs. U6 and H1 promoters do not carry the sequences necessary for transcribing anything downstream from the transcription start site (Makinen et al. (2006) *J. Gene Med.* 8:433-441). They are thus the most straightforward promoters for use in shRNA expression.

The use of other promoters such as type II pol III tRNA promoters, while successful in expressing shRNAs, results in longer dsRNA transcripts, which can induce an interferon response. RNA pol II promoters, such as the human cytomegalovirus (CMV) promoter also can be used (U.S. Pat. Nos. 8,202,846 and 8,383,599), but are more often utilized for expression of long RNA stretches. Studies have shown that the addition of the enhancer from the CMV promoter near the U6 promoter can increase its activity, increasing shRNA synthesis and improving gene silencing (Xia et al.

(2003) *Nucleic Acids Res.* 31(17):e100; Nie et al. (2010) *Genomics Proteomics Bioinformatics* 8(3):170-179). RNA pol II promoters are typically avoided in shRNA transcription due to the generation of cytoplasmic DNA, which leads to a pro-inflammatory interferon response. In this case, a cytoplasmic DNA mediated interferon response in *S. typhimurium*-infected tumor cells has anti-tumor benefit, especially in the context of TREX1 inhibition as provided herein. Prokaryotic promoters, including T7, pBAD and pepT promoters can be utilized when transcription occurs in a bacterial cell (Guo et al. (2011) *Gene Therapy* 18:95-105; U.S. Patent Publication Nos. 2012/0009153, and 2016/0369282; International Application Publication Nos. WO 2015/032165, and WO 2016/025582).

RNA pol III promoters generally are used for constitutive shRNA expression. For inducible expression, RNA pol II promoters are used. Examples include the pBAD promoter, which is inducible by L-arabinose; tetracycline-inducible promoters such as TRE-tight, IPT, TRE-CMV, Tet-ON and Tet-OFF; retroviral LTR; IPTG-inducible promoters such as Lad, Lac-O responsive promoters; LoxP-stop-LoxP system promoters (U.S. Pat. No. 8,426,675; International Application Publication No. WO 2016/025582); and pepT, which is a hypoxia-induced promoter (Yu et al. (2012) *Scientific Reports* 2:436). These promoters are well known. Exemplary of these promoters are human U6 (SEQ ID NO:73) and human H1 (SEQ ID NO:74).

dissociation of the transcription elongation complex. Transcriptional terminators shall be included in the plasmid in order to prevent expression of interfering RNAs by the *S. typhimurium* transcriptional machinery. This ensures that expression of the encoded interfering RNA, such as shRNA, micro-RNA and siRNA, is confined to the host cell transcriptional machinery.

Plasmids used for transformation of *Salmonella*, such as *S. typhimurium*, as a cancer therapy described herein, contain all or some of the following attributes: 1) a CpG island, 2) a bacterial origin of replication, 3) an asd gene selectable marker for plasmid maintenance, 4) one or more human interfering RNA expression cassettes, 5) DNA nuclear targeting sequence, and 6) transcriptional terminators.

9. CRISPR

An immunostimulatory bacterium, encoding a CRISPR cassette, can be used to infect human immune, myeloid, or hematopoietic cells in order to site-specifically knockout a target gene of interest. The strain used can be asd$^-$ and can contain a plasmid that lacks the complementary asd cassette and contains a kan cassette. In order to grow the strain in vitro in liquid media, DAP is added to complement the asd$^-$ genetic deficiency. After infection of human cells, the strain can no longer replicate, and the CRISPR cassette-encoded plasmid is delivered. The strain can also be hilA$^-$ or can lack one or more parts of SPI-1, or lack flagellin, or any combination thereof, which reduces or prevents pyroptosis (inflammatory-mediated cell death) of phagocytic cells.

| SEQ ID NO. | Name | Sequence |
|---|---|---|
| 73 | human U6 RNA pol III promoter | aa ggtcgggcag gaagagggcc<br>721 tatttcccat gattccttca tatttgcata tacgatacaa ggctgttaga gagataatta<br>781 gaattaattt gactgtaaac acaaagatat tagtacaaaa tacgtgacgt agaaagtaat<br>841 aatttcttgg gtagtttgca gttttaaaat tatgttttaa aatggactat catatgctta<br>901 ccgtaacttg aaagtatttc gatttcttgg ctttatatat cttgtggaaa ggacgaaact<br>961 ag |
| 74 | human H1 RNA pol III promoter | atatttgca tgtcgctatg<br>721 tgttctggga aatcaccata aacgtgaaat gtctttggat ttgggaatct tataagttct<br>781 gtatgagacc actccctagg |

Tissue-specific promoters include TRP2 promoter for melanoma cells and melanocytes, MMTV promoter or WAP promoter for breast and breast cancer cells, Villin promoter or FABP promoter for intestinal cells, RIP promoter for pancreatic beta cells, Keratin promoter for keratinocytes, Probasin promoter for prostatic epithelium, Nestin promoter or GFAP promoter for CNS cells/cancers, Tyrosine Hydroxylase S100 promoter or neurofilament promoter for neurons, Clara cell secretory protein promoter for lung cancer, and Alpha myosin promoter in cardiac cells (U.S. Pat. No. 8,426,675).

8. DNA Nuclear Targeting Sequences

DNA nuclear targeting sequences (DTS) such as the SV40 DTS mediate the translocation of DNA sequences through the nuclear pore complex. The mechanism of this transport is reported to be dependent on the binding of DNA binding proteins that contain nuclear localization sequences. The inclusion of a DTS on a plasmid to increase nuclear transport and expression has been demonstrated (Dean, D. A. et al. (1999) *Exp. Cell Res.* 253(2):713-722), and has been used to increase gene expression from plasmids delivered by *S. typhimurium* (Kong et al. (2012) *Proc. Natl. Acad. Sci. U.S.A.* 109(47):19414-19419).

Rho-independent or class I transcriptional terminators such as the T1 terminator of the rrnB gene of *E. coli* contain sequences of DNA that form secondary structures that cause G. Tumor-Targeting Immunostimulatory Bacteria Contain RNAi Against Exemplary Immune Target Genes to Stimulate Anti-Tumor Immunity RNAi against any immune target can be encoded in the plasmids. These include, but are not limited to, any discussed in the disclosure herein, and any known to those of skill in the art. The following discussion describes exemplary targets. The plasmids can contain any RNAi against such targets, including, but not limited to, shRNA, siRNA and microRNA.

1. TREX1

In certain embodiments provided herein, the immunostimulatory bacteria encode inhibitory RNA, such as shRNA, that inhibit or disrupt or suppress TREX1 expression. The enzyme product encoded by TREX1, located upstream from cGAS, is a mediator of the type I interferon pathway. TREX1 encodes the major 3' DNA exonuclease in mammalian cells (also called DNase III). Human TREX1 proteins are as catalytically efficient as bacterial exonucleases (Mazur and Perrino (2001) *J. Biol. Chem.* 276:17022-17029). Immunostimulatory bacterium that inhibit TREX1 expression by processes other than RNA silencing also are contemplated herein.

For the immunostimulatory bacteria provided herein, such as those that express shRNA against TREX1, loss of TREX1 activity and subsequent activation of cGAS/STING-induced vascular disruption enhances tumor colonization of *S. typhimurium*. The TREX1 gene encodes a protein that is 314 amino acids long (Mazur et al. (2001) *J. Biol. Chem.* 276:17022-17029), exists as a homodimer, and lacks endonuclease activity. TREX1 is among several proteins involved in the repair of DNA that is damaged by exogenous genotoxic stress, including UV irradiation and DNA-damaging compounds. TREX1 can function as an editing exonuclease for DNA pol β by excising mispaired nucleotides from the 3' end (Mazur et al. (2001) *J. Biol. Chem.* 276: 17022-17029). ssDNA is degraded 3-4 times more efficiently than dsDNA (Lindahl et al. (2009) *Biochem. Soc. Trans.* 37 (Pt 3), 535-538). Mutations in residues D18 and D200, frequently associated with autoimmune diseases, disable TREX1 enzyme from degrading dsDNA and reduces its ability to degrade ssDNA. TREX1 enzyme translocates from the endoplasmic reticulum to the nucleus following DNA damage, indicating its involvement in the replication of damaged DNA. Promoter activation and upregulation of TREX1 has been observed as a result of UVC exposure in mouse fibroblasts, and TREX1 null mouse cells have demonstrated hypersensitivity to UVC light (Tomicic et al. (2013) *Bioch. Biophys. Acta* 1833:1832-1843).

Mutations resulting in loss of TREX1 have been identified in patients with the inherited rare disease, Aicardi-Goutieres syndrome (AGS), which has phenotypic overlap with the autoimmune diseases systemic lupus erythematosus (SLE) and chilblain lupus (Aicardi and Goutieres, (2000) *Neuropediatrics* 31(3):113). Mutations in TREX1 also are associated with retinal vasculopathy with cerebral leukodystrophy. TREX1-mediated autoimmune diseases are associated with the cell's inability to prevent autoimmunity via the degradation of ssDNA and dsDNA that accumulates in the cytoplasm. TREX1 null mice suffer from inflammatory myocarditis, resulting in circulatory failure, which is caused by chronic cytokine production (Morita et al. (2004) *Mol. Cell Biol.* 24(15):6719-6727; Yang et al. (2007) *Cell* 131(5):873-886; Tomicic et al. (2013) *Bioch. Biophys. Acta* 1833(8): 1832-1843). Hence, TREX1 deficiency induces innate immunity following the cytoplasmic accumulation of DNA, resulting in an inflammatory response (Wang et al. (2009) DNA Repair (Amst) 8:1179-1189). The source of the DNA that accumulates in the cytosol of TREX1-deficient cells was found to be in part derived from endogenous retroelements that escape from the damaged nucleus, as TREX1 is known to metabolize reverse-transcribed (RT) DNA (Stetson et al. (2008) *Cell* 134(4):587-598). In HIV infection, HIV RT DNA accumulates in the cytosol of infected T cells and macrophages, and would normally trigger cGAS/STING activation of antiviral immunity. TREX1 digests this viral DNA and permits HIV immune escape (Yan et al. (2010) *Nat. Immunol.* 11(11):1005-1013). Thus, TREX1 acts as a negative regulator of STING, and can be exploited to evade detection by several retroviruses, such as murine leukemia virus (MLV), simian immunodeficiency virus (SIV), and many others (Hasan et al. (2014) *Front. Microbiol.* 5:193).

Like STING, TREX1 is expressed in most mammalian cell types, with the key producers of cytokines in TREX1 null mice originating from macrophages and dendritic cells (Ahn et al. (2014) *J. Immunol.* 193(9):4634-4642). Data indicate that TREX1 is responsible for degrading self-DNA that can leak from a damaged nucleus into the cytosol, where it would otherwise bind and activate cGAS and lead to autoimmunity (Barber (2015) *Nat. Rev. Immunol.* 15(12): 760-770). In support of this, TREX1 null mice and TREX1-deficient cells that also lack cGAS are completely protected from type I interferon activation and lethal autoimmunity (Ablasser et al. (2014) *J. Immunol.* 192(12):5993-5997; Gray et al. (2015) *J. Immunol.* 195(5):1939-1943). In a negative feedback loop, type I interferon and type II IFNγ can also induce TREX1, and TREX1 thus serves to limit aberrant autoimmune activation (Tomicic et al. (2013) *Bioch. Biophys. Acta* 1833:1832-1843).

Lymphocytes derived from an Aicardi-Goutieres syndrome patient, containing mutated TREX1, were found to inhibit angiogenesis and the growth of neuroblastoma cells, the effect being enhanced by the presence of IFN-α (Pulliero et al. (2012) *Oncology Reports* 27:1689-1694). The use of microRNA-103 also has been shown to inhibit the expression of TREX1, disrupting DNA repair and angiogenesis, and resulting in decreased tumor growth in vivo (see, U.S. Patent Publication No. 2014/0127284, Cheresh et al.).

TREX1 is a negative regulator of macrophage activation and pro-inflammatory function. TREX1 null macrophages were found to exhibit increased TNF-α and IFN-α production, higher levels of CD86, and increased antigen presentation to T cells, as well as impaired apoptotic T-cell clearance (Pereira-Lopes et al. (2013) *J. Immunol.* 191: 6128-6135). The inability to adequately digest apoptotic DNA in TREX1 null macrophages generates high amounts of aberrant cytosolic DNA, which binds to cGAS and activates the STING pathway to produce higher levels of type I interferon (Ahn et al. (2014) *J. Immunol.* 193:4634-4642). Not all cell types are sensitive to the immunostimulatory effects of Trex 1 knockdown, however. In a study of individual cell types, dendritic cells, macrophages, fibroblasts and keratinocytes were found to produce type I IFN upon TREX1 knockdown, while B cells, cardiomyocytes, neurons and astrocytes did not (Peschke et al. (2016) *J. Immunol.* 197:2157-2166). Thus, inhibiting the function of TREX1 in phagocytic cells that have engulfed *S. typhimurium* would enhance their pro-inflammatory activity, while driving an accumulation of cytosolic DNA from phagocytosed tumor cells that can then activate the cGAS/STING pathway. The use of microRNA-103 inhibits the expression of TREX1, disrupting DNA repair and angiogenesis, and resulting in decreased tumor growth in vivo (see, e.g., U.S. Publication No. 2014/0127284, Cheresh et al.).

Studies have found that the expression of cGAS and/or STING is inhibited in over a third of colorectal cancers, while STING expression is lost in many primary and metastatic melanomas and $HPV^+$ cancers. STING signaling remains intact in all tumor-resident APCs that continuously sample the antigenic milieu of the TME, including Batf3-lineage CD103/CD8$\alpha^+$ DCs that cross-present tumor antigens to $CD8^+$ T cells, and these APCs will also readily phagocytose *S. typhimurium* or be activated by type I IFN from neighboring macrophages that have phagocytosed *S. typhimurium* containing TREX1 gene knockdown.

Inactivation of TREX1 enhances an immune response by permitting cytosolic accumulation of dsDNA to bind to the enzyme cyclic GMP-AMP (cGAMP) synthase (cGAS), a cytosolic DNA sensor that triggers the production of type I interferons and other cytokines through activation of the STING signaling pathway (Sun et al. (2013) *Science* 339 (6121):786-791; Wu et al. (2013) *Science* 339(6121):826-830). Activation of the STING pathway has been shown to induce potent innate and adaptive antitumor immunity (Corrales et al. (2015) *Cell Reports* 11:1018-1030).

Hence, embodiments of the immunostimulatory bacterial strains, as provided herein, are administered to inhibit TREX1 in tumor-resident APCs and induce cGAS/STING activation, thereby activating these DCs to cross-present host tumor antigens to $CD8^+$ T cells and induce local and systemic tumor regression and durable anti-tumor immunity (Corrales et al. (2015) *Cell Reports* 11:1018-1030; Zitvogel et al. (2015) *Nat. Rev. Mol. Cell. Biol.* 16:393-405).

Immunostimulatory bacteria provided herein express RNAi against TREX1, and loss of TREX1 and subsequent activation of cGAS/STING-induced vascular disruption enhance tumor colonization of *S. typhimurium.*

2. PD-L1

Programmed cell death protein 1 (PD-1) is an immune-inhibitory receptor that is involved in the negative regulation of immune responses. Its cognate ligand, programmed death-ligand 1 (PD-L1), is expressed on APCs, and upon binding to PD-1 on T cells, leads to loss of $CD8^+$ T cell effector function, inducing T cell tolerance. The expression of PD-L1 is often associated with tumor aggressiveness and reduced survival in certain human cancers (Gao et al. (2009) *Clin. Cancer Res.* 15(3):971-979).

Antibodies designed to block immune checkpoints, such as anti-PD-1 (for example, pembrolizumab, nivolumab) and anti-PD-L1 (for example, atezolizumab, avelumab, durvalumab) antibodies have had durable success in preventing T cell anergy and breaking immune tolerance. Only a fraction of treated patients exhibit clinical benefit, and those that do often present with autoimmune-related toxicities (Ribas (2015)*N. Engl. J. Med.* 373(16):1490-1492; Topalian et al. (2012) *N. Engl. J. Med.* 366(26):2443-54). Besides acquiring toxicity, PD-1/PD-L1 therapy often leads to resistance, and the concomitant use of anti-CTLA-4 antibodies (for example, ipilimumab) has shown limited success in clinical trials with significantly additive toxicity. To limit the toxicity and enhance the potency of PD-L1 blockade, an immunostimulatory bacteria with an shRNA to PD-L1, as provided herein, will synergize with TLR activation of immune cells to both activate and potentiate anti-tumor immunity.

3. VISTA

Other non-redundant checkpoints in immune activation can synergize with PD-1/PD-L1 and CTLA-4, such as V-domain immunoglobulin (Ig) suppressor of T cell activation (VISTA). VISTA is expressed primarily on APCs, particularly on tumor-infiltrating myeloid cells and myeloid-derived suppressor cells (MDSC), and to a lesser extent on regulatory T cells ($CD4^+$ $Foxp3^+$ Tregs) (Wang et al. (2011) *J. Exp. Med.* 208(3):577-592). Similar to PD-L1, VISTA upregulation directly suppresses T cell proliferation and cytotoxic function (Liu et al. (2015) *Proc. Natl. Acad. Sci. U.S.A.* 112(21):6682-6687). Monoclonal antibody targeting of VISTA was shown to remodel the tumor microenvironment in mice, increasing APC activation and enhancing anti-tumor immunity (LeMercier et al. (2014) *Cancer Res.* 74(7):1933-1944). Clinically, VISTA expression was shown to be upregulated on tumor-resident macrophages following treatment with anti-CTLA-4 therapy in prostate cancer, demonstrating compensatory regulation of immune checkpoints (Gao et al. (2017) *Nat. Med.* 23(5):551-555). The majority of VISTA expression is purported to be located in the intracellular compartment of myeloid cells, rather than on the surface, which can limit the effectiveness of the monoclonal antibody approach (Deng et al. (2016) *J. Immunother. Cancer* 4:86). The ability to inhibit VISTA from within the APC using a tumor-targeting bacteria containing shRNA to VISTA, as provided herein, will more efficiently and completely inhibit the T cell-suppressing function of VISTA, leading to activation of T cell-mediated anti-tumor immunity and tumor regression.

4. SIRPα

One mechanism by which tumor cells evade removal is to prevent their phagocytosis by innate immune cells. Phagocytosis is inhibited by surface expression of CD47, which is widely expressed on hematopoietic and non-hematopoietic cells (Liu et al. (2015) *PLoS ONE* 10(9):e0137345). Upon CD47 binding its receptor, signal regulatory protein alpha (SIRPα), an inhibitory signal for phagocytosis, is initiated. SIRPα is abundantly expressed on phagocytic cells, including macrophages, granulocytes and DCs. As such, the protein-protein interaction between CD47 and SIRPα represents another class of immune checkpoints unique to APCs, and tumor-resident macrophages in particular. The effectiveness of CD47 in preventing phagocytosis is evidenced by the fact that it is often upregulated in a wide variety of tumors, which allow them to avoid being phagocytosed by APCs in the tumor microenvironment (Liu et al. (2015) *Nat. Med.* 21(10):1209-1215). Several methods to block the CD47/SIRPα interaction have been examined, including the development of anti-CD47 or anti-SIRPα antibodies or antibody fragments, the use of small peptides that bind either protein, or the knockdown of CD47 expression (U.S. Patent Publication Nos. 2013/0142786, 2014/0242095; International Application Publication No. WO 2015/191861; McCracken et al. (2015) *Clin. Cancer Res.* 21(16):3597-3601). To this end, several monoclonal antibodies that directly target SIRPα are in clinical development, either alone or in combination with tumor-targeting antibodies (e.g., Rituximab, Daratumumab, Alemtuzumab, Cetuximab) that can enhance phagocytosis of antibody-opsonized tumor cells, in a process known as antibody-dependent cellular phagocytosis (ADCP) (McCracken et al. (2015) *Clin. Cancer Res.* 21(16): 3597-3601; Yanagita et al. (2017) *JCI Insight* 2(1):e89140).

The CD47/SIRPα interaction also serves to preserve the longevity of red blood cells by preventing their phagocytic elimination (Murata et al. (2014) *J. Biochem.* 155(6):335-344). Thus, systemically administered therapies such as anti-CD47 antibodies that broadly disrupt this interaction have resulted in anemia toxicities (Huang et al. (2017) *J. Thorac. Dis.* 9(2):E168-E174). Systemic SIRPα-based therapies also risk adverse events, such as organ damage by creating systemic hyperphagocytic self-eating macrophages. Using a tumor-targeting immunostimulatory bacteria containing an shRNA to SIRPα, such as provided herein, will localize the CD47/SIRPα disruption to the tumor microenvironment and eliminate these adverse events. Further, inhibition of SIRPα in the context of bacterial activation of TLR-mediated pro-inflammatory signaling pathways will potently activate these macrophages to become hyperphagocytic towards neighboring tumor cells (Bian et al. (2016) *Proc. Natl. Acad. Sci. U.S.A.* 113(37): E5434-E5443).

5. β-Catenin

Immune checkpoint pathways exemplify the multiple layers of regulation that exist to prevent immune hyperactivation and autoimmunity, and the difficulties in subverting these pathways to promote anti-tumor immunity. One mechanism by which tumors have evolved to be refractory to checkpoint therapies is through their lack of T cell and dendritic cell (DC) infiltration, described as non-T-cell-inflamed, or "cold tumors" (Sharma et al. (2017) *Cell* 9; 168(4):707-723). Several tumor-intrinsic mechanisms have been identified that lead to the exclusion of anti-tumor T cells and resistance to immunotherapy. In melanoma, in particular, molecular profiling of checkpoint therapy-refractory tumors revealed a signature of elevated β-catenin and its downstream target genes, correlating with a lack of tumor-infiltrating lymphocytes (Gajewski et al. (2011) *Curr. Opin. Immunol.* 23(2):286-292).

CTNNB1 is an oncogene that encodes β-catenin, and can induce the expression of the genes c-Myc and cyclin D1, resulting in tumor proliferation. Mutations in CTNNB1 are associated with certain cancers. Gene silencing of CTNNB1/β-catenin using *S. typhimurium* shRNA vectors can be used in the treatment of cancer (Guo et al. (2011) *Gene Therapy* 18:95-105; U.S. Patent Publication Nos. 2012/0009153, and 2016/0369282; International Application Publication No. WO 2015/032165). For example, shRNA silencing of CTNNB1, using *S. typhimurium* strain SL7207 as a delivery vector, reduced tumor proliferation and growth in SW480 xenograft mice, when compared to control cells, and reduced expression of c-Myc and cyclin D1 (Guo et al. (2011) *Gene Therapy* 18:95-105). Silencing of CTNNB1 for the treatment of hepatoblastoma also can be achieved using miRNA, with or without antibody therapeutics against the immune checkpoints PD-land PD-L1 (International Application Publication No. WO 2017/005773). The use of siRNA or shRNA targeting CTNNB1, delivered via alternative vectors, such as liposomes, for the treatment of CTNNB1-related cancers, including adenocarcinomas and squamous cell carcinomas, also can be affected (U.S. Patent Publication Nos. 2009/0111762, and 2012/0294929).

Elevated β-catenin signaling directly inhibits the chemokine CCL4 from recruiting Batf3-lineage CD103/CD8$\alpha^+$ DCs, thereby preventing them from priming tumor antigen-specific CD8$^+$ T cells (Spranger et al. (2015) *Nature* 523 (7559):231-235). β-catenin is the major downstream mediator of the WNT signaling pathway, a key embryonic developmental pathway that is also critical for adult tissue regeneration, homeostasis and hematopoiesis (Clevers et al. (2012) *Cell* 149(6):1192-1205). Excessive WNT/β-catenin signaling has been implicated in a variety of cancers (Tai et al. (2015) *Oncologist* 20(10):1189-1198). Accordingly, several strategies to target WNT/β-catenin signaling have been pursued, but success has been hampered by a lack of specificity to the tumor microenvironment, resulting in off-target toxicities to intestinal stem cells, bone turnover and hematopoiesis (Kahn (2014) *Nat. Rev. Drug Dis.* 13(7): 513-532). The immunostimulatory bacteria provided herein overcome these problems.

For example, an advantage of using an immunostimulatory bacteria with shRNA to β-catenin as provided herein, is enhancing chemokine-mediated infiltration of T cell-priming DCs and the conversion of a cold tumor to a T-cell-inflamed tumor microenvironment, without the systemic toxicities of existing therapeutic modalities. Further, bacterial activation of TLR innate immune signaling pathways synergize with β-catenin inhibition to further promote immune activation and anti-tumor immunity.

6. TGF-β

Transforming growth factor beta (TGF-β) is a pleiotropic cytokine with numerous roles in embryogenesis, wound healing, angiogenesis and immune regulation. It exists in three isoforms in mammalian cells, TGF-β1, TGF-β2 and, TGF-β3; TGF-β1 is the most predominant in immune cells (Esebanmen et al. (2017) *Immunol Res.* 65:987-994). TGF-β's role as an immunosuppressant is arguably its most dominant function. Its activation from a latent form in the tumor microenvironment, in particular, has profound immunosuppressive effects on DCs and their ability to tolerize antigen-specific T cells. TGF-β can also directly convert Th1 CD4$^+$ T cells to immunosuppressive Tregs, furthering promoting tumor tolerance (Travis et al. (2014) *Annu. Rev. Immunol.* 32: 51-82). Based on its tumor-specific immunosuppressive functions, and irrespective of its known cancer cell growth and metastasis-promoting properties, inhibition of TGF-β is a cancer therapy target. High TGF-β signaling has been demonstrated in several human tumor types, including CRC, HCC, PDAC and NSCLC (Colak et al. (2017) *Trends in Cancer* 3:1). Systemic inhibition of TGF-β can lead to unacceptable autoimmune toxicities, and its inhibition should be localized to the tumor microenvironment. As such, a tumor-targeting immunostimulatory bacteria with RNAi, such as shRNA, to TGF-β, provided herein, or an shRNA to TGF-βRII, breaks tumor immune tolerance and stimulates anti-tumor immunity.

7. VEGF

Angiogenesis, or the development of new blood vessels, is an essential step for any tumor microenvironment to become established. Vascular endothelial growth factor (VEGF) is the critical mitogen for endothelial proliferation and angiogenesis, and inhibition of VEGF in the tumor microenvironment markedly decreases tumor vascularity, thereby starving the tumor of its blood supply (Kim et al. (1993) *Nature* 362(6423):841-844). This early research led to the development of the monoclonal antibody inhibitor of VEGF, bevacizumab (Avastin; Genentech), which in combination with chemotherapy, has become the standard of care for metastatic CRC. Systemic administration of bevacizumab also demonstrated significant toxicities, including multiple fatalities in a Phase II trial of NSCLC, largely due to hemorrhaging. As such, several next generation anti-angiogenics have been evaluated, such as the anti-VEGF receptor 2 antibody ramucirumab (Cyramza, Imclone) and the anti-angiogenic tyrosine kinase inhibitor axitinib (Inlyta, Pfizer), yet none have been able to overcome systemic toxicity or markedly improve progression-free survival (Alshangiti et al. (2018) *Curr. Oncol.* 25 (Suppl 1): S45-S58). While the anti-tumor activity of anti-VEGF therapy has shown some promise, systemic toxicity is clearly limiting. As such, a therapy that targets only the tumor microenvironment, such as an immunostimulatory tumor-targeting bacteria with shRNA to VEGF, provided herein, delivers local anti-angiogenic therapy while preventing systemic toxicity. This therapeutic modality has the additional advantage of being taken up into myeloid cells, which predominantly produce VEGF in the tumor microenvironment, where it will have maximum impact on tumor progression (Osterberg et al. (2016) *Neuro-Oncology.* 18(7):939-949).

8. Additional Exemplary Checkpoint Targets

Exemplary checkpoint targets for which RNAi, such as micro-RNA and shRNA, can be prepared or are exemplified herein include, but are not limited to:

| Checkpoint target |
|---|
| CTLA-4 |
| PD-L1 (B7-H1) |
| PD-L2 |
| PD-1, PD-2 |
| IDO1 |
| IDO2 |
| SIRP alpha, CD47 |
| VISTA (B7-H5) |
| LIGHT |
| HVEM |
| CD28 |
| LAG3, TIM3, TIGIT |
| Galectin-9 |
| CEACAM1, CD155, CD112, |

-continued

| Checkpoint target |
|---|
| CD226, CD244 (2B4) |
| B7-H2, B7-H3, CD137, ICOS, GITR, B7-H4, B7-H6 |
| CD137, CD27, CD40, CD40L, CD48, CD70, CD80, CD86, CD137 (4-1BB), CD200, CD272 (BTLA), CD160 |
| A2a receptor, A2b receptor, HHLA2, ILT-2, ILT-4, gp49B, PIR-B |
| OX40, OX-40L, BTLA, ICOS, HLA-G, ILT-2/4 |
| KIR, GITR, TIM1, TIM4 |

Other exemplary targets include, but are not limited to:

| Target |
|---|
| CTNNB1 (beta-catenin) |
| STAT3 |
| BCL-2 |
| MDR1 |
| Arginase1 |
| iNOS |
| TGF-β |
| IL-10 |
| pGE2 |
| VEGF |
| KSP |
| HER2 |
| KRAS |
| TAK1 |
| PLK1 |
| K-Ras (Ras) |
| Stablin-1/CLEVER-1 |
| RNase H2 |
| DNase II |

H. Pharmaceutical Production, Compositions, and Formulations

Provided herein are methods for manufacturing, pharmaceutical compositions and formulations containing any of the immunostimulatory bacteria provided herein and pharmaceutically acceptable excipients or additives. The pharmaceutical compositions can be used in treatment of diseases, such as hyperproliferative diseases or condition, such as a tumor or cancer. The immunostimulatory bacteria can be administered in a single agent therapy, or can be administered in a combination therapy with a further agent or treatment. The compositions can be formulated for single dosage administration or for multiple dosage administration. The agents can be formulated for direct administration. The compositions can be provided as a liquid or dried formulation.

1. Manufacturing a. Cell Bank Manufacturing

As the active ingredient of the immunotherapeutic described herein is composed of engineered self-replicating bacteria, the selected composition will be expanded into a series of cell banks that will be maintained for long-term storage and as the starting material for manufacturing of drug substance. Cell banks are produced under current good manufacturing practices (cGMP) in an appropriate manufacturing facility per the Code of Federal Regulations (CFR) 21 part 211 or other relevant regulatory authority. As the active agent of the immunotherapeutic is a live bacterium, the products described herein are, by definition, non-sterile and cannot be terminally sterilized. Care must be taken to ensure that aseptic procedures are used throughout the manufacturing process to prevent contamination. As such, all raw materials and solutions must be sterilized prior to use in the manufacturing process.

A master cell bank (MCB) is produced by sequential serial single colony isolation of the selected bacterial strain to ensure no contaminants are present in the starting material. A sterile culture vessel containing sterile media (can be complex media e.g., LB or MSB or defined media e.g., M9 supplemented with appropriate nutrients) is inoculated with a single well-isolated bacterial colony and the bacteria are allowed to replicate e.g., by incubation at 37° C. with shaking. The bacteria are then prepared for cryopreservation by suspension in a solution containing a cryoprotective agent or agents.

Examples of cryoprotective agents include: proteins such as human or bovine serum albumin, gelatin, and immunoglobulins; carbohydrates including monosaccharides (galactose, D-mannose, sorbose, etc.) and their non-reducing derivatives (e.g., methylglucoside), disaccharides (trehalose, sucrose, etc.), cyclodextrins, and polysaccharides (raffinose, maltodextrins, dextrans, etc.); amino-acids (glutamate, glycine, alanine, arginine or histidine, tryptophan, tyrosine, leucine, phenylalanine, etc.); methylamines such as betaine; polyols such as trihydric or higher sugar alcohols, e.g., glycerin, erythritol, glycerol, arabitol, xylitol, sorbitol, and mannitol; propylene glycol; polyethylene glycol; surfactants e.g., pluronic; or organo-sulfur compounds such as dimethyl sulfoxide (DMSO), and combinations thereof. Cryopreservation solutions can include one or more cryoprotective agents in a solution that can also contain salts (e.g., sodium chloride, potassium chloride, magnesium sulfate), and/or buffering agents such as sodium phosphate, tris(hydroxymethyl)aminomethane (TRIS), 4-(2-hydroxyethyl)-1-piperazineethanesulfonic acid (HEPES), and other such buffering agents known to those of skill.

Suspension of the bacteria in cryopropreservation solution can be achieved either by addition of a concentrated cryoprotective agent or agents to the culture material to achieve a final concentration that preserves viability of the bacteria during the freezing and thawing process (e.g., 0.5% to 20% final concentration of glycerol), or by harvesting the bacteria (e.g., by centrifugation) and suspending in a cryopreservative solution containing the appropriate final concentration of cryoprotective agent(s). The suspension of bacteria in cryopreservation solution is then filled into appropriate sterile vials (plastic or glass) with a container closure system that is capable of maintaining closure integrity under frozen conditions (e.g., butyl stoppers and crimp seals). The vials of master cell bank are then frozen (either slowly by means of a controlled rate freezer, or quickly by means of placing directly into a freezer). The MCB is then stored frozen at a temperature that preserves long-term viability (e.g., at or below −60° C.). Thawed master cell bank material is thoroughly characterized to ensure identity, purity, and activity per regulation by the appropriate authorities.

Working cell banks (WCBs) are produced much the same way as the master cell bank, but the starting material is derived from the MCB. MCB material can be directly transferred into a fermentation vessel containing sterile media and expanded as above. The bacteria are then suspended in a cryopreservation solution, filled into containers, sealed, and frozen at or below −20° C. Multiple WCBs can be produced from MCB material, and WCB material can be used to make additional cell banks (e.g., a manufacturer's working cell bank MWCB). WCBs are stored frozen and characterized to ensure identity, purity, and activity. WCB material is typically the starting material used in production of the drug substance of biologics such as engineered bacteria.

b. Drug Substance Manufacturing

Drug substance is manufactured using aseptic processes under cGMP as described above. Working cell bank material is typically used as starting material for manufacturing of drug substance under cGMP, however other cell banks can be used (e.g., MCB or MWCB). Aseptic processing is used for production of all cell therapies including bacterial cell-based therapies. The bacteria from the cell bank are expanded by fermentation, this can be achieved by production of a pre-culture (e.g., in a shake flask) or by direct inoculation of a fermenter. Fermentation is accomplished in a sterile bioreactor or flask that can be single-use disposable or re-usable. Bacteria are harvested by concentration (e.g., by centrifugation, continuous centrifugation, or tangential flow filtration). Concentrated bacteria are purified from media components and bacterial metabolites by exchange of the media with buffer (e.g., by diafiltration). The bulk drug product is formulated and preserved as an intermediate (e.g., by freezing or drying) or is processed directly into a drug product. Drug substance is tested for identity, strength, purity, potency, and quality.

c. Drug Product Manufacturing

Drug product is defined as the final formulation of the active substance contained in its final container. Drug product is manufactured using aseptic processes under cGMP. Drug product is produced from drug substance. Drug substance is thawed or reconstituted if necessary, then formulated at the appropriate target strength. Because the active component of the drug product is live, engineered bacteria, the strength is determined by the number of CFUs contained within the suspension. The bulk product is diluted in a final formulation appropriate for storage and use as described below. Containers are filled, and sealed with a container closure system and the drug product is labeled. The drug product is stored at an appropriate temperature to preserve stability and is tested for identity, strength, purity, potency, and quality and released for human use if it meets specified acceptance criteria.

2. Compositions

Pharmaceutically acceptable compositions are prepared in view of approvals for a regulatory agency or other agency prepared in accordance with generally recognized pharmacopeia for use in animals and in humans. The compositions can be prepared as solutions, suspensions, powders, or sustained release formulations. Typically, the compounds are formulated into pharmaceutical compositions using techniques and procedures well known in the art (see e.g., Ansel, *Introduction to Pharmaceutical Dosage Forms*, Fourth Edition, 1985, 126). The formulation should suit the mode of administration.

Compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. Other modes of administration also are contemplated. Administration can be local, topical or systemic depending upon the locus of treatment. Local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. Compositions also can be administered with other biologically active agents, either sequentially, intermittently or in the same composition. Administration also can include controlled release systems including controlled release formulations and device controlled release, such as by means of a pump.

The most suitable route in any given case depends on a variety of factors, such as the nature of the disease, the progress of the disease, the severity of the disease and the particular composition which is used. Pharmaceutical compositions can be formulated in dosage forms appropriate for each route of administration. In particular, the compositions can be formulated into any suitable pharmaceutical preparations for systemic, local intraperitoneal, oral or direct administration. For example, the compositions can be formulated for administration subcutaneously, intramuscularly, intratumorally, intravenously or intradermally. Administration methods can be employed to decrease the exposure of the active agent to degradative processes, such as immunological intervention via antigenic and immunogenic responses. Examples of such methods include local administration at the site of treatment or continuous infusion.

The immunostimulatory bacteria can be formulated into suitable pharmaceutical preparations such as solutions, suspensions, tablets, dispersible tablets, pills, capsules, powders, sustained release formulations or elixirs, for oral administrations, as well as transdermal patch preparation and dry powder inhalers. Typically, the compounds are formulated into pharmaceutical compositions using techniques and procedures well known in the art (see e.g., Ansel, *Introduction to Pharmaceutical Dosage Forms*, Fourth Edition, 1985, 126). Generally, the mode of formulation is a function of the route of administration. The compositions can be formulated in dried (lyophilized or other forms of vitrification) or liquid form. Where the compositions are provided in dried form they can be reconstituted just prior to use by addition of an appropriate buffer, for example, a sterile saline solution.

3. Formulations a. Liquids, Injectables, Emulsions

The formulation generally is made to suit the route of administration. Parenteral administration, generally characterized by injection or infusion, either subcutaneously, intramuscularly, intratumorally, intravenously or intradermally is contemplated herein. Preparations of bacteria for parenteral administration include suspensions ready for injection (direct administration) or frozen suspensions that are thawed prior to use, dry soluble products, such as lyophilized powders, ready to be combined with a resuspension solution just prior to use, and emulsions. Dried thermostable formulations such as lyophilized formulations can be used for storage of unit doses for later use.

The pharmaceutical preparation can be in a frozen liquid form, for example a suspension. If provided in frozen liquid form, the drug product can be provided as a concentrated preparation to be thawed and diluted to a therapeutically effective concentration before use.

The pharmaceutical preparations also can be provided in a dosage form that does not require thawing or dilution for use. Such liquid preparations can be prepared by conventional means with pharmaceutically acceptable additives, as appropriate, such as suspending agents (e.g., sorbitol, cellulose derivatives or hydrogenated edible fats); emulsifying agents (e.g., lecithin or acacia); non-aqueous vehicles (e.g., almond oil, oily esters, or fractionated vegetable oils); and preservatives suitable for use with microbial therapeutics. The pharmaceutical preparations can be presented in dried form, such as lyophilized or spray-dried, for reconstitution with water or other sterile suitable vehicle before use.

Suitable excipients are, for example, water, saline, dextrose, or glycerol. The solutions can be either aqueous or non-aqueous. If administered intravenously, suitable carriers include physiological saline or phosphate buffered saline (PBS), and other buffered solutions used for intravenous hydration. For intratumoral administration solutions containing thickening agents such as glucose, polyethylene glycol, and polypropylene glycol, oil emulsions and mixtures thereof can be appropriate to maintain localization of the injectant.

Pharmaceutical compositions can include carriers or other excipients. For example, pharmaceutical compositions provided herein can contain any one or more of a diluents(s), adjuvant(s), antiadherent(s), binder(s), coating(s), filler(s), flavor(s), color(s), lubricant(s), glidant(s), preservative(s), detergent(s), or sorbent(s) and a combination thereof or vehicle with which a modified therapeutic bacteria is administered. For example, pharmaceutically acceptable carriers or excipients used in parenteral preparations include aqueous vehicles, non-aqueous vehicles, isotonic agents, buffers, antioxidants, local anesthetics, suspending and dispersing agents, emulsifying agents, sequestering or chelating agents and other pharmaceutically acceptable substances. Formulations, including liquid preparations, can be prepared by conventional means with pharmaceutically acceptable additives or excipients.

Pharmaceutical compositions can include carriers such as a diluent, adjuvant, excipient, or vehicle with which the compositions are administered. Examples of suitable pharmaceutical carriers are described in "*Remington's Pharmaceutical Sciences*" by E. W. Martin. Such compositions will contain a therapeutically effective amount of the compound or agent, generally in purified form or partially purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. For example, suitable excipients are, for example, water, saline, dextrose, glycerol or ethanol. A composition, if desired, also can contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Pharmaceutically acceptable carriers used in parenteral preparations include aqueous vehicles, non-aqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Non-aqueous parenteral vehicles include fixed oils of vegetable origin, cottonseed oil, corn oil, sesame oil and peanut oil. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include, for example, polysorbates, such Polysorbate 80 (TWEEN 80). Sequestering or chelating agents of metal ions, such as EDTA, can be included. Pharmaceutical carriers also include polyethylene glycol and propylene glycol for water miscible vehicles and sodium hydroxide, hydrochloric acid, citric acid or lactic acid for pH adjustment. Non-anti-microbial preservatives can be included.

The pharmaceutical compositions also can contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. The percentage of active compound contained in such parenteral compositions is highly dependent on the specific nature thereof, as well as the activity of the compound and the needs of the subject.

b. Dried Thermostable Formulations

The bacteria can be dried. Dried thermostable formulations, such as lyophilized or spray dried powders and vitrified glass can be reconstituted for administration as solutions, emulsions and other mixtures. The dried thermostable formulation can be prepared from any of the liquid formulations, such as the suspensions, described above. The pharmaceutical preparations can be presented in lyophilized or vitrified form for reconstitution with water or other suitable vehicle before use.

The thermostable formulation is prepared for administration by reconstituting the dried compound with a sterile solution. The solution can contain an excipient which improves the stability or other pharmacological attribute of the active substance or reconstituted solution, prepared from the powder. The thermostable formulation is prepared by dissolving an excipient, such as dextrose, sorbitol, fructose, corn syrup, xylitol, glycerin, glucose, sucrose or other suitable agent, in a suitable buffer, such as citrate, sodium or potassium phosphate or other such buffer known to those of skill in the art. Then, the drug substance is added to the resulting mixture, and stirred until it is mixed. The resulting mixture is apportioned into vials for drying. Each vial will contain a single dosage containing $1\times10^5$ to $1\times10^{11}$ CFUs per vial. After drying, the product vial is sealed with a container closure system that prevents moisture or contaminants from entering the sealed vial. The dried product can be stored under appropriate conditions, such as at −20° C., 4° C., or room temperature. Reconstitution of this dried formulation with water or a buffer solution provides a formulation for use in parenteral administration. The precise amount depends upon the indication treated and selected compound. Such amount can be empirically determined.

4. Compositions for Other Routes of Administration

Depending upon the condition treated, other routes of administration in addition to parenteral, such as topical application, transdermal patches, oral and rectal administration are also contemplated herein. The suspensions and powders described above can be administered orally or can be reconstituted for oral administration. Pharmaceutical dosage forms for rectal administration are rectal suppositories, capsules and tablets and gel capsules for systemic effect. Rectal suppositories include solid bodies for insertion into the rectum which melt or soften at body temperature releasing one or more pharmacologically or therapeutically active ingredients. Pharmaceutically acceptable substances in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration are manufactured using the same pharmaceutically acceptable substance and by the same methods as for formulations for oral administration. Formulations suitable for rectal administration can be provided as unit dose suppositories. These can be prepared by admixing the drug substance with one or more conventional solid carriers, for example, cocoa butter, and then shaping the resulting mixture.

For oral administration, pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well-known in the art.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

Topical mixtures are prepared as described for local and systemic administration. The resulting mixtures can be solutions, suspensions, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compositions can be formulated as aerosols for topical application, such as by inhalation (see, e.g., U.S. Pat. Nos. 4,044,126; 4,414,209 and 4,364,923, which describe aerosols for delivery of a steroid useful for treatment of lung diseases). These formulations, for administration to the respiratory tract, can be in the form of an aerosol or solution for a nebulizer, or as a microfine powder for insufflation, alone or in combination with an inert carrier such as lactose. In such a case, the particles of the formulation will typically have diameters of less than 50 microns, or less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients also can be administered.

Formulations suitable for transdermal administration are provided. They can be provided in any suitable format, such as discrete patches adapted to remain in intimate contact with the epidermis of the recipient for a prolonged period of time. Such patches contain the active compound in an optionally buffered aqueous solution of, for example, 0.1 to 0.2 M concentration with respect to the active compound. Formulations suitable for transdermal administration also can be delivered by iontophoresis (see, e.g., Tyle, P., (1986) *Pharmaceutical Research* 3(6):318-326) and typically take the form of an optionally buffered aqueous solution of the active compound.

Pharmaceutical compositions also can be administered by controlled release formulations and/or delivery devices (see e.g., U.S. Pat. Nos. 3,536,809; 3,598,123; 3,630,200; 3,845,770; 3,916,899; 4,008,719; 4,769,027; 5,059,595; 5,073,543; 5,120,548; 5,591,767; 5,639,476; 5,674,533 and 5,733,566).

5. Dosages and Administration

The compositions can be formulated as pharmaceutical compositions for single dosage or multiple dosage administration. The immunostimulatory bacteria can be included in an amount sufficient to exert a therapeutically useful effect in the absence of undesirable side effects on the patient treated. For example, the concentration of the pharmaceutically active compound is adjusted so that an injection provides an effective amount to produce the desired pharmacological effect. The therapeutically effective concentration can be determined empirically by testing the immunostimulatory bacteria in known in vitro and in vivo systems such as by using the assays described herein or known in the art. For example, standard clinical techniques can be employed. In vitro assays and animal models can be employed to help identify optimal dosage ranges. The precise dose, which can be determined empirically, can depend on the age, weight, body surface area, and condition of the patient or animal, the particular immunostimulatory bacteria administered, the route of administration, the type of disease to be treated and the seriousness of the disease.

Hence, it is understood that the precise dosage and duration of treatment is a function of the disease being treated and can be determined empirically using known testing protocols or by extrapolation from in vivo or in vitro test data. Concentrations and dosage values also can vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of compositions and combinations containing them. The compositions can be administered hourly, daily, weekly, monthly, yearly or once. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects).

The immunostimulatory bacteria are included in the composition in an amount sufficient to exert a therapeutically useful effect. For example, the amount is one that achieves a therapeutic effect in the treatment of a hyperproliferative disease or condition, such as cancer.

Pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. Unit dosage forms, include, but are not limited to, tablets, capsules, pills, powders, granules, parenteral suspensions, and oral solutions or suspensions, and oil-in-water emulsions containing suitable quantities of the compounds or pharmaceutically acceptable derivatives thereof. Unit dose forms can be contained in vials, ampoules and syringes or individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses that are not segregated in packaging. Generally, dosage forms or compositions containing active ingredient in the range of 0.005% to 100% with the balance made up from non-toxic carrier can be prepared. Pharmaceutical compositions can be formulated in dosage forms appropriate for each route of administration.

The unit-dose parenteral preparations are packaged in an ampoule, a vial or a syringe with a needle. The volume of liquid solution or reconstituted powder preparation, containing the pharmaceutically active compound, is a function of the disease to be treated and the particular article of manufacture chosen for package. All preparations for parenteral administration must be sterile, as is known and practiced in the art.

As indicated, compositions provided herein can be formulated for any route known to those of skill in the art including, but not limited to, subcutaneous, intramuscular, intravenous, intradermal, intralesional, intraperitoneal, epidural, vaginal, rectal, local, otic, transdermal administration, or any route of administration. Formulations suited for such routes are known to one of skill in the art. Compositions also can be administered with other biologically active agents, either sequentially, intermittently or in the same composition.

Pharmaceutical compositions can be administered by controlled release formulations and/or delivery devices (see, e.g., U.S. Pat. Nos. 3,536,809; 3,598,123; 3,630,200; 3,845,770; 3,847,770; 3,916,899; 4,008,719; 4,687,660; 4,769,027; 5,059,595; 5,073,543; 5,120,548; 5,354,556; 5,591,767; 5,639,476; 5,674,533 and 5,733,566). Various delivery systems are known and can be used to administer selected compositions, are contemplated for use herein, and such particles can be easily made.

6. Packaging and Articles of Manufacture

Also provided are articles of manufacture containing packaging materials, any pharmaceutical composition provided herein, and a label that indicates that the compositions are to be used for treatment of diseases or conditions as described herein. For example, the label can indicate that the treatment is for a tumor or cancer.

Combinations of immunostimulatory bacteria described herein and another therapeutic agent also can be packaged in an article of manufacture. In one example, the article of manufacture contains a pharmaceutical composition containing the immunostimulatory bacteria composition and no further agent or treatment. In other examples, the article of manufacture includes another further therapeutic agent, such as a different anti-cancer agent. In this example, the agents can be provided together or separately, for packaging as articles of manufacture.

The articles of manufacture provided herein contain packaging materials. Packaging materials for use in packaging pharmaceutical products are well known to those of skill in the art. See, for example, U.S. Pat. Nos. 5,323,907, 5,052,558 and 5,033,252, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. Exemplary of articles of manufacture are containers including single chamber and dual chamber containers. The containers include, but are not limited to, tubes, bottles and syringes. The containers can further include a needle for intravenous administration.

The choice of package depends on the agents, and whether such compositions will be packaged together or separately. In general, the packaging is non-reactive with the compositions contained therein. In other examples, some of the components can be packaged as a mixture. In other examples, all components are packaged separately. Thus, for example, the components can be packaged as separate compositions that, upon mixing just prior to administration, can be directly administered together. Alternatively, the components can be packaged as separate compositions for administration separately.

Selected compositions including articles of manufacture thereof also can be provided as kits. Kits can include a pharmaceutical composition described herein and an item for administration provided as an article of manufacture. The compositions can be contained in the item for administration or can be provided separately to be added later. The kit can, optionally, include instructions for application including dosages, dosing regimens and instructions for modes of administration. Kits also can include a pharmaceutical composition described herein and an item for diagnosis.

I. Methods of Treatment and Uses

The methods provided herein include methods of administering or using the immunostimulatory bacteria, for treating subjects having a disease or condition whose symptoms can be ameliorated or lessened by administration of such bacteria, such as cancer. In particular examples, the disease or condition is a tumor or a cancer. Additionally, methods of combination therapies with one or more additional agents for treatment, such as an anti-cancer agent, such as an oncolytic virus, an immunotherapeutic agent, and/or an anti-hyaluronan agent, such as a hyaluronidase, also are provided. The bacteria can be administered by any suitable route, including, but not limited to, parenteral, systemic, topical and local, such as intra-tumoral, intravenous, rectal, oral, intramuscular, mucosal and other routes. Because of the modifications of the bacteria described herein, problems associated with systemic administration are solved. Formulations suitable for each route of administration are provided. The skilled person can establish suitable regimens and doses and select routes.

1. Tumors

The immunostimulatory bacteria, combinations, uses and methods provided herein are applicable to treating all types of tumors, including cancers, particularly solid tumors including lung cancer, bladder cancer, non-small cell lung cancer, gastric cancers, head and neck cancers, ovarian cancer, liver cancer, pancreatic cancer, kidney cancer, breast cancer, colorectal cancer, and prostate cancer. The methods also can be used for hematological cancers.

Tumors and cancers subject to treatment by the uses and methods provided herein include, but are not limited to, those that originate in the immune system, skeletal system, muscles and heart, breast, pancreas, gastrointestinal tract, central and peripheral nervous system, renal system, reproductive system, respiratory system, skin, connective tissue systems, including joints, fatty tissues, and circulatory system, including blood vessel walls. Examples of tumors that can be treated with the immunostimulatory bacteria provided herein include carcinomas, gliomas, sarcomas (including liposarcoma), adenocarcinomas, adenosarcomas, and adenomas. Such tumors can occur in virtually all parts of the body, including, for example, the breast, heart, lung, small intestine, colon, spleen, kidney, bladder, head and neck, ovary, prostate, brain, pancreas, skin, bone, bone marrow, blood, thymus, uterus, testicles, cervix, or liver.

Tumors of the skeletal system include, for example, sarcomas and blastomas such as osteosarcoma, chondrosarcoma, and chondroblastoma. Muscle and heart tumors include tumors of both skeletal and smooth muscles, e.g., leiomyomas (benign tumors of smooth muscle), leiomyosarcomas, rhabdomyomas (benign tumors of skeletal muscle), rhabdomyosarcomas, and cardiac sarcomas. Tumors of the gastrointestinal tract include, e.g., tumors of the mouth, esophagus, stomach, small intestine, colon and colorectal tumors, as well as tumors of gastrointestinal secretory organs such as the salivary glands, liver, pancreas, and the biliary tract. Tumors of the central nervous system include tumors of the brain, retina, and spinal cord, and can also originate in associated connective tissue, bone, blood vessels or nervous tissue. Treatment of tumors of the peripheral nervous system are also contemplated. Tumors of the peripheral nervous system include malignant peripheral nerve sheath tumors. Tumors of the renal system include those of the kidneys, e.g., renal cell carcinoma, as well as tumors of the ureters and bladder. Tumors of the reproductive system include tumors of the cervix, uterus, ovary, prostate, testes and related secretory glands. Tumors of the immune system include both blood-based and solid tumors, including lymphomas, e.g., both Hodgkin's and non-Hodgkin's. Tumors of the respiratory system include tumors of the nasal passages, bronchi and lungs. Tumors of the breast include, e.g., both lobular and ductal carcinoma.

Other examples of tumors that can be treated by the immunostimulatory bacteria and methods provided herein include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma (such as glioblastoma multiforme) and leiomyosarcoma. Examples of other cancers that can be treated as provided herein include, but are not limited to, lymphoma, blastoma, neuroendocrine tumors, mesothelioma, schwannoma, meningioma, melanoma, and leukemia or lymphoid malignancies. Examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (e.g., nasopharyngeal cancer, salivary gland carcinoma, and esophageal cancer), lung (e.g., small-cell lung cancer, non-small cell lung cancer, adenocarcinoma of the lung and squamous carcinoma of the lung), digestive system (e.g., gastric or stomach cancer including gastrointestinal cancer, cancer of the bile duct or biliary tract, colon cancer, rectal cancer, colorectal cancer, and anal carcinoma), reproductive system (e.g., testicular, penile, or prostate cancer, uterine, vaginal, vulval, cervical, ovarian, and endometrial cancer), skin (e.g., melanoma, basal cell carcinoma, squamous cell cancer, actinic keratosis, cutaneous melanoma), liver (e.g., liver cancer, hepatic carcinoma, hepatocellular cancer, and hepatoma), bone (e.g., osteoclastoma, and osteolytic bone cancers), additional tissues and organs (e.g., pancreatic cancer, bladder cancer, kidney or renal cancer, thyroid cancer, breast cancer, cancer of the peritoneum, and Kaposi's sarcoma), tumors of the vascular system (e.g., angiosarcoma and hemangiopericytoma), Wilms' tumor, retinoblastoma, osteosarcoma, and Ewing's sarcoma.

2. Administration

In practicing the uses and methods herein, immunostimulatory bacteria provided herein can be administered to a subject, including a subject having a tumor or having neoplastic cells, or a subject to be immunized. One or more steps can be performed prior to, simultaneously with or after administration of the immunostimulatory bacteria to the subject including, but not limited to, diagnosing the subject with a condition appropriate for administering immunostimulatory bacteria, determining the immunocompetence of the subject, immunizing the subject, treating the subject with a chemotherapeutic agent, treating the subject with radiation, or surgically treating the subject.

For embodiments that include administering immunostimulatory bacteria to a tumor-bearing subject for therapeutic purposes, the subject typically has previously been diagnosed with a neoplastic condition. Diagnostic methods also can include determining the type of neoplastic condition, determining the stage of the neoplastic conditions, determining the size of one or more tumors in the subject, determining the presence or absence of metastatic or neoplastic cells in the lymph nodes of the subject, or determining the presence of metastases of the subject.

Some embodiments of therapeutic methods for administering immunostimulatory bacteria to a subject can include a step of determination of the size of the primary tumor or the stage of the neoplastic disease, and if the size of the primary tumor is equal to or above a threshold volume, or if the stage of the neoplastic disease is at or above a threshold stage, an immunostimulatory bacterium is administered to the subject. In a similar embodiment, if the size of the primary tumor is below a threshold volume, or if the stage of the neoplastic disease is at or below a threshold stage, the immunostimulatory bacterium is not yet administered to the subject; such methods can include monitoring the subject until the tumor size or neoplastic disease stage reaches a threshold amount, and then administering the immunostimulatory bacterium to the subject. Threshold sizes can vary according to several factors, including rate of growth of the tumor, ability of the immunostimulatory bacterium to infect a tumor, and immunocompetence of the subject. Generally the threshold size will be a size sufficient for an immunostimulatory bacterium to accumulate and replicate in or near the tumor without being completely removed by the host's immune system, and will typically also be a size sufficient to sustain a bacterial infection for a time long enough for the host to mount an immune response against the tumor cells, typically about one week or more, about ten days or more, or about two weeks or more. Exemplary threshold stages are any stage beyond the lowest stage (e.g., Stage I or equivalent), or any stage where the primary tumor is larger than a threshold size, or any stage where metastatic cells are detected.

Any mode of administration of a microorganism to a subject can be used, provided the mode of administration permits the immunostimulatory bacteria to enter a tumor or metastasis. Modes of administration can include, but are not limited to, intravenous, intraperitoneal, subcutaneous, intramuscular, topical, intratumoral, multipuncture, inhalation, intranasal, oral, intracavity (e.g., administering to the bladder via a catheter, administering to the gut by suppository or enema), aural, rectal, and ocular administration.

One skilled in the art can select any mode of administration compatible with the subject and the bacteria, and that also is likely to result in the bacteria reaching tumors and/or metastases. The route of administration can be selected by one skilled in the art according to any of a variety of factors, including the nature of the disease, the kind of tumor, and the particular bacteria contained in the pharmaceutical composition. Administration to the target site can be performed, for example, by ballistic delivery, as a colloidal dispersion system, or systemic administration can be performed by injection into an artery.

The dosage regimen can be any of a variety of methods and amounts, and can be determined by one skilled in the art according to known clinical factors. A single dose can be therapeutically effective for treating a disease or disorder in which immune stimulation effects treatment. Exemplary of such stimulation is an immune response, that includes, but is not limited to, one or both of a specific immune response and non-specific immune response, both specific and non-specific responses, innate response, primary immune response, adaptive immunity, secondary immune response, memory immune response, immune cell activation, immune cell proliferation, immune cell differentiation, and cytokine expression.

As is known in the medical arts, dosages for a subject can depend on many factors, including the subject's species, size, body surface area, age, sex, immunocompetence, and general health, the particular bacteria to be administered, duration and route of administration, the kind and stage of the disease, for example, tumor size, and other compounds such as drugs being administered concurrently. In addition to the above factors, such levels can be affected by the infectivity of the bacteria and the nature of the bacteria, as can be determined by one skilled in the art. In the present methods, appropriate minimum dosage levels of bacteria can be levels sufficient for the bacteria to survive, grow and replicate in a tumor or metastasis. Exemplary minimum levels for administering a bacterium to a 65 kg human can include at least about $5\times10^6$ colony forming units (CFU), at least about $1\times10^7$ CFU, at least about $5\times10^7$ CFU, at least about $1\times10^8$ CFU, or at least about $1\times10^9$ CFU. In the present methods, appropriate maximum dosage levels of bacteria can be levels that are not toxic to the host, levels that do not cause splenomegaly of 3× or more, and/or levels that do not result in colonies or plaques in normal tissues or organs after about 1 day or after about 3 days or after about 7 days. Exemplary maximum levels for administering a bacterium to a 65 kg human can include no more than about $5\times10^{11}$ CFU, no more than about $1\times10^{11}$ CFU, no more than about $5\times10^{10}$ CFU, no more than about $1\times10^{10}$ CFU, or no more than about $1\times10^9$ CFU.

The methods and uses provided herein can include a single administration of immunostimulatory bacteria to a subject or multiple administrations of immunostimulatory bacteria to a subject or others of a variety of regimens, including combination therapies with other anti-tumor therapeutics and/or treatments. These include, cellular therapies, such as administration of modified immune cells; CAR-T therapy; CRISPR therapy; immunotherapy, such as immune checkpoint inhibitors, such as antibodies and antibody fragments; chemotherapy and chemotherapeutic compounds, such as nucleoside analogs; surgery; oncolytic virus therapy; and radiotherapy.

The immunostimulatory bacteria, or pharmaceutical compositions containing the immunostimulatory bacteria, can be used in methods of treatment, wherein the treatment comprises combination therapy, in which a second anti-cancer agent or treatment is administered. The second anti-cancer agent or treatment is administered before, concomitantly with, after, or intermittently with, the immunostimulatory bacterium or pharmaceutical composition, and can be an immunotherapy, oncolytic virus therapy, radiation, chemotherapy, or surgery, for example. The immunotherapy can be an antibody or antibody fragment, such as an antigen-binding fragment, including an anti-PD-1, or anti-PD-L1, or anti-CTLA4, or anti-IL6, or anti-VEGF, or anti-VEGFR, or anti-VEGFR2 antibody, or fragments thereof.

In some embodiments, a single administration is sufficient to establish immunostimulatory bacteria in a tumor, where the bacteria can colonize and can cause or enhance an anti-tumor response in the subject. In other embodiments, the immunostimulatory bacteria provided for use in the methods herein can be administered on different occasions, separated in time typically by at least one day. Separate administrations can increase the likelihood of delivering a bacterium to a tumor or metastasis, where a previous administration may have been ineffective in delivering the bacterium to a tumor or metastasis. In embodiments, separate administrations can increase the locations on a tumor or metastasis where bacterial colonization/proliferation can occur or can otherwise increase the titer of bacteria accumulated in the tumor, which can increase eliciting or enhancing a host's anti-tumor immune response.

When separate administrations are performed, each administration can be a dosage amount that is the same or different relative to other administration dosage amounts. In one embodiment, all administration dosage amounts are the same. In other embodiments, a first dosage amount can be a larger dosage amount than one or more subsequent dosage amounts, for example, at least 10× larger, at least 100× larger, or at least 1000× larger than subsequent dosage amounts. In one example of a method of separate administrations in which the first dosage amount is greater than one or more subsequent dosage amounts, all subsequent dosage amounts can be the same, smaller amount relative to the first administration.

Separate administrations can include any number of two or more administrations, including two, three, four, five or six administrations. One skilled in the art readily can determine the number of administrations to perform, or the desirability of performing one or more additional administrations, according to methods known in the art for monitoring therapeutic methods and other monitoring methods provided herein. Accordingly, the methods provided herein include methods of providing to the subject one or more administrations of immunostimulatory bacteria, where the number of administrations can be determined by monitoring the subject, and, based on the results of the monitoring, determining whether or not to provide one or more additional administrations. Deciding whether or not to provide one or more additional administrations can be based on a variety of monitoring results, including, but not limited to, indication of tumor growth or inhibition of tumor growth, appearance of new metastases or inhibition of metastasis, the subject's anti-bacterial antibody titer, the subject's anti-tumor antibody titer, the overall health of the subject and the weight of the subject.

The time period between administrations can be any of a variety of time periods. The time period between administrations can be a function of any of a variety of factors, including monitoring steps, as described in relation to the number of administrations, the time period for a subject to mount an immune response, the time period for a subject to clear bacteria from normal tissue, or the time period for bacterial colonization/proliferation in the tumor or metastasis. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for bacterial colonization/proliferation in the tumor or metastasis; for example, the time period can be more than the amount of time for a detectable signal to arise in a tumor or metastasis after administration of a microorganism expressing a detectable marker, such as about 3 days, about 5 days, about a week, about ten days, about two weeks, or about a month.

The methods used herein also can be performed by administering compositions, such as suspensions and other formulations, containing the immunostimulatory bacteria provided herein. Such compositions contain the bacteria and a pharmaceutically acceptable excipient or vehicle, as provided herein or known to those of skill in the art.

As discussed above, the uses and methods provided herein also can include administering one or more therapeutic compounds, such as anti-tumor compounds or other cancer therapeutics, to a subject in addition to administering immunostimulatory bacteria to the subject. The therapeutic compounds can act independently, or in conjunction with the immunostimulatory bacteria, for tumor therapeutic effects. Therapeutic compounds that can act independently include any of a variety of known chemotherapeutic compounds that can inhibit tumor growth, inhibit metastasis growth and/or formation, decrease the size of a tumor or metastasis, or eliminate a tumor or metastasis, without reducing the ability of the immunostimulatory bacteria to accumulate in a tumor, replicate in the tumor, and cause or enhance an anti-tumor immune response in the subject. Examples of such chemotherapeutic agents include, but are not limited to, alkylating agents, such as thiotepa and cyclophosphamide; alkyl sulfonates, such as busulfan, improsulfan and piposulfan; androgens, such as calusterone, dromostanolone propionate, epitiostanol, mepitiostane, and testolactone; anti-adrenals, such as aminoglutethimide, mitotane, and trilostane; anti-androgens, such as flutamide, nilutamide, bicalutamide, leuprolide, and goserelin; antibiotics, such as aclacinomycins, actinomycin, anthramycin, azaserine, bleomycin, cactinomycin, calicheamicin, carubicin, carminomycin, carzinophilin, chromomycin, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-estrogens, including for example, tamoxifen, raloxifene, aromatase inhibiting 4(5)-imidazoles, 4-hydroxytamoxifen, trioxifene, keoxifene, LY 117018, onapristone, and toremifene (Fareston); anti-metabolites, such as methotrexate and 5-fluorouracil (5-FU); folic acid analogues, such as denopterin, methotrexate, pteropterin, and trimetrexate; aziridines, such as benzodepa, carboquone, meturedepa, and uredepa; ethylenimines and methylmelamines, including altretamine, triethylenemelamine, triethylenephosphoramide, triethylenethiophosphoramide and trimethylol melamine; folic acid replenishers, such as folinic acid; nitrogen mustards, such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, and uracil mustard; nitrosoureas, such as carmustine, chlorozotocin, fotemustine, lomustine, nimustine, and ranimustine; platinum analogs, such as cisplatin and carboplatin; vinblastine; platinum; proteins, such as arginine deiminase and asparaginase; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, floxuridine, and 5-FU; taxanes, such as paclitaxel and docetaxel and albuminated forms thereof (i.e., nab-paclitaxel and nab-docetaxel); topoisomerase inhibitor, such as RFS 2000; thymidylate synthase inhibitors (such as Tomudex); and additional chemotherapeutics, including aceglatone; aldophosphamide glycoside; aminolevulinic acid; amsacrine; bestrabucil; bisantrene; edatrexate; defosfamide; demecolcine; diaziquone; difluoromethylornithine (DFMO); eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; Navelbine; Novantrone; teniposide;

daunomycin; aminopterin; Xeloda; ibandronate; CPT-11; retinoic acid; esperamycins; capecitabine; and topoisomerase inhibitors such as irinotecan. Pharmaceutically acceptable salts, acids or derivatives of any of the above can also be used.

Therapeutic compounds that act in conjunction with the immunostimulatory bacteria include, for example, compounds that increase the immune response eliciting properties of the bacteria, e.g., by increasing expression of the RNAi, such as shRNA and miRNA, that inhibit, suppress or disrupt expression of the checkpoint genes, such as PD-L1, or TREX1 or other checkpoint genes, or compounds that can further augment bacterial colonization/proliferation. For example, a gene expression-altering compound can induce or increase transcription of a gene in a bacterium, such as an exogenous gene, e.g., encoding shRNA that inhibit, suppress or disrupt expression of one or more checkpoint genes, thereby provoking an immune response. Any of a wide variety of compounds that can alter gene expression are known in the art, including IPTG and RU486. Exemplary genes whose expression can be up-regulated include proteins and RNA molecules, including toxins, enzymes that can convert a prodrug to an anti-tumor drug, cytokines, transcription regulating proteins, shRNA, siRNA, and ribozymes. In other embodiments, therapeutic compounds that can act in conjunction with the immunostimulatory bacteria to increase the colonization/proliferation or immune response eliciting properties of the bacteria are compounds that can interact with a bacteria-expressed gene product, and such interaction can result in an increased killing of tumor cells or an increased anti-tumor immune response in the subject. A therapeutic compound that can interact with a bacteria-expressed gene product can include, for example a prodrug or other compound that has little or no toxicity or other biological activity in its subject-administered form, but after interaction with a bacteria-expressed gene product, the compound can develop a property that results in tumor cell death, including but not limited to, cytotoxicity, ability to induce apoptosis, or ability to trigger an immune response. A variety of prodrug-like substances are known in the art, including ganciclovir, 5-fluorouracil, 6-methylpurine deoxyriboside, cephalosporin-doxorubicin, 4-[(2-chloroethyl)(2-mesuloxyethyl)amino]benzoyl-L-glutamic acid, acetaminophen, indole-3-acetic acid, CB1954, 7-ethyl-10-[4-(1-piperidino)-1-piperidino]carbonyloxycamptothecin, bis-(2-chloroethyl)amino-4-hydroxyphenylaminomethanone 28, 1-chloromethyl-5-hydroxy-1,2-dihyro-3H-benz[e]indole, epirubicin-glucuronide, 5'-deoxy-5-fluorouridine, cytosine arabinoside, and linamarin.

3. Monitoring

The methods provided herein can further include one or more steps of monitoring the subject, monitoring the tumor, and/or monitoring the immunostimulatory bacteria administered to the subject. Any of a variety of monitoring steps can be included in the methods provided herein, including, but not limited to, monitoring tumor size, monitoring the presence and/or size of metastases, monitoring the subject's lymph nodes, monitoring the subject's weight or other health indicators including blood or urine markers, monitoring anti-bacterial antibody titer, monitoring bacterial expression of a detectable gene product, and directly monitoring bacterial titer in a tumor, tissue or organ of a subject.

The purpose of the monitoring can be simply for assessing the health state of the subject or the progress of therapeutic treatment of the subject, or can be for determining whether or not further administration of the same or a different immunostimulatory bacterium is warranted, or for determining when or whether or not to administer a compound to the subject where the compound can act to increase the efficacy of the therapeutic method, or the compound can act to decrease the pathogenicity of the bacteria administered to the subject.

In some embodiments, the methods provided herein can include monitoring one or more bacterially expressed genes. Bacteria, such as those provided herein or otherwise known in the art, can express one or more detectable gene products, including but not limited to, detectable proteins.

As provided herein, measurement of a detectable gene product expressed in a bacterium can provide an accurate determination of the level of bacteria present in the subject. As further provided herein, measurement of the location of the detectable gene product, for example, by imaging methods including tomographic methods, can determine the localization of the bacteria in the subject. Accordingly, the methods provided herein that include monitoring a detectable bacterial gene product can be used to determine the presence or absence of the bacteria in one or more organs or tissues of a subject, and/or the presence or absence of the bacteria in a tumor or metastases of a subject. Further, the methods provided herein that include monitoring a detectable bacterial gene product can be used to determine the titer of bacteria present in one or more organs, tissues, tumors or metastases. Methods that include monitoring the localization and/or titer of bacteria in a subject can be used for determining the pathogenicity of bacteria since bacterial infection, and particularly the level of infection, of normal tissues and organs can indicate the pathogenicity of the bacteria. The methods that include monitoring the localization and/or titer of immunostimulatory bacteria in a subject can be performed at multiple time points and, accordingly, can determine the rate of bacterial replication in a subject, including the rate of bacterial replication in one or more organs or tissues of a subject; accordingly, methods that include monitoring a bacterial gene product can be used for determining the replication competence of the bacteria. The methods provided herein also can be used to quantitate the amount of immunostimulatory bacteria present in a variety of organs or tissues, and tumors or metastases, and can thereby indicate the degree of preferential accumulation of the bacteria in a subject; accordingly, the bacterial gene product monitoring can be used in methods of determining the ability of the bacteria to accumulate in tumors or metastases in preference to normal tissues or organs. Since the immunostimulatory bacteria used in the methods provided herein can accumulate in an entire tumor or can accumulate at multiple sites in a tumor, and can also accumulate in metastases, the methods provided herein for monitoring a bacterial gene product can be used to determine the size of a tumor or the number of metastases present in a subject. Monitoring such presence of bacterial gene product in a tumor or metastasis over a range of time can be used to assess changes in the tumor or metastases, including growth or shrinking of a tumor, or development of new metastases or disappearance of metastases, and also can be used to determine the rate of growth or shrinking of a tumor, or development of new metastases or disappearance of metastases, or the change in the rate of growth or shrinking of a tumor, or development of new metastases or disappearance of metastases. Accordingly, monitoring a bacterial gene product can be used for monitoring a neoplastic disease in a subject, or for determining the efficacy of treatment of a neoplastic disease, by determining the rate of growth or shrinking of a tumor, or development of new metastases or disappearance of metastases, or the change in the rate of growth or shrinking of a tumor, or development of new metastases or disappearance of metastases.

Any of a variety of detectable proteins can be detected by monitoring, exemplary of which are any of a variety of fluorescence proteins (e.g., green fluorescence proteins), any of a variety of luciferases, transferrin or other iron binding proteins; or receptors, binding proteins, and antibodies, where a compound that specifically binds the receptor, binding protein or antibody can be a detectable agent or can be labeled with a detectable substance (e.g., a radionuclide or imaging agent).

Tumor and/or metastasis size can be monitored by any of a variety of methods known in the art, including external assessment methods or tomographic or magnetic imaging methods. In addition to the methods known in the art, methods provided herein, for example, monitoring bacterial gene expression, can be used for monitoring tumor and/or metastasis size.

Monitoring size over several time points can provide information regarding the increase or decrease in size of a tumor or metastasis, and can also provide information regarding the presence of additional tumors and/or metastases in the subject. Monitoring tumor size over several time points can provide information regarding the development of a neoplastic disease in a subject, including the efficacy of treatment of a neoplastic disease in a subject.

The methods provided herein also can include monitoring the antibody titer in a subject, including antibodies produced in response to administration of immunostimulatory bacteria to a subject. The bacteria administered in the methods provided herein can elicit an immune response to endogenous bacterial antigens. The bacteria administered in the methods provided herein also can elicit an immune response to exogenous genes expressed by the bacteria. The bacteria administered in the methods provided herein also can elicit an immune response to tumor antigens. Monitoring antibody titer against bacterial antigens, bacterially expressed exogenous gene products, or tumor antigens can be used to monitor the toxicity of the bacteria, the efficacy of treatment methods, or the level of gene product or antibodies for production and/or harvesting.

Monitoring antibody titer can be used to monitor the toxicity of the bacteria. Antibody titer against a bacteria can vary over the time period after administration of the bacteria to the subject, where at some particular time points, a low anti-(bacterial antigen) antibody titer can indicate a higher toxicity, while at other time points a high anti-(bacterial antigen) antibody titer can indicate a higher toxicity. The bacteria used in the methods provided herein can be immunogenic, and can, therefore, elicit an immune response soon after administering the bacteria to the subject. Generally, immunostimulatory bacteria against which the immune system of a subject can mount a strong immune response can be bacteria that have low toxicity when the subject's immune system can remove the bacteria from all normal organs or tissues. Thus, in some embodiments, a high antibody titer against bacterial antigens soon after administering the bacteria to a subject can indicate low toxicity of the bacteria.

In other embodiments, monitoring antibody titer can be used to monitor the efficacy of treatment methods. In the methods provided herein, antibody titer, such as anti-(tumor antigen) antibody titer, can indicate the efficacy of a therapeutic method such as a therapeutic method to treat neoplastic disease. Therapeutic methods provided herein can include causing or enhancing an immune response against a tumor and/or metastasis. Thus, by monitoring the anti-(tumor antigen) antibody titer, it is possible to monitor the efficacy of a therapeutic method in causing or enhancing an immune response against a tumor and/or metastasis.

In other embodiments, monitoring antibody titer can be used for monitoring the level of gene product or antibodies for production and/or harvesting. As provided herein, methods can be used for producing proteins, RNA molecules or other compounds, particularly RNA molecules such as shRNA, by expressing an exogenous gene in a microorganism that has accumulated in a tumor. Monitoring antibody titer against the protein, RNA molecule or other compound can indicate the level of production of the protein, RNA molecule or other compound by the tumor-accumulated microorganism, and also can directly indicate the level of antibodies specific for such a protein, RNA molecule or other compound.

The methods provided herein also can include methods of monitoring the health of a subject. Some of the methods provided herein are therapeutic methods, including neoplastic disease therapeutic methods. Monitoring the health of a subject can be used to determine the efficacy of the therapeutic method, as is known in the art. The methods provided herein also can include a step of administering to a subject an immunostimulatory bacterium, as provided herein. Monitoring the health of a subject can be used to determine the pathogenicity of an immunostimulatory bacterium administered to a subject. Any of a variety of health diagnostic methods for monitoring disease such as neoplastic disease, infectious disease, or immune-related disease can be monitored, as is known in the art. For example, the weight, blood pressure, pulse, breathing, color, temperature or other observable state of a subject can indicate the health of a subject. In addition, the presence or absence or level of one or more components in a sample from a subject can indicate the health of a subject. Typical samples can include blood and urine samples, where the presence or absence or level of one or more components can be determined by performing, for example, a blood panel or a urine panel diagnostic test. Exemplary components indicative of a subject's health include, but are not limited to, white blood cell count, hematocrit, and c-reactive protein concentration.

The methods provided herein can include monitoring a therapy, where therapeutic decisions can be based on the results of the monitoring. Therapeutic methods provided herein can include administering to a subject immunostimulatory bacteria, where the bacteria can preferentially accumulate in a tumor and/or metastasis, and where the bacteria can cause or enhance an anti-tumor immune response. Such therapeutic methods can include a variety of steps including multiple administrations of a particular immunostimulatory bacterium, administration of a second immunostimulatory bacterium, or administration of a therapeutic compound. Determination of the amount, timing or type of immunostimulatory bacteria or compound to administer to the subject can be based on one or more results from monitoring the subject. For example, the antibody titer in a subject can be used to determine whether or not it is desirable to administer an immunostimulatory bacterium and, optionally, a compound, the quantity of bacteria and/or compound to administer, and the type of bacteria and/or compound to administer, where, for example, a low antibody titer can indicate the desirability of administering an additional immunostimulatory bacterium, a different immunostimulatory bacterium, and/or a therapeutic compound such as a compound that induces bacterial gene expression or a therapeutic compound that is effective independent of the immunostimulatory bacteria.

In another example, the overall health state of a subject can be used to determine whether or not it is desirable to administer an immunostimulatory bacterium and, optionally, a compound, the quantity of bacterium or compound to administer, and the type of bacterium and/or compound to administer where, for example, determining that the subject is healthy can indicate the desirability of administering additional bacteria, different bacteria, or a therapeutic compound such as a compound that induces bacterial gene (e.g., shRNA that inhibits one or more checkpoint gene(s)) expression. In another example, monitoring a detectable bacterially expressed gene product can be used to determine whether it is desirable to administer an immunostimulatory bacterium and, optionally, a compound, the quantity of bacterium and/or compound to administer, and the type of bacterium and/or compound to administer where, for example, determining that the subject is healthy can indicate the desirability of administering additional bacteria, different bacteria, or a therapeutic compound such as a compound that induces bacterial gene (e.g., shRNA that inhibits one or more checkpoint gene(s)) expression. Such monitoring methods can be used to determine whether or not the therapeutic method is effective, whether or not the therapeutic method is pathogenic to the subject, whether or not the bacteria have accumulated in a tumor or metastasis, and whether or not the bacteria have accumulated in normal tissues or organs. Based on such determinations, the desirability and form of further therapeutic methods can be derived.

In another example, monitoring can determine whether or not immunostimulatory bacteria have accumulated in a tumor or metastasis of a subject. Upon such a determination, a decision can be made to further administer additional bacteria, a different immunostimulatory bacterium and, optionally, a compound to the subject.

J. Examples

The following examples are included for illustrative purposes only and are not intended to limit the scope of the invention.

Summary of Some Exemplary Engineered Immunostimulatory Bacterial Strains and Nomenclature:

| Strain # | Plasmid | Strain Background | RNAi Targets | Alternate Name |
|---|---|---|---|---|
| AST-100 | None | YS1646 | none | VNP 20009 |
| AST-101 | None | YS1646-ASD | none | ASD (asd gene knockout) |
| AST-102 | pEQU6 | YS1646 | none | YS1646 (pEQU6-plasmid) |
| AST-103 | pEQU6 | YS1646 | Scrambled (shRNA) | YS1646 (pEQU6-shSCR) |
| AST-104 | pEQU6 | YS1646 | muTREX1 (shRNA) ARI-108 | YS1646 (pEQU6-shTREX1) |
| AST-105 | pEQU6 | YS1646 | muPD-L1 (shRNA) ARI-115 | YS1646 (pEQU6-shPDL1) |
| AST-106 | pEQU6 | YS1646 | muTREX1 (microRNA) ARI-203 | YS1646 (pEQU6-miTREX1) |
| AST-107 | pATI-U6 | YS1646-ASD | Scrambled (shRNA) | ASD (pATI-shSCR) |
| AST-108 | pATI-U6 | YS1646-ASD | muTREX1 (shRNA) ARI-108 | ASD (pATI- shTREX1) |
| AST-109 | pATIKAN-U6 | YS1646-ASD | Scrambled (shRNA) | ASD (pATIKan-shSCR) |
| AST-110 | pATIKAN-U6 | YS1646-ASD | muTREX1 (shRNA) ARI-108 | ASD (pATIKan-shTREX1) |
| AST-111 | None | YS1646-ASD-fljb-fliC | None | ASD/FLG (asd and flagellin knockout) |
| AST-112 | pATI-U6 | YS1646-ASD-fljb-fliC | muTREX1 (shRNA) ARI-108 | ASD/FLG (pATI-shTREX1) |
| AST-113 | pATI-U6 | YS1646-ASD-fljb-fliC | muTREX1 (shRNA) ARI-108 | ASD/FLG (pATI-U6 Kan shTREX1) |
| AST-114 | None | YS1646-ASD-LLO | None | ASD/LLO (asd knockout / cytoLLO knock-in) |
| AST-115 | pATI-U6 | YS1646-ASD-LLO | muTREX1 (shRNA) ARI-108 | ASD/LLO (pATIKan-shTREX1) |
| AST-116 | pATIKanpBRori-U6 | YS1646-ASD | Scrambled | ASD (pATIKanLow-shSCR) |
| AST-117 | pATIKanpBRori-U6 | YS1646-ASD | muTREX1 (shRNA) ARI-108 | ASD (pATIKanLow-shTREX1) |
| AST-118 | pATIKanpBRori-U6 | YS1646-ASD-fljb-fliC | muTREX1 (shRNA) ARI-108 | ASD/FLG (pATIKanLow-shTREX1) |
| AST-119 | pATIKanpBRori-U6 | YS1646-ASD-pMTL-LLO | muTREX1 (shRNA) ARI-108 | ASD/LLO (pATIKanLow-shTREX1) |

-continued

| Strain # | Plasmid | Strain Background | RNAi Targets | Alternate Name |
|---|---|---|---|---|
| AST-120 | pEQU6 pMTL-LLO | YS1646-ASD-(microRNA) | muTREX1 miTREX1) Suicidal ARI-203 | ASD/LLO(pEQU6- |
| AST-121 | pEQU6 | YS1646 | muVISTA ARI-157 | YS1646 (pEQU6-shVISTA) |
| AST-122 | pEQU6 | YS1646 | muTGF-beta ARI-149 | YS1646 (pEQU6-TGF-beta) |
| AST-123 | pEQU6 | YS1645 | muBeta-Catenin ARI-166 | YS1646 (pEQU6-Beta-Catenin) |

It is understood that these strains are listed for reference; the same deletions and insertions can be effected in a wild-type *Salmonella typhimurium* strain, such as the strain deposited under ATCC accession #14028, or a strain having all of the identifying characteristics thereof. The wild-type strain can additionally be made auxotrophic for adenosine by appropriate selection or deletions. The construction of and use of these strains is described in Published International PCT Application No. WO 2019/014398, and in U.S. Application Publication No. 2019/0017050.

Example 1

*Salmonella* asd Gene Knockout Strain Engineering

Strain AST-101 was prepared. It is an attenuated *Salmonella typhimurium* strain, derived from strain YS1646 (which can be purchased from ATCC, Catalog #202165) that has been engineered to be asd$^-$ (an asd gene knockout). In this example, the *Salmonella typhimurium* strain YS1646 asd$^-$ gene deletion was engineered using modifications of the method of Datsenko and Wanner (*Proc. Natl. Acad. Sci. U.S.A.* 97:6640-6645 (2000)) as outlined in FIG. 1, and described below. The methods and resulting products in this example and all examples below can be used with other starting bacteria, such as wild-type *Salmonella typhimurium*, such as the strain deposited under ATCC accession #14028.

Introduction of the Lambda Red Helper Plasmid into YS1646

The YS1646 strain was prepared to be electrocompetent as described previously (Sambrook J., (1998) *Molecular Cloning, A Laboratory Manual, 2nd Ed.* Cold Spring Harbor, N.Y.: Cold Spring Harbor Laboratory) by growing a culture in LB and concentrating 100-fold and washing three times with ice-cold 10% glycerol. The electrocompetent strain was electroporated with the Lambda red helper plasmid pKD46 (SEQ ID NO:218) using a 0.2 cm gap cuvette at the following settings: 2.5 kV, 186 ohms, 50 μF. Transformants carrying pKD46 were grown in 5 mL SOC medium with ampicillin and 1 mM L-arabinose at 30° C. and selected on LB agar plates containing ampicillin. A YS1646 clone containing the lambda red helper plasmid pKD46 then was made electrocompetent, as described above for strain YS1646.

Construction of asd Gene Knockout Cassette

The asd gene from the genome of YS1646 (Broadway et al. (2014) *J. Biotechnology* 192:177-178) was used for designing the asd gene knockout cassette. A plasmid containing 204 and 203 bp of homology to the left hand and right hand regions, respectively, of the asd gene, was transformed into DH5-alpha competent cells. A kanamycin gene cassette flanked by loxP sites was cloned into this plasmid. The asd gene knockout cassette then was PCR amplified using primers asd-1 and asd-2 (Table 1), and gel purified.

Execution of asd Gene Deletion

The YS1646 strain carrying plasmid pKD46 was electroporated with the gel-purified linear asd gene knock-out cassette. Electroporated cells were recovered in SOC medium and plated onto LB Agar plates supplemented with kanamycin (20 μg/mL) and diaminopimelic acid (DAP, 50 μg/ml). During this step, lambda red recombinase induces homologous recombination of the chromosomal asd gene with the kan cassette (due to the presence of homologous flanking sequences upstream and downstream of the chromosomal asd gene), and knockout of the chromosomal copy of the asd gene occurs. The presence of the disrupted asd gene in the selected kanamycin resistant clones was confirmed by PCR amplification with primers from the YS1646 genome flanking the sites of disruption (primer asd-3) and from the multi-cloning site (primer scFv-3) (Table 1). Colonies were also replica plated onto LB plates with and without supplemental DAP to demonstrate DAP auxotrophy. All clones with the asd gene deletion were unable to grow in the absence of supplemental DAP, demonstrating DAP auxotrophy.

TABLE 1

Primer Information

| Primer Name | Primer Sequence | SEQ ID NO. |
|---|---|---|
| asd-1 | ccttcctaacgcaaattccctg | 219 |
| asd-2 | ccaatgctctgcttaactcctg | 220 |
| asd-3 | gcctcgccatgtttcagtacg | 221 |
| asd-4 | ggtctggtgcattccgagtac | 222 |
| scFv-3 | cataatctgggtccttggtctgc | 223 |

Kanamycin Gene Cassette Removal

The kan selectable marker was removed by using the Cre/loxP site-specific recombination system. The YS1646 asd$^-$ gene Kan$^R$ mutant was transformed with pJW168, a temperature sensitive plasmid expressing the Cre recombinase (SEQ ID NO:224). Amp$^R$ colonies were selected at 30° C.; pJW168 was subsequently eliminated by growth at 42° C. A selected clone (AST-101) then was tested for loss of kan by replica plating on LB agar plates with and without kanamycin, and confirmed by PCR verification using primers from the YS1646 genome flanking the sites of disruption (primer asd-3 and asd-4, for primer sequence, see Table 1).

Characterization of the asd Deletion Mutant Strain AST-101

The asd$^-$ mutant AST-101 was unable to grow on LB agar plates at 37° C., but was able to grow on LB plates containing 50 μg/mL diaminopimelic acid (DAP). The $asd^-$ mutant growth rate was evaluated in LB liquid media; it was unable to grow in liquid LB, but was able to grow in LB supplemented with 50 μg/mL DAP, as determined by measuring absorbance at 600 nM.

Sequence Confirmation of the AST-101 Asd Locus Sequence after Asd Gene Deletion

The AST-101 asd gene deletion strain was verified by DNA sequencing using primers asd-3 and asd-4. Sequencing of the region flanking the asd locus was performed, and the sequence confirmed that the asd gene was deleted from the YS1646 chromosome.

Example 2

Generation of Modified *Salmonella typhimurium* Strains from Wild-Type *Salmonella typhimurium*

The purI, msbB and asd genes were individually deleted from the genome of wild-type *Salmonella typhimurium* strain ATCC 14028 using the lambda-derived Red recombination system as described in Datsenko and Wanner (*Proc. Natl. Acad. Sci. U.S.A.* 97:6640-6645 (2000)), to generate a base-strain designated 14028:ΔpurI/ΔmsbB/Δasd. The flagellin genes fljB and fliC were subsequently deleted to generate the strain 14028:ΔpurI/ΔmsbB/Δasd/ΔfljB/ΔfliC, and the pagP gene was then deleted to generate the strain 14028: ΔpurI/ΔmsbB/Δasd/ΔfljB/ΔfliC/ΔpagP. Strains 14028: ΔpurI/ΔmsbB/Δasd/ΔfljB/ΔfliC and 14028: ΔpurI/ΔmsbB/Δasd/ΔfljB/ΔfliC/ΔpagP were electroporated with a plasmid containing a functional asd gene, to complement the chromosomal deletion of asd and ensure plasmid maintenance in vivo, and a eukaryotic expression cassette encoding the red fluorescent protein mCherry under control of the EF1-α promoter.

Example 3

Modified *Salmonella typhimurium* Targets Demonstrate Robust Tumor Growth

Inhibition in Multiple Syngeneic Murine Tumor Models

PD-L1

The immune system has evolved several checks and balances to limit autoimmunity. Programmed cell death protein 1 (PD-1) and programmed death-ligand 1 (PD-L1) are two examples of numerous inhibitory "immune checkpoints," which function by downregulating immune responses. The binding of PD-L1 to PD-1 interferes with $CD8^+$ T cell signaling pathways, impairing the proliferation and effector function of $CD8^+$ T cells, and inducing T cell tolerance (see, e.g., Topalian et al. (2012) *N. Engl. J. Med.* 366:2443-2454).

Tumor colonization of a modified *Salmonella typhimurium* strain delivering shRNA to knockdown the PD-L1 gene disrupts the binding of PD-L1 to PD-1, and its inhibition of $CD8^+$ T cell function. PD-L1/PD-1 checkpoint inhibition synergizes well with the immunostimulatory *S. typhimurium* containing CpG plasmid DNA, all in one therapeutic modality. In place of an RNAi, the immunostimulatory bacterium can be modified to encode an antigen-binding fragment or single-chain antibody that inhibits PD-L1 or PD-1, to inhibit the PD-1 pathway.

To demonstrate the in vivo efficacy of the YS1646 strain containing a plasmid encoding shRNA against PD-L1 (AST-105), or other inhibitor of PD-L1 or the PD-1 pathway, this strain, in comparison to the AST-102 strain (containing a control plasmid that also contains CpG motifs) was evaluated in a murine colon carcinoma model. For this experiment, 6-8 week-old female BALB/c mice (10 mice per group) were inoculated subcutaneously (SC) in the right flank with CT26 murine colon carcinoma cells ($2\times10^5$ cells in 100 μL PBS). Mice bearing established flank tumors were intravenously (IV) injected twice, four days apart, with $5\times10^6$ CFUs of AST-105 or AST-102, or were IV administered an anti-PD-L1 antibody (4 mg/kg, BioXCell clone 10F.9G2). Six hours following the first IV dose, mice were bled, and plasma was collected and assessed for pro-inflammatory cytokines using the Mouse Inflammation Cytometric Bead Array (CBA) kit and analyzed by FACS (BD Biosciences).

Treatment with strain AST-105 demonstrated statistically significant tumor control compared to treatment with the plasmid-containing control strain AST-102 (69% TGI, p=0.05, day 25). Tumor growth inhibition was also greater for treatment with AST-105 (expressing shPD-L1) than from systemic administration of an anti-PD-L1 antibody (68% TGI vs. anti-PD-L1).

Comparing the production of innate pro-inflammatory cytokines at 6 hours post IV injection, the cytokines elicited by strain AST-105 were significantly higher compared to the anti-PD-L1 antibody ($p<0.05$), and much higher than those from strain AST-102. These data demonstrate that inhibiting PD-L1 within the tumor microenvironment, compared to systemic administration of an anti-PD-L1 antibody, uniquely activates potent pro-inflammatory cytokines that induce anti-tumor immunity and promote tumor growth inhibition in a murine model of colon carcinoma.

Example 4

Intratumoral Administration of Modified *S. typhimurium* Encoding shTREX1 Provides Distal Tumor Colonization and Complete Anti-Tumor Responses in a Dual Flank Murine Colon Carcinoma Model A hallmark of inducing adaptive immunity to a tumor is the ability to induce regression of a distal, untreated tumor. To assess the ability of the YS1646 strain containing the pEQU6 shRNA plasmids to induce primary and distal tumor growth inhibition in a dual flank murine colon carcinoma model, 6-8 week-old female BALB/c mice (10 mice per group) were inoculated SC in the right and left flanks with CT26 murine colon carcinoma cells ($2\times10^5$ cells in 100 μL PBS). Mice bearing established flank tumors were intratumorally (IT) injected twice, four days apart, into the right flank tumor with $5\times10^6$ CFUs of strain AST-104, (pEQU6-shTREX1 in YS1646), strain AST-105 (pEQU6-shPD-L1 in YS1646), or strain AST-102 (pEQU6 plasmid control in YS1646), and compared to PBS control.

IT injection of strains AST-104 and AST-105 induced significant tumor growth inhibition in the injected tumor, compared to the PBS control (AST-105: 60.5% TGI, p=0.03; AST-104: 61.4% TGI, p=0.03 day 25). Unlike AST-105, only AST-104 induced significant growth inhibition of the distal, untreated tumor compared to PBS (60% TGI, $p<0.0001$, day 25), and significant distal tumor growth inhibition compared to AST-102 containing the plasmid control (p=0.004, day 25). The AST-104 strain also demonstrated significant tumor regression and increased survival compared to PBS control (p=0.0076, Log-rank (Mantel-Cox) test), with 2/10 complete remissions.

Figure 2:
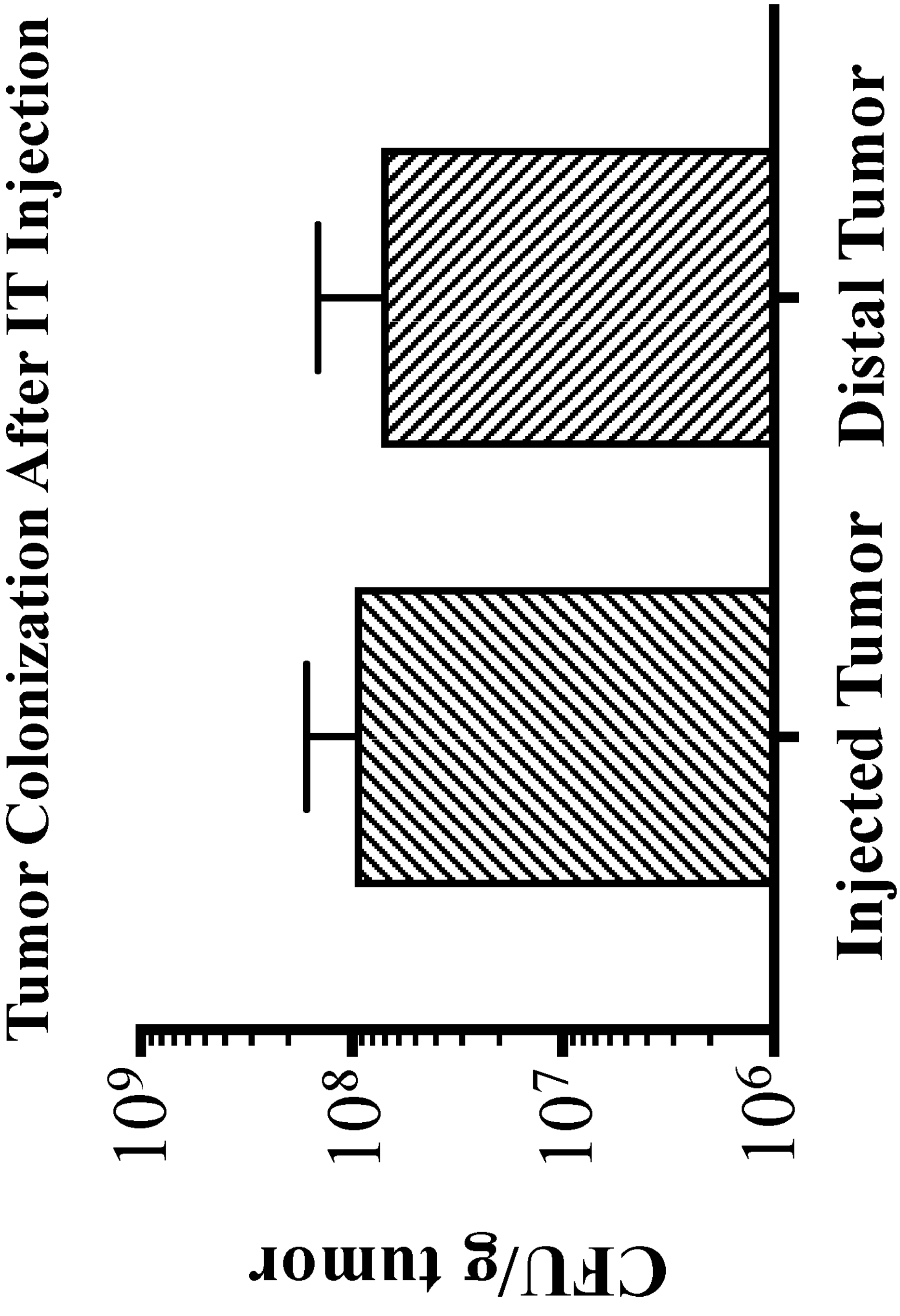
FIG. 2 depicts the levels of tumor colonization in injected and distal tumors after IT administration of AST-104. BALB/c mice (6-8 week old) were implanted with dual CT26 ($2\times10^5$ cells) subcutaneous flank tumors on the right and left flanks (n=10 per group). Mice with established tumors were IT injected into the right flank with $5\times10^6$ CFUs of the YS1646 strain containing a TREX1 shRNA plasmid (AST-104). At 35 days post tumor implantation (12 days after the last dose of AST-104), three mice were sacrificed, and injected and distal tumors were homogenized (GentleMACs™, Miltenyi Biotec) and plated on LB plates to enumerate the number of colony forming units (CFUs) per gram of tumor tissue. The figure depicts the mean CFUs per gram of tissue, ±SD.

To determine whether the bacteria colonize injected, as well as distal tumors, tumor-bearing mice treated with AST-104 were sacrificed and tumors were collected. Injected and distal tumors were transferred to M tubes and were homogenized in PBS using a gentleMACS™ Dissociator (Miltenyi Biotec). Tumor homogenates were serially diluted and plated on LB agar plates and incubated at 37° C. for colony forming unit (CFU) determination. As shown in FIG. 2, the distal tumor was colonized to the same extent as the injected tumor, indicating that the engineered *Salmonella* strains dosed with an intratumoral route of administration are able to transit and colonize distal lesions. These data demonstrate the potency of administering an immunostimulatory bacteria intratumorally with the ability to systemically colonize distal tumor lesions preferentially over other organs, and the potency of activating the STING type I Interferon pathway, leading to systemic tumor regression and complete remission.

Example 5

Modified *S. typhimurium* Strains with Plasmids Containing CpG Elements Demonstrate Enhanced Anti-Tumor Activity Compared to YS1646 Parental Strain Toll-like receptors (TLRs) are key receptors for sensing pathogen-associated molecular patterns (PAMPs) and activating innate immunity against pathogens (see, e.g., Akira et al. (2001) *Nat. Immunol.* 2(8):675-680). Of these, TLR9 is responsible for recognizing hypomethylated CpG motifs in pathogenic DNA which do not occur naturally in mammalian DNA (see, e.g., McKelvey et al. (2011) *J. Autoimmunity* 36:76). Recognition of CpG motifs upon phagocytosis of pathogens into endosomes in immune cell subsets induces IFR7-dependent type I interferon (IFN) signaling and activates innate and adaptive immunity. It is shown herein, that the *S. typhimurium* strain YS1646 carrying modified *Salmonella typhimurium* plasmids containing CpG motifs (YS1646 pEQU6 Scramble) similarly activate TLR9 and induce type I IFN-mediated innate and adaptive immunity, as compared to the YS1646 strain without a plasmid.

The CpG motifs in the engineered plasmids used here are shown in Table 2. The pEQU6-shSCR (non-cognate shRNA) plasmid in strain AST-103 possesses 362 CpG motifs, indicating that *Salmonella*-based plasmid delivery can be immuno-stimulatory and can have an anti-tumor effect, when compared to the same *Salmonella* strain lacking transformation with this plasmid. To assess the ability of CpG-containing plasmids within strain YS1646 to induce tumor growth inhibition (TGI) in a murine colon carcinoma model, 6-8 week-old female BALB/c mice (9 mice per group) were inoculated subcutaneously (SC) in the right flank with CT26 cells ($2\times10^5$ cells in 100 μL PBS). Mice bearing established flank tumors were IV injected weekly with three doses of $5\times10^6$ CFUs of strains YS1646 (AST-100), or YS1646 containing an shRNA scrambled plasmid with CpG motifs (AST-103), and compared to PBS control.

TABLE 2

CpG Motifs in the Engineered Plasmids

| Sequence Name | Number of CpG Motifs | SEQ ID NO. |
|---|---|---|
| pBR322 Origin | 80 | 243 |
| pEQU6 (shSCR) | 362 | 244 |
| asd Gene ORF | 234 | 242 |
| pATI-2.0 | 538 | 245 |

Figure 3:
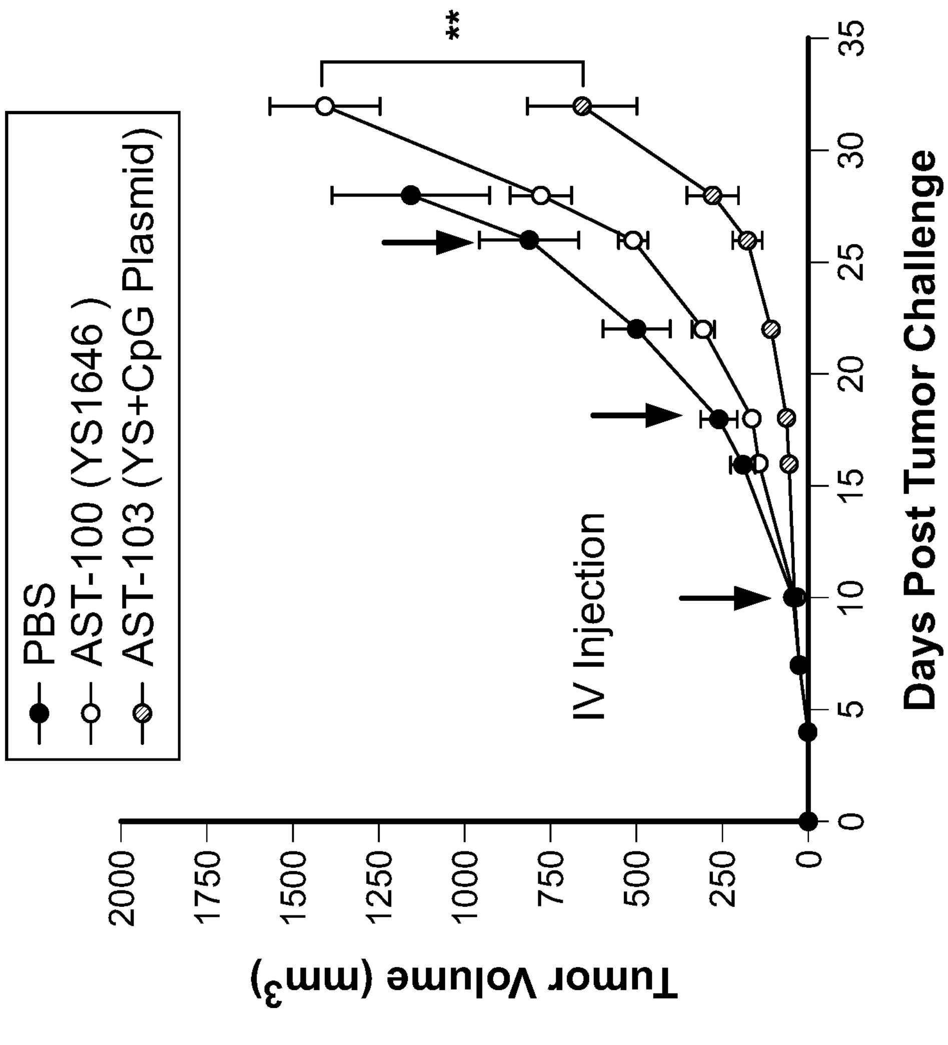
FIG. 3 depicts that a CpG scrambled plasmid has immuno-stimulatory anti-tumor properties. BALB/c mice (6-8 week old) were implanted with a single CT26 ($2\times10^5$ cells) subcutaneous flank tumor (n=9 per group). Mice with established tumors were IV injected with $5\times10^6$ CFUs of the YS1646 strain (AST-100), or the YS1646 strain containing the scrambled shRNA control plasmid (AST-103), or PBS control, on the days indicated by the arrows. Tumor measurements were performed using electronic calipers (Fowler, Newton, Mass.). Tumor volume was calculated using the modified ellipsoid formula, ½ (length×width$^2$). Mice were euthanized when tumor size reached >20% of body weight or became necrotic, as per IACUC regulations. TGI is calculated as 1-(mean test tumor volume/mean control tumor volume)×100. The figure depicts mean tumor growth of each group, ±SEM. **p<0.01, student's t-test.

As shown in FIG. 3, the YS1646 (AST-100) strain demonstrated modest tumor control (32% TGI, p=ns, day 28) as compared to PBS. The AST-103 strain, that varies from YS1646 only by the addition of the CpG-containing plasmid encoding a non-cognate scrambled shRNA (pEQU6-shSCR), demonstrated highly significant tumor growth inhibition compared to YS1646 alone, untransformed, and therefore lacking a plasmid (p=0.004, day 32).

Figure 16:
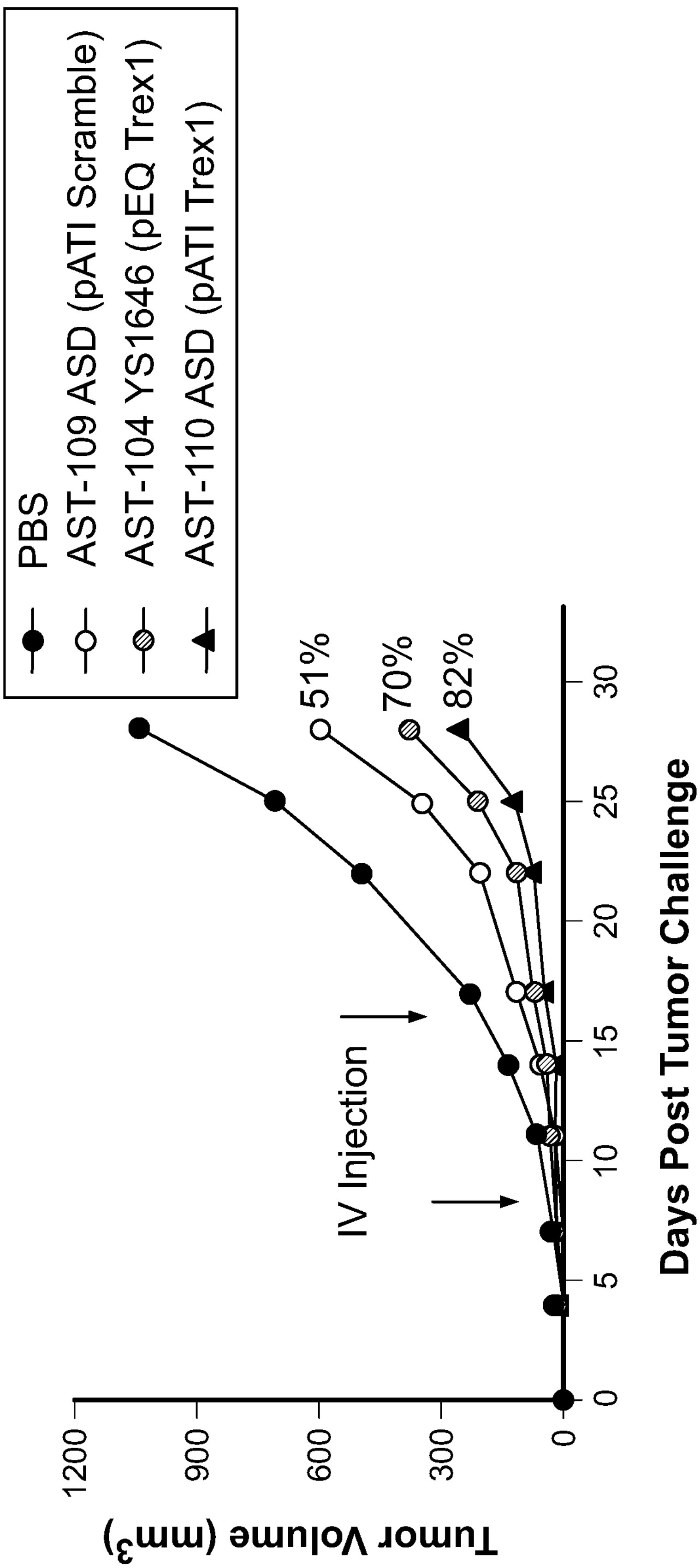
FIG. 16 depicts that the therapeutic efficacy of a strain containing a plasmid with an asd gene complementation system and shTREX1 (AST-110) is improved. BALB/c mice (6-8 week old) were implanted with a single CT26 ($2\times10^5$ cells) subcutaneous flank tumor (n=9 per group). Mice with established tumors were IV injected with $5\times10^6$ CFUs of the asd knockout strain containing the pATI-shTREX1 plasmid (AST-110), or the asd knockout strain containing the pATI-scramble plasmid (AST-109), or the YS1646 strain containing a pEQ-shTREX1 plasmid without an asd gene (AST-104), or PBS control, on the days indicated by the arrows. Tumor measurements were performed using electronic calipers (Fowler, Newton, Mass.). Tumor volume was calculated using the modified ellipsoid formula, ½(length× width). Mice were euthanized when tumor size reaches >20% of body weight or became necrotic, as per IACUC regulations. TGI was calculated as 1-(mean test tumor volume/mean control tumor volume)×100. The figure depicts the mean tumor growth of each group, ±SEM.

The asd gene possesses 234 CpG motifs (see, Table 2), indicating that a plasmid containing this gene can have immunostimulatory properties. As shown in FIG. 16, strain AST-109 (YS1646-ASD with scrambled shRNA, containing plasmid pATI-shSCR; see Example 6) had 51% tumor growth inhibition versus PBS alone, indicative of a strong immuno-stimulatory effect.

These data demonstrate the potent immunostimulatory properties of plasmid DNA containing TLR9-activating CpG motifs within a tumor-targeting attenuated strain of *S. typhimurium.*

Example 6

Vector Synthesis

Complementation of Asd Deletion by Asd Expression from Plasmids

A plasmid (pATIU6) was chemically synthesized and assembled (SEQ ID NO:225). The plasmid contained the following features: a high copy (pUC19) origin of replication, a U6 promoter for driving expression of a short hairpin RNA, an ampicillin resistance gene flanked by HindIII restriction sites for subsequent removal, and the asd gene containing 85 base pairs of sequence upstream of the start codon (SEQ ID NO:246). Into this vector, shRNAs targeting murine TREX1 or a scrambled, non-cognate shRNA sequence, were introduced by restriction digestion with SpeI and XhoI and ligation and cloning into *E. coli* DH5-alpha. The resulting plasmids, designated pATI-shTREX1 and pATI-shSCR, respectively, were amplified in *E. coli* and purified for transformation into the asd knockout strain AST-101 by electroporation and clonal selection on LB amp plates to produce strains AST-108, and AST-107, respectively. $asd^-$ mutants complemented with the pATIU6-derived plasmids were able to grow on LB agar and liquid media in the absence of DAP.

In a subsequent iteration, the ampicillin resistance gene ($Amp^R$) from pATI-shTREX1 was replaced with a kanamycin resistance gene. This was accomplished by digestion of the pATI-shTREX1 plasmid with HindIII, followed by gel purification to remove the $Amp^R$ gene, and then PCR amplification of the kanamycin resistance ($Kan^R$) gene using primers APR-001 and APR-002 (SEQ ID NO:226 and SEQ ID NO:227, respectively), digestion with HindIII, and ligation into the gel purified, digested pATIU6 plasmid.

In subsequent iterations, a single point mutation was introduced into the pATIKan plasmid at the pUC19 origin of replication using the Q5® Site-Directed Mutagenesis Kit (New England Biolabs) and the primers APR-003 (SEQ ID NO:228) and APR-004 (SEQ ID NO:229) to change the nucleotide T at position 148 to a C. This mutation makes the origin of replication homologous to the pBR322 origin of replication, in order to reduce the plasmid copy number.

| Primer ID | Description | Sequence | SEQ ID NO |
|---|---|---|---|
| APR-001 | Kan primerF | AAAAAAGCTTGCAGCTCTGGCCCGTG | 226 |
| APR-002 | Kan PrimerR | AAAAAAGCTTTTAGAAAAACTCATCG AGCATCAAATGA | 227 |
| APR-003 | pATI ori T148CF | ACACTAGAAGgACAGTATTTGGTATC TG | 228 |
| APR-004 | pATI ori T148CR | AGCCGTAGTTAGGCCACC | 229 |

pATI2.0

A plasmid was designed and synthesized that contains the following features: a pBR322 origin of replication, an SV40 DNA nuclear targeting sequence (DTS), an rrnB terminator, a U6 promoter for driving expression of shRNAs followed by flanking restriction sites for cloning the promoter and shRNAs or microRNAs, the asd gene, an rrnG terminator, a kanamycin resistance gene flanked by HindIII sites for curing, and a multicloning site (plasmid pATI2.0; SEQ ID NO:247). In addition, a plasmid was designed and synthesized for expression of two separate shRNAs or microRNAs. This plasmid contains the following features: a pBR322 origin of replication, an SV40 DNA nuclear targeting sequence (DTS), an rrnB terminator, a U6 promoter for driving expression of shRNAs followed by flanking restriction sites for cloning the promoter and shRNAs or microRNAs, an H1 promoter for driving the expression of a $2^{nd}$ shRNA or microRNA, a 450 bp randomly generated stuffer sequence placed between the H1 and U6 promoters, the asd gene, an rrnG terminator, and a kanamycin resistance gene flanked by HindIII sites for curing, and a multicloning site (SEQ ID NO:245).

Example 7

*S. typhimurium* Flagellin Knockout Strain Engineering by Deletion of the fliC and fljB Genes In the example herein, *S. typhimurium* strains were engineered to lack both flagellin subunits FliC and FljB, to reduce pro-inflammatory signaling. Deletions of the fliC and fljB genes were sequentially engineered into the chromosome of the asd gene-deleted strain of YS1646 (AST-101).

Deletion of fliC

Figure 4:
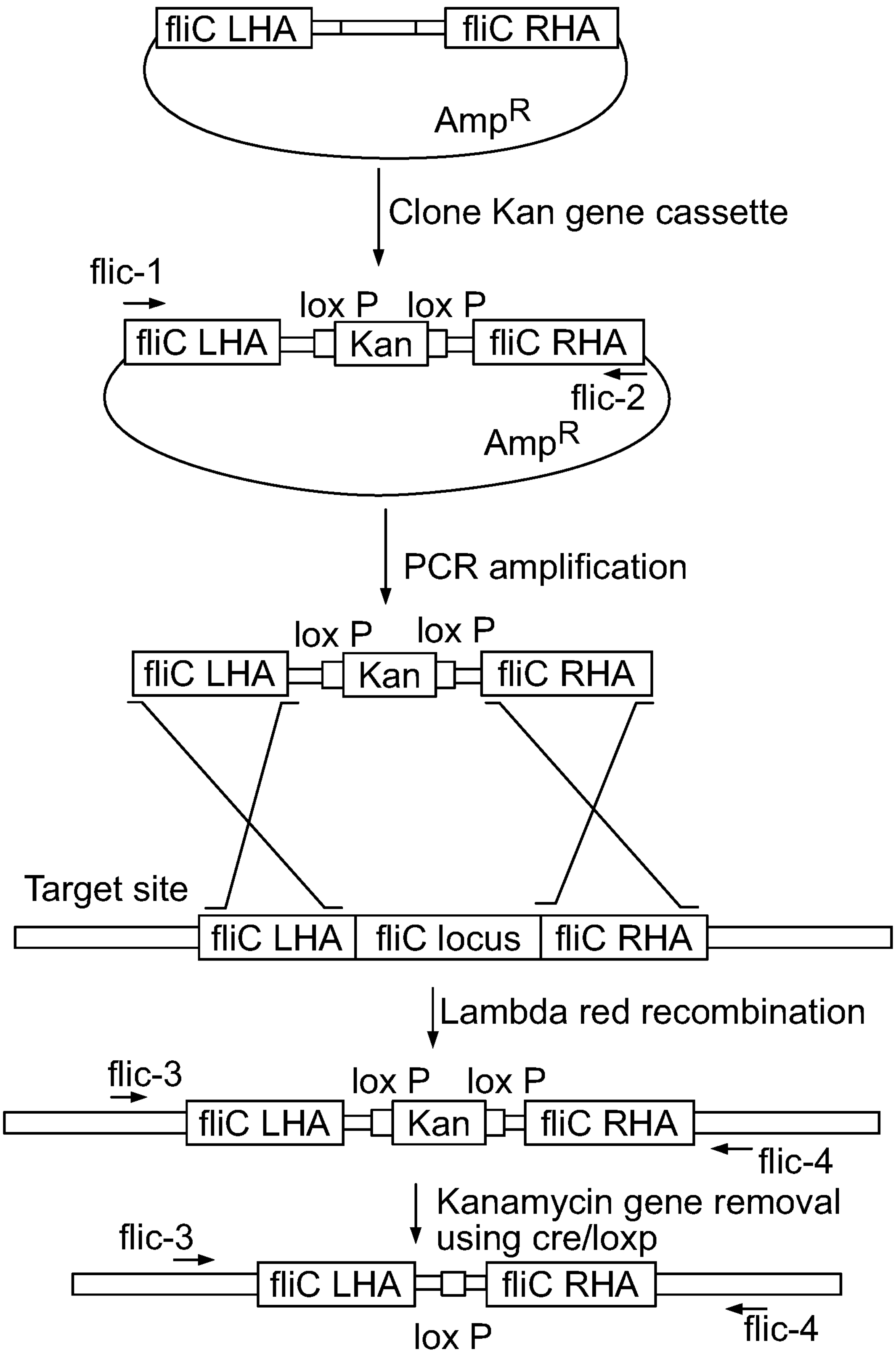
FIG. 4 depicts a schematic of the process used to delete the fliC gene. The flic gene was deleted from the chromosome of *S. typhimurium* strain AST-101 (asd deleted strain of YS1646) using the lambda-derived Red recombination system, as described in Datsenko and Wanner (*Proc. Natl. Acad. Sci. U.S.A.* 97:6640-6645 (2000)).

In this example, fliC was deleted from the chromosome of the AST-101 strain using modifications of the method of Datsenko and Wanner (*Proc. Natl. Acad. Sci. U.S.A.* 97:6640-6645 (2000)), as described in detail in Example 1, and schematically depicted in FIG. 4. Synthetic fliC gene homology arm sequences were ordered that contained 224 and 245 bases of homologous sequence flanking the fliC gene, cloned into a plasmid called pSL0147 (SEQ ID NO:230). A kanamycin gene cassette flanked by Cre/loxP sites then was cloned into pSL0147, the fliC gene knockout cassette was then PCR amplified with primer flic-1 (SEQ ID NO:232) and flic-2 (SEQ ID NO:233), and gel purified and introduced into the AST-101 strain carrying the temperature sensitive lambda red recombination plasmid pKD46 by electroporation. Electroporated cells were recovered in SOC+DAP medium and plated onto LB Agar plates supplemented with kanamycin (20 μg/mL) and diaminopimelic acid (DAP, 50 μg/ml). Colonies were selected and screened for insertion of the knockout fragment by PCR, using primers flic-3 (SEQ ID NO:234) and flic-4 (SEQ ID NO:235). pKD46 then was cured by culturing the selected kanamycin resistant strain at 42° C., and screening for loss of ampicillin resistance. The kanamycin resistance marker then was cured by electroporation of a temperature sensitive plasmid expressing the Cre recombinase (pJW1680) and $Amp^R$ colonies were selected at 30° C.; pJW168 was subsequently eliminated by growing cultures at 42° C. Selected fliC knockout clones were then tested for loss of the kanamycin marker by PCR, using primers flanking the sites of disruption (flic-3 and flic-4), and evaluation of the electrophoretic mobility on agarose gels.

Deletion of fljB fljB was then deleted in the asd/fliC deleted YS1646 strain using modifications of the methods described above. Synthetic fljB gene homology arm sequences that contained 249 and 213 bases of the left hand and right hand sequence, respectively, flanking the fljB gene, were synthesized and cloned into a plasmid called pSL0148 (SEQ ID NO:231). A kanamycin gene cassette flanked by Cre/loxP sites then was cloned into pSL0148 and the fljB gene knockout cassette then was PCR amplified with primer fljb-1 (SEQ ID NO:236) and fljb-2 (SEQ ID NO:237), and gel purified and introduced into strain AST-101 carrying the temperature sensitive lambda red recombination plasmid pKD46 by electroporation. The kanamycin resistance gene then was cured by Cre-mediated recombination as described above, and the temperature-sensitive plasmids were cured by growth at non-permissive temperature. The fliC and fljB gene knockout sequences were amplified by PCR using primers flic-3 and flic-4, or fljb-3 (SEQ ID NO:238) and fljb-4 (SEQ ID NO:239), and verified by DNA sequencing. This $asd^-$/$fliC^-$/$fljB^-$ mutant derivative of YS1646 was designated AST-111.

Primer Sequence Information

| Primer Name | Primer Sequence | SEQ ID NO. |
|---|---|---|
| flic-1 | CGTTATCGGCAATCTGGAGGC | 232 |
| flic-2 | CCAGCCCTTACAACAGTGGTC | 233 |
| flic-3 | GTCTGTCAACAACTGGTCTAACGG | 234 |
| flic-4 | AGACGGTCCTCATCCAGATAAGG | 235 |
| fljb-1 | TTCCAGACGACAAGAGTATCGC | 236 |
| fljb-2 | CCTTTAGGTTTATCCGAAGCCAGA ATC | 237 |
| fljb-3 | CACCAGGTTTTTCACGCTGC | 238 |
| fljb-4 | ACACGCATTTACGCCTGTCG | 239 |

Figure 5:
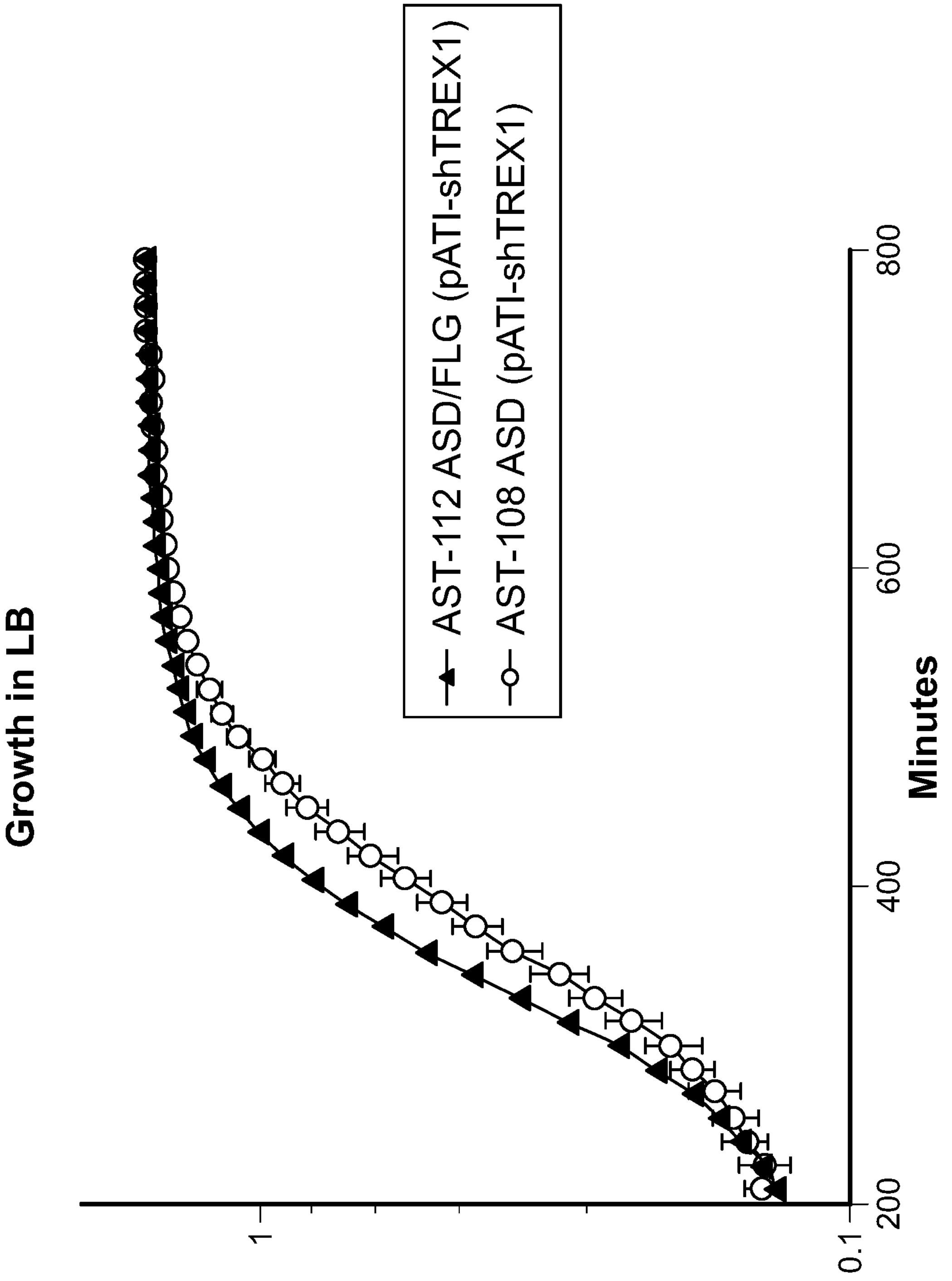
FIG. 5 depicts that the flagellin deletion strain grows normally in LB. The figure depicts the growth of strains AST-108 ASD (pATI-shTREX1) and AST-112 ASD/FLG (pATI-shTREX1) at 37° C. in LB broth, as measured by $OD_{600}$ using a SpectraMax® 96-well plate reader (Molecular Devices).

In Vitro Characterization of Engineered *S. typhimurium* Flagellin Knockout Strain The YS1646 derived $asd^-$ mutant strain, harboring the deletions of both fliC and fljB, herein referred to as AST-111 or ASD/FLG, was evaluated for swimming motility by spotting 10 microliters of overnight cultures onto swimming plates (LB containing 0.3% agar and 50 mg/mL DAP). While motility was observed for strain YS1646 and the asd-deleted strain AST-101, no motility was evident with the asd/fliC/fljB-deleted strain AST-111. The AST-111 strain then was electroporated with pATI-shTREX1 (a plasmid containing an asd gene and an shRNA targeting TREX1), to produce strain AST-112, and its growth rate in the absence of DAP was assessed. As shown in FIG. 5, ASD/FLG (pATI-shTREX1) strain AST-112 was able to replicate in LB in the absence of supplemental DAP, and grew at a rate comparable to the asd strain containing pATI-shTREX1 (AST-108). These data demonstrate that the elimination of flagellin does not decrease the fitness of *S. typhimurium* in vitro.

Elimination of flagellin subunits decreases pyroptosis in macrophages. To demonstrate this, $5\times10^5$ mouse RAW-Dual™ macrophage cells (InvivoGen, San Diego, Ca.) were infected with the asd/fliC/fljB-deleted strain harboring a low copy shTREX1 plasmid, designated AST-118, or the asd-deleted strain harboring the same plasmid (AST-117), at a multiplicity of infection (MOI) of approximately 100 in a gentamicin protection assay. After 24 hours of infection, culture supernatants were collected and assessed for lactate dehydrogenase release as a marker of cell death using a Pierce™ LDH Cytotoxicity Assay Kit (Thermo Fisher Scientific, Waltham, Ma.). Strain AST-117 induced 75% maximal LDH release, while strain AST-118 induced 54% maximal LDH release, demonstrating that the deletion of the flagellin genes reduces the *S. typhimurium*-induced pyroptosis of infected macrophages.

ASD/FLG Knockout Strain Containing shTrex1 Plasmid Demonstrates Enhanced Anti-Tumor Activity, Enhanced Interferon Gamma Responses, and Increased Tumor Colonization in Mice Compared to Parental Asd Strain To assess the impact of the flagellin knockout strains when administered in a murine model of colon carcinoma, 6-8 week-old female BALB/c mice (10 mice per group) were inoculated SC in the right flank with CT26 cells ($2\times10^5$ cells in 100 PBS). Mice bearing established flank tumors were IV injected with three weekly doses of $5\times10^6$ CFUs of the ASD/FLG strain containing the pATIKan-shTREX1 plasmid (AST-113), or the ASD strain with the same pATI-Kan-shTREX1 plasmid (AST-110), and compared to PBS control. Six hours following the first IV dose, mice were bled, and plasma was collected and assessed for pro-inflammatory cytokines using the Mouse Inflammation Cytometric Bead Array kit and analyzed by FACS (BD Biosciences).

Figure 6:
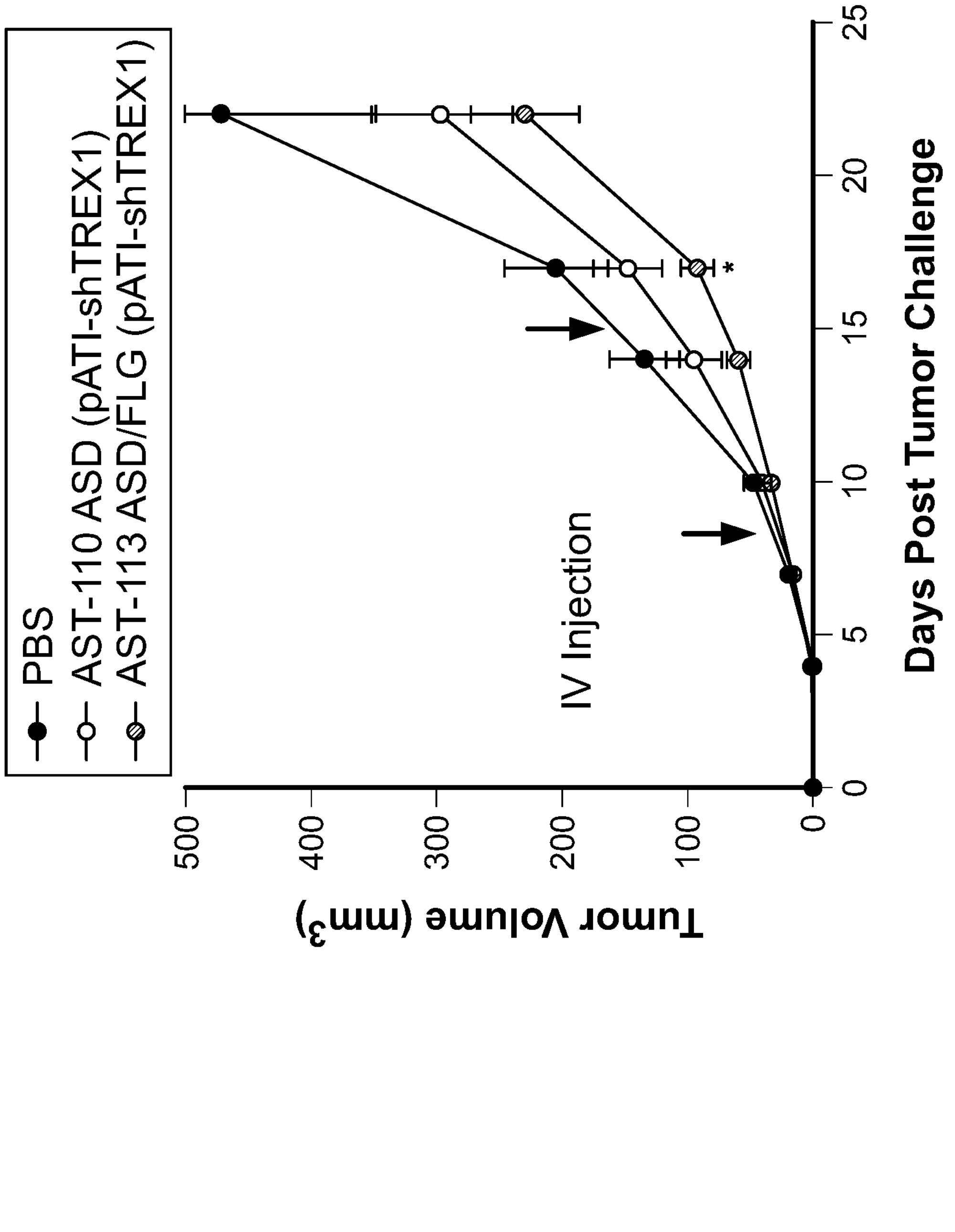
FIG. 6 depicts that flagellin knockout improves anti-tumor efficacy. BALB/c mice (6-8 week old) were implanted with a single CT26 ($2\times10^5$ cells) subcutaneous flank tumor (n=9 per group). Mice with established tumors were IV injected with $5\times10^6$ CFUs of the asd/fljB/fliC knockout strain containing the pATI shTREX1 plasmid (AST-113), or the asd knockout strain containing the pATI shTREX1 plasmid (AST-110), or PBS control, on the days indicated by the arrows. Tumor measurements were performed using electronic calipers (Fowler, Newton, Mass.). Tumor volume was calculated using the modified ellipsoid formula, ½(length×width$^2$). Mice were euthanized when tumor size reached >20% of body weight or became necrotic, as per IACUC regulations. TGI was calculated as 1-(mean test tumor volume/mean control tumor volume)×100. The figure depicts the mean tumor growth of each group, ±SEM. * $p<0.05$, student's t-test.

As shown in FIG. 6, the AST-113 strain, incapable of making flagella and containing the pATI-shTREX1 plasmid (ASD/FLG pATI-shTREX1), demonstrated enhanced tumor control compared to the parental ASD pATI-shTREX1 strain, AST-110, and significant tumor control compared to the PBS control (54% TGI, p=0.02, day 17).

Figure 7:
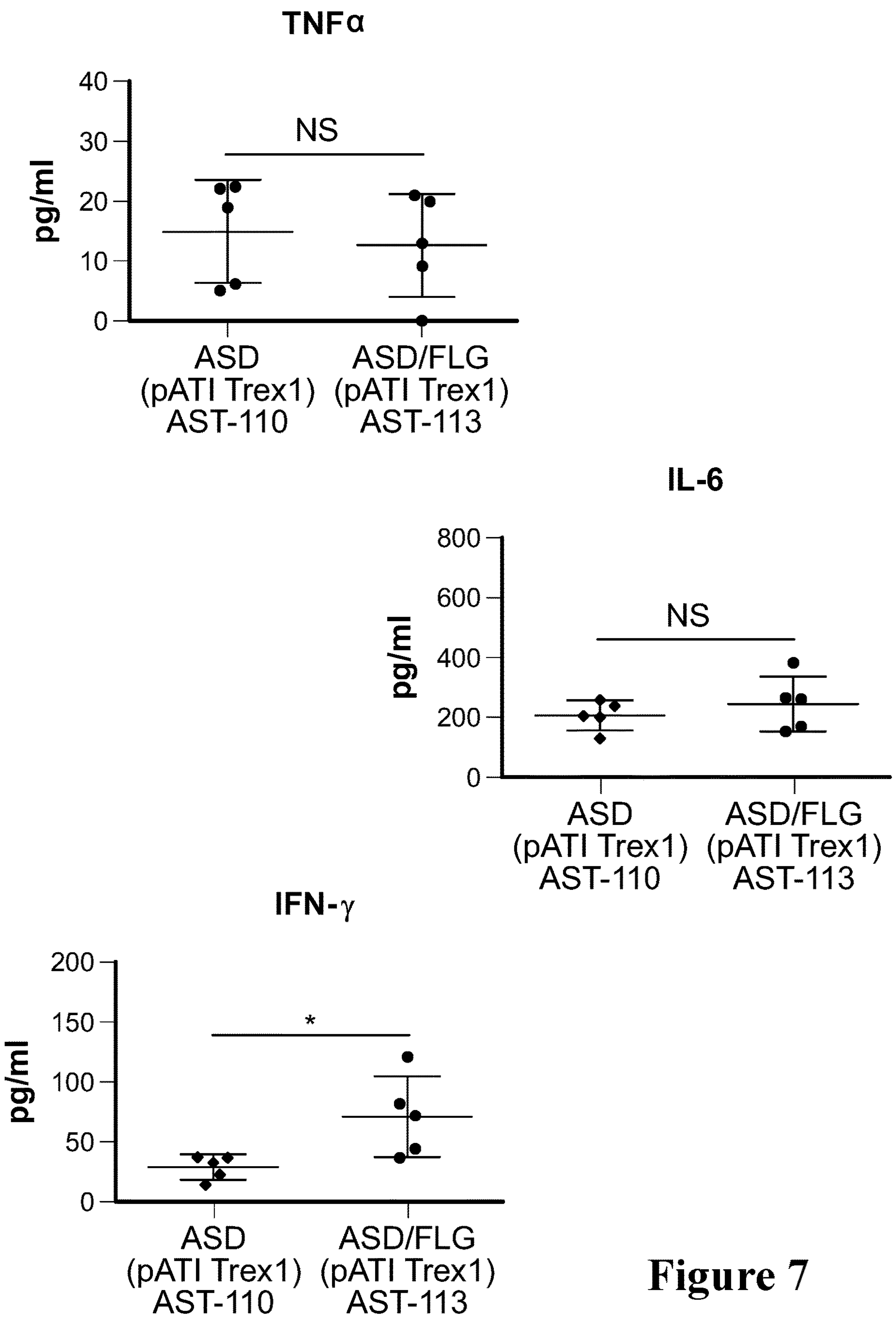
FIG. 7 depicts that flagellin knockout shows an increased IFN-gamma signature. BALB/c mice (6-8 week old) were implanted with a single CT26 ($2\times10^5$ cells) subcutaneous flank tumor (n=9 per group). Mice with established tumors were IV injected with $5\times10^6$ CFUs of the asd/fljB/fliC knockout strain containing the pATI shTREX1 plasmid (AST-113), or the asd knockout strain containing the pATI shTREX1 plasmid (AST-110), or PBS control. Mice were bled 6 hours following the first dose, and systemic serum cytokines were tested by Luminex 200 device (Luminex Corporation) and mouse cytometric bead array (BD bead array, FACS Fortessa, FCAP software, all BD Biosciences). * $p<0.05$,  $p<0.01$, * $p<0.001$, student's t-test.

Comparing the levels of systemic serum cytokines at 6 hours post IV injection, the cytokines elicited by the AST-113 strain were comparable for TNF-α and IL-6, as compared to the parental AST-110 strain that is capable of making flagella. The levels of the potent anti-tumor immune cytokine IFN-γ were significantly higher with AST-113 compared to AST-110, indicating that the flagellin-deficient strain can provide for superior anti-tumor potency over the parental asd knockout strain (FIG. 7).

Figure 8:
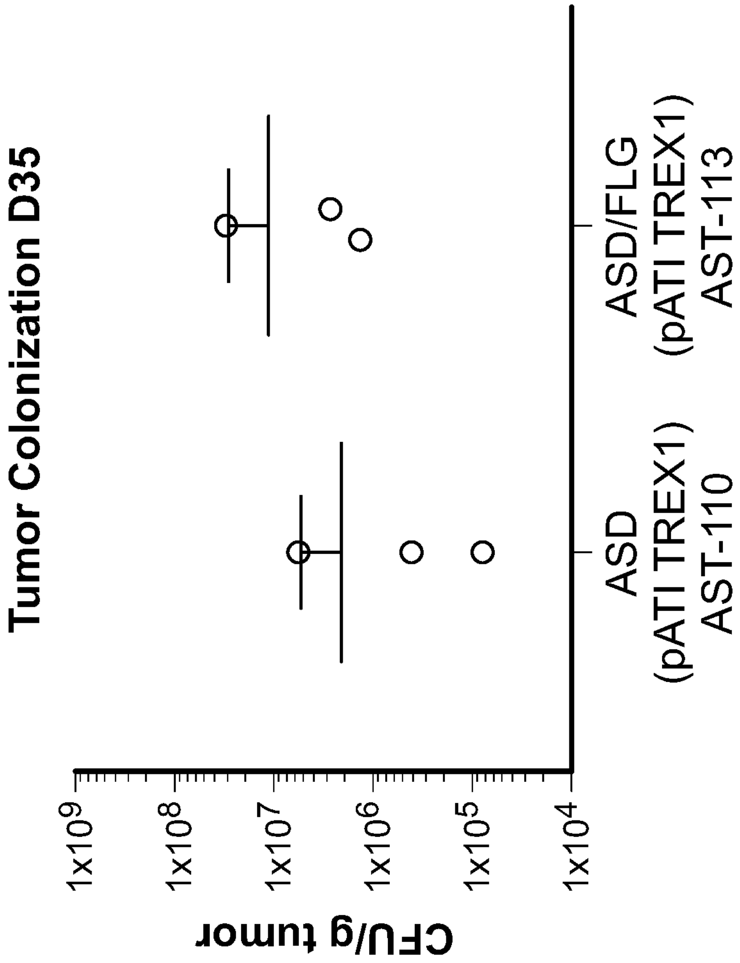
FIG. 8 depicts that flagellin is not required for tumor colonization. BALB/c mice (6-8 week old) were implanted with a single CT26 ($2\times10^5$ cells) subcutaneous flank tumor (n=9 per group). Mice with established tumors were IV injected with $5\times10^6$ CFUs of the asd/fljB/fliC knockout strain containing the pATI shTREX1 plasmid (AST-113), or the asd knockout strain containing the pATI shTREX1 plasmid (AST-110), or PBS control. At 35 days (D35) post tumor implantation (12 days after the last dose of engineered *Salmonella* therapy), three mice per group were sacrificed, and tumors were homogenized (GentleMACs™, Miltenyi Biotec) and plated on LB plates to enumerate the number of colony forming units per gram of tumor tissue. The figure depicts the mean colony forming units (CFUs) per gram of tissue, ±SD.

At 35 days post tumor implantation (12 days after the last dose of engineered *Salmonella* therapy), three mice per group were euthanized, and tumors were homogenized and plated on LB plates to enumerate the number of colony forming units (CFUs) per gram of tumor tissue as described above. As shown in FIG. 8, the AST-113 strain, deleted of fliC and fljB and containing the pATI-shTREX1 plasmid, was able to colonize tumors at least as well as the strain that only had the asd gene deletion and contained the same plasmid (AST-110). AST-113 colonized tumors with a mean of $1.2\times10^7$ CFUs per gram of tissue compared with a mean of $2.1\times10^6$ CFUs/g of tumor for AST-110, indicating that the absence of flagellin can lead to an increased tumor colonization by greater than 5 times that of strains with a functional flagella. Together, these data demonstrate that, contrary to the expectation from the art, not only is the flagella not required for tumor colonization, but its loss can enhance tumor colonization and anti-tumor immunity.

Example 8

*S. typhimurium* Engineered to Express cytoLLO for Enhanced Plasmid Delivery In this example, the asd-deleted strain of YS1646 described in Example 1 (AST-101) was further modified to express the listeriolysin O (LLO) protein lacking the signal sequence, that accumulates in the cytoplasm of the *Salmonella* strain (referred to herein as cytoLLO). LLO is a cholesterol-dependent pore-forming cytolysin that is secreted from *Listeria monocytogenes* and mediates phagosomal escape of bacteria. A gene encoding LLO, with codons 2-24 deleted, was synthesized with codons optimized for expression in *Salmonella*. The sequence of the open reading frame of cytoLLO is shown in SEQ ID NO:240. The cytoLLO gene was placed under control of a promoter that induces transcription in *S. typhimurium* (SEQ ID NO:241, reproduced below). The cytoLLO expression cassette was inserted in single copy into the knockout asd locus of the asd-deleted strain AST-101, using modifications of the method of Datsenko and Wanner (*Proc. Natl. Acad. Sci. U.S.A.* (2000) 97:6640-6645), as described in Example 1.

| Sequence of Promoter Driving Expression of cytoLLO | | |
|---|---|---|
| LLO promoter | attatgtcttgacatgtagtgagtgggctgg tataatgcagcaag | SEQ ID NO: 241 |

Figure 9:
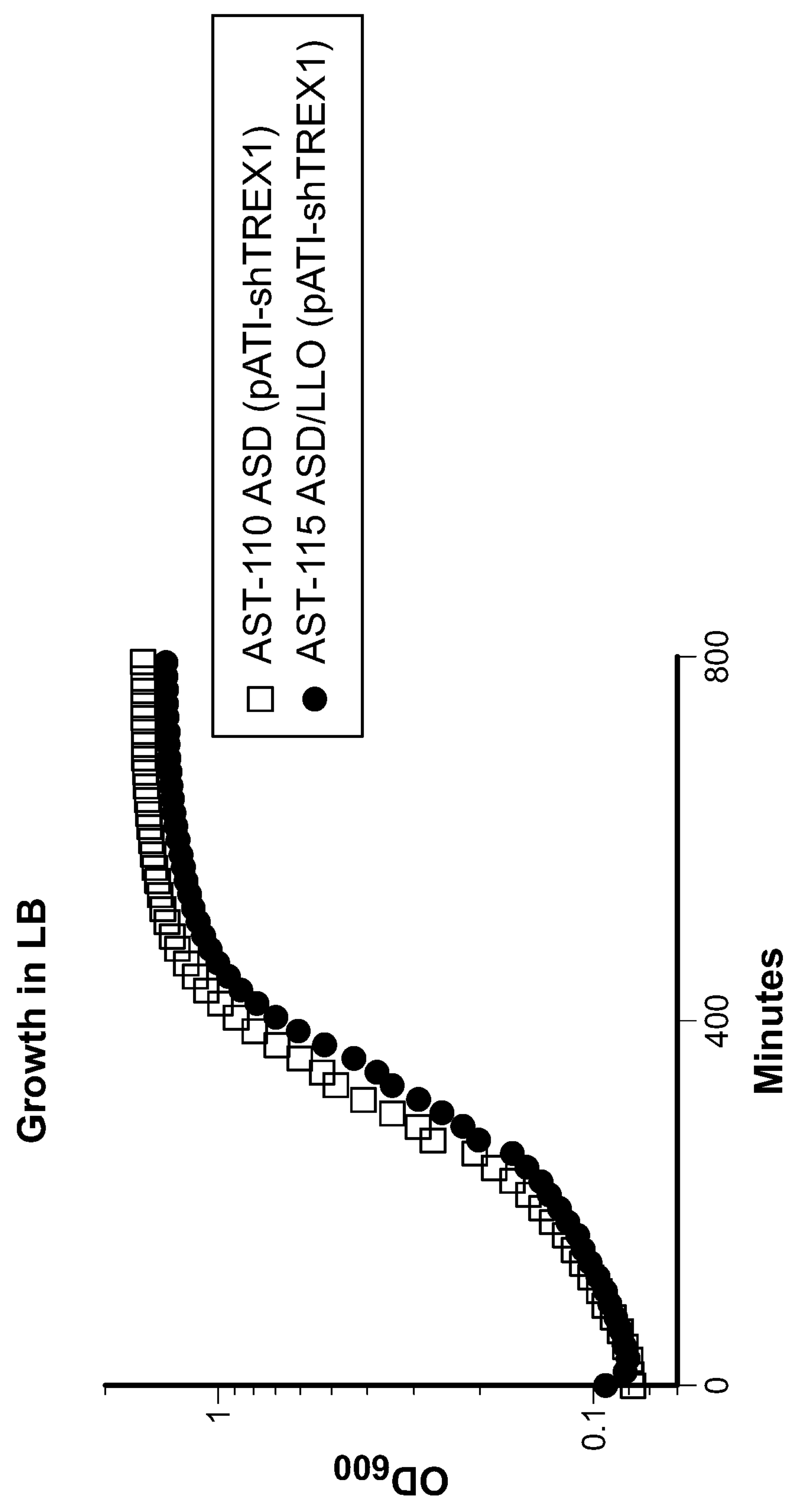
FIG. 9 depicts that a cytoLLO expressing strain grows normally in vitro. The figure depicts the growth of strains AST-110 (YS1646 with asd deletion containing (pATI-shTREX1)), and AST-115 (YS1646 with asd deletion and knock-in of cytoLLO expression cassette containing (pATI-shTREX1)) at 37° C. in LB broth, as measured by $OD_{600}$ using a SpectraMax® 96-well plate reader (Molecular Devices).

The asd-deleted strain with the cytoLLO expression cassette inserted at the asd locus (referred to herein as ASD/LLO or AST-114) was further modified by electroporation with a pATI plasmid encoding an asd gene that allows the strain to grow in the absence of exogenous DAP and selects for plasmid maintenance, and that also contains a U6 promoter driving expression of shTREX1 as described in Example 6 (referred to herein as ASD/LLO (pATI-shTREX1), or AST-115). As shown in FIG. 9, the ASD/LLO (pATI-shTREX1) strain AST-115 grew at a comparable rate to the asd-deleted strain containing the same plasmid (pATI-shTREX1), AST-110, demonstrating that the LLO knock-in does not impact bacterial fitness in vitro.

*S. typhimurium* Strains Engineered to Produce cytoLLO Demonstrate Potent Anti-Tumor Activity To determine whether the cytoLLO gene knock-in provided anti-tumor efficacy, the ASD/LLO (pATI-shTREX1) strain AST-115 was evaluated in a murine model of colon carcinoma. For this study, 6-8 week-old female BALB/c mice (8 mice per group) were inoculated SC in the right flank with CT26 cells ($2\times10^5$ cells in 100 PBS). Mice bearing established flank tumors were IV injected with a single dose of $5\times10^6$ CFUs of AST-115, and compared to PBS control.

Figure 10:
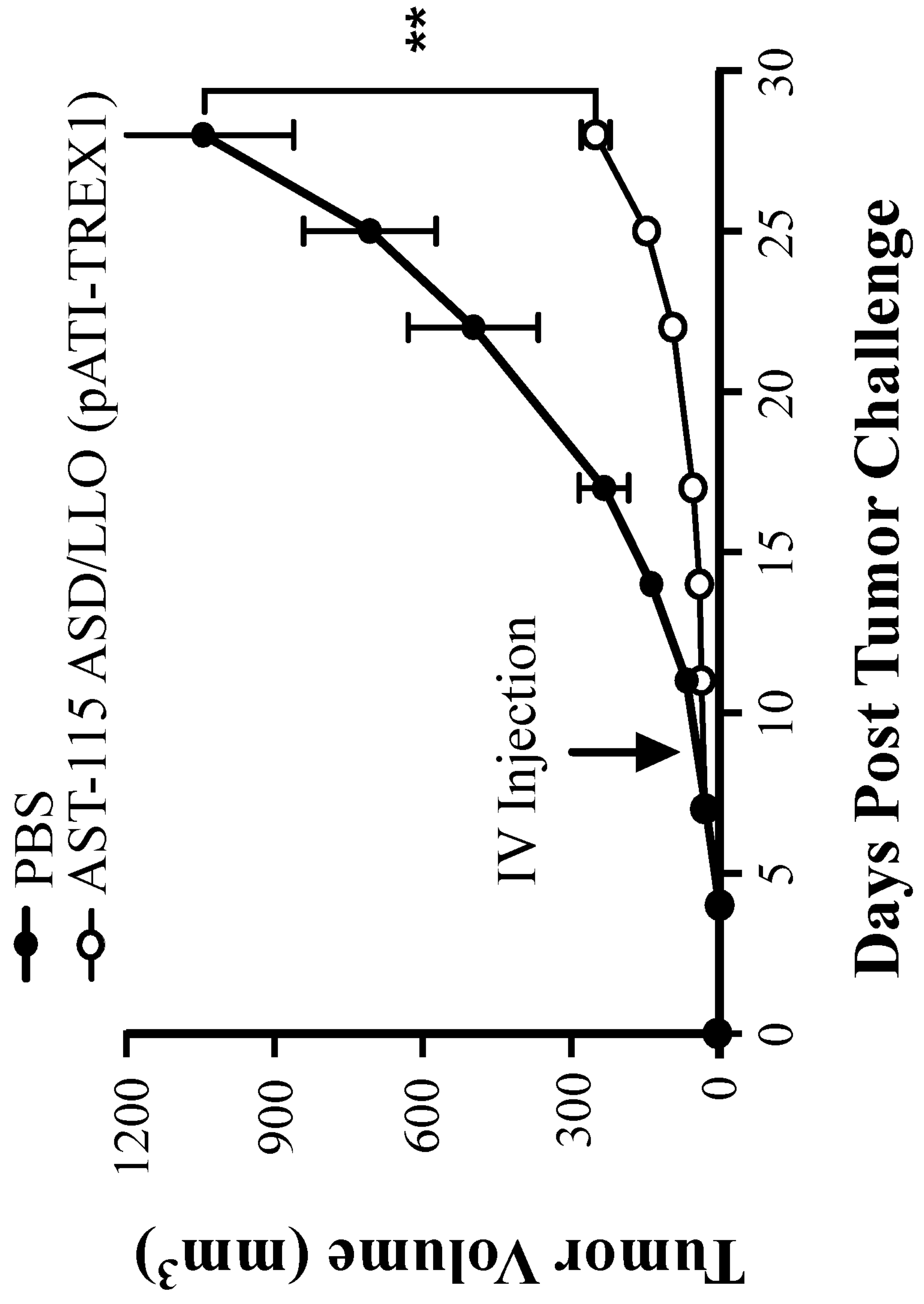
FIG. 10 depicts that strain AST-115 (ASD knockout+cytoLLO knock-in strain, carrying shTREX1 plasmid) demonstrates potent, single-dose efficacy in a murine CT26 tumor model. BALB/c mice (6-8 week old) were implanted with a single CT26 ($2\times10^5$ cells) subcutaneous flank tumor (n=9 per group). Mice with established tumors were IV injected with $5\times10^6$ CFUs of AST-115 (YS1646 with asd deletion and knock-in of cytoLLO expression cassette at asd locus, and containing plasmid (pATI-shTREX1)), or PBS control, on the days indicated by the arrows. Tumor measurements were performed using electronic calipers (Fowler, Newton, Mass.). Tumor volume was calculated using the modified ellipsoid formula, ½(length×width). Mice were euthanized when tumor size reached >20% of body weight or became necrotic, as per IACUC regulations. TGI was calculated as 1-(mean test tumor volume/mean control tumor volume)×100. The figure depicts the mean tumor growth of each group, ±SEM. ** $p<0.01$, student's t-test.

As shown in FIG. 10, the addition of the cytoLLO gene into the asd$^-$ strain ASD/LLO (pATI-shTREX1) demonstrated highly significant tumor control compared to PBS control (76% TGI, p=0.002, day 28), and comparable efficacy after a single dose to previous studies where the TREX1 shRNA plasmid-containing strains were given at multiple doses. These data demonstrate the cytoLLO-mediated advantage of delivering more plasmid into the cytosol, resulting in greater gene knockdown, thereby improving the therapeutic efficacy of RNAi against targets such as TREX1.

Example 9

Adenosine Auxotrophic Strains of *S. typhimurium*

Strains provided herein are engineered to be auxotrophic for adenosine. As a result, they are attenuated in vivo because they are unable to replicate in the low adenosine concentrations of normal tissue, and colonization occurs primarily in the solid tumor microenvironment (TME), where adenosine levels are high. The *Salmonella* strain YS1646 (AST-100) is a derivative of the wild-type strain ATCC 14028, and was engineered to be auxotrophic for purine due to disruption of the purI gene (see, e.g., Low et al., (2004) *Methods Mol. Med.* 90:47-60). Subsequent analysis of the entire genome of YS1646 demonstrated that the purI gene (synonymous with purM) was not in fact deleted, but was instead disrupted by a chromosomal inversion (see, e.g., Broadway et al. (2014) *J. Biotechnol.* 192:177-178), and that the entire gene is still contained within two parts of the YS1646 chromosome that is flanked by insertion sequences (one of which has an active transposase). The presence of the complete genetic sequence of the purI gene disrupted by means of a chromosomal reengagement leaves open the possibility of reversion to a wild-type gene. While it has previously been demonstrated that purine auxotrophy of YS1646 was stable after serial passage in vitro, it was not clear what the reversion rate is (see, e.g., Clairmont et al. (2000) *J. Infect. Dis.* 181:1996-2002).

It is shown herein that, when provided with adenosine, YS1646 is able to replicate in minimal medium, whereas the wild-type parental strain ATCC 14028 can grow in minimal media that is not supplemented with adenosine. YS1646 was grown overnight in LB medium, washed with M9 minimal medium, and diluted into M9 minimal media containing no adenosine, or increasing concentrations of adenosine. Growth was measured using a SpectraMax® M3 spectrophotometer (Molecular Devices) at 37° C., reading the $OD_{600}$ every 15 minutes.

Figure 11:
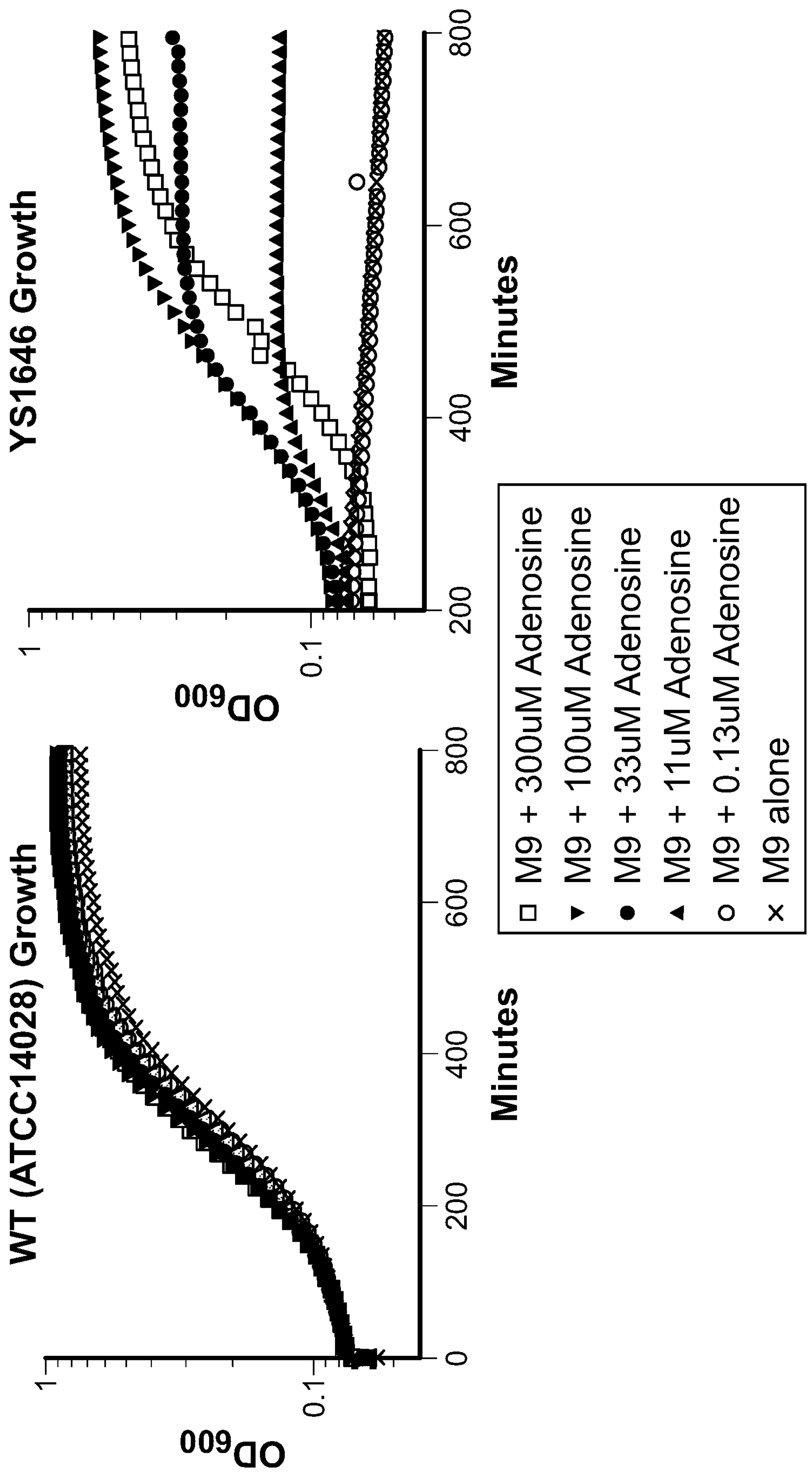
FIG. 11 depicts that strain YS1646 requires tumor microenvironment levels of adenosine for growth. Growth of strains YS1646 (purI$^-$/msbB$^-$), and the wild-type parental strain, ATCC 14028, at 37° C. in LB broth are shown, as measured by $OD_{600}$ using a SpectraMax® 96-well plate reader (Molecular Devices).

As shown in FIG. 11, strain YS1646 was able to replicate when adenosine was provided at concentrations ranging from 11 to 300 micromolar, but was completely unable to replicate in M9 alone, or in M9 supplemented with 130 nanomolar adenosine. These data demonstrate that purI mutants are able to replicate in concentrations of adenosine that are found in the tumor microenvironment, but not at concentrations found in normal tissues. Engineered adenosine auxotrophic strains exemplified herein include strains wherein all, or portions of the purI open reading frame are deleted from the chromosome, to prevent reversion to wild-type. Such gene deletions can be achieved utilizing the lambda red system as described in Example 1.

Figure 12:
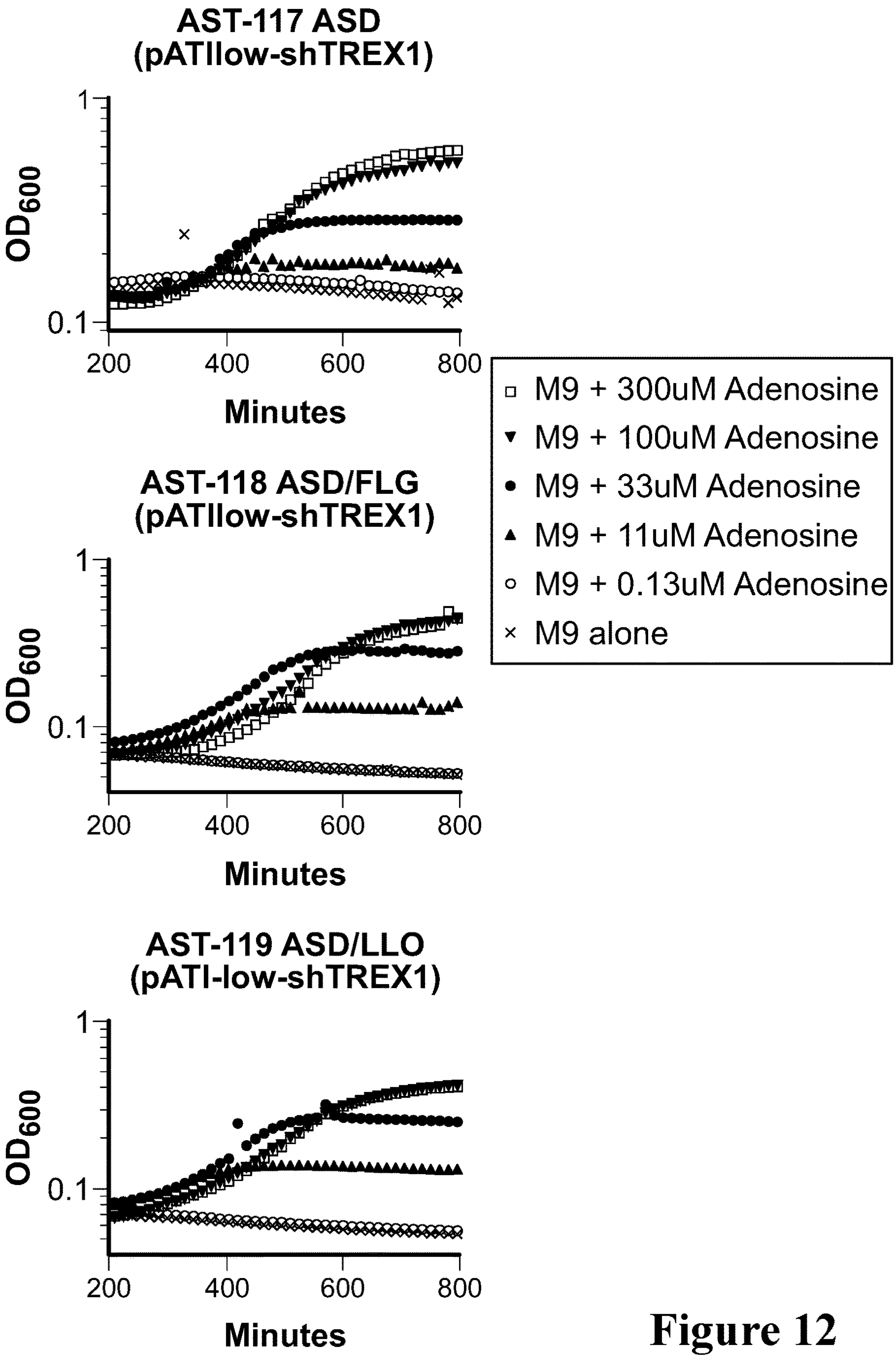
FIG. 12 depicts that ASD, FLG, and cytoLLO engineered strains require high adenosine concentrations for growth. The growth of strains AST-117 (YS1646 Δasd, containing a low copy shTREX-1 plasmid), AST-118 (YS1646 Δasd/ΔfliC/ΔfljB, containing a low copy shTREX-1 plasmid), and AST-119 (YS1646 Δasd:LLO, containing a low copy shTREX-1 plasmid) at 37° C. in LB broth are shown, as measured by $OD_{600}$ using a SpectraMax® 96-well plate reader (Molecular Devices).

*Salmonella* strains containing a purI disruption, further engineered to contain an asd gene deletion (ASD) as described in Example 1, or containing an asd gene deletion further engineered to have deletions of fliC and fljB (ASD/FLG), as described in Example 7, or asd$^-$ mutants further engineered to express cytoLLO (ASD/LLO) as described in Example 8, and complemented with a low copy number plasmid (pATIlow) expressing asd as described in Example 6 (Strains AST-117, AST-118, and AST-119, respectively), were also evaluated for growth in M9 minimal media. The data in FIG. 12 show that each strain was able to replicate when adenosine was provided at concentrations ranging from 11 to 300 micromolar, but was completely unable to replicate in M9 alone, or in M9 supplemented with 130 nanomolar adenosine.

Example 10

Figure 13:
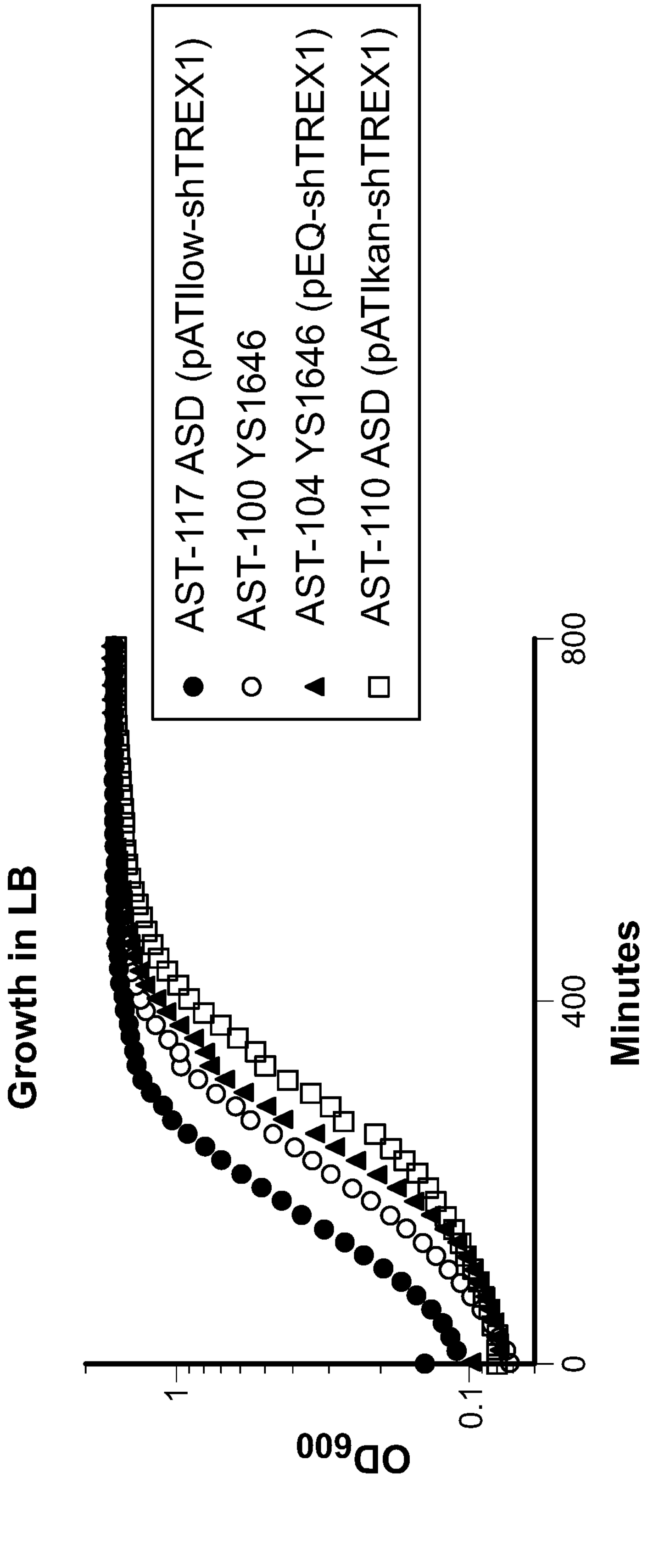
FIG. 13 depicts that a strain with a low copy origin of replication asd-encoding plasmid has superior growth kinetics than a strain with a high copy origin of replication asd-encoding plasmid. The growth of strains YS1646 (AST-100), AST-117 (YS1646 Δasd, containing a low copy shTREX-1 plasmid with a functional asd gene), AST-104 (YS1646 containing a low copy pEQU6-shTREX1 plasmid without an asd gene), and AST-110 (YS1646 Δasd, containing a high copy pATI-shTREX1 plasmid with a functional asd gene) at 37° C. in LB broth are shown, as measured by $OD_{600}$ using a SpectraMax® 96-well plate reader (Molecular Devices).

Characterization and Use of the asd Gene Complementation System In Vitro Growth of Strains with asd Gene Complementation To assess fitness of the bacterial strains containing plasmids, growth curves were performed in LB liquid media using a SpectraMax® plate reader at 37° C., reading the $OD_{600}$ every 15 minutes. As shown in FIG. 13, strain YS1646 containing a low copy plasmid, pEQU6-shTREX1 (AST-104), grew comparably to strain YS1646 that did not contain a plasmid (AST-100). An asd$^-$ mutant strain harboring a high copy shTREX1 plasmid with an asd gene that can complement the asd deletion (AST-110) was able to replicate in LB in the absence of DAP, but grew slower than strain YS1646. An asd-deleted strain, containing an shTREX1 expression plasmid with a low copy number origin of replication and an asd gene that can complement the asd deletion (pATIlow-shTREX1), strain AST-117, grew at a faster rate than strain AST-110. These data demonstrate that low copy number plasmids that complement the asd gene deletion are superior to high copy number plasmids, as they allow for more rapid replication rates of *S. typhimurium* in vitro.

Intracellular Growth of asd Complemented Strains

To measure fitness of the asd$^-$ mutants complemented with asd on high and low copy plasmids, the ability of bacterial strains to replicate intracellularly in mouse tumor cell lines was assessed using a gentamicin protection assay. In this assay, mouse melanoma B16.F10 cells, or mouse colon cancer CT26 cells, were infected with asd$^-$ mutant *Salmonella* strains containing plasmids that contain a complementary asd gene and that have either a high copy origin of replication, AST-110 (ASD pATI-shTREX1), or a low copy origin of replication, AST-117 (ASD pATIlow-shTREX1). Cells were infected at a multiplicity of approximately 5 bacteria per cell for 30 minutes, then cells were washed with PBS, and medium containing gentamicin was added to kill extracellular bacteria. Intracellular bacteria are not killed by gentamicin, as it cannot cross the cell membrane. At various time points after infection, cell monolayers were lysed by osmotic shock with water, and the cell lysates were diluted and plated on LB agar to enumerate surviving colony forming units (CFUs).

Figure 14:
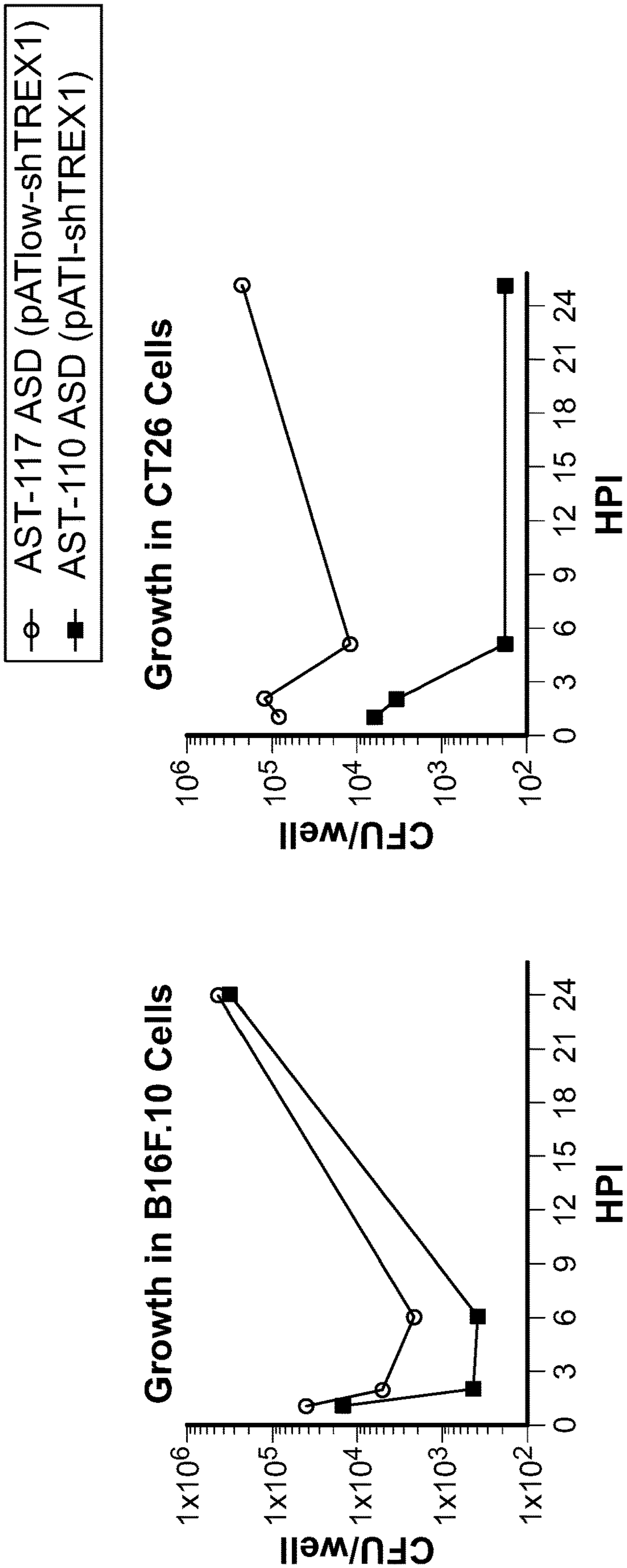
FIG. 14 depicts that a strain with a low copy asd plasmid is more fit than a strain with a high copy asd plasmid in mouse tumor cells. The intracellular growth of strains AST-117 (YS1646 Δasd, containing a low copy shTREX1 plasmid with a functional asd gene), and AST-110 (YS1646 Δasd, containing a high copy pATI-shTREX1 plasmid with a functional asd gene) are shown in B16F.10 mouse melanoma cells and CT26 mouse colon carcinoma cells. $5\times10^5$ cells in a 24-well dish were infected with the *S. typhimurium* strains at a multiplicity of infection (MOI) of 5. After 30 minutes of infection, media was replaced with media containing gentamicin to kill extracellular bacteria. At indicated time points, cell monolayers were lysed by osmotic shock the cell lysates were diluted and plated on LB agar to enumerate CFUs.

As shown in FIG. 14, the asd$^-$ mutant strain complemented with a high copy plasmid, AST-110, had an initial decline in CFUs, and was able to grow in B16.F10 cells but not in CT26 cells, demonstrating that the asd gene complementation system is sufficient to support growth inside mammalian tumor cells. The asd$^-$ mutant strain containing the low copy plasmid, AST-117, was able to invade and replicate in both cell types, demonstrating that asd gene complementation on a low copy plasmid allows for robust asd$^-$ mutant growth inside mammalian tumor cells. The strain with a low copy plasmid replicated to higher numbers in both tumor cell types, compared to the strain with a high copy plasmid. This demonstrates that *Salmonella* strains with low copy plasmids have enhanced fitness over strains with high copy plasmids.

Plasmid Maintenance in Tumors Using Asd Complementation System

In this example, CT26 tumor-bearing mice were treated with strain YS1646 containing a plasmid that expresses an shRNA targeting TREX1 (pEQU6-TREX1), strain AST-104, or an asd-deleted strain of YS1646 containing a plasmid with a functional asd gene and an shRNA targeting TREX1 (pATI-shTREX1), strain AST-110. At 12 days after the final *Salmonella* injection, tumors were homogenized, and homogenates were serially diluted and plated on LB agar plates to enumerate the total number of CFUs present, or on LB plates containing kanamycin to enumerate the number of kanamycin resistant colonies.

Figure 15:
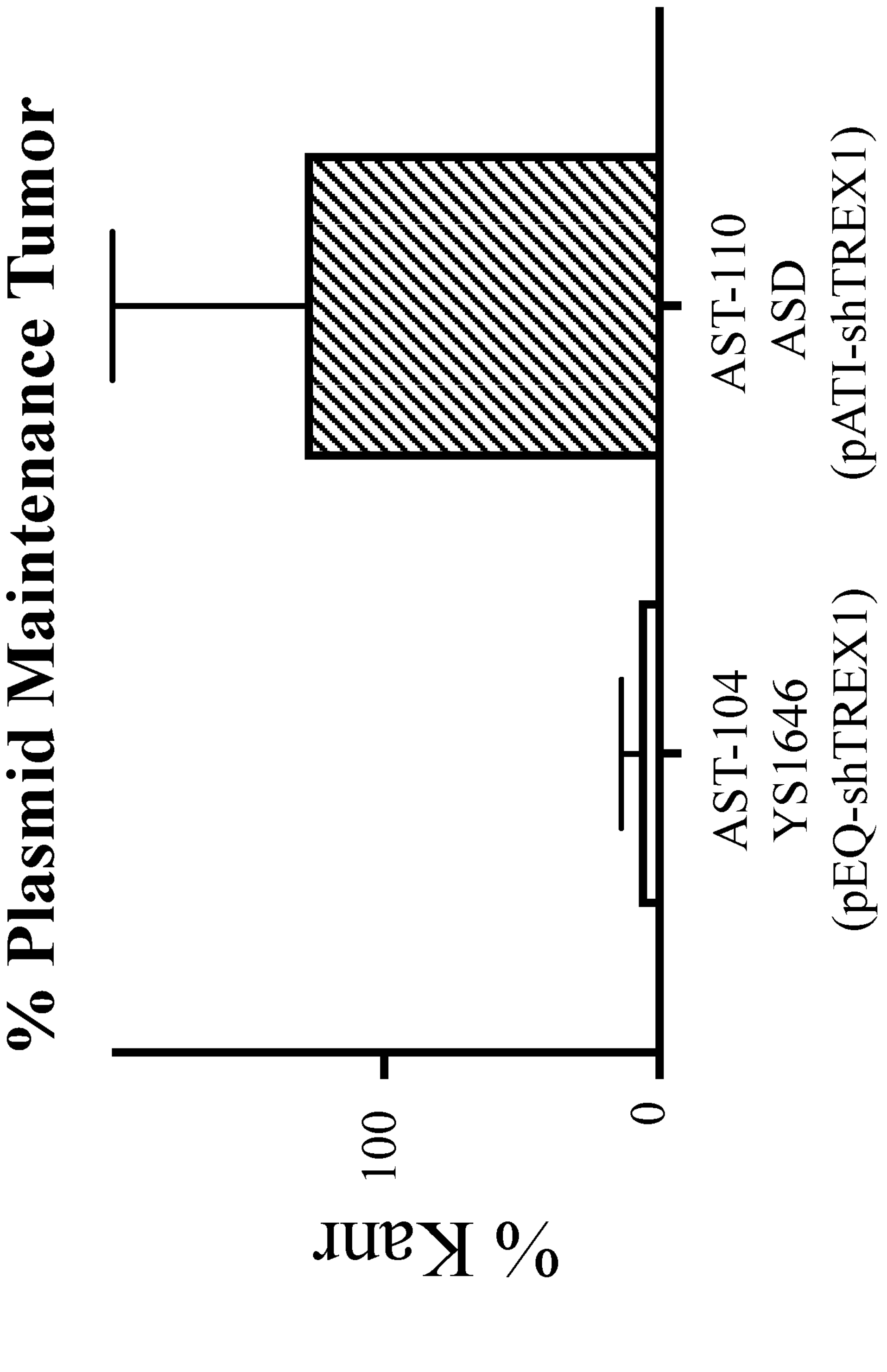
FIG. 15 depicts that in vivo, asd gene complementation systems result in retention of plasmids in *S. typhimurium*-infected tumors. BALB/c mice (6-8 week old) were implanted with a single CT26 ($2\times10^5$ cells) subcutaneous flank tumor (n=9 per group). Mice with established tumors were IV injected with $5\times10^6$ CFUs of the asd knockout strain containing the pATI-shTREX1 plasmid (AST-110), or the YS1646 strain containing a pEQ shTREX1 plasmid without an asd gene (AST-104). At 35 days post tumor implantation (12 days after the last dose of engineered *Salmonella* therapy), three mice per group were sacrificed, and tumors were homogenized using a GentleMACs™ homogenizer (Miltenyi Biotec) and plated on LB agar plates or LB agar plates with 50 μg/mL of kanamycin. The figure depicts the percentage of kanamycin resistant CFUs in tumor tissue homogenates, ±SD.

As shown in FIG. 15, *S. typhimurium* that did not have selective pressure to maintain the shRNA plasmid, i.e., strain AST-104, demonstrated plasmid loss, as the percent kanamycin resistant ($Kan^R$) colonies was less than 10%. The strain that used the asd gene complementation system for plasmid maintenance, AST-110, had nearly identical numbers of kanamycin resistant and kanamycin sensitive CFUs. These data demonstrate that the asd gene complementation system is sufficient to maintain the plasmid in the context of the tumor microenvironment in mice.

Enhanced Anti-Tumor Efficacy Using asd Complementation System

The asd complementation system is designed to prevent plasmid loss and potentiate the anti-tumor efficacy of the inhibitory RNA delivery by *S. typhimurium* strains in vivo. To test this, asd-deleted strains containing the shTREX1 plasmid (AST-110), or scrambled control (AST-109), that contain a functional asd gene cassette, were compared to strain YS1646 containing plasmid pEQU6-shTREX1 (strain AST-104, containing a plasmid that lacks an asd gene cassette, and therefore, does not have a mechanism for plasmid maintenance), for anti-tumor efficacy in a murine colon carcinoma model. For this experiment, 6-8 week-old female BALB/c mice (8 mice per group) were inoculated SC in the right flank with CT26 cells ($2\times10^5$ cells in 100 μL PBS). Mice bearing established flank tumors were IV injected twice, on day 8 and day 18, with $5\times10^6$ CFUs of strain AST-109 (ASD transformed with pATI-shScramble), strain AST-110 (ASD transformed with pATI-shTREX1), or strain AST-104 (YS1646 transformed with pEQU6-shTREX1), and compared to PBS control.

As shown in FIG. 16, the YS1646 strain AST-104 demonstrated tumor control compared to PBS (70% TGI, day 28), despite its demonstrated plasmid loss over time. The $asd^-$ strain containing the scramble control in a pATI plasmid with the asd gene complementation system (strain AST-109) demonstrated tumor control compared to PBS (51% TGI, day 25), indicating that maintained delivery of CpG-containing plasmids stimulates an anti-tumor response. The $asd^-$ strain containing the plasmid with the asd gene complementation system and shTREX1 (strain AST-110) demonstrated the highest tumor growth inhibition compared to PBS (82% TGI, p=0.002, day 25). These data demonstrate that improved potency is achieved by preventing plasmid loss using the asd complementation system, and by delivery of shTREX1, as compared to YS1646 containing plasmids without asd gene complementation systems, or without shTREX1.

Figure 17:
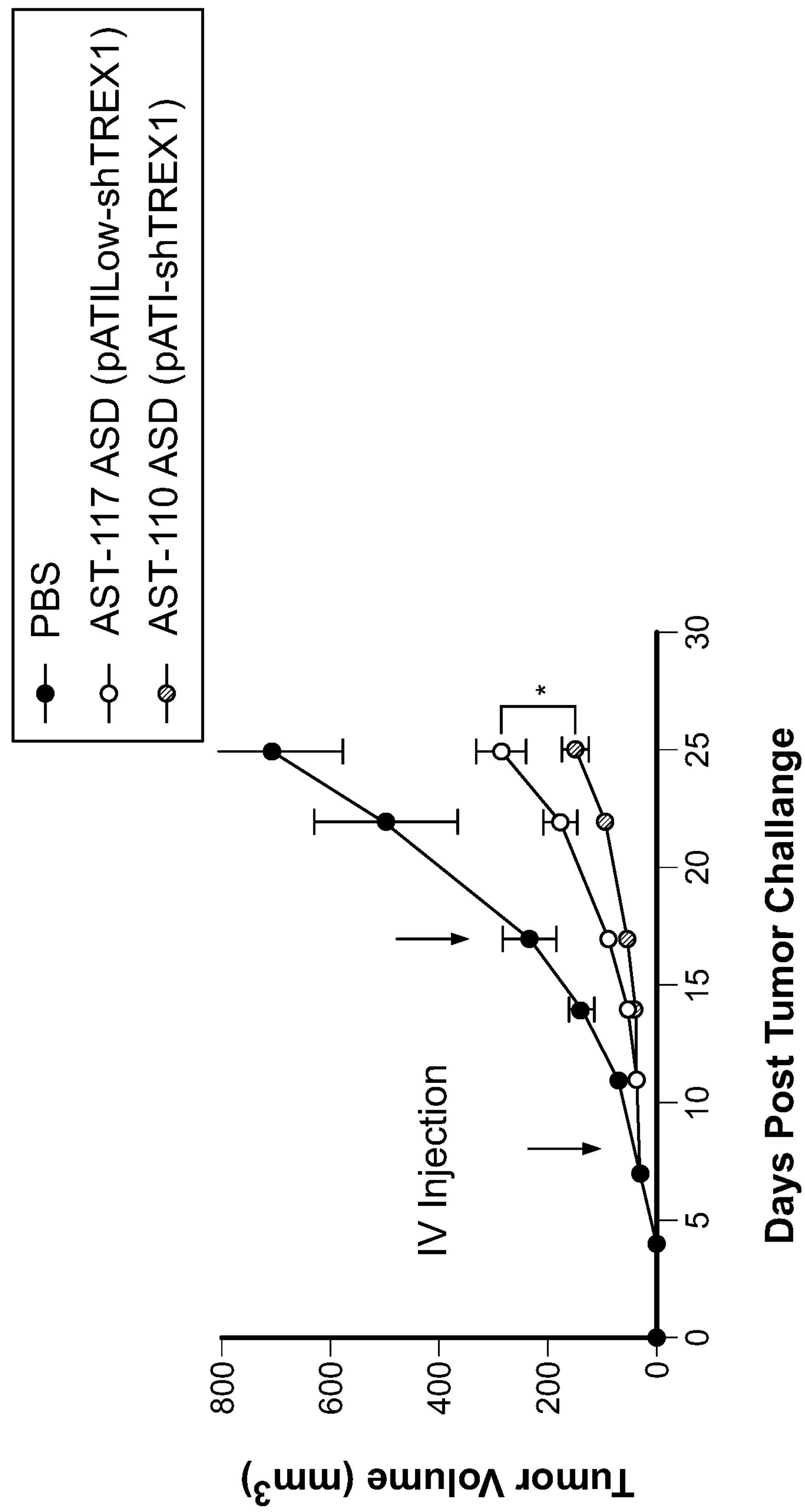
FIG. 17 depicts that a strain containing a low copy shTREX1 plasmid (AST-117) has superior anti-tumor properties compared to a strain containing a high copy shTREX1 plasmid (AST-110). BALB/c mice (6-8 week old) were implanted with a single CT26 ($2\times10^5$ cells) subcutaneous flank tumor (n=9 per group). Mice with established tumors were IV injected with $5\times10^6$ CFUs of the asd knockout strain containing the pATI-shTREX1 plasmid with a high copy number origin of replication (AST-110), or the asd knockout strain containing the pATI-shTREX1 plasmid with a low copy number origin of replication (AST-117), or PBS control, on the days indicated by the arrows. Tumor measurements were performed using electronic calipers (Fowler, Newton, Mass.). Tumor volume was calculated using the modified ellipsoid formula, ½(length×width$^2$). Mice were euthanized when tumor size reached >20% of body weight or became necrotic, as per IACUC regulations. TGI was calculated as 1-(mean test tumor volume/mean control tumor volume)×100. The figure depicts the mean tumor growth of each group, ±SEM. * $p<0.05$, student's t-test.

*S. typhimurium* Strains with Low Copy Plasmids Demonstrate Superior Anti-Tumor Efficacy and Tumor Colonization Compared to High Copy Plasmids In order to compare the anti-tumor efficacy of the low copy shTREX1 plasmid with the asd complementation system, relative to the high copy shTREX1 plasmid, in a murine model of colon carcinoma, 6-8 week-old female BALB/c mice (10 mice per group) were inoculated SC in the right flank with CT26 cells ($2\times10^5$ cells in 100 PBS). Mice bearing established flank tumors were IV injected with two weekly doses of $5\times10^6$ CFUs of strain AST-117 (ASD (pATI Low-shTREX1)), or strain AST-110 (ASD (pATI-shTREX1)), and were compared to PBS injections as a negative control. As shown in FIG. 17, the strain with the low copy plasmid, AST-117, demonstrated superior anti-tumor efficacy compared to the strain with the high copy plasmid, AST-110 (High: 59% TGI, Low: 79% TGI, p=0.042, day 25).

Figure 18B:
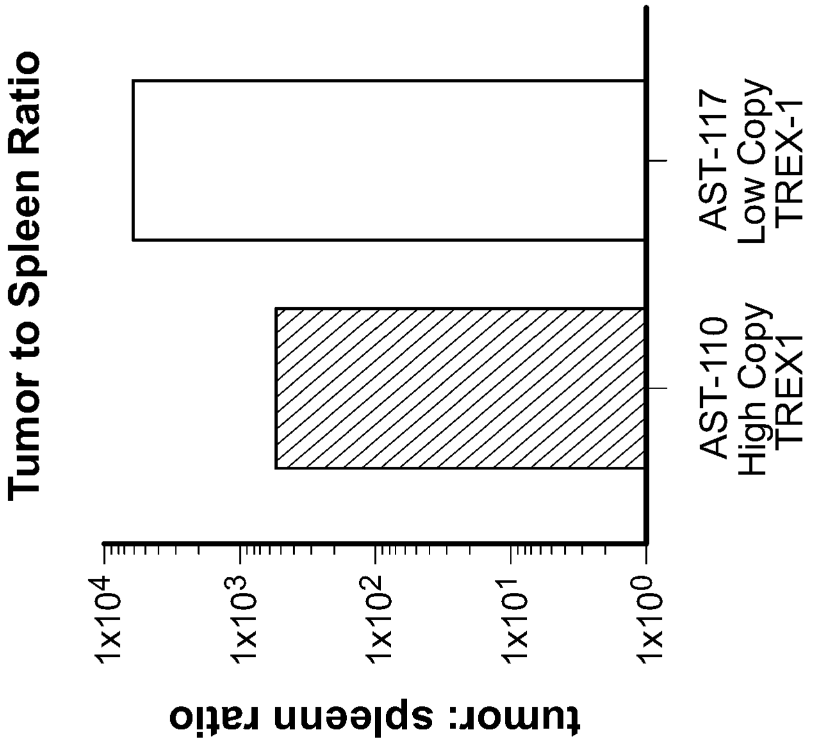
FIGS. 18A and 18B depict that the AST-117 low copy plasmid strain colonizes tumors better, and has a higher tumor to spleen colonization ratio, than the AST-110 high copy plasmid strain. BALB/c mice (6-8 week old) were implanted with a single CT26 ($2\times10^5$ cells) subcutaneous flank tumor (n=9 per group). Mice with established tumors were IV injected with $5\times10^6$ CFUs of the asd knockout strain containing the pATI-shTREX1 plasmid with a high copy number origin of replication (AST-110), or the asd knockout strain containing the pATI-shTREX1 plasmid with a low copy number origin of replication (AST-117). At 35 days post tumor implantation (12 days after the last dose of engineered *Salmonella* therapy), 3 mice per group were sacrificed, and tumors were homogenized using a GentleMACs™ homogenizer (Miltenyi Biotec) and plated on LB plates to enumerate the number of CFUs per gram of tumor tissue.
Figure 18A:
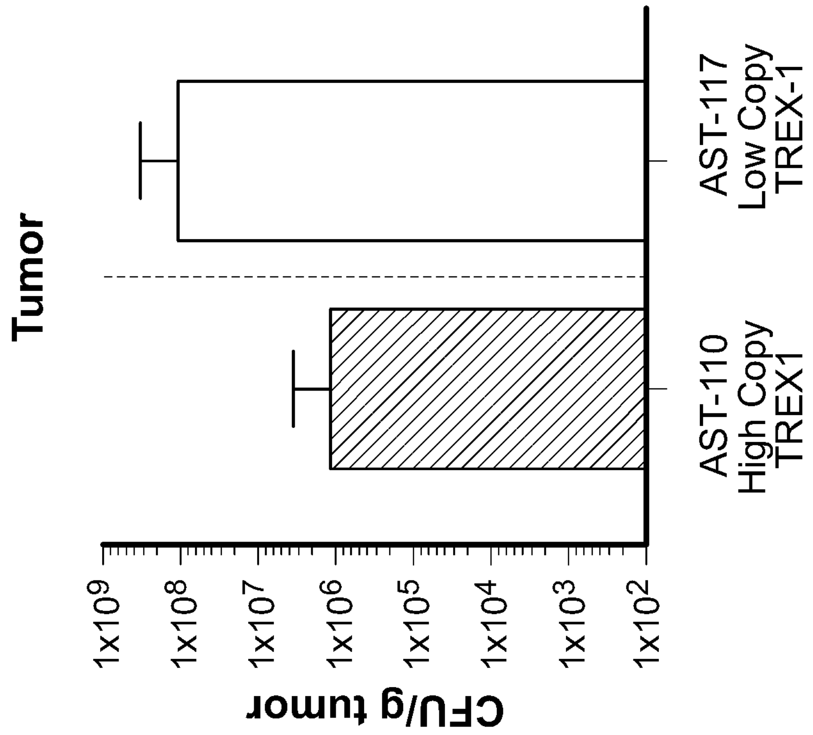

At the end of this tumor growth inhibition study, 4 mice from each group were euthanized, and tumors and spleens were homogenized as described above, to evaluate tumor colonization, and tumor to spleen colonization ratios. As shown in FIG. 18A, the strain containing the low copy plasmid, AST-117, colonized tumors at a level greater than 100 times higher than the strain with the high copy plasmid, AST-110. When the ratio of colonies recovered from tumor and spleen were calculated, strain AST-117 had a greater than 10-fold higher tumor to spleen colonization ratio compared to strain AST-110 (FIG. 18B), demonstrating that the strain with the low copy plasmid had greater specificity for tumor colonization than the strain with the high copy plasmid.

These data demonstrate a previously unknown attribute that *S typhimurium* engineered to deliver plasmids encoding interfering RNAs have improved tumor colonizing capabilities and anti-tumor efficacy when the plasmids have low copy number origins of replication.

Example 11

Engineering of an Autolytic *S. typhimurium* Strain for Delivery of RNAi

As described above, the asd gene in *S. typhimurium* encodes aspartate-semialdehyde dehydrogenase. Deletion of this gene renders the bacteria auxotrophic for diaminopimelic acid (DAP) when grown in vitro or in vivo. This example employs an asd-deleted strain (described in Example 1) that is auxotrophic for DAP and that contains a plasmid suitable for delivery of RNAi, but that does not contain an asd complementing gene, so that the strain is defective for replication in vivo. This strain is propagated in vitro in the presence of DAP and grows normally, and then is administered as an immunotherapeutic agent to mammalian hosts where DAP is not present, which results in autolysis of the bacteria. Autolytic strains are able to invade host cells, but are not able to replicate due to the absence of DAP in mammalian tissues; this combination of attributes allows for RNAi-mediated gene knockdown and increased safety relative to replicating strains.

In this example, the asd-deleted strain of YS1646 (strain AST-101, described in Example 1) was further modified to express cytoLLO, to generate strain AST-114 (described in Example 8), and was electroporated to contain a plasmid encoding ARI-203 (a microRNA targeting TREX1), to generate strain AST-120 (ASD/LLO (pEQU6-miTREX1)). When this strain is introduced into tumor bearing mice, the bacteria are taken up by host cells, and enter the *Salmonella*-containing vacuole (SCV). In this environment, the lack of DAP prevents replication, and result in lysis of the bacteria in the SCV. Lysis of strain AST-120 allows for release of the plasmid, and the accumulated cytoLLO that form pores in the cholesterol-containing SVC membrane, resulting in efficient delivery of the plasmid into the cytosol of the host cell.

Figure 19:
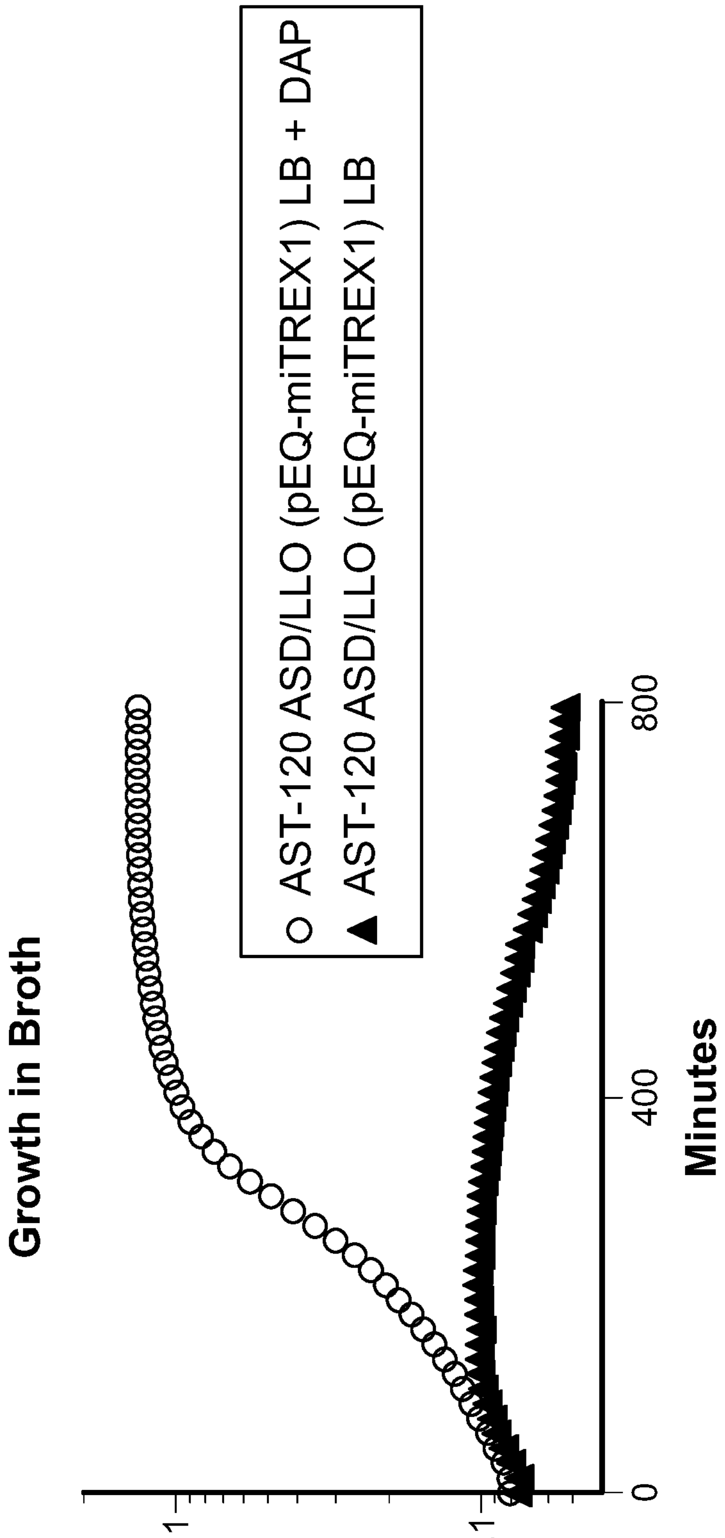
FIG. 19 depicts that an autolytic strain (AST-120) cannot grow in the absence of DAP. The figure depicts the growth of the Δasd:cytoLLO strain, containing a pEQU6-miTREX1 plasmid that does not contain an asd gene (AST-120), over time in LB broth alone, or in LB broth supplemented with 50 μg/mL DAP, as measured by $OD_{600}$ using a SpectraMax® 96-well plate reader (Molecular Devices).

The ability of the autolytic strain, AST-120, to replicate in LB in the presence or absence of DAP was assessed using a SpectraMax® M3 spectrophotometer (Molecular Devices) at 37° C., reading the $OD_{600}$ every 15 minutes. As shown in FIG. 19, strain AST-120 is able to grow robustly in LB supplemented with 50 μg/mL DAP, but cannot replicate in LB alone.

Increased Attenuation of Autolytic *S. typhimurium* in Mice

To determine whether the autolytic strain, AST-120, engineered to deliver cytoLLO and a microRNA targeting TREX1, was attenuated for virulence, a median lethal dose ($LD_{50}$) study was performed. Increasing doses of strain AST-120, ranging from $1\times10^6$ to $5\times10^7$ CFUs, were administered IV to C57BL/6 mice (a strain of mouse that is highly sensitive to LPS). After IV administration, strain AST-120 was well tolerated at all doses, with transient weight loss observed after a single dose. A second dose was administered 7 days after the first dose, and one mouse out of four, at the highest dose level ($5\times10^7$ CFUs), was found moribund and required euthanasia. All other mice administered strain AST-120 experienced transient weight loss, but recovered. These data indicate that the $LD_{50}$ for the autolytic strain of *S. typhimurium*, delivering a micro-RNA targeting TREX1 (AST-120), is greater than $5\times10^7$ CFUs. The $LD_{50}$ for the VNP20009 strain is known to be approximately $5\times10^6$ CFUs in C57BL/6 mice (see, e.g., Lee et al. (2000) *International Journal of Toxicology* 19:19-25), demonstrating that strain AST-120 is at least 10-fold attenuated compared to VNP20009.

Antitumor Activity of Autolytic *S. typhimurium*

Figure 20:
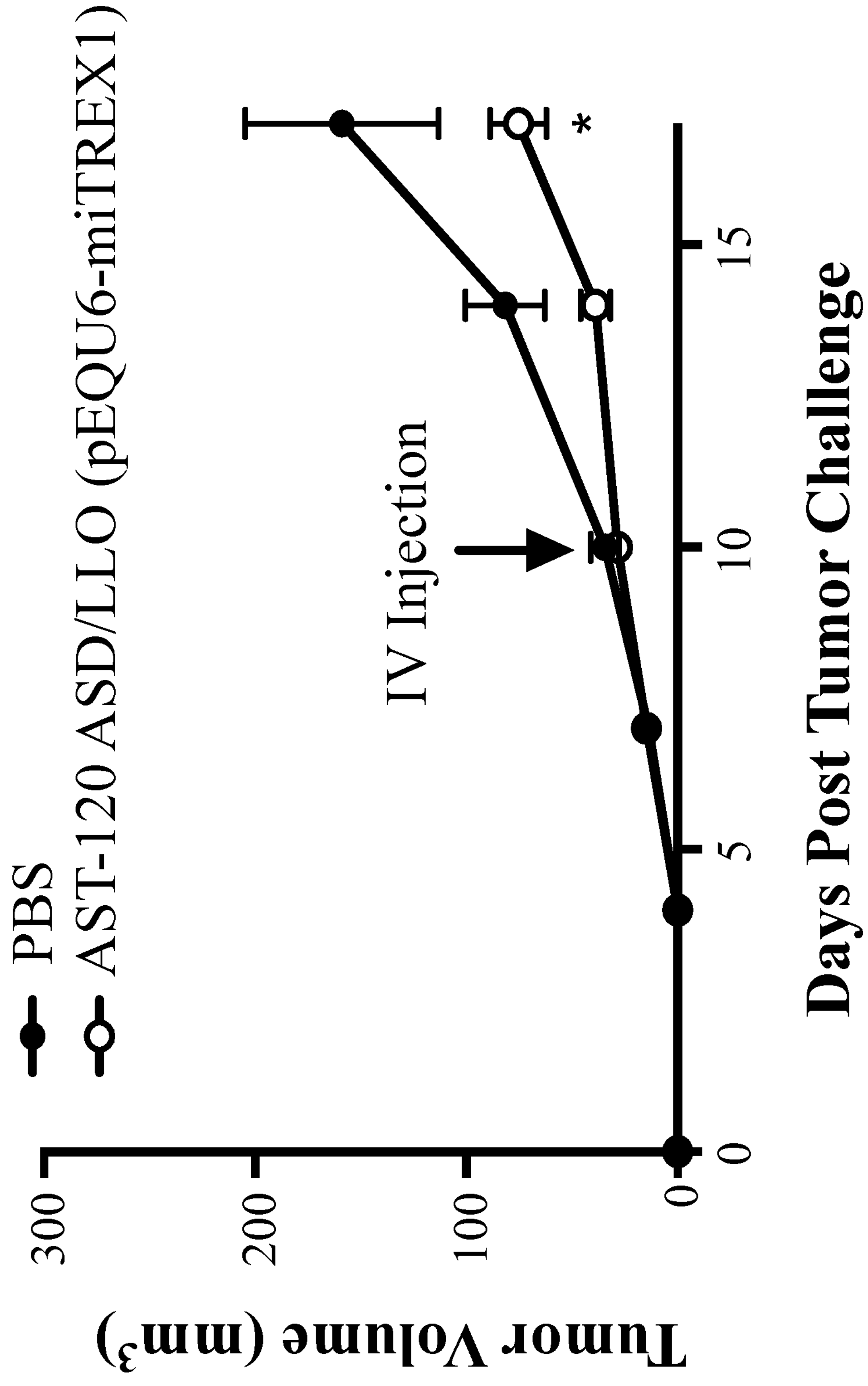
FIG. 20 depicts the anti-tumor activity of the autolytic strain (AST-120). BALB/c mice (6-8 week old) were implanted with a single CT26 ($2\times10^5$ cells) subcutaneous flank tumor (n=9 per group). Mice with established tumors were IV injected with $5\times10^6$ CFUs of the of Δasd:cytoLLO strain containing a pEQU6-miTREX1 plasmid that does not contain an asd gene (AST-120), or PBS control, on the days indicated by the arrows. Tumor measurements were performed using electronic calipers (Fowler, Newton, Mass.). Tumor volume was calculated using the modified ellipsoid formula, ½(length×width$^2$). Mice were euthanized when tumor size reached >20% of body weight or became necrotic, as per IACUC regulations. TGI was calculated as 1-(mean test tumor volume/mean control tumor volume)× 100. The figure depicts the mean tumor growth of each group, ±SEM. * $p<0.05$, student's t-test.
Figure 21:
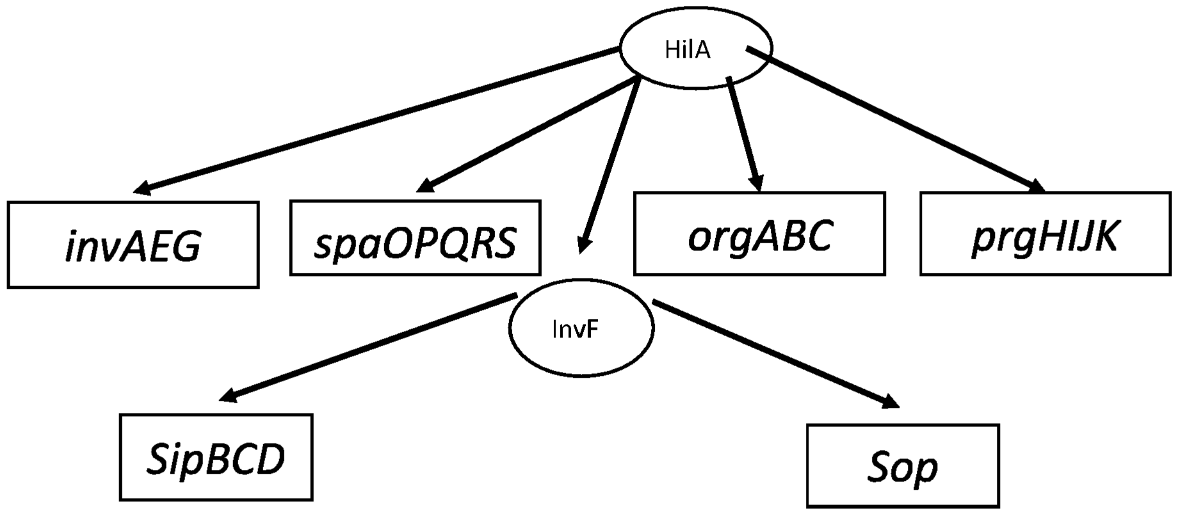
FIG. 21 depicts proteins that act downstream of HilA in the SPI-1 pathway.

To determine whether the autolytic strain, AST-120, engineered to deliver cytoLLO and a microRNA targeting TREX1, was able to provide an anti-tumor response, 6-8 week-old female BALB/c mice (10 mice per group) were inoculated SC in the right flank with CT26 cells ($2\times10^5$ cells in 100 μL PBS). Mice bearing established flank tumors were IV injected with a single dose of $5\times10^6$ CFUs of the autolytic strain AST-120 (ASD/LLO (pEQU6-miTREX1)), and compared to mice treated with PBS as a control. As shown in FIG. 20, an anti-tumor response was detected after only a single dose, compared to animals treated with PBS alone (52.4% TGI, p=0.02, day 17). Together, these data demonstrate that *S. typhimurium* engineered to be autolytic by means of DAP auxotrophy, and engineered to contain a plasmid for delivery of RNAi targeting TREX1, are exquisitely attenuated and can elicit an anti-tumor response.

Example 12

Exemplary Strains Engineered for Increased Tolerability adrA or csgD Deletion In this example, a live attenuated strain of *Salmonella typhimurium*, that contains a purI deletion, an msbB deletion, and an asd gene deletion, and that is engineered to deliver plasmids encoding interfering RNA, is further modified to delete adrA, a gene required for *Salmonella typhimurium* biofilm formation. *Salmonella* that cannot form biofilms are taken up more rapidly by host phagocytic cells, and are cleared more rapidly. This increase in intracellular localization enhances the effectiveness of plasmid delivery and gene knockdown by RNA interference. The increased clearance rate from tumors/tissues increases the tolerability of the therapy, and the lack of biofilm formation prevents colonization of prosthetics and gall bladders in patients.

In another example, a live attenuated strain of *Salmonella typhimurium*, that contains a purI deletion, an msbB deletion, and an asd gene deletion, and that is engineered to deliver plasmids encoding interfering RNA, is further modified to delete csgD. This gene is responsible for activation of adrA, and also induces expression of the curli fimbriae, a TLR2 agonist. Loss of csgD also prevents biofilm formation, with the added benefit of inhibiting TLR2 activation, thereby further reducing the bacterial virulence, and enhancing delivery of RNAi.

pagP Deletion

In this example, a live attenuated strain of *S. typhimurium*, that contains a purI deletion, an msbB deletion, and an asd gene deletion, and that is engineered to deliver plasmids encoding interfering RNA, is further modified to delete pagP. The pagP gene is induced during the infectious life cycle of *S. typhimurium* and encodes an enzyme that palmitoylates lipid A. In wild type *S. typhimurium*, expression of pagP results in a lipid A that is hepta-acylated. In an $msbB^-$ mutant, in which the terminal acyl chain of the lipid A cannot be added, the expression of pagP results in a hexa-acylated LPS. Hexa-acylated LPS has been shown to be the most pro-inflammatory. In this example, a strain deleted of pagP and msbB can produce only penta-acylated LPS, allowing for lower pro-inflammatory cytokines, enhanced tolerability, and increased adaptive immunity when the bacteria are engineered to deliver interfering RNAs.

hilA Deletion

In this example, a live attenuated strain of *Salmonella typhimurium*, that contains a purI deletion, an msbB deletion, and an asd gene deletion, and that is engineered to deliver plasmids encoding interfering RNA, is further modified to delete hilA. hilA is a regulatory gene that is required for expression of the *Salmonella* pathogenicity island 1 (SPI-1)-associated type 3 secretion system (T3SS). This secretion system is responsible for injecting effector proteins into the cytosol of non-phagocytic host cells, such as epithelial cells, that cause the uptake of modified *S. typhimurium*. The SPI-1 T3SS has been shown to be essential for crossing the gut epithelial layer, but is dispensable for infection when bacteria are injected parenterally. The injection of some proteins, and the needle complex itself, can also induce inflammasome activation and pyroptosis of phagocytic cells. This pro-inflammatory cell death can limit the initiation of a robust adaptive immune response by directly inducing the death of antigen-presenting cells (APCs), as well as by modifying the cytokine milieu to prevent the generation of memory T-cells. In this example, the additional deletion of the hilA gene from a therapeutic *Salmonella typhimurium* strain that is administered either intravenously or intratumorally, focuses the *Salmonella typhimurium* infection towards phagocytic cells that do not require the SPI-1 T3SS for uptake, and then prolongs the longevity of these phagocytic cells. The hilA mutation reduces the quantity of pro-inflammatory cytokines, increasing the tolerability of the therapy, as well as the quality of the adaptive immune response.

Example 13 hilA Deletion Mutants Grow Normally In Vitro

The hilA gene was deleted from the YS1646 strain of *S. typhimurium* with the asd gene deleted, and the YS1646 strain deleted of asd, and of flagellin genes fljB and fliC, using the lambda-derived Red recombination system as described in Datsenko and Wanner (*Proc. Natl. Acad. Sci. U.S.A.* 97:6640-6645(2000)), to generate the strains HilA/ASD and HilA/FLG/ASD, respectively. These strains were then electroporated with a plasmid containing a functional asd gene (to complement the deleted asd gene and to ensure plasmid maintenance in vivo) and a eukaryotic expression cassette containing the U6 promoter driving expression of a microRNA targeting murine TREX-1 (pATI-miTREX1). The in vitro growth rates of strains HilA/ASD (pATI-miTREX1) and HilA/FLG/ASD (pATI-miTREX1) were then determined and compared to the strains ASD (pATI-miTREX1) and YS1646 at 37° C. in LB broth, as measured by $OD_{600}$ using a SpectraMax® 96-well plate reader (Molecular Devices). Each modified strain grew at a rate comparable to the parental YS1646 strain in vitro, indicating that the hilA deletion does not reduce the fitness of the bacteria in vitro.

Example 14 hilA Deletion Mutants Induce Less Cell Death in Human Monocytic Cells

To assess whether a hilA deletion mutant induced less pyroptosis than strains capable of producing SPI-1, human THP-1 monocytic cells were infected with a multiplicity of infection (MOI) of 1000 bacteria with strains YS1646, ASD (pATI-miTREX1), FLG/ASD (pATI-miTREX1), and HilA/ASD (pATI-miTREX1). After 1 hour of infection, extracellular bacteria were removed and the media was replaced with media containing gentamicin at 100 μg/mL to kill extracellular bacteria. At 4 hours post infection, cells were harvested, and THP-1 cell viability was assessed using CellTiter-Glo® reagent (Promega) uptake, and measuring luminescence using a SpectraMax® 96-well plate reader (Molecular Devices). While infection with strain YS1646 resulted in 86% cell death, infection with strain HilA/ASD (pATI-miTREX1) only resulted in 46% cell death. The % dead cells for strain ASD (pATI-miTREX1) and strain FLG/ASD (pATI-miTREX1) demonstrated intermediate phenotypes, with 77% and 68% cell death, respectively. These data demonstrate that hilA-deleted strains induce less cell death in human monocytic cells than *S. typhimurium* strains capable of expressing SPI-1.

Example 15 hilA Deletion Mutants Have Reduced Capacity to Infect Human Epithelial Cells HeLa cells were infected with a multiplicity of infection of 500 bacteria, with strains YS1646, ASD (pATI-miTREX1), FLG/ASD (pATI-miTREX1), and HilA/ASD (pATI-miTREX1). After 1 hour, extracellular bacteria were removed and the media was replaced with media containing gentamicin at 100 μg/mL to kill extracellular bacteria. At 4 hours post infection, cells were harvested and lysed by osmotic shock, and the number of viable colony forming units (CFUs) of bacteria were enumerated by serial dilution and plating on LB agar plates. $4.6\times10^3$ CFUs per well were recovered with strain YS1646, and only $2.0\times10^2$ CFUs were recovered with the HilA/ASD (pATI-miTREX1) strain. Strains ASD (pATI-miTREX1) and FLG/ASD (pATI-miTREX1) demonstrated intermediate phenotypes, with $8.0\times10^2$ CFUs and $6.0\times10^2$ CFUs recovered, respectively. These data demonstrate that hilA-deleted strains induce less uptake in human epithelial cells than *S. typhimurium* strains capable of expressing SPI-1.

Example 16 pagP Deletion Mutants have Penta-Acylated LPS and Induce Reduced Inflammatory Cytokines The pagP gene was deleted from the asd gene-deleted strain of *S. typhimurium* YS1646 (which contains a purI/purM and msbB deletion), using the lambda-derived Red recombination system, as described in Datsenko and Wanner (*Proc. Natl. Acad. Sci. U.S.A.* 97:6640-6645 (2000)) to generate the strain PagP/ASD. This strain was then electroporated with a plasmid containing a functional asd gene (to complement the deleted asd gene and to ensure plasmid maintenance in vivo) and a eukaryotic expression cassette containing the U6 promoter driving expression of a microRNA targeting murine TREX-1 (pATI-miTREX1), to generate the strain PagP/ASD (pATI-miTREX1). The lipid A was then extracted from this strain, and evaluated by matrix-assisted laser desorption/ionization mass spectrometry (MALDI MS), and compared to lipid A from wild-type *S. typhimurium* strain ATCC 14028, strain YS1646 (which is deleted for msbB and purI/purM), and strain YS1646 deleted for the asd gene and complemented with the pATI-miTREX1 plasmid. Wild-type *Salmonella* had a minor lipid A peak with a mass of 2034, and a major peak with a mass of 1796, corresponding to the hepta-acylated and hexa-acylated species, respectively, due to the presence of functional msbB and purI/purM genes. The msbB-deleted strains, YS1646 and ASD (pATI-miTREX1), had major peaks at 1828 and 1585, corresponding to a mixture of hexa-acylated and penta-acylated LPS. The msbB- and pagP-deleted strain, PagP/ASD (pATI-TREX1) had only a single peak with a mass of 1585. These data demonstrate that deletion of pagP prevents palmitoylation of the LPS, thereby restricting it to a single penta-acylated species.

To determine whether the penta-acylated LPS from the pagP-deleted mutant strains reduced TLR-4 signaling, 4 μg of purified LPS from the strains described above were added to THP-1 human monocytic cells, and the supernatants were evaluated 24 hours later for the presence of inflammatory cytokines using a cytometric bead array (CBA) kit (BD Biosciences). The LPS from the $pagP^-$ strain induced ¼ the amount of TNF-alpha compared to wild-type LPS, and 7-fold less IL-6 than wild-type LPS. The $pagP^-$ mutant LPS induced 22-fold less IL-6 than YS1646 LPS, demonstrating that the penta-acylated LPS species from a $pagP^-$ mutant is significantly less inflammatory in human cells, and indicating that the $pagP^-$ mutant would be better tolerated in humans.

Example 17

FLG, hilA and pagP Deletion Mutants are More Attenuated than Strain YS1646 in Mice To determine whether the modified strains described above are more attenuated than strain YS1646, a median lethal dose ($LD_{50}$) study was conducted. C57BL/6 mice were injected intravenously with increasing concentrations of strains YS1646, FLG/ASD (pATI-TREX1), HilA/ASD (pATI-TREX1), or PagP/ASD (pATI-TREX1). The $LD_{50}$ for strain YS1646 was found to be $1.6\times10^6$ CFUs, which is consistent with published reports of this strain. The $LD_{50}$ for the HilA/ASD (pATI-TREX1) strain was determined to be $5.3\times10^6$ CFUs, demonstrating a 3-fold reduction in virulence. The $LD_{50}$ for the PagP/ASD (pATI-TREX1) strain was determined to be $6.9\times10^6$ CFUs, demonstrating a 4-fold reduction in virulence. The $LD_{50}$ for the FLG/ASD (pATI-TREX1) strain was determined to be $>7\times10^6$ CFUs, demonstrating a >4.4-fold reduction in virulence compared to strain YS1646. These data indicate that the genetic modifications described above reduce the virulence of the *S. typhimurium* therapy, and will lead to increased tolerability in humans. In the Phase I clinical trial of VNP20009 (see, Toso et al. (2002) *J. Clin. Oncol.* 20(1):142-152), the presence of the bacteria in patients' tumors was only partially observed at the two highest doses tested, 3E8 CFU/$m^2$ (33% presence), and 1E9 CFU/$m^2$ (50% presence), indicating that the tolerable dose of VNP20009 was too low to achieve colonization. By improving the tolerability of the strains through the modifications described above, higher doses can be administered than VNP20009. This improves both the percentage of patients that will have their tumors colonized, and the level of therapeutic colonization per tumor.

Example 18 hilA Deletion Mutants Demonstrate Significant Anti-Tumor Activity in Mice, and Comparable Activity to the fljB/fliC Deletion Mutants The $hilA^-$ mutation should prevent upregulation of the T3SS, and prevent pyroptotic cell death of infected macrophages. This should enhance tolerability and anti-tumor efficacy of the plasmid-containing target strains in vivo. To test this, ΔhilA/Δasd strains, containing the miTREX1 plasmid (HilA/ASD (pATI-miTREX1)), or vehicle control, were compared to ΔfljB/ΔfliC/Δasd strains, containing the miTREX1 plasmid (FLG/ASD (pATI-miTREX1)), for anti-tumor efficacy in a murine colon carcinoma model. 6-8 week-old female C57BL/6 mice (9 mice per group) were inoculated S.C. in the right flank with MC38 cells ($5\times10^5$ cells in 100 μL PBS). Mice bearing established flank tumors were I.V. injected on day 8 with $3\times10^5$ CFUs of strains HilA/ASD (pATI-miTREX1), FLG/ASD (pATI-miTREX1), or PBS vehicle control. Body weights and tumors were measured twice weekly. Tumor measurements were performed using electronic calipers (Fowler, Newton, Mass.). Tumor volume was calculated using the modified ellipsoid formula, ½(length×width). Mice were euthanized when tumor size reached >20% of body weight or became necrotic, as per IACUC regulations.

The data demonstrate that the HilA/ASD (pATI-miTREX1) strain induces potent tumor control compared to PBS (83.6% TGI, day 25), including ⅑ complete tumor regressions. These data were comparable to those observed with the FLG/ASD (pATI-miTREX1) strain compared to PBS (82.8% TGI, day 25). Thus, the ΔhilA strain provides comparable or greater potency in a murine tumor model as the ΔfljB/ΔfliC strain.

Example 19 hilA Deletion Mutants Demonstrate Significantly Lower Systemic Cytokines than the Parental VNP20009 Strain, and Enhanced Colonization Compared to the fljB/fliC Deletion Mutants To test the impact of the ΔhilA/Δasd and ΔfljB/ΔfliC/Δasd strains on tumor colonization and tolerability, compared to the parental VNP20009 strain, these strains, containing the miTREX1 plasmid, were evaluated in a murine colon carcinoma model. 6-8 week-old female C57BL/6 mice (3 mice per group) were inoculated S.C. in the right flank with MC38 cells ($5\times10^5$ cells in 100 μL PBS). Mice bearing established flank tumors were I.V. injected on day 8 with $3\times10^5$ and $1\times10^5$ CFUs of HilA/ASD (pATI-miTREX1), FLG/ASD (pATI-miTREX1), VNP20009, or PBS vehicle control. Mice were bled 2 hours post-dosing, and serum was assessed for systemic cytokines, using a mouse inflammation cytometric bead array (BD Biosciences) on a flow cytometer (NovoCyte®). On day 3 post I.V. dosing, mice were sacrificed, and the tumors, spleens and livers were harvested and weighed. Tissues were homogenized in 10 mL sterile PBS (M tubes, GentleMACS™, Miltenyi Biotec), and then 10-fold serial dilutions were performed and plated on LB (Luria Broth) agar plates containing LB+kanamycin (Sigma). The following day, colony forming units (CFUs) were counted, and total CFUs were assessed per gram of tissue.

Serum cytokine IL-6 levels in mice have been shown to be the most accurate correlate of clinical tolerability. The IL-6 levels from VNP20009 at the 3e5 CFU dose averaged 11,755 μg/mL, compared to the baseline 18 μg/mL of PBS control. The HilA/ASD (pATI-miTREX1) and FLG/ASD (pATI-miTREX1) IL-6 levels at the 3e5 CFU dose were both significantly lower than the VNP20009 levels (3,570 μg/mL and 3,850 μg/mL, respectively). These data demonstrate the significantly enhanced tolerability of the mutant strains compared to the parental VNP20009 strain. Comparing the colonization of tumors, spleens and livers 3 days post I.V. dosing of 1e5 CFU, the overall colonization of the spleens between HilA/ASD (pATI-miTREX1) and FLG/ASD (pATI-miTREX1) was comparable (HilA: 2.1e4 CFU/g, vs. FLG: 1.2e4 CFU/g), while the FLG/ASD (pATI-miTREX1) strain had somewhat lower colonization in the liver (HilA: 7.4e3 CFU/g, vs. FLG: 1.5e3 CFU/g). The tumor colonization of the HilA/ASD (pATI-miTREX1) strain was shown to be an average of 2.6e4 CFU/g, which was significantly higher than the undetectable levels found in the FLG/ASD (pATI-miTREX1) tumors at the same time point. These data demonstrate the high degree of tolerability and enhanced tumor colonization properties of the ΔhilA/Δasd strain.

Example 20

*S. typhimurium* Immune Modulator Strains Demonstrate Expression of Heterologous Proteins in Human Monocytes As described above, the hilA gene and flagellin genes fljB and fliC were deleted from the YS1646 strain of *S. typhimurium* with the asd gene deleted, generating the strains HilA/ASD and FLG/ASD, respectively. In addition, the FLG/ASD strain was further modified to express the listeriolysin O (LLO) protein lacking the signal sequence (cytoLLO), that accumulates in the cytoplasm of the *Salmonella* strain (FLG/ASD/cytoLLO). These strains were electroporated with a plasmid containing an expression cassette for the EF1a promoter and the murine cytokine IL-2 (muIL-2). In addition, the FLG/ASD strain was electroporated with an expression plasmid for IL-15δ, as a control for a non-cognate cytokine. Additional constructs were created using the CMV promoter.

To determine whether these strains containing expression plasmids could infect human monocytes and induce the production of murine IL-2, THP-1 human monocytic cells were plated at 50,000 cells/well in RPMI (Corning®)+10% Nu-Serum™ (Gibco™), one day prior to infection. The cells were infected at an MOI of 50 for one hour in RPMI, then washed 3 times with PBS, and resuspended in RPMI+100 μg/ml gentamicin (Sigma). Supernatants were collected 48 hours later from a 96-well plate, and assessed for the concentration of murine IL-2 by ELISA (R&D Systems). The concentration of IL-2 detected in the FLG/ASD-IL-150 control wells was found to be very low as expected, and likely reflective of some cross-reactivity to endogenous human IL-2 (6.52 μg/mL). In contrast, the FLG/ASD-IL-2 strain induced an average of 35.1 pg/ml IL-2, and an even higher concentration of IL-2, 59.8 μg/mL, was measured with the FLG/ASD/cytoLLO strain. The highest levels of IL-2, 103.4 μg/mL, were detected in the HilA/ASD-IL-2 strain. These data demonstrate the feasibility of expressing and secreting functional heterologous proteins, such as IL-2, from the *S. typhimurium* immune modulator platform strains.

Example 21

Cell Infection with ΔhilA Mutant Leads to Less Human Epithelial Cell Infection To demonstrate that hilA-deleted *S. typhimurium* strains are reduced in their ability to infect epithelial cells, HeLa cervical carcinoma cells were infected with the following *S. typhimurium* strains: YS1646, YS1646Δasd and YS1646Δasd/ΔhilA, containing plasmids encoding a functional asd gene for plasmid maintenance. $1\times10^6$ HeLa cells were placed in a 24-well dish with DMEM and 10% FBS. Cells were infected with log-phase cultures of *S. typhimurium* for 1 hour, then the cells were washed with PBS and the media was replaced with media containing 50 μg/mL gentamicin to kill extracellular bacteria. After 4 hours, the HeLa cell monolayers were washed with PBS and lysed with 1% Triton™ X-100 lysis buffer to release intracellular bacteria. The lysates were serially diluted and plated on LB agar plates to quantify the number of intracellular bacteria. The strain with the hilA deletion had a 90% reduction in recovered CFUs compared to the strains with a functional hilA gene, demonstrating that deletion of hilA significantly decreases *S. typhimurium* infection of epithelial-derived cells.

Example 22

Cell Infection with ΔhilA or ΔfljB/ΔfliC Mutants Leads to Less Pyroptosis in Human Macrophages To demonstrate that ΔhilA or ΔfljB/ΔfliC *S. typhimurium* strains are reduced in their ability cause cell death in macrophages, THP-1 human macrophage cells were infected with the following *S. typhimurium* strains: YS1646, YS1646Δasd, YS1646Δasd/ΔfljB/ΔfliC, and YS1646Δasd/ΔhilA, containing plasmids encoding a functional asd gene to ensure plasmid maintenance. $5\times10^4$ cells were placed in a 96-well dish with DMEM and 10% FBS. Cells were infected with washed log-phase cultures of *S. typhimurium* for 1 hour at an MOI of 100 CFUs per cell, then the cells were washed with PBS, and the media was replaced with media containing 50 μg/mL gentamicin to kill extracellular bacteria, and 50 ng/mL of interferon gamma. After 24 hours, the THP-1 cells were stained with CellTiter-Glo® reagent (Promega), and the percentage of viable cells was determined using a luminescent cell viability assay using a SpectraMax® plate reader to quantify the luminescence. The cells infected with the hilA deletion strain had approximately 72% viable cells, whereas the YS1646-infected cells had only 38% viability, demonstrating that deletion of hilA prevents cell death of human macrophages. Cells infected with the plasmid-containing strains YS1646Δasd and YS1646Δasd/ΔfljB/ΔfliC had 40% and 51% viability, respectively, indicating that the deletion of the flagellin genes also prevented cell death of human macrophages.

Example 23

Infection of Human Macrophages with an Immunostimulatory *S. typhimurium* Strain Containing a Plasmid Encoding IL-2 Expression Cassette Leads to Secretion of IL-2

Human THP-1 macrophages were infected with the following *S. typhimurium* strains: YS1646Δasd/ΔfljB/ΔfliC, YS1646Δasd-cytoLLO, and YS1646Δasd/ΔhilA, containing plasmids encoding an expression cassette for murine IL-2 under a eukaryotic promoter, and a functional asd gene to ensure plasmid maintenance. $5\times10^4$ cells were placed in a 96-well dish with DMEM and 10% FBS. Cells were infected with washed log-phase cultures of *S. typhimurium* for 1 hour at an MOI of 50 CFUs per cell, then the cells were washed with PBS, and the media was replaced with media containing 50 μg/mL gentamicin to kill extracellular bacteria. After 48 hours, the cellular supernatants were removed and tested for murine IL-2 using an R&D Systems™ Mouse IL-2 Quantikine® ELISA Kit. The remaining cells were stained with CellTiter-Glo® reagent (Promega), and the percentage of viable cells was determined using a luminescent cell viability assay using a SpectraMax® plate reader to quantify the luminescence. The YS1646Δasd/ΔfljB/ΔfliC, YS1646Δasd-cytoLLO, and YS1646Δasd/ΔhilA strains, containing plasmids encoding an expression cassette for murine IL-2, expressed 35 μg/mL, 60 μg/mL, and 103 μg/mL of IL-2, respectively.

Example 24

*S. typhimurium* Strains Expressing Murine IL-2 Demonstrate Potent Tumor Growth Inhibition In Vivo The immunostimulatory *S. typhimurium* strains containing deletions in hilA or the flagellin genes fljB and fliC in the YS1646 strain of *S. typhimurium* were combined with the asd gene deletion, to form the strains YS1646Δasd/ΔhilA and YS1646Δasd/ΔfljB/ΔfliC, respectively. These strains were electroporated with a plasmid containing an expression cassette for the EF1α promoter and the murine cytokine IL-2.

To show that the *S. typhimurium* strains containing the IL-2 expression plasmids induce anti-tumor efficacy, the Δasd/ΔhilA strains containing the muIL-2 plasmid, or the Δasd/ΔfljB/ΔfliC strains containing the muIL-2 plasmid, were compared to vehicle control. 6-8 week-old female C57BL/6 mice (5 mice per group) were inoculated S.C. in the right flank with MC38 cells ($5\times10^5$ cells in 100 μL PBS). Mice bearing established flank tumors were IV injected on day 8 with $5\times10^5$ CFUs of strain Δasd/ΔhilA (pATI-muIL-2), strain Δasd/ΔfljB/ΔfliC (pATI-muIL-2), or PBS vehicle control. Body weights and tumors were measured twice weekly. Tumor measurements were performed using electronic calipers (Fowler, Newton, Mass.). Tumor volume was calculated using the modified ellipsoid formula, ½(length× width$^2$). Mice were euthanized when tumor size reached >20% of body weight or became necrotic, as per IACUC regulations.

The experiment demonstrated that the Δasd/ΔhilA (pATI-muIL-2) strain elicited significant tumor control compared to PBS (P=0.003, day 21). These data were comparable to those observed with the Δasd/ΔfljB/ΔfliC (pATI-muIL-2) strain, which also demonstrated significant tumor growth inhibition compared to PBS (P=0.005, day 21). Thus, both strains demonstrate the ability of expressed IL-2 to potently inhibit tumor growth inhibition in a model of colorectal carcinoma.

Example 25 pagP$^-$, fljB$^-$/fliC$^-$, and pagP$^-$/fljB$^-$/fliC$^-$ Strains Demonstrate Significantly Higher Viability in Human Serum Compared to VNP20009 (YS1646)

As described herein, VNP20009 (YS1646) exhibits limited tumor colonization in humans after systemic administration. It is shown herein that VNP20009 is inactivated by complement factors in human blood. To demonstrate this, strains YS1646 and *E. coli* D10B were compared to exemplary immunostimulatory bacteria provided herein that contain additional mutations that alter the surface of the bacteria. These strains were YS1646(pagP$^-$), YS1646(fljB$^-$/fliC$^-$), and YS1646(pagP$^-$/fljB$^-$/fliC$^-$). These three strains, in addition to YS1646 and *E. coli* D10B cultures, were incubated with serum or heat-inactivated (HI) serum from either pooled mouse blood, or pooled healthy human donors (n=3), for 3 hours at 37° C. After incubation with serum, bacteria were serially diluted and plated on LB agar plates, and the colony forming units (CFUs) were measured.

In mouse serum, all strains remained 100% viable and were completely resistant to complement inactivation. In human serum, all strains were 100% viable in the heat-inactivated serum. The *E. coli* D10B strain was completely eliminated after 3 hours in whole human serum. The YS1646 strain exhibited only 6.37% of live colonies, demonstrating that tumor colonization of the YS1646 clinical strain was limited due to complement inactivation in human blood. For the YS1646(fljB$^-$/fliC$^-$) strain, 31.47% of live colonies remained, and for the YS1646(pagP$^-$) strain, 72.9% of live colonies remained, after incubation with human serum for 3 hours. The combined YS1646(pagP$^-$/fljB$^-$/fliC$^-$) strain was completely resistant to complement in human serum.

These data explain why VNP20009 had very low tumor colonization when systemically administered. It is shown herein that VNP20009 (YS1646) is highly sensitive to complement inactivation in human serum, but not in mouse serum. These data explain why limited tumor colonization was observed in humans, while mouse tumors were colonized at a high level. The fljB/fliC or pagP deletions, or the combination of these mutations, partially or completely rescues this phenotype. Thus, the enhanced stability observed in human serum with the fljB/fliC, pagP, or pagP/fljB/fliC deletion strains provides for increased human tumor colonization.

These data and other provided herein (see, e.g., Examples 7, 16 and 17, above) show that deletion of the flagella and/or pagP increases tumor colonization, improves tolerability, and increases the anti-tumor activity of the immunostimulatory bacteria. Example 16 demonstrates that LPS from immunostimulatory bacteria that are pagP$^-$ induced 22-fold less IL-6 than LPS from YS1646, and therefore pagP$^-$ bacteria are less inflammatory in human cells. Example 17 demonstrates that each and all of FLG, hilA and pagP deletion mutants are more attenuated than strain YS1646.

Immunostimulatory bacteria, such as *Salmonella* strains, including wild-type strains, that are one or both of flagellin$^-$ and pagP$^-$ exhibit properties that increase tumor/tumor microenvironment colonization, and that increase anti-tumor activity. Such strains can be used to deliver a therapeutic payload, such as an immunotherapeutic product and/or other anti-tumor product, and also can include modifications that improve therapeutic properties, such as deletion of hilA, and/or msbB, adenosine auxotrophy, and other properties as described elsewhere herein. The resulting strains are more effectively targeted to the tumor/tumor microenvironment, by virtue of the modifications that alter infectivity, toxicity to certain cells, and nutritional requirements, such as auxotrophy for purines, that are provided in the tumor environment.

Example 26 fljB$^-$/fliC$^-$ Immunostimulatory Bacterial Strain Demonstrates Tumor Myeloid Cell-Specific Colonization In Vivo The asd and flagellin (fljB/fliC) genes were deleted from strain YS1646, which is purI$^-$/msbB$^-$, using the lambda-derived Red recombination system as described previously (see, Datsenko and Wanner (2000) *Proc. Natl. Acad. Sci. U.S.A.* 97:6640-6645), to generate the strain YS1646ΔFLG/ΔASD. Strain YS1646ΔFLG/ΔASD was then transformed by electroporation with the bacterial plasmid pRPSM-mCherry, containing 1) a functional asd expression cassette to complement the chromosomal deletion of asd for in vivo plasmid maintenance, and 2) a constitutive mCherry expression cassette under control of the bacterial rpsM promoter (rpsM-mCherry). Bacterial colonies transformed with this plasmid were visibly red in color, due to expression of the mCherry red fluorescent protein. To evaluate tumor colonization, the transformed bacterial strain (YS1646ΔFLG/ΔASD (pRPSM-mCherry)) was tested in vivo in a murine colon carcinoma model. 6-8 week-old female C57BL/6 mice (3 mice per group) were inoculated subcutaneously in the right flank with MC38 cells ($5\times10^5$ cells in 100 μL PBS). Mice bearing large, established flank tumors were intravenously injected with $1\times10^6$ CFUs of strain YS1646ΔFLG/ΔASD (pRPSM-mCherry). Tumors were harvested 3 days later and dissociated into a single cell suspension (Miltenyi Biotec). Cells were stained with Zombie Aqua™ fixable viability dye (BioLegend), which penetrates dead, but not live, cells. The cells were incubated with the following antibodies: Brilliant Violet 510™ anti-mouse CD45 (clone 30-F11, BioLegend); Brilliant Violet 421™ anti-mouse CD8a (clone 53-6.7, BioLegend); PE anti-mouse CD3c (clone 145-2C11, BioLegend); FITC anti-mouse CD4 (clone RM4-5, BioLegend); PE/Cy7 anti-mouse/human CD11b (clone M1/70, BioLegend); Brilliant Violet 785™ anti-mouse Ly6C (clone HK1.4, BioLegend); Brilliant Violet 605™ anti-mouse Ly6G (clone 1A8, BioLegend); APC anti-mouse F4/80 (clone BM8, BioLegend); and PercP/Cy5.5 anti-mouse CD24 (clone M1/69, BioLegend). The cells were then sorted by flow cytometry (NovoCyte®) using the various surface markers and mCherry$^+$ (PE Texas Red), to determine/localize bacterial uptake by the harvested cells.

$CD45^-$ cells, which include stromal and tumor cells, demonstrated no detectable bacterial colonization, with 0.076% cells being positive for mCherry, compared to a background staining level of 0.067%. $CD45^+$ tumor-infiltrating myeloid cells were positive for mCherry, with 7.27% of monocytes, 3.33% of dendritic cells (DCs), and 8.96% of macrophages being positive for mCherry, indicating uptake of the YS1646ΔFLG/ΔASD (pRPSM-mCherry) bacteria. A control strain, containing intact flagella, was tested in parallel. Unlike the ΔFLG strain, the flagellin control strain infected CD45" cells, with 0.36% of CD45" cells being positive for mCherry, which was 5.37-fold greater than background staining (0.067%). The flagellin control strain also infected $CD45^+$ myeloid populations, with 5.71% of monocytes, 5.56% of DCs, and 9.52% of macrophages being positive for mCherry. These data indicate that flagella knockout strains accumulate in the myeloid cell populations of the tumor, but not in the tumor or stromal cells, whereas strains with intact flagella infect all cell types. Thus, flagella knockout strains demonstrate tumor myeloid-specific colonization in vivo.

Example 27

Flagella Knockout (ΔfljB/ΔfliC) and ΔpagP Strains Demonstrate Increased Tolerability and Decreased Immunogenicity In Vivo The pagP gene was deleted from the *S. typhimurium* strains YS1646ΔASD and YS1646ΔFLG/ΔASD, generating the strains YS1646ΔPagP/ΔASD and YS1646ΔPagP/ΔFLG/ΔASD, respectively. Strains YS1646ΔFLG/ΔASD, YS1646ΔPagP/ΔASD, and YS1646ΔPagP/ΔFLG/ΔASD were transformed by electroporation with plasmids encoding the asd gene, as well as a eukaryotic expression cassette encoding murine IL-2 (muIL-2). To test the tolerability of these strains in vivo, an $LD_{50}$ study was performed in 6-8 week old female BALB/c mice. The mice were intravenously injected with $3\times10^5$, $1\times10^6$, $3\times10^6$, $1\times10^7$, or $3\times10^7$ CFUs of strains YS1646, YS1646ΔFLG/ΔASD (muIL-2), YS1646ΔPagP/ΔASD (muIL-2), or YS1646ΔPagP/ΔFLG/ΔASD (muIL-2). The mice were then monitored for morbidity and mortality, and the $LD_{50}$ values were calculated. The results are shown in the table below.

| Bacterial Strain | $LD_{50}$ (CFUs) |
|---|---|
| YS1646 | $7.24 \times 10^6$ |
| YS1646ΔFLG/AASD (muIL-2) | $2.07 \times 10^7$ |
| YS1646ΔPagP/AASD (muIL-2) | $1.39 \times 10^7$ |
| YS1646ΔPagP/AFLG/AASD (muIL-2) | Not calculated |

The $LD_{50}$ values for the YS1646ΔFLG/ΔASD (muIL-2) and YS1646ΔPagP/ΔASD (muIL-2) strains were higher than the $LD_{50}$ value for the parental YS1646 strain, indicating that the tolerability of the $flagellin^-$ and pagP deletion mutants, expressing murine IL-2, was higher in vivo. The $LD_{50}$ for strain YS1646ΔPagP/ΔFLG/ΔASD (muIL-2) was not calculated, as no animals died during the duration of the study, but was greater than $6.2\times10^7$ CFUs, representing a near 10-fold improvement in the tolerability, compared to the parental YS1646 strain.

To compare the immunogenicity of the different bacterial strains, mice that survived the $3\times10^6$ CFU dose (N=5, except YS1646, where N=4) were bled at day 40 post intravenous dosing, and anti-*Salmonella* serum antibodies were titered. Sera from mice treated with the various mutant bacterial strains, and from control mice, were seeded in a 96-well PCR plate and serially diluted in PBS. Cultures of the *S. typhimurium* strains containing the pRPSM-mCherry plasmid were spun down and washed, then resuspended in flow-cytometry fixation buffer. For the assay, 25 μl of the $mCherry^+$ bacterial cultures, containing $1\times10^6$ CFUs, were added to the sera and incubated for 25 minutes at room temperature. Following incubation, the bacterial samples were centrifuged and washed twice with PBS by spinning them at 4000 RPM for 5 min, and then resuspended in PBS containing a secondary goat anti-mouse Fc Alexa Fluor® 488 antibody (1/400 dilution from stock), and incubated for 25 minutes at room temperature in the dark. The samples were then washed three times with PBS by spinning them at 4000 RPM for 5 min, resuspended in PBS, and analyzed by flow cytometry (NovoCyte®). The results showed that the mice injected with parental strain YS1646 had the highest anti-*Salmonella* serum antibody titers, with an average mean fluorescence intensity (MFI) of 29, 196±20,730. Sera from mice injected with strain YS1646ΔFLG/ΔASD (muIL-2) had an MFI of 7,941±9,290; sera from mice injected with strain YS1646ΔPagP/ΔASD (muIL-2) had an MFI of 3,454±3,860; and sera from mice injected with strain YS1646ΔPagP/ΔFLG/ΔASD (muIL-2), had the lowest serum antibody titers, with an MFI of 2,295±2,444. The data demonstrate that deletion of the genes encoding the flagella (fljB/fliC) or PagP result in strains with decreased immunogenicity, and that the combination of mutations (ΔPagP/ΔFLG), further decreases the immunogenicity, compared to the parental strain without the deletions.

Overall, the data demonstrate the improved tolerability and decreased immunogenicity of the ΔFLG and ΔPagP strains, with the ΔPagP/ΔFLG/ΔASD strain demonstrating the most favorable tolerability and lowest immunogenicity.

Since modifications will be apparent to those of skill in the art, it is intended that this invention be limited only by the scope of the appended claims.

What is claimed:

1. An immunostimulatory bacterium, comprising a plasmid encoding a therapeutic product under control of a eukaryotic promoter, wherein:
   - the therapeutic product is an anti-cancer product;
   - the bacterium comprises genome modifications whereby the bacterium is $csgD^-$;
   - the genome of the immunostimulatory bacterium is modified to eliminate flagella, whereby:
     - the ability of the immunostimulatory bacterium to infect epithelial cells is eliminated;
     - uptake by phagocytic cells is retained or increased; and
     - accumulation of the immunostimulatory bacterium in tumor-resident immune cells is increased compared to accumulation in tumor-resident immune cells in the absence of the genome modification(s); and
   - the wild-type bacterium comprises flagella.

2. The immunostimulatory bacterium of claim 1 that is a Gram-negative bacterium, wherein the genome of the immunostimulatory bacterium is modified, whereby lipopolysaccharide (LPS) of the bacterium is penta-acylated.

3. The immunostimulatory bacterium of claim 1 that is an adenosine auxotroph.

4. The immunostimulatory bacterium of claim 1 that comprises genome modifications, whereby the bacterium is $pagP^-$.

5. The immunostimulatory bacterium of claim 1 that comprises genome modifications, whereby the immunostimulatory bacterium is $pagP^-$and $msbB^-$.

6. The immunostimulatory bacterium of claim 1, wherein the anti-cancer therapeutic product is an immunostimulatory protein that confers or contributes to an anti-tumor immune response in the tumor microenvironment.

7. The immunostimulatory bacterium of claim 6, wherein the immunostimulatory protein that confers or contributes to an anti-tumor immune response in the tumor microenvironment is a cytokine.

8. The immunostimulatory bacterium of claim 6, wherein the immunostimulatory protein that confers or contributes to an anti-tumor immune response in the tumor microenvironment is a chemokine.

9. The immunostimulatory bacterium of claim 6, wherein the immunostimulatory protein that confers or contributes to an anti-tumor immune response in the tumor microenvironment is selected from among one or more of: IL-2, IL-7, IL-12p70 (IL-12p40+IL-12p35), IL-15, IL-36 gamma, IL-15/IL-15R alpha chain complex, IL-18, IL-21, IL-23, IL-2 that is modified so that it has attenuated binding or does not bind to IL-2Ra, CXCL9, CXCL10, CXCL11, interferon-α, interferon-β, interferon-γ, CCL3, CCL4, CCL5, proteins that are involved in or that effect or potentiate the recruitment or persistence of T cells, CD40, CD40 ligand (CD40L), CD28, OX40, OX40 ligand (OX40L), 4-1BB, 4-1BB ligand (4-1BBL), members of the B7-CD28 family, CD47 antagonists, TGF-beta polypeptide antagonists, and members of the tumor necrosis factor receptor (TNFR) superfamily.

10. The immunostimulatory bacterium of claim 1, wherein the therapeutic product is an antibody or antigen-binding fragment thereof.

11. The immunostimulatory bacterium of claim 10, wherein the antibody or antigen-binding fragment thereof is an antigen-binding fragment that is selected from among a Fab, Fab', F(ab')$_2$, single-chain Fv (scFv), Fv, dsFv, nanobody, diabody fragment, and a single-chain antibody.

12. The immunostimulatory bacterium of claim 10, wherein the antibody or antigen-binding fragment thereof is a humanized antibody or antigen-binding fragment thereof or is a human antibody or antigen-binding fragment thereof.

13. The immunostimulatory bacterium of claim 1, wherein nucleic acid encoding the therapeutic product is operatively linked for expression to a nucleic acid encoding a secretory signal, whereby, upon expression in a host, the therapeutic product is secreted.

14. The immunostimulatory bacterium of claim 1, wherein the bacterium is auxotrophic for adenosine, or for adenosine and adenine.

15. The immunostimulatory bacterium of claim 1 that is aspartate-semialdehyde dehydrogenase" (asd$^-$), wherein the bacterium is asd$^-$by virtue of disruption or deletion of all or a portion of the endogenous gene encoding aspartate-semialdehyde dehydrogenase (asd), whereby endogenous asd encoded in the bacterial genome is not expressed.

16. The immunostimulatory bacterium of claim 1, wherein the plasmid is present in fewer than 150 copies.

17. The immunostimulatory bacterium of claim 1, wherein the eukaryotic promoter is an RNA polymerase II promoter that is a viral promoter or a mammalian RNA polymerase II promoter.

18. The immunostimulatory bacterium of claim 17, wherein the promoter is active in hypoxic conditions, or in conditions where the pH is less than 7.

19. An immunostimulatory bacterium, comprising a plasmid encoding an anti-cancer therapeutic product, wherein:

the immunostimulatory bacterium is a *Salmonella* species;

the immunostimulatory bacterium is an adenosine auxotroph;

the immunostimulatory bacterium comprises genome modifications, whereby the bacterium is fliC$^-$/fljB$^-$and thereby lacks flagellin and flagella; and the anti-cancer therapeutic product encoded on the plasmid is expressed under the control of a eukaryotic promoter or eukaryotic regulatory sequences.

20. The immunostimulatory bacterium of claim 1, wherein the bacterium prior to the genome modifications is an attenuated bacterium.

21. The immunostimulatory bacterium claim 1, wherein the bacterium prior to the genome modifications is a wild-type strain.

22. The immunostimulatory bacterium of claim 1, wherein the bacterium prior to the genome modifications is a strain of *Salmonella*.

23. The immunostimulatory bacterium of claim 22, wherein the bacterium prior to the genome modifications is a *Salmonella typhimurium* strain.

24. The immunostimulatory bacterium of claim 23, wherein the bacterium prior to the genome modifications is a *Salmonella typhimurium* strain selected from among strains designated as YS1646 (ATCC #202165), RE88, SL7207, $\chi$ 8429, $\chi$ 8431, $\chi$ 8468, and wild-type strain ATCC 14028.

25. A pharmaceutical composition, comprising the immunostimulatory bacterium of claim 1 in a pharmaceutically acceptable vehicle.

26. An isolated eukaryotic cell, comprising the immunostimulatory bacterium of claim 1.

27. The cell of claim 26 that is an immune cell, a stem cell, a tumor cell, or a primary cell line.

28. The cell of claim 26 that is a hematopoietic cell.

29. The cell of claim 26 that is a T-cell.

30. An immunostimulatory bacterium, comprising genome modifications whereby the bacterium lacks flagella and is pagP$^-$/msbB$^-$, wherein the wild-type bacterium comprises flagella.

31. The immunostimulatory bacterium of claim 30, comprising a plasmid encoding a therapeutic product under control of a eukaryotic promoter.

32. The immunostimulatory bacterium of claim 30, comprising a plasmid encoding a cytokine.

33. The immunostimulatory bacterium of claim 32, wherein the cytokine is IL-15 or IL-15/IL-15R alpha chain complex.

34. An immunostimulatory bacterium, comprising a plasmid encoding a therapeutic product under control of a eukaryotic promoter, wherein:

the therapeutic product is an anti-cancer product that is an immunostimulatory protein that confers or contributes to an anti-tumor immune response in the tumor microenvironment;

the genome of the immunostimulatory bacterium is modified, whereby the bacterium is pagP$^-$/ImsbB$^-$, and lacks flagella; and the wild-type bacterium has flagella.

35. The immunostimulatory bacterium of claim 34 that is a *Salmonella* strain that comprises genome modifications whereby the bacterium is purI$^-$, asd$^-$, and csgD$^-$.

36. The immunostimulatory bacterium of claim 33, wherein the therapeutic product is selected from among one or more of: IL-2, IL-7, IL-12p70, IL-15, IL-36 gamma, IL-15/IL-15R alpha chain complex, IL-18, IL-21, IL-23, IL-2 that is modified so that it has attenuated binding or does not bind to IL-2Ra, CXCL9, CXCL10, CXCL11, interferon-$\alpha$, interferon-$\beta$, interferon-$\gamma$, CCL3, CCL4, CCL5, proteins that are involved in or that effect or potentiate the recruitment or persistence of T cells, CD40, CD40 ligand (CD40L), CD28, OX40, OX40 ligand (OX40L), 4-1BB, 4-1BB ligand (4-1BBL), members of the B7-CD28 family, CD47 antagonists, TGF-beta polypeptide antagonists, and members of the tumor necrosis factor receptor (TNFR) superfamily.

37. The immunostimulatory bacterium of claim 35, wherein the therapeutic product is selected from among one or more of: IL-2, IL-7, IL-12p70,IL-15, IL-36 gamma, IL-15/IL-15R alpha chain complex, IL-18, IL-21, IL-23, IL-2 that is modified so that it has attenuated binding or does not bind to IL-2Ra, CXCL9, CXCL10,CXCL11, interferon-$\alpha$, interferon-$\beta$, interferon-$\gamma$, CCL3, CCL4, CCL5, proteins that are involved in or that effect or potentiate the recruitment or persistence of T cells, CD40, CD40ligand (CD40L), CD28, OX40, OX40 ligand (OX40L), 4-1BB, 4-1BB ligand (4-1BBL), members of the B7-CD28 family, CD47 antagonists, TGF-beta polypeptide antagonists, and members of the tumor necrosis factor receptor (TNFR) superfamily.

* * * * *

SEQUENCE LISTING

<160> NUMBER OF SEQ ID NOS: 304

<210> SEQ ID NO 1
<211> LENGTH: 19
<212> TYPE: DNA
<213> ORGANISM: Homo sapiens
<220> FEATURE:
<223> OTHER INFORMATION: Human PD-L1 shRNA target 1

<400> SEQUENCE: 1

-continued

```
gtagagtatg gtagcaata                                                  19


<210> SEQ ID NO 2
<211> LENGTH: 19
<212> TYPE: DNA
<213> ORGANISM: Homo sapiens
<220> FEATURE:
<223> OTHER INFORMATION: Human PD-L1 shRNA target 2

<400> SEQUENCE: 2

gccgactaca agcgaatta                                                  19


<210> SEQ ID NO 3
<211> LENGTH: 19
<212> TYPE: DNA
<213> ORGANISM: Homo sapiens
<220> FEATURE:
<223> OTHER INFORMATION: Human PD-L1 shRNA target 3

<400> SEQUENCE: 3

gacaagcagt gaccatcaa                                                  19


<210> SEQ ID NO 4
<211> LENGTH: 19
<212> TYPE: DNA
<213> ORGANISM: Homo sapiens
<220> FEATURE:
<223> OTHER INFORMATION: Human PD-L1 shRNA target 4

<400> SEQUENCE: 4

gaatcaacac aacaactaa                                                  19


<210> SEQ ID NO 5
<211> LENGTH: 19
<212> TYPE: DNA
<213> ORGANISM: Homo sapiens
<220> FEATURE:
<223> OTHER INFORMATION: Human PD-L1 shRNA target 5

<400> SEQUENCE: 5

gcacatcctc caaatgaaa                                                  19


<210> SEQ ID NO 6
<211> LENGTH: 19
<212> TYPE: DNA
<213> ORGANISM: Homo sapiens
<220> FEATURE:
<223> OTHER INFORMATION: Human PD-L1 shRNA target 6

<400> SEQUENCE: 6

gtagcactga cattcatct                                                  19


<210> SEQ ID NO 7
<211> LENGTH: 19
<212> TYPE: DNA
<213> ORGANISM: Homo sapiens
<220> FEATURE:
<223> OTHER INFORMATION: Human CTNNB1 shRNA target 1

<400> SEQUENCE: 7

gacagactgc cttcaaatt                                                  19


<210> SEQ ID NO 8
<211> LENGTH: 19
<212> TYPE: DNA
<213> ORGANISM: Homo sapiens
```

```
<220> FEATURE:
<223> OTHER INFORMATION: Human CTNNB1 shRNA target 2

<400> SEQUENCE: 8

gcagctggaa ttctttcta                                              19


<210> SEQ ID NO 9
<211> LENGTH: 19
<212> TYPE: DNA
<213> ORGANISM: Homo sapiens
<220> FEATURE:
<223> OTHER INFORMATION: Human CTNNB1 shRNA target 3

<400> SEQUENCE: 9

gactaccagt tgtggttaa                                              19


<210> SEQ ID NO 10
<211> LENGTH: 19
<212> TYPE: DNA
<213> ORGANISM: Homo sapiens
<220> FEATURE:
<223> OTHER INFORMATION: Human CTNNB1 shRNA target 4

<400> SEQUENCE: 10

ggacacagca gcaatttgt                                              19


<210> SEQ ID NO 11
<211> LENGTH: 19
<212> TYPE: DNA
<213> ORGANISM: Homo sapiens
<220> FEATURE:
<223> OTHER INFORMATION: Human CTNNB1 shRNA target 5

<400> SEQUENCE: 11

ggatgttcac aaccgaatt                                              19


<210> SEQ ID NO 12
<211> LENGTH: 19
<212> TYPE: DNA
<213> ORGANISM: Homo sapiens
<220> FEATURE:
<223> OTHER INFORMATION: Human CTNNB1 shRNA target 6

<400> SEQUENCE: 12

gccacaagat tacaagaaa                                              19


<210> SEQ ID NO 13
<211> LENGTH: 19
<212> TYPE: DNA
<213> ORGANISM: Homo sapiens
<220> FEATURE:
<223> OTHER INFORMATION: Human SIRP-alpha shRNA target 1

<400> SEQUENCE: 13

gccaggtgag gaagttcta                                              19


<210> SEQ ID NO 14
<211> LENGTH: 19
<212> TYPE: DNA
<213> ORGANISM: Homo sapiens
<220> FEATURE:
<223> OTHER INFORMATION: Human SIRP-alpha shRNA target 2

<400> SEQUENCE: 14

gagctggctc ctggtgaat                                              19
```

<210> SEQ ID NO 15
<211> LENGTH: 19
<212> TYPE: DNA
<213> ORGANISM: Homo sapiens
<220> FEATURE:
<223> OTHER INFORMATION: Human SIRP-alpha shRNA target 3

<400> SEQUENCE: 15
gctgagaaca ctggatcta 19

<210> SEQ ID NO 16
<211> LENGTH: 19
<212> TYPE: DNA
<213> ORGANISM: Homo sapiens
<220> FEATURE:
<223> OTHER INFORMATION: Human SIRP-alpha shRNA target 4

<400> SEQUENCE: 16
gaagaatgcc agagaaata 19

<210> SEQ ID NO 17
<211> LENGTH: 19
<212> TYPE: DNA
<213> ORGANISM: Homo sapiens
<220> FEATURE:
<223> OTHER INFORMATION: Human SIRP-alpha shRNA target 5

<400> SEQUENCE: 17
ggacacaaat gatatcaca 19

<210> SEQ ID NO 18
<211> LENGTH: 19
<212> TYPE: DNA
<213> ORGANISM: Homo sapiens
<220> FEATURE:
<223> OTHER INFORMATION: Human SIRP-alpha shRNA target 6

<400> SEQUENCE: 18
ggagtatgcc agcattcag 19

<210> SEQ ID NO 19
<211> LENGTH: 19
<212> TYPE: DNA
<213> ORGANISM: Homo sapiens
<220> FEATURE:
<223> OTHER INFORMATION: Human Trex1 shRNA target 1

<400> SEQUENCE: 19
gcagcgcatg ggcgtcaat 19

<210> SEQ ID NO 20
<211> LENGTH: 19
<212> TYPE: DNA
<213> ORGANISM: Homo sapiens
<220> FEATURE:
<223> OTHER INFORMATION: Human Trex1 shRNA target 2

<400> SEQUENCE: 20
ggcccaagga agagctata 19

<210> SEQ ID NO 21
<211> LENGTH: 19
<212> TYPE: DNA
<213> ORGANISM: Homo sapiens
<220> FEATURE:
<223> OTHER INFORMATION: Human Trex1 shRNA target 3

<400> SEQUENCE: 21
gcaccatcag gcccatgta 19

<210> SEQ ID NO 22
<211> LENGTH: 19
<212> TYPE: DNA
<213> ORGANISM: Homo sapiens
<220> FEATURE:
<223> OTHER INFORMATION: Human Trex1 shRNA target 4

<400> SEQUENCE: 22
gccacaacca ggaacacta 19

<210> SEQ ID NO 23
<211> LENGTH: 19
<212> TYPE: DNA
<213> ORGANISM: Homo sapiens
<220> FEATURE:
<223> OTHER INFORMATION: Human Trex1 shRNA target 5

<400> SEQUENCE: 23
gcaggggtac caaggatct 19

<210> SEQ ID NO 24
<211> LENGTH: 19
<212> TYPE: DNA
<213> ORGANISM: Homo sapiens
<220> FEATURE:
<223> OTHER INFORMATION: Human Trex1 shRNA target 6

<400> SEQUENCE: 24
gccacactgt atggactat 19

<210> SEQ ID NO 25
<211> LENGTH: 19
<212> TYPE: DNA
<213> ORGANISM: Homo sapiens
<220> FEATURE:
<223> OTHER INFORMATION: Human VISTA shRNA target 1

<400> SEQUENCE: 25
gatgtgacct tctacaaga 19

<210> SEQ ID NO 26
<211> LENGTH: 19
<212> TYPE: DNA
<213> ORGANISM: Homo sapiens
<220> FEATURE:
<223> OTHER INFORMATION: Human VISTA shRNA target 2

<400> SEQUENCE: 26
gaccaccatg gcaacttct 19

<210> SEQ ID NO 27
<211> LENGTH: 19
<212> TYPE: DNA
<213> ORGANISM: Homo sapiens
<220> FEATURE:
<223> OTHER INFORMATION: Human VISTA shRNA target 3

<400> SEQUENCE: 27
ggtgcagaca ggcaaagat 19

<210> SEQ ID NO 28

<211> LENGTH: 19
<212> TYPE: DNA
<213> ORGANISM: Homo sapiens
<220> FEATURE:
<223> OTHER INFORMATION: Human VISTA shRNA target 4

<400> SEQUENCE: 28
gtgcctgcat cgtaggaat 19

<210> SEQ ID NO 29
<211> LENGTH: 19
<212> TYPE: DNA
<213> ORGANISM: Homo sapiens
<220> FEATURE:
<223> OTHER INFORMATION: Human VISTA shRNA target 5

<400> SEQUENCE: 29
gcaacattca agggattga 19

<210> SEQ ID NO 30
<211> LENGTH: 19
<212> TYPE: DNA
<213> ORGANISM: Homo sapiens
<220> FEATURE:
<223> OTHER INFORMATION: Human VISTA shRNA target 6

<400> SEQUENCE: 30
gtccctgact ctccaaact 19

<210> SEQ ID NO 31
<211> LENGTH: 870
<212> TYPE: DNA
<213> ORGANISM: Homo sapiens
<220> FEATURE:
<223> OTHER INFORMATION: programmed death-ligand 1 (PD-L1), isoform 1

<400> SEQUENCE: 31
atgaggatat ttgctgtctt tatattcatg acctactggc atttgctgaa cgcatttact 60
gtcacggttc ccaaggacct atatgtggta gagtatggta gcaatatgac aattgaatgc 120
aaattcccag tagaaaaaca attagacctg gctgcactaa ttgtctattg ggaaatggag 180
gataagaaca ttattcaatt tgtgcatgga gaggaagacc tgaaggttca gcatagtagc 240
tacagacaga gggcccggct gttgaaggac cagctctccc tgggaaatgc tgcacttcag 300
atcacagatg tgaaattgca ggatgcaggg gtgtaccgct gcatgatcag ctatggtggt 360
gccgactaca agcgaattac tgtgaaagtc aatgccccat acaacaaaat caaccaaaga 420
attttggttg tggatccagt cacctctgaa catgaactga catgtcaggc tgagggctac 480
cccaaggccg aagtcatctg gacaagcagt gaccatcaag tcctgagtgg taagaccacc 540
accaccaatt ccaagagaga ggagaagctt ttcaatgtga ccagcacact gagaatcaac 600
acaacaacta atgagatttt ctactgcact tttaggagat tagatcctga ggaaaaccat 660
acagctgaat tggtcatccc agaactacct ctggcacatc ctccaaatga aaggactcac 720
ttggtaattc tgggagccat cttattatgc cttggtgtag cactgacatt catcttccgt 780
ttaagaaaag ggagaatgat ggatgtgaaa aaatgtggca tccaagatac aaactcaaag 840
aagcaaagtg atacacattt ggaggagacg 870

<210> SEQ ID NO 32
<211> LENGTH: 2343
<212> TYPE: DNA
<213> ORGANISM: Homo sapiens
<220> FEATURE:
<223> OTHER INFORMATION: CTNNB1 (Beta-catenin), isoform 1

<400> SEQUENCE: 32
atggctactc aagctgattt gatggagttg gacatggcca tggaaccaga cagaaaagcg 60
gctgttagtc actggcagca acagtcttac ctggactctg gaatccattc tggtgccact 120
accacagctc cttctctgag tggtaaaggc aatcctgagg aagaggatgt ggatacctcc 180
caagtcctgt atgagtggga acagggattt tctcagtcct tcactcaaga acaagtagct 240
gatattgatg gacagtatgc aatgactcga gctcagaggg tacgagctgc tatgttccct 300
gagacattag atgagggcat gcagatccca tctacacagt ttgatgctgc tcatcccact 360
aatgtccagc gtttggctga accatcacag atgctgaaac atgcagttgt aaacttgatt 420
aactatcaag atgatgcaga acttgccaca cgtgcaatcc ctgaactgac aaaactgcta 480
aatgacgagg accaggtggt ggttaataag gctgcagtta tggtccatca gctttctaaa 540
aaggaagctt ccagacacgc tatcatgcgt tctcctcaga tggtgtctgc tattgtacgt 600
accatgcaga atacaaatga tgtagaaaca gctcgttgta ccgctgggac cttgcataac 660
ctttcccatc atcgtgaggg cttactggcc atctttaagt ctggaggcat tcctgccctg 720
gtgaaaatgc ttggttcacc agtggattct gtgttgtttt atgccattac aactctccac 780
aaccttttat tacatcaaga aggagctaaa atggcagtgc gtttagctgg tgggctgcag 840
aaaatggttg ccttgctcaa caaaacaaat gttaaattct tggctattac gacagactgc 900
cttcaaattt tagcttatgg caaccaagaa agcaagctca tcatactggc tagtggtgga 960
ccccaagctt tagtaaatat aatgaggacc tatacttacg aaaaactact gtggaccaca 1020
agcagagtgc tgaaggtgct atctgtctgc tctagtaata agccggctat tgtagaagct 1080
ggtggaatgc aagctttagg acttcacctg acagatccaa gtcaacgtct tgttcagaac 1140
tgtctttgga ctctcaggaa tctttcagat gctgcaacta aacaggaagg gatggaaggt 1200
ctccttggga ctcttgttca gcttctgggt tcagatgata taaatgtggt cacctgtgca 1260
gctggaattc tttctaacct cacttgcaat aattataaga acaagatgat ggtctgccaa 1320
gtgggtggta tagaggctct tgtgcgtact gtccttcggg ctggtgacag ggaagacatc 1380
actgagcctg ccatctgtgc tcttcgtcat ctgaccagcc gacaccaaga agcagagatg 1440
gcccagaatg cagttcgcct tcactatgga ctaccagttg tggttaagct cttacaccca 1500
ccatcccact ggcctctgat aaaggctact gttggattga ttcgaaatct tgccctttgt 1560
cccgcaaatc atgcaccttt gcgtgagcag ggtgccattc cacgactagt tcagttgctt 1620
gttcgtgcac atcaggatac ccagcgccgt acgtccatgg gtgggacaca gcagcaattt 1680
gtggaggggg tccgcatgga agaaatagtt gaaggttgta ccggagccct tcacatccta 1740
gctcgggatg ttcacaaccg aattgttatc agaggactaa ataccattcc attgtttgtg 1800
cagctgcttt attctcccat tgaaaacatc caaagagtag ctgcaggggt cctctgtgaa 1860
cttgctcagg acaaggaagc tgcagaagct attgaagctg agggagccac agctcctctg 1920
acagagttac ttcactctag gaatgaaggt gtggcgacat atgcagctgc tgttttgttc 1980
cgaatgtctg aggacaagcc acaagattac aagaaacggc tttcagttga gctgaccagc 2040
tctctcttca gaacagagcc aatggcttgg aatgagactg ctgatcttgg acttgatatt 2100
ggtgcccagg gagaacccct tggatatcgc caggatgatc ctagctatcg ttcttttcac 2160
tctggtggat atggccagga tgccttgggt atggacccca tgatggaaca tgagatgggt 2220

-continued

```
ggccaccacc ctggtgctga ctatccagtt gatgggctgc cagatctggg gcatgcccag   2280

gacctcatgg atgggctgcc tccaggtgac agcaatcagc tggcctggtt tgatactgac   2340

ctg                                                                 2343
```

<210> SEQ ID NO 33
<211> LENGTH: 1512
<212> TYPE: DNA
<213> ORGANISM: Homo sapiens
<220> FEATURE:
<223> OTHER INFORMATION: signal regulatory protein alpha (SIRP-alpha) isoform 1

<400> SEQUENCE: 33

```
atggagcccg ccggcccggc ccccggccgc ctcgggccgc tgctctgcct gctgctcgcc     60

gcgtcctgcg cctggtcagg agtggcgggt gaggaggagc tgcaggtgat tcagcctgac    120

aagtccgtgt tggttgcagc tggagagaca gccactctgc gctgcactgc gacctctctg    180

atccctgtgg ggcccatcca gtggttcaga ggagctggac caggccggga attaatctac    240

aatcaaaaag aaggccactt cccccgggta acaactgttt cagacctcac aaagagaaac    300

aacatggact ttccatccg catcggtaac atcaccccag cagatgccgg cacctactac    360

tgtgtgaagt tccggaaagg gagccccgat gacgtggagt ttaagtctgg agcaggcact    420

gagctgtctg tgcgcgccaa accctctgcc cccgtggtat cgggccctgc ggcgagggcc    480

acacctcagc acacagtgag cttcacctgc gagtcccacg gcttctcacc cagagacatc    540

accctgaaat ggttcaaaaa tgggaatgag ctctcagact tccagaccaa cgtggacccc    600

gtaggagaga gcgtgtccta cagcatccac agcacagcca aggtggtgct gacccgcgag    660

gacgttcact ctcaagtcat ctgcgaggtg gcccacgtca ccttgcaggg ggaccctctt    720

cgtgggactg ccaacttgtc tgagaccatc cgagttccac ccaccttgga ggttactcaa    780

cagcccgtga gggcagagaa ccaggtgaat gtcacctgcc aggtgaggaa gttctacccc    840

cagagactac agctgacctg gttggagaat ggaaacgtgt cccggacaga aacggcctca    900

accgttacag agaacaagga tggtacctac aactggatga gctggctcct ggtgaatgta    960

tctgcccaca gggatgatgt gaagctcacc tgccaggtgg agcatgacgg gcagccagcg   1020

gtcagcaaaa gccatgacct gaaggtctca gcccacccga aggagcaggg ctcaaatacc   1080

gccgctgaga acactggatc taatgaacgg aacatctata ttgtggtggg tgtggtgtgc   1140

accttgctgg tggccctact gatggcggcc ctctacctcg tccgaatcag acagaagaaa   1200

gcccagggct ccacttcttc tacaaggttg catgagcccg agaagaatgc cagagaaata   1260

acacaggaca caaatgatat cacatatgca gacctgaacc tgcccaaggg gaagaagcct   1320

gctccccagg ctgcggagcc caacaaccac acggagtatg ccagcattca gaccagcccg   1380

cagcccgcgt cggaggacac cctcacctat gctgacctgg acatggtcca cctcaaccgg   1440

acccccaagc agccggcccc caagcctgag ccgtccttct cagagtacgc cagcgtccag   1500

gtcccgagga ag                                                       1512
```

<210> SEQ ID NO 34
<211> LENGTH: 1108
<212> TYPE: DNA
<213> ORGANISM: Homo sapiens
<220> FEATURE:
<223> OTHER INFORMATION: TREX1 isoform 1

<400> SEQUENCE: 34

-continued

```
aatgggccct ggagctcgca gacagggcag gattgtgcag ggaaggcctg agatgtgctt     60

ctgcccaccc cctaccccac tccctcccct tcggatctta acactgggca ctcacacacc    120

caccccatgc tcctctccag gctcagcagc aggtacgtac ccaaccatgg gctcgcaggc    180

cctgcccccg gggcccatgc agaccctcat ctttttcgac atggaggcca ctggcttgcc    240

cttctcccag cccaaggtca cggagctgtg cctgctggct gtccacagat gtgccctgga    300

gagccccccc acctctcagg ggccacctcc cacagttcct ccaccaccgc gtgtggtaga    360

caagctctcc ctgtgtgtgg ctccggggaa ggcctgcagc cctgcagcca gcgagatcac    420

aggtctgagc acagctgtgc tggcagcgca tgggcgtcaa tgttttgatg acaacctggc    480

caacctgctc ctagccttcc tgcggcgcca gccacagccc tggtgcctgg tggcacacaa    540

tggtgaccgc tacgacttcc ccctgctcca agcagagctg gctatgctgg gcctcaccag    600

tgctctggat ggtgccttct gtgtggatag catcactgcg ctgaaggccc tggagcgagc    660

aagcagcccc tcagaacacg gcccaaggaa gagctatagc ctaggcagca tctacactcg    720

cctgtatggg cagtcccctc cagactcgca cacggctgag ggtgatgtcc tggccctgct    780

cagcatctgt cagtggagac cacaggccct gctgcggtgg gtggatgctc acgccaggcc    840

tttcggcacc atcaggccca tgtatggggt cacagcctct gctaggacca agccaagacc    900

atctgctgtc acaaccactg cacacctggc cacaaccagg aacactagtc ccagccttgg    960

agagagcagg ggtaccaagg atcttcctcc agtgaaggac cctggagccc tatccaggga   1020

ggggctgctg gccccactgg gtctgctggc catcctgacc ttggcagtag ccacactgta   1080

tggactatcc ctggccacac ctggggag                                      1108
```

<210> SEQ ID NO 35
<211> LENGTH: 933
<212> TYPE: DNA
<213> ORGANISM: Homo sapiens
<220> FEATURE:
<223> OTHER INFORMATION: V-domain Ig suppressor of T cell activation (VISTA)

<400> SEQUENCE: 35

```
atgggcgtcc ccacggccct ggaggccggc agctggcgct ggggatccct gctcttcgct     60

ctcttcctgg ctgcgtccct aggtccggtg gcagccttca aggtcgccac gccgtattcc    120

ctgtatgtct gtcccgaggg gcagaacgtc accctcacct gcaggctctt gggccctgtg    180

gacaaagggc acgatgtgac cttctacaag acgtggtacc gcagctcgag gggcgaggtg    240

cagacctgct cagagcgccg gcccatccgc aacctcacgt tccaggacct tcacctgcac    300

catggaggcc accaggctgc caacaccagc cacgacctgg ctcagcgcca cgggctggag    360

tcggcctccg accaccatgg caacttctcc atcaccatgc gcaacctgac cctgctggat    420

agcggcctct actgctgcct ggtggtggag atcaggcacc accactcgga gcacagggtc    480

catggtgcca tggagctgca ggtgcagaca ggcaaagatg caccatccaa ctgtgtggtg    540

tacccatcct cctcccagga tagtgaaaac atcacggctg cagccctggc tacgggtgcc    600

tgcatcgtag gaatcctctg cctccccctc atcctgctcc tggtctacaa gcaaaggcag    660

gcagcctcca accgccgtgc ccaggagctg gtgcggatgg acagcaacat tcaagggatt    720

gaaaaccccg gctttgaagc ctcaccacct gcccagggga tacccgaggc caaagtcagg    780

cacccccctgt cctatgtggc ccagcggcag ccttctgagt ctgggcggca tctgctttcg    840

gagcccagca ccccccctgtc tcctccaggc cccggagacg tcttcttccc atccctggac    900
```

cctgtccctg actctccaaa ctttgaggtc atc 933

<210> SEQ ID NO 36
<211> LENGTH: 45
<212> TYPE: DNA
<213> ORGANISM: Artificial Sequence
<220> FEATURE:
<223> OTHER INFORMATION: shRNA-encoding sequence for huPD-L1

<400> SEQUENCE: 36
gtagagtatg gtagcaatat ctagagtatt gctaccatac tctac 45

<210> SEQ ID NO 37
<211> LENGTH: 45
<212> TYPE: DNA
<213> ORGANISM: Artificial Sequence
<220> FEATURE:
<223> OTHER INFORMATION: shRNA-encoding sequence for huCTNNB1

<400> SEQUENCE: 37
gacagactgc cttcaaattt ctagagaatt tgaaggcagt ctgtc 45

<210> SEQ ID NO 38
<211> LENGTH: 45
<212> TYPE: DNA
<213> ORGANISM: Artificial Sequence
<220> FEATURE:
<223> OTHER INFORMATION: shRNA-encoding sequence for huSIRPalpha

<400> SEQUENCE: 38
gccaggtgag gaagttctat ctagagtaga acttcctcac ctggc 45

<210> SEQ ID NO 39
<211> LENGTH: 45
<212> TYPE: DNA
<213> ORGANISM: Artificial Sequence
<220> FEATURE:
<223> OTHER INFORMATION: shRNA-encoding sequence for huTREX1

<400> SEQUENCE: 39
gcagcgcatg ggcgtcaatt ctagagattg acgcccatgc gctgc 45

<210> SEQ ID NO 40
<211> LENGTH: 45
<212> TYPE: DNA
<213> ORGANISM: Artificial Sequence
<220> FEATURE:
<223> OTHER INFORMATION: shRNA-encoding sequence for huVISTA

<400> SEQUENCE: 40
gaccaccatg gcaacttctt ctagagagaa gttgccatgg tggtc 45

<210> SEQ ID NO 41
<211> LENGTH: 3220
<212> TYPE: DNA
<213> ORGANISM: Artificial Sequence
<220> FEATURE:
<223> OTHER INFORMATION: pEQU6 vector

<400> SEQUENCE: 41
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240

-continued

```
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga ctggatccaa ggtcgggcag gaagagggcc    720
tatttcccat gattccttca tatttgcata tacgatacaa ggctgttaga gagataatta    780
gaattaattt gactgtaaac acaaagatat tagtacaaaa tacgtgacgt agaaagtaat    840
aatttcttgg gtagtttgca gttttaaaat tatgttttaa aatggactat catatgctta    900
ccgtaacttg aaagtatttc gatttcttgg ctttatatat cttgtggaaa ggacgaaact    960
agtttttct cgagtagcta gagaattcat ggtaatagcg atgactaata cgtagatgta   1020
ctgccaagta ggaaagtccc ataaggtcat gtactgggca taatgccagg cgggccattt   1080
accgtcattg acgtcaatag ggggcgtact tggcatatga tacacttgat gtactgccaa   1140
gtgggcagtt taccgtaaat agtccaccca ttgacgtcaa tggaaagtcc ctattggcgt   1200
tactatggga acatacgtca ttattgacgt caatgggcgg gggtcgttgg gcggtcagcc   1260
aggcgggcca tttaccgtaa gttatgtaac gcggaactcc atatatgggc tatgaactaa   1320
tgaccccgta attgattact attaataact agacccagct ttcttgtaca aagttggcat   1380
tataagaaag cattgcttat caatttgttg caacgaacag gtcactatca gtcaaaataa   1440
aatcattatt tgccatccag ctgatatccc ctatagtgag tcgtattaca tggtcatagc   1500
tgtttcctgg cagctctggc ccgtgtctca aaatctctga tgttacattg cacaagataa   1560
aaatatatca tcatgaacaa taaaactgtc tgcttacata aacagtaata caaggggtgt   1620
tatgagccat attcaacggg aaacgtcgag gccgcgatta aattccaaca tggatgctga   1680
tttatatggg tataaatggg ctcgcgataa tgtcgggcaa tcaggtgcga caatctatcg   1740
cttgtatggg aagcccgatg cgccagagtt gtttctgaaa catggcaaag gtagcgttgc   1800
caatgatgtt acagatgaga tggtcagact aaactggctg acggaattta tgcctcttcc   1860
gaccatcaag cattttatcc gtactcctga tgatgcatgg ttactcacca ctgcgatccc   1920
cggaaaaaca gcattccagg tattagaaga atatcctgat tcaggtgaaa atattgttga   1980
tgcgctggca gtgttcctgc gccggttgca ttcgattcct gtttgtaatt gtccttttaa   2040
cagcgatcgc gtatttcgtc tcgctcaggc gcaatcacga atgaataacg gtttggttga   2100
tgcgagtgat tttgatgacg agcgtaatgg ctggcctgtt gaacaagtct ggaaagaaat   2160
gcataaactt ttgccattct caccggattc agtcgtcact catggtgatt tctcacttga   2220
taaccttatt tttgacgagg ggaaattaat aggttgtatt gatgttggac gagtcggaat   2280
cgcagaccga taccaggatc ttgccatcct atggaactgc ctcggtgagt tttctccttc   2340
attacagaaa cggctttttc aaaaatatgg tattgataat cctgatatga ataaattgca   2400
gtttcatttg atgctcgatg agtttttcta atcagaattg gttaattggt tgtaacactg   2460
gcagagcatt acgctgactt gacgggacgg cgcaagctca tgaccaaaat cccttaacgt   2520
gagttacgcg tcgttccact gagcgtcaga ccccgtagaa aagatcaaag gatcttcttg   2580
```

-continued agatcctttt tttctgcgcg taatctgctg cttgcaaaca aaaaaaccac cgctaccagc 2640
ggtggtttgt ttgccggatc aagagctacc aactcttttt ccgaaggtaa ctggcttcag 2700
cagagcgcag ataccaaata ctgtccttct agtgtagccg tagttaggcc accacttcaa 2760
gaactctgta gcaccgccta catacctcgc tctgctaatc ctgttaccag tggctgctgc 2820
cagtggcgat aagtcgtgtc ttaccgggtt ggactcaaga cgatagttac cggataaggc 2880
gcagcggtcg ggctgaacgg ggggttcgtg cacacagccc agcttggagc gaacgaccta 2940
caccgaactg agatacctac agcgtgagca ttgagaaagc gccacgcttc ccgaagggag 3000
aaaggcggac aggtatccgg taagcggcag ggtcggaaca ggagagcgca cgagggagct 3060
tccaggggga aacgcctggt atctttatag tcctgtcggg tttcgccacc tctgacttga 3120
gcgtcgattt ttgtgatgct cgtcaggggg gcggagccta tggaaaaacg ccagcaacgc 3180
ggccttttta cggttcctgg ccttttgctg gccttttgct 3220

<210> SEQ ID NO 42
<211> LENGTH: 3802
<212> TYPE: DNA
<213> ORGANISM: Artificial Sequence
<220> FEATURE:
<223> OTHER INFORMATION: pEQU6-H1 Vector

<400> SEQUENCE: 42
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga gaattggtac catatttgca tgtcgctatg 720
tgttctggga aatcaccata aacgtgaaat gtctttggat ttgggaatct tataagttct 780
gtatgagacc actccctagg tttttgtcga cagatctggc gcgccatagt ggccagcggc 840
cgcaggtaag ccagcccagg cctcgccctc cagctcaagg cgggacaggt gccctagagt 900
agcctgcatc cagggacagg ccccagccgg gtgctgacac gtccacctcc atctcttcct 960
caggtctgcc cgggtggcat ccctgtgacc cctccccagt gcctctcctg gccctggaag 1020
ttgccactcc agtgcccacc agccttgtcc taataaaatt aagttgcatc attttgtctg 1080
actaggtgtc cttctataat attatggggt ggaggggggt ggtatggagc aaggggccca 1140
agttaacttg tttattgcag cttataatgg ttacaaataa agcaatagca tcacaaattt 1200
cacaaataaa gcattttttt cactgcattc tagttgtggt ttgtccaaac tcatcaatgt 1260
atcttatcat gtctggatcc aaggtcgggc aggaagaggg cctatttccc atgattcctt 1320
catatttgca tatacgatac aaggctgtta gagagataat tagaattaat ttgactgtaa 1380
acacaaagat attagtacaa aatacgtgac gtagaaagta ataatttctt gggtagtttg 1440

-continued cagttttaaa attatgtttt aaaatggact atcatatgct taccgtaact tgaaagtatt 1500
tcgatttctt ggctttatat atcttgtgga aaggacgaaa ctagtttttt ctcgagtagc 1560
tagagaattc atggtaatag cgatgactaa tacgtagatg tactgccaag taggaaagtc 1620
ccataaggtc atgtactggg cataatgcca ggcgggccat ttaccgtcat tgacgtcaat 1680
agggggcgta cttggcatat gatacacttg atgtactgcc aagtgggcag tttaccgtaa 1740
atagtccacc cattgacgtc aatggaaagt ccctattggc gttactatgg gaacatacgt 1800
cattattgac gtcaatgggc gggggtcgtt gggcggtcag ccaggcgggc catttaccgt 1860
aagttatgta acgcggaact ccatatatgg gctatgaact aatgaccccg taattgatta 1920
ctattaataa ctagacccag ctttcttgta caaagttggc attataagaa agcattgctt 1980
atcaatttgt tgcaacgaac aggtcactat cagtcaaaat aaaatcatta tttgccatcc 2040
agctgatatc ccctatagtg agtcgtatta catggtcata gctgtttcct ggcagctctg 2100
gcccgtgtct caaaatctct gatgttacat tgcacaagat aaaaatatat catcatgaac 2160
aataaaactg tctgcttaca taaacagtaa tacaaggggt gttatgagcc atattcaacg 2220
ggaaacgtcg aggccgcgat taaattccaa catggatgct gatttatatg ggtataaatg 2280
ggctcgcgat aatgtcgggc aatcaggtgc gacaatctat cgcttgtatg ggaagcccga 2340
tgcgccagag ttgtttctga aacatggcaa aggtagcgtt gccaatgatg ttacagatga 2400
gatggtcaga ctaaactggc tgacggaatt tatgcctctt ccgaccatca agcattttat 2460
ccgtactcct gatgatgcat ggttactcac cactgcgatc cccggaaaaa cagcattcca 2520
ggtattagaa gaatatcctg attcaggtga aaatattgtt gatgcgctgg cagtgttcct 2580
gcgccggttg cattcgattc ctgtttgtaa ttgtcctttt aacagcgatc gcgtatttcg 2640
tctcgctcag gcgcaatcac gaatgaataa cggtttggtt gatgcgagtg attttgatga 2700
cgagcgtaat ggctggcctg ttgaacaagt ctggaaagaa atgcataaac ttttgccatt 2760
ctcaccggat tcagtcgtca ctcatggtga tttctcactt gataacctta tttttgacga 2820
ggggaaatta ataggttgta ttgatgttgg acgagtcgga atcgcagacc gataccagga 2880
tcttgccatc ctatggaact gcctcggtga gttttctcct tcattacaga aacggctttt 2940
tcaaaaatat ggtattgata atcctgatat gaataaattg cagtttcatt tgatgctcga 3000
tgagtttttc taatcagaat tggttaattg gttgtaacac tggcagagca ttacgctgac 3060
ttgacgggac ggcgcaagct catgaccaaa atcccttaac gtgagttacg cgtcgttcca 3120
ctgagcgtca gaccccgtag aaaagatcaa aggatcttct tgagatcctt tttttctgcg 3180
cgtaatctgc tgcttgcaaa caaaaaaacc accgctacca gcggtggttt gtttgccgga 3240
tcaagagcta ccaactcttt ttccgaaggt aactggcttc agcagagcgc agataccaaa 3300
tactgtcctt ctagtgtagc cgtagttagg ccaccacttc aagaactctg tagcaccgcc 3360
tacatacctc gctctgctaa tcctgttacc agtggctgct gccagtggcg ataagtcgtg 3420
tcttaccggg ttggactcaa gacgatagtt accggataag gcgcagcggt cgggctgaac 3480
ggggggttcg tgcacacagc ccagcttgga gcgaacgacc tacaccgaac tgagatacct 3540
acagcgtgag cattgagaaa gcgccacgct tcccgaaggg agaaaggcgg acaggtatcc 3600
ggtaagcggc agggtcggaa caggagagcg cacgagggag cttccagggg gaaacgcctg 3660
gtatctttat agtcctgtcg ggtttcgcca cctctgactt gagcgtcgat ttttgtgatg 3720
ctcgtcaggg gggcggagcc tatggaaaaa cgccagcaac gcggcctttt tacggttcct 3780

```
ggccttttgc tggccttttg ct                                           3802


<210> SEQ ID NO 43
<211> LENGTH: 3263
<212> TYPE: DNA
<213> ORGANISM: Artificial Sequence
<220> FEATURE:
<223> OTHER INFORMATION: pEQU6-shPDL1-shRNA Vector

<400> SEQUENCE: 43

ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccca aataatgatt ttattttgac tgatagtgac    600

ctgttcgttg caacaaattg atgagcaatg cttttttata atgccaactt tgtacaaaaa    660

agcaggcttt aaaggaacca attcagtcga ctggatccaa ggtcgggcag gaagagggcc    720

tatttcccat gattccttca tatttgcata tacgatacaa ggctgttaga gagataatta    780

gaattaattt gactgtaaac acaaagatat tagtacaaaa tacgtgacgt agaaagtaat    840

aatttcttgg gtagtttgca gttttaaaat tatgttttaa aatggactat catatgctta    900

ccgtaacttg aaagtatttc gatttcttgg ctttatatat cttgtggaaa ggacgaaact    960

aggtagagta tggtagcaat atctagagta ttgctaccat actctacttt tttcgagtag   1020

ctagagaatt catggtaata gcgatgacta atacgtagat gtactgccaa gtaggaaagt   1080

cccataaggt catgtactgg gcataatgcc aggcgggcca tttaccgtca ttgacgtcaa   1140

tagggggcgt acttggcata tgatacactt gatgtactgc caagtgggca gtttaccgta   1200

aatagtccac ccattgacgt caatggaaag tccctattgg cgttactatg ggaacatacg   1260

tcattattga cgtcaatggg cgggggtcgt tgggcggtca gccaggcggg ccatttaccg   1320

taagttatgt aacgcggaac tccatatatg ggctatgaac taatgacccc gtaattgatt   1380

actattaata actagaccca gctttcttgt acaaagttgg cattataaga aagcattgct   1440

tatcaatttg ttgcaacgaa caggtcacta tcagtcaaaa taaaatcatt atttgccatc   1500

cagctgatat cccctatagt gagtcgtatt acatggtcat agctgtttcc tggcagctct   1560

ggcccgtgtc tcaaaatctc tgatgttaca ttgcacaaga taaaaatata tcatcatgaa   1620

caataaaact gtctgcttac ataaacagta atacaagggg tgttatgagc catattcaac   1680

gggaaacgtc gaggccgcga ttaaattcca acatggatgc tgatttatat gggtataaat   1740

gggctcgcga taatgtcggg caatcaggtg cgacaatcta tcgcttgtat gggaagcccg   1800

atgcgccaga gttgtttctg aaacatggca aaggtagcgt tgccaatgat gttacagatg   1860

agatggtcag actaaactgg ctgacggaat ttatgcctct tccgaccatc aagcatttta   1920

tccgtactcc tgatgatgca tggttactca ccactgcgat ccccggaaaa acagcattcc   1980

aggtattaga agaatatcct gattcaggtg aaaatattgt tgatgcgctg gcagtgttcc   2040
```

tgcgccggtt gcattcgatt cctgtttgta attgtccttt taacagcgat cgcgtatttc 2100
gtctcgctca ggcgcaatca cgaatgaata acggtttggt tgatgcgagt gattttgatg 2160
acgagcgtaa tggctggcct gttgaacaag tctggaaaga aatgcataaa cttttgccat 2220
tctcaccgga ttcagtcgtc actcatggtg atttctcact tgataacctt atttttgacg 2280
aggggaaatt aataggttgt attgatgttg gacgagtcgg aatcgcagac cgataccagg 2340
atcttgccat cctatggaac tgcctcggtg agttttctcc ttcattacag aaacggcttt 2400
ttcaaaaata tggtattgat aatcctgata tgaataaatt gcagtttcat ttgatgctcg 2460
atgagttttt ctaatcagaa ttggttaatt ggttgtaaca ctggcagagc attacgctga 2520
cttgacggga cggcgcaagc tcatgaccaa aatcccttaa cgtgagttac gcgtcgttcc 2580
actgagcgtc agaccccgta gaaaagatca aaggatcttc ttgagatcct ttttttctgc 2640
gcgtaatctg ctgcttgcaa acaaaaaaac caccgctacc agcggtggtt tgtttgccgg 2700
atcaagagct accaactctt tttccgaagg taactggctt cagcagagcg cagataccaa 2760
atactgtcct tctagtgtag ccgtagttag gccaccactt caagaactct gtagcaccgc 2820
ctacatacct cgctctgcta atcctgttac cagtggctgc tgccagtggc gataagtcgt 2880
gtcttaccgg gttggactca agacgatagt taccggataa ggcgcagcgg tcgggctgaa 2940
cggggggttc gtgcacacag cccagcttgg agcgaacgac ctacaccgaa ctgagatacc 3000
tacagcgtga gcattgagaa agcgccacgc ttcccgaagg gagaaaggcg gacaggtatc 3060
cggtaagcgg cagggtcgga acaggagagc gcacgaggga gcttccaggg ggaaacgcct 3120
ggtatcttta tagtcctgtc gggtttcgcc acctctgact tgagcgtcga tttttgtgat 3180
gctcgtcagg ggggcggagc ctatggaaaa acgccagcaa cgcggccttt ttacggttcc 3240
tggccttttg ctggcctttt gct 3263

<210> SEQ ID NO 44
<211> LENGTH: 3888
<212> TYPE: DNA
<213> ORGANISM: Artificial Sequence
<220> FEATURE:
<223> OTHER INFORMATION: pEQU6-shPDL1-H1-shCTNNB1 Vector

<400> SEQUENCE: 44
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga gaattggtac catatttgca tgtcgctatg 720
tgttctggga aatcaccata aacgtgaaat gtctttggat ttgggaatct tataagttct 780

-continued

```
gtatgagacc actccctagg acagactgcc ttcaaatttc tagagaattt gaaggcagtc    840
tgtctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gcccgggtgg   1020
catccctgtg accccctccc agtgcctctc ctggccctgg aagttgccac tccagtgccc   1080
accagccttg tcctaataaa attaagttgc atcattttgt ctgactaggt gtccttctat   1140
aatattatgg ggtggagggg ggtggtatgg agcaaggggc ccaagttaac ttgtttattg   1200
cagcttataa tggttacaaa taaagcaata gcatcacaaa tttcacaaat aaagcatttt   1260
tttcactgca ttctagttgt ggtttgtcca aactcatcaa tgtatcttat catgtctgga   1320
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggta gagtatggta gcaatatcta gagtattgct   1620
accatactct actttttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
```

-continued

```
cttaacgtga gttacgcgtc gttccactga gcgtcagacc ccgtagaaaa gatcaaagga   3240

tcttcttgag atcctttttt tctgcgcgta atctgctgct tgcaaacaaa aaaaccaccg   3300

ctaccagcgg tggtttgttt gccggatcaa gagctaccaa ctctttttcc gaaggtaact   3360

ggcttcagca gagcgcagat accaaatact gtccttctag tgtagccgta gttaggccac   3420

cacttcaaga actctgtagc accgcctaca tacctcgctc tgctaatcct gttaccagtg   3480

gctgctgcca gtggcgataa gtcgtgtctt accgggttgg actcaagacg atagttaccg   3540

gataaggcgc agcggtcggg ctgaacgggg ggttcgtgca cacagcccag cttggagcga   3600

acgacctaca ccgaactgag atacctacag cgtgagcatt gagaaagcgc cacgcttccc   3660

gaagggagaa aggcggacag gtatccggta agcggcaggg tcggaacagg agagcgcacg   3720

agggagcttc cagggggaaa cgcctggtat ctttatagtc ctgtcgggtt tcgccacctc   3780

tgacttgagc gtcgattttt gtgatgctcg tcaggggggc ggagcctatg gaaaaacgcc   3840

agcaacgcgg cctttttacg gttcctggcc ttttgctggc cttttgct                3888
```

<210> SEQ ID NO 45
<211> LENGTH: 3888
<212> TYPE: DNA
<213> ORGANISM: Artificial Sequence
<220> FEATURE:
<223> OTHER INFORMATION: pEQU6-shPDL1-H1-shSIRPalpha Vector

<400> SEQUENCE: 45

```
ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccca aataatgatt ttattttgac tgatagtgac    600

ctgttcgttg caacaaattg atgagcaatg cttttttata atgccaactt tgtacaaaaa    660

agcaggcttt aaaggaacca attcagtcga gaattggtac catatttgca tgtcgctatg    720

tgttctggga aatcaccata aacgtgaaat gtctttggat ttgggaatct tataagttct    780

gtatgagacc actccctagg ccaggtgagg aagttctatc tagagtagaa cttcctcacc    840

tggctttttt cgacagatct ggcgcgccat agtggccagc ggccgcaggt aagccagccc    900

aggcctcgcc ctccagctca aggcgggaca ggtgccctag agtagcctgc atccagggac    960

aggccccagc cgggtgctga cacgtccacc tccatctctt cctcaggtct gcccgggtgg   1020

catccctgtg acccctcccc agtgcctctc ctggccctgg aagttgccac tccagtgccc   1080

accagccttg tcctaataaa attaagttgc atcattttgt ctgactaggt gtccttctat   1140

aatattatgg ggtggagggg ggtggtatgg agcaaggggc ccaagttaac ttgtttattg   1200

cagcttataa tggttacaaa taaagcaata gcatcacaaa tttcacaaat aaagcatttt   1260

tttcactgca ttctagttgt ggtttgtcca aactcatcaa tgtatcttat catgtctgga   1320
```

-continued

```
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggta gagtatggta gcaatatcta gagtattgct   1620
accatactct actttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctctttttcc gaaggtaact   3360
ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
```

agggagcttc caggggggaaa cgcctggtat ctttatagtc ctgtcgggtt tcgccacctc 3780
tgacttgagc gtcgattttt gtgatgctcg tcaggggggc ggagcctatg gaaaaacgcc 3840
agcaacgcgg cctttttacg gttcctggcc ttttgctggc cttttgct 3888

<210> SEQ ID NO 46
<211> LENGTH: 3888
<212> TYPE: DNA
<213> ORGANISM: Artificial Sequence
<220> FEATURE:
<223> OTHER INFORMATION: pEQU6-shPDL1-H1-shTREX1

<400> SEQUENCE: 46
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga gaattggtac catatttgca tgtcgctatg 720
tgttctggga aatcaccata aacgtgaaat gtctttggat ttgggaatct tataagttct 780
gtatgagacc actccctagg cagcgcatgg gcgtcaattc tagagattga cgcccatgcg 840
ctgctttttt cgacagatct ggcgcgccat agtggccagc ggccgcaggt aagccagccc 900
aggcctcgcc ctccagctca aggcgggaca ggtgccctag agtagcctgc atccagggac 960
aggccccagc cgggtgctga cacgtccacc tccatctctt cctcaggtct gcccgggtgg 1020
catccctgtg accccctccc agtgcctctc ctggccctgg aagttgccac tccagtgccc 1080
accagccttg tcctaataaa attaagttgc atcattttgt ctgactaggt gtccttctat 1140
aatattatgg ggtggagggg ggtggtatgg agcaaggggc ccaagttaac ttgtttattg 1200
cagcttataa tggttacaaa taaagcaata gcatcacaaa tttcacaaat aaagcatttt 1260
tttcactgca ttctagttgt ggtttgtcca aactcatcaa tgtatcttat catgtctgga 1320
tccaaggtcg ggcaggaaga gggcctattt cccatgattc cttcatattt gcatatacga 1380
tacaaggctg ttagagagat aattagaatt aatttgactg taaacacaaa gatattagta 1440
caaaatacgt gacgtagaaa gtaataattt cttgggtagt ttgcagtttt aaaattatgt 1500
tttaaaatgg actatcatat gcttaccgta acttgaaagt atttcgattt cttggcttta 1560
tatatcttgt ggaaaggacg aaactaggta gagtatggta gcaatatcta gagtattgct 1620
accatactct actttttttcg agtagctaga gaattcatgg taatagcgat gactaatacg 1680
tagatgtact gccaagtagg aaagtcccat aaggtcatgt actgggcata atgccaggcg 1740
ggccatttac cgtcattgac gtcaataggg ggcgtacttg gcatatgata cacttgatgt 1800
actgccaagt gggcagttta ccgtaaatag tccacccatt gacgtcaatg gaaagtccct 1860

-continued

```
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctctttttcc gaaggtaact   3360
ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
agggagcttc cagggggaaa cgcctggtat ctttatagtc ctgtcgggtt tcgccacctc   3780
tgacttgagc gtcgattttt gtgatgctcg tcaggggggc ggagcctatg gaaaaacgcc   3840
agcaacgcgg cctttttacg gttcctggcc ttttgctggc cttttgct                3888
```

<210> SEQ ID NO 47
<211> LENGTH: 3888
<212> TYPE: DNA
<213> ORGANISM: Artificial Sequence
<220> FEATURE:
<223> OTHER INFORMATION: pEQU6-shPDL1-H1-shVISTA

<400> SEQUENCE: 47

```
ctttcctgcg ttatcccctg attctgtgga taaccgtatt accgcctttg agtgagctga     60
```

-continued

```
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg ctttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg accaccatgg caacttcttc tagagagaag ttgccatggt    840
ggtctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gcccgggtgg   1020
catccctgtg acccctcccc agtgcctctc ctggccctgg aagttgccac tccagtgccc   1080
accagccttg tcctaataaa attaagttgc atcattttgt ctgactaggt gtccttctat   1140
aatattatgg ggtggagggg ggtggtatgg agcaaggggc ccaagttaac ttgtttattg   1200
cagcttataa tggttacaaa taaagcaata gcatcacaaa tttcacaaat aaagcatttt   1260
tttcactgca ttctagttgt ggtttgtcca aactcatcaa tgtatcttat catgtctgga   1320
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggta gagtatggta gcaatatcta gagtattgct   1620
accatactct acttttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
```

-continued

```
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctctttttcc gaaggtaact   3360
ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
agggagcttc caggggggaaa cgcctggtat ctttatagtc ctgtcgggtt tcgccacctc   3780
tgacttgagc gtcgattttt gtgatgctcg tcaggggggc ggagcctatg gaaaaacgcc   3840
agcaacgcgg cctttttacg gttcctggcc ttttgctggc cttttgct              3888
```

<210> SEQ ID NO 48
<211> LENGTH: 1104
<212> TYPE: DNA
<213> ORGANISM: Salmonella typhimurium
<220> FEATURE:
<223> OTHER INFORMATION: Strain LT2 Aspartate-semialdehyde dehydrogenase (asd)

<400> SEQUENCE: 48

```
atgaaaaatg ttggttttat cggctggcgc ggaatggtcg gctctgttct catgcaacgc     60
atggtagagg agcgcgattt cgacgctatt cgccctgttt tcttttctac ctcccagttt    120
ggacaggcgg cgcccacctt cggcgacacc tccaccggca cgctacagga cgcttttgat    180
ctggatgcgc taaaagcgct cgatatcatc gtgacctgcc agggcggcga ttataccaac    240
gaaatttatc caaagctgcg cgaaagcgga tggcagggtt actggattga tgcggcttct    300
acgctgcgca tgaaagatga tgccattatt attctcgacc cggtcaacca ggacgtgatt    360
accgacggcc tgaacaatgg cgtgaagacc tttgtgggcg gtaactgtac cgttagcctg    420
atgttgatgt cgctgggcgg tctctttgcc cataatctcg ttgactgggt atccgtcgcg    480
acctatcagg ccgcctccgg cggcggcgcg cgccatatgc gcgagctgtt aacccagatg    540
```

-continued ggtcagttgt atggccatgt cgccgatgaa ctggcgacgc cgtcttccgc aattcttgat 600
attgaacgca aagttacggc attgacccgc agcggcgagc tgccggttga taactttggc 660
gtaccgctgg cgggaagcct gatcccctgg atcgacaaac agctcgataa cggccagagc 720
cgcgaagagt ggaaaggcca ggcggaaacc aacaagattc tcaatactgc ctctgtgatt 780
ccggttgatg gtttgtgtgt gcgcgtcggc gcgctgcgct gtcacagcca ggcgttcacc 840
atcaagctga aaaaagaggt atccattccg acggtggaag aactgctggc ggcacataat 900
ccgtgggcga aagtggtgcc gaacgatcgt gatatcacta tgcgcgaatt aaccccggcg 960
gcggtgaccg gcacgttgac tacgccggtt ggtcgtctgc gtaagctgaa catggggcca 1020
gagttcttgt cggcgtttac cgtaggcgac cagttgttat ggggcgccgc cgagccgctg 1080
cgtcgaatgc tgcgccagtt ggcg 1104

<210> SEQ ID NO 49
<211> LENGTH: 861
<212> TYPE: DNA
<213> ORGANISM: Salmonella typhimurium
<220> FEATURE:
<223> OTHER INFORMATION: Strain LT2 TSX

<400> SEQUENCE: 49
atgaaaaaaa ctttactcgc agtcagcgca gcgctggcgc tcacctcatc ttttactgct 60
aacgcagcag aaaatgatca gccgcagtat ttgtccgact ggtggcacca gagcgtaaac 120
gtggtaggca gctaccatac ccgtttctcg ccgaaattga acaacgacgt ctatctggaa 180
tatgaagcat ttgccaaaaa agactggttt gatttctacg gctatatcga tattcccaaa 240
acctttgatt ggggtaacgg caacgataaa ggtatctggt ccgacggttc tccgctgttc 300
atggaaatcg aaccgcgttt ctcaattgat aagctgaccg gcgcagacct gagcttcggc 360
ccgtttaaag agtggtattt cgccaacaac tacatctacg atatgggcga taacaaagcc 420
agccgccaga gcacgtggta tatgggtctg ggaccgata tcgacaccgg cctgccgatg 480
ggtctgtcgc tgaacgtgta tgcgaaatat cagtggcaaa actacggcgc gtccaatgaa 540
aacgaatggg acggctaccg tttcaaagtg aaatacttcg tccccatcac cgatctgtgg 600
ggcggtaaac tgagctatat cggctttacc aactttgact ggggatctga tttaggcgac 660
gatccgaacc gtaccagcaa ctccatcgct tccagccata tcctggcgct gaactacgat 720
cactggcact actcggtcgt tgcgcgttac ttccataacg gcggacagtg gcagaatggc 780
gcaaaactga actggggcga cggcgatttc agcgcgaaat ctaccggctg ggcggctac 840 ctggtcgtgg gttacaactt c 861

<210> SEQ ID NO 50
<211> LENGTH: 864
<212> TYPE: DNA
<213> ORGANISM: Homo sapiens
<220> FEATURE:
<223> OTHER INFORMATION: programmed cell death protein 1 (PD-1)

<400> SEQUENCE: 50
atgcagatcc cacaggcgcc ctggccagtc gtctgggcgg tgctacaact gggctggcgg 60
ccaggatggt tcttagactc cccagacagg ccctggaacc cccccacctt ctccccagcc 120
ctgctcgtgg tgaccgaagg ggacaacgcc accttcacct gcagcttctc caacacatcg 180
gagagcttcg tgctaaactg gtaccgcatg agccccagca accagacgga caagctggcc 240
gccttccccg aggaccgcag ccagcccggc caggactgcc gcttccgtgt cacacaactg 300

```
cccaacgggc gtgacttcca catgagcgtg gtcagggccc ggcgcaatga cagcggcacc    360

tacctctgtg gggccatctc cctggccccc aaggcgcaga tcaaagagag cctgcgggca    420

gagctcaggg tgacagagag aagggcagaa gtgcccacag cccaccccag cccctcaccc    480

aggccagccg gccagttcca aaccctggtg gttggtgtcg tgggcggcct gctgggcagc    540

ctggtgctgc tagtctgggt cctggccgtc atctgctccc gggccgcacg agggacaata    600

ggagccaggc gcaccggcca gcccctgaag gaggacccct cagccgtgcc tgtgttctct    660

gtggactatg gggagctgga tttccagtgg cgagagaaga ccccggagcc ccccgtgccc    720

tgtgtccctg agcagacgga gtatgccacc attgtctttc ctagcggaat gggcacctca    780

tcccccgccc gcaggggctc agctgacggc cctcggagtg cccagccact gaggcctgag    840

gatggacact gctcttggcc cctc                                           864
```

```
<210> SEQ ID NO 51
<211> LENGTH: 933
<212> TYPE: DNA
<213> ORGANISM: Homo sapiens
<220> FEATURE:
<223> OTHER INFORMATION: programmed cell death protein 2 (PD-2), isoform
      1

<400> SEQUENCE: 51

atggctgccg ccggggccag gcctgtggag ctgggcttcg ccgagtcggc gccggcgtgg     60

cgactgcgca gcgagcagtt ccccagcaag gtgtatgcgc cgctgcctgg ccgcccggac    120

gccttccacc gctgcatctt cctcttctgc tgccgcgagc agccgtgctg tgccggcctg    180

cgagttttta ggaatcaact acccaggaaa aacgattttt actcatatga gccaccttct    240

gagaatcctc ccccagaaac aggagaatca gtgtgtctcc agcttaagtc tggtgctcat    300

ctctgcaggg tttgtggctg tttaggcccc aaaacgtgct ccagatgcca caaagcatat    360

tactgcagca aggagcatca gaccctagac tggagattgg gacataagca ggcttgtgca    420

caaccagatc atctggacca tataattcca gaccacaact tcctttttcc agaatttgaa    480

attgtaatag aaacagaaga tgagattatg cctgaggttg tggaaaagga agattactca    540

gagattatag ggagcatggg tgaagcactt gaggaagaac tggattccat ggcaaaacat    600

gaatccaggg aagataaaat ttttcagaag tttaaaactc agatagccct tgaaccagaa    660

cagattctta gatatggcag aggtattgcc cccatctgga tttctggtga aaatattcct    720

caagaaaagg atattccaga ttgcccctgt ggtgccaaga gaatattgga attccaggtc    780

atgcctcagc tcctaaacta cctgaaggct gacagactgg gcaagagcat tgactggggc    840

atcctggctg tcttcacctg tgctgagagc tgcagcttgg gtactggcta tacagaagaa    900

tttgtgtgga agcaggatgt aacagataca ccg                                 933
```

```
<210> SEQ ID NO 52
<211> LENGTH: 819
<212> TYPE: DNA
<213> ORGANISM: Homo sapiens
<220> FEATURE:
<223> OTHER INFORMATION: programmed death-ligand 2 (PD-L2), isoform 1

<400> SEQUENCE: 52

atgatcttcc tcctgctaat gttgagcctg gaattgcagc ttcaccagat agcagcttta     60

ttcacagtga cagtccctaa ggaactgtac ataatagagc atggcagcaa tgtgaccctg    120

gaatgcaact ttgacactgg aagtcatgtg aaccttggag caataacagc cagtttgcaa    180
```

aaggtggaaa atgatacatc cccacaccgt gaaagagcca ctttgctgga ggagcagctg 240
cccctaggga aggcctcgtt ccacatacct caagtccaag tgagggacga aggacagtac 300
caatgcataa tcatctatgg ggtcgcctgg gactacaagt acctgactct gaaagtcaaa 360
gcttcctaca ggaaaataaa cactcacatc ctaaaggttc cagaaacaga tgaggtagag 420
ctcacctgcc aggctacagg ttatcctctg gcagaagtat cctggccaaa cgtcagcgtt 480
cctgccaaca ccagccactc caggacccct gaaggcctct accaggtcac cagtgttctg 540
cgcctaaagc cacccccctgg cagaaacttc agctgtgtgt tctggaatac tcacgtgagg 600
gaacttactt tggccagcat tgaccttcaa agtcagatgg aacccaggac ccatccaact 660
tggctgcttc acattttcat cccctcctgc atcattgctt tcattttcat agccacagtg 720
atagccctaa gaaaacaact ctgtcaaaag ctgtattctt caaaagacac aacaaaaaga 780
cctgtcacca caacaaagag ggaagtgaac agtgctatc 819

<210> SEQ ID NO 53
<211> LENGTH: 669
<212> TYPE: DNA
<213> ORGANISM: Homo sapiens
<220> FEATURE:
<223> OTHER INFORMATION: cytotoxic T-lymphocyte-associated protein 4
(CTLA-4), isoform 1

<400> SEQUENCE: 53
atggcttgcc ttggatttca gcggcacaag gctcagctga acctggctac caggacctgg 60
ccctgcactc tcctgttttt tcttctcttc atccctgtct tctgcaaagc aatgcacgtg 120
gcccagcctg ctgtggtact ggccagcagc cgaggcatcg ccagctttgt gtgtgagtat 180
gcatctccag gcaaagccac tgaggtccgg gtgacagtgc ttcggcaggc tgacagccag 240
gtgactgaag tctgtgcggc aacctacatg atggggaatg agttgacctt cctagatgat 300
tccatctgca cgggcacctc cagtggaaat caagtgaacc tcactatcca aggactgagg 360
gccatggaca cgggactcta catctgcaag gtggagctca tgtacccacc gccatactac 420
ctgggcatag gcaacggaac ccagatttat gtaattgatc cagaaccgtg cccagattct 480
gacttcctcc tctggatcct tgcagcagtt agttcggggt tgttttttta tagctttctc 540
ctcacagctg tttctttgag caaaatgcta aagaaaagaa gccctcttac aacaggggtc 600
tatgtgaaaa tgcccccaac agagccagaa tgtgaaaagc aatttcagcc ttattttatt 660
cccatcaat 669

<210> SEQ ID NO 54
<211> LENGTH: 969
<212> TYPE: DNA
<213> ORGANISM: Homo sapiens
<220> FEATURE:
<223> OTHER INFORMATION: CD47 transcript variant 1

<400> SEQUENCE: 54
atgtggcccc tggtagcggc gctgttgctg ggctcggcgt gctgcggatc agctcagcta 60
ctatttaata aaacaaaatc tgtagaattc acgttttgta atgacactgt cgtcattcca 120
tgctttgtta ctaatatgga ggcacaaaac actactgaag tatacgtaaa gtggaaattt 180
aaaggaagag atatttacac ctttgatgga gctctaaaca agtccactgt ccccactgac 240
tttagtagtg caaaaattga agtctcacaa ttactaaaag gagatgcctc tttgaagatg 300
gataagagtg atgctgtctc acacacagga aactacactt gtgaagtaac agaattaacc 360
agagaaggtg aaacgatcat cgagctaaaa tatcgtgttg tttcatggtt ttctccaaat 420
gaaaatattc ttattgttat tttcccaatt tttgctatac tcctgttctg ggacagttt 480 ggtattaaaa cacttaaata tagatccggt ggtatggatg agaaaacaat tgctttactt 540
gttgctggac tagtgatcac tgtcattgtc attgttggag ccattctttt cgtcccaggt 600
gaatattcat taaagaatgc tactggcctt ggtttaattg tgacttctac agggatatta 660
atattacttc actactatgt gtttagtaca gcgattggat taacctcctt cgtcattgcc 720
atattggtta ttcaggtgat agcctatatc ctcgctgtgg ttggactgag tctctgtatt 780
gcggcgtgta taccaatgca tggccctctt ctgatttcag gtttgagtat cttagctcta 840
gcacaattac ttggactagt ttatatgaaa tttgtggctt ccaatcagaa gactatacaa 900
cctcctagga aagctgtaga ggaacccctt aatgcattca aagaatcaaa aggaatgatg 960
aatgatgaa 969

<210> SEQ ID NO 55
<211> LENGTH: 1209
<212> TYPE: DNA
<213> ORGANISM: Homo sapiens
<220> FEATURE:
<223> OTHER INFORMATION: indoleamine 2,3-dioxygenase (IDO) 1

<400> SEQUENCE: 55
atggcacacg ctatggaaaa ctcctggaca atcagtaaag agtaccatat tgatgaagaa 60
gtgggctttg ctctgccaaa tccacaggaa aatctacctg atttttataa tgactggatg 120
ttcattgcta aacatctgcc tgatctcata gagtctggcc agcttcgaga aagagttgag 180
aagttaaaca tgctcagcat tgatcatctc acagaccaca agtcacagcg ccttgcacgt 240
ctagttctgg gatgcatcac catggcatat gtgtggggca aaggtcatgg agatgtccgt 300
aaggtcttgc caagaaatat tgctgttcct tactgccaac tctccaagaa actggaactg 360
cctcctattt tggtttatgc agactgtgtc ttggcaaact ggaagaaaaa ggatcctaat 420
aagcccctga cttatgagaa catggacgtt ttgttctcat ttcgtgatgg agactgcagt 480
aaaggattct tcctggtctc tctattggtg gaaatagcag ctgcttctgc aatcaaagta 540
attcctactg tattcaaggc aatgcaaatg caagaacggg acactttgct aaaggcgctg 600
ttggaaatag cttcttgctt ggagaaagcc cttcaagtgt ttcaccaaat ccacgatcat 660
gtgaacccaa aagcattttt cagtgttctt cgcatatatt tgtctggctg gaaaggcaac 720
ccccagctat cagacggtct ggtgtatgaa aggttctggg aagacccaaa ggagtttgca 780
gggggcagtg caggccaaag cagcgtcttt cagtgctttg acgtcctgct gggcatccag 840
cagactgctg gtggaggaca tgctgctcag ttcctccagg acatgagaag atatatgcca 900
ccagctcaca ggaacttcct gtgctcatta gagtcaaatc cctcagtccg tgagtttgtc 960
ctttcaaaag gtgatgctgg cctgcgggaa gcttatgacg cctgtgtgaa agctctggtc 1020
tccctgagga gctaccatct gcaaatcgtg actaagtaca tcctgattcc tgcaagccag 1080
cagccaaagg agaataagac ctctgaagac ccttcaaaac tggaagccaa aggaactgga 1140
ggcactgatt taatgaattt cctgaagact gtaagaagta caactgagaa atcccttttg 1200
aaggaaggt 1209

<210> SEQ ID NO 56
<211> LENGTH: 1260
<212> TYPE: DNA

<213> ORGANISM: Homo sapiens
<220> FEATURE:
<223> OTHER INFORMATION: indoleamine 2,3-dioxygenase (IDO) 2

<400> SEQUENCE: 56
atgttgcatt ttcattatta tgatacttca aacaaaataa tggagcccca cagaccgaat 60
gtgaagacag cagtgccatt gtctttggaa agctatcaca tatctgaaga gtatggcttt 120
cttcttccag attctctgaa agaacttcca gatcattata ggccttggat ggaaattgcc 180
aacaaacttc ctcaattgat tgatgctcac cagcttcaag ctcatgtgga caagatgccc 240
ctgctgagct gccagttcct gaagggtcac cgggagcagc gcctggccca cctggtcctg 300
agcttcctca ccatgggtta tgtctggcag gaaggagagg cgcagcctgc agaggtcctg 360
ccaaggaatc ttgcccttcc atttgtcgaa gtctccagga acttggggct ccctcctatc 420
ctggtccact cagacttggt gctgacgaac tggaccaaaa aagatccaga cggattcctg 480
gaaattggga acctggagac catcatctca tttcctgggg gagagagcct gcatggtttt 540
atactggtga ctgctttggt agagaaagaa gcagtgcctg ggataaaggc tcttgttcag 600
gccacgaatg ctatcttgca gcccaaccag gaggccctgc tccaagccct gcagcgactg 660
agactgtcta ttcaggacat caccaaaacc ttaggacaga tgcatgatta tgtagatcca 720
gacatatttt atgcaggcat ccggatcttt ctctctggat ggaaagacaa cccagcaatg 780
cctgcagggc tgatgtatga aggagtttcc caagagcccc tgaaatactc cggcgggagt 840
gcagctcaga gcacagtgct tcatgccttt gatgagttct taggcattcg tcatagcaag 900
gaaagtggtg actttctgta cagaatgagg gattacatgc ctccttccca taaggccttc 960
atagaagaca tccactcagc accttccctg agggactaca tcctgtcatc tggacaggac 1020
cacttgctga cagcttataa ccagtgtgtg caggccctgg cagagctgcg gagctatcac 1080
atcaccatgg tcaccaaata cctcatcaca gctgcagcca aggcaaagca tgggaagcca 1140
aaccatctcc cagggcctcc tcaggcttta aaagacaggg gcacaggtgg aaccgcagtt 1200
atgagctttc ttaagagtgt cagggataag accttggagt caatccttca cccacgtggt 1260

<210> SEQ ID NO 57
<211> LENGTH: 2310
<212> TYPE: DNA
<213> ORGANISM: Homo sapiens
<220> FEATURE:
<223> OTHER INFORMATION: signal transducer and activator of
transcription 3 (STAT3)

<400> SEQUENCE: 57
atggcccaat ggaatcagct acagcagctt gacacacggt acctggagca gctccatcag 60
ctctacagtg acagcttccc aatggagctg cggcagtttc tggccccttg gattgagagt 120
caagattggg catatgcggc cagcaaagaa tcacatgcca ctttggtgtt tcataatctc 180
ctgggagaga ttgaccagca gtatagccgc ttcctgcaag agtcgaatgt tctctatcag 240
cacaatctac gaagaatcaa gcagtttctt cagagcaggt atcttgagaa gccaatggag 300
attgcccgga ttgtggcccg gtgcctgtgg gaagaatcac gccttctaca gactgcagcc 360
actgcggccc agcaaggggg ccaggccaac caccccacag cagccgtggt gacggagaag 420
cagcagatgc tggagcagca ccttcaggat gtccggaaga gagtgcagga tctagaacag 480
aaaatgaaag tggtagagaa tctccaggat gactttgatt tcaactataa aaccctcaag 540
agtcaaggag acatgcaaga tctgaatgga aacaaccagt cagtgaccag gcagaagatg 600

```
cagcagctgg aacagatgct cactgcgctg gaccagatgc ggagaagcat cgtgagtgag    660

ctggcggggc ttttgtcagc gatggagtac gtgcagaaaa ctctcacgga cgaggagctg    720

gctgactgga agaggcggca acagattgcc tgcattggag gcccgcccaa catctgccta    780

gatcggctag aaaactggat aacgtcatta gcagaatctc aacttcagac ccgtcaacaa    840

attaagaaac tggaggagtt gcagcaaaaa gtttcctaca aaggggaccc cattgtacag    900

caccggccga tgctggagga gagaatcgtg gagctgttta gaaacttaat gaaaagtgcc    960

tttgtggtgg agcggcagcc ctgcatgccc atgcatcctg accggcccct cgtcatcaag   1020

accggcgtcc agttcactac taaagtcagg ttgctggtca aattccctga gttgaattat   1080

cagcttaaaa ttaaagtgtg cattgacaaa gactctgggg acgttgcagc tctcagagga   1140

tcccggaaat ttaacattct gggcacaaac acaaaagtga tgaacatgga agaatccaac   1200

aacggcagcc tctctgcaga attcaaacac ttgaccctga gggagcagag atgtgggaat   1260

gggggccgag ccaattgtga tgcttccctg attgtgactg aggagctgca cctgatcacc   1320

tttgagaccg aggtgtatca ccaaggcctc aagattgacc tagagaccca ctccttgcca   1380

gttgtggtga tctccaacat ctgtcagatg ccaaatgcct gggcgtccat cctgtggtac   1440

aacatgctga ccaacaatcc caagaatgta aacttttttta ccaagccccc aattggaacc   1500

tgggatcaag tggccgaggt cctgagctgg cagttctcct ccaccaccaa gcgaggactg   1560

agcatcgagc agctgactac actggcagag aaactcttgg gacctggtgt gaattattca   1620

gggtgtcaga tcacatgggc taaattttgc aaagaaaaca tggctggcaa gggcttctcc   1680

ttctgggtct ggctggacaa tatcattgac cttgtgaaaa agtacatcct ggccctttgg   1740

aacgaagggt acatcatggg ctttatcagt aaggagcggg agcgggccat cttgagcact   1800

aagcctccag gcaccttcct gctaagattc agtgaaagca gcaaagaagg aggcgtcact   1860

ttcacttggg tggagaagga catcagcggt aagacccaga tccagtccgt ggaaccatac   1920

acaaagcagc agctgaacaa catgtcattt gctgaaatca tcatgggcta taagatcatg   1980

gatgctacca atatcctggt gtctccactg gtctatctct atcctgacat tcccaaggag   2040

gaggcattcg gaaagtattg tcggccagag agccaggagc atcctgaagc tgacccaggt   2100

agcgctgccc catacctgaa gaccaagttt atctgtgtga caccaacgac ctgcagcaat   2160

accattgacc tgccgatgtc cccccgcact ttagattcat tgatgcagtt tggaaataat   2220

ggtgaaggtg ctgaaccctc agcaggaggg cagtttgagt ccctcacctt tgacatggag   2280

ttgacctcgg agtgcgctac ctcccccatg                                    2310
```

<210> SEQ ID NO 58
<211> LENGTH: 1575
<212> TYPE: DNA
<213> ORGANISM: Homo sapiens
<220> FEATURE:
<223> OTHER INFORMATION: lymphocyte-activation gene 3 (LAG3)

<400> SEQUENCE: 58

```
atgtgggagg ctcagttcct gggcttgctg tttctgcagc cgctttgggt ggctccagtg     60

aagcctctcc agccaggggc tgaggtcccg gtggtgtggg cccaggaggg ggctcctgcc    120

cagctcccct gcagccccac aatccccctc caggatctca gccttctgcg aagagcaggg    180

gtcacttggc agcatcagcc agacagtggc ccgcccgctg ccgcccccgg ccatcccctg    240

gcccccggcc ctcacccggc ggcgccctcc tcctgggggc ccaggccccg ccgctacacg    300

gtgctgagcg tgggtcccgg aggcctgcgc agcgggaggc tgccccctgca gccccgcgtc    360
```

cagctggatg agcgcggccg gcagcgcggg gacttctcgc tatggctgcg cccagcccgg 420
cgcgcggacg ccggcgagta ccgcgccgcg gtgcacctca gggaccgcgc cctctcctgc 480
cgcctccgtc tgcgcctggg ccaggcctcg atgactgcca gcccccccagg atctctcaga 540 gcctccgact gggtcatttt gaactgctcc ttcagccgcc ctgaccgccc agcctctgtg 600
cattggttcc ggaaccgggg ccagggccga gtccctgtcc gggagtcccc ccatcaccac 660
ttagcggaaa gcttcctctt cctgccccaa gtcagcccca tggactctgg gccctggggc 720
tgcatcctca cctacagaga tggcttcaac gtctccatca tgtataacct cactgttctg 780
ggtctggagc cccaactcc cttgacagtg tacgctggag caggttccag ggtggggctg 840
ccctgccgcc tgcctgctgg tgtggggacc cggtctttcc tcactgccaa gtggactcct 900
cctgggggag gccctgacct cctggtgact ggagacaatg gcgactttac ccttcgacta 960
gaggatgtga gccaggccca ggctgggacc tacacctgcc atatccatct gcaggaacag 1020
cagctcaatg ccactgtcac attggcaatc atcacagtga ctcccaaatc ctttgggtca 1080
cctggatccc tggggaagct gctttgtgag gtgactccag tatctggaca agaacgcttt 1140
gtgtggagct ctctggacac cccatcccag aggagtttct caggaccttg gctggaggca 1200
caggaggccc agctcctttc ccagccttgg caatgccagc tgtaccaggg ggagaggctt 1260
cttggagcag cagtgtactt cacagagctg tctagcccag gtgcccaacg ctctgggaga 1320
gccccaggtg ccctcccagc aggccacctc ctgctgtttc tcatccttgg tgtcctttct 1380
ctgctccttt tggtgactgg agcctttggc tttcaccttt ggagaagaca gtggcgacca 1440
agacgatttt ctgccttaga gcaagggatt caccctccgc aggctcagag caagatagag 1500
gagctggagc aagaaccgga gccggagccg gagccggaac cggagcccga gcccgagccc 1560
gagccggagc agctc 1575

<210> SEQ ID NO 59
<211> LENGTH: 903
<212> TYPE: DNA
<213> ORGANISM: Homo sapiens
<220> FEATURE:
<223> OTHER INFORMATION: T cell immunoglobulin and mucin-domain containing-3 (TIM-3)

<400> SEQUENCE: 59
atgttttcac atcttccctt tgactgtgtc ctgctgctgc tgctgctact acttacaagg 60
tcctcagaag tggaatacag agcggaggtc ggtcagaatg cctatctgcc ctgcttctac 120
accccagccg ccccagggaa cctcgtgccc gtctgctggg gcaaaggagc ctgtcctgtg 180
tttgaatgtg gcaacgtggt gctcaggact gatgaaaggg atgtgaatta ttggacatcc 240
agatactggc taaatgggga tttccgcaaa ggagatgtgt ccctgaccat agagaatgtg 300
actctagcag acagtgggat ctactgctgc cggatccaaa tcccaggcat aatgaatgat 360
gaaaaattta acctgaagtt ggtcatcaaa ccagccaagg tcacccctgc accgactcgg 420
cagagagact tcactgcagc ctttccaagg atgcttacca ccaggggaca tggcccagca 480
gagacacaga cactggggag cctccctgat ataaatctaa cacaaatatc cacattggcc 540
aatgagttac gggactctag attggccaat gacttacggg actctggagc aaccatcaga 600
ataggcatct acatcggagc agggatctgt gctgggctgg ctctggctct tatcttcggc 660
gctttaattt tcaaatggta ttctcatagc aaagagaaga tacagaattt aagcctcatc 720
tctttggcca acctccctcc ctcaggattg gcaaatgcag tagcagaggg aattcgctca 780
gaagaaaaca tctataccat tgaagagaac gtatatgaag tggaggagcc caatgagtat 840
tattgctatg tcagcagcag gcagcaaccc tcacaacctt tgggttgtcg ctttgcaatg 900
cca 903

<210> SEQ ID NO 60
<211> LENGTH: 732
<212> TYPE: DNA
<213> ORGANISM: Homo sapiens
<220> FEATURE:
<223> OTHER INFORMATION: T cell immunoreceptor with Ig and ITIM domains (TIGIT), isoform 1

<400> SEQUENCE: 60
atgcgctggt gtctcctcct gatctgggcc caggggctga ggcaggctcc cctcgcctca 60
ggaatgatga caggcacaat agaaacaacg ggaacattt ctgcagagaa aggtggctct 120
atcatcttac aatgtcacct ctcctccacc acggcacaag tgacccaggt caactgggag 180
cagcaggacc agcttctggc catttgtaat gctgacttgg ggtggcacat ctccccatcc 240
ttcaaggatc gagtggcccc aggtcccggc ctgggcctca ccctccagtc gctgaccgtg 300
aacgatacag gggagtactt ctgcatctat cacacctacc ctgatgggac gtacactggg 360
agaatcttcc tggaggtcct agaaagctca gtggctgagc acggtgccag gttccagatt 420
ccattgcttg gagccatggc cgcgacgctg gtggtcatct gcacagcagt catcgtggtg 480
gtcgcgttga ctagaaagaa gaaagccctc agaatccatt ctgtggaagg tgacctcagg 540
agaaaatcag ctggacagga ggaatggagc cccagtgctc cctcaccccc aggaagctgt 600
gtccaggcag aagctgcacc tgctgggctc tgtggagagc agcggggaga ggactgtgcc 660
gagctgcatg actacttcaa tgtcctgagt tacagaagcc tgggtaactg cagcttcttc 720
acagagactg gt 732

<210> SEQ ID NO 61
<211> LENGTH: 1065
<212> TYPE: DNA
<213> ORGANISM: Homo sapiens
<220> FEATURE:
<223> OTHER INFORMATION: GALECTIN-9/LGALS9, isoform 1

<400> SEQUENCE: 61
atggccttca gcggttccca ggctccctac ctgagtccag ctgtcccctt ttctgggact 60
attcaaggag gtctccagga cggacttcag atcactgtca atgggaccgt tctcagctcc 120
agtggaacca ggtttgctgt gaactttcag actggcttca gtggaaatga cattgccttc 180
cacttcaacc ctcggtttga agatggaggg tacgtggtgt gcaacacgag gcagaacgga 240
agctgggggc ccgaggagag gaagacacac atgcctttcc agaaggggat gccctttgac 300
ctctgcttcc tggtgcagag ctcagatttc aaggtgatgg tgaacgggat cctcttcgtg 360
cagtacttcc accgcgtgcc cttccaccgt gtggacacca tctccgtcaa tggctctgtg 420
cagctgtcct acatcagctt ccagaacccc cgcacagtcc ctgttcagcc tgccttctcc 480
acggtgccgt tctcccagcc tgtctgtttc ccacccaggc ccagggggcg cagacaaaaa 540
cctcccggcg tgtggcctgc caacccggct cccattaccc agacagtcat ccacacagtg 600
cagagcgccc ctggacagat gttctctact cccgccatcc cacctatgat gtaccccac 660 cccgcctatc cgatgccttt catcaccacc attctgggag ggctgtaccc atccaagtcc 720
atcctcctgt caggcactgt cctgcccagt gctcagaggt tccacatcaa cctgtgctct 780

```
gggaaccaca tcgccttcca cctgaacccc cgttttgatg agaatgctgt ggtccgcaac    840

acccagatcg acaactcctg gggtctgag gagcgaagtc tgccccgaaa aatgcccttc    900

gtccgtggcc agagcttctc agtgtggatc ttgtgtgaag ctcactgcct caaggtggcc    960

gtggatggtc agcacctgtt tgaatactac catcgcctga ggaacctgcc caccatcaac   1020

agactggaag tgggggcga catccagctg acccatgtgc agaca                    1065
```

<210> SEQ ID NO 62
<211> LENGTH: 720
<212> TYPE: DNA
<213> ORGANISM: Homo sapiens
<220> FEATURE:
<223> OTHER INFORMATION: LIGHT/TNSF14

<400> SEQUENCE: 62

```
atggaggaga gtgtcgtacg gccctcagtg tttgtggtgg atggacagac cgacatccca     60

ttcacgaggc tgggacgaag ccaccggaga cagtcgtgca gtgtggcccg ggtgggtctg    120

ggtctcttgc tgttgctgat gggggccggg ctggccgtcc aaggctggtt cctcctgcag    180

ctgcactggc gtctaggaga gatggtcacc cgcctgcctg acggacctgc aggctcctgg    240

gagcagctga tacaagagcg aaggtctcac gaggtcaacc cagcagcgca tctcacaggg    300

gccaactcca gcttgaccgg cagcgggggg ccgctgttat gggagactca gctgggcctg    360

gccttcctga ggggcctcag ctaccacgat ggggcccttg tggtcaccaa agctggctac    420

tactacatct actccaaggt gcagctgggc ggtgtgggct gcccgctggg cctggccagc    480

accatcaccc acggcctcta caagcgcaca ccccgctacc ccgaggagct ggagctgttg    540

gtcagccagc agtcaccctg cggacgggcc accagcagct cccgggtctg gtgggacagc    600

agcttcctgg gtggtgtggt acacctggag gctggggaga aggtggtcgt ccgtgtgctg    660

gatgaacgcc tggttcgact gcgtgatggt acccggtctt acttcggggc tttcatggtg    720
```

<210> SEQ ID NO 63
<211> LENGTH: 849
<212> TYPE: DNA
<213> ORGANISM: Homo sapiens
<220> FEATURE:
<223> OTHER INFORMATION: HVEM/TNSFR14 (receptor for LIGHT ligand)

<400> SEQUENCE: 63

```
atggagcctc ctggagactg gggcctcct ccctggagat ccaccccaa aaccgacgtc     60

ttgaggctgg tgctgtatct caccttcctg ggagccccct gctacgcccc agctctgccg    120

tcctgcaagg aggacgagta cccagtgggc tccgagtgct gccccaagtg cagtccaggt    180

tatcgtgtga aggaggcctg cggggagctg acgggcacag tgtgtgaacc ctgccctcca    240

ggcacctaca ttgcccacct caatggccta agcaagtgtc tgcagtgcca aatgtgtgac    300

ccagccatgg gcctgcgcgc gagccggaac tgctccagga cagagaacgc cgtgtgtggc    360

tgcagcccag gccacttctg catcgtccag gacggggacc actgcgccgc gtgccgcgct    420

tacgccacct ccagcccggg ccagagggtg cagaagggag gcaccgagag tcaggacacc    480

ctgtgtcaga actgcccccc ggggaccttc tctcccaatg ggaccctgga ggaatgtcag    540

caccagacca agtgcagctg gctggtgacg aaggccggag ctgggaccag cagctcccac    600

tgggtatggt ggtttctctc agggagcctc gtcatcgtca ttgtttgctc cacagttggc    660

ctaatcatat gtgtgaaaag aagaaagcca aggggtgatg tagtcaaggt gatcgtctcc    720
```

-continued

```
gtccagcgga aaagacagga ggcagaaggt gaggccacag tcattgaggc cctgcaggcc    780

cctccggacg tcaccacggt ggccgtggag gagacaatac cctcattcac ggggaggagc    840

ccaaaccac                                                            849


<210> SEQ ID NO 64
<211> LENGTH: 660
<212> TYPE: DNA
<213> ORGANISM: Homo sapiens
<220> FEATURE:
<223> OTHER INFORMATION: CD28

<400> SEQUENCE: 64

atgctcaggc tgctcttggc tctcaactta ttcccttcaa ttcaagtaac aggaaacaag     60

attttggtga agcagtcgcc catgcttgta gcgtacgaca atgcggtcaa ccttagctgc    120

aagtattcct acaatctctt ctcaagggag ttccgggcat cccttcacaa aggactggat    180

agtgctgtgg aagtctgtgt tgtatatggg aattactccc agcagcttca ggtttactca    240

aaaacggggt tcaactgtga tgggaaattg ggcaatgaat cagtgacatt ctacctccag    300

aatttgtatg ttaaccaaac agatatttac ttctgcaaaa ttgaagttat gtatcctcct    360

ccttacctag acaatgagaa gagcaatgga accattatcc atgtgaaagg gaaacacctt    420

tgtccaagtc ccctatttcc cggaccttct aagccctttt gggtgctggt ggtggttggt    480

ggagtcctgg cttgctatag cttgctagta acagtggcct ttattatttt ctgggtgagg    540

agtaagagga gcaggctcct gcacagtgac tacatgaaca tgactccccg ccgccccggg    600

cccacccgca agcattacca gccctatgcc ccaccacgcg acttcgcagc ctatcgctcc    660


<210> SEQ ID NO 65
<211> LENGTH: 1578
<212> TYPE: DNA
<213> ORGANISM: Homo sapiens
<220> FEATURE:
<223> OTHER INFORMATION: carcinoembryonic antigen-related cell adhesion
      molecule 1 (CEACAM1, or CD66a)

<400> SEQUENCE: 65

atggggcacc tctcagcccc acttcacaga gtgcgtgtac cctggcaggg gcttctgctc     60

acagcctcac ttctaacctt ctggaacccg cccaccactg cccagctcac tactgaatcc    120

atgccattca atgttgcaga ggggaaggag gttcttctcc ttgtccacaa tctgccccag    180

caactttttg gctacagctg gtacaaaggg gaaagagtgg atggcaaccg tcaaattgta    240

ggatatgcaa taggaactca acaagctacc ccagggcccg caaacagcgg tcgagagaca    300

atataccccca atgcatccct gctgatccag aacgtcaccc agaatgacac aggattctac   360

accctacaag tcataaagtc agatcttgtg aatgaagaag caactggaca gttccatgta    420

tacccggagc tgcccaagcc ctccatctcc agcaacaact ccaaccctgt ggaggacaag    480

gatgctgtgg ccttcacctg tgaacctgag actcaggaca caacctacct gtggtggata    540

aacaatcaga gcctcccggt cagtcccagg ctgcagctgt ccaatggcaa caggaccctc    600

actctactca gtgtcacaag gaatgacaca ggaccctatg agtgtgaaat acagaaccca    660

gtgagtgcga accgcagtga cccagtcacc ttgaatgtca cctatggccc ggacaccccc    720

accatttccc cttcagacac ctattaccgt ccaggggcaa acctcagcct ctcctgctat    780

gcagcctcta acccacctgc acagtactcc tggcttatca atggaacatt ccagcaaagc    840

acacaagagc tctttatccc taacatcact gtgaataata gtggatccta tacctgccac    900
```

gccaataact cagtcactgg ctgcaacagg accacagtca agacgatcat agtcactgag 960
ctaagtccag tagtagcaaa gccccaaatc aaagccagca agaccacagt cacaggagat 1020
aaggactctg tgaacctgac ctgctccaca aatgacactg gaatctccat ccgttggttc 1080
ttcaaaaacc agagtctccc gtcctcggag aggatgaagc tgtcccaggg caacaccacc 1140
ctcagcataa accctgtcaa gagggaggat gctgggacgt attggtgtga ggtcttcaac 1200
ccaatcagta agaaccaaag cgaccccatc atgctgaacg taaactataa tgctctacca 1260
caagaaaatg gcctctcacc tggggccatt gctggcattg tgattggagt agtggccctg 1320
gttgctctga tagcagtagc cctggcatgt tttctgcatt tcgggaagac cggcagggca 1380
agcgaccagc gtgatctcac agagcacaaa ccctcagtct ccaaccacac tcaggaccac 1440
tccaatgacc cacctaacaa gatgaatgaa gttacttatt ctaccctgaa ctttgaagcc 1500
cagcaaccca cacaaccaac ttcagcctcc ccatccctaa cagccacaga aataatttat 1560
tcagaagtaa aaaagcag 1578

<210> SEQ ID NO 66
<211> LENGTH: 864
<212> TYPE: DNA
<213> ORGANISM: Homo sapiens
<220> FEATURE:
<223> OTHER INFORMATION: CD80/B7-1

<400> SEQUENCE: 66
atgggccaca cacggaggca gggaacatca ccatccaagt gtccatacct caatttcttt 60
cagctcttgg tgctggctgg tctttctcac ttctgttcag gtgttatcca cgtgaccaag 120
gaagtgaaag aagtggcaac gctgtcctgt ggtcacaatg tttctgttga agagctggca 180
caaactcgca tctactggca aaaggagaag aaaatggtgc tgactatgat gtctggggac 240
atgaatatat ggcccgagta caagaaccgg accatctttg atatcactaa taacctctcc 300
attgtgatcc tggctctgcg cccatctgac gagggcacat acgagtgtgt tgttctgaag 360
tatgaaaaag acgctttcaa gcgggaacac ctggctgaag tgacgttatc agtcaaagct 420
gacttcccta cacctagtat atctgacttt gaaattccaa cttctaatat tagaaggata 480
atttgctcaa cctctggagg ttttccagag cctcacctct cctggttgga aaatggagaa 540
gaattaaatg ccatcaacac aacagtttcc caagatcctg aaactgagct ctatgctgtt 600
agcagcaaac tggatttcaa tatgacaacc aaccacagct tcatgtgtct catcaagtat 660
ggacatttaa gagtgaatca gaccttcaac tggaatacaa ccaagcaaga gcattttcct 720
gataacctgc tcccatcctg ggccattacc ttaatctcag taaatggaat ttttgtgata 780
tgctgcctga cctactgctt tgccccaaga tgcagagaga gaaggaggaa tgagagattg 840
agaagggaaa gtgtacgccc tgta 864

<210> SEQ ID NO 67
<211> LENGTH: 995
<212> TYPE: DNA
<213> ORGANISM: Homo sapiens
<220> FEATURE:
<223> OTHER INFORMATION: CD86/B7-2

<400> SEQUENCE: 67
cagccaaaat ggatccccag tgcactatgg gactgagtaa cattctcttt gtgatggcct 60
tcctgctctc tggtgctgct cctctgaaga ttcaagctta tttcaatgag actgcagacc 120
tgccatgcca atttgcaaac tctcaaaacc aaagcctgag tgagctagta gtattttggc 180
aggaccagga aaacttggtt ctgaatgagg tatacttagg caaagagaaa tttgacagtg 240
ttcattccaa gtatatgggc cgcacaagtt ttgattcgga cagttggacc ctgagacttc 300
acaatcttca gatcaaggac aagggcttgt atcaatgtat catccatcac aaaaagccca 360
caggaatgat tcgcatccac cagatgaatt ctgaactgtc agtgcttgct aacttcagtc 420
aacctgaaat agtaccaatt tctaatataa cagaaaatgt gtacataaat ttgacctgct 480
catctataca cggttaccca gaacctaaga agatgagtgt tttgctaaga accaagaatt 540
caactatcga gtatgatggt attatgcaga aatctcaaga taatgtcaca gaactgtacg 600
acgtttccat cagcttgtct gtttcattcc ctgatgttac gagcaatatg accatcttct 660
gtattctgga aactgacaag acgcggcttt tatcttcacc tttctctata gagcttgagg 720
accctcagcc tcccccagac cacattcctt ggattacagc tgtacttcca acagttatta 780
tatgtgtgat ggttttctgt ctaattctat ggaaatggaa gaagaagaag cggcctcgca 840
actcttataa atgtggaacc aacacaatgg agagggaaga gagtgaacag accaagaaaa 900
gagaaaaaat ccatatacct gaaagatctg atgaagccca gcgtgttttt aaaagttcga 960
agacatcttc atgcgacaaa agtgatacat gtttt 995

<210> SEQ ID NO 68
<211> LENGTH: 1095
<212> TYPE: DNA
<213> ORGANISM: Homo sapiens
<220> FEATURE:
<223> OTHER INFORMATION: CD244/2B4

<400> SEQUENCE: 68
atgctggggc aagtggtcac cctcatactc ctcctgctcc tcaaggtgta tcagggcaaa 60
ggatgccagg gatcagctga ccatgtggtt agcatctcgg gagtgcctct tcagttacaa 120
ccaaacagca tacagacgaa ggttgacagc attgcatgga agaagttgct gccctcacaa 180
aatggatttc atcacatatt gaagtgggag aatggctctt tgccttccaa tacttccaat 240
gatagattca gttttatagt caagaacttg agtcttctca tcaaggcagc tcagcagcag 300
gacagtggcc tctactgcct ggaggtcacc agtatatctg gaaaagttca gacagccacg 360
ttccaggttt ttgtatttga taaagttgag aaaccccgcc tacaggggca ggggaagatc 420
ctggacagag ggagatgcca agtggctctg tcttgcttgg tctccaggga tggcaatgtg 480
tcctatgctt ggtacagagg gagcaagctg atccagacag cagggaacct cacctacctg 540
gacgaggagg ttgacattaa tggcactcac acatatacct gcaatgtcag caatcctgtt 600
agctgggaaa gccacaccct gaatctcact caggactgtc agaatgccca tcaggaattc 660
agattttggc cgtttttggt gatcatcgtg attctaagcg cactgttcct tggcaccctt 720
gcctgcttct gtgtgtggag gagaaagagg aaggagaagc agtcagagac cagtcccaag 780
gaatttttga caatttacga agatgtcaag gatctgaaaa ccaggagaaa tcacgagcag 840
gagcagactt ttcctggagg ggggagcacc atctactcta tgatccagtc ccagtcttct 900
gctcccacgt cacaagaacc tgcatataca ttatattcat taattcagcc ttccaggaag 960
tctggatcca ggaagaggaa ccacagccct tccttcaata gcactatcta tgaagtgatt 1020
ggaaagagtc aacctaaagc ccagaaccct gctcgattga gccgcaaaga gctggagaac 1080
tttgatgttt attcc 1095

<210> SEQ ID NO 69

<211> LENGTH: 1251
<212> TYPE: DNA
<213> ORGANISM: Homo sapiens
<220> FEATURE:
<223> OTHER INFORMATION: CD155/PVR

<400> SEQUENCE: 69
atggcccgag ccatggccgc cgcgtggccg ctgctgctgg tggcgctact ggtgctgtcc 60
tggccacccc caggaaccgg ggacgtcgtc gtgcaggcgc ccacccaggt gcccggcttc 120
ttgggcgact ccgtgacgct gccctgctac ctacaggtgc ccaacatgga ggtgacgcat 180
gtgtcacagc tgacttgggc gcggcatggt gaatctggca gcatggccgt cttccaccaa 240
acgcagggcc ccagctattc ggagtccaaa cggctggaat tcgtggcagc cagactgggc 300
gcggagctgc ggaatgcctc gctgaggatg ttcgggttgc gcgtagagga tgaaggcaac 360
tacacctgcc tgttcgtcac gttcccgcag ggcagcagga gcgtggatat ctggctccga 420
gtgcttgcca agccccagaa cacagctgag gttcagaagg tccagctcac tggagagcca 480
gtgcccatgg cccgctgcgt ctccacaggg ggtcgcccgc cagcccaaat cacctggcac 540
tcagacctgg gcgggatgcc caatacgagc caggtgccag ggttcctgtc tggcacagtc 600
actgtcacca gcctctggat attggtgccc tcaagccagg tggacggcaa gaatgtgacc 660
tgcaaggtgg agcacgagag ctttgagaag cctcagctgc tgactgtgaa cctcaccgtg 720
tactaccccc cagaggtatc catctctggc tatgataaca actggtacct tggccagaat 780
gaggccaccc tgacctgcga tgctcgcagc aacccagagc ccacaggcta taattggagc 840
acgaccatgg gtcccctgcc accctttgct gtggcccagg gcgcccagct cctgatccgt 900
cctgtggaca aaccaatcaa cacaacttta atctgcaacg tcaccaatgc cctaggagct 960
cgccaggcag aactgaccgt ccaggtcaaa gagggacctc ccagtgagca ctcaggcatg 1020
tcccgtaacg ccatcatctt cctggttctg ggaatcctgg tttttctgat cctgctgggg 1080
atcgggattt atttctattg gtccaaatgt tcccgtgagg tcctttggca ctgtcatctg 1140
tgtccctcga gtacagagca tgccagcgcc tcagctaatg ggcatgtctc ctattcagct 1200
gtgagcagag agaacagctc ttcccaggat ccacagacag agggcacaag g 1251

<210> SEQ ID NO 70
<211> LENGTH: 1614
<212> TYPE: DNA
<213> ORGANISM: Homo sapiens
<220> FEATURE:
<223> OTHER INFORMATION: CD122/nectin-2

<400> SEQUENCE: 70
atggcccggg ccgctgccct cctgccgtcg agatcgccgc cgacgccgct gctgtggccg 60
ctgctgctgc tgctgctcct ggaaaccgga gcccaggatg tgcgagttca agtgctaccc 120
gaggtgcgag gccagctcgg gggcaccgtg gagctgccgt gccacctgct gccacctgtt 180
cctggactgt acatctccct ggtgacctgg cagcgcccag atgcacctgc gaaccaccag 240
aatgtggccg ccttccaccc taagatgggt cccagcttcc ccagcccgaa gcctggcagc 300
gagcggctgt ccttcgtctc tgccaagcag agcactgggc aagacacaga ggcagagctc 360
caggacgcca cgctggccct ccacgggctc acggtggagg acgagggcaa ctacacttgc 420
gagtttgcca ccttccccaa ggggtccgtc cgagggatga cctggctcag agtcatagcc 480
aagcccaaga accaagctga ggcccagaag gtcacgttca gccaggaccc tacgacagtg 540
gccctctgca tctccaaaga gggccgccca cctgcccgga tctcctggct ctcatccctg 600

```
gactgggaag ccaaagagac tcaggtgtca gggaccctgg ccggaactgt cactgtcacc    660

agccgcttca ccttggtgcc ctcgggccga gcagatggtg tcacggtcac ctgcaaagtg    720

gagcatgaga gcttcgagga accagccctg atacctgtga ccctctctgt acgctaccct    780

cctgaagtgt ccatctccgg ctatgatgac aactggtacc tcggccgtac tgatgccacc    840

ctgagctgtg acgtccgcag caacccagag cccacgggct atgactggag cacgacctca    900

ggcaccttcc cgacctccgc agtggcccag ggctcccagc tggtcatcca cgcagtggac    960

agtctgttca ataccacctt cgtctgcaca gtcaccaatg ccgtgggcat gggccgcgct   1020

gagcaggtca tctttgtccg agagaccccc aacacagcag gcgcaggggc cacaggcggc   1080

atcatcgggg gcatcatcgc cgccatcatt gctactgctg tggctgccac gggcatcctt   1140

atctgccggc agcagcggaa ggagcagacg ctgcaggggg cagaggagga cgaagacctg   1200

gagggacctc cctcctacaa gccaccgacc ccaaaagcga agctggaggc acaggagatg   1260

ccctcccagc tcttcactct gggggcctcg gagcacagcc cactcaagac cccctacttt   1320

gatgctggcg cctcatgcac tgagcaggaa atgcctcgat accatgagct gcccaccttg   1380

gaagaacggt caggaccctt gcaccctgga gccacaagcc tggggtcccc catcccggtg   1440

cctccagggc cacctgctgt ggaagacgtt tccctggatc tagaggatga ggagggggag   1500

gaggaggaag agtatctgga caagatcaac cccatctatg atgctctgtc ctatagcagc   1560

ccctctgatt cctaccaggg caaaggcttt gtcatgtccc gggccatgta tgtg         1614
```

```
<210> SEQ ID NO 71
<211> LENGTH: 1008
<212> TYPE: DNA
<213> ORGANISM: Homo sapiens
<220> FEATURE:
<223> OTHER INFORMATION: CD226 antigen

<400> SEQUENCE: 71

atggattatc ctactttact tttggctctt cttcatgtat acagagctct atgtgaagag     60

gtgctttggc atacatcagt tccctttgcc gagaacatgt ctctagaatg tgtgtatcca    120

tcaatgggca tcttaacaca ggtggagtgg ttcaagatcg ggacccagca ggattccata    180

gccattttca gccctactca tggcatggtc ataaggaagc cctatgctga gagggtttac    240

tttttgaatt caacgatggc ttccaataac atgactcttt tctttcggaa tgcctctgaa    300

gatgatgttg gctactattc ctgctctctt tacacttacc cacagggaac ttggcagaag    360

gtgatacagg tggttcagtc agatagtttt gaggcagctg tgccatcaaa tagccacatt    420

gtttcggaac ctggaaagaa tgtcacactc acttgtcagc ctcagatgac gtggcctgtg    480

caggcagtga ggtgggaaaa gatccagccc cgtcagatcg acctcttaac ttactgcaac    540

ttggtccatg gcagaaattt cacctccaag ttcccaagac aaatagtgag caactgcagc    600

cacggaaggt ggagcgtcat cgtcatcccc gatgtcacag tctcagactc ggggctttac    660

cgctgctact tgcaggccag cgcaggagaa aacgaaacct tcgtgatgag attgactgta    720

gccgagggta aaaccgataa ccaatatacc ctctttgtgg ctggagggac agttttattg    780

ttgttgtttg ttatctcaat taccaccatc attgtcattt tccttaacag aaggagaagg    840

agagagagaa gagatctatt tacagagtcc tgggatacac agaaggcacc caataactat    900

agaagtccca tctctaccag tcaacctacc aatcaatcca tggatgatac aagagaggat    960

atttatgtca actatccaac cttctctcgc agaccaaaga ctagagtt                1008
```

-continued

<210> SEQ ID NO 72
<211> LENGTH: 545
<212> TYPE: DNA
<213> ORGANISM: Homo sapiens
<220> FEATURE:
<223> OTHER INFORMATION: CD160 antigen

<400> SEQUENCE: 72
ggatgctgtt ggaacccggc agaggctgct gtgccctggc catcctgctg gcaattgtgg 60
acatccagtc tggtggatgc attaacatca ccagctcagc ttcccaggaa ggaacgcgac 120
taaacttaat ctgtactgta tggcataaga aagaagaggc tgaggggttt gtagtgtttt 180
tgtgcaagga caggtctgga gactgttctc ctgagaccag tttaaaacag ctgagactta 240
aaagggatcc tgggatagat ggtgttggtg aaatatcatc tcagttgatg ttcaccataa 300
gccaagtcac accgttgcac agtgggacct accagtgttg tgccagaagc cagaagtcag 360
gtatccgcct tcagggccat tttttctcca ttctattcac agagacaggg aactacacag 420
tgacgggatt gaaacaaaga caacaccttg agttcagcca taatgaaggc actctcagtt 480
caggcttcct acaagaaaag gtctgggtaa tgctggtcac cagccttgtg gcccttcaag 540
ctttg 545

<210> SEQ ID NO 73
<211> LENGTH: 264
<212> TYPE: DNA
<213> ORGANISM: Homo sapiens
<220> FEATURE:
<223> OTHER INFORMATION: human U6 RNA Pol III promoter

<400> SEQUENCE: 73
aaggtcgggc aggaagaggg cctatttccc atgattcctt catatttgca tatacgatac 60
aaggctgtta gagagataat tagaattaat ttgactgtaa acacaaagat attagtacaa 120
aatacgtgac gtagaaagta ataatttctt gggtagtttg cagttttaaa attatgtttt 180
aaaatggact atcatatgct taccgtaact tgaaagtatt tcgatttctt ggctttatat 240
atcttgtgga aaggacgaaa ctag 264

<210> SEQ ID NO 74
<211> LENGTH: 99
<212> TYPE: DNA
<213> ORGANISM: Homo sapiens
<220> FEATURE:
<223> OTHER INFORMATION: human H1 RNA Pol III promoter

<400> SEQUENCE: 74
atatttgcat gtcgctatgt gttctgggaa atcaccataa acgtgaaatg tctttggatt 60
tgggaatctt ataagttctg tatgagacca ctccctagg 99

<210> SEQ ID NO 75
<211> LENGTH: 58
<212> TYPE: DNA
<213> ORGANISM: Artificial Sequence
<220> FEATURE:
<223> OTHER INFORMATION: shRNA-encoding sequence targeting muPD-L1

<400> SEQUENCE: 75
ccggccgaaa tgatacacaa ttcgactcga gtcgaattgt gtatcatttc ggtttttg 58

<210> SEQ ID NO 76
<211> LENGTH: 57

<212> TYPE: DNA
<213> ORGANISM: Artificial Sequence
<220> FEATURE:
<223> OTHER INFORMATION: shRNA-encoding sequence targeting muSIRPA

<400> SEQUENCE: 76
ccggccacaa ctggaatgtc ttcatctcga gatgaagaca ttccagttgt ggtttt 57

<210> SEQ ID NO 77
<211> LENGTH: 58
<212> TYPE: DNA
<213> ORGANISM: Artificial Sequence
<220> FEATURE:
<223> OTHER INFORMATION: shRNA-encoding sequence targeting muTREX1, clone 1

<400> SEQUENCE: 77
ccggacaacc aacctaaggc cacatctcga gatgtggcct taggttggtt gttttttg 58

<210> SEQ ID NO 78
<211> LENGTH: 58
<212> TYPE: DNA
<213> ORGANISM: Artificial Sequence
<220> FEATURE:
<223> OTHER INFORMATION: shRNA-encoding sequence targeting muTREX1, clone 2

<400> SEQUENCE: 78
ccggcctaga tggtaccttc tgtgtctcga gacacagaag gtaccatcta ggtttttg 58

<210> SEQ ID NO 79
<211> LENGTH: 3966
<212> TYPE: DNA
<213> ORGANISM: Artificial Sequence
<220> FEATURE:
<223> OTHER INFORMATION: Vector1-human shTREX1-1_shPDL1-1

<400> SEQUENCE: 79
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccctt aaaggaacca attcagtcga gaattggtac 600
catatttgca tgtcgctatg tgttctggga aatcaccata aacgtgaaat gtctttggat 660
ttgggaatct tataagttct gtatgagacc actccctagg cagcgcatgg gcgtcaattc 720
tagagattga cgcccatgcg ctgctttttt cgacagatct ggcgcgccat agtggccagc 780
ggccgcaggt aagccagccc aggcctcgcc ctccagctca aggcgggaca ggtgccctag 840
agtagcctgc atccagggac aggccccagc cgggtgctga cacgtccacc tccatctctt 900
cctcaggtct gcccgggtgg catccctgtg acccctcccc agtgcctctc ctggccctgg 960
aagttgccac tccagtgccc accagccttg tcctaataaa attaagttgc atcattttgt 1020

-continued

```
ctgactaggt gtccttctat aatattatgg ggtggagggg ggtggtatgg agcaaggggc   1080
ccaagttaac ttgtttattg cagcttataa tggttacaaa taaagcaata gcatcacaaa   1140
tttcacaaat aaagcatttt tttcactgca ttctagttgt ggtttgtcca aactcatcaa   1200
tgtatcttat catgtctgga tccaaggtcg ggcaggaaga gggcctattt cccatgattc   1260
cttcatattt gcatatacga tacaaggctg ttagagagat aattagaatt aatttgactg   1320
taaacacaaa gatattagta caaaatacgt gacgtagaaa gtaataattt cttgggtagt   1380
ttgcagtttt aaaattatgt tttaaaatgg actatcatat gcttaccgta acttgaaagt   1440
atttcgattt cttggcttta tatatcttgt ggaaaggacg aaactaggta gagtatggta   1500
gcaatatcta gagtattgct accatactct actttttttcg agtagctaga gaattcatgg   1560
taatagcgat gactaatacg tagatgtact gccaagtagg aaagtcccat aaggtcatgt   1620
actgggcata atgccaggcg ggccatttac cgtcattgac gtcaataggg ggcgtacttg   1680
gcatatgata cacttgatgt actgccaagt gggcagttta ccgtaaatag tccacccatt   1740
gacgtcaatg gaaagtccct attggcgtta ctatgggaac atacgtcatt attgacgtca   1800
atgggcgggg gtcgttgggc ggtcagccag gcgggccatt taccgtaagt tatgtaacgc   1860
ggaactccat atatgggcta tgaactaatg accccgtaat tgattactat taataactag   1920
ccatccagct gatatcccat ggtcatagct gtttcctggc agctctggcc cgtgtctcaa   1980
aatctctgat gttacattgc acaagataaa aatatatcat catgaacaat aaaactgtct   2040
gcttacataa acagtaatac aaggggtgtt atgaaaaatg ttggttttat cggctggcgc   2100
ggaatggtcg gctctgttct catgcaacgc atggtagagg agcgcgattt cgacgctatt   2160
cgccctgttt tcttttctac ctcccagttt ggacaggcgg cgcccacctt cggcgacacc   2220
tccaccggca cgctacagga cgcttttgat ctggatgcgc taaaagcgct cgatatcatc   2280
gtgacctgcc agggcggcga ttataccaac gaaatttatc caaagctgcg cgaaagcgga   2340
tggcagggtt actggattga tgcggcttct acgctgcgca tgaaagatga tgccattatt   2400
attctcgacc cggtcaacca ggacgtgatt accgacggcc tgaacaatgg cgtgaagacc   2460
tttgtgggcg gtaactgtac cgttagcctg atgttgatgt cgctgggcgg tctctttgcc   2520
cataatctcg ttgactgggt atccgtcgcg acctatcagg ccgcctccgg cggcggcgcg   2580
cgccatatgc gcgagctgtt aacccagatg ggtcagttgt atggccatgt cgccgatgaa   2640
ctggcgacgc cgtcttccgc aattcttgat attgaacgca aagttacggc attgacccgc   2700
agcggcgagc tgccggttga taactttggc gtaccgctgg cgggaagcct gatcccctgg   2760
atcgacaaac agctcgataa cggccagagc cgcgaagagt ggaaaggcca ggcggaaacc   2820
aacaagattc tcaatactgc ctctgtgatt ccggttgatg gtttgtgtgt gcgcgtcggc   2880
gcgctgcgct gtcacagcca ggcgttcacc atcaagctga aaaaagaggt atccattccg   2940
acggtggaag aactgctggc ggcacataat ccgtgggcga aagtggtgcc gaacgatcgt   3000
gatatcacta tgcgcgaatt aaccccggcg gcggtgaccg gcacgttgac tacgccggtt   3060
ggtcgtctgc gtaagctgaa catggggcca gagttcttgt cggcgtttac cgtaggcgac   3120
cagttgttat ggggcgccgc cgagccgctg cgtcgaatgc tgcgccagtt ggcgtagtca   3180
gaattggtta attggttgta acactggcag agcattacgc tgacttgacg ggacggcgca   3240
agctcatgac caaaatccct taacgtgagt tacgcgtcgt tccactgagc gtcagacccc   3300
gtagaaaaga tcaaaggatc ttcttgagat cctttttttc tgcgcgtaat ctgctgcttg   3360
caaacaaaaa aaccaccgct accagcggtg gtttgtttgc cggatcaaga gctaccaact   3420
```

```
cttttttccga aggtaactgg cttcagcaga gcgcagatac caaatactgt ccttctagtg   3480

tagccgtagt taggccacca cttcaagaac tctgtagcac cgcctacata cctcgctctg   3540

ctaatcctgt taccagtggc tgctgccagt ggcgataagt cgtgtcttac cgggttggac   3600

tcaagacgat agttaccgga taaggcgcag cggtcgggct gaacgggggg ttcgtgcaca   3660

cagcccagct tggagcgaac gacctacacc gaactgagat acctacagcg tgagcattga   3720

gaaagcgcca cgcttcccga agggagaaag gcggacaggt atccggtaag cggcagggtc   3780

ggaacaggag agcgcacgag ggagcttcca gggggaaacg cctggtatct ttatagtcct   3840

gtcgggtttc gccacctctg acttgagcgt cgatttttgt gatgctcgtc aggggggcgg   3900

agcctatgga aaaacgccag caacgcggcc tttttacggt tcctggcctt ttgctggcct   3960

tttgct                                                               3966
```

<210> SEQ ID NO 80
<211> LENGTH: 3972
<212> TYPE: DNA
<213> ORGANISM: Artificial Sequence
<220> FEATURE:
<223> OTHER INFORMATION: Vector2-mouse shTREX1-1_shPDL1-1

<400> SEQUENCE: 80

```
ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccct aaaggaacca attcagtcga gaattggtac    600

catatttgca tgtcgctatg tgttctggga aatcaccata aacgtgaaat gtctttggat    660

ttgggaatct tataagttct gtatgagacc actccctaga caaccaacct aaggccacat    720

ctcgagatgt ggccttaggt tggttgtttt tttcgacaga tctggcgcgc catagtggcc    780

agcggccgca ggtaagccag cccaggcctc gccctccagc tcaaggcggg acaggtgccc    840

tagagtagcc tgcatccagg gacaggcccc agccgggtgc tgacacgtcc acctccatct    900

cttcctcagg tctgcccggg tggcatccct gtgacccctc cccagtgcct ctcctggccc    960

tggaagttgc cactccagtg cccaccagcc ttgtcctaat aaaattaagt tgcatcattt   1020

tgtctgacta ggtgtccttc tataatatta tggggtggag gggggtggta tggagcaagg   1080

ggcccaagtt aacttgttta ttgcagctta taatggttac aaataaagca atagcatcac   1140

aaatttcaca aataaagcat ttttttcact gcattctagt tgtggtttgt ccaaactcat   1200

caatgtatct tatcatgtct ggatccaagg tcgggcagga agagggccta tttcccatga   1260

ttccttcata tttgcatata cgatacaagg ctgttagaga gataattaga attaatttga   1320

ctgtaaacac aaagatatta gtacaaaata cgtgacgtag aaagtaataa tttcttgggt   1380

agtttgcagt tttaaaatta tgttttaaaa tggactatca tatgcttacc gtaacttgaa   1440
```

-continued

```
agtatttcga tttcttggct ttatatatct tgtggaaagg acgaaactag ccgaaatgat   1500
acacaattcg actcgagtcg aattgtgtat catttcggtt ttttcgagta gctagagaat   1560
tcatggtaat agcgatgact aatacgtaga tgtactgcca agtaggaaag tcccataagg   1620
tcatgtactg ggcataatgc caggcgggcc atttaccgtc attgacgtca atagggggcg   1680
tacttggcat atgatacact tgatgtactg ccaagtgggc agtttaccgt aaatagtcca   1740
cccattgacg tcaatggaaa gtccctattg gcgttactat gggaacatac gtcattattg   1800
acgtcaatgg gcgggggtcg ttgggcggtc agccaggcgg gccatttacc gtaagttatg   1860
taacgcggaa ctccatatat gggctatgaa ctaatgaccc cgtaattgat tactattaat   1920
aactagccat ccagctgata tcccatggtc atagctgttt cctggcagct ctggcccgtg   1980
tctcaaaatc tctgatgtta cattgcacaa gataaaaata tatcatcatg aacaataaaa   2040
ctgtctgctt acataaacag taatacaagg ggtgttatga aaatgttgg ttttatcggc   2100
tggcgcggaa tggtcggctc tgttctcatg caacgcatgg tagaggagcg cgatttcgac   2160
gctattcgcc ctgttttctt ttctacctcc cagtttggac aggcggcgcc caccttcggc   2220
gacacctcca ccggcacgct acaggacgct tttgatctgg atgcgctaaa agcgctcgat   2280
atcatcgtga cctgccaggg cggcgattat accaacgaaa tttatccaaa gctgcgcgaa   2340
agcggatggc agggttactg gattgatgcg gcttctacgc tgcgcatgaa agatgatgcc   2400
attattattc tcgacccggt caaccaggac gtgattaccg acggcctgaa caatggcgtg   2460
aagacctttg tgggcggtaa ctgtaccgtt agcctgatgt tgatgtcgct gggcggtctc   2520
tttgcccata atctcgttga ctgggtatcc gtcgcgacct atcaggccgc ctccggcggc   2580
ggcgcgcgcc atatgcgcga gctgttaacc cagatgggtc agttgtatgg ccatgtcgcc   2640
gatgaactgg cgacgccgtc ttccgcaatt cttgatattg aacgcaaagt tacggcattg   2700
acccgcagcg gcgagctgcc ggttgataac tttggcgtac cgctggcggg aagcctgatc   2760
ccctggatcg acaaacagct cgataacggc cagagccgcg aagagtggaa aggccaggcg   2820
gaaaccaaca agattctcaa tactgcctct gtgattccgg ttgatggttt gtgtgtgcgc   2880
gtcggcgcgc tgcgctgtca cagccaggcg ttcaccatca agctgaaaaa agaggtatcc   2940
attccgacgg tggaagaact gctggcggca cataatccgt gggcgaaagt ggtgccgaac   3000
gatcgtgata tcactatgcg cgaattaacc ccggcggcgg tgaccggcac gttgactacg   3060
ccggttggtc gtctgcgtaa gctgaacatg gggccagagt tcttgtcggc gtttaccgta   3120
ggcgaccagt tgttatgggg cgccgccgag ccgctgcgtc gaatgctgcg ccagttggcg   3180
tagtcagaat tggttaattg gttgtaacac tggcagagca ttacgctgac ttgacgggac   3240
ggcgcaagct catgaccaaa atcccttaac gtgagttacg cgtcgttcca ctgagcgtca   3300
gaccccgtag aaaagatcaa aggatcttct tgagatcctt tttttctgcg cgtaatctgc   3360
tgcttgcaaa caaaaaaacc accgctacca gcggtggttt gtttgccgga tcaagagcta   3420
ccaactcttt ttccgaaggt aactggcttc agcagagcgc agataccaaa tactgtcctt   3480
ctagtgtagc cgtagttagg ccaccacttc aagaactctg tagcaccgcc tacatacctc   3540
gctctgctaa tcctgttacc agtggctgct gccagtggcg ataagtcgtg tcttaccggg   3600
ttggactcaa gacgatagtt accggataag gcgcagcggt cgggctgaac ggggggttcg   3660
tgcacacagc ccagcttgga gcgaacgacc tacaccgaac tgagatacct acagcgtgag   3720
cattgagaaa gcgccacgct tcccgaaggg agaaaggcgg acaggtatcc ggtaagcggc   3780
agggtcggaa caggagagcg cacgagggag cttccagggg gaaacgcctg gtatctttat   3840
```

agtcctgtcg ggtttcgcca cctctgactt gagcgtcgat ttttgtgatg ctcgtcaggg 3900
gggcggagcc tatggaaaaa cgccagcaac gcggcctttt tacggttcct ggccttttgc 3960
tggccttttg ct 3972

<210> SEQ ID NO 81
<211> LENGTH: 1281
<212> TYPE: DNA
<213> ORGANISM: Salmonella typhimurium
<220> FEATURE:
<223> OTHER INFORMATION: aroA

<400> SEQUENCE: 81
atggaatccc tgacgttaca acccatcgcg cgggtcgatg gcgccattaa tttacctggc 60
tccaaaagtg tttcaaaccg tgctttgctc ctggcggctt tagcttgtgg taaaaccgct 120
ctgacgaatc tgctggatag cgatgacgtc cgccatatgc tcaatgccct gagcgcgttg 180
gggatcaatt acaccctttc tgccgatcgc acccgctgtg atatcacggg taatggcggc 240
gcattacgtg cgccaggcgc tctggaactg tttctcggta atgccggaac cgcgatgcgt 300
ccgttagcgg cagcgctatg tctggggcaa aatgagatag tgttaaccgg cgaaccgcgt 360
atgaaagagc gtccgatagg ccatctggtc gattcgctgc gtcagggcgg ggcgaatatt 420
gattacctgg agcaggaaaa ctatccgccc ctgcgtctgc gcggcggttt taccggcggc 480
gacattgagg ttgatggtag cgtttccagc cagttcctga ccgctctgct gatgacggcg 540
ccgctggccc ctaaagacac aattattcgc gttaaaggcg aactggtatc aaaaccttac 600
atcgatatca cgctaaattt aatgaaaacc tttggcgtgg agatagcgaa ccaccactac 660
caacaatttg tcgtgaaggg aggtcaacag tatcactctc caggtcgcta tctggtcgag 720
ggcgatgcct cgtcagcgtc ctattttctc gccgctgggg cgataaaagg cggcacggta 780
aaagtgaccg gaattggccg caaaagtatg cagggcgata ttcgttttgc cgatgtgctg 840
gagaaaatgg gcgcgaccat tacctggggc gatgatttta ttgcctgcac gcgcggtgaa 900
ttgcacgcca tagatatgga tatgaaccat attccggatg cggcgatgac gattgccacc 960
acggcgctgt ttgcgaaagg aaccacgacg ttgcgcaata tttataactg gcgagtgaaa 1020
gaaaccgatc gcctgttcgc gatggcgacc gagctacgta aagtgggcgc tgaagtcgaa 1080
gaagggcacg actatattcg tatcacgccg ccggcgaagc tccaacacgc ggatattggc 1140
acgtacaacg accaccgtat ggcgatgtgc ttctcactgg tcgcactgtc cgatacgcca 1200
gttacgatcc tggaccctaa atgtaccgca aaaacgttcc ctgattattt cgaacaactg 1260
gcgcgaatga gtacgcctgc c 1281

<210> SEQ ID NO 82
<211> LENGTH: 1094
<212> TYPE: DNA
<213> ORGANISM: Salmonella typhimurium
<220> FEATURE:
<223> OTHER INFORMATION: aroC

<400> SEQUENCE: 82
acggagccgt gatggcagga aacacaattg gacaactctt tcgcgtaacc actttcggcg 60
aatcacacgg gctggcgctt gggtgtatcg tcgatggcgt gccgcccggc atcccgttga 120
cggaggccga tctgcaacac gatctcgaca gacgccgccc cggcacctcg cgctatacta 180
cccagcgccg cgaaccggac caggtaaaaa ttctctccgg cgtgtttgat ggcgtgacga 240

```
ccggcaccag cattggccta ctgattgaaa acaccgatca gcgctcgcag gactacagcg    300

cgattaaaga tgtttttcgt ccgggacacg cggattacac ctatgagcag aaatacggcc    360

tgcgcgatta ccgtggcggt ggacgttctt ccgcgcgtga aaccgcgatg cgcgtagcgg    420

caggggcgat cgccaagaaa tacctggcgg aaaagttcgg catcgaaatc cgcggctgcc    480

tgacccagat gggcgacatt ccgctggaga ttaaagactg gcgtcaggtt gagcttaatc    540

cgttcttttg tcccgatgcg gacaaacttg acgcgctgga cgaactgatg cgcgcgctga    600

aaaaagaggg tgactccatc ggcgcgaaag tgacggtgat ggcgagcggc gtgccggcag    660

ggcttggcga accggtattt gaccgactgg atgcggacat cgcccatgcg ctgatgagca    720

ttaatgcggt gaaaggcgtg gagatcggcg aaggatttaa cgtggtggcg ctgcgcggca    780

gccagaatcg cgatgaaatc acggcgcagg gttttcagag caaccacgct ggcggcatcc    840

tcggtggcat cagtagcggg caacacattg tggcgcatat ggcgctgaaa cctacctcca    900

gcattaccgt gccgggacgt acgatcaacc gggcaggtga agaagtcgaa atgatcacca    960

aagggcgcca cgatccgtgt gtggggattc gcgcagtgcc gatcgcagaa gccatgctgg   1020

cgatcgtgct gatggatcac ctgctgcgcc atcgggcaca gaatgcggat gtaaagacag   1080

agattccacg ctgg                                                     1094
```

<210> SEQ ID NO 83
<211> LENGTH: 767
<212> TYPE: DNA
<213> ORGANISM: Salmonella typhimurium
<220> FEATURE:
<223> OTHER INFORMATION: aroD

<400> SEQUENCE: 83

```
aagggtacca aatgaaaacc gtaactgtaa gagatctcgt ggttggcgaa ggcgcgccaa     60

agatcattgt gtcgctaatg ggaaaaacca ttaccgatgt gaaatcggaa gcactcgcct    120

accgtgaagc ggatttcgat attctggagt ggcgcgttga ccattttgcc aacgtgacaa    180

cggcggaaag cgtacttgag gccgccggcg ccatccggga gattattacc gataaaccct    240

tgctatttac cttccgcagc gcgaaagaag gcggcgaaca ggcgctaacc accggacagt    300

atatcgatct gaatcgtgca gcggttgaca gcggtctggt cgatatgatc gatcttgagc    360

tttttaccgg cgacgatgag gtgaaagcca ccgtcggcta tgctcatcaa cacaatgttg    420

cggtgatcat gtctaaccat gattttcata aaacgcccgc agcggaagag attgttcagc    480

gtctgcgtaa aatgcaggaa ctgggcgctg atattccgaa gatcgccgtc atgccacaga    540

ctaaagccga tgtcctgacc ttacttaccg ccactgtaga aatgcaggag cgctatgcgg    600

atcgtccgat tattaccatg tcgatgtcga aaaccggggt aatatctcgt cttgccggcg    660

aagtgttcgg ttctgcggca acgtttggcg cggtgaaaaa agcatctgcg ccgggacaaa    720

tatcggtagc cgatctgcgt accgtattaa ctatattgca ccaggcg                  767
```

<210> SEQ ID NO 84
<211> LENGTH: 684
<212> TYPE: DNA
<213> ORGANISM: Salmonella typhimurium
<220> FEATURE:
<223> OTHER INFORMATION: PhoP

<400> SEQUENCE: 84

```
aagggagaag agatgatgcg cgtactggtt gtagaggata atgcattatt acgccaccac     60

ctgaaggttc agctccagga ttcaggtcac caggtcgatg ccgcagaaga tgccagggaa    120
```

-continued

```
gctgattact accttaatga acaccttccg gatatcgcta ttgtcgattt aggtctgccg    180

gatgaagacg gcctttcctt aatacgccgc tggcgcagca gtgatgtttc actgccggtt    240

ctggtgttaa ccgcgcgcga aggctggcag gataaagtcg aggttctcag ctccggggcc    300

gatgactacg tgacgaagcc attccacatc gaagaggtaa tggcgcgtat gcaggcgtta    360

atgcgccgta atagcggtct ggcctcccag gtgatcaaca tcccgccgtt ccaggtggat    420

ctctcacgcc gggaattatc cgtcaatgaa gaggtcatca aactcacggc gttcgaatac    480

accattatgg aaacgcttat ccgtaacaac ggtaaagtgg tcagcaaaga ttcgctgatg    540

cttcagctgt atccggatgc ggaactgcgg gaaagtcata ccattgatgt tctcatgggg    600

cgtctgcgga aaaaaataca ggcccagtat ccgcacgatg tcattaccac cgtacgcgga    660

caaggatatc tttttgaatt gcgc                                           684
```

<210> SEQ ID NO 85
<211> LENGTH: 1461
<212> TYPE: DNA
<213> ORGANISM: Salmonella typhimurium
<220> FEATURE:
<223> OTHER INFORMATION: PhoQ

<400> SEQUENCE: 85

```
atgaataaat ttgctcgcca ttttctgccg ctgtcgctgc gggttcgttt tttgctggcg     60

acagccggcg tcgtgctggt gctttctttg gcatatggca tagtggcgct ggtcggctat    120

agcgtaagtt ttgataaaac cacctttcgt ttgctgcgcg gcgaaagcaa cctgttttat    180

accctcgcca aatgggaaaa taataaaatc agcgttgagc tgcctgaaaa tctggacatg    240

caaagcccga ccatgacgct gatttacgat gaaacgggca aattattatg gacgcagcgc    300

aacattccct ggctgattaa aagcattcaa ccggaatggt taaaaacgaa cggcttccat    360

gaaattgaaa ccaacgtaga cgccaccagc acgctgttga gcgaagacca ttccgcgcag    420

gaaaaactca aagaagtacg tgaagatgac gatgatgccg agatgaccca ctcggtagcg    480

gtaaatattt atcctgccac ggcgcggatg ccgcagttaa ccatcgtggt ggtcgatacc    540

attccgatag aactaaaacg ctcctatatg gtgtggagct ggttcgtata cgtgctggcc    600

gccaatttac tgttagtcat tcctttactg tggatcgccg cctggtggag cttacgccct    660

atcgaggcgc tggcgcggga agtccgcgag cttgaagatc atcaccgcga aatgctcaat    720

ccggagacga cgcgtgagct gaccagcctt gtgcgcaacc ttaatcaact gctcaaaagc    780

gagcgtgaac gttataacaa ataccgcacg accctgaccg acctgacgca cagtttaaaa    840

acgccgctcg cggttttgca gagtacgtta cgctctttac gcaacgaaaa gatgagcgtc    900

agcaaagctg aaccggtgat gctggaacag atcagccgga tttcccagca gatcggctat    960

tatctgcatc gcgccagtat gcgcggtagc ggcgtgttgt taagccgcga actgcatccc   1020

gtcgcgccgt tgttagataa cctgatttct gcgctaaata aagtttatca gcgtaaaggg   1080

gtgaatatca gtatggatat ttcaccagaa atcagttttg tcggcgagca aaacgacttt   1140

gtcgaagtga tgggcaacgt actggacaac gcttgtaaat attgtctgga gtttgtcgag   1200

atttcggctc gccagaccga cgatcatttg catattttcg tcgaagatga cggcccaggc   1260

attccccaca gcaaacgttc cctggtgttt gatcgcggtc agcgcgccga taccctacga   1320

ccaggacaag gcgtggggct ggctgtcgcg cgcgagatta cggaacaata cgccgggcag   1380

atcattgcca gcgacagtct gctcggtggc gcccgtatgg aggtcgtttt tggccgacag   1440
```

catcccacac agaaagagga a 1461

<210> SEQ ID NO 86
<211> LENGTH: 2731
<212> TYPE: DNA
<213> ORGANISM: Salmonella typhimurium
<220> FEATURE:
<223> OTHER INFORMATION: Adenylate cyclase (cyaA)

<400> SEQUENCE: 86
tctttcttta cggtcaatga gcaaggtgtt aaattgatca cgttttagac catttttttcg 60 tcggtattag ataaaaatat gcaggcgaga aagggtaacg gttatttttg acatacggtt 120
tatcccgaat ggcgacggtc aagtactgac ctgcaccatg acgggtagca acatcaggcg 180
atacgtcttg tacctctata ttgagactct gaaacagaga ctggatgcca taaatcaact 240
gcgtgtggat cgcgcgcttg ctgccatggg acccgctttt cagcaggttt acagtcttct 300
gccgacatta ttgcactatc accatccact gatgccgggt taccttgatg gtaacgttcc 360
cagcggtatt tgcttctaca cgcctgatga aacccaacgc cactatctga acgaacttga 420
gctgtaccgc ggtatgacgc cgcaggaccc gccgaagggc gagctgccga ttaccggcgt 480
ttacaccatg ggcagcacct cctcggtcgg gcagagctgc tcgtccgacc tggatatctg 540
ggtgtgccat cagtcctggc tcgacggcga agagcgtcag ttgctgcaac gtaagtgtag 600
cctgctggaa agctgggccg cctcgcttgg cgttgaggtg agcttcttcc tgatcgacga 660
gaaccgtttc cgccataacg aaagcggcag tctgggcggg gaagactgtg gttctacgca 720
gcatatcctg ttgcttgatg agttttatcg taccgctgtg cgcctggccg ggaagcgtat 780
cctgtggagt atggtgccgt gcgacgaaga agagcattac gacgactatg tcatgacgct 840
ctatgcgcag ggcgtattaa cgccaaacga atggctggat ctggggggct taagctcgct 900
ctccgccgaa gagtactttg gcgccagcct gtggcagcta tacaagagca ttgactcgcc 960
gtacaaagcg gtgctgaaaa cgctgctgct ggaagcctat tcatgggaat atcctaaccc 1020
acgtctgctg gcgaaagata ttaaacaacg tctgcatgac ggtgaaatcg tatcgtttgg 1080
actcgatccc tactgcatga tgctggaacg ggtcactgaa tacctgacgg cgattgaaga 1140
tccgacgcgg ctggatttag tccgccgctg cttttacctg aaagtgtgcg agaaattaag 1200
tcgcgagcgt gcctgcgtag gctggcgtcg ggaagtatta agccagttag tcagcgagtg 1260
gggatgggac gacgcgcgtc tgaccatgct cgataatcgc gcaaactgga aaatcgatca 1320
ggtgcgcgaa gcccacaacg aattgctcga cgccatgatg caaagctatc gtaatctgat 1380
tcgctttgcg cggcgcaaca acctcagcgt gagtgccagc ccgcaggata tcggcgtact 1440
gacgcgtaag ctgtacgcgg cttttgaagc gttgccgggt aaagtcacgc tggtgaaccc 1500
gcagatatcg ccggatctgt ccgagccgaa tttaaccttt atccatgtgc cgccgggacg 1560
cgccaaccgt tcaggctggt atctctacaa ccgcgcgccg aacatggatt ccatcatcag 1620
ccatcagccg ctggaatata accgttatct taataagctg gtcgcgtggg cgtggttcaa 1680
cggcctgctg acgtcgcgaa cgcatctgtt tattaagggc aacggtattg tcgacctgcc 1740
taagttacag gagatggtcg ccgatgtttc gcaccatttc ccgctgcgct tgcctgctcc 1800
gacgccgaaa gcgctctaca gcccctgtga aattcgccat ctggcgatta tcgttaacct 1860
cgaatatgac ccgacggcgg cgtttcgcaa taaagtggtc cattttgact tccgtaagct 1920
ggacgttttc agctttggcg aagagcaaaa ctgtctgata ggcagtatcg acttgttata 1980
tcgcaactcg tggaacgaag tgcgtactct gcactttaac ggcgagcagg cgatgatcga 2040
agcgctgaaa acgattctgg ggaaaatgca ccaggatgcc gcgccgccgg atagcgtgga 2100
ggtgttctgc tacagtcagc atcttcgcgg cctgattcgc acccgtgtgc agcaactggt 2160
ctccgaatgt attgagctac gtctttccag cacccgtcag gagaccggtc gcttcaaggc 2220
gctgcgggtt tccgggcaga cgtgggggct attcttcgaa cgcttgaatg tctcggtgca 2280
gaagctggag aacgctatcg aattctacgg cgcgatttcg cataacaagc tgcacgggct 2340
gtcggtacag gtggaaacca accaggtgaa attgccgtca gtggtggatg gcttcgccag 2400
cgaagggatt atccagttct tctttgaaga aacaggcgat gagaaaggct ttaacattta 2460
tattctggat gaaagtaacc gggcggaagt atatcaccac tgcgaaggta gcaaggaaga 2520
actggtgcgc gacgtcagtc gcttctattc gtcatcgcac gatcgcttca cgtatggctc 2580
cagttttatc aactttaacc tgccgcagtt ctaccagata gtgaaaaccg atggccgcgc 2640
gcaggtgatc ccattccgta cgcagcctat caacaccgtg ccgccagcaa accaggatca 2700
tgacgcgccg ctattgcagc agtatttttc g 2731

<210> SEQ ID NO 87
<211> LENGTH: 826
<212> TYPE: DNA
<213> ORGANISM: Salmonella typhimurium
<220> FEATURE:
<223> OTHER INFORMATION: cAMP-activated global transcriptional regulator (crp)

<400> SEQUENCE: 87
aagctatgct aaaacagaca agatgctaca gtaatacatt gacgtactgc atgtatgcag 60
aggacatcac attacaggct acaatctatt ttcgtagccc ccttcccagg tagcgggaag 120
tatatttttg caaccccaga gacagtgccg ttttctggct ctggagacag cttataacag 180
aggataaccg cgcatggtgc ttggcaaacc gcaaacagac ccgactcttg aatggttctt 240
gtctcattgc cacattcata agtacccgtc aaagagcacg ctgattcacc agggtgaaaa 300
agcagaaacg ctgtactaca tcgttaaagg ctccgtggca gtgctgatca aagatgaaga 360
agggaaagaa atgatccttt cttatctgaa tcagggtgat tttattggtg aactgggcct 420
gtttgaagaa ggccaggaac gcagcgcctg ggtacgtgcg aaaaccgcat gtgaggtcgc 480
tgaaatttcc tacaaaaaat ttcgccaatt aatccaggtc aacccggata ttctgatgcg 540
cctctcttcc cagatggctc gtcgcttaca agtcacctct gaaaaagtag gtaacctcgc 600
cttccttgac gtcaccgggc gtatcgctca gacgctgctg aatctggcga aacagcccga 660
tgccatgacg cacccggatg ggatgcagat caaaatcact cgtcaggaaa tcggccagat 720
cgtcggctgc tcccgcgaaa ccgttggtcg tattttgaaa atgctggaag atcaaaacct 780
gatctccgcg catggcaaga ccatcgtcgt ctacggcacc cgttaa 826

<210> SEQ ID NO 88
<211> LENGTH: 1566
<212> TYPE: DNA
<213> ORGANISM: Homo sapiens
<220> FEATURE:
<223> OTHER INFORMATION: cyclic GMP-AMP (cGAMP) synthase (cGAS), isoform 1

<400> SEQUENCE: 88
atgcagcctt ggcacggaaa ggccatgcag agagcttccg aggccggagc cactgccccc 60
aaggcttccg cacggaatgc caggggcgcc ccgatggatc ccaccgagtc tccggctgcc 120

-continued

```
cccgaggccg ccctgcctaa ggcgggaaag ttcggccccg ccaggaagtc gggatcccgg    180

cagaaaaaga gcgccccgga cacccaggag aggccgcccg tccgcgcaac tggggcccgc    240

gccaaaaagg cccctcagcg cgcccaggac acgcagccgt ctgacgccac cagcgcccct    300

ggggcagagg ggctggagcc tcctgcggct cgggagccgg ctctttccag ggctggttct    360

tgccgccaga ggggcgcgcg ctgctccacg aagccaagac ctccgcccgg gccctgggac    420

gtgcccagcc ccggcctgcc ggtctcggcc cccattctcg tacggaggga tgcggcgcct    480

ggggcctcga agctccgggc ggttttggag aagttgaagc tcagccgcga tgatatctcc    540

acggcggcgg ggatggtgaa aggggttgtg gaccacctgc tgctcagact gaagtgcgac    600

tccgcgttca gaggcgtcgg gctgctgaac accgggagct actatgagca cgtgaagatt    660

tctgcaccta atgaatttga tgtcatgttt aaactggaag tccccagaat tcaactagaa    720

gaatattcca acactcgtgc atattacttt gtgaaattta aaagaaatcc gaaagaaaat    780

cctctgagtc agtttttaga aggtgaaata ttatcagctt ctaagatgct gtcaaagttt    840

aggaaaatca ttaaggaaga aattaacgac attaaagata cagatgtcat catgaagagg    900

aaaagaggag ggagccctgc tgtaacactt cttattagtg aaaaaatatc tgtggatata    960

accctggctt tggaatcaaa aagtagctgg cctgctagca cccaagaagg cctgcgcatt   1020

caaaactggc tttcagcaaa agttaggaag caactacgac taaagccatt ttaccttgta   1080

cccaagcatg caaaggaagg aaatggtttc caagaagaaa catggcggct atccttctct   1140

cacatcgaaa aggaaatttt gaacaatcat ggaaaatcta aaacgtgctg tgaaaacaaa   1200

gaagagaaat gttgcaggaa agattgttta aaactaatga aataccttt  agaacagctg   1260

aaagaaaggt ttaaagacaa aaaacatctg gataaattct cttcttatca tgtgaaaact   1320

gccttctttc acgtatgtac ccagaaccct caagacagtc agtgggaccg caaagacctg   1380

ggcctctgct ttgataactg cgtgacatac tttcttcagt gcctcaggac agaaaaactt   1440

gagaattatt ttattcctga attcaatcta ttctctagca acttaattga caaaagaagt   1500

aaagaatttc tgacaaagca aattgaatat gaaagaaaca atgagtttcc agtttttgat   1560

gaattt                                                              1566
```

```
<210> SEQ ID NO 89
<211> LENGTH: 1137
<212> TYPE: DNA
<213> ORGANISM: Homo sapiens
<220> FEATURE:
<223> OTHER INFORMATION: Stimulator of Interferon Genes (STING)(H232
      Allele)

<400> SEQUENCE: 89

atgccccact ccagcctgca tccatccatc ccgtgtccca ggggtcacgg ggcccagaag     60

gcagccttgg ttctgctgag tgcctgcctg gtgacccttt gggggctagg agagccacca    120

gagcacactc tccggtacct ggtgctccac ctagcctccc tgcagctggg actgctgtta    180

aacggggtct gcagcctggc tgaggagctg cgccacatcc actccaggta ccggggcagc    240

tactggagga ctgtgcgggc ctgcctgggc tgcccccctcc gccgtggggc cctgttgctg    300

ctgtccatct atttctacta ctccctccca aatgcggtcg gcccgccctt cacttggatg    360

cttgccctcc tgggcctctc gcaggcactg aacatcctcc tgggcctcaa gggcctggcc    420

ccagctgaga tctctgcagt gtgtgaaaaa gggaatttca acgtggccca tgggctggca    480

tggtcatatt acatcggata tctgcggctg atcctgccag agctccaggc ccggattcga    540
```

```
acttacaatc agcattacaa caacctgcta cggggtgcag tgagccagcg gctgtatatt    600

ctcctcccat tggactgtgg ggtgcctgat aacctgagta tggctgaccc caacattcgc    660

ttcctggata aactgcccca gcagaccggt gaccatgctg gcatcaagga tcgggtttac    720

agcaacagca tctatgagct tctggagaac gggcagcggg cgggcacctg tgtcctggag    780

tacgccaccc ccttgcagac tttgtttgcc atgtcacaat acagtcaagc tggctttagc    840

cgggaggata ggcttgagca ggccaaactc ttctgccgga cacttgagga catcctggca    900

gatgcccctg agtctcagaa caactgccgc ctcattgcct accaggaacc tgcagatgac    960

agcagcttct cgctgtccca ggaggttctc cggcacctgc ggcaggagga aaaggaagag   1020

gttactgtgg gcagcttgaa gacctcagcg gtgcccagta cctccacgat gtcccaagag   1080

cctgagctcc tcatcagtgg aatggaaaag cccctccctc tccgcacgga tttctct      1137
```

<210> SEQ ID NO 90
<211> LENGTH: 972
<212> TYPE: DNA
<213> ORGANISM: Salmonella typhimurium
<220> FEATURE:
<223> OTHER INFORMATION: lipid A biosynthesis myristoyltransferase (msbB)

<400> SEQUENCE: 90

```
ttatttgatg ggataaagat ctttacgctt atacggctga atctcgcctg gcttgcgggt     60

tttgagcagc ttcaggatcc aggtgtactg ttccggatgc gggccgacaa aaatttcgac    120

ctcttcgttc atccgtctgg cgatagtgtg gtcgtcagcc gtgagcagat cgtccattgg    180

cgggcgaatc tggatagtca ggcgatgcgt tttaccatta tacaccggga aaagcggtat    240

cacgcgtgcg cggcacactt tcatcagccg accaattgca ggcagcgtcg ctttgtatgt    300

cgcaaagaaa tcaacgaatt cactatgctc cgggccgtga tcctggtccg gcaggtagta    360

accccagtag ccctgacgaa cagactgaat aaagggttta atcccgtcat tacgcgcatg    420

caaacgtccg ccgaaacgcc gacgcactgt gttccagata tagtcaaaaa ccggattacc    480

ctgattatga aacatcgccg ccattttttg cccctgagag gccatcagca tggctggaat    540

gtcgacgccc cagccatgcg gtacgagaaa aatgactttt tcgtcgttac gacgcatctc    600

ctcgataatc tccagacctt cccagtcaac acgctgttga atttttttcg gaccgcgcat    660

cgccaactca gccatcatcg ccattgcctg tggcgcggtg gcgaacatct catcgacaat    720

cgcttcgcgc tcagcttcgc tacgctgcgg aaagcacaac gacagattaa ttagcgcccg    780

gcgacgagaa ctcttcccca gccgtccggc aaaacgcccc agcgtcgcca gcaaagggtc    840

gcggaatgat gccggtgtta atgcgatccc cgccattgcc gccgcgccca accaggcgcc    900

ccaatactgt ggatagcgaa aggatttttc gaattcaggg atatactcac tattattttt    960

tttggtttcc at                                                        972
```

<210> SEQ ID NO 91
<211> LENGTH: 1038
<212> TYPE: DNA
<213> ORGANISM: Salmonella typhimurium
<220> FEATURE:
<223> OTHER INFORMATION: Phosphoribosylaminoimidazole synthetase (purI)

<400> SEQUENCE: 91

```
ttattcaata accacacgct gttcggaatc agaggctttg atgataccga ttttccatgc     60

gttttcacct ttctcgttta gcagagcaag cgctttgtcc gcttccggag cggagagcgc    120
```

-continued

```
aatcaccatg ccgacgccgc agttaaaggt acggtacatt tcatgtcggc tgacattacc    180

ggcggtttgc agccaggtaa agatggcggg ccactgccag gacgactcat taattaccgc    240

ctgggtattc tccggcagaa cgcgcggaat attttcccaa aagcccccgc cggtgaggtg    300

ggcgatagcg tgtacatcga cgttttcaat cagttccaga accgatttta cgtagatacg    360

ggtcggttca agcagatgat cggccagcgg cttcccttcc agcagagtgg tttgtgggtc    420

gcagccgcta acgtcaataa ttttccgcac cagcgaatat ccattcgagt gcgggccgct    480

ggagccgagt gcaatcagca cgtcgccttc ggcaacccgg gagccgtcga tgatttctga    540

tttttcgact acgccgacgc agaaacccgc cacatcgtaa tcttcgccgt gatacatgcc    600

cggcatttcc gccgtctcgc cgccgaccag cgcgcagccg gattgcaggc agccttcggc    660

aataccgttg atcacgctgg cggcggtatc gacatccagt ttacccgtgg catagtaatc    720

gaggaaaaac agcggttccg cgccctgaac gaccagatcg tttacgcaca ttgccaccag    780

atcaataccg atagcgtcgt gacgctttaa gtccatcgcc aggcgaagtt tggtacctac    840

gccgtcagtg ccggaaacca gtaccggttc acgatatttt tgcggcaacg cgcacagcgc    900

accgaaaccg cccagaccgc ccataacctc cgggcggcga gttttcttca ctacgccttt    960

gattcgatca accagagcgt tacccgcatc aatatcgacg ccggcatctt tatagctaag   1020

agaggtctta tcggtcac                                                 1038
```

<210> SEQ ID NO 92
<211> LENGTH: 426
<212> TYPE: DNA
<213> ORGANISM: Homo sapiens
<220> FEATURE:
<223> OTHER INFORMATION: Survivin (SVN)/BIRC5, isoform 1

<400> SEQUENCE: 92

```
atgggtgccc cgacgttgcc ccctgcctgg cagccctttc tcaaggacca ccgcatctct     60

acattcaaga actggccctt cttggagggc tgcgcctgca ccccggagcg gatggccgag    120

gctggcttca tccactgccc cactgagaac gagccagact tggcccagtg tttcttctgc    180

ttcaaggagc tggaaggctg ggagccagat gacgacccca tagaggaaca taaaaagcat    240

tcgtccggtt gcgctttcct ttctgtcaag aagcagtttg aagaattaac ccttggtgaa    300

tttttgaaac tggacagaga aagagccaag aacaaaattg caaaggaaac caacaataag    360

aagaaagaat ttgaggaaac tgcggagaaa gtgcgccgtg ccatcgagca gctggctgcc    420

atggat                                                               426
```

<210> SEQ ID NO 93
<211> LENGTH: 285
<212> TYPE: DNA
<213> ORGANISM: E. coli
<220> FEATURE:
<223> OTHER INFORMATION: araBAD promoter (pBAD)

<400> SEQUENCE: 93

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcttacctg acgcttttta tcgcaactct ctactgtttc tccat                    285
```

<210> SEQ ID NO 94
<211> LENGTH: 459
<212> TYPE: DNA
<213> ORGANISM: Homo sapiens
<220> FEATURE:
<223> OTHER INFORMATION: Interleukin 2 (IL-2)

<400> SEQUENCE: 94
atgtacagga tgcaactcct gtcttgcatt gcactaagtc ttgcacttgt cacaaacagt 60
gcacctactt caagttctac aaagaaaaca cagctacaac tggagcattt actgctggat 120
ttacagatga ttttgaatgg aattaataat tacaagaatc ccaaactcac caggatgctc 180
acatttaagt tttacatgcc caagaaggcc acagaactga aacatcttca gtgtctagaa 240
gaagaactca aacctctgga ggaagtgcta aatttagctc aaagcaaaaa ctttcactta 300
agacccaggg acttaatcag caatatcaac gtaatagttc tggaactaaa gggatctgaa 360
acaacattca tgtgtgaata tgctgatgag acagcaacca ttgtagaatt tctgaacaga 420
tggattacct tttgtcaaag catcatctca acactgact 459

<210> SEQ ID NO 95
<211> LENGTH: 567
<212> TYPE: DNA
<213> ORGANISM: Homo sapiens
<220> FEATURE:
<223> OTHER INFORMATION: Interferon (IFN) alpha

<400> SEQUENCE: 95
atggcctcgc cctttgcttt actgatggtc ctggtggtgc tcagctgcaa gtcaagctgc 60
tctctgggct gtgatctccc tgagacccac agcctggata acaggaggac cttgatgctc 120
ctggcacaaa tgagcagaat ctctccttcc tcctgtctga tggacagaca tgactttgga 180
tttccccagg aggagtttga tggcaaccag ttccagaagg ctccagccat ctctgtcctc 240
catgagctga tccagcagat cttcaacctc tttaccacaa aagattcatc tgctgcttgg 300
gatgaggacc tcctagacaa attctgcacc gaactctacc agcagctgaa tgacttggaa 360
gcctgtgtga tgcaggagga gagggtggga gaaactcccc tgatgaatgc ggactccatc 420
ttggctgtga agaaatactt ccgaagaatc actctctatc tgacagagaa gaaatacagc 480
ccttgtgcct gggaggttgt cagagcagaa atcatgagat ccctctcttt atcaacaaac 540
ttgcaagaaa gattaaggag gaaggaa 567

<210> SEQ ID NO 96
<211> LENGTH: 729
<212> TYPE: DNA
<213> ORGANISM: Homo sapiens
<220> FEATURE:
<223> OTHER INFORMATION: CD48, isoform 1

<400> SEQUENCE: 96
atgtgctcca gaggttggga ttcgtgtctg gctctggaat tgctactgct gcctctgtca 60
ctcctggtga ccagcattca aggtcacttg gtacatatga ccgtggtctc cggcagcaac 120
gtgactctga acatctctga gagcctgcct gagaactaca aacaactaac ctggttttat 180
actttcgacc agaagattgt agaatgggat tccagaaaat ctaagtactt tgaatccaaa 240
tttaaaggca gggtcagact tgatcctcag agtggcgcac tgtacatctc taaggtccag 300
aaagaggaca acagcaccta catcatgagg gtgttgaaaa agactgggaa tgagcaagaa 360
tggaagatca agctgcaagt gcttgaccct gtacccaagc ctgtcatcaa aattgagaag 420

-continued atagaagaca tggatgacaa ctgttatctg aaactgtcat gtgtgatacc tggcgagtct 480
gtaaactaca cctggtatgg ggacaaaagg cccttcccaa aggagctcca gaacagtgtg 540
cttgaaacca cccttatgcc acataattac tccaggtgtt atacttgcca agtcagcaat 600
tctgtgagca gcaagaatgg cacggtctgc ctcagtccac cctgtaccct ggcccggtcc 660
tttggagtag aatggattgc aagttggcta gtggtcacgg tgcccaccat tcttggcctg 720
ttacttacc 729

<210> SEQ ID NO 97
<211> LENGTH: 1602
<212> TYPE: DNA
<213> ORGANISM: Homo sapiens
<220> FEATURE:
<223> OTHER INFORMATION: CD276/B7-H3, isoform 1

<400> SEQUENCE: 97
atgctgcgtc ggcggggcag ccctggcatg ggtgtgcatg tgggtgcagc cctgggagca 60
ctgtggttct gcctcacagg agccctggag gtccaggtcc ctgaagaccc agtggtggca 120
ctggtgggca ccgatgccac cctgtgctgc tccttctccc ctgagcctgg cttcagcctg 180
gcacagctca acctcatctg gcagctgaca gataccaaac agctggtgca cagctttgct 240
gagggccagg accagggcag cgcctatgcc aaccgcacgg ccctcttccc ggacctgctg 300
gcacagggca acgcatccct gaggctgcag cgcgtgcgtg tggcggacga gggcagcttc 360
acctgcttcg tgagcatccg ggatttcggc agcgctgccg tcagcctgca ggtggccgct 420
ccctactcga agcccagcat gaccctggag cccaacaagg acctgcggcc aggggacacg 480
gtgaccatca cgtgctccag ctaccagggc taccctgagg ctgaggtgtt ctggcaggat 540
gggcagggtg tgcccctgac tggcaacgtg accacgtcgc agatggccaa cgagcagggc 600
ttgtttgatg tgcacagcat cctgcgggtg gtgctgggtg caaatggcac ctacagctgc 660
ctggtgcgca accccgtgct gcagcaggat gcgcacagct ctgtcaccat cacaccccag 720
agaagcccca caggagccgt ggaggtccag gtccctgagg acccggtggt ggccctagtg 780
ggcaccgatg ccaccctgcg ctgctccttc tcccccgagc ctggcttcag cctggcacag 840
ctcaacctca tctggcagct gacagacacc aaacagctgg tgcacagttt caccgaaggc 900
cgggaccagg gcagcgccta tgccaaccgc acggccctct tcccggacct gctggcacaa 960
ggcaatgcat ccctgaggct gcagcgcgtg cgtgtggcgg acgagggcag cttcacctgc 1020
ttcgtgagca tccgggattt cggcagcgct gccgtcagcc tgcaggtggc cgctccctac 1080
tcgaagccca gcatgaccct ggagcccaac aaggacctgc ggccagggga cacggtgacc 1140
atcacgtgct ccagctaccg gggctaccct gaggctgagg tgttctggca ggatgggcag 1200
ggtgtgcccc tgactggcaa cgtgaccacg tcgcagatgg ccaacgagca gggcttgttt 1260
gatgtgcaca gcgtcctgcg ggtggtgctg ggtgcgaatg gcacctacag ctgcctggtg 1320
cgcaaccccg tgctgcagca ggatgcgcac ggctctgtca ccatcacagg gcagcctatg 1380
acattccccc cagaggccct gtgggtgacc gtggggctgt ctgtctgtct cattgcactg 1440
ctggtggccc tggctttcgt gtgctggaga aagatcaaac agagctgtga ggaggagaat 1500
gcaggagctg aggaccagga tggggaggga gaaggctcca agacagccct gcagcctctg 1560
aaacactctg acagcaaaga agatgatgga caagaaatag cc 1602

<210> SEQ ID NO 98
<211> LENGTH: 846

<212> TYPE: DNA
<213> ORGANISM: Homo sapiens
<220> FEATURE:
<223> OTHER INFORMATION: B7-H4/VTCN1

<400> SEQUENCE: 98

```
atggcttccc tggggcagat cctcttctgg agcataatta gcatcatcat tattctggct     60

ggagcaattg cactcatcat tggctttggt atttcaggga gacactccat cacagtcact    120

actgtcgcct cagctgggaa cattggggag gatggaatcc tgagctgcac ttttgaacct    180

gacatcaaac tttctgatat cgtgatacaa tggctgaagg aaggtgtttt aggcttggtc    240

catgagttca aagaaggcaa agatgagctg tcggagcagg atgaaatgtt cagaggccgg    300

acagcagtgt ttgctgatca agtgatagtt ggcaatgcct ctttgcggct gaaaaacgtg    360

caactcacag atgctggcac ctacaaatgt tatatcatca cttctaaagg caaggggaat    420

gctaaccttg agtataaaac tggagccttc agcatgccgg aagtgaatgt ggactataat    480

gccagctcag agaccttgcg gtgtgaggct ccccgatggt tcccccagcc cacagtggtc    540

tgggcatccc aagttgacca gggagccaac ttctcggaag tctccaatac cagctttgag    600

ctgaactctg agaatgtgac catgaaggtt gtgtctgtgc tctacaatgt tacgatcaac    660

aacacatact cctgtatgat tgaaaatgac attgccaaag caacagggga tatcaaagtg    720

acagaatcgg agatcaaaag gcggagtcac ctacagctgc taaactcaaa ggcttctctg    780

tgtgtctctt ctttctttgc catcagctgg gcacttctgc ctctcagccc ttacctgatg    840

ctaaaa                                                               846
```

<210> SEQ ID NO 99
<211> LENGTH: 867
<212> TYPE: DNA
<213> ORGANISM: Homo sapiens
<220> FEATURE:
<223> OTHER INFORMATION: BTLA/CD272, isoform 1

<400> SEQUENCE: 99

```
atgaagacat tgcctgccat gcttggaact gggaaattat tttgggtctt cttcttaatc     60

ccatatctgg acatctggaa catccatggg aaagaatcat gtgatgtaca gctttatata    120

aagagacaat ctgaacactc catcttagca ggagatccct ttgaactaga atgccctgtg    180

aaatactgtg ctaacaggcc tcatgtgact tggtgcaagc tcaatggaac aacatgtgta    240

aaacttgaag atagacaaac aagttggaag gaagagaaga acatttcatt tttcattcta    300

cattttgaac cagtgcttcc taatgacaat gggtcatacc gctgttctgc aaattttcag    360

tctaatctca ttgaaagcca ctcaacaact ctttatgtga cagatgtaaa aagtgcctca    420

gaacgaccct ccaaggacga aatggcaagc agaccctggc tcctgtatag tttacttcct    480

ttgggggggat tgcctctact catcactacc tgtttctgcc tgttctgctg cctgagaagg    540

caccaaggaa agcaaaatga actctctgac acagcaggaa gggaaattaa cctggttgat    600

gctcacctta agagtgagca aacagaagca agcaccaggc aaaattccca agtactgcta    660

tcagaaactg gaatttatga taatgaccct gacctttgtt tcaggatgca ggaagggtct    720

gaagtttatt ctaatccatg cctggaagaa aacaaaccag gcattgttta tgcttccctg    780

aaccattctg tcattggacc gaactcaaga ctggcaagaa atgtaaaaga agcaccaaca    840

gaatatgcat ccatatgtgt gaggagt                                        867
```

<210> SEQ ID NO 100

<211> LENGTH: 276
<212> TYPE: DNA
<213> ORGANISM: Homo sapiens
<220> FEATURE:
<223> OTHER INFORMATION: Chemokine (C-C motif) ligand 4 (CCL4)

<400> SEQUENCE: 100
atgaagctct gcgtgactgt cctgtctctc ctcatgctag tagctgcctt ctgctctcca 60
gcgctctcag caccaatggg ctcagaccct cccaccgcct gctgcttttc ttacaccgcg 120
aggaagcttc ctcgcaactt tgtggtagat tactatgaga ccagcagcct ctgctcccag 180
ccagctgtgg tattccaaac caaaagaagc aagcaagtct gtgctgatcc cagtgaatcc 240
tgggtccagg agtacgtgta tgacctggaa ctgaac 276

<210> SEQ ID NO 101
<211> LENGTH: 3537
<212> TYPE: DNA
<213> ORGANISM: Homo sapiens
<220> FEATURE:
<223> OTHER INFORMATION: CD103/ITGAE

<400> SEQUENCE: 101
atgtggctct tccacactct gctctgcata gccagcctgg ccctgctggc cgctttcaat 60
gtggatgtgg cccggccctg gctcacgccc aagggaggtg cccctttcgt gctcagctcc 120
cttctgcacc aagaccccag caccaaccag acctggctcc tggtcaccag ccccagaacc 180
aagaggacac cagggcccct ccatcgatgt tcccttgtcc aggatgaaat cctttgccat 240
cctgtagagc atgtccccat ccccaagggg aggcaccggg gagtgaccgt tgtccggagc 300
caccacggtg ttttgatatg cattcaagtg ctggtccggc ggcctcacag cctcagctca 360
gaactcacag gcacctgtag cctcctgggc cctgacctcc gtccccaggc tcaggccaac 420
ttcttcgacc ttgaaaatct cctggatcca gatgcacgtg tggacactgg agactgctac 480
agcaacaaag aaggcggtgg agaagacgat gtgaacacag ccaggcagcg ccgggctctg 540
gagaaggagg aggaggaaga caaggaggag gaggaagacg aggaggagga ggaagctggc 600
accgagattg ccatcatcct ggatggctca ggaagcattg atcccccaga ctttcagaga 660
gccaaagact tcatctccaa catgatgagg aacttctatg aaaagtgttt tgagtgcaac 720
tttgccttgg tgcagtatgg aggagtgatc cagactgagt ttgaccttcg ggacagccag 780
gatgtgatgg cctccctcgc cagagtccag aacatcactc aagtggggag tgtcaccaag 840
actgcctcag ccatgcaaca cgtcttagac agcatcttca cctcaagcca cggctccagg 900
agaaaggcat ccaaggtcat ggtggtgctc accgatggtg gcatattcga ggaccccctc 960
aaccttacga cagtcatcaa ctcccccaaa atgcagggtg ttgagcgctt tgccattggg 1020
gtgggagaag aatttaagag tgctaggact gcgagggaac tgaacctgat cgcctcagac 1080
ccggatgaga cccatgcttt caaggtgacc aactacatgg cgctggatgg gctgctgagc 1140
aaactgcggt acaacatcat cagcatggaa ggcacggttg gagacgccct tcactaccag 1200
ctggcacaga ttggcttcag tgctcagatc ctggatgagc ggcaggtgct gctcggcgcc 1260
gtcggggcct ttgactggtc cggaggggcg ttgctctacg acacacgcag ccgccggggc 1320
cgcttcctga accagacagc ggcggcggcg gcagacgcgg aggctgcgca gtacagctac 1380
ctgggttacg ctgtggccgt gctgcacaag acctgcagcc tctcctacat cgcgggggct 1440
ccacggtaca aacatcatgg ggccgtgttt gagctccaga aggagggcag agaggccagc 1500
ttcctgccag tgctggaggg agagcagatg gggtcctatt ttggctctga gctgtgccct 1560

```
gtggacattg acatggatgg aagcacggac ttcttgctgg tggctgctcc attttaccac   1620
gttcatggag aagaaggcag agtctacgtg taccgtctca gcgagcagga tggttctttc   1680
tccttggcac gcatactgag tgggcacccc gggttcacca atgcccgctt tggctttgcc   1740
atggcggcta tgggggatct cagtcaggat aagctcacag atgtggccat cggggccccc   1800
ctggaaggtt ttggggcaga tgatggtgcc agcttcggca gtgtgtatat ctacaatgga   1860
cactgggacg gcctctccgc cagcccctcg cagcggatca gagcctccac ggtggcccca   1920
ggactccagt acttcggcat gtccatggct ggtggctttg atattagtgg cgacggcctt   1980
gccgacatca ccgtgggcac tctgggccag gcggttgtgt tccgctcccg gcctgtggtt   2040
cgcctgaagg tctccatggc cttcaccccc agcgcactgc ccatcggctt caacggcgtc   2100
gtgaatgtcc gtttatgttt tgaaatcagc tctgtaacca cagcctctga gtcaggcctc   2160
cgcgaggcac ttctcaactt cacgctggat gtggatgtgg ggaagcagag gagacggctg   2220
cagtgttcag acgtaagaag ctgtctgggc tgcctgaggg agtggagcag cggatcccag   2280
ctttgtgagg acctcctgct catgcccaca gagggagagc tctgtgagga ggactgcttc   2340
tccaatgcca gtgtcaaagt cagctaccag ctccagaccc ctgagggaca gacggaccat   2400
ccccagccca tcctggaccg ctacactgag ccctttgcca tcttccagct gccctatgag   2460
aaggcctgca agaataagct gttttgtgtc gcagaattac agttggccac caccgtctct   2520
cagcaggagt tggtggtggg tctcacaaag gagctgaccc tgaacattaa cctaactaac   2580
tccggggaag attcctacat gacaagcatg gccttgaatt accccagaaa cctgcagttg   2640
aagaggatgc aaaagcctcc ctctccaaac attcagtgtg atgaccctca gccggttgct   2700
tctgtcctga tcatgaactg caggattggt caccccgtcc tcaagaggtc atctgctcat   2760
gtttcagtcg tttggcagct agaggagaat gcctttccaa acaggacagc agacatcact   2820
gtgactgtca ccaattccaa tgaaagacgg tctttggcca acgagaccca cacccttcaa   2880
ttcaggcatg gcttcgttgc agttctgtcc aaaccatcca taatgtacgt gaacacaggc   2940
caggggcttt ctcaccacaa agaattcctc ttccatgtac atggggagaa cctctttgga   3000
gcagaatacc agttgcaaat ttgcgtccca accaaattac gaggtctcca ggttgtagca   3060
gtgaagaagc tgacgaggac tcaggcctcc acggtgtgca cctggagtca ggagcgcgct   3120
tgtgcgtaca gttcggttca gcatgtggaa gaatggcatt cagtgagctg tgtcatcgct   3180
tcagataaag aaaatgtcac cgtggctgca gagatctcct gggatcactc tgaggagtta   3240
ctaaaagatg taactgaact gcagatcctt ggtgaaatat ctttcaacaa atctctatat   3300
gagggactga atgcagagaa ccacagaact aagatcactg tcgtcttcct gaaagatgag   3360
aagtaccatt ctttgcctat catcattaaa ggcagcgttg gtggacttct ggtgttgatc   3420
gtgattctgg tcatcctgtt caagtgtggc tttttttaaaa gaaaatatca acaactgaac   3480
ttggagagca tcaggaaggc ccagctgaaa tcagagaatc tgctcgaaga agagaat      3537
```

<210> SEQ ID NO 102
<211> LENGTH: 1671
<212> TYPE: DNA
<213> ORGANISM: Homo sapiens
<220> FEATURE:
<223> OTHER INFORMATION: CD19, isoform 1

<400> SEQUENCE: 102

```
atgccacctc ctcgcctcct cttcttcctc ctcttcctca cccccatgga agtcaggccc     60
```

gaggaacctc tagtggtgaa ggtggaagag ggagataacg ctgtgctgca gtgcctcaag 120
gggacctcag atggccccac tcagcagctg acctggtctc gggagtcccc gcttaaaccc 180
ttcttaaaac tcagcctggg gctgccaggc ctgggaatcc acatgaggcc cctggccatc 240
tggcttttca tcttcaacgt ctctcaacag atggggggct tctacctgtg ccagccgggg 300 ccccctctg agaaggcctg gcagcctggc tggacagtca atgtggaggg cagcggggag 360
ctgttccggt ggaatgtttc ggacctaggt ggcctgggct gtggcctgaa gaacaggtcc 420
tcagagggcc ccagctcccc ttccgggaag ctcatgagcc ccaagctgta tgtgtgggcc 480
aaagaccgcc ctgagatctg ggagggagag cctccgtgtc tcccaccgag ggacagcctg 540
aaccagagcc tcagccagga cctcaccatg gcccctggct ccacactctg gctgtcctgt 600
ggggtacccc ctgactctgt gtccaggggc cccctctcct ggacccatgt gcaccccaag 660
gggcctaagt cattgctgag cctagagctg aaggacgatc gcccggccag agatatgtgg 720
gtaatggaga cgggtctgtt gttgccccgg gccacagctc aagacgctgg aaagtattat 780
tgtcaccgtg gcaacctgac catgtcattc cacctggaga tcactgctcg gccagtacta 840
tggcactggc tgctgaggac tggtggctgg aaggtctcag ctgtgacttt ggcttatctg 900
atcttctgcc tgtgttccct tgtgggcatt cttcatcttc aaagagccct ggtcctgagg 960
aggaaaagaa agcgaatgac tgaccccacc aggagattct tcaaagtgac gcctccccca 1020
ggaagcgggc cccagaacca gtacgggaac gtgctgtctc tccccacacc cacctcaggc 1080
ctcggacgcg cccagcgttg ggccgcaggc ctgggggca ctgccccgtc ttatggaaac 1140
ccgagcagcg acgtccaggc ggatggagcc ttggggtccc ggagcccgcc gggagtgggc 1200
ccagaagaag aggaagggga gggctatgag gaacctgaca gtgaggagga ctccgagttc 1260
tatgagaacg actccaacct tgggcaggac cagctctccc aggatggcag cggctacgag 1320
aaccctgagg atgagcccct gggtcctgag gatgaagact ccttctccaa cgctgagtct 1380
tatgagaacg aggatgaaga gctgacccag ccggtcgcca ggacaatgga cttcctgagc 1440
cctcatgggt cagcctggga ccccagccgg gaagcaacct ccctggcagg gtcccagtcc 1500
tatgaggata tgagaggaat cctgtatgca gcccccagc tccgctccat tcggggccag 1560
cctggaccca atcatgagga agatgcagac tcttatgaga acatggataa tcccgatggg 1620
ccagacccag cctggggagg agggggccgc atgggcacct ggagcaccag g 1671

<210> SEQ ID NO 103
<211> LENGTH: 579
<212> TYPE: DNA
<213> ORGANISM: Homo sapiens
<220> FEATURE:
<223> OTHER INFORMATION: Interleukin 18 (IL-18), isoform 1

<400> SEQUENCE: 103
atggctgctg aaccagtaga agacaattgc atcaactttg tggcaatgaa atttattgac 60
aatacgcttt actttatagc tgaagatgat gaaaacctgg aatcagatta ctttggcaag 120
cttgaatcta aattatcagt cataagaaat ttgaatgacc aagttctctt cattgaccaa 180
ggaaatcggc ctctatttga agatatgact gattctgact gtagagataa tgcaccccgg 240
accatattta ttataagtat gtataaagat agccagccta gaggtatggc tgtaactatc 300
tctgtgaagt gtgagaaaat ttcaactctc tcctgtgaga acaaaattat ttcctttaag 360
gaaatgaatc ctcctgataa catcaaggat acaaaaagtg acatcatatt ctttcagaga 420
agtgtcccag gacatgataa taagatgcaa tttgaatctt catcatacga aggatacttt 480
ctagcttgtg aaaaagagag agaccttttt aaactcattt tgaaaaaaga ggatgaattg 540
ggggatagat ctataatgtt cactgttcaa aacgaagac 579

<210> SEQ ID NO 104
<211> LENGTH: 1005
<212> TYPE: DNA
<213> ORGANISM: Homo sapiens
<220> FEATURE:
<223> OTHER INFORMATION: Fas ligand

<400> SEQUENCE: 104
atgctgggca tctggaccct cctacctctg gttcttacgt ctgttgctag attatcgtcc 60
aaaagtgtta atgcccaagt gactgacatc aactccaagg gattggaatt gaggaagact 120
gttactacag ttgagactca gaacttggaa ggcctgcatc atgatggcca attctgccat 180
aagccctgtc ctccaggtga aaggaaagct agggactgca cagtcaatgg ggatgaacca 240
gactgcgtgc cctgccaaga agggaaggag tacacagaca aagcccattt ttcttccaaa 300
tgcagaagat gtagattgtg tgatgaagga catggcttag aagtggaaat aaactgcacc 360
cggacccaga ataccaagtg cagatgtaaa ccaaactttt tttgtaactc tactgtatgt 420
gaacactgtg acccttgcac caaatgtgaa catggaatca tcaaggaatg cacactcacc 480
agcaacacca agtgcaaaga ggaaggatcc agatctaact tggggtggct ttgtcttctt 540
cttttgccaa ttccactaat tgtttgggtg aagagaaagg aagtacagaa aacatgcaga 600
aagcacagaa aggaaaacca aggttctcat gaatctccaa ctttaaatcc tgaaacagtg 660
gcaataaatt tatctgatgt tgacttgagt aaatatatca ccactattgc tggagtcatg 720
acactaagtc aagttaaagg ctttgttcga aagaatggtg tcaatgaagc caaaatagat 780
gagatcaaga atgacaatgt ccaagacaca gcagaacaga aagttcaact gcttcgtaat 840
tggcatcaac ttcatggaaa gaaagaagcg tatgacacat tgattaaaga tctcaaaaaa 900
gccaatcttt gtactcttgc agagaaaatt cagactatca tcctcaagga cattactagt 960
gactcagaaa attcaaactt cagaaatgaa atccaaagct tggtc 1005

<210> SEQ ID NO 105
<211> LENGTH: 1023
<212> TYPE: DNA
<213> ORGANISM: Salmonella typhimurium
<220> FEATURE:
<223> OTHER INFORMATION: firA/SSC

<400> SEQUENCE: 105
atgccttcaa ttcgactggc tgacttagca gaacagttgg atgcagaatt acacggtgat 60
ggcgatatcg tcatcaccgg cgttgcgtcc atgcaatctg caacaacagg ccacattacg 120
tttatggtga atcctaagta ccgtgaacac ttaggtttat gccaggcttc tgcggttgtc 180
atgacgcagg acgatcttcc ttttgctaag agtgcggcgc tggtagttaa aaatccctac 240
ctgacctacg cgcgcatggc gcaaatttta gatactacgc cgcagcccgc gcagaatatc 300
gcgccaagcg ccgtgattga tgcgacggca acgctgggta gcaatgtttc agtcggcgcg 360
aatgcggtga ttgaatctgg cgtacaactg ggcgataacg tggttatcgg cgcaggctgt 420
ttcgtcggaa aaaatagcaa aatcggggcg ggttcacgct tgtgggcgaa cgtaacgatt 480
taccacgaca ttcagatcgg tgagaattgc ctgatccagt ccagtacggt gatcggcgcg 540
gacggttttg gctacgctaa cgatcgtggc aactgggtga agatcccaca actgggccgg 600

-continued

```
gtcattattg gcgatcgtgt cgagatcggc gcttgtacca ccattgaccg tggcgcgttg    660

gatgatactg ttattggcaa tggcgtgatt attgataatc agtgccagat tgcacataac    720

gtcgtgattg gcgacaatac ggcagttgcc ggtggcgtca ttatggcggg tagcctgaag    780

attggccgtt actgcatgat tggcggcgcc agcgtgatca atgggcatat ggaaatatgc    840

gacaaagtca cggtaactgg catgggtatg gtgatgcgtc ccatcacgga accgggcgtc    900

tactcctcag gcattccgct gcaacccaac aaagtatggc gtaaaactgc tgcactggtg    960

atgaacattg atgatatgag caagcgtctc aaagcgattg agcgcaaggt taatcaacaa   1020

gac                                                                 1023
```

<210> SEQ ID NO 106
<211> LENGTH: 918
<212> TYPE: DNA
<213> ORGANISM: E. coli
<220> FEATURE:
<223> OTHER INFORMATION: htrB

<400> SEQUENCE: 106

```
atgacgaatc tacccaagtt ctccaccgca ctgcttcatc cgcgttattg gttaacctgg     60

ttgggtattg gcgtactttg gttagtcgtg caattgccct acccggttat ctaccgcctc    120

ggttgtggat taggaaaact ggcgttacgt tttatgaaac gacgcgcaaa aattgtgcat    180

cgcaacctgg aactgtgctt cccggaaatg agcgaacaag aacgccgtaa aatggtggtg    240

aagaatttcg aatccgttgg catgggcctg atggaaaccg gcatggcgtg gttctggccg    300

gaccgccgaa tcgcccgctg gacggaagtg atcggcatgg aacacattcg tgacgtgcag    360

gcgcaaaaac gcggcatcct gttagttggc atccattttc tgacactgga gctgggtgcg    420

cggcagtttg gtatgcagga accgggtatt ggcgtttatc gcccgaacga taatccactg    480

attgactggc tacaaacctg ggccgtttg cgctcaaata aatcgatgct cgaccgcaaa     540

gatttaaaag gcatgattaa agccctgaaa aaaggcgaag tggtctggta cgcaccggat    600

catgattacg gcccgcgctc aagcgttttc gtcccgttgt ttgccgttga gcaggctgcg    660

accacgaccg gaacctggat gctggcacgg atgtccggcg catgtctggt gcccttcgtt    720

ccacgccgta agccagatgg caaagggtat caattgatta tgctgccgcc agagtgttct    780

ccgccactgg atgatgccga aactaccgcc gcgtggatga acaaagtggt cgaaaaatgc    840

atcatgatgg caccagagca gtatatgtgg ttacaccgtc gctttaaaac acgcccggaa    900

ggcgttcctt cacgctat                                                  918
```

<210> SEQ ID NO 107
<211> LENGTH: 717
<212> TYPE: DNA
<213> ORGANISM: Salmonella typhimurium
<220> FEATURE:
<223> OTHER INFORMATION: ompR

<400> SEQUENCE: 107

```
atgcaagaga attataagat tctggtggtt gatgacgata tgcgtctgcg ggcgctactg     60

gaacgttatc tgaccgagca gggcttccag gttcgaagcg tcgctaacgc tgagcagatg    120

gatcgtctgc tgacccgtga atctttccat ctcatggtac tggatttaat gctgccaggt    180

gaagatggtc tgtcgatttg tcgtcgcctg cgtagtcaaa gtaatccaat gccgatcatt    240

atggtcacgg cgaagggtga agaggttgac cgtatcgtcg ggctggaaat cggcgccgat    300

gactacattc ctaaaccgtt taacccgcgc gagctgttgg cgcgtattcg gcccgtgtta    360
```

cgtcgtcagg caaacgaact gcccggcgcg ccgtcgcagg aagaggccgt tatcgcgttc 420
ggtaagttta aactgaacct cggtacgcgc gagatgttcc gtgaagatga accgatgccg 480
ctgaccagcg gggagtttgc ggtactgaaa gcgttagtca gccatccgcg cgagccgctc 540
tctcgcgata agctgatgaa tctggcccgt ggccgcgagt attccgcgat ggaacgctcc 600
atcgacgtcc agatctcccg cctgcgccgt atggtggaag aagatccggc acatccgcgt 660
tatattcaga ccgtctgggg cctgggctac gtctttgtac cggacggttc taaagca 717

<210> SEQ ID NO 108
<211> LENGTH: 498
<212> TYPE: DNA
<213> ORGANISM: Homo sapiens
<220> FEATURE:
<223> OTHER INFORMATION: Inteferon (IFN) gamma

<400> SEQUENCE: 108
atgaaatata caagttatat cttggctttt cagctctgca tcgttttggg ttctcttggc 60
tgttactgcc aggacccata tgtaaaagaa gcagaaaacc ttaagaaata ttttaatgca 120
ggtcattcag atgtagcgga taatggaact cttttcttag gcattttgaa gaattggaaa 180
gaggagagtg acagaaaaat aatgcagagc caaattgtct ccttttactt caaacttttt 240
aaaaacttta aagatgacca gagcatccaa aagagtgtgg agaccatcaa ggaagacatg 300
aatgtcaagt tttcaatag caacaaaaag aaacgagatg acttcgaaaa gctgactaat 360
tattcggtaa ctgacttgaa tgtccaacgc aaagcaatac atgaactcat ccaagtgatg 420
gctgaactgt cgccagcagc taaaacaggg aagcgaaaaa ggagtcagat gctgtttcga 480
ggtcgaagag catcccag 498

<210> SEQ ID NO 109
<211> LENGTH: 699
<212> TYPE: DNA
<213> ORGANISM: Homo sapiens
<220> FEATURE:
<223> OTHER INFORMATION: Tumor necrosis factor (TNF) alpha

<400> SEQUENCE: 109
atgagcactg aaagcatgat ccgggacgtg gagctggccg aggaggcgct ccccaagaag 60
acaggggggc cccagggctc caggcggtgc ttgttcctca gcctcttctc cttcctgatc 120
gtggcaggcg ccaccacgct cttctgcctg ctgcactttg gagtgatcgg cccccagagg 180
gaagagttcc ccagggacct ctctctaatc agccctctgg cccaggcagt cagatcatct 240
tctcgaaccc cgagtgacaa gcctgtagcc catgttgtag caaaccctca agctgagggg 300
cagctccagt ggctgaaccg ccgggccaat gccctcctgg ccaatggcgt ggagctgaga 360
gataaccagc tggtggtgcc atcagagggc ctgtacctca tctactccca ggtcctcttc 420
aagggccaag gctgcccctc cacccatgtg ctcctcaccc acaccatcag ccgcatcgcc 480
gtctcctacc agaccaaggt caacctcctc tctgccatca agagcccctg ccagagggag 540
accccagagg gggctgaggc caagccctgg tatgagccca tctatctggg aggggtcttc 600
cagctggaga agggtgaccg actcagcgct gagatcaatc ggcccgacta tctcgacttt 660
gccgagtctg ggcaggtcta ctttgggatc attgccctg 699

<210> SEQ ID NO 110
<211> LENGTH: 825
<212> TYPE: DNA

<213> ORGANISM: Homo sapiens
<220> FEATURE:
<223> OTHER INFORMATION: Atg5 long isoform

<400> SEQUENCE: 110
atgacagatg acaaagatgt gcttcgagat gtgtggtttg gacgaattcc aacttgtttc 60
acgctatatc aggatgagat aactgaaagg gaagcagaac catactattt gcttttgcca 120
agagtaagtt atttgacgtt ggtaactgac aaagtgaaaa agcactttca gaaggttatg 180
agacaagaag acattagtga gatatggttt gaatatgaag gcacaccact gaaatggcat 240
tatccaattg gtttgctatt tgatcttctt gcatcaagtt cagctcttcc ttggaacatc 300
acagtacatt ttaagagttt tccagaaaaa gaccttctgc actgtccatc taaggatgca 360
attgaagctc attttatgtc atgtatgaaa gaagctgatg ctttaaaaca taaaagtcaa 420
gtaatcaatg aaatgcagaa aaaagatcac aagcaactct ggatgggatt gcaaaatgac 480
agatttgacc agttttgggc catcaatcgg aaactcatgg aatatcctgc agaagaaaat 540
ggatttcgtt atatcccctt tagaatatat cagacaacga ctgaaagacc tttcattcag 600
aagctgtttc gtcctgtggc tgcagatgga cagttgcaca cactaggaga tctcctcaaa 660
gaagtttgtc cttctgctat tgatcctgaa gatggggaaa aaaagaatca agtgatgatt 720
catggaattg agccaatgtt ggaaacacct ctgcagtggc tgagtgaaca tctgagctac 780
ccggataatt ttcttcatat tagtatcatc ccacagccaa cagat 825

<210> SEQ ID NO 111
<211> LENGTH: 1350
<212> TYPE: DNA
<213> ORGANISM: Homo sapiens
<220> FEATURE:
<223> OTHER INFORMATION: Beclin1

<400> SEQUENCE: 111
atggaagggt ctaagacgtc caacaacagc accatgcagg tgagcttcgt gtgccagcgc 60
tgcagccagc ccctgaaact ggacacgagt ttcaagatcc tggaccgtgt caccatccag 120
gaactcacag ctccattact taccacagcc caggcgaaac caggagagac ccaggaggaa 180
gagactaact caggagagga gccatttatt gaaactcctc gccaggatgg tgtctctcgc 240
agattcatcc ccccagccag gatgatgtcc acagaaagtg ccaacagctt cactctgatt 300
ggggaggcat ctgatggcgg caccatggag aacctcagcc gaagactgaa ggtcactggg 360
gacctttttg acatcatgtc gggccagaca gatgtggatc acccactctg tgaggaatgc 420
acagatactc ttttagacca gctggacact cagctcaacg tcactgaaaa tgagtgtcag 480
aactacaaac gctgtttgga gatcttagag caaatgaatg aggatgacag tgaacagtta 540
cagatggagc taaaggagct ggcactagag gaggagaggc tgatccagga gctggaagac 600
gtggaaaaga accgcaagat agtggcagaa aatctcgaga aggtccaggc tgaggctgag 660
agactggatc aggaggaagc tcagtatcag agagaataca gtgaatttaa acgacagcag 720
ctggagctgg atgatgagct gaagagtgtt gaaaaccaga tgcgttatgc ccagacgcag 780
ctggataagc tgaagaaaac caacgtcttt aatgcaacct tccacatctg gcacagtgga 840
cagtttggca caatcaataa cttcaggctg ggtcgcctgc ccagtgttcc cgtggaatgg 900
aatgagatta atgctgcttg gggccagact gtgttgctgc tccatgctct ggccaataag 960
atgggtctga aatttcagag ataccgactt gttccttacg gaaaccattc atatctggag 1020
tctctgacag acaaatctaa ggagctgccg ttatactgtt ctgggggggtt gcggtttttc 1080

```
tgggacaaca agtttgacca tgcaatggtg gctttcctgg actgtgtgca gcagttcaaa   1140

gaagaggttg agaaaggcga gacacgtttt tgtcttccct acaggatgga tgtggagaaa   1200

ggcaagattg aagacacagg aggcagtggc ggctcctatt ccatcaaaac ccagtttaac   1260

tctgaggagc agtggacaaa agctctcaag ttcatgctga cgaatcttaa gtggggtctt   1320

gcttgggtgt cctcacaatt ttataacaaa                                    1350


<210> SEQ ID NO 112
<211> LENGTH: 2352
<212> TYPE: DNA
<213> ORGANISM: Homo sapiens
<220> FEATURE:
<223> OTHER INFORMATION: Toll-like receptor 2 (TLR2)

<400> SEQUENCE: 112

atgccacata ctttgtggat ggtgtgggtc ttgggggtca tcatcagcct ctccaaggaa     60

gaatcctcca atcaggcttc tctgtcttgt gaccgcaatg gtatctgcaa gggcagctca    120

ggatctttaa actccattcc ctcagggctc acagaagctg taaaaagcct tgacctgtcc    180

aacaacagga tcacctacat tagcaacagt gacctacaga ggtgtgtgaa cctccaggct    240

ctggtgctga catccaatgg aattaacaca atagaggaag attctttttc ttccctgggc    300

agtcttgaac atttagactt atcctataat tacttatcta atttatcgtc ttcctggttc    360

aagcccottt cttctttaac attcttaaac ttactgggaa atccttacaa aaccctaggg    420

gaaacatctc tttttctca tctcacaaaa ttgcaaatcc tgagagtggg aaatatggac    480

accttcacta agattcaaag aaaagatttt gctggactta ccttccttga ggaacttgag    540

attgatgctt cagatctaca gagctatgag ccaaaaagtt tgaagtcaat tcagaatgta    600

agtcatctga tccttcatat gaagcagcat attttactgc tggagatttt tgtagatgtt    660

acaagttccg tggaatgttt ggaactgcga gatactgatt tggacacttt ccatttttca    720

gaactatcca ctggtgaaac aaattcattg attaaaaagt ttacatttag aaatgtgaaa    780

atcaccgatg aaagtttgtt tcaggttatg aaacttttga atcagatttc tggattgtta    840

gaattagagt ttgatgactg taccottaat ggagttggta attttagagc atctgataat    900

gacagagtta tagatccagg taaagtggaa acgttaacaa tccggaggct gcatattcca    960

aggttttact tattttatga tctgagcact ttatattcac ttacagaaag agttaaaaga   1020

atcacagtag aaaacagtaa agtttttctg gttccttgtt tactttcaca acatttaaaa   1080

tcattagaat acttggatct cagtgaaaat ttgatggttg aagaatactt gaaaaattca   1140

gcctgtgagg atgcctggcc ctctctacaa actttaattt taaggcaaaa tcatttggca   1200

tcattggaaa aaaccggaga gactttgctc actctgaaaa acttgactaa cattgatatc   1260

agtaagaata gttttcattc tatgcctgaa acttgtcagt ggccagaaaa gatgaaatat   1320

ttgaacttat ccagcacacg aatacacagt gtaacaggct gcattcccaa gacactggaa   1380

attttagatg ttagcaacaa caatctcaat ttattttctt tgaatttgcc gcaactcaaa   1440

gaactttata tttccagaaa taagttgatg actctaccag atgcctccct cttacccatg   1500

ttactagtat tgaaaatcag taggaatgca ataactacgt tttctaagga gcaacttgac   1560

tcatttcaca cactgaagac tttggaagct ggtggcaata acttcatttg ctcctgtgaa   1620

ttcctctcct tcactcagga gcagcaagca ctggccaaag tcttgattga ttggccagca   1680

aattacctgt gtgactctcc atcccatgtg cgtggccagc aggttcagga tgtccgcctc   1740
```

tcggtgtcgg aatgtcacag gacagcactg gtgtctggca tgtgctgtgc tctgttcctg 1800
ctgatcctgc tcacgggggt cctgtgccac cgtttccatg gcctgtggta tatgaaaatg 1860
atgtgggcct ggctccaggc caaaaggaag cccaggaaag ctcccagcag gaacatctgc 1920
tatgatgcat ttgtttctta cagtgagcgg gatgcctact gggtggagaa ccttatggtc 1980
caggagctgg agaacttcaa tccccccttc aagttgtgtc ttcataagcg ggacttcatt 2040
cctggcaagt ggatcattga caatatcatt gactccattg aaaagagcca caaaactgtc 2100
tttgtgcttt ctgaaaactt tgtgaagagt gagtggtgca agtatgaact ggacttctcc 2160
catttccgtc tttttgatga gaacaatgat gctgccattc tcattcttct ggagcccatt 2220
gagaaaaaag ccattcccca gcgcttctgc aagctgcgga agataatgaa caccaagacc 2280
tacctggagt ggcccatgga cgaggctcag cgggaaggat tttgggtaaa tctgagagct 2340
gcgataaagt cc 2352

<210> SEQ ID NO 113
<211> LENGTH: 2517
<212> TYPE: DNA
<213> ORGANISM: Homo sapiens
<220> FEATURE:
<223> OTHER INFORMATION: TLR4, isoform 1

<400> SEQUENCE: 113
atgatgtctg cctcgcgcct ggctgggact ctgatcccag ccatggcctt cctctcctgc 60
gtgagaccag aaagctggga gccctgcgtg gaggtggttc ctaatattac ttatcaatgc 120
atggagctga atttctacaa aatccccgac aacctcccct tctcaaccaa gaacctggac 180
ctgagcttta atcccctgag gcatttaggc agctatagct tcttcagttt cccagaactg 240
caggtgctgg atttatccag gtgtgaaatc cagacaattg aagatggggc atatcagagc 300
ctaagccacc tctctacctt aatattgaca ggaaacccca tccagagttt agccctggga 360
gccttttctg gactatcaag tttacagaag ctggtggctg tggagacaaa tctagcatct 420
ctagagaact tccccattgg acatctcaaa actttgaaag aacttaatgt ggctcacaat 480
cttatccaat ctttcaaatt acctgagtat ttttctaatc tgaccaatct agagcacttg 540
gacctttcca gcaacaagat tcaaagtatt tattgcacag acttgcgggt tctacatcaa 600
atgcccctac tcaatctctc tttagacctg tccctgaacc ctatgaactt tatccaacca 660
ggtgcattta aagaaattag gcttcataag ctgactttaa gaaataattt tgatagttta 720
aatgtaatga aaacttgtat tcaaggtctg gctggtttag aagtccatcg tttggttctg 780
ggagaattta gaaatgaagg aaacttggaa aagtttgaca aatctgctct agagggcctg 840
tgcaatttga ccattgaaga attccgatta gcatacttag actactacct cgatgatatt 900
attgacttat ttaattgttt gacaaatgtt tcttcatttt ccctggtgag tgtgactatt 960
gaaagggtaa aagacttttc ttataatttc ggatggcaac atttagaatt agttaactgt 1020
aaatttggac agtttcccac attgaaactc aaatctctca aaaggcttac tttcacttcc 1080
aacaaaggtg ggaatgcttt ttcagaagtt gatctaccaa gccttgagtt tctagatctc 1140
agtagaaatg gcttgagttt caaaggttgc tgttctcaaa gtgattttgg gacaaccagc 1200
ctaaagtatt tagatctgag cttcaatggt gttattacca tgagttcaaa cttcttgggc 1260
ttagaacaac tagaacatct ggatttccag cattccaatt tgaaacaaat gagtgagttt 1320
tcagtattcc tatcactcag aaacctcatt taccttgaca tttctcatac tcacaccaga 1380
gttgctttca atggcatctt caatggcttg tccagtctcg aagtcttgaa aatggctggc 1440

```
aattctttcc aggaaaactt ccttccagat atcttcacag agctgagaaa cttgaccttc   1500

ctggacctct ctcagtgtca actggagcag ttgtctccaa cagcatttaa ctcactctcc   1560

agtcttcagg tactaaatat gagccacaac aacttctttt cattggatac gtttccttat   1620

aagtgtctga actccctcca ggttcttgat tacagtctca atcacataat gacttccaaa   1680

aaacaggaac tacagcattt tccaagtagt ctagctttct taaatcttac tcagaatgac   1740

tttgcttgta cttgtgaaca ccagagtttc ctgcaatgga tcaaggacca gaggcagctc   1800

ttggtggaag ttgaacgaat ggaatgtgca acaccttcag ataagcaggg catgcctgtg   1860

ctgagtttga atatcacctg tcagatgaat aagaccatca ttggtgtgtc ggtcctcagt   1920

gtgcttgtag tatctgttgt agcagttctg gtctataagt tctattttca cctgatgctt   1980

cttgctggct gcataaagta tggtagaggt gaaaacatct atgatgcctt tgttatctac   2040

tcaagccagg atgaggactg ggtaaggaat gagctagtaa agaatttaga agaaggggtg   2100

cctccatttc agctctgcct tcactacaga gactttattc ccggtgtggc cattgctgcc   2160

aacatcatcc atgaaggttt ccataaaagc cgaaaggtga ttgttgtggt gtcccagcac   2220

ttcatccaga gccgctggtg tatctttgaa tatgagattg ctcagacctg gcagtttctg   2280

agcagtcgtg ctggtatcat cttcattgtc ctgcagaagg tggagaagac cctgctcagg   2340

cagcaggtgg agctgtaccg ccttctcagc aggaacactt acctggagtg ggaggacagt   2400

gtcctggggc ggcacatctt ctggagacga ctcagaaaag ccctgctgga tggtaaatca   2460

tggaatccag aaggaacagt gggtacagga tgcaattggc aggaagcaac atctatc      2517
```

```
<210> SEQ ID NO 114
<211> LENGTH: 2574
<212> TYPE: DNA
<213> ORGANISM: Homo sapiens
<220> FEATURE:
<223> OTHER INFORMATION: TLR5

<400> SEQUENCE: 114

atgggagacc acctggacct tctcctagga gtggtgctca tggccggtcc tgtgtttgga     60

attccttcct gctcctttga tggccgaata gccttttatc gtttctgcaa cctcacccag    120

gtcccccagg tcctcaacac cactgagagg ctcctgctga gcttcaacta tatcaggaca    180

gtcactgctt catccttccc ctttctggaa cagctgcagc tgctggagct cgggagccag    240

tataccccct tgactattga caaggaggcc ttcagaaacc tgcccaacct tagaatcttg    300

gacctgggaa gtagtaagat atacttcttg catccagatg cttttcaggg actgttccat    360

ctgtttgaac ttagactgta tttctgtggt ctctctgatg ctgtattgaa agatggttat    420

ttcagaaatt taaaggcttt aactcgcttg gatctatcca aaaatcagat tcgtagcctt    480

taccttcatc cttcatttgg gaagttgaat tccttaaagt ccatagattt ttcctccaac    540

caaatattcc ttgtatgtga acatgagctc gagcccctac aagggaaaac gctctccttt    600

tttagcctcg cagctaatag cttgtatagc agagtctcag tggactgggg aaaatgtatg    660

aacccattca gaaacatggt gctggagata ctagatgttt ctggaaatgg ctggacagtg    720

gacatcacag gaaactttag caatgccatc agcaaaagcc aggccttctc tttgattctt    780

gcccaccaca tcatgggtgc cgggtttggc ttccataaca tcaaagatcc tgaccagaac    840

acatttgctg gcctggccag aagttcagtg agacacctgg atctttcaca tgggtttgtc    900

ttctccctga actcacgagt ctttgagaca ctcaaggatt tgaaggttct gaaccttgcc    960
```

-continued tacaacaaga taaataagat tgcagatgaa gcattttacg gacttgacaa cctccaagtt 1020
ctcaatttgt catataacct tctgggggaa ctttacagtt cgaatttcta tggactacct 1080
aaggtagcct acattgattt gcaaaagaat cacattgcaa taattcaaga ccaaacattc 1140
aaattcctgg aaaaattaca gaccttggat ctccgagaca atgctcttac aaccattcat 1200
tttattccaa gcatacccga tatcttcttg agtggcaata aactagtgac tttgccaaag 1260
atcaacctta cagcgaacct catccactta tcagaaaaca ggctagaaaa tctagatatt 1320
ctctactttc tcctacgggt acctcatctc cagattctca ttttaaatca aaatcgcttc 1380
tcctcctgta gtggagatca aacccccttca gagaatccca gcttagaaca gcttttcctt 1440
ggagaaaata tgttgcaact tgcctgggaa actgagctct gttgggatgt tttgagggga 1500
ctttctcatc ttcaagttct gtatttgaat cataactatc ttaattccct tccaccagga 1560
gtatttagcc atctgactgc attaagggga ctaagcctca actccaacag gctgacagtt 1620
ctttctcaca atgatttacc tgctaattta gagatcctgg acatatccag gaaccagctc 1680
ctagctccta atcctgatgt atttgtatca cttagtgtct tggatataac tcataacaag 1740
ttcatttgtg aatgtgaact tagcactttt atcaattggc ttaatcacac caatgtcact 1800
atagctgggc ctcctgcaga catatattgt gtgtaccctg actcgttctc tggggtttcc 1860
ctcttctctc tttccacgga aggttgtgat gaagaggaag tcttaaagtc cctaaagttc 1920 tccctttca ttgtatgcac tgtcactctg actctgttcc tcatgaccat cctcacagtc 1980
acaaagttcc ggggcttctg ttttatctgt tataagacag cccagagact ggtgttcaag 2040
gaccatcccc agggcacaga acctgatatg tacaaatatg atgcctattt gtgcttcagc 2100
agcaaagact tcacatgggt gcagaatgct ttgctcaaac acctggacac tcaatacagt 2160
gaccaaaaca gattcaacct gtgctttgaa gaaagagact ttgtcccagg agaaaaccgc 2220
attgccaata tccaggatgc catctggaac agtagaaaga tcgtttgtct tgtgagcaga 2280
cacttcctta gagatggctg gtgccttgaa gccttcagtt atgcccaggg caggtgctta 2340
tctgacctta acagtgctct catcatggtg gtggttgggt ccttgtccca gtaccagttg 2400
atgaaacatc aatccatcag aggctttgta cagaaacagc agtatttgag gtggcctgag 2460
gatctccagg atgttggctg gtttcttcat aaactctctc aacagatact aaagaaagaa 2520
aaagaaaaga agaaagacaa taacattccg ttgcaaactg tagcaaccat ctcc 2574

<210> SEQ ID NO 115
<211> LENGTH: 2712
<212> TYPE: DNA
<213> ORGANISM: Homo sapiens
<220> FEATURE:
<223> OTHER INFORMATION: TLR3, isoform 1

<400> SEQUENCE: 115
atgagacaga ctttgccttg tatctacttt tgggggggcc ttttgccctt tgggatgctg 60
tgtgcatcct ccaccaccaa gtgcactgtt agccatgaag ttgctgactg cagccacctg 120
aagttgactc aggtacccga tgatctaccc acaaacataa cagtgttgaa ccttacccat 180
aatcaactca gaagattacc agccgccaac ttcacaaggt atagccagct aactagcttg 240
gatgtaggat ttaacaccat ctcaaaactg gagccagaat tgtgccagaa acttcccatg 300
ttaaaagttt tgaacctcca gcacaatgag ctatctcaac tttctgataa aacctttgcc 360
ttctgcacga atttgactga actccatctc atgtccaact caatccagaa aattaaaaat 420
aatccctttg tcaagcagaa gaatttaatc acattagatc tgtctcataa tggcttgtca 480

```
tctacaaaat taggaactca ggttcagctg gaaaatctcc aagagcttct attatcaaac    540
aataaaattc aagcgctaaa aagtgaagaa ctggatatct ttgccaattc atctttaaaa    600
aaattagagt tgtcatcgaa tcaaattaaa gagttttctc cagggtgttt tcacgcaatt    660
ggaagattat ttggcctctt tctgaacaat gtccagctgg gtcccagcct tacagagaag    720
ctatgtttgg aattagcaaa cacaagcatt cggaatctgt ctctgagtaa cagccagctg    780
tccaccacca gcaatacaac tttcttggga ctaaagtgga caaatctcac tatgctcgat    840
ctttcctaca acaacttaaa tgtggttggt aacgattcct ttgcttggct tccacaacta    900
gaatatttct tcctagagta taataatata cagcatttgt tttctcactc tttgcacggg    960
cttttcaatg tgaggtacct gaatttgaaa cggtctttta ctaaacaaag tatttccctt   1020
gcctcactcc ccaagattga tgatttttct tttcagtggc taaaatgttt ggagcacctt   1080
aacatggaag ataatgatat tccaggcata aaaagcaata tgttcacagg attgataaac   1140
ctgaaatact taagtctatc caactccttt acaagtttgc gaactttgac aaatgaaaca   1200
tttgtatcac ttgctcattc tcccttacac atactcaacc taaccaagaa taaaatctca   1260
aaaatagaga gtgatgcttt ctcttggttg ggccacctag aagtacttga cctgggcctt   1320
aatgaaattg ggcaagaact cacaggccag gaatggagag gtctagaaaa tattttcgaa   1380
atctatcttt cctacaacaa gtacctgcag ctgactagga actcctttgc cttggtccca   1440
agccttcaac gactgatgct ccgaagggtg gcccttaaaa atgtggatag ctctccttca   1500
ccattccagc ctcttcgtaa cttgaccatt ctggatctaa gcaacaacaa catagccaac   1560
ataaatgatg acatgttgga gggtcttgag aaactagaaa ttctcgattt gcagcataac   1620
aacttagcac ggctctggaa acacgcaaac cctggtggtc ccatttattt cctaaagggt   1680
ctgtctcacc tccacatcct taacttggag tccaacggct ttgacgagat cccagttgag   1740
gtcttcaagg atttatttga actaaagatc atcgatttag gattgaataa tttaaacaca   1800
cttccagcat ctgtctttaa taatcaggtg tctctaaagt cattgaacct tcagaagaat   1860
ctcataacat ccgttgagaa gaaggttttc gggccagctt tcaggaacct gactgagtta   1920
gatatgcgct ttaatccctt tgattgcacg tgtgaaagta ttgcctggtt tgttaattgg   1980
attaacgaga cccataccaa catccctgag ctgtcaagcc actacctttg caacactcca   2040
cctcactatc atgggttccc agtgagactt tttgatacat catcttgcaa agacagtgcc   2100
ccctttgaac tctttttcat gatcaatacc agtatcctgt tgatttttat ctttattgta   2160
cttctcatcc actttgaggg ctggaggata tctttttatt ggaatgtttc agtacatcga   2220
gttcttggtt tcaaagaaat agacagacag acagaacagt ttgaatatgc agcatatata   2280
attcatgcct ataaagataa ggattgggtc tgggaacatt tctcttcaat ggaaaaggaa   2340
gaccaatctc tcaaattttg tctggaagaa agggactttg aggcgggtgt ttttgaacta   2400
gaagcaattg ttaacagcat caaaagaagc agaaaaatta tttttgttat aacacaccat   2460
ctattaaaag acccattatg caaaagattc aaggtacatc atgcagttca acaagctatt   2520
gaacaaaatc tggattccat tatattggtt ttccttgagg agattccaga ttataaactg   2580
aaccatgcac tctgtttgcg aagaggaatg tttaaatctc actgcatctt gaactggcca   2640
gttcagaaag aacggatagg tgcctttcgt cataaattgc aagtagcact tggatccaaa   2700
aactctgtac at                                                       2712
```

<210> SEQ ID NO 116

<211> LENGTH: 3096
<212> TYPE: DNA
<213> ORGANISM: Homo sapiens
<220> FEATURE:
<223> OTHER INFORMATION: TLR9

<400> SEQUENCE: 116
atgggtttct gccgcagcgc cctgcacccg ctgtctctcc tggtgcaggc catcatgctg 60
gccatgaccc tggccctggg taccttgcct gccttcctac cctgtgagct ccagccccac 120
ggcctggtga actgcaactg gctgttcctg aagtctgtgc cccacttctc catggcagca 180
ccccgtggca atgtcaccag cctttccttg tcctccaacc gcatccacca cctccatgat 240
tctgactttg cccacctgcc cagcctgcgg catctcaacc tcaagtggaa ctgcccgccg 300
gttggcctca gccccatgca cttcccctgc cacatgacca tcgagcccag caccttcttg 360
gctgtgccca ccctggaaga gctaaacctg agctacaaca acatcatgac tgtgcctgcg 420
ctgcccaaat ccctcatatc cctgtccctc agccatacca acatcctgat gctagactct 480
gccagcctcg ccggcctgca tgccctgcgc ttcctattca tggacggcaa ctgttattac 540
aagaacccct gcaggcaggc actggaggtg gccccgggtg ccctccttgg cctgggcaac 600
ctcacccacc tgtcactcaa gtacaacaac ctcactgtgg tgccccgcaa cctgccttcc 660
agcctggagt atctgctgtt gtcctacaac cgcatcgtca aactggcgcc tgaggacctg 720
gccaatctga ccgccctgcg tgtgctcgat gtgggcggaa attgccgccg ctgcgaccac 780
gctcccaacc cctgcatgga gtgccctcgt cacttccccc agctacatcc cgataccttc 840
agccacctga gccgtcttga aggcctggtg ttgaaggaca gttctctctc ctggctgaat 900
gccagttggt tccgtgggct gggaaacctc cgagtgctgg acctgagtga gaacttcctc 960
tacaaatgca tcactaaaac caaggccttc cagggcctaa cacagctgcg caagcttaac 1020
ctgtccttca attaccaaaa gagggtgtcc tttgcccacc tgtctctggc cccttccttc 1080
gggagcctgg tcgccctgaa ggagctggac atgcacggca tcttcttccg ctcactcgat 1140
gagaccacgc tccggccact ggcccgcctg cccatgctcc agactctgcg tctgcagatg 1200
aacttcatca accaggccca gctcggcatc ttcagggcct tccctggcct gcgctacgtg 1260
gacctgtcgg acaaccgcat cagcggagct tcggagctga cagccaccat gggggaggca 1320
gatggagggg agaaggtctg gctgcagcct ggggaccttg ctccggcccc agtggacact 1380
cccagctctg aagacttcag gcccaactgc agcaccctca acttcacctt ggatctgtca 1440
cggaacaacc tggtgaccgt gcagccggag atgtttgccc agctctcgca cctgcagtgc 1500
ctgcgcctga gccacaactg catctcgcag gcagtcaatg gctcccagtt cctgccgctg 1560
accggtctgc aggtgctaga cctgtcccac aataagctgg acctctacca cgagcactca 1620
ttcacggagc taccgcgact ggaggccctg gacctcagct acaacagcca gccctttggc 1680
atgcagggcg tgggccacaa cttcagcttc gtggctcacc tgcgcaccct gcgccacctc 1740
agcctggccc acaacaacat ccacagccaa gtgtcccagc agctctgcag tacgtcgctg 1800
cgggccctgg acttcagcgg caatgcactg ggccatatgt gggccgaggg agacctctat 1860
ctgcacttct tccaaggcct gagcggtttg atctggctgg acttgtccca gaaccgcctg 1920
cacaccctcc tgccccaaac cctgcgcaac ctccccaaga gcctacaggt gctgcgtctc 1980
cgtgacaatt acctggcctt ctttaagtgg tggagcctcc acttcctgcc caaactggaa 2040
gtcctcgacc tggcaggaaa ccagctgaag gccctgacca atggcagcct gcctgctggc 2100
acccggctcc ggaggctgga tgtcagctgc aacagcatca gcttcgtggc ccccggcttc 2160

```
ttttccaagg ccaaggagct gcgagagctc aaccttagcg ccaacgccct caagacagtg   2220
gaccactcct ggtttgggcc cctggcgagt gccctgcaaa tactagatgt aagcgccaac   2280
cctctgcact gcgcctgtgg ggcggccttt atggacttcc tgctggaggt gcaggctgcc   2340
gtgcccggtc tgcccagccg ggtgaagtgt ggcagtccgg gccagctcca gggcctcagc   2400
atctttgcac aggacctgcg cctctgcctg gatgaggccc tctcctggga ctgtttcgcc   2460
ctctcgctgc tggctgtggc tctgggcctg ggtgtgccca tgctgcatca cctctgtggc   2520
tgggacctct ggtactgctt ccacctgtgc ctggcctggc ttccctggcg ggggcggcaa   2580
agtgggcgag atgaggatgc cctgccctac gatgccttcg tggtcttcga caaaacgcag   2640
agcgcagtgg cagactgggt gtacaacgag cttcgggggc agctggagga gtgccgtggg   2700
cgctgggcac tccgcctgtg cctggaggaa cgcgactggc tgcctggcaa aaccctcttt   2760
gagaacctgt gggcctcggt ctatggcagc cgcaagacgc tgtttgtgct ggcccacacg   2820
gaccgggtca gtggtctctt gcgcgccagc ttcctgctgg cccagcagcg cctgctggag   2880
gaccgcaagg acgtcgtggt gctggtgatc ctgagccctg acggccgccg ctcccgctac   2940
gtgcggctgc gccagcgcct ctgccgccag agtgtcctcc tctggcccca ccagcccagt   3000
ggtcagcgca gcttctgggc ccagctgggc atggccctga ccagggacaa ccaccacttc   3060
tataaccgga acttctgcca gggacccacg gccgaa                             3096
```

<210> SEQ ID NO 117
<211> LENGTH: 3147
<212> TYPE: DNA
<213> ORGANISM: Homo sapiens
<220> FEATURE:
<223> OTHER INFORMATION: TLR7

<400> SEQUENCE: 117

```
atggtgtttc caatgtggac actgaagaga caaattctta tcctttttaa cataatccta     60
atttccaaac tccttggggc tagatggttt cctaaaactc tgccctgtga tgtcactctg    120
gatgttccaa agaaccatgt gatcgtggac tgcacagaca agcatttgac agaaattcct    180
ggaggtattc ccacgaacac cacgaacctc accctcacca ttaaccacat accagacatc    240
tccccagcgt cctttcacag actggaccat ctggtagaga tcgatttcag atgcaactgt    300
gtacctattc cactggggtc aaaaaacaac atgtgcatca agaggctgca gattaaaccc    360
agaagcttta gtggactcac ttatttaaaa tccctttacc tggatggaaa ccagctacta    420
gagataccgc agggcctccc gcctagctta cagcttctca gccttgaggc caacaacatc    480
ttttccatca gaaaagagaa tctaacagaa ctggccaaca tagaaatact ctacctgggc    540
caaaactgtt attatcgaaa tccttgttat gtttcatatt caatagagaa agatgccttc    600
ctaaacttga caaagttaaa agtgctctcc ctgaaagata acaatgtcac agccgtccct    660
actgttttgc catctacttt aacagaacta tatctctaca acaacatgat tgcaaaaatc    720
caagaagatg attttaataa cctcaaccaa ttacaaattc ttgacctaag tggaaattgc    780
cctcgttgtt ataatgcccc atttccttgt gcgccgtgta aaaataattc tcccctacag    840
atccctgtaa atgcttttga tgcgctgaca gaattaaaag ttttacgtct acacagtaac    900
tctcttcagc atgtgccccc aagatggttt aagaacatca acaaactcca ggaactggat    960
ctgtcccaaa acttcttggc caaagaaatt ggggatgcta aatttctgca ttttctcccc   1020
agcctcatcc aattggatct gtctttcaat tttgaacttc aggtctatcg tgcatctatg   1080
```

-continued

```
aatctatcac aagcattttc ttcactgaaa agcctgaaaa ttctgcggat cagaggatat   1140
gtctttaaag agttgaaaag ctttaacctc tcgccattac ataatcttca aaatcttgaa   1200
gttcttgatc ttggcactaa ctttataaaa attgctaacc tcagcatgtt taaacaattt   1260
aaaagactga aagtcataga tctttcagtg aataaaatat caccttcagg agattcaagt   1320
gaagttggct tctgctcaaa tgccagaact tctgtagaaa gttatgaacc ccaggtcctg   1380
gaacaattac attatttcag atatgataag tatgcaagga gttgcagatt caaaaacaaa   1440
gaggcttctt tcatgtctgt taatgaaagc tgctacaagt atgggcagac cttggatcta   1500
agtaaaaata gtatattttt tgtcaagtcc tctgattttc agcatctttc tttcctcaaa   1560
tgcctgaatc tgtcaggaaa tctcattagc caaactctta atggcagtga attccaacct   1620
ttagcagagc tgagatattt ggacttctcc aacaaccggc ttgatttact ccattcaaca   1680
gcatttgaag agcttcacaa actggaagtt ctggatataa gcagtaatag ccattatttt   1740
caatcagaag gaattactca tatgctaaac tttaccaaga acctaaaggt tctgcagaaa   1800
ctgatgatga acgacaatga catctcttcc tccaccagca ggaccatgga gagtgagtct   1860
cttagaactc tggaattcag aggaaatcac ttagatgttt tatggagaga aggtgataac   1920
agatacttac aattattcaa gaatctgcta aaattagagg aattagacat ctctaaaaat   1980
tccctaagtt tcttgccttc tggagttttt gatggtatgc ctccaaatct aaagaatctc   2040
tctttggcca aaaatgggct caaatctttc agttggaaga aactccagtg tctaaagaac   2100
ctggaaactt tggacctcag ccacaaccaa ctgaccactg tccctgagag attatccaac   2160
tgttccagaa gcctcaagaa tctgattctt aagaataatc aaatcaggag tctgacgaag   2220
tattttctac aagatgcctt ccagttgcga tatctggatc tcagctcaaa taaaatccag   2280
atgatccaaa agaccagctt cccagaaaat gtcctcaaca atctgaagat gttgcttttg   2340
catcataatc ggtttctgtg cacctgtgat gctgtgtggt ttgtctggtg ggttaaccat   2400
acggaggtga ctattcctta cctggccaca gatgtgactt gtgtggggcc aggagcacac   2460
aagggccaaa gtgtgatctc cctggatctg tacacctgtg agttagatct gactaacctg   2520
attctgttct cactttccat atctgtatct ctctttctca tggtgatgat gacagcaagt   2580
cacctctatt tctgggatgt gtggtatatt taccatttct gtaaggccaa gataaagggg   2640
tatcagcgtc taatatcacc agactgttgc tatgatgctt ttattgtgta tgacactaaa   2700
gacccagctg tgaccgagtg ggttttggct gagctggtgg ccaaactgga agacccaaga   2760
gagaaacatt ttaatttatg tctcgaggaa agggactggt taccagggca gccagttctg   2820
gaaaaccttt cccagagcat acagcttagc aaaaagacag tgtttgtgat gacagacaag   2880
tatgcaaaga ctgaaaattt taagatagca ttttacttgt cccatcagag gctcatggat   2940
gaaaaagttg atgtgattat cttgatattt cttgagaagc cctttcagaa gtccaagttc   3000
ctccagctcc ggaaaaggct ctgtgggagt tctgtccttg agtggccaac aaacccgcaa   3060
gctcacccat acttctggca gtgtctaaag aacgccctgg ccacagacaa tcatgtggcc   3120
tatagtcagg tgttcaagga aacggtc                                       3147
```

<210> SEQ ID NO 118
<211> LENGTH: 3177
<212> TYPE: DNA
<213> ORGANISM: Homo sapiens
<220> FEATURE:
<223> OTHER INFORMATION: TLR8, isoform 1

<400> SEQUENCE: 118

```
atgaaggagt catctttgca aaatagctcc tgcagcctgg gaaaggagac taaaaaggaa     60
aacatgttcc ttcagtcgtc aatgctgacc tgcattttcc tgctaatatc tggttcctgt    120
gagttatgcg ccgaagaaaa tttttctaga agctatcctt gtgatgagaa aaagcaaaat    180
gactcagtta ttgcagagtg cagcaatcgt cgactacagg aagttcccca aacggtgggc    240
aaatatgtga cagaactaga cctgtctgat aatttcatca cacacataac gaatgaatca    300
tttcaagggc tgcaaaatct cactaaaata aatctaaacc acaaccccaa tgtacagcac    360
cagaacggaa atcccggtat acaatcaaat ggcttgaata tcacagacgg ggcattcctc    420
aacctaaaaa acctaaggga gttactgctt gaagacaacc agttacccca aataccctct    480
ggtttgccag agtctttgac agaacttagt ctaattcaaa acaatatata caacataact    540
aaagagggca tttcaagact tataaacttg aaaaatctct atttggcctg gaactgctat    600
tttaacaaag tttgcgagaa aactaacata gaagatggag tatttgaaac gctgacaaat    660
ttggagttgc tatcactatc tttcaattct ctttcacacg tgccacccaa actgccaagc    720
tccctacgca aactttttct gagcaacacc cagatcaaat acattagtga agaagatttc    780
aagggattga taaatttaac attactagat ttaagcggga actgtccgag gtgcttcaat    840
gccccatttc catgcgtgcc ttgtgatggt ggtgcttcaa ttaatataga tcgttttgct    900
tttcaaaact tgacccaact tcgataccta aacctctcta gcacttccct caggaagatt    960
aatgctgcct ggtttaaaaa tatgcctcat ctgaaggtgc tggatcttga attcaactat   1020
ttagtgggag aaatagcctc tggggcattt ttaacgatgc tgccccgctt agaaatactt   1080
gacttgtctt ttaactatat aaaggggagt tatccacagc atattaatat ttccagaaac   1140
ttctctaaac ttttgtctct acgggcattg catttaagag gttatgtgtt ccaggaactc   1200
agagaagatg atttccagcc cctgatgcag cttccaaact tatcgactat caacttgggt   1260
attaatttta ttaagcaaat cgatttcaaa cttttccaaa atttctccaa tctggaaatt   1320
atttacttgt cagaaaacag aatatcaccg ttggtaaaag atacccggca gagttatgca   1380
aatagttcct cttttcaacg tcatatccgg aaacgacgct caacagattt tgagtttgac   1440
ccacattcga acttttatca tttcacccgt cctttaataa agccacaatg tgctgcttat   1500
ggaaaagcct tagatttaag cctcaacagt attttcttca ttgggccaaa ccaatttgaa   1560
aatcttcctg acattgcctg tttaaatctg tctgcaaata gcaatgctca agtgttaagt   1620
ggaactgaat tttcagccat tcctcatgtc aaatatttgg atttgacaaa caatagacta   1680
gactttgata atgctagtgc tcttactgaa ttgtccgact tggaagttct agatctcagc   1740
tataattcac actatttcag aatagcaggc gtaacacatc atctagaatt tattcaaaat   1800
ttcacaaatc taaaagtttt aaacttgagc cacaacaaca tttatacttt aacagataag   1860
tataacctgg aaagcaagtc cctggtagaa ttagttttca gtggcaatcg ccttgacatt   1920
ttgtggaatg atgatgacaa caggtatatc tccattttca aaggtctcaa gaatctgaca   1980
cgtctggatt tatcccttaa taggctgaag cacatcccaa atgaagcatt ccttaatttg   2040
ccagcgagtc tcactgaact acatataaat gataatatgt taaagttttt taactggaca   2100
ttactccagc agtttcctcg tctcgagttg cttgacttac gtggaaacaa actactcttt   2160
ttaactgata gcctatctga ctttacatct tcccttcgga cactgctgct gagtcataac   2220
aggatttccc acctaccctc tggctttctt tctgaagtca gtagtctgaa gcacctcgat   2280
ttaagttcca atctgctaaa aacaatcaac aaatccgcac ttgaaactaa gaccaccacc   2340
```

-continued aaattatcta tgttggaact acacggaaac ccctttgaat gcacctgtga cattggagat 2400
ttccgaagat ggatggatga acatctgaat gtcaaaattc ccagactggt agatgtcatt 2460
tgtgccagtc ctggggatca aagagggaag agtattgtga gtctggagct aacaacttgt 2520
gtttcagatg tcactgcagt gatattattt ttcttcacgt tctttatcac caccatggtt 2580
atgttggctg ccctggctca ccatttgttt tactgggatg tttggtttat atataatgtg 2640
tgtttagcta aggtaaaagg ctacaggtct ctttccacat cccaaacttt ctatgatgct 2700
tacatttctt atgacaccaa agatgcctct gttactgact gggtgataaa tgagctgcgc 2760
taccaccttg aagagagccg agacaaaaac gttctccttt gtctagagga gagggattgg 2820
gacccgggat tggccatcat cgacaacctc atgcagagca tcaaccaaag caagaaaaca 2880
gtatttgttt taaccaaaaa atatgcaaaa agctggaact ttaaaacagc tttttacttg 2940
gctttgcaga ggctaatgga tgagaacatg gatgtgatta tatttatcct gctggagcca 3000
gtgttacagc attctcagta tttgaggcta cggcagcgga tctgtaagag ctccatcctc 3060
cagtggcctg acaacccgaa ggcagaaggc ttgttttggc aaactctgag aaatgtggtc 3120
ttgactgaaa atgattcacg gtataacaat atgtatgtcg attccattaa gcaatac 3177

<210> SEQ ID NO 119
<211> LENGTH: 636
<212> TYPE: DNA
<213> ORGANISM: Homo sapiens
<220> FEATURE:
<223> OTHER INFORMATION: Interleukin 6 (IL-6)

<400> SEQUENCE: 119
atgaactcct tctccacaag cgccttcggt ccagttgcct tctccctggg gctgctcctg 60
gtgttgcctg ctgccttccc tgccccagta cccccaggag aagattccaa agatgtagcc 120
gccccacaca gacagccact cacctcttca gaacgaattg acaaacaaat tcggtacatc 180
ctcgacggca tctcagccct gagaaaggag acatgtaaca agagtaacat gtgtgaaagc 240
agcaaagagg cactggcaga aaacaacctg aaccttccaa agatggctga aaaagatgga 300
tgcttccaat ctggattcaa tgaggagact tgcctggtga aaatcatcac tggtcttttg 360
gagtttgagg tatacctaga gtacctccag aacagatttg agagtagtga ggaacaagcc 420
agagctgtgc agatgagtac aaaagtcctg atccagttcc tgcagaaaaa ggcaaagaat 480
ctagatgcaa taaccacccc tgacccaacc acaaatgcca gcctgctgac gaagctgcag 540
gcacagaacc agtggctgca ggacatgaca actcatctca ttctgcgcag ctttaaggag 600
ttcctgcagt ccagcctgag ggctcttcgg caaatg 636

<210> SEQ ID NO 120
<211> LENGTH: 951
<212> TYPE: DNA
<213> ORGANISM: Homo sapiens
<220> FEATURE:
<223> OTHER INFORMATION: MyD88, isoform 1

<400> SEQUENCE: 120
atgcgacccg accgcgctga ggctccagga ccgcccgcca tggctgcagg aggtcccggc 60
gcggggtctg cggccccggt ctcctccaca tcctcccttc cctggctgc tctcaacatg 120 cgagtgcggc gccgcctgtc tctgttcttg aacgtgcgga cacaggtggc ggccgactgg 180
accgcgctgg cggaggagat ggactttgag tacttggaga tccggcaact ggagacacaa 240
gcggacccca ctggcaggct gctggacgcc tggcagggac gccctggcgc ctctgtaggc 300
cgactgctcg agctgcttac caagctgggc cgcgacgacg tgctgctgga gctgggaccc 360
agcattgagg aggattgcca aaagtatatc ttgaagcagc agcaggagga ggctgagaag 420
cctttacagg tggccgctgt agacagcagt gtcccacgga cagcagagct ggcgggcatc 480
accacacttg atgacccct ggggcatatg cctgagcgtt tcgatgcctt catctgctat 540
tgccccagcg acatccagtt tgtgcaggag atgatccggc aactggaaca gacaaactat 600
cgactgaagt tgtgtgtgtc tgaccgcgat gtcctgcctg gcacctgtgt ctggtctatt 660
gctagtgagc tcatcgaaaa gaggttggct agaaggccac ggggtgggtg ccgccggatg 720
gtggtggttg tctctgatga ttacctgcag agcaaggaat gtgacttcca gaccaaattt 780
gcactcagcc tctctccagg tgcccatcag aagcgactga tccccatcaa gtacaaggca 840
atgaagaaag agttccccag catcctgagg ttcatcactg tctgcgacta caccaacccc 900
tgcaccaaat cttggttctg gactcgcctt gccaaggcct tgtccctgcc c 951

<210> SEQ ID NO 121
<211> LENGTH: 807
<212> TYPE: DNA
<213> ORGANISM: Homo sapiens
<220> FEATURE:
<223> OTHER INFORMATION: Interleukin 1-beta (IL-1beta)

<400> SEQUENCE: 121
atggcagaag tacctgagct cgccagtgaa atgatggctt attacagtgg caatgaggat 60
gacttgttct ttgaagctga tggccctaaa cagatgaagt gctccttcca ggacctggac 120
ctctgccctc tggatggcgg catccagcta cgaatctccg accaccacta cagcaagggc 180
ttcaggcagg ccgcgtcagt tgttgtggcc atggacaagc tgaggaagat gctggttccc 240
tgcccacaga ccttccagga gaatgacctg agcaccttct ttcccttcat ctttgaagaa 300
gaacctatct tcttcgacac atgggataac gaggcttatg tgcacgatgc acctgtacga 360
tcactgaact gcacgctccg ggactcacag caaaaaagct tggtgatgtc tggtccatat 420
gaactgaaag ctctccacct ccagggacag gatatggagc aacaagtggt gttctccatg 480
tcctttgtac aaggagaaga aagtaatgac aaaatacctg tggccttggg cctcaaggaa 540
aagaatctgt acctgtcctg cgtgttgaaa gatgataagc ccactctaca gctggagagt 600
gtagatccca aaaattaccc aaagaagaag atggaaaagc gatttgtctt caacaagata 660
gaaatcaata acaagctgga atttgagtct gcccagttcc ccaactggta catcagcacc 720
tctcaagcag aaaacatgcc cgtcttcctg ggagggacca aaggcggcca ggatataact 780
gacttcacca tgcaatttgt gtcttcc 807

<210> SEQ ID NO 122
<211> LENGTH: 3075
<212> TYPE: DNA
<213> ORGANISM: Homo sapiens
<220> FEATURE:
<223> OTHER INFORMATION: MDA5/IFIH1, isoform 1

<400> SEQUENCE: 122
atgtcgaatg ggtattccac agacgagaat ttccgctatc tcatctcgtg cttcagggcc 60
agggtgaaaa tgtacatcca ggtggagcct gtgctggact acctgacctt tctgcctgca 120
gaggtgaagg agcagattca gaggacagtc gccacctccg ggaacatgca ggcagttgaa 180
ctgctgctga gcaccttgga gaagggagtc tggcaccttg gttggactcg ggaattcgtg 240

-continued

```
gaggccctcc ggagaaccgg cagccctctg gccgcccgct acatgaaccc tgagctcacg    300

gacttgccct ctccatcgtt tgagaacgct catgatgaat atctccaact gctgaacctc    360

cttcagccca ctctggtgga caagcttcta gttagagacg tcttggataa gtgcatggag    420

gaggaactgt tgacaattga agacagaaac cggattgctg ctgcagaaaa caatggaaat    480

gaatcaggtg taagagagct actaaaaagg attgtgcaga aagaaaactg gttctctgca    540

tttctgaatg ttcttcgtca aacaggaaac aatgaacttg tccaagagtt aacaggctct    600

gattgctcag aaagcaatgc agagattgag aatttatcac aagttgatgg tcctcaagtg    660

gaagagcaac ttctttcaac cacagttcag ccaaatctgg agaaggaggt ctggggcatg    720

gagaataact catcagaatc atcttttgca gattcttctg tagtttcaga atcagacaca    780

agtttggcag aaggaagtgt cagctgctta gatgaaagtc ttggacataa cagcaacatg    840

ggcagtgatt caggcaccat gggaagtgat tcagatgaag agaatgtggc agcaagagca    900

tccccggagc cagaactcca gctcaggcct taccaaatgg aagttgccca gccagccttg    960

gaagggaaga atatcatcat ctgcctccct acagggagtg gaaaaaccag agtggctgtt   1020

tacattgcca aggatcactt agacaagaag aaaaaagcat ctgagcctgg aaaagttata   1080

gttcttgtca ataaggtact gctagttgaa cagctcttcc gcaaggagtt ccaaccattt   1140

ttgaagaaat ggtatcgtgt tattggatta agtggtgata cccaactgaa aatatcattt   1200

ccagaagttg tcaagtcctg tgatattatt atcagtacag ctcaaatcct tgaaaactcc   1260

ctcttaaact tggaaaatgg agaagatgct ggtgttcaat tgtcagactt ttccctcatt   1320

atcattgatg aatgtcatca caccaacaaa gaagcagtgt ataataacat catgaggcat   1380

tatttgatgc agaagttgaa aaacaataga ctcaagaaag aaaacaaacc agtgattccc   1440

cttcctcaga tactgggact aacagcttca cctggtgttg gaggggccac gaagcaagcc   1500

aaagctgaag aacacatttt aaaactatgt gccaatcttg atgcatttac tattaaaact   1560

gttaaagaaa accttgatca actgaaaaac caaatacagg agccatgcaa gaagtttgcc   1620

attgcagatg caaccagaga agatccattt aaagagaaac ttctagaaat aatgacaagg   1680

attcaaactt attgtcaaat gagtccaatg tcagattttg gaactcaacc ctatgaacaa   1740

tgggccattc aaatggaaaa aaaagctgca aaagaaggaa atcgcaaaga acgtgtttgt   1800

gcagaacatt tgaggaagta caatgaggcc ctacaaatta atgacacaat tcgaatgata   1860

gatgcgtata ctcatcttga aactttctat aatgaagaga aagataagaa gtttgcagtc   1920

atagaagatg atagtgatga gggtggtgat gatgagtatt gtgatggtga tgaagatgag   1980

gatgatttaa agaaaccttt gaaactggat gaaacagata gatttctcat gactttattt   2040

tttgaaaaca ataaaatgtt gaaaaggctg gctgaaaacc cagaatatga aaatgaaaag   2100

ctgaccaaat taagaaatac cataatggag caatatacta ggactgagga atcagcacga   2160

ggaataatct ttacaaaaac acgacagagt gcatatgcgc tttcccagtg gattactgaa   2220

aatgaaaaat ttgctgaagt aggagtcaaa gcccaccatc tgattggagc tggacacagc   2280

agtgagttca aacccatgac acagaatgaa caaaaagaag tcattagtaa atttcgcact   2340

ggaaaaataa atctgcttat cgctaccaca gtggcagaag aaggtctgga tattaaagaa   2400

tgtaacattg ttatccgtta tggtctcgtc accaatgaaa tagccatggt ccaggcccgt   2460

ggtcgagcca gagctgatga gagcacctac gtcctggttg ctcacagtgg ttcaggagtt   2520

atcgaacatg agacagttaa tgatttccga gagaagatga tgtataaagc tatacattgt   2580

gttcaaaata tgaaaccaga ggagtatgct cataagattt tggaattaca gatgcaaagt   2640
```

ataatggaaa agaaaatgaa aaccaagaga aatattgcca agcattacaa gaataaccca 2700
tcactaataa ctttcctttg caaaaactgc agtgtgctag cctgttctgg ggaagatatc 2760
catgtaattg agaaaatgca tcacgtcaat atgaccccag aattcaagga actttacatt 2820
gtaagagaaa acaaagcact gcaaaagaag tgtgccgact atcaaataaa tggtgaaatc 2880
atctgcaaat gtggccaggc ttggggaaca atgatggtgc acaaaggctt agatttgcct 2940
tgtctcaaaa taaggaattt tgtagtggtt ttcaaaaata attcaacaaa gaaacaatac 3000
aaaaagtggg tagaattacc tatcacattt cccaatcttg actattcaga atgctgttta 3060
tttagtgatg aggat 3075

<210> SEQ ID NO 123
<211> LENGTH: 1620
<212> TYPE: DNA
<213> ORGANISM: Homo sapiens
<220> FEATURE:
<223> OTHER INFORMATION: IPS-1/MAVS, isoform 1

<400> SEQUENCE: 123
atgccgtttg ctgaagacaa gacctataag tatatctgcc gcaatttcag caatttttgc 60
aatgtggatg ttgtagagat tctgccttac ctgccctgcc tcacagcaag agaccaggat 120
cgactgcggg ccacctgcac actctcaggg aaccgggaca ccctctggca tctcttcaat 180
acccttcagc ggcggcccgg ctgggtggag tacttcattg cggcactgag ggctgtgag 240 ctagttgatc tcgcggacga agtggcctct gtctaccaga gctaccagcc tcggacctcg 300
gaccgtcccc cagacccact ggagccaccg tcacttcctg ctgagaggcc agggcccccc 360
acacctgctg cggcccacag catcccctac aacagctgca gagagaagga gccaagttac 420
cccatgcctg tccaggagac ccaggcgcca gagtccccag gagagaattc agagcaagcc 480
ctgcagacgc tcagccccag agccatccca aggaatccag atggtggccc cctggagtcc 540
tcctctgacc tggcagccct cagccctctg acctccagcg ggcatcagga gcaggacaca 600
gaactgggca gtacccacac agcaggtgcg acctccagcc tcacaccatc ccgtgggcct 660
gtgtctccat ctgtctcctt ccagcccctg gcccgttcca cccccagggc aagccgcttg 720
cctggaccca cagggtcagt tgtatctact ggcacctcct tctcctcctc atcccctggc 780
ttggcctctg caggggctgc agagggtaaa cagggtgcag agagtgacca ggccgagcct 840
atcatctgct ccagtggggc agaggcacct gccaactctc tgccctccaa agtgcctacc 900
accttgatgc ctgtgaacac agtggccctg aaagtgcctg ccaacccagc atctgtcagc 960
acagtgccct ccaagttgcc aactagctca aagcccctg gtgcagtgcc ttctaatgcg 1020
ctcaccaatc cagcaccatc caaattgccc atcaactcaa cccgtgctgg catggtgcca 1080
tccaaagtgc ctactagcat ggtgctcacc aaggtgtctg ccagcacagt ccccactgac 1140
gggagcagca gaaatgagga gaccccagca gctccaacac ccgccggcgc cactggaggc 1200
agctcagcct ggctagacag cagctctgag aatagggggcc ttgggtcgga gctgagtaag 1260
cctggcgtgc tggcatccca ggtagacagc ccgttctcgg gctgcttcga ggatcttgcc 1320
atcagtgcca gcacctcctt gggcatgggg ccctgccatg gcccagagga gaatgagtat 1380
aagtccgagg gcacctttgg gatccacgtg gctgagaacc ccagcatcca gctcctggag 1440
ggcaaccctg ggccacctgc ggacccggat ggcggcccca ggccacaagc cgaccggaag 1500
ttccaggaga gggaggtgcc atgccacagg ccctcacctg ggctctgtg gctccaggtg 1560

-continued gctgtgacag gggtgctggt agtcacactc ctggtggtgc tgtaccggcg gcgtctgcac 1620

<210> SEQ ID NO 124
<211> LENGTH: 2775
<212> TYPE: DNA
<213> ORGANISM: Homo sapiens
<220> FEATURE:
<223> OTHER INFORMATION: RIG-1/DDX58, isoform 1

<400> SEQUENCE: 124
atgaccaccg agcagcgacg cagcctgcaa gccttccagg attatatccg gaagaccctg 60
gaccctacct acatcctgag ctacatggcc ccctggttta gggaggaaga ggtgcagtat 120
attcaggctg agaaaaacaa caagggccca atggaggctg ccacactttt tctcaagttc 180
ctgttggagc tccaggagga aggctggttc cgtggctttt tggatgccct agaccatgca 240
ggttattctg gactttatga agccattgaa agttgggatt tcaaaaaaat tgaaaagttg 300
gaggagtata gattactttt aaaacgttta caaccagaat ttaaaaccag aattatccca 360
accgatatca tttctgatct gtctgaatgt ttaattaatc aggaatgtga agaaattcta 420
cagatttgct ctactaaggg gatgatggca ggtgcagaga aattggtgga atgccttctc 480
agatcagaca aggaaaactg gcccaaaact ttgaaacttg ctttggagaa agaaaggaac 540
aagttcagtg aactgtggat tgtagagaaa ggtataaaag atgttgaaac agaagatctt 600
gaggataaga tggaaacttc tgacatacag attttctacc aagaagatcc agaatgccag 660
aatcttagtg agaattcatg tccaccttca gaagtgtctg atacaaactt gtacagccca 720
tttaaaccaa gaaattacca attagagctt gctttgcctg ctatgaaagg aaaaaacaca 780
ataatatgtg ctcctacagg ttgtggaaaa acctttgttt cactgcttat atgtgaacat 840
catcttaaaa aattcccaca aggacaaaag gggaaagttg tctttttttgc gaatcagatc 900 ccagtgtatg aacagcagaa atctgtattc tcaaaatact ttgaaagaca tgggtataga 960
gttacaggca tttctggagc aacagctgag aatgtcccag tggaacagat tgttgagaac 1020
aatgacatca tcattttaac tccacagatt cttgtgaaca accttaaaaa gggaacgatt 1080
ccatcactat ccatctttac tttgatgata tttgatgaat gccacaacac tagtaaacaa 1140
cacccgtaca atatgatcat gtttaattat ctagatcaga aacttggagg atcttcaggc 1200
ccactgcccc aggtcattgg gctgactgcc tcggttggtg ttggggatgc caaaaacaca 1260
gatgaagcct tggattatat ctgcaagctg tgtgcttctc ttgatgcgtc agtgatagca 1320
acagtcaaac acaatctgga ggaactggag caagttgttt ataagcccca gaagtttttc 1380
aggaaagtgg aatcacggat tagcgacaaa tttaaataca tcatagctca gctgatgagg 1440
gacacagaga gtctggcaaa gagaatctgc aaagacctcg aaaacttatc tcaaattcaa 1500
aatagggaat ttggaacaca gaaatatgaa caatggattg ttacagttca gaaagcatgc 1560
atggtgttcc agatgccaga caaagatgaa gagagcagga tttgtaaagc cctgttttta 1620
tacacttcac atttgcggaa atataatgat gccctcatta tcagtgagca tgcacgaatg 1680
aaagatgctc tggattactt gaaagacttc ttcagcaatg tccgagcagc aggattcgat 1740
gagattgagc aagatcttac tcagagattt gaagaaaagc tgcaggaact agaaagtgtt 1800
tccagggatc ccagcaatga gaatcctaaa cttgaagacc tctgcttcat cttacaagaa 1860
gagtaccact taaacccaga gacaataaca attctctttg tgaaaaccag agcacttgtg 1920
gacgctttaa aaaattggat tgaaggaaat cctaaactca gttttctaaa acctggcata 1980
ttgactggac gtggcaaaac aaatcagaac acaggaatga ccctcccggc acagaagtgt 2040

```
atattggatg cattcaaagc cagtggagat cacaatattc tgattgccac ctcagttgct   2100

gatgaaggca ttgacattgc acagtgcaat cttgtcatcc tttatgagta tgtgggcaat   2160

gtcatcaaaa tgatccaaac cagaggcaga ggaagagcaa gaggtagcaa gtgcttcctt   2220

ctgactagta atgctggtgt aattgaaaaa gaacaaataa acatgtacaa agaaaaaatg   2280

atgaatgact ctattttacg ccttcagaca tgggacgaag cagtatttag ggaaaagatt   2340

ctgcatatac agactcatga aaaattcatc agagatagtc aagaaaaacc aaaacctgta   2400

cctgataagg aaaataaaaa actgctctgc agaaagtgca aagccttggc atgttacaca   2460

gctgacgtaa gagtgataga ggaatgccat tacactgtgc ttggagatgc ttttaaggaa   2520

tgctttgtga gtagaccaca tcccaagcca aagcagtttt caagttttga aaaaagagca   2580

aagatattct gtgcccgaca gaactgcagc catgactggg gaatccatgt gaagtacaag   2640

acatttgaga ttccagttat aaaaattgaa agttttgtgg tggaggatat tgcaactgga   2700

gttcagacac tgtactcgaa gtggaaggac tttcattttg agaagatacc atttgatcca   2760

gcagaaatgt ccaaa                                                   2775
```

<210> SEQ ID NO 125
<211> LENGTH: 1494
<212> TYPE: DNA
<213> ORGANISM: Homo sapiens
<220> FEATURE:
<223> OTHER INFORMATION: IRF5, transcript variant 2

<400> SEQUENCE: 125

```
atgaaccagt ccatcccagt ggctcccacc ccaccccgcc gcgtgcggct gaagccctgg     60

ctggtggccc aggtgaacag ctgccagtac ccagggcttc aatgggtcaa cggggaaaag    120

aaattattct gcatcccctg gaggcatgcc acaaggcatg gtcccagcca ggacggagat    180

aacaccatct tcaaggcctg ggccaaggag acagggaaat acaccgaagg cgtggatgaa    240

gccgatccgg ccaagtggaa ggccaacctg cgctgtgccc ttaacaagag ccgggacttc    300

cgcctcatct acgacgggcc ccgggacatg ccacctcagc cctacaagat ctacgaggtc    360

tgctccaatg gccctgctcc cacagactcc cagcccccctg aggattactc ttttggtgca    420

ggagaggagg aggaagaaga ggaagagctg cagaggatgt tgccaagcct gagcctcaca    480

gaggatgtca agtggccgcc cactctgcag ccgcccactc tgcggccgcc tactctgcag    540

ccgcccactc tgcagccgcc cgtggtgctg ggtccccctg ctccagaccc cagccccctg    600

gctcctcccc ctggcaaccc tgctggcttc agggagcttc tctctgaggt cctggagcct    660

gggcccctgc ctgccagcct gcccccctgca ggcgaacagc tcctgccaga cctgctgatc    720

agcccccaca tgctgcctct gaccgacctg gagatcaagt ttcagtaccg gggggcggcca    780

ccccgggccc tcaccatcag caacccccat ggctgccggc tcttctacag ccagctggag    840

gccacccagg agcaggtgga actcttcggc cccataagcc tggagcaagt gcgcttcccc    900

agccctgagg acatccccag tgacaagcag cgcttctaca cgaaccagct gctggatgtc    960

ctggaccgcg ggctcatcct ccagctacag ggccaggacc tttatgccat ccgcctgtgt   1020

cagtgcaagg tgttctggag cgggccttgt gcctcagccc atgactcatg ccccaacccc   1080

atccagcggg aggtcaagac caagcttttc agcctggagc attttctcaa tgagctcatc   1140

ctgttccaaa agggccagac caacacccca ccacccttcg agatcttctt ctgctttggg   1200

gaagaatggc ctgaccgcaa accccgagag aagaagctca ttactgtaca ggtggtgcct   1260
```

```
gtagcagctc gactgctgct ggagatgttc tcaggggagc tatcttggtc agctgatagt   1320

atccggctac agatctcaaa cccagacctc aaagaccgca tggtggagca attcaaggag   1380

ctccatcaca tctggcagtc ccagcagcgg ttgcagcctg tggcccaggc ccctcctgga   1440

gcaggccttg gtgttggcca ggggccctgg cctatgcacc cagctggcat gcaa         1494
```

```
<210> SEQ ID NO 126
<211> LENGTH: 1284
<212> TYPE: DNA
<213> ORGANISM: Homo sapiens
<220> FEATURE:
<223> OTHER INFORMATION: IRF3, isoform 1

<400> SEQUENCE: 126

accatgggaa ccccaaagcc acggatcctg ccctggctgg tgtcgcagct ggacctgggg     60

caactggagg gcgtggcctg ggtgaacaag agccgcacgc gcttccgcat cccttggaag    120

cacggcctac ggcaggatgc acagcaggag gatttcggaa tcttccaggc ctgggccgag    180

gccactggtg catatgttcc cgggagggat aagccagacc tgccaacctg gaagaggaat    240

ttccgctctg ccctcaaccg caaagaaggg ttgcgtttag cagaggaccg gagcaaggac    300

cctcacgacc cacataaaat ctacgagttt gtgaactcag gagttgggga cttttcccag    360

ccagacacct ctccggacac caatggtgga ggcagtactt ctgataccca ggaagacatt    420

ctggatgagt tactgggtaa catggtgttg gccccactcc cagatccggg accccccaagc   480

ctggctgtag cccctgagcc ctgccctcag cccctgcgga gccccagctt ggacaatccc    540

actcccttcc caaacctggg gccctctgag aacccactga agcggctgtt ggtgccgggg    600

gaagagtggg agttcgaggt gacagccttc taccggggcc gccaagtctt ccagcagacc    660

atctcctgcc cggagggcct gcggctggtg gggtccgaag tgggagacag gacgctgcct    720

ggatggccag tcacactgcc agaccctggc atgtccctga cagacagggg agtgatgagc    780

tacgtgaggc atgtgctgag ctgcctgggt gggggactgg ctctctggcg ggccgggcag    840

tggctctggg cccagcggct ggggcactgc cacacatact gggcagtgag cgaggagctg    900

ctccccaaca gcgggcatgg gcctgatggc gaggtcccca aggacaagga aggaggcgtg    960

tttgacctgg ggcccttcat tgtagatctg attaccttca cggaaggaag cggacgctca   1020

ccacgctatg ccctctggtt ctgtgtgggg gagtcatggc cccaggacca gccgtggacc   1080

aagaggctcg tgatggtcaa ggttgtgccc acgtgcctca gggccttggt agaaatggcc   1140

cgggtagggg gtgcctcctc cctggagaat actgtggacc tgcacatttc caacagccac   1200

ccactctccc tcacctccga ccagtacaag gcctacctgc aggacttggt ggagggcatg   1260

gatttccagg gccctgggga gagc                                          1284
```

```
<210> SEQ ID NO 127
<211> LENGTH: 1275
<212> TYPE: DNA
<213> ORGANISM: Homo sapiens
<220> FEATURE:
<223> OTHER INFORMATION: TANK

<400> SEQUENCE: 127

atggataaaa acattggcga gcaactcaat aaagcgtatg aagccttccg gcaggcatgc     60

atggatagag attctgcagt aaaagaatta cagcaaaaga ctgagaacta tgagcagaga    120

atacgtgaac aacaggaaca gctgtcactt caacagacta ttattgacaa gctaaaatct    180

cagttacttc ttgtgaattc cactcaagat aacaattatg gctgtgttcc tctgcttgaa    240
```

gacagtgaaa caagaaagaa taatttgact cttgatcagc cacaagataa agtgatttca 300
ggaatagcaa gagaaaaact accaaaggta agaagacaag aggtttcttc tcctagaaaa 360
gaaacttcag caaggagtct tggcagtcct ttgctccatg aaaggggtaa tatagagaag 420
actttctggg atctgaaaga agaatttcat aaaatatgca tgctagcaaa agcacagaaa 480
gaccacttaa gcaaacttaa tataccagac actgcaactg aaacacagtg ctctgtgcct 540
atacagtgta cggataaaac agataaacaa gaagcgctgt ttaagcctca ggctaaagat 600
gatataaata gaggtgcacc atccatcaca tctgtcacac caagaggact gtgcagagat 660
gaggaagaca cctcttttga atcactttct aaattcaatg tcaagtttcc acctatggac 720
aatgactcaa ctttcttaca tagcactcca gagagacccg gcatccttag tcctgccacg 780
tctgaggcag tgtgccaaga gaaatttaat atggagttca gagacaaccc agggaacttt 840
gttaaaacag aagaaacttt atttgaaatt cagggaattg accccatagc ttcagctata 900
caaaacctta aaacaactga caaaacaaag ccctcaaatc tcgtaaacac ttgtatcagg 960
acaactctgg atagagctgc gtgtttgcca cctggagacc ataatgcatt atatgtaaat 1020
agcttcccac ttctggaccc atctgatgca ccttttccct cactcgattc cccgggaaaa 1080
gcaatccgag gaccacagca gcccatttgg aagccctttc ctaatcaaga cagtgactcg 1140
gtggtactaa gtggcacaga ctcagaactg catatacctc gagtatgtga attctgtcaa 1200
gcagttttcc caccatccat tacatccagg ggggatttcc ttcggcatct taattcacac 1260
ttcaatggag agact 1275

<210> SEQ ID NO 128
<211> LENGTH: 2136
<212> TYPE: DNA
<213> ORGANISM: Homo sapiens
<220> FEATURE:
<223> OTHER INFORMATION: TRIF/TICAM1

<400> SEQUENCE: 128
atggcctgca caggcccatc acttcctagc gccttcgaca ttctaggtgc agcaggccag 60
gacaagctct tgtatctgaa gcacaaactg aagaccccac gcccaggctg ccaggggcag 120
gacctcctgc atgccatggt tctcctgaag ctgggccagg aaactgaggc caggatctct 180
ctagaggcat tgaaggccga tgcggtggcc cggctggtgg cccgccagtg ggctggcgtg 240
gacagcaccg aggacccaga ggagcccccca gatgtgtcct gggctgtggc ccgcttgtac 300
cacctgctgg ctgaggagaa gctgtgcccc gcctcgctgc gggacgtggc ctaccaggaa 360
gccgtccgca ccctcagctc cagggacgac caccggctgg gggaacttca ggatgaggcc 420
cgaaaccggt gtgggtggga cattgctggg gatccaggga gcatccggac gctccagtcc 480
aatctgggct gcctcccacc atcctcggct ttgccctctg ggaccaggag cctcccacgc 540
cccattgacg gtgtttcgga ctggagccaa gggtgctccc tgcgatccac tggcagccct 600
gcctccctgg ccagcaactt ggaaatcagc cagtccccta ccatgccctt cctcagcctg 660
caccgcagcc cacatgggcc cagcaagctc tgtgacgacc cccaggccag cttggtgccc 720
gagcctgtcc ccggtggctg ccaggagcct gaggagatga gctggccgcc atcgggggag 780
attgccagcc caccagagct gccaagcagc ccacctcctg ggcttcccga agtggcccca 840
gatgcaacct ccactggcct ccctgatacc cccgcagctc cagaaaccag caccaactac 900
ccagtggagt gcaccgaggg gtctgcaggc ccccagtctc tccccttgcc tattctggag 960
ccggtcaaaa accccctgctc tgtcaaagac cagacgccac tccaactttc tgtagaagat 1020
accacctctc caaataccaa gccgtgccca cctactccca ccaccccaga aacatcccct 1080
cctcctcctc ctcctcctcc ttcatctact ccttgttcag ctcacctgac cccctcctcc 1140
ctgttccctt cctccctgga atcatcatcg gaacagaaat tctataactt tgtgatcctc 1200
cacgccaggg cagacgaaca catcgccctg cgggttcggg agaagctgga ggcccttggc 1260
gtgcccgacg gggccacctt ctgcgaggat ttccaggtgc cggggcgcgg ggagctgagc 1320
tgcctgcagg acgccataga ccactcagct ttcatcatcc tacttctcac ctccaacttc 1380
gactgtcgcc tgagcctgca ccaggtgaac caagccatga tgagcaacct cacgcgacag 1440
gggtcgccag actgtgtcat ccccttcctg cccctggaga gctccccggc ccagctcagc 1500
tccgacacgg ccagcctgct ctccgggctg gtgcggctgg acgaacactc ccagatcttc 1560
gccaggaagg tggccaacac cttcaagccc cacaggcttc aggcccgaaa ggccatgtgg 1620
aggaaggaac aggacacccg agccctgcgg gaacagagcc aacacctgga cggtgagcgg 1680
atgcaggcgg cggcactgaa cgcagcctac tcagcctacc tccagagcta cttgtcctac 1740
caggcacaga tggagcagct ccaggtggct tttgggagcc acatgtcatt tgggactggg 1800
gcgccctatg gggctcgaat gccctttggg ggccaggtgc ccctgggagc cccgccaccc 1860
tttcccactt ggccggggtg cccgcagccg ccacccctgc acgcatggca ggctggcacc 1920
cccccaccgc cctccccaca gccagcagcc tttccacagt cactgccctt cccgcagtcc 1980
ccagccttcc ctacggcctc acccgcaccc cctcagagcc cagggctgca acccctcatt 2040
atccaccacg cacagatggt acagctgggg ctgaacaacc acatgtggaa ccagagaggg 2100
tcccaggcgc ccgaggacaa gacgcaggag gcagaa 2136

<210> SEQ ID NO 129
<211> LENGTH: 381
<212> TYPE: DNA
<213> ORGANISM: Homo sapiens
<220> FEATURE:
<223> OTHER INFORMATION: Batf3

<400> SEQUENCE: 129
atgtcgcaag ggctcccggc cgccggcagc gtcctgcaga ggagcgtcgc ggcgcccggg 60
aaccagccgc agccgcagcc gcagcagcag agccctgagg atgatgacag gaaggtccga 120
aggagagaaa aaaaccgagt tgctgctcag agaagtcgga agaagcagac ccagaaggct 180
gacaagctcc atgaggaata tgagagcctg gagcaagaaa acaccatgct gcggagagag 240
atcgggaagc tgacagagga gctgaagcac ctgacagagg cactgaagga gcacgagaag 300
atgtgcccgc tgctgctctg ccctatgaac tttgtgccag tgcctccccg gccggaccct 360
gtggccggct gcttgccccg a 381

<210> SEQ ID NO 130
<211> LENGTH: 459
<212> TYPE: DNA
<213> ORGANISM: Homo sapiens
<220> FEATURE:
<223> OTHER INFORMATION: IL-4, isoform 1

<400> SEQUENCE: 130
atgggtctca cctcccaact gcttcccccct ctgttcttcc tgctagcatg tgccggcaac 60
tttgtccacg gacacaagtg cgatatcacc ttacaggaga tcatcaaaac tttgaacagc 120
ctcacagagc agaagactct gtgcaccgag ttgaccgtaa cagacatctt tgctgcctcc 180

```
aagaacacaa ctgagaagga aaccttctgc agggctgcga ctgtgctccg gcagttctac    240

agccaccatg agaaggacac tcgctgcctg ggtgcgactg cacagcagtt ccacaggcac    300

aagcagctga tccgattcct gaaacggctc gacaggaacc tctggggcct ggcgggcttg    360

aattcctgtc ctgtgaagga agccaaccag agtacgttgg aaaacttctt ggaaaggcta    420

aagacgatca tgagagagaa atattcaaag tgttcgagc                           459


<210> SEQ ID NO 131
<211> LENGTH: 534
<212> TYPE: DNA
<213> ORGANISM: Homo sapiens
<220> FEATURE:
<223> OTHER INFORMATION: IL-10

<400> SEQUENCE: 131

atgcacagct cagcactgct ctgttgcctg gtcctcctga ctggggtgag ggccagccca     60

ggccagggca cccagtctga gaacagctgc acccacttcc caggcaacct gcctaacatg    120

cttcgagatc tccgagatgc cttcagcaga gtgaagactt tctttcaaat gaaggatcag    180

ctggacaact tgttgttaaa ggagtccttg ctggaggact ttaagggtta cctgggttgc    240

caagccttgt ctgagatgat ccagttttac ctggaggagg tgatgcccca agctgagaac    300

caagacccag acatcaaggc gcatgtgaac tccctggggg agaacctgaa gaccctcagg    360

ctgaggctac ggcgctgtca tcgatttctt ccctgtgaaa acaagagcaa ggccgtggag    420

caggtgaaga atgcctttaa taagctccaa gagaaaggca tctacaaagc catgagtgag    480

tttgacatct tcatcaacta catagaagcc tacatgacaa tgaagatacg aaac          534


<210> SEQ ID NO 132
<211> LENGTH: 759
<212> TYPE: DNA
<213> ORGANISM: Homo sapiens
<220> FEATURE:
<223> OTHER INFORMATION: IL-12 alpha

<400> SEQUENCE: 132

atgtggcccc ctgggtcagc ctcccagcca ccgccctcac ctgccgcggc cacaggtctg     60

catccagcgg ctcgccctgt gtccctgcag tgccggctca gcatgtgtcc agcgcgcagc    120

ctcctccttg tggctaccct ggtcctcctg gaccacctca gtttggccag aaacctcccc    180

gtggccactc cagacccagg aatgttccca tgccttcacc actcccaaaa cctgctgagg    240

gccgtcagca acatgctcca gaaggccaga caaactctag aattttaccc ttgcacttct    300

gaagagattg atcatgaaga tatcacaaaa gataaaacca gcacagtgga ggcctgttta    360

ccattggaat taaccaagaa tgagagttgc ctaaattcca gagagacctc tttcataact    420

aatgggagtt gcctggcctc cagaaagacc tcttttatga tggccctgtg ccttagtagt    480

atttatgaag acttgaagat gtaccaggtg gagttcaaga ccatgaatgc aaagcttctg    540

atggatccta agaggcagat ctttctagat caaaacatgc tggcagttat tgatgagctg    600

atgcaggccc tgaatttcaa cagtgagact gtgccacaaa aatcctccct tgaagaaccg    660

gatttttata aaactaaaat caagctctgc atacttcttc atgctttcag aattcgggca    720

gtgactattg atagagtgat gagctatctg aatgcttcc                           759


<210> SEQ ID NO 133
<211> LENGTH: 986
<212> TYPE: DNA
```

<213> ORGANISM: Homo sapiens
<220> FEATURE:
<223> OTHER INFORMATION: IL-12 beta

<400> SEQUENCE: 133
agatgtgtca ccagcagttg gtcatctctt ggttttccct ggtttttctg gcatctcccc 60
tcgtggccat atgggaactg aagaaagatg tttatgtcgt agaattggat tggtatccgg 120
atgcccctgg agaaatggtg gtcctcacct gtgacacccc tgaagaagat ggtatcacct 180
ggaccttgga ccagagcagt gaggtcttag gctctggcaa aaccctgacc atccaagtca 240
aagagtttgg agatgctggc cagtacacct gtcacaaagg aggcgaggtt ctaagccatt 300
cgctcctgct gcttcacaaa aaggaagatg gaatttggtc cactgatatt ttaaaggacc 360
agaaagaacc caaaaataag acctttctaa gatgcgaggc caagaattat tctggacgtt 420
tcacctgctg gtggctgacg acaatcagta ctgatttgac attcagtgtc aaaagcagca 480
gaggctcttc tgacccccaa ggggtgacgt gcggagctgc tacactctct gcagagagag 540
tcagagggga caacaaggag tatgagtact cagtggagtg ccaggaggac agtgcctgcc 600
cagctgctga ggagagtctg cccattgagg tcatggtgga tgccgttcac aagctcaagt 660
atgaaaacta caccagcagc ttcttcatca gggacatcat caaacctgac ccacccaaga 720
acttgcagct gaagccatta aagaattctc ggcaggtgga ggtcagctgg gagtaccctg 780
acacctggag tactccacat tcctacttct ccctgacatt ctgcgttcag gtccagggca 840
agagcaagag agaaaagaaa gatagagtct tcacggacaa gacctcagcc acggtcatct 900
gccgcaaaaa tgccagcatt agcgtgcggg cccaggaccg ctactatagc tcatcttgga 960
gcgaatgggc atctgtgccc tgcagt 986

<210> SEQ ID NO 134
<211> LENGTH: 276
<212> TYPE: DNA
<213> ORGANISM: Homo sapiens
<220> FEATURE:
<223> OTHER INFORMATION: MIP-1 alpha/ CCL3

<400> SEQUENCE: 134
atgcaggtct ccactgctgc ccttgctgtc ctcctctgca ccatggctct ctgcaaccag 60
ttctctgcat cacttgctgc tgacacgccg accgcctgct gcttcagcta cacctcccgg 120
cagattccac agaatttcat agctgactac tttgagacga gcagccagtg ctccaagccc 180
ggtgtcatct tcctaaccaa gcgaagccgg caggtctgtg ctgaccccag tgaggagtgg 240
gtccagaaat atgtcagcga cctggagctg agtgcc 276

<210> SEQ ID NO 135
<211> LENGTH: 1530
<212> TYPE: DNA
<213> ORGANISM: Homo sapiens
<220> FEATURE:
<223> OTHER INFORMATION: CD39/ENTPD1, isoform 1

<400> SEQUENCE: 135
atggaagata caaaggagtc taacgtgaag acattttgct ccaagaatat cctagccatc 60
cttggcttct cctctatcat agctgtgata gctttgcttg ctgtggggtt gacccagaac 120
aaagcattgc cagaaaacgt taagtatggg attgtgctgg atgcgggttc ttctcacaca 180
agtttataca tctataagtg gccagcagaa aaggagaatg acacaggcgt ggtgcatcaa 240
gtagaagaat gcagggttaa aggtcctgga atctcaaaat ttgttcagaa agtaaatgaa 300

```
ataggcattt acctgactga ttgcatggaa agagctaggg aagtgattcc aaggtcccag    360

caccaagaga cacccgttta cctgggagcc acggcaggca tgcggttgct caggatggaa    420

agtgaagagt tggcagacag ggttctggat gtggtggaga ggagcctcag caactacccc    480

tttgacttcc agggtgccag gatcattact ggccaagagg aaggtgccta tggctggatt    540

actatcaact atctgctggg caaattcagt cagaaaacaa ggtggttcag catagtccca    600

tatgaaacca ataatcagga aacctttgga gctttggacc ttgggggagc ctctacacaa    660

gtcacttttg taccccaaaa ccagactatc gagtccccag ataatgctct gcaatttcgc    720

ctctatggca aggactacaa tgtctacaca catagcttct tgtgctatgg gaaggatcag    780

gcactctggc agaaactggc caaggacatt caggttgcaa gtaatgaaat tctcagggac    840

ccatgctttc atcctggata taagaaggta gtgaacgtaa gtgaccttta caagaccccc    900

tgcaccaaga gatttgagat gactcttcca ttccagcagt ttgaaatcca gggtattgga    960

aactatcaac aatgccatca aagcatcctg gagctcttca acaccagtta ctgcccttac   1020

tcccagtgtg ccttcaatgg gattttcttg ccaccactcc aggggggattt tggggcattt   1080

tcagcttttt actttgtgat gaagttttta aacttgacat cagagaaagt ctctcaggaa   1140

aaggtgactg agatgatgaa aaagttctgt gctcagcctt gggaggagat aaaaacatct   1200

tacgctggag taaaggagaa gtacctgagt gaatactgct tttctggtac ctacattctc   1260

tccctccttc tgcaaggcta tcatttcaca gctgattcct gggagcacat ccatttcatt   1320

ggcaagatcc agggcagcga cgccggctgg actttgggct acatgctgaa cctgaccaac   1380

atgatcccag ctgagcaacc attgtccaca cctctctccc actccaccta tgtcttcctc   1440

atggttctat tctccctggt ccttttcaca gtggccatca taggcttgct tatctttcac   1500

aagccttcat atttctggaa agatatggta                                    1530
```

```
<210> SEQ ID NO 136
<211> LENGTH: 1722
<212> TYPE: DNA
<213> ORGANISM: Homo sapiens
<220> FEATURE:
<223> OTHER INFORMATION: CD73/NT5E, isoform 1

<400> SEQUENCE: 136

atgtgtcccc gagccgcgcg ggcgcccgcg acgctactcc tcgccctggg cgcggtgctg     60

tggcctgcgg ctggcgcctg ggagcttacg attttgcaca ccaacgacgt gcacagccgg    120

ctggagcaga ccagcgagga ctccagcaag tgcgtcaacg ccagccgctg catgggtggc    180

gtggctcggc tcttcaccaa ggttcagcag atccgccgcg ccgaacccaa cgtgctgctg    240

ctggacgccg gcgaccagta ccagggcact atctggttca ccgtgtacaa gggcgccgag    300

gtggcgcact tcatgaacgc cctgcgctac gatgccatgg cactgggaaa tcatgaattt    360

gataatggtg tggaaggact gatcgagcca ctcctcaaag aggccaaatt tccaattctg    420

agtgcaaaca ttaaagcaaa ggggccacta gcatctcaaa tatcaggact ttatttgcca    480

tataaagttc ttcctgttgg tgatgaagtt gtgggaatcg ttggatacac ttccaaagaa    540

accccttttc tctcaaatcc agggacaaat ttagtgtttg aagatgaaat cactgcatta    600

caacctgaag tagataagtt aaaaactcta aatgtgaaca aaattattgc actgggacat    660

tcgggttttg aaatggataa actcatcgct cagaaagtga ggggtgtgga cgtcgtggtg    720

ggaggacact ccaacacatt tctttacaca ggcaatccac cttccaaaga ggtgcctgct    780
```

gggaagtacc cattcatagt cacttctgat gatgggcgga aggttcctgt agtccaggcc 840
tatgcttttg gcaaatacct aggctatctg aagatcgagt ttgatgaaag aggaaacgtc 900
atctcttccc atggaaatcc cattcttcta aacagcagca ttcctgaaga tccaagcata 960
aaagcagaca ttaacaaatg gaggataaaa ttggataatt attctaccca ggaattaggg 1020
aaaacaattg tctatctgga tggctcctct caatcatgcc gctttagaga atgcaacatg 1080
ggcaacctga tttgtgatgc aatgattaac aacaacctga gacacacgga tgaaatgttc 1140
tggaaccacg tatccatgtg cattttaaat ggaggtggta tccggtcgcc cattgatgaa 1200
cgcaacaatg gcacaattac ctgggagaac ctggctgctg tattgccctt tggaggcaca 1260
tttgacctag tccagttaaa aggttccacc ctgaagaagg cctttgagca tagcgtgcac 1320
cgctacggcc agtccactgg agagttcctg caggtgggcg gaatccatgt ggtgtatgat 1380
ctttcccgaa aacctggaga cagagtagtc aaattagatg ttctttgcac caagtgtcga 1440
gtgcccagtt atgaccctct caaaatggac gaggtatata aggtgatcct cccaaacttc 1500
ctggccaatg gtggagatgg gttccagatg ataaaagatg aattattaag acatgactct 1560
ggtgaccaag atatcaacgt ggtttctaca tatatctcca aaatgaaagt aatttatcca 1620
gcagttgaag gtcggatcaa gttttccaca ggaagtcact gccatggaag cttttcttta 1680
atatttcttt cactttgggc agtgatcttt gttttatacc aa 1722

<210> SEQ ID NO 137
<211> LENGTH: 297
<212> TYPE: DNA
<213> ORGANISM: Homo sapiens
<220> FEATURE:
<223> OTHER INFORMATION: IL-8 (CXCL8)

<400> SEQUENCE: 137
atgacttcca agctggccgt ggctctcttg gcagccttcc tgatttctgc agctctgtgt 60
gaaggtgcag ttttgccaag gagtgctaaa gaacttagat gtcagtgcat aaagacatac 120
tccaaacctt tccaccccaa atttatcaaa gaactgagag tgattgagag tggaccacac 180
tgcgccaaca cagaaattat tgtaaagctt tctgatggaa gagagctctg tctggacccc 240
aaggaaaact gggtgcagag ggttgtggag aagtttttga agagggctga gaattca 297

<210> SEQ ID NO 138
<211> LENGTH: 1596
<212> TYPE: DNA
<213> ORGANISM: Homo sapiens
<220> FEATURE:
<223> OTHER INFORMATION: ICAM1

<400> SEQUENCE: 138
atggctccca gcagcccccg gcccgcgctg cccgcactcc tggtcctgct cggggctctg 60
ttcccaggac ctggcaatgc ccagacatct gtgtcccccct caaaagtcat cctgccccgg 120
ggaggctccg tgctggtgac atgcagcacc tcctgtgacc agcccaagtt gttgggcata 180
gagaccccgt tgcctaaaaa ggagttgctc ctgcctggga acaaccggaa ggtgtatgaa 240
ctgagcaatg tgcaagaaga tagccaacca atgtgctatt caaactgccc tgatgggcag 300
tcaacagcta aaaccttcct caccgtgtac tggactccag aacgggtgga actggcaccc 360
ctcccctctt ggcagccagt gggcaagaac cttaccctac gctgccaggt ggagggtggg 420
gcaccccggg ccaacctcac cgtggtgctg ctccgtgggg agaaggagct gaaacgggag 480
ccagctgtgg gggagcccgc tgaggtcacg accacggtgc tggtgaggag agatcaccat 540

```
ggagccaatt tctcgtgccg cactgaactg gacctgcggc cccaagggct ggagctgttt    600
gagaacacct cggcccccta ccagctccag acctttgtcc tgccagcgac tcccccacaa    660
cttgtcagcc cccgggtcct agaggtggac acgcagggga ccgtggtctg ttccctggac    720
gggctgttcc cagtctcgga ggcccaggtc cacctggcac tgggggacca gaggttgaac    780
cccacagtca cctatggcaa cgactccttc tcggccaagg cctcagtcag tgtgaccgca    840
gaggacgagg gcacccagcg gctgacgtgt gcagtaatac tggggaacca gagccaggag    900
acactgcaga cagtgaccat ctacagcttt ccggcgccca acgtgattct gacgaagcca    960
gaggtctcag aagggaccga ggtgacagtg aagtgtgagg cccaccctag agccaaggtg   1020
acgctgaatg gggttccagc ccagccactg ggcccgaggg cccagctcct gctgaaggcc   1080
accccagagg acaacgggcg cagcttctcc tgctctgcaa ccctggaggt ggccggccag   1140
cttatacaca agaaccagac ccgggagctt cgtgtcctgt atggcccccg actggacgag   1200
agggattgtc cgggaaactg gacgtggcca gaaaattccc agcagactcc aatgtgccag   1260
gcttggggga acccattgcc cgagctcaag tgtctaaagg atggcacttt cccactgccc   1320
atcggggaat cagtgactgt cactcgagat cttgagggca cctacctctg tcgggccagg   1380
agcactcaag gggaggtcac ccgcaaggtg accgtgaatg tgctctcccc ccggtatgag   1440
attgtcatca tcactgtggt agcagccgca gtcataatgg gcactgcagg cctcagcacg   1500
tacctctata accgccagcg gaagatcaag aaatacagac tacaacaggc ccaaaaaggg   1560
acccccatga aaccgaacac acaagccacg cctccc                             1596
```

<210> SEQ ID NO 139
<211> LENGTH: 1488
<212> TYPE: DNA
<213> ORGANISM: Homo sapiens
<220> FEATURE:
<223> OTHER INFORMATION: angiopoietin 2, isoform 1

<400> SEQUENCE: 139

```
atgtggcaga ttgttttctt tactctgagc tgtgatcttg tcttggccgc agcctataac     60
aactttcgga agagcatgga cagcatagga aagaagcaat atcaggtcca gcatgggtcc    120
tgcagctaca ctttcctcct gccagagatg gacaactgcc gctcttcctc cagcccctac    180
gtgtccaatg ctgtgcagag ggacgcgccg ctcgaatacg atgactcggt gcagaggctg    240
caagtgctgg agaacatcat ggaaaacaac actcagtggc taatgaagct tgagaattat    300
atccaggaca acatgaagaa agaaatggta gagatacagc agaatgcagt acagaaccag    360
acggctgtga tgatagaaat agggacaaac ctgttgaacc aaacagcgga gcaaacgcgg    420
aagttaactg atgtggaagc ccaagtatta aatcagacca cgagacttga acttcagctc    480
ttggaacact ccctctcgac aaacaaattg gaaaaacaga ttttggacca gaccagtgaa    540
ataaacaaat tgcaagataa gaacagtttc ctagaaaaga aggtgctagc tatggaagac    600
aagcacatca tccaactaca gtcaataaaa gaagagaaag atcagctaca ggtgttagta    660
tccaagcaaa attccatcat tgaagaacta gaaaaaaaaa tagtgactgc cacggtgaat    720
aattcagttc ttcagaagca gcaacatgat ctcatggaga cagttaataa cttactgact    780
atgatgtcca catcaaactc agctaaggac cccactgttg ctaaagaaga acaaatcagc    840
ttcagagact gtgctgaagt attcaaatca ggacacacca cgaatggcat ctacacgtta    900
acattcccta attctacaga agagatcaag gcctactgtg acatggaagc tggaggaggc    960
```

-continued

```
gggtggacaa ttattcagcg acgtgaggat ggcagcgttg attttcagag gacttggaaa   1020

gaatataaag tgggatttgg taacccttca ggagaatatt ggctgggaaa tgagtttgtt   1080

tcgcaactga ctaatcagca acgctatgtg cttaaaatac accttaaaga ctgggaaggg   1140

aatgaggctt actcattgta tgaacatttc tatctctcaa gtgaagaact caattatagg   1200

attcacctta aaggacttac agggacagcc ggcaaaataa gcagcatcag ccaaccagga   1260

aatgatttta gcacaaagga tggagacaac gacaaatgta tttgcaaatg ttcacaaatg   1320

ctaacaggag gctggtggtt tgatgcatgt ggtccttcca acttgaacgg aatgtactat   1380

ccacagaggc agaacacaaa taagttcaac ggcattaaat ggtactactg gaaaggctca   1440

ggctattcgc tcaaggccac aaccatgatg atccgaccag cagatttc                1488
```

<210> SEQ ID NO 140
<211> LENGTH: 2766
<212> TYPE: DNA
<213> ORGANISM: Homo sapiens
<220> FEATURE:
<223> OTHER INFORMATION: NLRP3, isoform 2

<400> SEQUENCE: 140

```
atgaagatgg caagcacccg ctgcaagctg gccaggtacc tggaggacct ggaggatgtg     60

gacttgaaga aatttaagat gcacttagag gactatcctc cccagaaggg ctgcatcccc    120

ctcccgaggg gtcagacaga gaaggcagac catgtggatc tagccacgct aatgatcgac    180

ttcaatgggg aggagaaggc gtgggccatg gccgtgtgga tcttcgctgc gatcaacagg    240

agagaccttt atgagaaagc aaaaagagat gagccgaagt ggggttcaga taatgcacgt    300

gtttcgaatc ccactgtgat atgccaggaa gacagcattg aagaggagtg gatgggttta    360

ctggagtacc tttcgagaat ctctatttgt aaaatgaaga aagattaccg taagaagtac    420

agaaagtacg tgagaagcag attccagtgc attgaagaca ggaatgcccg tctgggtgag    480

agtgtgagcc tcaacaaacg ctacacacga ctgcgtctca tcaaggagca ccggagccag    540

caggagaggg agcaggagct tctggccatc ggcaagacca agacgtgtga gagccccgtg    600

agtcccatta agatggagtt gctgtttgac cccgatgatg agcattctga gcctgtgcac    660

accgtggtgt tccagggggc ggcagggatt gggaaaacaa tcctggccag gaagatgatg    720

ttggactggg cgtcggggac actctaccaa gacaggtttg actatctgtt ctatatccac    780

tgtcgggagg tgagccttgt gacacagagg agcctggggg acctgatcat gagctgctgc    840

cccgacccaa acccacccat ccacaagatc gtgagaaaac cctccagaat cctcttcctc    900

atggacggct tcgatgagct gcaaggtgcc tttgacgagc acataggacc gctctgcact    960

gactggcaga aggccgagcg gggagacatt ctcctgagca gcctcatcag aaagaagctg   1020

cttcccgagg cctctctgct catcaccacg agacctgtgg ccctggagaa actgcagcac   1080

ttgctggacc atcctcggca tgtggagatc ctgggtttct ccgaggccaa aaggaaagag   1140

tacttcttca agtacttctc tgatgaggcc caagccaggg cagccttcag tctgattcag   1200

gagaacgagg tcctcttcac catgtgcttc atcccccctgg tctgctggat cgtgtgcact   1260

ggactgaaac agcagatgga gagtggcaag agccttgccc agacatccaa gaccaccacc   1320

gcggtgtacg tcttcttcct ttccagtttg ctgcagcccc ggggagggag ccaggagcac   1380

ggcctctgcg cccacctctg ggggctctgc tctttggctg cagatggaat ctggaaccag   1440

aaaatcctgt ttgaggagtc cgacctcagg aatcatggac tgcagaaggc ggatgtgtct   1500

gctttcctga ggatgaacct gttccaaaag gaagtggact gcgagaagtt ctacagcttc   1560
```

-continued atccacatga ctttccagga gttctttgcc gccatgtact acctgctgga agaggaaaag 1620
gaaggaagga cgaacgttcc agggagtcgt ttgaagcttc ccagccgaga cgtgacagtc 1680
cttctggaaa actatggcaa attcgaaaag ggtatttga tttttgttgt acgtttcctc 1740
tttggcctgg taaaccagga gaggacctcc tacttggaga agaaattaag ttgcaagatc 1800
tctcagcaaa tcaggctgga gctgctgaaa tggattgaag tgaaagccaa agctaaaaag 1860
ctgcagatcc agcccagcca gctggaattg ttctactgtt tgtacgagat gcaggaggag 1920
gacttcgtgc aaagggccat ggactatttc cccaagattg agatcaatct ctccaccaga 1980
atggaccaca tggtttcttc cttttgcatt gagaactgtc atcgggtgga gtcactgtcc 2040
ctggggtttc tccataacat gcccaaggag gaagaggagg aggaaaagga aggccgacac 2100
cttgatatgg tgcagtgtgt cctcccaagc tcctctcatg ctgcctgttc tcatgggttg 2160
gggcgctgtg gcctctcgca tgagtgctgc ttcgacatct ccttggtcct cagcagcaac 2220
cagaagctgg tggagctgga cctgagtgac aacgccctcg gtgacttcgg aatcagactt 2280
ctgtgtgtgg gactgaagca cctgttgtgc aatctgaaga agctctggtt ggtgaattct 2340
ggccttacgt cagtctgttg ttcagctttg tcctcggtac tcagcactaa tcagaatctc 2400
acgcaccttt acctgcgagg caacactctc ggagacaagg ggatcaaact actctgtgag 2460
ggactcttgc accccgactg caagcttcag gtgttggaat tagacaactg caacctcacg 2520
tcacactgct gctgggatct ttccacactt ctgacctcca gccagagcct gcgaaagctg 2580
agcctgggca acaatgacct gggcgacctg ggggtcatga tgttctgtga agtgctgaaa 2640
cagcagagct gcctcctgca gaacctgggg ttgtctgaaa tgtatttcaa ttatgagaca 2700
aaaagtgcgt tagaaacact tcaagaagaa aagcctgagc tgaccgtcgt ctttgagcct 2760
tcttgg 2766

<210> SEQ ID NO 141
<211> LENGTH: 831
<212> TYPE: DNA
<213> ORGANISM: Homo sapiens
<220> FEATURE:
<223> OTHER INFORMATION: CD40, isoform 1

<400> SEQUENCE: 141
atggttcgtc tgcctctgca gtgcgtcctc tggggctgct tgctgaccgc tgtccatcca 60
gaaccaccca ctgcatgcag agaaaaacag tacctaataa acagtcagtg ctgttctttg 120
tgccagccag gacagaaact ggtgagtgac tgcacagagt tcactgaaac ggaatgcctt 180
ccttgcggtg aaagcgaatt cctagacacc tggaacagag agacacactg ccaccagcac 240
aaatactgcg accccaacct agggcttcgg gtccagcaga agggcacctc agaaacagac 300
accatctgca cctgtgaaga aggctggcac tgtacgagtg aggcctgtga gagctgtgtc 360
ctgcaccgct catgctcgcc cggctttggg gtcaagcaga ttgctacagg ggtttctgat 420
accatctgcg agccctgccc agtcggcttc ttctccaatg tgtcatctgc tttcgaaaaa 480
tgtcaccctt ggacaagctg tgagaccaaa gacctggttg tgcaacaggc aggcacaaac 540
aagactgatg ttgtctgtgg tccccaggat cggctgagag ccctggtggt gatccccatc 600
atcttcggga tcctgtttgc catcctcttg gtgctggtct ttatcaaaaa ggtggccaag 660
aagccaacca ataaggcccc ccaccccaag caggaacccc aggagatcaa ttttcccgac 720
gatcttcctg gctccaacac tgctgctcca gtgcaggaga ctttacatgg atgccaaccg 780
gtcacccagg aggatggcaa agagagtcgc atctcagtgc aggagagaca g 831

<210> SEQ ID NO 142
<211> LENGTH: 783
<212> TYPE: DNA
<213> ORGANISM: Homo sapiens
<220> FEATURE:
<223> OTHER INFORMATION: CD40 ligand (CD40L)

<400> SEQUENCE: 142
atgatcgaaa catacaacca aacttctccc cgatctgcgg ccactggact gcccatcagc 60
atgaaaattt ttatgtattt acttactgtt tttcttatca cccagatgat tgggtcagca 120
ctttttgctg tgtatcttca tagaaggttg gacaagatag aagatgaaag gaatcttcat 180
gaagattttg tattcatgaa aacgatacag agatgcaaca caggagaaag atccttatcc 240
ttactgaact gtgaggagat taaaagccag tttgaaggct ttgtgaagga tataatgtta 300
aacaaagagg agacgaagaa agaaaacagc tttgaaatgc aaaaaggtga tcagaatcct 360
caaattgcgg cacatgtcat aagtgaggcc agcagtaaaa caacatctgt gttacagtgg 420
gctgaaaaag gatactacac catgagcaac aacttggtaa ccctggaaaa tgggaaacag 480
ctgaccgtta aaagacaagg actctattat atctatgccc aagtcacctt ctgttccaat 540
cgggaagctt cgagtcaagc tccatttata gccagcctct gcctaaagtc ccccggtaga 600
ttcgagagaa tcttactcag agctgcaaat acccacagtt ccgccaaacc ttgcgggcaa 660
caatccattc acttgggagg agtatttgaa ttgcaaccag gtgcttcggt gtttgtcaat 720
gtgactgatc caagccaagt gagccatggc actggcttca cgtcctttgg cttactcaaa 780
ctc 783

<210> SEQ ID NO 143
<211> LENGTH: 579
<212> TYPE: DNA
<213> ORGANISM: Homo sapiens
<220> FEATURE:
<223> OTHER INFORMATION: CD-70 antigen, isoform 1

<400> SEQUENCE: 143
atgccggagg agggttcggg ctgctcggtg cggcgcaggc cctatgggtg cgtcctgcgg 60
gctgctttgg tcccattggt cgcgggcttg gtgatctgcc tcgtggtgtg catccagcgc 120
ttcgcacagg ctcagcagca gctgccgctc gagtcacttg ggtgggacgt agctgagctg 180
cagctgaatc acacaggacc tcagcaggac cccaggctat actggcaggg gggcccagca 240
ctgggccgct ccttcctgca tggaccagag ctggacaagg ggcagctacg tatccatcgt 300
gatggcatct acatggtaca catccaggtg acgctggcca tctgctcctc cacgacggcc 360
tccaggcacc accccaccac cctggccgtg ggaatctgct ctcccgcctc ccgtagcatc 420
agcctgctgc gtctcagctt ccaccaaggt tgtaccattg cctcccagcg cctgacgccc 480
ctggcccgag ggacacact ctgcaccaac ctcactggga cacttttgcc ttcccgaaac 540
actgatgaga ccttctttgg agtgcagtgg gtgcgcccc 579

<210> SEQ ID NO 144
<211> LENGTH: 765
<212> TYPE: DNA
<213> ORGANISM: Homo sapiens
<220> FEATURE:
<223> OTHER INFORMATION: CD137 (4-1BB, TNFRSF9)

<400> SEQUENCE: 144
atgggaaaca gctgttacaa catagtagcc actctgttgc tggtcctcaa ctttgagagg 60
acaagatcat tgcaggatcc ttgtagtaac tgcccagctg gtacattctg tgataataac 120
aggaatcaga tttgcagtcc ctgtcctcca aatagtttct ccagcgcagg tggacaaagg 180
acctgtgaca tatgcaggca gtgtaaaggt gttttcagga ccaggaagga gtgttcctcc 240
accagcaatg cagagtgtga ctgcactcca gggtttcact gcctgggggc aggatgcagc 300
atgtgtgaac aggattgtaa acaaggtcaa gaactgacaa aaaaaggttg taaagactgt 360
tgctttggga catttaacga tcagaaacgt ggcatctgtc gaccctggac aaactgttct 420
ttggatggaa agtctgtgct tgtgaatggg acgaaggaga gggacgtggt ctgtggacca 480
tctccagccg acctctctcc gggagcatcc tctgtgaccc cgcctgcccc tgcgagagag 540
ccaggacact ctccgcagat catctccttc tttcttgcgc tgacgtcgac tgcgttgctc 600
ttcctgctgt tcttcctcac gctccgtttc tctgttgtta aacggggcag aaagaaactc 660
ctgtatatat tcaaacaacc atttatgaga ccagtacaaa ctactcaaga ggaagatggc 720
tgtagctgcc gatttccaga agaagaagaa ggaggatgtg aactg 765

<210> SEQ ID NO 145
<211> LENGTH: 807
<212> TYPE: DNA
<213> ORGANISM: Homo sapiens
<220> FEATURE:
<223> OTHER INFORMATION: CD200, isoform 1

<400> SEQUENCE: 145
atggagaggc tggtgatcag gatgcccttc tctcatctgt ctacctacag cctggtttgg 60
gtcatggcag cagtggtgct gtgcacagca caagtgcaag tggtgaccca ggatgaaaga 120
gagcagctgt acacacctgc ttccttaaaa tgctctctgc aaaatgccca ggaagccctc 180
attgtgacat ggcagaaaaa gaaagctgta agcccagaaa acatggtcac cttcagcgag 240
aaccatgggg tggtgatcca gcctgcctat aaggacaaga taaacattac ccagctggga 300
ctccaaaact caaccatcac cttctggaat atcaccctgg aggatgaagg gtgttacatg 360
tgtctcttca ataccttttgg ttttgggaag atctcaggaa cggcctgcct caccgtctat 420
gtacagccca tagtatccct tcactacaaa ttctctgaag accacctaaa tatcacttgc 480
tctgccactg cccgcccagc ccccatggtc ttctggaagg tccctcggtc agggattgaa 540
aatagtacag tgactctgtc tcacccaaat gggaccacgt ctgttaccag catcctccat 600
atcaaagacc ctaagaatca ggtggggaag gaggtgatct gccaggtgct gcacctgggg 660
actgtgaccg actttaagca aaccgtcaac aaaggctatt ggttttcagt tccgctattg 720
ctaagcattg tttccctggt aattcttctc gtcctaatct caatcttact gtactggaaa 780
cgtcaccgga atcaggaccg agagccc 807

<210> SEQ ID NO 146
<211> LENGTH: 1236
<212> TYPE: DNA
<213> ORGANISM: Homo sapiens
<220> FEATURE:
<223> OTHER INFORMATION: A2aR (ADORA2A)

<400> SEQUENCE: 146
atgcccatca tgggctcctc ggtgtacatc acggtggagc tggccattgc tgtgctggcc 60
atcctgggca atgtgctggt gtgctgggcc gtgtggctca acagcaacct gcagaacgtc 120

-continued

```
accaactact ttgtggtgtc actggcggcg gccgacatcg cagtgggtgt gctcgccatc    180

ccctttgcca tcaccatcag caccgggttc tgcgctgcct gccacggctg cctcttcatt    240

gcctgcttcg tcctggtcct cacgcagagc tccatcttca gtctcctggc catcgccatt    300

gaccgctaca ttgccatccg catcccgctc cggtacaatg gcttggtgac cggcacgagg    360

gctaagggca tcattgccat ctgctgggtg ctgtcgtttg ccatcggcct gactcccatg    420

ctaggttgga acaactgcgg tcagccaaag gagggcaaga accactccca gggctgcggg    480

gagggccaag tggcctgtct ctttgaggat gtggtcccca tgaactacat ggtgtacttc    540

aacttctttg cctgtgtgct ggtgcccctg ctgctcatgc tgggtgtcta tttgcggatc    600

ttcctggcgg cgcgacgaca gctgaagcag atggagagcc agcctctgcc gggggagcgg    660

gcacggtcca cactgcagaa ggaggtccat gctgccaagt cactggccat cattgtgggg    720

ctctttgccc tctgctggct gcccctacac atcatcaact gcttcacttt cttctgcccc    780

gactgcagcc acgcccctct ctggctcatg tacctggcca tcgtcctctc ccacaccaat    840

tcggttgtga atcccttcat ctacgcctac cgtatccgcg agttccgcca gaccttccgc    900

aagatcattc gcagccacgt cctgaggcag caagaacctt tcaaggcagc tggcaccagt    960

gcccgggtct tggcagctca tggcagtgac ggagagcagg tcagcctccg tctcaacggc   1020

cacccgccag gagtgtgggc caacggcagt gctccccacc ctgagcggag gcccaatggc   1080

tatgccctgg ggctggtgag tggagggagt gcccaagagt cccaggggaa cacgggcctc   1140

ccagacgtgg agctccttag ccatgagctc aagggagtgt gcccagagcc ccctggccta   1200

gatgaccccc tggcccagga tggagcagga gtgtcc                             1236
```

<210> SEQ ID NO 147
<211> LENGTH: 723
<212> TYPE: DNA
<213> ORGANISM: Homo sapiens
<220> FEATURE:
<223> OTHER INFORMATION: GITR/TNFRSF18, isoform 1

<400> SEQUENCE: 147

```
atggcacagc acggggcgat gggcgcgttt cgggccctgt gcggcctggc gctgctgtgc     60

gcgctcagcc tgggtcagcg ccccaccggg ggtcccgggt gcggccctgg gcgcctcctg    120

cttgggacgg gaacggacgc gcgctgctgc cgggttcaca cgacgcgctg ctgccgcgat    180

tacccgggcg aggagtgctg ttccgagtgg gactgcatgt gtgtccagcc tgaattccac    240

tgcggagacc cttgctgcac gacctgccgg caccaccctt gtcccccagg ccagggggta    300

cagtcccagg ggaaattcag ttttggcttc cagtgtatcg actgtgcctc ggggaccttc    360

tccgggggcc acgaaggcca ctgcaaacct tggacagact gcacccagtt cgggtttctc    420

actgtgttcc ctgggaacaa gacccacaac gctgtgtgcg tcccagggtc cccgccggca    480

gagccgcttg ggtggctgac cgtcgtcctc ctggccgtgg ccgcctgcgt cctcctcctg    540

acctcggccc agcttggact gcacatctgg cagctgagga gtcagtgcat gtggccccga    600

gagacccagc tgctgctgga ggtgccgccg tcgaccgaag acgccagaag ctgccagttc    660

cccgaggaag agcggggcga gcgatcggca gaggagaagg ggcggctggg agacctgtgg    720

gtg                                                                  723
```

<210> SEQ ID NO 148
<211> LENGTH: 1362
<212> TYPE: DNA
<213> ORGANISM: Homo sapiens

<220> FEATURE:
<223> OTHER INFORMATION: B7-H6 (NCR3LG1)

<400> SEQUENCE: 148

```
atgacgtgga gggctgccgc ctccacgtgc gcggcgctcc tgattctgct gtgggcgctg      60
acgaccgaag gtgatctgaa agtagagatg atggcagggg ggactcagat cacacccctg     120
aatgacaatg tcaccatatt ctgcaatatc ttttattccc aacccctcaa catcacgtct     180
atgggtatca cctggttttg gaagagtctg acgtttgaca aagaagtcaa agtctttgaa     240
ttttttggag atcaccaaga ggcattccga cctggagcca ttgtgtctcc atggaggctg     300
aagagtgggg acgcctcact gcggctgcct ggaatccagc tggaggaagc aggagagtac     360
cgatgtgagg tggtggtcac ccctctgaag gcacagggaa cagtccagct tgaagttgtg     420
gcttccccag ccagcagatt gttgctggat caagtgggca tgaaagagaa tgaagacaaa     480
tatatgtgtg agtcaagtgg gttctaccca gaggctatta atataacatg ggagaagcag     540
acccagaagt ttccccatcc catagagatt tctgaggatg tcatcactgg tcccaccatc     600
aagaatatgg atggcacatt taatgtcact agctgcttga agctgaactc ctctcaggaa     660
gaccctggga ctgtctacca gtgtgtggta cggcatgcgt ccttgcatac cccccttgagg     720
agcaacttta ccctgactgc tgctcggcac agtctttctg aaactgagaa gacagataat     780
ttttccattc attggtggcc tatttcattc attggtgttg gactggtttt attaattgtt     840
ttgattcctt ggaaaaagat atgtaacaaa tcatcttcag cctatactcc tctcaagtgc     900
attctgaaac actggaactc ctttgacact cagactctga agaaagagca cctcatattc     960
ttttgcactc gggcatggcc gtcttaccag ctgcaggatg gggaggcttg gcctcctgag    1020
ggaagtgtta atattaatac tattcaacaa ctagatgttt tctgcagaca ggagggcaaa    1080
tggtccgagg ttccttatgt gcaagccttc tttgccttgc gagacaaccc agatctttgt    1140
cagtgttgta gaattgaccc tgctctccta acagttacat caggcaagtc catagatgat    1200
aattccacaa agtctgagaa acaaacccct agggaacact cggatgcagt tccggatgcc    1260
ccaatccttc ctgtctcccc tatctgggaa cctcctccag ccacaacatc aacaactcca    1320
gttctatcct cccaaccccc aactttactg ttacccctac ag                       1362
```

<210> SEQ ID NO 149
<211> LENGTH: 597
<212> TYPE: DNA
<213> ORGANISM: Homo sapiens
<220> FEATURE:
<223> OTHER INFORMATION: ICOS, isoform 1

<400> SEQUENCE: 149

```
atgaagtcag gcctctggta tttctttctc ttctgcttgc gcattaaagt tttaacagga      60
gaaatcaatg gttctgccaa ttatgagatg tttatatttc acaacggagg tgtacaaatt     120
ttatgcaaat atcctgacat tgtccagcaa tttaaaatgc agttgctgaa agggggggcaa     180
atactctgcg atctcactaa gacaaaagga agtggaaaca cagtgtccat taagagtctg     240
aaattctgcc attctcagtt atccaacaac agtgtctctt tttttctata caacttggac     300
cattctcatg ccaactatta cttctgcaac ctatcaattt ttgatcctcc tccttttaaa     360
gtaactctta caggaggata tttgcatatt tatgaatcac aactttgttg ccagctgaag     420
ttctggttac ccataggatg tgcagccttt gttgtagtct gcattttggg atgcatactt     480
atttgttggc ttacaaaaaa gaagtattca tccagtgtgc acgaccctaa cggtgaatac     540
```

atgttcatga gagcagtgaa cacagccaaa aaatctagac tcacagatgt gaccccta 597

<210> SEQ ID NO 150
<211> LENGTH: 906
<212> TYPE: DNA
<213> ORGANISM: Homo sapiens
<220> FEATURE:
<223> OTHER INFORMATION: ICOS ligand, isoform 1

<400> SEQUENCE: 150
atgcggctgg gcagtcctgg actgctcttc ctgctcttca gcagccttcg agctgatact 60
caggagaagg aagtcagagc gatggtaggc agcgacgtgg agctcagctg cgcttgccct 120
gaaggaagcc gttttgattt aaatgatgtt tacgtatatt ggcaaaccag tgagtcgaaa 180
accgtggtga cctaccacat cccacagaac agctccttgg aaaacgtgga cagccgctac 240
cggaaccgag ccctgatgtc accggccggc atgctgcggg gcgacttctc cctgcgcttg 300
ttcaacgtca ccccccagga cgagcagaag tttcactgcc tggtgttgag ccaatccctg 360
ggattccagg aggttttgag cgttgaggtt acactgcatg tggcagcaaa cttcagcgtg 420
cccgtcgtca gcgcccccca cagcccctcc caggatgagc tcaccttcac gtgtacatcc 480
ataaacggct accccaggcc caacgtgtac tggatcaata agacggacaa cagcctgctg 540
gaccaggctc tgcagaatga caccgtcttc ttgaacatgc ggggcttgta tgacgtggtc 600
agcgtgctga ggatcgcacg gacccccagc gtgaacattg gctgctgcat agagaacgtg 660
cttctgcagc agaacctgac tgtcggcagc cagacaggaa atgacatcgg agagagagac 720
aagatcacag agaatccagt cagtaccggc gagaaaaacg cggccacgtg gagcatcctg 780
gctgtcctgt gcctgcttgt ggtcgtggcg gtggccatag gctgggtgtg cagggaccga 840
tgcctccaac acagctatgc aggtgcctgg gctgtgagtc cggagacaga gctcactggc 900
cacgtt 906

<210> SEQ ID NO 151
<211> LENGTH: 1344
<212> TYPE: DNA
<213> ORGANISM: Homo sapiens
<220> FEATURE:
<223> OTHER INFORMATION: gp49B/LILRB4, isoform 1

<400> SEQUENCE: 151
atgatcccca ccttcacggc tctgctctgc ctcgggctga gtctgggccc caggacccac 60
atgcaggcag ggcccctccc caaacccacc ctctgggctg agccaggctc tgtgatcagc 120
tgggggaact ctgtgaccat ctggtgtcag ggggaccctgg aggctcggga gtaccgtctg 180
gataaagagg aaagcccagc accctgggac agacagaacc cactggagcc caagaacaag 240
gccagattct ccatcccatc catgacagag gactatgcag ggagataccg ctgttactat 300
cgcagccctg taggctggtc acagcccagt gacccccctgg agctggtgat gacaggagcc 360
tacagtaaac ccaccctttc agccctgccg agtcctcttg tgacctcagg aaagagcgtg 420
accctgctgt gtcagtcacg gagcccaatg gacacttttc ttctgatcaa ggagcgggca 480
gcccatcccc tactgcatct gagatcagag cacggagctc agcagcacca ggctgaattc 540
cccatgagtc ctgtgacctc agtgcacggg gggacctaca ggtgcttcag ctcacacggc 600
ttctcccact acctgctgtc acaccccagt gacccccctgg agctcatagt ctcaggatcc 660
ttggagggtc ccaggccctc acccacaagg tccgtctcaa cagctgcagg ccctgaggac 720
cagcccctca tgcctacagg gtcagtcccc cacagtggtc tgagaaggca ctgggaggta 780
ctgatcgggg tcttggtggt ctccatcctg cttctctccc tcctcctctt cctcctcctc 840
caacactggc gtcagggaaa acacaggaca ttggcccaga gacaggctga tttccaacgt 900
cctccagggg ctgccgagcc agagcccaag gacgggggcc tacagaggag gtccagccca 960
gctgctgacg tccagggaga aaacttctgt gctgccgtga agaacacaca gcctgaggac 1020
ggggtggaaa tggacactcg gcagagccca cacgatgaag acccccaggc agtgacgtat 1080
gccaaggtga aacactccag acctaggaga gaaatggcct ctcctccctc cccactgtct 1140
ggggaattcc tggacacaaa ggacagacag gcagaagagg acagacagat ggacactgag 1200
gctgctgcat ctgaagcccc ccaggatgtg acctacgccc ggctgcacag ctttaccctc 1260
agacagaagg caactgagcc tcctccatcc caggaagggg cctctccagc tgagcccagt 1320
gtctatgcca ctctggccat ccac 1344

<210> SEQ ID NO 152
<211> LENGTH: 1896
<212> TYPE: DNA
<213> ORGANISM: Homo sapiens
<220> FEATURE:
<223> OTHER INFORMATION: PIR-B/LILRB3, isoform 1

<400> SEQUENCE: 152
atgacgcccg ccctcacagc cctgctctgc cttgggctga gtctgggccc caggacccgc 60
atgcaggcag ggcccttccc caaacccacc ctctgggctg agccaggctc tgtgatcagc 120
tgggggagcc ccgtgaccat ctggtgtcag ggggagcctgg aggcccagga gtaccaactg 180
gataaagagg gaagcccaga gccctgggac agaaataacc cactggaacc caagaacaag 240
gccagattct ccatcccatc catgacacag caccatgcag ggagataccg ctgccactat 300
tacagctctg caggctggtc agagcccagc gaccccctgg agctggtgat gacaggattc 360
tacaacaaac ccaccctctc agccctgccc agccctgtgg tggcctcagg ggggaatatg 420
accctccgat gtggctcaca gaagggatat caccattttg ttctgatgaa ggaaggagaa 480
caccagctcc cccggaccct ggactcacag cagctccaca gtgggggggtt ccaggccctg 540 ttccctgtgg gccccgtgac ccccagccac aggtggaggt tcacatgcta ttactattat 600
acaaacaccc cctgggtgtg gtcccacccc agtgaccccc tggagattct gccctcaggc 660
gtgtctagga agccctccct cctgaccctg cagggccctg tcctggcccc tgggcagagc 720
ctgaccctcc agtgtggctc tgatgtcggc tacgacagat ttgttctgta taaggagggg 780
gaacgtgact tcctccagcg ccctggccag cagccccagg ctgggctctc ccaggccaac 840
ttcaccctgg gccctgtgag ccgctcctac gggggccagt acaggtgcta tggtgcacac 900
aacctctcct ccgagtggtc ggcccccagt gacccccctgg acatcctgat cacaggacag 960
atctatgaca ccgtctccct gtcagcacag ccgggcccca cagtggcctc aggagagaac 1020
atgaccctgc tgtgtcagtc acgggggtat tttgacactt tccttctgac caaagaaggg 1080
gcagcccatc ccccactgcg tctgagatca atgtacggag ctcataagta ccaggctgaa 1140
ttccccatga gtcctgtgac ctcagcccac gcggggacct acaggtgcta cggctcacgc 1200
agctccaacc cccacctgct gtctttcccc agtgagcccc tggaactcat ggtctcagga 1260
cactctggag gctccagcct cccacccaca gggccgccct ccacacctgg tctgggaaga 1320
tacctggagg ttttgattgg ggtctcggtg gccttcgtcc tgctgctctt cctcctcctc 1380
ttcctcctcc tcctccgtca gcgtcacagc aaacacagga catctgacca gagaaagact 1440

-continued gatttccagc gtcctgcagg ggctgcggag acagagccca aggacagggg cctgctgagg 1500
aggtccagcc cagctgctga cgtccaggaa gaaaacctct atgctgctgt gaaggacaca 1560
cagtctgagg acagggtgga gctggacagt cagcagagcc cacacgatga agaccccccag 1620 gcagtgacgt atgccccggt gaaacactcc agtcctagga gagaaatggc ctctcctccc 1680
tcctcactgt ctggggaatt cctggacaca aaggacagac aggtggaaga ggacaggcag 1740
atggacactg aggctgctgc atctgaagcc tcccaggatg tgacctacgc ccagctgcac 1800
agcttgaccc ttagacggaa ggcaactgag cctcctccat cccaggaagg ggaacctcca 1860
gctgagccca gcatctacgc cactctggcc atccac 1896

<210> SEQ ID NO 153
<211> LENGTH: 1014
<212> TYPE: DNA
<213> ORGANISM: Homo sapiens
<220> FEATURE:
<223> OTHER INFORMATION: HLA-G alpha chain

<400> SEQUENCE: 153
atggtggtca tggcgccccg aaccctcttc ctgctgctct cgggggccct gaccctgacc 60
gagacctggg cgggctccca ctccatgagg tatttcagcg ccgccgtgtc ccggcccggc 120
cgcggggagc cccgcttcat cgccatgggc tacgtggacg acacgcagtt cgtgcggttc 180
gacagcgact cggcgtgtcc gaggatggag ccgcgggcgc cgtgggtgga gcaggagggg 240
ccggagtatt gggaagagga gacacggaac accaaggccc acgcacagac tgacagaatg 300
aacctgcaga ccctgcgcgg ctactacaac cagagcgagg ccagttctca caccctccag 360
tggatgattg gctgcgacct ggggtccgac ggacgcctcc tccgcgggta tgaacagtat 420
gcctacgatg gcaaggatta cctcgccctg aacgaggacc tgcgctcctg gaccgcagcg 480
gacactgcgg ctcagatctc caagcgcaag tgtgaggcgg ccaatgtggc tgaacaaagg 540
agagcctacc tggagggcac gtgcgtggag tggctccaca gatacctgga gaacgggaag 600
gagatgctgc agcgcgcgga cccccccaag acacacgtga cccaccaccc tgtctttgac 660
tatgaggcca ccctgaggtg ctgggccctg ggcttctacc ctgcggagat catactgacc 720
tggcagcggg atggggagga ccagacccag gacgtggagc tcgtggagac caggcctgca 780
ggggatggaa ccttccagaa gtgggcagct gtggtggtgc cttctggaga ggagcagaga 840
tacacgtgcc atgtgcagca tgaggggctg ccggagcccc tcatgctgag atggaagcag 900
tcttccctgc ccaccatccc catcatgggt atcgttgctg gcctggttgt ccttgcagct 960
gtagtcactg gagctgcggt cgctgctgtg ctgtggagaa agaagagctc agat 1014

<210> SEQ ID NO 154
<211> LENGTH: 1092
<212> TYPE: DNA
<213> ORGANISM: Homo sapiens
<220> FEATURE:
<223> OTHER INFORMATION: TIM1/HAVCR1

<400> SEQUENCE: 154
atgcatcctc aagtggtcat cttaagcctc atcctacatc tggcagattc tgtagctggt 60
tctgtaaagg ttggtggaga ggcaggtcca tctgtcacac taccctgcca ctacagtgga 120
gctgtcacat ccatgtgctg gaatagaggc tcatgttctc tattcacatg ccaaaatggc 180
attgtctgga ccaatggaac ccacgtcacc tatcggaagg acacacgcta taagctattg 240
ggggaccttt caagaaggga tgtctctttg accatagaaa atacagctgt gtctgacagt 300
ggcgtatatt gttgccgtgt tgagcaccgt gggtggttca atgacatgaa aatcaccgta 360
tcattggaga ttgtgccacc caaggtcacg actactccaa ttgtcacaac tgttccaacc 420
gtcacgactg ttcgaacgag caccactgtt ccaacgacaa cgactgttcc aatgacgact 480
gttccaacga caactgttcc aacaacaatg agcattccaa cgacaacgac tgttctgacg 540
acaatgactg tttcaacgac aacgagcgtt ccaacgacaa cgagcattcc aacaacaaca 600
agtgttccag tgacaacaac tgtctctacc tttgttcctc caatgccttt gcccaggcag 660
aaccatgaac cagtagccac ttcaccatct tcacctcagc cagcagaaac ccaccctacg 720
acactgcagg gagcaataag gagagaaccc accagctcac cattgtactc ttacacaaca 780
gatgggaatg acaccgtgac agagtcttca gatggccttt ggaataacaa tcaaactcaa 840
ctgttcctag aacatagtct actgacggcc aataccacta aaggaatcta tgctggagtc 900
tgtatttctg tcttggtgct tcttgctctt ttgggtgtca tcattgccaa aaagtatttc 960
ttcaaaaagg aggttcaaca actaagtgtt tcatttagca gccttcaaat taaagctttg 1020
caaaatgcag ttgaaaagga agtccaagca gaagacaata tctacattga gaatagtctt 1080
tatgccacgg ac 1092

<210> SEQ ID NO 155
<211> LENGTH: 1134
<212> TYPE: DNA
<213> ORGANISM: Homo sapiens
<220> FEATURE:
<223> OTHER INFORMATION: TIM4/TIMD4, isoform 1

<400> SEQUENCE: 155
atgtccaaag aacctctcat tctctggctg atgattgagt tttggtggct ttacctgaca 60
ccagtcactt cagagactgt tgtgacggag gttttgggtc accgggtgac tttgccctgt 120
ctgtactcat cctggtctca caacagcaac agcatgtgct gggggaaaga ccagtgcccc 180
tactccggtt gcaaggaggc gctcatccgc actgatggaa tgagggtgac ctcaagaaag 240
tcagcaaaat atagacttca ggggactatc ccgagaggtg atgtctcctt gaccatctta 300
aaccccagtg aaagtgacag cggtgtgtac tgctgccgca tagaagtgcc tggctggttc 360
aacgatgtaa agataaacgt gcgcctgaat ctacagagag cctcaacaac cacgcacaga 420
acagcaacca ccaccacacg cagaacaaca acaacaagcc ccaccaccac ccgacaaatg 480
acaacaaccc cagctgcact tccaacaaca gtcgtgacca cacccgatct cacaaccgga 540
acaccactcc agatgacaac cattgccgtc ttcacaacag caaacacgtg cctttcacta 600
accccaagca cccttccgga ggaagccaca ggtcttctga ctcccgagcc ttctaaggaa 660
gggcccatcc tcactgcaga atcagaaact gtcctcccca gtgattcctg gagtagtgtt 720
gagtctactt ctgctgacac tgtcctgctg acatccaaag agtccaaagt ttgggatctc 780
ccatcaacat cccacgtgtc aatgtggaaa acgagtgatt ctgtgtcttc tcctcagcct 840
ggagcatctg atacagcagt tcctgagcag aacaaaaacaa caaaaacagg acagatggat 900
ggaataccca tgtcaatgaa gaatgaaatg cccatctccc aactactgat gatcatcgcc 960
ccctccttgg gatttgtgct cttcgcattg tttgtggcgt ttctcctgag agggaaactc 1020
atggaaacct attgttcgca gaaacacaca aggctagact acattggaga tagtaaaaat 1080
gtcctcaatg acgtgcagca tggaagggaa gacgaagacg gcctttttac cctc 1134

<210> SEQ ID NO 156

<211> LENGTH: 831
<212> TYPE: DNA
<213> ORGANISM: Homo sapiens
<220> FEATURE:
<223> OTHER INFORMATION: OX-40/CD134/TNFRSF4

<400> SEQUENCE: 156
atgtgcgtgg gggctcggcg gctgggccgc gggccgtgtg cggctctgct cctcctgggc 60
ctggggctga gcaccgtgac ggggctccac tgtgtcgggg acacctaccc cagcaacgac 120
cggtgctgcc acgagtgcag gccaggcaac gggatggtga gccgctgcag ccgctcccag 180
aacacggtgt gccgtccgtg cgggccgggc ttctacaacg acgtggtcag ctccaagccg 240
tgcaagccct gcacgtggtg taacctcaga agtgggagtg agcggaagca gctgtgcacg 300
gccacacagg acacagtctg ccgctgccgg gcgggcaccc agcccctgga cagctacaag 360
cctggagttg actgtgcccc ctgccctcca gggcacttct ccccaggcga caaccaggcc 420
tgcaagccct ggaccaactg caccttggct gggaagcaca ccctgcagcc ggccagcaat 480
agctcggacg caatctgtga ggacagggac cccccagcca cgcagcccca ggagacccag 540
ggccccccgg ccaggcccat cactgtccag cccactgaag cctggcccag aacctcacag 600
ggaccctcca cccggcccgt ggaggtcccc gggggccgtg cggttgccgc catcctgggc 660
ctgggcctgg tgctggggct gctgggcccc ctggccatcc tgctggccct gtacctgctc 720
cggagggacc agaggctgcc ccccgatgcc cacaagcccc ctgggggagg cagtttccgg 780
acccccatcc aagaggagca ggccgacgcc cactccaccc tggccaagat c 831

<210> SEQ ID NO 157
<211> LENGTH: 549
<212> TYPE: DNA
<213> ORGANISM: Homo sapiens
<220> FEATURE:
<223> OTHER INFORMATION: OX-40L/CD252/TNFSF4, isoform 1

<400> SEQUENCE: 157
atggaaaggg tccaacccct ggaagagaat gtgggaaatg cagccaggcc aagattcgag 60
aggaacaagc tattgctggt ggcctctgta attcagggac tggggctgct cctgtgcttc 120
acctacatct gcctgcactt ctctgctctt caggtatcac atcggtatcc tcgaattcaa 180
agtatcaaag tacaatttac cgaatataag aaggagaaag gtttcatcct cacttcccaa 240
aaggaggatg aaatcatgaa ggtgcagaac aactcagtca tcatcaactg tgatgggttt 300
tatctcatct ccctgaaggg ctacttctcc caggaagtca acattagcct tcattaccag 360
aaggatgagg agcccctctt ccaactgaag aaggtcaggt ctgtcaactc cttgatggtg 420
gcctctctga cttacaaaga caaagtctac ttgaatgtga ccactgacaa tacctccctg 480
gatgacttcc atgtgaatgg cggagaactg attcttatcc atcaaaatcc tggtgaattc 540
tgtgtcctt 549

<210> SEQ ID NO 158
<211> LENGTH: 1950
<212> TYPE: DNA
<213> ORGANISM: Homo sapiens
<220> FEATURE:
<223> OTHER INFORMATION: ILT-2/LILRB1, isoform 1

<400> SEQUENCE: 158
atgaccccca tcctcacggt cctgatctgt ctcgggctga gtctgggccc ccggacccac 60
gtgcaggcag ggcacctccc caagcccacc ctctgggctg aaccaggctc tgtgatcacc 120

```
caggggagtc ctgtgaccct caggtgtcag gggggccagg agacccagga gtaccgtcta    180
tatagagaaa agaaaacagc accctggatt acacggatcc cacaggagct tgtgaagaag    240
ggccagttcc ccatcccatc catcacctgg gaacacacag ggcggtatcg ctgttactat    300
ggtagcgaca ctgcaggccg ctcagagagc agtgaccccc tggagctggt ggtgacagga    360
gcctacatca aacccaccct ctcagcccag cccagccccg tggtgaactc aggagggaat    420
gtaaccctcc agtgtgactc acaggtggca tttgatggct tcattctgtg taaggaagga    480
gaagatgaac acccacaatg cctgaactcc cagccccatg cccgtgggtc gtcccgcgcc    540
atcttctccg tgggccccgt gagcccgagt cgcaggtggt ggtacaggtg ctatgcttat    600
gactcgaact ctccctatga gtggtctcta cccagtgatc tcctggagct cctggtccta    660
ggtgtttcta agaagccatc actctcagtg cagccaggtc ctatcgtggc ccctgaggag    720
accctgactc tgcagtgtgg ctctgatgct ggctacaaca gatttgttct gtataaggac    780
ggggaacgtg acttccttca gctcgctggc gcacagcccc aggctgggct ctcccaggcc    840
aacttcaccc tgggccctgt gagccgctcc tacgggggcc agtacagatg ctacggtgca    900
cacaacctct cctccgagtg gtcggccccc agcgaccccc tggacatcct gatcgcagga    960
cagttctatg acagagtctc cctctcggtg cagccgggcc ccacggtggc ctcaggagag   1020
aacgtgaccc tgctgtgtca gtcacaggga tggatgcaaa ctttccttct gaccaaggag   1080
ggggcagctg atgacccatg gcgtctaaga tcaacgtacc aatctcaaaa ataccaggct   1140
gaattcccca tgggtcctgt gacctcagcc catgcgggga cctacaggtg ctacggctca   1200
cagagctcca aaccctacct gctgactcac cccagtgacc ccctggagct cgtggtctca   1260
ggaccgtctg gggggcccag ctccccgaca acaggcccca cctccacatc tggccctgag   1320
gaccagcccc tcacccccac cgggtcggat ccccagagtg gtctgggaag gcacctgggg   1380
gttgtgatcg gcatcttggt ggccgtcatc ctactgctcc tcctcctcct cctcctcttc   1440
ctcatcctcc gacatcgacg tcagggcaaa cactggacat cgacccagag aaaggctgat   1500
ttccaacatc ctgcaggggc tgtggggcca gagcccacag acagaggcct gcagtggagg   1560
tccagcccag ctgccgatgc ccaggaagaa aacctctatg ctgccgtgaa gcacacacag   1620
cctgaggatg gggtggagat ggacactcgg agcccacacg atgaagaccc ccaggcagtg   1680
acgtatgccg aggtgaaaca ctccagacct aggagagaaa tggcctctcc tccttcccca   1740
ctgtctgggg aattcctgga cacaaaggac agacaggcgg aagaggacag gcagatggac   1800
actgaggctg ctgcatctga agccccccag gatgtgacct acgcccagct gcacagcttg   1860
accctcagac gggaggcaac tgagcctcct ccatcccagg aagggccctc tccagctgtg   1920
cccagcatct acgccactct ggccatccac                                    1950
```

<210> SEQ ID NO 159
<211> LENGTH: 1794
<212> TYPE: DNA
<213> ORGANISM: Homo sapiens
<220> FEATURE:
<223> OTHER INFORMATION: ILT-4/LILRB2, isoform 1

<400> SEQUENCE: 159

```
atgaccccca tcgtcacagt cctgatctgt ctcgggctga gtctgggccc caggacccgc     60
gtgcagacag ggaccatccc caagcccacc ctgtgggctg agccagactc tgtgatcacc    120
caggggagtc ccgtcaccct cagttgtcag ggggagccttg aagcccagga gtaccgtcta    180
```

```
tatagggaga aaaaatcagc atcttggatt acacggatac gaccagagct tgtgaagaac    240
ggccagttcc acatcccatc catcacctgg gaacacacag ggcgatatgg ctgtcagtat    300
tacagccgcg ctcggtggtc tgagctcagt gaccccctgg tgctggtgat gacaggagcc    360
tacccaaaac ccaccctctc agcccagccc agccctgtgg tgacctcagg aggaagggtg    420
accctccagt gtgagtcaca ggtggcattt ggcggcttca ttctgtgtaa ggaaggagaa    480
gatgaacacc cacaatgcct gaactcccag ccccatgccc gtgggtcgtc ccgcgccatc    540
ttctccgtgg gccccgtgag cccgaatcgc aggtggtcgc acaggtgcta tggttatgac    600
ttgaactctc cctatgtgtg gtcttcaccc agtgatctcc tggagctcct ggtcccaggt    660
gtttctaaga agccatcact ctcagtgcag ccgggtcctg tcatggcccc tggggaaagc    720
ctgaccctcc agtgtgtctc tgatgtcggc tatgacagat ttgttctgta caaggagggg    780
gaacgtgacc ttcgccagct ccctggccgg cagccccagg ctgggctctc ccaggccaac    840
ttcaccctgg gccctgtgag ccgctcctac gggggccagt acagatgcta cggtgcacac    900
aacctctcct ctgagtgctc ggcccccagc gacccccctgg acatcctgat cacaggacag    960
atccgtggca cacccttcat ctcagtgcag ccaggcccca cagtggcctc aggagagaac   1020
gtgaccctgc tgtgtcagtc atggcggcag ttccacactt tccttctgac caaggcggga   1080
gcagctgatg ccccactccg tctaagatca atacacgaat atcctaagta ccaggctgaa   1140
ttccccatga gtcctgtgac ctcagcccac gcggggacct acaggtgcta cggctcactc   1200
aactccgacc cctacctgct gtctcacccc agtgagcccc tggagctcgt ggtctcagga   1260
ccctccatgg gttccagccc cccacccacc ggtcccatct ccacacctgc aggccctgag   1320
gaccagcccc tcacccccac tgggtcggat ccccaaagtg gtctgggaag gcacctgggg   1380
gttgtgatcg gcatcttggt ggccgtcgtc ctactgctcc tcctcctcct cctcctcttc   1440
ctcatcctcc gacatcgacg tcagggcaaa cactggacat cgacccagag aaaggctgat   1500
ttccaacatc ctgcaggggc tgtggggcca gagcccacag acagaggcct gcagtggagg   1560
tccagcccag ctgccgacgc ccaggaagaa aacctctatg ctgccgtgaa ggacacacag   1620
cctgaagatg gggtggagat ggacactcgg gctgctgcat ctgaagcccc ccaggatgtg   1680
acctacgccc agctgcacag cttgaccctc agacggaagg caactgagcc tcctccatcc   1740
caggaaaggg aacctccagc tgagcccagc atctacgcca ccctggccat ccac         1794
```

<210> SEQ ID NO 160
<211> LENGTH: 717
<212> TYPE: DNA
<213> ORGANISM: Homo sapiens
<220> FEATURE:
<223> OTHER INFORMATION: BCL-2 isoform alpha

<400> SEQUENCE: 160

```
atggcgcacg ctgggagaac agggtacgat aaccgggaga tagtgatgaa gtacatccat     60
tataagctgt cgcagagggg ctacgagtgg gatgcgggag atgtgggcgc cgcgcccccg    120
ggggccgccc ccgcaccggg catcttctcc tcccagcccg ggcacacgcc ccatccagcc    180
gcatcccggg acccggtcgc caggacctcg ccgctgcaga ccccggctgc ccccggcgcc    240
gccgcggggc ctgcgctcag cccggtgcca cctgtggtcc acctgaccct ccgccaggcc    300
ggcgacgact tctcccgccg ctaccgccgc gacttcgccg agatgtccag ccagctgcac    360
ctgacgccct tcaccgcgcg gggacgcttt gccacggtgg tggaggagct cttcagggac    420
ggggtgaact gggggaggat tgtggccttc tttgagttcg gtggggtcat gtgtgtggag    480
```

agcgtcaacc gggagatgtc gcccctggtg gacaacatcg ccctgtggat gactgagtac 540
ctgaaccggc acctgcacac ctggatccag gataacggag gctgggatgc ctttgtggaa 600
ctgtacggcc ccagcatgcg gcctctgttt gatttctcct ggctgtctct gaagactctg 660
ctcagtttgg ccctggtggg agcttgcatc accctgggtg cctatctggg ccacaag 717

<210> SEQ ID NO 161
<211> LENGTH: 4050
<212> TYPE: DNA
<213> ORGANISM: Homo sapiens
<220> FEATURE:
<223> OTHER INFORMATION: MDR1/ABCB1, isoform 1

<400> SEQUENCE: 161
atgagtgtca acttgcaagg ggaccagaga ggtgcaacgg aagccagaac attcctcctg 60
gaaattcaac ctgtttcgca gtttctcgag gaatcagcat tcagtcaatc cgggccggga 120
gcagtcatct gtggtctttc cactaaagtc ggagtatctt cttccaaaat ttcacgtctt 180
ggtggccgtt ccaaggagcg cgaggtcgga atggatcttg aaggggaccg caatggagga 240
gcaaagaaga agaacttttt taaactgaac aataaaagtg aaaaagataa gaaggaaaag 300
aaaccaactg tcagtgtatt ttcaatgttt cgctattcaa attggcttga caagttgtat 360
atggtggtgg gaactttggc tgccatcatc catggggctg gacttcctct catgatgctg 420
gtgtttggag aaatgacaga tatctttgca aatgcaggaa atttagaaga tctgatgtca 480
aacatcacta atagaagtga tatcaatgat acagggttct tcatgaatct ggaggaagac 540
atgaccaggt atgcctatta ttacagtgga attggtgctg gggtgctggt tgctgcttac 600
attcaggttt cattttggtg cctggcagct ggaagacaaa tacacaaaat tagaaaacag 660
ttttttcatg ctataatgcg acaggagata ggctggtttg atgtgcacga tgttggggag 720
cttaacaccc gacttacaga tgatgtctcc aagattaatg aaggaattgg tgacaaaatt 780
ggaatgttct ttcagtcaat ggcaacattt ttcactgggt ttatagtagg atttacacgt 840
ggttggaagc taacccttgt gattttggcc atcagtcctg ttcttggact gtcagctgct 900
gtctgggcaa agatactatc ttcatttact gataaagaac tcttagcgta tgcaaaagct 960
ggagcagtag ctgaagaggt cttggcagca attagaactg tgattgcatt tggaggacaa 1020
aagaaagaac ttgaaaggta caacaaaaat ttagaagaag ctaaaagaat tgggataaag 1080
aaagctatta cagccaatat ttctataggt gctgctttcc tgctgatcta tgcatcttat 1140
gctctggcct tctggtatgg gaccaccttg gtcctctcag gggaatattc tattggacaa 1200
gtactcactg tattcttttc tgtattaatt ggggctttta gtgttggaca ggcatctcca 1260
agcattgaag catttgcaaa tgcaagagga gcagcttatg aaatcttcaa gataattgat 1320
aataagccaa gtattgacag ctattcgaag agtgggcaca aaccagataa tattaaggga 1380
aatttggaat tcagaaatgt tcacttcagt tacccatctc gaaaagaagt taagatcttg 1440
aagggtctga acctgaaggt gcagagtggg cagacggtgg ccctggttgg aaacagtggc 1500
tgtgggaaga gcacaacagt ccagctgatg cagaggctct atgaccccac agaggggatg 1560
gtcagtgttg atggacagga tattaggacc ataaatgtaa ggtttctacg ggaaatcatt 1620
ggtgtggtga gtcaggaacc tgtattgttt gccaccacga tagctgaaaa cattcgctat 1680
ggccgtgaaa atgtcaccat ggatgagatt gagaaagctg tcaaggaagc caatgcctat 1740
gactttatca tgaaactgcc tcataaattt gacaccctgg ttggagagag aggggcccag 1800
ttgagtggtg ggcagaagca gaggatcgcc attgcacgtg ccctggttcg caaccccaag 1860
atcctcctgc tggatgaggc cacgtcagcc ttggacacag aaagcgaagc agtggttcag 1920
gtggctctgg ataaggccag aaaaggtcgg accaccattg tgatagctca tcgtttgtct 1980
acagttcgta atgctgacgt catcgctggt ttcgatgatg gagtcattgt ggagaaagga 2040
aatcatgatg aactcatgaa agagaaaggc atttacttca aacttgtcac aatgcagaca 2100
gcaggaaatg aagttgaatt agaaaatgca gctgatgaat ccaaaagtga aattgatgcc 2160
ttggaaatgt cttcaaatga ttcaagatcc agtctaataa gaaaaagatc aactcgtagg 2220
agtgtccgtg gatcacaagc ccaagacaga aagcttagta ccaaagaggc tctggatgaa 2280
agtatacctc cagtttcctt ttggaggatt atgaagctaa atttaactga atggccttat 2340
tttgttgttg gtgtattttg tgccattata aatggaggcc tgcaaccagc atttgcaata 2400
atattttcaa agattatagg ggtttttaca agaattgatg atcctgaaac aaaacgacag 2460
aatagtaact tgttttcact attgtttcta gcccttggaa ttatttcttt tattacattt 2520
ttccttcagg gtttcacatt tggcaaagct ggagagatcc tcaccaagcg gctccgatac 2580
atggttttcc gatccatgct cagacaggat gtgagttggt ttgatgaccc taaaaacacc 2640
actggagcat tgactaccag gctcgccaat gatgctgctc aagttaaagg ggctataggt 2700
tccaggcttg ctgtaattac ccagaatata gcaaatcttg ggacaggaat aattatatcc 2760
ttcatctatg gttggcaact aacactgtta ctcttagcaa ttgtacccat cattgcaata 2820
gcaggagttg ttgaaatgaa aatgttgtct ggacaagcac tgaaagataa gaaagaacta 2880
gaaggttctg ggaagatcgc tactgaagca atagaaaact tccgaaccgt tgtttctttg 2940
actcaggagc agaagtttga acatatgtat gctcagagtt tgcaggtacc atacagaaac 3000
tctttgagga aagcacacat ctttggaatt acattttcct tcacccaggc aatgatgtat 3060
ttttcctatg ctggatgttt ccggtttgga gcctacttgg tggcacataa actcatgagc 3120
tttgaggatg ttctgttagt attttcagct gttgtctttg gtgccatggc cgtggggcaa 3180
gtcagttcat ttgctcctga ctatgccaaa gccaaaatat cagcagccca catcatcatg 3240
atcattgaaa aaaccccttt gattgacagc tacagcacgg aaggcctaat gccgaacaca 3300
ttggaaggaa atgtcacatt tggtgaagtt gtattcaact atcccacccg accggacatc 3360
ccagtgcttc agggactgag cctggaggtg aagaagggcc agacgctggc tctggtgggc 3420
agcagtggct gtgggaagag cacagtggtc cagctcctgg agcggttcta cgaccccttg 3480
gcagggaaag tgctgcttga tggcaaagaa ataaagcgac tgaatgttca gtggctccga 3540
gcacacctgg gcatcgtgtc ccaggagccc atcctgtttg actgcagcat tgctgagaac 3600
attgcctatg gagacaacag ccgggtggtg tcacaggaag agattgtgag ggcagcaaag 3660
gaggccaaca tacatgcctt catcgagtca ctgcctaata aatatagcac taaagtagga 3720
gacaaaggaa ctcagctctc tggtggccag aaacaacgca ttgccatagc tcgtgccctt 3780
gttagacagc ctcatatttt gcttttggat gaagccacgt cagctctgga tacagaaagt 3840
gaaaaggttg tccaagaagc cctggacaaa gccagagaag gccgcacctg cattgtgatt 3900
gctcaccgcc tgtccaccat ccagaatgca gacttaatag tggtgtttca gaatggcaga 3960
gtcaaggagc atggcacgca tcagcagctg ctggcacaga aaggcatcta tttttcaatg 4020
gtcagtgtcc aggctggaac aaagcgccag 4050

<210> SEQ ID NO 162
<211> LENGTH: 990

<212> TYPE: DNA
<213> ORGANISM: Homo sapiens
<220> FEATURE:
<223> OTHER INFORMATION: Arginase1, isoform 1

<400> SEQUENCE: 162
atgagcgcca agtccagaac catagggatt attggagctc ctttctcaaa gggacagcca 60
cgaggagggg tggaagaagg ccctacagta ttgagaaagg ctggtctgct tgagaaactt 120
aaagaacaag taactcaaaa ctttttaatt ttagagtgtg atgtgaagga ttatggggac 180
ctgccctttg ctgacatccc taatgacagt ccctttcaaa ttgtgaagaa tccaaggtct 240
gtgggaaaag caagcgagca gctggctggc aaggtggcag aagtcaagaa gaacggaaga 300
atcagcctgg tgctgggcgg agaccacagt ttggcaattg gaagcatctc tggccatgcc 360
agggtccacc ctgatcttgg agtcatctgg gtggatgctc acactgatat caacactcca 420
ctgacaacca caagtggaaa cttgcatgga caacctgtat ctttcctcct gaaggaacta 480
aaaggaaaga ttcccgatgt gccaggattc tcctgggtga ctccctgtat atctgccaag 540
gatattgtgt atattggctt gagagacgtg gaccctgggg aacactacat tttgaaaact 600
ctaggcatta aatacttttc aatgactgaa gtggacagac taggaattgg caaggtgatg 660
gaagaaacac tcagctatct actaggaaga aagaaaaggc caattcatct aagttttgat 720
gttgacggac tggacccatc tttcacacca gctactggca caccagtcgt gggaggtctg 780
acatacagag aaggtctcta catcacagaa gaaatctaca aaacagggct actctcagga 840
ttagatataa tggaagtgaa cccatccctg ggaagacac cagaagaagt aactcgaaca 900
gtgaacacag cagttgcaat aaccttggct tgtttcggac ttgctcggga gggtaatcac 960
aagcctattg actaccttaa cccacctaag 990

<210> SEQ ID NO 163
<211> LENGTH: 3459
<212> TYPE: DNA
<213> ORGANISM: Homo sapiens
<220> FEATURE:
<223> OTHER INFORMATION: nitric oxide synthase, inducible (iNOS/NOS2), isoform 1

<400> SEQUENCE: 163
atggcctgtc cttggaaatt tctgttcaag accaaattcc accagtatgc aatgaatggg 60
gaaaaagaca tcaacaacaa tgtggagaaa gccccctgtg ccacctccag tccagtgaca 120
caggatgacc ttcagtatca caacctcagc aagcagcaga atgagtcccc gcagcccctc 180
gtggagacgg gaaagaagtc tccagaatct ctggtcaagc tggatgcaac cccattgtcc 240
tccccacggc atgtgaggat caaaaactgg ggcagcggga tgactttcca agacacactt 300
caccataagg ccaaagggat tttaacttgc aggtccaaat cttgcctggg gtccattatg 360
actcccaaaa gtttgaccag aggacccagg gacaagccta cccctccaga tgagcttcta 420
cctcaagcta tcgaatttgt caaccaatat tacggctcct tcaaagaggc aaaaatagag 480
gaacatctgg ccagggtgga agcggtaaca aaggagatag aaacaacagg aacctaccaa 540
ctgacgggag atgagctcat cttcgccacc aagcaggcct ggcgcaatgc cccacgctgc 600
attgggagga tccagtggtc caacctgcag gtcttcgatg cccgcagctg ttccactgcc 660
cgggaaatgt ttgaacacat ctgcagacac gtgcgttact ccaccaacaa tggcaacatc 720
aggtcggcca tcaccgtgtt cccccagcgg agtgatggca agcacgactt ccgggtgtgg 780
aatgctcagc tcatccgcta tgctggctac cagatgccag atggcagcat cagaggggac 840

-continued cctgccaacg tggaattcac tcagctgtgc atcgacctgg gctggaagcc caagtacggc 900
cgcttcgatg tggtccccct ggtcctgcag gccaatggcc gtgaccctga gctcttcgaa 960
atcccacctg accttgtgct tgaggtggcc atggaacatc ccaaatacga gtggtttcgg 1020
gaactggagc taaagtggta cgccctgcct gcagtggcca acatgctgct tgaggtgggc 1080
ggcctggagt tcccagggtg ccccttcaat ggctggtaca tgggcacaga gatcggagtc 1140
cgggacttct gtgacgtcca gcgctacaac atcctggagg aagtgggcag gagaatgggc 1200
ctggaaacgc acaagctggc ctcgctctgg aaagaccagg ctgtcgttga gatcaacatt 1260
gctgtgctcc atagtttcca gaagcagaat gtgaccatca tggaccacca ctcggctgca 1320
gaatccttca tgaagtacat gcagaatgaa taccggtccc gtgggggctg cccggcagac 1380
tggatttggc tggtccctcc catgtctggg agcatcaccc ccgtgtttca ccaggagatg 1440
ctgaactacg tcctgtcccc tttctactac tatcaggtag aggcctggaa aacccatgtc 1500
tggcaggacg agaagcggag acccaagaga agagagattc cattgaaagt cttggtcaaa 1560
gctgtgctct ttgcctgtat gctgatgcgc aagacaatgg cgtcccgagt cagagtcacc 1620
atcctctttg cgacagagac aggaaaatca gaggcgctgg cctgggacct gggggcctta 1680
ttcagctgtg ccttcaaccc caaggttgtc tgcatggata agtacaggct gagctgcctg 1740
gaggaggaac ggctgctgtt ggtggtgacc agtacgtttg gcaatggaga ctgccctggc 1800
aatggagaga aactgaagaa atcgctcttc atgctgaaag agctcaacaa caaattcagg 1860
tacgctgtgt ttggcctcgg ctccagcatg taccctcggt tctgcgcctt tgctcatgac 1920
attgatcaga agctgtccca cctgggggcc tctcagctca ccccgatggg agaaggggat 1980
gagctcagtg ggcaggagga cgccttccgc agctgggccg tgcaaacctt caaggcagcc 2040
tgtgagacgt ttgatgtccg aggcaaacag cacattcaga tccccaagct ctacacctcc 2100
aatgtgacct gggacccgca ccactacagg ctcgtgcagg actcacagcc tttggacctc 2160
agcaaagccc tcagcagcat gcatgccaag aacgtgttca ccatgaggct caaatctcgg 2220
cagaatctac aaagtccgac atccagccgt gccaccatcc tggtggaact ctcctgtgag 2280
gatggccaag gcctgaacta cctgccgggg gagcaccttg gggtttgccc aggcaaccag 2340
ccggccctgg tccaaggtat cctggagcga gtggtggatg gccccacacc ccaccagaca 2400
gtgcgcctgg aggccctgga tgagagtggc agctactggg tcagtgacaa gaggctgccc 2460
ccctgctcac tcagccaggc cctcacctac ttcctggaca tcaccacacc cccaacccag 2520
ctgctgctcc aaaagctggc ccaggtggcc acagaagagc ctgagagaca gaggctggag 2580
gccctgtgcc agccctcaga gtacagcaag tggaagttca ccaacagccc cacattcctg 2640
gaggtgctag aggagttccc gtccctgcgg gtgtctgctg gcttcctgct ttcccagctc 2700
cccattctga agcccaggtt ctactccatc agctcctccc gggatcacac gcccacagag 2760
atccacctga ctgtggccgt ggtcacctac cacacccgag atggccaggg tcccctgcac 2820
cacggcgtct gcagcacatg gctcaacagc ctgaagcccc aagacccagt gccctgcttt 2880
gtgcggaatg ccagcggctt ccacctcccc gaggatccct cccatccttg catcctcatc 2940
gggcctggca caggcatcgc gcccttccgc agtttctggc agcaacggct ccatgactcc 3000
cagcacaagg gagtgcgggg aggccgcatg accttggtgt ttgggtgccg ccgcccagat 3060
gaggaccaca tctaccagga ggagatgctg gagatggccc agaagggggt gctgcatgcg 3120
gtgcacacag cctattcccg cctgcctggc aagcccaagg tctatgttca ggacatcctg 3180

```
cggcagcagc tggccagcga ggtgctccgt gtgctccaca aggagccagg ccacctctat   3240

gtttgcgggg atgtgcgcat ggcccgggac gtggcccaca ccctgaagca gctggtggct   3300

gccaagctga aattgaatga ggagcaggtc gaggactatt tctttcagct caagagccag   3360

aagcgctatc acgaagatat ctttggtgct gtatttcctt acgaggcgaa gaaggacagg   3420

gtggcggtgc agcccagcag cctggagatg tcagcgctc                         3459


<210> SEQ ID NO 164
<211> LENGTH: 3765
<212> TYPE: DNA
<213> ORGANISM: Homo sapiens
<220> FEATURE:
<223> OTHER INFORMATION: Her2

<400> SEQUENCE: 164

atggagctgg cggccttgtg ccgctggggg ctcctcctcg ccctcttgcc ccccggagcc     60

gcgagcaccc aagtgtgcac cggcacagac atgaagctgc ggctccctgc cagtcccgag    120

acccacctgg acatgctccg ccacctctac cagggctgcc aggtggtgca gggaaacctg    180

gaactcacct acctgcccac caatgccagc ctgtccttcc tgcaggatat ccaggaggtg    240

cagggctacg tgctcatcgc tcacaaccaa gtgaggcagg tcccactgca gaggctgcgg    300

attgtgcgag gcacccagct ctttgaggac aactatgccc tggccgtgct agacaatgga    360

gacccgctga acaataccac ccctgtcaca ggggcctccc caggaggcct gcgggagctg    420

cagcttcgaa gcctcacaga gatcttgaaa ggaggggtct tgatccagcg gaacccccag    480

ctctgctacc aggacacgat tttgtggaag gacatcttcc acaagaacaa ccagctggct    540

ctcacactga tagacaccaa ccgctctcgg gcctgccacc cctgttctcc gatgtgtaag    600

ggctcccgct gctggggaga gagttctgag gattgtcaga gcctgacgcg cactgtctgt    660

gccggtggct gtgcccgctg caaggggcca ctgcccactg actgctgcca tgagcagtgt    720

gctgccggct gcacgggccc caagcactct gactgcctgg cctgcctcca cttcaaccac    780

agtggcatct gtgagctgca ctgcccagcc ctggtcacct acaacacaga cacgtttgag    840

tccatgccca atcccgaggg ccggtataca ttcggcgcca gctgtgtgac tgcctgtccc    900

tacaactacc tttctacgga cgtgggatcc tgcaccctcg tctgccccct gcacaaccaa    960

gaggtgacag cagaggatgg aacacagcgg tgtgagaagt gcagcaagcc ctgtgcccga   1020

gtgtgctatg gtctgggcat ggagcacttg cgagaggtga gggcagttac cagtgccaat   1080

atccaggagt ttgctggctg caagaagatc tttgggagcc tggcatttct gccggagagc   1140

tttgatgggg acccagcctc caacactgcc ccgctccagc cagagcagct ccaagtgttt   1200

gagactctgg aagagatcac aggttaccta tacatctcag catggccgga cagcctgcct   1260

gacctcagcg tcttccagaa cctgcaagta atccggggac gaattctgca caatggcgcc   1320

tactcgctga ccctgcaagg gctgggcatc agctggctgg ggctgcgctc actgagggaa   1380

ctgggcagtg gactggccct catccaccat aacacccacc tctgcttcgt gcacacggtg   1440

ccctgggacc agctctttcg gaacccgcac caagctctgc tccacactgc caaccggcca   1500

gaggacgagt gtgtgggcga gggcctggcc tgccaccagc tgtgcgcccg agggcactgc   1560

tggggtccag ggcccaccca gtgtgtcaac tgcagccagt tccttcgggg ccaggagtgc   1620

gtggaggaat gccgagtact gcaggggctc cccagggagt atgtgaatgc caggcactgt   1680

ttgccgtgcc accctgagtg tcagccccag aatggctcag tgacctgttt tggaccggag   1740

gctgaccagt gtgtggcctg tgcccactat aaggaccctc ccttctgcgt ggcccgctgc   1800
```

-continued cccagcggtg tgaaacctga cctctcctac atgcccatct ggaagtttcc agatgaggag 1860
ggcgcatgcc agccttgccc catcaactgc acccactcct gtgtggacct ggatgacaag 1920
ggctgccccg ccgagcagag agccagccct ctgacgtcca tcatctctgc ggtggttggc 1980
attctgctgg tcgtggtctt gggggtggtc tttgggatcc tcatcaagcg acggcagcag 2040
aagatccgga agtacacgat gcggagactg ctgcaggaaa cggagctggt ggagccgctg 2100
acacctagcg gagcgatgcc caaccaggcg cagatgcgga tcctgaaaga gacggagctg 2160
aggaaggtga aggtgcttgg atctggcgct tttggcacag tctacaaggg catctggatc 2220
cctgatgggg agaatgtgaa aattccagtg gccatcaaag tgttgaggga aaacacatcc 2280
cccaaagcca acaaagaaat cttagacgaa gcatacgtga tggctggtgt gggctcccca 2340
tatgtctccc gccttctggg catctgcctg acatccacgg tgcagctggt gacacagctt 2400
atgccctatg gctgcctctt agaccatgtc cgggaaaacc gcggacgcct gggctcccag 2460
gacctgctga actggtgtat gcagattgcc aaggggatga gctacctgga ggatgtgcgg 2520
ctcgtacaca gggacttggc cgctcggaac gtgctggtca agagtcccaa ccatgtcaaa 2580
attacagact tcgggctggc tcggctgctg gacattgacg agacagagta ccatgcagat 2640
gggggcaagg tgcccatcaa gtggatggcg ctggagtcca ttctccgccg gcggttcacc 2700
caccagagtg atgtgtggag ttatggtgtg actgtgtggg agctgatgac ttttggggcc 2760
aaaccttacg atgggatccc agcccgggag atccctgacc tgctggaaaa gggggagcgg 2820
ctgccccagc cccccatctg caccattgat gtctacatga tcatggtcaa atgttggatg 2880
attgactctg aatgtcggcc aagattccgg gagttggtgt ctgaattctc ccgcatggcc 2940
agggaccccc agcgctttgt ggtcatccag aatgaggact tgggcccagc cagtcccttg 3000
gacagcacct tctaccgctc actgctggag gacgatgaca tgggggacct ggtggatgct 3060
gaggagtatc tggtacccca gcagggcttc ttctgtccag accctgcccc gggcgctggg 3120
ggcatggtcc accacaggca ccgcagctca tctaccagga gtggcggtgg ggacctgaca 3180
ctagggctgg agccctctga agaggaggcc cccaggtctc cactggcacc ctccgaaggg 3240
gctggctccg atgtatttga tggtgacctg ggaatggggg cagccaaggg gctgcaaagc 3300
ctccccacac atgaccccag ccctctacag cggtacagtg aggaccccac agtacccctg 3360
ccctctgaga ctgatggcta cgttgccccc ctgacctgca gcccccagcc tgaatatgtg 3420
aaccagccag atgttcggcc ccagccccct tcgccccgag agggccctct gcctgctgcc 3480
cgacctgctg gtgccactct ggaaaggccc aagactctct ccccagggaa gaatggggtc 3540
gtcaaagacg tttttgcctt tgggggtgcc gtggagaacc ccgagtactt gacaccccag 3600
ggaggagctg cccctcagcc ccaccctcct cctgccttca gcccagcctt cgacaacctc 3660
tattactggg accaggaccc accagagcgg ggggctccac ccagcacctt caaagggaca 3720
cctacggcag agaacccaga gtacctgggt ctggacgtgc cagtg 3765

<210> SEQ ID NO 165
<211> LENGTH: 567
<212> TYPE: DNA
<213> ORGANISM: Homo sapiens
<220> FEATURE:
<223> OTHER INFORMATION: KRAS

<400> SEQUENCE: 165
atgactgaat ataaacttgt ggtagttgga gctggtggcg taggcaagag tgccttgacg 60

```
atacagctaa ttcagaatca ttttgtggac gaatatgatc caacaataga ggattcctac    120

aggaagcaag tagtaattga tggagaaacc tgtctcttgg atattctcga cacagcaggt    180

caagaggagt acagtgcaat gagggaccag tacatgagga ctggggaggg ctttctttgt    240

gtatttgcca taaataatac taaatcattt gaagatattc accattatag agaacaaatt    300

aaaagagtta aggactctga agatgtacct atggtcctag taggaaataa atgtgatttg    360

ccttctagaa cagtagacac aaaacaggct caggacttag caagaagtta tggaattcct    420

tttattgaaa catcagcaaa gacaagacag agagtggagg atgcttttta tacattggtg    480

agggagatcc gacaatacag attgaaaaaa atcagcaaag aagaaaagac tcctggctgt    540

gtgaaaatta aaaaatgcat tataatg                                        567
```

<210> SEQ ID NO 166
<211> LENGTH: 1809
<212> TYPE: DNA
<213> ORGANISM: Homo sapiens
<220> FEATURE:
<223> OTHER INFORMATION: PLK1

<400> SEQUENCE: 166

```
atgagtgctg cagtgactgc agggaagctg gcacgggcac cggccgaccc tgggaaagcc     60

ggggtccccg gagttgcagc tcccggagct ccggcggcgg ctccaccggc gaaagagatc    120

ccggaggtcc tagtggaccc acgcagccgg cggcgctatg tgcggggccg ctttttgggc    180

aagggcggct ttgccaagtg cttcgagatc tcggacgcgg acaccaagga ggtgttcgcg    240

ggcaagattg tgcctaagtc tctgctgctc aagccgcacc agagggagaa gatgtccatg    300

gaaatatcca ttcaccgcag cctcgcccac cagcacgtcg taggattcca cggctttttc    360

gaggacaacg acttcgtgtt cgtggtgttg gagctctgcc gccggaggtc tctcctggag    420

ctgcacaaga ggaggaaagc cctgactgag cctgaggccc gatactacct acggcaaatt    480

gtgcttggct gccagtacct gcaccgaaac cgagttattc atcgagacct caagctgggc    540

aaccttttcc tgaatgaaga tctggaggtg aaaatagggg attttggact ggcaaccaaa    600

gtcgaatatg acggggagag gaagaagacc ctgtgtggga ctcctaatta catagctccc    660

gaggtgctga gcaagaaagg gcacagtttc gaggtggatg tgtggtccat tgggtgtatc    720

atgtatacct tgttagtggg caaaccacct tttgagactt cttgcctaaa agagacctac    780

ctccggatca agaagaatga atacagtatt cccaagcaca tcaaccccgt ggccgcctcc    840

ctcatccaga agatgcttca gacagatccc actgcccgcc caaccattaa cgagctgctt    900

aatgacgagt tctttacttc tggctatatc cctgcccgtc tccccatcac ctgcctgacc    960

attccaccaa ggttttcgat tgctcccagc agcctggacc ccagcaaccg gaagcccctc   1020

acagtcctca ataaaggctt ggagaacccc ctgcctgagc gtccccggga aaaagaagaa   1080

ccagtggttc gagagacagg tgaggtggtc gactgccacc tcagtgacat gctgcagcag   1140

ctgcacagtg tcaatgcctc caagccctcg gagcgtgggc tggtcaggca agaggaggct   1200

gaggatcctg cctgcatccc catcttctgg gtcagcaagt gggtggacta ttcggacaag   1260

tacggccttg ggtatcagct ctgtgataac agcgtggggg tgctcttcaa tgactcaaca   1320

cgcctcatcc tctacaatga tggtgacagc ctgcagtaca tagagcgtga cggcactgag   1380

tcctacctca ccgtgagttc ccatcccaac tccttgatga agaagatcac cctccttaaa   1440

tatttccgca attacatgag cgagcacttg ctgaaggcag gtgccaacat cacgccgcgc   1500

gaaggtgatg agctcgcccg gctgccctac ctacggacct ggttccgcac ccgcagcgcc   1560
```

atcatcctgc acctcagcaa cggcagcgtg cagatcaact tcttccagga tcacaccaag 1620
ctcatcttgt gcccactgat ggcagccgtg acctacatcg acgagaagcg ggacttccgc 1680
acataccgcc tgagtctcct ggaggagtac ggctgctgca aggagctggc cagccggctc 1740
cgctacgccc gcactatggt ggacaagctg ctgagctcac gctcggccag caaccgtctc 1800
aaggcctcc 1809

<210> SEQ ID NO 167
<211> LENGTH: 876
<212> TYPE: DNA
<213> ORGANISM: Salmonella typhimurium
<220> FEATURE:
<223> OTHER INFORMATION: dapA, strain LT2

<400> SEQUENCE: 167
atgttcacgg gaagtattgt cgcgcttgtt acgccgatgg atgagaaagg taacgtcagt 60
aggtcttgcc tgaaaaaact cattgattat catgtcgcca acggtacctc ggcgattgtt 120
tcggttggca ctaccggcga gtctgccacg ctaagccatg atgaacatgg cgatgtcgtg 180
atgatgacgc tggaactggc tgacggacgt attccggtta tcgccggcac gggcgcaaac 240
gcgaccgcgg aagcgattag cctgacgcag cgttttaacg atagcggtat tgtaggctgc 300
ctgacggtaa cgccgtacta caatcgcccc acgcaggaag gtttgttcca gcatttcaaa 360
gccatcgcgg aacacactga cttgccgcaa attctgtata atgtgccgtc ccgtaccggt 420
tgcgatatgt tgccggaaac cgtgggtcgt ctggcggaaa taaaaaatat tatcgctatc 480
aaagaggcga cagggaactt aacccgcgtt caccagatca aagagctggt ttcagacgat 540
tttattctgc ttagcggcga tgacgcgtct gcgctggact ttatgcaact gggtggtcat 600
ggcgtgattt ccgttacggc taacgtagcg gcgcgcgaga tggctgacat gtgcaaactg 660
gcggcggaag ggcaatttgc cgaggcgcgc gctatcaacc agcgtctgat gccgttacac 720
aacaaactat ttgtcgaacc caatcctatc ccggtgaaat gggcatgtaa ggcattgggt 780
cttgtggcga ccgacacgct gcgcctgcca atgacgccta tcacggacca tggtcgtgac 840
atcgtcaaag cagcgcttca gcatgctggc ctgctg 876

<210> SEQ ID NO 168
<211> LENGTH: 819
<212> TYPE: DNA
<213> ORGANISM: Salmonella typhimurium
<220> FEATURE:
<223> OTHER INFORMATION: dapB, strain LT2

<400> SEQUENCE: 168
atgcatgaag cacaaatccg cgtcgccatt gccggcgccg gtggccgcat gggacggcag 60
ttaatccagg ccgccatggc gatggaaggt gttcagctgg gtgccgcgct ggagcgcgaa 120
ggctcttcct tgctgggcag cgatgctggc gaactggcag ggcgggaaa gtccggcgtg 180 atcgttcaaa gcagccttga ggcggtaaaa gatgattttg acgttttcat cgattttacc 240
cgtccggaag gcacgttgac gcatctggcg ttttgccgcc agcatggtaa agggatggtg 300
attggtacta ccggctttga cgacgccggt aaacaagcca ttcgcgaggc gtcacaagag 360
attgcgatcg ttttcgccgc aaactttagc gtcggcgtta acgtcatgct caagctgctg 420
gagaaagccg cgaaggtaat gggcgactat agcgatattg aaattattga agcgcaccac 480
cgccataaag tggatgcacc gtcgggtacg gcgctggcaa tgggcgaggc aatcgccggg 540
gcgctggata aaaatctgaa ggactgcgcg gtctactcgc gtgaaggtta taccggcgag 600
cgcgtagcgg gcacgattgg ctttgcgacc gttcgggcgg gcgacatcgt cggcgaacat 660
accgcgatgt ttgccgatat tggcgagcgc gtagagatta cgcataaagc ttccagccgc 720
atgacgtttg caaatggcgc gttgcgatcg gcgttatggc taaaaacgaa gaaaaatggg 780
ctatttgaca tgcgggatgt gctggggctg gatgtatta 819

<210> SEQ ID NO 169
<211> LENGTH: 876
<212> TYPE: DNA
<213> ORGANISM: E. coli
<220> FEATURE:
<223> OTHER INFORMATION: dapA

<400> SEQUENCE: 169
atgttcacgg gaagtattgt cgcgattgtt actccgatgg atgaaaaagg taatgtctgt 60
cgggctagct tgaaaaaact gattgattat catgtcgcca gcggtacttc ggcgatcgtt 120
tctgttggca ccactggcga gtccgctacc ttaaatcatg acgaacatgc tgatgtggtg 180
atgatgacgc tggatctggc tgatgggcgc attccggtaa ttgccgggac cggcgctaac 240
gctactgcgg aagccattag cctgacgcag cgcttcaatg acagtggtat cgtcggctgc 300
ctgacggtaa ccccttacta caatcgtccg tcgcaagaag gtttgtatca gcatttcaaa 360
gccatcgctg agcatactga cctgccgcaa attctgtata atgtgccgtc ccgtactggc 420
tgcgatctgc tcccggaaac ggtgggccgt ctggcgaaag taaaaaatat tatcggaatc 480
aaagaggcaa cagggaactt aacgcgtgta aaccagatca aagagctggt ttcagatgat 540
tttgttctgc tgagcggcga tgatgcgagc gcgctggact tcatgcaatt gggcggtcat 600
ggggttattt ccgttacgac taacgtcgca gcgcgtgata tggcccagat gtgcaaactg 660
gcagcagaag aacattttgc cgaggcacgc gttattaatc agcgtctgat gccattacac 720
aacaaactat ttgtcgaacc caatccaatc ccggtgaaat gggcatgtaa ggaactgggt 780
cttgtggcga ccgatacgct gcgcctgcca atgacaccaa tcaccgacag tggtcgtgag 840
acggtcagag cggcgcttaa gcatgccggt ttgctg 876

<210> SEQ ID NO 170
<211> LENGTH: 819
<212> TYPE: DNA
<213> ORGANISM: E. coli
<220> FEATURE:
<223> OTHER INFORMATION: dapB

<400> SEQUENCE: 170
atgcatgatg caaacatccg cgttgccatc gcgggagccg gggggcgtat gggccgccag 60
ttgattcagg cggcgctggc attagagggc gtgcagttgg gcgctgcgct ggagcgtgaa 120
ggatcttctt tactgggcag cgacgccggt gagctggccg gagccgggaa aacaggcgtt 180
accgtgcaaa gcagcctcga tgcggtaaaa gatgattttg atgtgtttat cgattttacc 240
cgtccggaag gtacgctgaa ccatctcgct ttttgtcgcc agcatggcaa agggatggtg 300
atcggcacta cggggtttga cgaagccggt aaacaagcaa ttcgtgacgc cgctgccgat 360
attgcgattg tctttgcggc caattttagc gttggcgtta acgtcatgct taagctgctg 420
gagaaagcag ccaaagtgat gggtgactac accgatatcg aaattattga agcacatcat 480
agacataaag ttgatgcgcc gtcaggcacc gcactggcaa tgggagaggc gatcgcccac 540
gcccttgata aagatctgaa agattgcgcg gtctacagtc gtgaaggcca caccggtgaa 600
cgtgtgcctg gcaccattgg ttttgccacc gtgcgtgcag gtgacatcgt tggtgaacat 660
accgcgatgt ttgccgatat tggcgagcgt ctggagatca cccataaggc gtccagccgt 720
atgacatttg ctaacggcgc ggtaagatcg gctttgtggt tgagtggtaa ggaaagcggt 780
ctttttgata tgcgagatgt acttgatctc aataatttg 819

<210> SEQ ID NO 171
<211> LENGTH: 1218
<212> TYPE: DNA
<213> ORGANISM: E. coli
<220> FEATURE:
<223> OTHER INFORMATION: dapC

<400> SEQUENCE: 171
atggcaattg aacaaacagc aattacacgc gcgactttcg atgaagtgat cctgccgatt 60
tatgctccgg cagagtttat tccggtaaaa ggtcagggca gccgaatctg ggatcagcaa 120
ggcaaggagt atgtcgattt cgcgggtggc attgcagtta cggcgttggg ccattgccat 180
cctgcgctgg tgaacgcgtt aaaaacccag ggcgaaactc tgtggcatat cagtaacgtt 240
ttcaccaatg aaccggcgct gcgtcttggg cgtaaactga ttgaggcaac gtttgccgaa 300
cgcgtggtgt ttatgaactc cggcacggaa gctaacgaaa ccgcctttaa actggcacgc 360
cattacgcct gtgtgcgtca tagcccgttc aaaaccaaaa ttattgcctt ccataacgct 420
tttcatggtc gctcgctgtt taccgtttcg gtgggtggcc agccaaaata ttccgacggc 480
tttgggccga aaccggcaga catcatccac gttcccttta acgatctcca tgcagtgaaa 540
gcggtgatgg atgatcacac ctgtgcggtg gtggttgagc cgatccaggg cgagggcggt 600
gtgacggcag cgacgccaga gtttttgcag ggcttgcgcg agctgtgcga tcaacatcag 660
gcattattgg tgtttgatga agtgcagtgc gggatggggc ggaccggcga tttgtttgct 720
tacatgcact acgcgttagc gccggatatt ctgacctctg cgaaagcgtt aggcggcggc 780
ttcccgatta gcgccatgct gaccacggcg gaaattgctt ctgcgtttca tcctggttct 840
cacggttcca cctacggcgg taatcctctg gcctgtgcag tagcgggggc ggcgtttgat 900
atcatcaata cccctgaagt gctggaaggc attcaggcga aacgccagcg ttttgttgac 960
catctgcaga agatcgatca gcagtacgat gtatttagcg atattcgcgg tatggggctg 1020
ttgattggcg cagagctgaa accacagtac aaaggtcggg cgcgtgattt cctgtatgcg 1080
ggcgcagagg ctggcgtaat ggtgctgaat gccggaccgg atgtgatgcg ttttgcaccg 1140
tcgctggtgg tggaagatgc ggatatcgat gaagggatgc aacgtttcgc ccacgcggtg 1200
gcgaaggtgg ttggggcg 1218

<210> SEQ ID NO 172
<211> LENGTH: 822
<212> TYPE: DNA
<213> ORGANISM: E. coli
<220> FEATURE:
<223> OTHER INFORMATION: dapD

<400> SEQUENCE: 172
atgcagcagt tacagaacat tattgaaacc gcttttgaac gccgtgccga gatcacgcca 60
gccaatgcag acaccgttac ccgcgaagcg gataatcagg tgatcgccct gctggattcc 120
ggcgcactgc gtgtagcgga aaaaattgac ggtcagtggg tgacgcatca gtggttgaaa 180
aaagcggtgc tgctctcttt ccgtattaat gataatcagg tgatcgaagg ggcagaaagc 240

```
cgctacttcg acaaagtgcc gatgaaattc gccgactacg acgaagcacg tttccagaaa    300

gaaggcttcc gcgttgtgcc accagcggcg gtacgtcagg gtgcgtttat tgcccgtaac    360

accgtgctga tgccgtctta cgtcaacatc ggcgcatatg ttgatgaagg caccatggtt    420

gatacctggg cgaccgtcgg ttcttgtgcg cagattggta aaaacgttca cctttccggt    480

ggcgtgcgca tcggcggcgt gctggaaccg ctgcaggcta acccaaccat gattgaagat    540

aattgcttca tcggcgcgcg ctctgaactg gttgaagggg tgattgtcga agaaggttcc    600

gtcatttcca tgggcgtata cattggtcag agcacccgta tttacgaccg tgaaaccggc    660

gaaatccact acggtcgcgt tccggcgggg tctgtggttg tttcaggtaa tctgccgtca    720

aaagatggca aatacagcct ctactgtgcg gttatcgtta agaaagttga cgcgaaaact    780

cgcggcaaag tcggcattaa cgaactgctg cgtaccatcg ac                       822
```

```
<210> SEQ ID NO 173
<211> LENGTH: 1125
<212> TYPE: DNA
<213> ORGANISM: E. coli
<220> FEATURE:
<223> OTHER INFORMATION: dapE

<400> SEQUENCE: 173

atgtcgtgcc cggttattga gctgacacaa cagcttattc gccgcccttc cctgagtcct     60

gatgatgcag gatgccaggc tttgttgatt gaacgtttgc aggcgatcgg ttttaccgtt    120

gaacgcatgg actttgccga tacgcagaat ttttgggcat ggcgtgggca gggtgaaacg    180

ttagcctttg ccgggcatac cgacgtggtg ccgcctggcg acgccgatcg ttggatcaat    240

cccccgtttg aacccaccat tcgtgacggc atgttattcg ggcgcggtgc ggcagatatg    300

aaaggctcgc tggcggcgat ggtggtggcg gcagaacgtt ttgtcgcaca acatcccaac    360

catacggggc gactggcatt tctgatcacc tctgatgaag aagccagtgc ccacaacggt    420

acggtaaaag tcgtcgaagc gttaatggca cgtaatgagc gtctcgatta ctgcctggtt    480

ggcgaaccgt cgagtatcga agtggtaggt gatgtggtga aaaatggtcg tcgcggatca    540

ttaacctgca accttaccat tcatggcgtt caggggcatg ttgcctaccc acatctggct    600

gacaatccgg tacatcgcgc agcacctttc cttaatgaat tagtggctat tgagtgggat    660

cagggcaatg aattcttccc ggcgaccagt atgcagattg ccaatattca ggcgggaacg    720

ggcagtaaca acgttattcc gggtgaactg tttgtgcagt ttaacttccg cttcagcacc    780

gaactgactg atgagatgat caaagcgcag gtgcttgccc tgcttgaaaa acatcaactg    840

cgctatacgg tggattggtg gctttccggg cagccatttt tgaccgcgcg cggtaaactg    900

gtggatgcgg tcgttaacgc ggttgagcac tataatgaaa ttaaaccgca gctactgacc    960

acaggcggaa cgtccgacgg gcgctttatt gcccgcatgg gggcgcaggt ggtggaactc   1020

gggccggtca atgccactat tcataaaatt aatgaatgtg tgaacgctgc cgacctgcag   1080

ctacttgccc gtatgtatca acgtatcatg gaacagctcg tcgcc                   1125
```

```
<210> SEQ ID NO 174
<211> LENGTH: 1179
<212> TYPE: DNA
<213> ORGANISM: Homo sapiens
<220> FEATURE:
<223> OTHER INFORMATION: p53

<400> SEQUENCE: 174

atggaggagc cgcagtcaga tcctagcgtc gagccccctc tgagtcagga aacattttca     60
```

```
gacctatgga aactacttcc tgaaaacaac gttctgtccc ccttgccgtc ccaagcaatg    120
gatgatttga tgctgtcccc ggacgatatt gaacaatggt tcactgaaga cccaggtcca    180
gatgaagctc ccagaatgcc agaggctgct ccccgcgtgg cccctgcacc agcagctcct    240
acaccggcgg cccctgcacc agccccctcc tggcccctgt catcttctgt cccttcccag    300
aaaacctacc agggcagcta cggtttccgt ctgggcttct tgcattctgg gacagccaag    360
tctgtgactt gcacgtactc ccctgccctc aacaagatgt tttgccaact ggccaagacc    420
tgccctgtgc agctgtgggt tgattccaca cccccgcccg gcacccgcgt ccgcgccatg    480
gccatctaca agcagtcaca gcacatgacg gaggttgtga ggcgctgccc ccaccatgag    540
cgctgctcag atagcgatgg tctggcccct cctcagcatc ttatccgagt ggaaggaaat    600
ttgcgtgtgg agtatttgga tgacagaaac acttttcgac atagtgtggt ggtgccctat    660
gagccgcctg aggttggctc tgactgtacc accatccact acaactacat gtgtaacagt    720
tcctgcatgg gcggcatgaa ccggaggccc atcctcacca tcatcacact ggaagactcc    780
agtggtaatc tactgggacg gaacagcttt gaggtgcatg tttgtgcctg tcctgggaga    840
gaccggcgca cagaggaaga gaatctccgc aagaaagggg agcctcacca cgagctgccc    900
ccagggagca ctaagcgagc actgtccaac aacaccagct cctctcccca gccaaagaag    960
aaaccactgg atggagaata tttcaccctt cagatccgtg ggcgtgagcg cttcgagatg   1020
ttccgagagc tgaatgaggc cttggaactc aaggatgccc aggctgggaa ggagccaggg   1080
gggagcaggg ctcactccag ccacctgaag tccaaaaagg gtcagtctac ctcccgccat   1140
aaaaaactca tgttcaagac agaagggcct gactcagac                          1179
```

<210> SEQ ID NO 175
<211> LENGTH: 1470
<212> TYPE: DNA
<213> ORGANISM: Homo sapiens
<220> FEATURE:
<223> OTHER INFORMATION: ERBA

<400> SEQUENCE: 175

```
atggaacaga agccaagcaa ggtggagtgt gggtcagacc cagaggagaa cagtgccagg     60
tcaccagatg gaaagcgaaa aagaaagaac ggccaatgtt ccctgaaaac cagcatgtca    120
gggtatatcc ctagttacct ggacaaagac gagcagtgtg tcgtgtgtgg ggacaaggca    180
actggttatc actaccgctg tatcacttgt gagggctgca agggcttctt tcgccgcaca    240
atccagaaga acctccatcc cacctattcc tgcaaatatg acagctgctg tgtcattgac    300
aagatcaccc gcaatcagtg ccagctgtgc cgcttcaaga agtgcatcgc cgtgggcatg    360
gccatggact tggttctaga tgactcgaag cgggtggcca agcgtaagct gattgagcag    420
aaccgggagc ggcggcggaa ggaggagatg atccgatcac tgcagcagcg accagagccc    480
actcctgaag agtgggatct gatccacatt gccacagagg cccatcgcag caccaatgcc    540
cagggcagcc attggaaaca gaggcggaaa ttcctgcccg atgacattgg ccagtcaccc    600
attgtctcca tgccggacgg agacaaggtg gacctggaag ccttcagcga gtttaccaag    660
atcatcaccc cggccatcac ccgtgtggtg gactttgcca aaaaactgcc catgttctcc    720
gagctgcctt gcgaagacca gatcatcctc ctgaaggggt gctgcatgga gatcatgtcc    780
ctgcgggcgg ctgtccgcta cgaccctgag agcgacaccc tgacgctgag tggggagatg    840
gctgtcaagc gggagcagct caagaatggc ggcctgggcg tagtctccga cgccatcttt    900
```

-continued

```
gaactgggca agtcactctc tgcctttaac ctggatgaca cggaagtggc tctgctgcag    960

gctgtgctgc taatgtcaac agaccgctcg ggcctgctgt gtgtggacaa gatcgagaag   1020

agtcaggagg cgtacctgct ggcgttcgag cactacgtca accaccgcaa acacaacatt   1080

ccgcacttct ggcccaagct gctgatgaag gagagagaag tgcagagttc gattctgtac   1140

aagggggcag cggcagaagg ccggccgggc gggtcactgg gcgtccaccc ggaaggacag   1200

cagcttctcg gaatgcatgt tgttcagggt ccgcaggtcc ggcagcttga gcagcagctt   1260

ggtgaagcgg gaagtctcca agggccggtt cttcagcacc agagcccgaa gagcccgcag   1320

cagcgtctcc tggagctgct ccaccgaagc ggaattctcc atgcccgagc ggtctgtggg   1380

gaagacgaca gcagtgaggc ggactccccg agctcctctg aggaggaacc ggaggtctgc   1440

gaggacctgg caggcaatgc agcctctccc                                    1470
```

<210> SEQ ID NO 176
<211> LENGTH: 1317
<212> TYPE: DNA
<213> ORGANISM: Homo sapiens
<220> FEATURE:
<223> OTHER INFORMATION: myc

<400> SEQUENCE: 176

```
atgcccctca acgttagctt caccaacagg aactatgacc tcgactacga ctcggtgcag     60

ccgtatttct actgcgacga ggaggagaac ttctaccagc agcagcagca gagcgagctg    120

cagcccccgg cgcccagcga ggatatctgg aagaaattcg agctgctgcc caccccgccc    180

ctgtccccta gccgccgctc cgggctctgc tcgccctcct acgttgcggt cacacccttc    240

tcccttcggg gagacaacga cggcggtggc gggagcttct ccacggccga ccagctggag    300

atggtgaccg agctgctggg aggagacatg gtgaaccaga gtttcatctg cgacccggac    360

gacgagacct tcatcaaaaa catcatcatc caggactgta tgtggagcgg cttctcggcc    420

gccgccaagc tcgtctcaga gaagctggcc tcctaccagg ctgcgcgcaa agacagcggc    480

agcccgaacc ccgcccgcgg ccacagcgtc tgctccacct ccagcttgta cctgcaggat    540

ctgagcgccg ccgcctcaga gtgcatcgac ccctcggtgg tcttccccta ccctctcaac    600

gacagcagct cgcccaagtc ctgcgcctcg caagactcca gcgccttctc tccgtcctcg    660

gattctctgc tctcctcgac ggagtcctcc ccgcagggca gccccgagcc cctggtgctc    720

catgaggaga caccgcccac caccagcagc gactctgagg aggaacaaga agatgaggaa    780

gaaatcgatg ttgtttctgt ggaaaagagg caggctcctg gcaaaaggtc agagtctgga    840

tcaccttctg ctggaggcca cagcaaacct cctcacagcc cactggtcct caagaggtgc    900

cacgtctcca cacatcagca caactacgca gcgcctccct ccactcggaa ggactatcct    960

gctgccaaga gggtcaagtt ggacagtgtc agagtcctga gacagatcag caacaaccga   1020

aaatgcacca gccccaggtc ctcggacacc gaggagaatg tcaagaggcg aacacacaac   1080

gtcttggagc gccagaggag gaacgagcta aaacggagct tttttgccct gcgtgaccag   1140

atcccggagt tggaaaacaa tgaaaaggcc cccaaggtag ttatccttaa aaaagccaca   1200

gcatacatcc tgtccgtcca agcagaggag caaaagctca tttctgaaga ggacttgttg   1260

cggaaacgac gagaacagtt gaaacacaaa cttgaacagc tacggaactc ttgtgcg      1317
```

<210> SEQ ID NO 177
<211> LENGTH: 2283
<212> TYPE: DNA
<213> ORGANISM: Homo sapiens -continued

<220> FEATURE:
<223> OTHER INFORMATION: MYB

<400> SEQUENCE: 177

```
atggcccgaa gaccccggca cagcatatat agcagtgacg aggatgatga ggactttgag     60
atgtgtgacc atgactatga tgggctgctt cccaagtctg gaaagcgtca cttggggaaa    120
acaaggtgga cccgggaaga ggatgaaaaa ctgaagaagc tggtggaaca gaatggaaca    180
gatgactgga aagttattgc caattatctc ccgaatcgaa cagatgtgca gtgccagcac    240
cgatggcaga aagtactaaa ccctgagctc atcaagggtc cttggaccaa agaagaagat    300
cagagagtga tagagcttgt acagaaatac ggtccgaaac gttggtctgt tattgccaag    360
cacttaaagg ggagaattgg aaaacaatgt agggagaggt ggcataacca cttgaatcca    420
gaagttaaga aaacctcctg gacagaagag gaagacagaa ttatttacca ggcacacaag    480
agactgggga acagatgggc agaaatcgca aagctactgc ctggacgaac tgataatgct    540
atcaagaacc actggaattc tacaatgcgt cggaaggtcg aacaggaagg ttatctgcag    600
gagtcttcaa aagccagcca gccagcagtg gccacaagct tccagaagaa cagtcatttg    660
atgggttttg ctcaggctcc gcctacagct caactccctg ccactggcca gcccactgtt    720
aacaacgact attcctatta ccacatttct gaagcacaaa atgtctccag tcatgttcca    780
taccctgtag cgttacatgt aaatatagtc aatgtccctc agccagctgc cgcagccatt    840
cagagacact ataatgatga agaccctgag aaggaaaagc gaataaagga attagaattg    900
ctcctaatgt caaccgagaa tgagctaaaa ggacagcagg tgctaccaac acagaaccac    960
acatgcagct accccgggtg gcacagcacc accattgccg accacaccag acctcatgga   1020
gacagtgcac ctgtttcctg tttgggagaa caccactcca ctccatctct gccagcggat   1080
cctggctccc tacctgaaga aagcgcctcg ccagcaaggt gcatgatcgt ccaccagggc   1140
accattctgg ataatgttaa gaacctctta gaatttgcag aaacactcca atttatagat   1200
tctgattctt catcatggtg tgatctcagc agttttgaat tctttgaaga agcagatttt   1260
tcacctagcc aacatcacac aggcaaagcc ctacagcttc agcaaagaga gggcaatggg   1320
actaaacctg caggagaacc tagcccaagg gtgaacaaac gtatgttgag tgagagttca   1380
cttgacccac ccaaggtctt acctcctgca aggcacagca caattccact ggtcatcctt   1440
cgaaaaaaac ggggccaggc cagcccctta gccactggag actgtagctc cttcatattt   1500
gctgacgtca gcagttcaac tcccaagcgt tcccctgtca aaagcctacc cttctctccc   1560
tcgcagttct taaacacttc cagtaaccat gaaaactcag acttggaaat gccttcttta   1620
acttccaccc ccctcattgg tcacaaattg actgttacaa caccatttca tagagaccag   1680
actgtgaaaa ctcaaaagga aaatactgtt tttagaaccc cagctatcaa aaggtcaatc   1740
ttagaaagct ctccaagaac tcctacacca ttcaaacatg cacttgcagc tcaagaaatt   1800
aaatacggtc ccctgaagat gctacctcag acaccctctc atctagtaga agatctgcag   1860
gatgtgatca aacaggaatc tgatgaatct ggaattgttg ctgagtttca agaaaatgga   1920
ccacccttac tgaagaaaat caaacaagag gtggaatctc caactgataa atcaggaaac   1980
ttcttctgct cacaccactg ggaaggggac agtctgaata cccaactgtt cacgcagacc   2040
tcgcctgtgg cagatgcacc gaatattctt acaagctccg ttttaatggc accagcatca   2100
gaagatgaag acaatgttct caaagcattt acagtaccta aaaacaggtc cctggcgagc   2160
cccttgcagc cttgtagcag tacctgggaa cctgcatcct gtggaaagat ggaggagcag   2220
```

atgacatctt ccagtcaagc tcgtaaatac gtgaatgcat tctcagcccg gacgctggtc 2280
atg 2283

<210> SEQ ID NO 178
<211> LENGTH: 993
<212> TYPE: DNA
<213> ORGANISM: Homo sapiens
<220> FEATURE:
<223> OTHER INFORMATION: JUN

<400> SEQUENCE: 178
atgactgcaa agatggaaac gaccttctat gacgatgccc tcaacgcctc gttcctcccg 60
tccgagagcg gaccttatgg ctacagtaac cccaagatcc tgaaacagag catgaccctg 120
aacctggccg acccagtggg gagcctgaag ccgcacctcc gcgccaagaa ctcggacctc 180
ctcacctcgc ccgacgtggg gctgctcaag ctggcgtcgc ccgagctgga gcgcctgata 240
atccagtcca gcaacgggca catcaccacc acgccgaccc ccacccagtt cctgtgcccc 300
aagaacgtga cagatgagca ggagggcttc gccgagggct tcgtgcgcgc cctggccgaa 360
ctgcacagcc agaacacgct gcccagcgtc acgtcggcgg cgcagccggt caacggggca 420
ggcatggtgg ctcccgcggt agcctcggtg gcagggggca gcggcagcgg cggcttcagc 480
gccagcctgc acagcgagcc gccggtctac gcaaacctca gcaacttcaa cccaggcgcg 540
ctgagcagcg gcggcggggc gccctcctac ggcgcggccg gcctggcctt tcccgcgcaa 600
ccccagcagc agcagcagcc gccgcaccac ctgccccagc agatgcccgt gcagcacccg 660
cggctgcagg ccctgaagga ggagcctcag acagtgcccg agatgcccgg cgagacaccg 720
cccctgtccc ccatcgacat ggagtcccag gagcggatca aggcggagag gaagcgcatg 780
aggaaccgca tcgctgcctc caagtgccga aaaaggaagc tggagagaat cgcccggctg 840
gaggaaaaag tgaaaacctt gaaagctcag aactcggagc tggcgtccac ggccaacatg 900
ctcagggaac aggtggcaca gcttaaacag aaagtcatga accacgttaa cagtgggtgc 960
caactcatgc taacgcagca gttgcaaaca ttt 993

<210> SEQ ID NO 179
<211> LENGTH: 3633
<212> TYPE: DNA
<213> ORGANISM: Homo sapiens
<220> FEATURE:
<223> OTHER INFORMATION: ERBB

<400> SEQUENCE: 179
atgcgaccct ccgggacggc cggggcagcg ctcctggcgc tgctggctgc gctctgcccg 60
gcgagtcggg ctctggagga aaagaaagtt tgccaaggca cgagtaacaa gctcacgcag 120
ttgggcactt ttgaagatca ttttctcagc ctccagagga tgttcaataa ctgtgaggtg 180
gtccttggga atttggaaat tacctatgtg cagaggaatt atgatctttc cttcttaaag 240
accatccagg aggtggctgg ttatgtcctc attgccctca acacagtgga gcgaattcct 300
ttggaaaacc tgcagatcat cagaggaaat atgtactacg aaaattccta tgccttagca 360
gtcttatcta actatgatgc aaataaaacc ggactgaagg agctgcccat gagaaattta 420
caggaaatcc tgcatggcgc cgtgcggttc agcaacaacc ctgccctgtg caacgtggag 480
agcatccagt ggcgggacat agtcagcagt gactttctca gcaacatgtc gatggacttc 540
cagaaccacc tgggcagctg ccaaaagtgt gatccaagct gtcccaatgg gagctgctgg 600
ggtgcaggag aggagaactg ccagaaactg accaaaatca tctgtgccca gcagtgctcc 660

```
gggcgctgcc gtggcaagtc ccccagtgac tgctgccaca accagtgtgc tgcaggctgc    720
acaggccccc gggagagcga ctgcctggtc tgccgcaaat tccgagacga agccacgtgc    780
aaggacacct gccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag ggtgactcc    1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaac   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
tgcctcacct ccaccgtgca gctcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgactg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag acccccagcg ctaccttgtc   2940
attcaggggg atgaaagaat gcatttgcca agtcctacag actccaactt ctaccgtgcc   3000
```

-continued

```
ctgatggatg aagaagacat ggacgacgtg gtggatgccg acgagtacct catcccacag   3060

cagggcttct tcagcagccc ctccacgtca cggactcccc tcctgagctc tctgagtgca   3120

accagcaaca attccaccgt ggcttgcatt gatagaaatg ggctgcaaag ctgtcccatc   3180

aaggaagaca gcttcttgca gcgatacagc tcagacccca caggcgcctt gactgaggac   3240

agcatagacg acaccttcct cccagtgcct gaatacataa accagtccgt tcccaaaagg   3300

cccgctggct ctgtgcagaa tcctgtctat cacaatcagc ctctgaaccc cgcgcccagc   3360

agagacccac actaccagga cccccacagc actgcagtgg gcaaccccga gtatctcaac   3420

actgtccagc ccacctgtgt caacagcaca ttcgacagcc ctgcccactg ggcccagaaa   3480

ggcagccacc aaattagcct ggacaaccct gactaccagc aggacttctt tcccaaggaa   3540

gccaagccaa atggcatctt taagggctcc acagctgaaa atgcagaata cctaagggtc   3600

gcgccacaaa gcagtgaatt tattggagca tga                                3633
```

<210> SEQ ID NO 180
<211> LENGTH: 5589
<212> TYPE: DNA
<213> ORGANISM: Homo sapiens
<220> FEATURE:
<223> OTHER INFORMATION: BRCA1

<400> SEQUENCE: 180

```
atggatttat ctgctcttcg cgttgaagaa gtacaaaatg tcattaatgc tatgcagaaa     60

atcttagagt gtcccatctg tctggagttg atcaaggaac ctgtctccac aaagtgtgac    120

cacatatttt gcaaattttg catgctgaaa cttctcaacc agaagaaagg gccttcacag    180

tgtcctttat gtaagaatga tataaccaaa aggagcctac aagaaagtac gagatttagt    240

caacttgttg aagagctatt gaaaatcatt tgtgcttttc agcttgacac aggtttggag    300

tatgcaaaca gctataattt tgcaaaaaag gaaaataact ctcctgaaca tctaaaagat    360

gaagtttcta tcatccaaag tatgggctac agaaaccgtg ccaaaagact tctacagagt    420

gaacccgaaa atccttcctt gcaggaaacc agtctcagtg tccaactctc taaccttgga    480

actgtgagaa ctctgaggac aaagcagcgg atacaacctc aaaagacgtc tgtctacatt    540

gaattgggat ctgattcttc tgaagatacc gttaataagg caacttattg cagtgtggga    600

gatcaagaat tgttacaaat cacccctcaa ggaaccaggg atgaaatcag tttggattct    660

gcaaaaaagg ctgcttgtga attttctgag acggatgtaa caaatactga acatcatcaa    720

cccagtaata atgatttgaa caccactgag aagcgtgcag ctgagaggca tccagaaaag    780

tatcagggta gttctgtttc aaacttgcat gtggagccat gtggcacaaa tactcatgcc    840

agctcattac agcatgagaa cagcagttta ttactcacta aagacagaat gaatgtagaa    900

aaggctgaat tctgtaataa aagcaaacag cctggcttag caaggagcca acataacaga    960

tgggctggaa gtaaggaaac atgtaatgat aggcggactc ccagcacaga aaaaaaggta   1020

gatctgaatg ctgatcccct gtgtgagaga aaagaatgga ataagcagaa actgccatgc   1080

tcagagaatc ctagagatac tgaagatgtt ccttggataa cactaaatag cagcattcag   1140

aaagttaatg agtggttttc cagaagtgat gaactgttag gttctgatga ctcacatgat   1200

ggggagtctg aatcaaatgc caaagtagct gatgtattgg acgttctaaa tgaggtagat   1260

gaatattctg gttcttcaga gaaaatagac ttactggcca gtgatcctca tgaggcttta   1320

atatgtaaaa gtgaaagagt tcactccaaa tcagtagaga gtaatattga agacaaaata   1380

tttgggaaaa cctatcggaa gaaggcaagc ctccccaact taagccatgt aactgaaaat   1440
```

ctaattatag gagcatttgt tactgagcca cagataatac aagagcgtcc cctcacaaat 1500
aaattaaagc gtaaaaggag acctacatca ggccttcatc ctgaggattt tatcaagaaa 1560
gcagatttgg cagttcaaaa gactcctgaa atgataaatc agggaactaa ccaaacggag 1620
cagaatggtc aagtgatgaa tattactaat agtggtcatg agaataaaac aaaaggtgat 1680
tctattcaga atgagaaaaa tcctaaccca atagaatcac tcgaaaaaga atctgctttc 1740
aaaacgaaag ctgaacctat aagcagcagt ataagcaata tggaactcga attaaatatc 1800
cacaattcaa aagcacctaa aaagaatagg ctgaggagga agtcttctac caggcatatt 1860
catgcgcttg aactagtagt cagtagaaat ctaagcccac ctaattgtac tgaattgcaa 1920
attgatagtt gttctagcag tgaagagata aagaaaaaaa agtacaacca aatgccagtc 1980
aggcacagca gaaacctaca actcatggaa ggtaaagaac ctgcaactgg agccaagaag 2040
agtaacaagc caaatgaaca gacaagtaaa agacatgaca gcgatacttt cccagagctg 2100
aagttaacaa atgcacctgg ttcttttact aagtgttcaa ataccagtga acttaaagaa 2160
tttgtcaatc ctagccttcc aagagaagaa aaagaagaga aactagaaac agttaaagtg 2220
tctaataatg ctgaagaccc caaagatctc atgttaagtg gagaaagggt tttgcaaact 2280
gaaagatctg tagagagtag cagtatttca ttggtacctg gtactgatta tggcactcag 2340
gaaagtatct cgttactgga agttagcact ctagggaagg caaaaacaga accaaataaa 2400
tgtgtgagtc agtgtgcagc atttgaaaac cccaagggac taattcatgg ttgttccaaa 2460
gataatagaa atgacacaga aggctttaag tatccattgg gacatgaagt taaccacagt 2520
cgggaaacaa gcatagaaat ggaagaaagt gaacttgatg ctcagtattt gcagaataca 2580
ttcaaggttt caaagcgcca gtcatttgct ccgttttcaa atccaggaaa tgcagaagag 2640
gaatgtgcaa cattctctgc ccactctggg tccttaaaga aacaaagtcc aaaagtcact 2700
tttgaatgtg aacaaaagga agaaaatcaa ggaaagaatg agtctaatat caagcctgta 2760
cagacagtta atatcactgc aggctttcct gtggttggtc agaaagataa gccagttgat 2820
aatgccaaat gtagtatcaa aggaggctct aggttttgtc tatcatctca gttcagaggc 2880
aacgaaactg gactcattac tccaaataaa catggacttt tacaaaaccc atatcgtata 2940
ccaccacttt ttcccatcaa gtcatttgtt aaaactaaat gtaagaaaaa tctgctagag 3000
gaaaactttg aggaacattc aatgtcacct gaaagagaaa tgggaaatga gaacattcca 3060
agtacagtga gcacaattag ccgtaataac attagagaaa atgtttttaa agaagccagc 3120
tcaagcaata ttaatgaagt aggttccagt actaatgaag tgggctccag tattaatgaa 3180
ataggttcca gtgatgaaaa cattcaagca gaactaggta gaaacagagg gccaaaattg 3240
aatgctatgc ttagattagg ggttttgcaa cctgaggtct ataaacaaag tcttcctgga 3300
agtaattgta agcatcctga aataaaaaag caagaatatg aagaagtagt tcagactgtt 3360
aatacagatt tctctccata tctgatttca gataacttag aacagcctat gggaagtagt 3420
catgcatctc aggtttgttc tgagacacct gatgacctgt tagatgatgg tgaaataaag 3480
gaagatacta gttttgctga aaatgacatt aaggaaagtt ctgctgtttt tagcaaaagc 3540
gtccagaaag gagagcttag caggagtcct agccctttca cccatacaca tttggctcag 3600
ggttaccgaa gaggggccaa gaaattagag tcctcagaag agaacttatc tagtgaggat 3660
gaagagcttc cctgcttcca acacttgtta tttggtaaag taaacaatat accttctcag 3720
tctactaggc atagcaccgt tgctaccgag tgtctgtcta agaacacaga ggagaattta 3780

```
ttatcattga agaatagctt aaatgactgc agtaaccagg taatattggc aaaggcatct   3840
caggaacatc accttagtga ggaaacaaaa tgttctgcta gcttgttttc ttcacagtgc   3900
agtgaattgg aagacttgac tgcaaataca aacacccagg atcctttctt gattggttct   3960
tccaaacaaa tgaggcatca gtctgaaagc cagggagttg gtctgagtga caaggaattg   4020
gtttcagatg atgaagaaag aggaacgggc ttggaagaaa ataatcaaga agagcaaagc   4080
atggattcaa acttaggtga agcagcatct gggtgtgaga gtgaaacaag cgtctctgaa   4140
gactgctcag ggctatcctc tcagagtgac attttaacca ctcagcagag ggataccatg   4200
caacataacc tgataaagct ccagcaggaa atggctgaac tagaagctgt gttagaacag   4260
catgggagcc agccttctaa cagctaccct tccatcataa gtgactcttc tgcccttgag   4320
gacctgcgaa atccagaaca aagcacatca gaaaaagcag tattaacttc acagaaaagt   4380
agtgaatacc ctataagcca gaatccagaa ggcctttctg ctgacaagtt tgaggtgtct   4440
gcagatagtt ctaccagtaa aaataaagaa ccaggagtgg aaaggtcatc cccttctaaa   4500
tgcccatcat tagatgatag gtggtacatg cacagttgct ctgggagtct tcagaataga   4560
aactacccat ctcaagagga gctcattaag gttgttgatg tggaggagca acagctggaa   4620
gagtctgggc cacacgattt gacggaaaca tcttacttgc caaggcaaga tctagaggga   4680
accccttacc tggaatctgg aatcagcctc ttctctgatg accctgaatc tgatccttct   4740
gaagacagag ccccagagtc agctcgtgtt ggcaacatac catcttcaac ctctgcattg   4800
aaagttcccc aattgaaagt tgcagaatct gcccagagtc cagctgctgc tcatactact   4860
gatactgctg ggtataatgc aatggaagaa agtgtgagca gggagaagcc agaattgaca   4920
gcttcaacag aaagggtcaa caaaagaatg tccatggtgg tgtctggcct gaccccagaa   4980
gaatttatgc tcgtgtacaa gtttgccaga aaacaccaca tcactttaac taatctaatt   5040
actgaagaga ctactcatgt tgttatgaaa acagatgctg agtttgtgtg tgaacggaca   5100
ctgaaatatt ttctaggaat tgcgggagga aaatgggtag ttagctattt ctgggtgacc   5160
cagtctatta aagaaagaaa aatgctgaat gagcatgatt ttgaagtcag aggagatgtg   5220
gtcaatggaa gaaaccacca aggtccaaag cgagcaagag aatcccagga cagaaagatc   5280
ttcagggggc tagaaatctg ttgctatggg cccttcacca acatgcccac agatcaactg   5340
gaatggatgg tacagctgtg tggtgcttct gtggtgaagg agctttcatc attcaccctt   5400
ggcacaggtg tccacccaat tgtggttgtg cagccagatg cctggacaga ggacaatggc   5460
ttccatgcaa ttgggcagat gtgtgaggca cctgtggtga cccgagagtg ggtgttggac   5520
agtgtagcac tctaccagtg ccaggagctg gacacctacc tgataccccca gatcccccac   5580
agccactac                                                           5589
```

<210> SEQ ID NO 181
<211> LENGTH: 10254
<212> TYPE: DNA
<213> ORGANISM: Homo sapiens
<220> FEATURE:
<223> OTHER INFORMATION: BRCA2

<400> SEQUENCE: 181

```
atgcctattg gatccaaaga gaggccaaca ttttttgaaa tttttaagac acgctgcaac     60
aaagcagatt taggaccaat aagtcttaat tggtttgaag aactttcttc agaagctcca    120
ccctataatt ctgaacctgc agaagaatct gaacataaaa acaacaatta cgaaccaaac    180
ctatttaaaa ctccacaaag gaaaccatct tataatcagc tggcttcaac tccaataata    240
```

-continued

```
ttcaaagagc aagggctgac tctgccgctg taccaatctc ctgtaaaaga attagataaa    300
ttcaaattag acttaggaag gaatgttccc aatagtagac ataaaagtct tcgcacagtg    360
aaaactaaaa tggatcaagc agatgatgtt tcctgtccac ttctaaattc ttgtcttagt    420
gaaagtcctg ttgttctaca atgtacacat gtaacaccac aaagagataa gtcagtggta    480
tgtgggagtt tgtttcatac accaaagttt gtgaagggtc gtcagacacc aaaacatatt    540
tctgaaagtc taggagctga ggtggatcct gatatgtctt ggtcaagttc tttagctaca    600
ccacccaccc ttagttctac tgtgctcata gtcagaaatg aagaagcatc tgaaactgta    660
tttcctcatg atactactgc taatgtgaaa agctattttt ccaatcatga tgaaagtctg    720
aagaaaaatg atagatttat cgcttctgtg acagacagtg aaaacacaaa tcaaagagaa    780
gctgcaagtc atggatttgg aaaaacatca gggaattcat ttaaagtaaa tagctgcaaa    840
gaccacattg gaaagtcaat gccaaatgtc ctagaagatg aagtatatga aacagttgta    900
gatacctctg aagaagatag tttttcatta tgtttttcta aatgtagaac aaaaaatcta    960
caaaaagtaa gaactagcaa gactaggaaa aaaattttcc atgaagcaaa cgctgatgaa   1020
tgtgaaaaat ctaaaaacca agtgaaagaa aaatactcat ttgtatctga agtggaacca   1080
aatgatactg atccattaga ttcaaatgta gcaaatcaga agccctttga gagtggaagt   1140
gacaaaatct ccaaggaagt tgtaccgtct ttggcctgtg aatggtctca actaaccctt   1200
tcaggtctaa atggagccca gatggagaaa ataccctat tgcatatttc ttcatgtgac   1260
caaaatattt cagaaaaaga cctattagac acagagaaca aaagaaagaa agattttctt   1320
acttcagaga attctttgcc acgtatttct agcctaccaa aatcagagaa gccattaaat   1380
gaggaaacag tggtaaataa gagagatgaa gagcagcatc ttgaatctca tacagactgc   1440
attcttgcag taaagcaggc aatatctgga acttctccag tggcttcttc atttcagggt   1500
atcaaaaagt ctatattcag aataagagaa tcacctaaag agactttcaa tgcaagtttt   1560
tcaggtcata tgactgatcc aaactttaaa aaagaaactg aagcctctga aagtggactg   1620
gaaatacata ctgtttgctc acagaaggag gactccttat gtccaaattt aattgataat   1680
ggaagctggc cagccaccac cacacagaat tctgtagctt tgaagaatgc aggtttaata   1740
tccactttga aaaagaaaac aaataagttt atttatgcta tacatgatga aacatcttat   1800
aaaggaaaaa aaataccgaa agaccaaaaa tcagaactaa ttaactgttc agcccagttt   1860
gaagcaaatg cttttgaagc accacttaca tttgcaaatg ctgattcagg tttattgcat   1920
tcttctgtga aaagaagctg ttcacagaat gattctgaag aaccaacttt gtccttaact   1980
agctcttttg ggacaattct gaggaaatgt tctagaaatg aaacatgttc taataataca   2040
gtaatctctc aggatcttga ttataaagaa gcaaaatgta ataaggaaaa actacagtta   2100
tttattaccc cagaagctga ttctctgtca tgcctgcagg aaggacagtg tgaaaatgat   2160
ccaaaaagca aaaaagtttc agatataaaa gaagaggtct tggctgcagc atgtcaccca   2220
gtacaacatt caaaagtgga atacagtgat actgactttc aatcccagaa aagtctttta   2280
tatgatcatg aaaatgccag cactcttatt ttaactccta cttccaagga tgttctgtca   2340
aacctagtca tgatttctag aggcaaagaa tcatacaaaa tgtcagacaa gctcaaaggt   2400
aacaattatg aatctgatgt tgaattaacc aaaaatattc ccatggaaaa gaatcaagat   2460
gtatgtgctt taaatgaaaa ttataaaaac gttgagctgt tgccacctga aaaatacatg   2520
agagtagcat caccttcaag aaaggtacaa ttcaaccaaa acacaaatct aagagtaatc   2580
```

-continued

```
caaaaaaatc aagaagaaac tacttcaatt tcaaaaataa ctgtcaatcc agactctgaa   2640
gaacttttct cagacaatga gaataatttt gtcttccaag tagctaatga aaggaataat   2700
cttgctttag gaaatactaa ggaacttcat gaaacagact tgacttgtgt aaacgaaccc   2760
attttcaaga actctaccat ggttttatat ggagacacag gtgataaaca agcaacccaa   2820
gtgtcaatta aaaaagattt ggtttatgtt cttgcagagg agaacaaaaa tagtgtaaag   2880
cagcatataa aaatgactct aggtcaagat ttaaaatcgg acatctcctt gaatatagat   2940
aaaataccag aaaaaaataa tgattacatg aacaaatggg caggactctt aggtccaatt   3000
tcaaatcaca gttttggagg tagcttcaga acagcttcaa ataaggaaat caagctctct   3060
gaacataaca ttaagaagag caaaatgttc ttcaaagata ttgaagaaca atatcctact   3120
agtttagctt gtgttgaaat tgtaaatacc ttggcattag ataatcaaaa gaaactgagc   3180
aagcctcagt caattaatac tgtatctgca catttacaga gtagtgtagt tgtttctgat   3240
tgtaaaaata gtcatataac ccctcagatg ttattttcca agcaggattt taattcaaac   3300
cataatttaa cacctagcca aaaggcagaa attacagaac tttctactat attagaagaa   3360
tcaggaagtc agtttgaatt tactcagttt agaaaaccaa gctacatatt gcagaagagt   3420
acatttgaag tgcctgaaaa ccagatgact atcttaaaga ccacttctga ggaatgcaga   3480
gatgctgatc ttcatgtcat aatgaatgcc ccatcgattg gtcaggtaga cagcagcaag   3540
caatttgaag gtacagttga aattaaacgg aagtttgctg gcctgttgaa aaatgactgt   3600
aacaaaagtg cttctggtta tttaacagat gaaaatgaag tggggtttag ggggctttttat   3660
tctgctcatg gcacaaaact gaatgtttct actgaagctc tgcaaaaagc tgtgaaactg   3720
tttagtgata ttgagaatat tagtgaggaa acttctgcag aggtacatcc aataagttta   3780
tcttcaagta aatgtcatga ttctgttgtt tcaatgttta agatagaaaa tcataatgat   3840
aaaactgtaa gtgaaaaaaa taataaatgc caactgatat tacaaaataa tattgaaatg   3900
actactggca cttttgttga agaaattact gaaaattaca agagaaatac tgaaaatgaa   3960
gataacaaat atactgctgc cagtagaaat tctcataact tagaatttga tggcagtgat   4020
tcaagtaaaa atgatactgt ttgtattcat aaagatgaaa cggacttgct atttactgat   4080
cagcacaaca tatgtcttaa attatctggc cagtttatga aggagggaaa cactcagatt   4140
aaagaagatt tgtcagattt aactttttg gaagttgcga aagctcaaga agcatgtcat   4200
ggtaatactt caaataaaga acagttaact gctactaaaa cggagcaaaa tataaaagat   4260
tttgagactt ctgatacatt ttttcagact gcaagtggga aaaatattag tgtcgccaaa   4320
gagtcattta ataaaattgt aaatttcttt gatcagaaac cagaagaatt gcataacttt   4380
tccttaaatt ctgaattaca ttctgacata agaaagaaca aaatggacat tctaagttat   4440
gaggaaacag acatagttaa acacaaaata ctgaaagaaa gtgtcccagt tggtactgga   4500
aatcaactag tgaccttcca gggacaaccc gaacgtgatg aaaagatcaa agaacctact   4560
ctattgggtt ttcatacagc tagcgggaaa aaagttaaaa ttgcaaagga atctttggac   4620
aaagtgaaaa acctttttga tgaaaaagag caaggtacta gtgaaatcac cagttttagc   4680
catcaatggg caaagaccct aaagtacaga gaggcctgta aagaccttga attagcatgt   4740
gagaccattg agatcacagc tgccccaaag tgtaaagaaa tgcagaattc tctcaataat   4800
gataaaaacc ttgtttctat tgagactgtg gtgccaccta agctcttaag tgataattta   4860
tgtagacaaa ctgaaaatct caaaacatca aaaagtatct tttgaaagt taaagtacat   4920
gaaaatgtag aaaaagaaac agcaaaaagt cctgcaactt gttacacaaa tcagtcccct   4980
```

```
tattcagtca ttgaaaattc agccttagct ttttacacaa gttgtagtag aaaaacttct   5040
gtgagtcaga cttcattact tgaagcaaaa aaatggctta gagaaggaat atttgatggt   5100
caaccagaaa gaataaatac tgcagattat gtaggaaatt atttgtatga aaataattca   5160
aacagtacta tagctgaaaa tgacaaaaat catctctccg aaaaacaaga tacttattta   5220
agtaacagta gcatgtctaa cagctattcc taccattctg atgaggtata taatgattca   5280
ggatatctct caaaaaataa acttgattct ggtattgagc cagtattgaa gaatgttgaa   5340
gatcaaaaaa acactagttt ttccaaagta atatccaatg taaaagatgc aaatgcatac   5400
ccacaaactg taaatgaaga tatttgcgtt gaggaacttg tgactagctc ttcaccctgc   5460
aaaaataaaa atgcagccat taaattgtcc atatctaata gtaataattt tgaggtaggg   5520
ccacctgcat ttaggatagc cagtggtaaa atcgtttgtg tttcacatga aacaattaaa   5580
aaagtgaaag acatatttac agacagtttc agtaaagtaa ttaaggaaaa caacgagaat   5640
aaatcaaaaa tttgccaaac gaaaattatg gcaggttgtt acgaggcatt ggatgattca   5700
gaggatattc ttcataactc tctagataat gatgaatgta gcacgcattc acataaggtt   5760
tttgctgaca ttcagagtga agaaatttta caacataacc aaaatatgtc tggattggag   5820
aaagtttcta aaatatcacc ttgtgatgtt agtttggaaa cttcagatat atgtaaatgt   5880
agtataggga agcttcataa gtcagtctca tctgcaaata cttgtgggat ttttagcaca   5940
gcaagtggaa aatctgtcca ggtatcagat gcttcattac aaaacgcaag acaagtgttt   6000
tctgaaatag aagatagtac caagcaagtc ttttccaaag tattgtttaa aagtaacgaa   6060
cattcagacc agctcacaag agaagaaaat actgctatac gtactccaga acatttaata   6120
tcccaaaaag gcttttcata taatgtggta aattcatctg ctttctctgg atttagtaca   6180
gcaagtggaa agcaagtttc cattttagaa agttccttac acaaagttaa gggagtgtta   6240
gaggaatttg atttaatcag aactgagcat agtcttcact attcacctac gtctagacaa   6300
aatgtatcaa aaatacttcc tcgtgttgat aagagaaacc cagagcactg tgtaaactca   6360
gaaatggaaa aaacctgcag taaagaattt aaattatcaa ataacttaaa tgttgaaggt   6420
ggttcttcag aaaataatca ctctattaaa gtttctccat atctctctca atttcaacaa   6480
gacaaacaac agttggtatt aggaaccaaa gtgtcacttg ttgagaacat tcatgttttg   6540
ggaaaagaac aggcttcacc taaaaacgta aaaatggaaa ttggtaaaac tgaaactttt   6600
tctgatgttc ctgtgaaaac aaatatagaa gtttgttcta cttactccaa agattcagaa   6660
aactactttg aaacagaagc agtagaaatt gctaaagctt ttatggaaga tgatgaactg   6720
acagattcta aactgccaag tcatgccaca cattctcttt ttacatgtcc cgaaaatgag   6780
gaaatggttt tgtcaaattc aagaattgga aaaagaagag gagagcccct tatcttagtg   6840
ggagaaccct caatcaaaag aaacttatta aatgaatttg acaggataat agaaaatcaa   6900
gaaaaatcct taaaggcttc aaaaagcact ccagatggca caataaaaga tcgaagattg   6960
tttatgcatc atgtttcttt agagccgatt acctgtgtac cctttcgcac aactaaggaa   7020
cgtcaagaga tacagaatcc aaattttacc gcacctggtc aagaatttct gtctaaatct   7080
catttgtatg aacatctgac tttggaaaaa tcttcaagca atttagcagt ttcaggacat   7140
ccattttatc aagtttctgc tacaagaaat gaaaaaatga gacacttgat tactacaggc   7200
agaccaacca aagtctttgt tccacctttt aaaactaaat cacattttca cagagttgaa   7260
cagtgtgtta ggaatattaa cttggaggaa aacagacaaa agcaaaacat tgatggacat   7320
```

-continued

```
ggctctgatg atagtaaaaa taagattaat gacaatgaga ttcatcagtt taacaaaaac   7380
aactccaatc aagcagcagc tgtaactttc acaaagtgtg aagaagaacc tttagattta   7440
attacaagtc ttcagaatgc cagagatata caggatatgc gaattaagaa gaaacaaagg   7500
caacgcgtct ttccacagcc aggcagtctg tatcttgcaa aaacatccac tctgcctcga   7560
atctctctga aagcagcagt aggaggccaa gttccctctg cgtgttctca taaacagctg   7620
tatacgtatg gcgtttctaa acattgcata aaaattaaca gcaaaaatgc agagtctttt   7680
cagtttcaca ctgaagatta ttttggtaag gaaagtttat ggactggaaa aggaatacag   7740
ttggctgatg gtggatggct cataccctcc aatgatggaa aggctggaaa agaagaattt   7800
tatagggctc tgtgtgacac tccaggtgtg gatccaaagc ttatttctag aatttgggtt   7860
tataatcact atagatggat catatggaaa ctggcagcta tggaatgtgc ctttcctaag   7920
gaatttgcta atagatgcct aagcccagaa agggtgcttc ttcaactaaa atacagatat   7980
gatacggaaa ttgatagaag cagaagatcg gctataaaaa agataatgga aagggatgac   8040
acagctgcaa aaacacttgt tctctgtgtt tctgacataa tttcattgag cgcaaatata   8100
tctgaaactt ctagcaataa aactagtagt gcagataccc aaaaagtggc cattattgaa   8160
cttacagatg ggtggtatgc tgttaaggcc cagttagatc ctcccctctt agctgtctta   8220
aagaatggca gactgacagt tggtcagaag attattcttc atggagcaga actggtgggc   8280
tctcctgatg cctgtacacc tcttgaagcc ccagaatctc ttatgttaaa gatttctgct   8340
aacagtactc ggcctgctcg ctggtatacc aaacttggat tctttcctga ccctagacct   8400
tttcctctgc ccttatcatc gcttttcagt gatggaggaa atgttggttg tgttgatgta   8460
attattcaaa gagcataccc tatacagtgg atggagaaga catcatctgg attatacata   8520
tttcgcaatg aaagagagga agaaaaggaa gcagcaaaat atgtggaggc ccaacaaaag   8580
agactagaag ccttattcac taaaattcag gaggaatttg aagaacatga agaaaacaca   8640
acaaaaccat atttaccatc acgtgcacta acaagacagc aagttcgtgc tttgcaagat   8700
ggtgcagagc tttatgaagc agtgaagaat gcagcagacc cagcttacct tgagggttat   8760
ttcagtgaag agcagttaag agccttgaat aatcacaggc aaatgttgaa tgataagaaa   8820
caagctcaga tccagttgga aattaggaag gccatggaat ctgctgaaca aaaggaacaa   8880
ggtttatcaa gggatgtcac aaccgtgtgg aagttgcgta ttgtaagcta ttcaaaaaaa   8940
gaaaaagatt cagttatact gagtatttgg cgtccatcat cagatttata ttctctgtta   9000
acagaaggaa agagatacag aatttatcat cttgcaactt caaaatctaa aagtaaatct   9060
gaaagagcta acatacagtt agcagcgaca aaaaaaactc agtatcaaca actaccggtt   9120
tcagatgaaa ttttatttca gatttaccag ccacgggagc cccttcactt cagcaaattt   9180
ttagatccag actttcagcc atcttgttct gaggtggacc taataggatt tgtcgtttct   9240
gttgtgaaaa aaacaggact tgccccttc gtctatttgt cagacgaatg ttacaattta   9300
ctggcaataa agttttggat agaccttaat gaggacatta ttaagcctca tatgttaatt   9360
gctgcaagca acctccagtg gcgaccagaa tccaaatcag gccttcttac tttatttgct   9420
ggagattttt ctgtgtttttc tgctagtcca aaagagggcc actttcaaga gacattcaac   9480
aaaatgaaaa atactgttga gaatattgac atactttgca atgaagcaga aaacaagctt   9540
atgcatatac tgcatgcaaa tgatcccaag tggtccaccc caactaaaga ctgtacttca   9600
gggccgtaca ctgctcaaat cattcctggt acaggaaaca agcttctgat gtcttctcct   9660
aattgtgaga tatattatca aagtccttta tcactttgta tggccaaaag gaagtctgtt   9720
```

```
tccacacctg tctcagccca gatgacttca aagtcttgta aaggggagaa agagattgat   9780

gaccaaaaga actgcaaaaa gagaagagcc ttggatttct tgagtagact gcctttacct   9840

ccacctgtta gtcccatttg tacatttgtt tctccggctg cacagaaggc atttcagcca   9900

ccaaggagtt gtggcaccaa atacgaaaca cccataaaga aaaaagaact gaattctcct   9960

cagatgactc catttaaaaa attcaatgaa atttctcttt tggaaagtaa ttcaatagct  10020

gacgaagaac ttgcattgat aaatacccaa gctcttttgt ctggttcaac aggagaaaaa  10080

caatttatat ctgtcagtga atccactagg actgctccca ccagttcaga agattatctc  10140

agactgaaac gacgttgtac tacatctctg atcaaagaac aggagagttc ccaggccagt  10200

acggaagaat gtgagaaaaa taagcaggac acaattacaa ctaaaaaata tatc        10254
```

<210> SEQ ID NO 182
<211> LENGTH: 2487
<212> TYPE: DNA
<213> ORGANISM: Homo sapiens
<220> FEATURE:
<223> OTHER INFORMATION: MCC

<400> SEQUENCE: 182

```
atgaattccg gagttgccat gaaatatgga aacgactcct cggccgagct gagtgagctc     60

cattcagcag ccctggcatc actaaaggga gatatagtgg aacttaataa acgtctccag    120

caaacagaga gggaacggga ccttctggaa aagaaattgg ccaaggcaca gtgcgagcag    180

tcccacctca tgagagagca tgaggatgtc caggagcgaa cgacgcttcg ctatgaggaa    240

cgcatcacag agctccacag cgtcattgcg gagctcaaca agaagataga ccgtctgcaa    300

ggcaccacca tcagggagga agatgagtac tcagaactgc gatcagaact cagccagagc    360

caacacgagg tcaacgagga ctctcgaagc atggaccaag accagacctc tgtctctatc    420

cccgaaaacc agtctaccat ggttactgct gacatggaca actgcagtga cctgaactca    480

gaactgcaga gggtgctgac agggctggag aatgttgtct gcggcaggaa gaagagcagc    540

tgcagcctct ccgtggccga ggtggacagg cacattgagc agctcaccac agccagcgag    600

cactgtgacc tggctattaa gacagtcgag gagattgagg gggtgcttgg ccgggacctg    660

tatcccaacc tggctgaaga gaggtctcgg tgggagaagg agctggctgg gctgagggaa    720

gagaatgaga gcctgactgc catgctgtgc agcaaagagg aagaactgaa ccggactaag    780

gccaccatga atgccatccg ggaagagcgg gaccggctcc ggaggcgggt cagagagctt    840

caaactcgac tacagagcgt gcaggccaca ggtccctcca gccctggccg cctcacttcc    900

accaaccgcc cgattaaccc cagcactggg gagctgagca caagcagcag cagcaatgac    960

attcccatcg ccaagattgc tgagagggtg aagctatcaa agacaaggtc cgaatcgtca   1020

tcatctgatc ggccagtcct gggctcagaa atcagtagca taggggtatc cagcagtgtg   1080

gctgaacacc tggcccactc acttcaggac tgctccaata tccaagagat tttccaaaca   1140

ctctactcac acggatctgc catctcagaa agcaagatta gagagtttga ggtggaaaca   1200

gaacggctga atagccggat tgagcacctc aaatcccaaa atgacctcct gaccataacc   1260

ttggaggaat gtaaaagcaa tgctgagagg atgagcatgc tggtgggaaa atacgaatcc   1320

aatgccacag cgctgaggct ggccttgcag tacagcgagc agtgcatcga agcctacgaa   1380

ctcctcctgg cgctggcaga gagtgagcag agcctcatcc tggggcagtt ccgagcggcg   1440

ggcgtggggt cctcccctgg agaccagtcg gggatgaaa acatcactca gatgctcaag   1500
```

```
cgagctcatg actgccggaa gacagctgag aacgctgcca aggccctgct catgaagctg   1560

gacggcagct gtgggggagc ctttgccgtg gccggctgca gcgtgcagcc ctgggagagc   1620

ctttcctcca acagccacac cagcacaacc agctccacag ccagtagttg cgacaccgag   1680

ttcactaaag aagacgagca gaggctgaag gattatatcc agcagctcaa gaatgacagg   1740

gctgcggtca agctgaccat gctggagctg gaaagcatcc acatcgatcc tctcagctat   1800

gacgtcaagc ctcggggaga cagccagagg ctggatctgg aaaacgcagt gcttatgcag   1860

gagctcatgg ccatgaagga ggagatggcc gagttgaagg cccagctcta cctactggag   1920

aaagagaaga aggccctgga gctgaagctg agcacgcggg aggcccagga gcaggcctac   1980

ctggtgcaca ttgagcacct gaagtccgag gtggaggagc agaaggagca gcggatgcga   2040

tccctcagct ccaccagcag cggcagcaaa gataaacctg gcaaggagtg tgctgatgct   2100

gcctccccag ctctgtccct agctgaactc aggacaacgt gcagcgagaa tgagctggct   2160

gcggagttca ccaacgccat tcgtcgagaa aagaagttga aggccagagt tcaagagctg   2220

gtgagtgcct tggagagact caccaagagc agtgaaatcc gacatcagca atctgcagag   2280

ttcgtgaatg atctaaagcg ggccaacagc aacctggtgg ctgcctatga gaaagcaaag   2340

aaaaagcatc aaaacaaact gaagaagtta gagtcgcaga tgatggccat ggtggagaga   2400

catgagaccc aagtgaggat gctcaagcaa agaatagctc tgctagagga ggagaactcc   2460

aggccacaca ccaatgaaac ttcgctt                                       2487
```

```
<210> SEQ ID NO 183
<211> LENGTH: 2253
<212> TYPE: DNA
<213> ORGANISM: Homo sapiens
<220> FEATURE:
<223> OTHER INFORMATION: EZH2, isoform 1

<400> SEQUENCE: 183

atgggccaga ctgggaagaa atctgagaag ggaccagttt gttggcggaa gcgtgtaaaa     60

tcagagtaca tgcgactgag acagctcaag aggttcagac gagctgatga agtaaagagt    120

atgtttagtt ccaatcgtca gaaaattttg gaaagaacgg aaatcttaaa ccaagaatgg    180

aaacagcgaa ggatacagcc tgtgcacatc ctgacttctg tgagctcatt gcgcgggact    240

agggagtgtt cggtgaccag tgacttggat tttccaacac aagtcatccc attaaagact    300

ctgaatgcag ttgcttcagt acccataatg tattcttggt ctcccctaca gcagaatttt    360

atggtggaag atgaaactgt tttacataac attccttata tgggagatga agttttagat    420

caggatggta ctttcattga agaactaata aaaaattatg atgggaaagt acacggggat    480

agagaatgtg ggtttataaa tgatgaaatt tttgtggagt tggtgaatgc ccttggtcaa    540

tataatgatg atgacgatga tgatgatgga gacgatcctg aagaaagaga agaaaagcag    600

aaagatctgg aggatcaccg agatgataaa gaaagccgcc cacctcggaa atttccttct    660

gataaaattt ttgaagccat ttcctcaatg tttccagata agggcacagc agaagaacta    720

aaggaaaaat ataaagaact caccgaacag cagctcccag gcgcacttcc tcctgaatgt    780

acccccaaca tagatggacc aaatgctaaa tctgttcaga gagagcaaag cttacactcc    840

tttcatacgc ttttctgtag gcgatgtttt aaatatgact gcttcctaca tcgtaagtgc    900

aattattctt ttcatgcaac acccaacact tataagcgga agaacacaga aacagctcta    960

gacaacaaac cttgtggacc acagtgttac cagcatttgg agggagcaaa ggagtttgct   1020

gctgctctca ccgctgagcg gataaagacc ccaccaaaac gtccaggagg ccgcagaaga   1080
```

ggacggcttc ccaataacag tagcaggccc agcaccccca ccattaatgt gctggaatca 1140
aaggatacag acagtgatag ggaagcaggg actgaaacgg ggggagagaa caatgataaa 1200
gaagaagaag agaagaaaga tgaaacttcg agctcctctg aagcaaattc tcggtgtcaa 1260
acaccaataa agatgaagcc aaatattgaa cctcctgaga atgtggagtg gagtggtgct 1320
gaagcctcaa tgtttagagt cctcattggc acttactatg acaatttctg tgccattgct 1380
aggttaattg ggaccaaaac atgtagacag gtgtatgagt ttagagtcaa agaatctagc 1440
atcatagctc cagctcccgc tgaggatgtg gatactcctc caaggaaaaa gaagaggaaa 1500
caccggttgt gggctgcaca ctgcagaaag atacagctga aaaaggacgg ctcctctaac 1560
catgtttaca actatcaacc ctgtgatcat ccacggcagc cttgtgacag ttcgtgccct 1620
tgtgtgatag cacaaaattt ttgtgaaaag ttttgtcaat gtagttcaga gtgtcaaaac 1680
cgctttccgg gatgccgctg caaagcacag tgcaacacca agcagtgccc gtgctacctg 1740
gctgtccgag agtgtgaccc tgacctctgt cttacttgtg gagccgctga ccattgggac 1800
agtaaaaatg tgtcctgcaa gaactgcagt attcagcggg gctccaaaaa gcatctattg 1860
ctggcaccat ctgacgtggc aggctggggg atttttatca aagatcctgt gcagaaaaat 1920
gaattcatct cagaatactg tggagagatt atttctcaag atgaagctga cagaagaggg 1980
aaagtgtatg ataaatacat gtgcagcttt ctgttcaact tgaacaatga ttttgtggtg 2040
gatgcaaccc gcaagggtaa caaaattcgt tttgcaaatc attcggtaaa tccaaactgc 2100
tatgcaaaag ttatgatggt taacggtgat cacaggatag gtatttttgc caagagagcc 2160
atccagactg gcgaagagct gtttttttgat tacagataca gccaggctga tgccctgaag 2220
tatgtcggca tcgaaagaga aatggaaatc cct 2253

<210> SEQ ID NO 184
<211> LENGTH: 1053
<212> TYPE: DNA
<213> ORGANISM: Homo sapiens
<220> FEATURE:
<223> OTHER INFORMATION: NIPP1/PPP1R8, isoform alpha

<400> SEQUENCE: 184
atggcggcag ccgcgaactc cggctctagc ctcccgctgt tcgactgccc aacctgggca 60
ggtaagcccc ctcccggttt acatctggat gtagtcaaag gagacaaact aattgagaaa 120
ctgattattg atgagaagaa gtattactta tttgggagaa accctgattt gtgtgacttt 180
accattgacc accagtcttg ctctcgggtc catgctgcac ttgtctacca caagcatctg 240
aagagagttt tcctgataga tctcaacagt acacacggca ctttcttggg tcacattcgg 300
ttggaacctc acaagcctca gcaaattccc atcgattcca cggtctcatt tggcgcatcc 360
acaagggcat acactctgcg cgagaagcct cagacattgc catcggctgt gaaaggagat 420
gagaagatgg gtggagagga tgatgaactc aagggcttac tggggcttcc agaggaggaa 480
actgagcttg ataacctgac agagttcaac actgcccaca acaagcggat ttctaccctt 540
accattgagg agggaaatct ggacattcaa agaccaaaga ggaagaggaa gaactcacgg 600
gtgacattca gtgaggatga tgagatcatc aacccagagg atgtggatcc ctcagttggt 660
cgattcagga acatggtgca aactgcagtg gtcccagtca agaagaagcg tgtggagggc 720
cctggctccc tgggcctgga ggaatcaggg agcaggcgca tgcagaactt tgccttcagc 780
ggaggactct acgggggcct gccccccaca cacagtgaag caggctccca gccacatggc 840

```
atccatggga cagcactcat cggtggcttg cccatgccat acccaaacct tgcccctgat    900

gtggacttga ctcctgttgt gccgtcagca gtgaacatga accctgcacc aaaccctgca    960

gtctataacc ctgaagctgt aaatgaaccc aagaagaaga aatatgcaaa agaggcttgg   1020

ccaggcaaga agcccacacc ttccttgctg att                                1053


<210> SEQ ID NO 185
<211> LENGTH: 990
<212> TYPE: DNA
<213> ORGANISM: Homo sapiens
<220> FEATURE:
<223> OTHER INFORMATION: PPP1CA, isoform 1

<400> SEQUENCE: 185

atgtccgaca gcgagaagct caacctggac tcgatcatcg ggcgcctgct ggaagtgcag     60

ggctcgcggc ctggcaagaa tgtacagctg acagagaacg agatccgcgg tctgtgcctg    120

aaatcccggg agatttttct gagccagccc attcttctgg agctggaggc acccctcaag    180

atctgcggtg acatacacgg ccagtactac gaccttctgc gactatttga gtatggcggt    240

ttccctcccg agagcaacta cctctttctg gggggactatg tggacagggg caagcagtcc    300

ttggagacca tctgcctgct gctggcctat aagatcaagt accccgagaa cttcttcctg    360

ctccgtggga accacgagtg tgccagcatc aaccgcatct atggtttcta cgatgagtgc    420

aagagacgct acaacatcaa actgtggaaa accttcactg actgcttcaa ctgcctgccc    480

atcgcggcca tagtggacga aaagatcttc tgctgccacg gaggcctgtc cccggacctg    540

cagtctatgg agcagattcg gcggatcatg cggcccacag atgtgcctga ccagggcctg    600

ctgtgtgacc tgctgtggtc tgaccctgac aaggacgtgc agggctgggg cgagaacgac    660

cgtggcgtct cttttacctt tggagccgag gtggtggcca agttcctcca caagcacgac    720

ttggacctca tctgccgagc acaccaggtg gtagaagacg gctacgagtt ctttgccaag    780

cggcagctgg tgacactttt ctcagctccc aactactgtg gcgagtttga caatgctggc    840

gccatgatga gtgtggacga gaccctcatg tgctctttcc agatcctcaa gcccgccgac    900

aagaacaagg ggaagtacgg gcagttcagt ggcctgaacc ctggaggccg acccatcacc    960

ccaccccgca attccgccaa agccaagaaa                                     990


<210> SEQ ID NO 186
<211> LENGTH: 1818
<212> TYPE: DNA
<213> ORGANISM: Homo sapiens
<220> FEATURE:
<223> OTHER INFORMATION: TAK1/MAP3K7, isoform 1B

<400> SEQUENCE: 186

atgtctacag cctctgccgc ctcctcctcc tcctcgtctt cggccggtga gatgatcgaa     60

gccccttccc aggtcctcaa ctttgaagag atcgactaca aggagatcga ggtggaagag    120

gttgttggaa gaggagcctt tggagttgtt tgcaaagcta agtggagagc aaaagatgtt    180

gctattaaac aaatagaaag tgaatctgag aggaaagcgt ttattgtaga gcttcggcag    240

ttatcccgtg tgaaccatcc taatattgta aagctttatg gagcctgctt gaatccagtg    300

tgtcttgtga tggaatatgc tgaagggggc tctttatata atgtgctgca tggtgctgaa    360

ccattgccat attatactgc tgcccacgca atgagttggt gtttacagtg ttcccaagga    420

gtggcttatc ttcacagcat gcaacccaaa gcgctaattc acagggacct gaaaccacca    480

aacttactgc tggttgcagg ggggacagtt ctaaaaattt gtgattttgg tacagcctgt    540
```

```
gacattcaga cacacatgac caataacaag gggagtgctg cttggatggc acctgaagtt    600

tttgaaggta gtaattacag tgaaaaatgt gacgtcttca gctggggtat tattctttgg    660

gaagtgataa cgcgtcggaa accctttgat gagattggtg gcccagcttt ccgaatcatg    720

tgggctgttc ataatggtac tcgaccacca ctgataaaaa atttacctaa gcccattgag    780

agcctgatga ctcgttgttg gtctaaagat ccttcccagc gcccttcaat ggaggaaatt    840

gtgaaaataa tgactcactt gatgcggtac tttccaggag cagatgagcc attacagtat    900

ccttgtcagt attcagatga aggacagagc aactctgcca ccagtacagg ctcattcatg    960

gacattgctt ctacaaatac gagtaacaaa agtgacacta atatggagca agttcctgcc   1020

acaaatgata ctattaagcg cttagaatca aaattgttga aaaatcaggc aaagcaacag   1080

agtgaatctg gacgtttaag cttgggagcc tcccgtggga gcagtgtgga gagcttgccc   1140

ccaacctctg agggcaagag gatgagtgct gacatgtctg aaatagaagc taggatcgcc   1200

gcaaccacag cctattccaa gcctaaacgg ggccaccgta aaactgcttc atttggcaac   1260

attctggatg tccctgagat cgtcatatca ggcaacggac agccaagacg tagatccatc   1320

caagacttga ctgtaactgg aacagaacct ggtcaggtga gcagtaggtc atccagtccc   1380

agtgtcagaa tgattactac ctcaggacca acctcagaaa agccaactcg aagtcatcca   1440

tggacccctg atgattccac agataccaat ggatcagata actccatccc aatggcttat   1500

cttacactgg atcaccaact acagcctcta gcaccgtgcc caaactccaa agaatctatg   1560

gcagtgtttg aacagcattg taaaatggca caagaatata tgaaagttca aacagaaatt   1620

gcattgttat tacagagaaa gcaagaacta gttgcagaac tggaccagga tgaaaaggac   1680

cagcaaaata catctcgcct ggtacaggaa cataaaaagc ttttagatga aaacaaaagc   1740

ctttctactt actaccagca atgcaaaaaa caactagagg tcatcagaag tcagcagcag   1800

aaacgacaag gcacttca                                                1818
```

<210> SEQ ID NO 187
<211> LENGTH: 204
<212> TYPE: DNA
<213> ORGANISM: Unknown
<220> FEATURE:
<223> OTHER INFORMATION: CMV promoter

<400> SEQUENCE: 187

```
gtgatgcggt tttggcagta catcaatggg cgtggatagc ggtttgactc acggggattt     60

ccaagtctcc accccattga cgtcaatggg agtttgtttt ggcaccaaaa tcaacgggac    120

tttccaaaat gtcgtaacaa ctccgcccca ttgacgcaaa tgggcggtag gcgtgtacgg    180

tgggaggtct atataagcag agct                                          204
```

<210> SEQ ID NO 188
<211> LENGTH: 1212
<212> TYPE: DNA
<213> ORGANISM: Homo sapiens
<220> FEATURE:
<223> OTHER INFORMATION: Caspase-1, isoform alpha

<400> SEQUENCE: 188

```
atggccgaca aggtcctgaa ggagaagaga aagctgttta tccgttccat gggtgaaggt     60

acaataaatg gcttactgga tgaattatta cagacaaggg tgctgaacaa ggaagagatg    120

gagaaagtaa aacgtgaaaa tgctacagtt atggataaga cccgagcttt gattgactcc    180
```

-continued

```
gttattccga aaggggcaca ggcatgccaa atttgcatca catacatttg tgaagaagac    240

agttacctgg cagggacgct gggactctca gcagatcaaa catctggaaa ttaccttaat    300

atgcaagact ctcaaggagt actttcttcc tttccagctc ctcaggcagt gcaggacaac    360

ccagctatgc ccacatcctc aggctcagaa gggaatgtca agctttgctc cctagaagaa    420

gctcaaagga tatggaaaca aaagtcggca gagatttatc caataatgga caagtcaagc    480

cgcacacgtc ttgctctcat tatctgcaat gaagaatttg acagtattcc tagaagaact    540

ggagctgagg ttgacatcac aggcatgaca atgctgctac aaaatctggg gtacagcgta    600

gatgtgaaaa aaaatctcac tgcttcggac atgactacag agctggaggc atttgcacac    660

cgcccagagc acaagacctc tgacagcacg ttcctggtgt tcatgtctca tggtattcgg    720

gaaggcattt gtgggaagaa acactctgag caagtcccag atatactaca actcaatgca    780

atctttaaca tgttgaatac caagaactgc ccaagtttga aggacaaacc gaaggtgatc    840

atcatccagg cctgccgtgg tgacagccct ggtgtggtgt ggtttaaaga ttcagtagga    900

gtttctggaa acctatcttt accaactaca gaagagtttg aggatgatgc tattaagaaa    960

gcccacatag agaaggattt tatcgctttc tgctcttcca caccagataa tgtttcttgg   1020

agacatccca caatgggctc tgtttttatt ggaagactca ttgaacatat gcaagaatat   1080

gcctgttcct gtgatgtgga ggaaattttc cgcaaggttc gattttcatt tgagcagcca   1140

gatggtagag cgcagatgcc caccactgaa agagtgactt tgacaagatg tttctacctc   1200

ttcccaggac at                                                       1212
```

<210> SEQ ID NO 189
<211> LENGTH: 885
<212> TYPE: DNA
<213> ORGANISM: Homo sapiens
<220> FEATURE:
<223> OTHER INFORMATION: cyclin-D1/CCND1

<400> SEQUENCE: 189

```
atggaacacc agctcctgtg ctgcgaagtg gaaaccatcc gccgcgcgta ccccgatgcc     60

aacctcctca acgaccgggt gctgcgggcc atgctgaagg cggaggagac ctgcgcgccc    120

tcggtgtcct acttcaaatg tgtgcagaag gaggtcctgc cgtccatgcg gaagatcgtc    180

gccacctgga tgctggaggt ctgcgaggaa cagaagtgcg aggaggaggt cttcccgctg    240

gccatgaact acctggaccg cttcctgtcg ctggagcccg tgaaaaagag ccgcctgcag    300

ctgctggggg ccacttgcat gttcgtggcc tctaagatga aggagaccat ccccctgacg    360

gccgagaagc tgtgcatcta caccgacaac tccatccggc ccgaggagct gctgcaaatg    420

gagctgctcc tggtgaacaa gctcaagtgg aacctggccg caatgacccc gcacgatttc    480

attgaacact tcctctccaa aatgccagag gcggaggaga acaaacagat catccgcaaa    540

cacgcgcaga ccttcgttgc cctctgtgcc acagatgtga agttcatttc caatccgccc    600

tccatggtgg cagcggggag cgtggtggcc gcagtgcaag gcctgaacct gaggagcccc    660

aacaacttcc tgtcctacta ccgcctcaca cgcttcctct ccagagtgat caagtgtgac    720

ccggactgcc tccgggcctg ccaggagcag atcgaagccc tgctggagtc aagcctgcgc    780

caggcccagc agaacatgga ccccaaggcc gccgaggagg aggaagagga ggaggaggag    840

gtggacctgg cttgcacacc caccgacgtg cgggacgtgg acatc                    885
```

<210> SEQ ID NO 190
<211> LENGTH: 996

<212> TYPE: DNA
<213> ORGANISM: Homo sapiens
<220> FEATURE:
<223> OTHER INFORMATION: A2b receptor (ADORA2B)

<400> SEQUENCE: 190
atgctgctgg agacacagga cgcgctgtac gtggcgctgg agctggtcat cgccgcgctt 60
tcggtggcgg gcaacgtgct ggtgtgcgcc gcggtgggca cggcgaacac tctgcagacg 120
cccaccaact acttcctggt gtccctggct gcggccgacg tggccgtggg gctcttcgcc 180
atcccctttg ccatcaccat cagcctgggc ttctgcactg acttctacgg ctgcctcttc 240
ctcgcctgct tcgtgctggt gctcacgcag agctccatct tcagccttct ggccgtggca 300
gtcgacagat acctggccat ctgtgtcccg ctcaggtata aaagtttggt cacggggacc 360
cgagcaagag ggtcattgc tgtcctctgg gtccttgcct ttggcatcgg attgactcca 420
ttcctggggt ggaacagtaa agacagtgcc accaacaact gcacagaacc ctgggatgga 480
accacgaatg aaagctgctg ccttgtgaag tgtctctttg agaatgtggt ccccatgagc 540
tacatggtat atttcaattt ctttgggtgt gttctgcccc cactgcttat aatgctggtg 600
atctacatta agatcttcct ggtggcctgc aggcagcttc agcgcactga gctgatggac 660
cactcgagga ccaccctcca gcgggagatc catgcagcca agtcactggc catgattgtg 720
gggatttttg ccctgtgctg gttacctgtg catgctgtta actgtgtcac tcttttccag 780
ccagctcagg gtaaaaataa gcccaagtgg gcaatgaata tggccattct tctgtcacat 840
gccaattcag ttgtcaatcc cattgtctat gcttaccgga accgagactt ccgctacact 900
tttcacaaaa ttatctccag gtatcttctc tgccaagcag atgtcaagag tgggaatggt 960
caggctgggg tacagcctgc tctcggtgtg ggccta 996

<210> SEQ ID NO 191
<211> LENGTH: 1242
<212> TYPE: DNA
<213> ORGANISM: Homo sapiens
<220> FEATURE:
<223> OTHER INFORMATION: HHLA2, isoform 1

<400> SEQUENCE: 191
atgaaggcac agacagcact gtctttcttc ctcattctca taacatctct gagtggatct 60
caaggcatat tccctttggc tttcttcatt tatgttccta tgaatgaaca aatcgtcatt 120
ggaagacttg atgaagatat aattctccct tcttcatttg agaggggatc cgaagtcgta 180
atacactgga agtatcaaga tagctataag gttcacagtt actacaaagg cagtgaccat 240
ttggaaagcc aagatcccag atatgcaaac aggacatccc ttttctataa tgagattcaa 300
aatgggaatg cgtcgctatt tttcagaaga gtaagccttc tggacgaagg aatttacacc 360
tgctatgtag gaacagcaat tcaagtgatt acaaacaaag tggtgctaaa ggtgggagtt 420
tttctcacac ccgtgatgaa gtatgaaaag aggaacacaa acagcttctt aatatgcagc 480
gtgttaagtg tttatcctcg tccaattatc acgtggaaaa tggacaacac acctatctct 540
gaaaacaaca tggaagaaac agggtctttg gattcttttt ctattaacag cccactgaat 600
attacaggat caaattcatc ttatgaatgt acaattgaaa attcactgct gaagcaaaca 660
tggacagggc gctggacgat gaaagatggc cttcataaaa tgcaaagtga acacgtttca 720
ctctcatgtc aacctgtaaa tgattatttt tcaccaaacc aagacttcaa agttacttgg 780
tccagaatga aaagtgggac tttctctgtc ctggcttact atctgagctc ctcacaaaat 840

```
acaattatca atgaatcccg attctcatgg aacaaagagc tgataaacca gagtgacttc    900

tctatgaatt tgatggatct taatctttca gacagtgggg aatatttatg caatatttct    960

tcggatgaat atactttact taccatccac acagtgcatg tagaaccgag ccaagaaaca   1020

gcttcccata acaaaggctt atggattttg gtgccctctg cgattttggc agcttttctg   1080

ctgatttgga gcgtaaaatg ttgcagagcc cagctagaag ccaggaggag cagacaccct   1140

gctgatggag cccaacaaga aagatgttgt gtccctcctg gtgagcgctg tcccagtgca   1200

cccgataatg gcgaagaaaa tgtgcctctt tcaggaaaag ta                      1242
```

```
<210> SEQ ID NO 192
<211> LENGTH: 1128
<212> TYPE: DNA
<213> ORGANISM: Herpes simplex
<220> FEATURE:
<223> OTHER INFORMATION: herpes simplex virus thymidine kinase (HSV-TK)

<400> SEQUENCE: 192

atggcttcgt accccctgcca tcaacacgcg tctgcgttcg accaggctgc gcgttctcgc     60

ggccatagca accgacgtac ggcgttgcgc cctcgccggc agcaagaagc cacggaagtc    120

cgcctggagc agaaaatgcc cacgctactg cgggtttata tagacggtcc tcacgggatg    180

gggaaaacca ccaccacgca actgctggtg gccctgggtt cgcgcgacga tatcgtctac    240

gtacccgagc cgatgactta ctggcaggtg ctgggggctt ccgagacaat cgcgaacatc    300

tacaccacac aacaccgcct cgaccagggt gagatatcgg ccggggacgc ggcggtggta    360

atgacaagcg cccagataac aatgggcatg ccttatgccg tgaccgacgc cgttctggct    420

cctcatgtcg ggggggaggc tgggagttca catgccccgc ccccggccct caccctcatc    480

ttcgaccgcc atcccatcgc cgccctcctg tgctacccgg ccgcgcgata ccttatgggc    540

agcatgaccc cccaggccgt gctggcgttc gtggccctca tcccgccgac cttgcccggc    600

acaaacatcg tgttgggggc ccttccggag gacagacaca tcgaccgcct ggccaaacgc    660

cagcgccccg gcgagcggct tgacctggct atgctggccg cgattcgccg cgtttacggg    720

ctgcttgcca atacggtgcg gtatctgcag ggcggcgggt cgtggtggga ggattgggga    780

cagctttcgg ggacggccgt gccgccccag ggtgccgagc cccagagcaa cgcgggccca    840

cgaccccata tcggggacac gttatttacc ctgtttcggg cccccgagtt gctggccccc    900

aacggcgacc tgtataacgt gtttgcctgg gccttggacg tcttggccaa acgcctccgt    960

cccatgcacg tctttatcct ggattacgac caatcgcccg ccggctgccg ggacgccctg   1020

ctgcaactta cctccgggat ggtccagacc cacgtcacca ccccaggctc cataccgacg   1080

atctgcgacc tggcgcgcac gtttgcccgg gagatggggg aggctaac                1128
```

```
<210> SEQ ID NO 193
<211> LENGTH: 1173
<212> TYPE: DNA
<213> ORGANISM: Homo sapiens
<220> FEATURE:
<223> OTHER INFORMATION: Human TGF-beta isoform 1

<400> SEQUENCE: 193

atgccgccct ccgggctgcg gctgctgccg ctgctgctac cgctgctgtg gctactggtg     60

ctgacgcctg gccggccggc cgcgggacta tccacctgca agactatcga catggagctg    120

gtgaagcgga agcgcatcga ggccatccgc ggccagatcc tgtccaagct gcggctcgcc    180

agccccccga gccaggggga ggtgccgccc ggcccgctgc ccgaggccgt gctcgccctg    240
```

```
tacaacagca cccgcgaccg ggtggccggg gagagtgcag aaccggagcc cgagcctgag    300

gccgactact acgccaagga ggtcacccgc gtgctaatgg tggaaaccca caacgaaatc    360

tatgacaagt tcaagcagag tacacacagc atatatatgt tcttcaacac atcagagctc    420

cgagaagcgg tacctgaacc cgtgttgctc tcccgggcag agctgcgtct gctgaggctc    480

aagttaaaag tggagcagca cgtggagctg taccagaaat acagcaacaa ttcctggcga    540

tacctcagca accggctgct ggcacccagc gactcgccag agtggttatc ttttgatgtc    600

accggagttg tgcggcagtg gttgagccgt ggaggggaaa ttgagggctt tcgccttagc    660

gcccactgct cctgtgacag cagggataac acactgcaag tggacatcaa cgggttcact    720

accggccgcc gaggtgacct ggccaccatt catggcatga accggccttt cctgcttctc    780

atggccaccc cgctggagag ggcccagcat ctgcaaagct cccggcaccg ccgagccctg    840

gacaccaact attgcttcag ctccacggag aagaactgct gcgtgcggca gctgtacatt    900

gacttccgca aggacctcgg ctggaagtgg atccacgagc ccaagggcta ccatgccaac    960

ttctgcctcg ggccctgccc ctacatttgg agcctggaca cgcagtacag caaggtcctg   1020

gccctgtaca accagcataa cccgggcgcc tcggcggcgc cgtgctgcgt gccgcaggcg   1080

ctggagccgc tgcccatcgt gtactacgtg ggccgcaagc ccaaggtgga gcagctgtcc   1140

aacatgatcg tgcgctcctg caagtgcagc tga                                1173
```

<210> SEQ ID NO 194
<211> LENGTH: 699
<212> TYPE: DNA
<213> ORGANISM: Homo sapiens
<220> FEATURE:
<223> OTHER INFORMATION: Human VEGF

<400> SEQUENCE: 194

```
atgaactttc tgctgtcttg ggtgcattgg agccttgcct tgctgctcta cctccaccat     60

gccaagtggt cccaggctgc acccatggca gaaggaggag ggcagaatca tcacgaagtg    120

gtgaagttca tggatgtcta tcagcgcagc tactgccatc caatcgagac cctggtggac    180

atcttccagg agtaccctga tgagatcgag tacatcttca agccatcctg tgtgcccctg    240

atgcgatgcg gggctgctg caatgacgag ggcctggagt gtgtgcccac tgaggagtcc    300

aacatcacca tgcagattat gcggatcaaa cctcaccaag gccagcacat aggagagatg    360

agcttcctac agcacaacaa atgtgaatgc agaccaaaga aagatagagc aagacaagaa    420

aaaaaatcag ttcgaggaaa gggaaagggg caaaaacgaa agcgcaagaa atcccggtat    480

aagtcctgga gcgtgtacgt tggtgcccgc tgctgtctaa tgccctggag cctccctggc    540

ccccatccct gtgggccttg ctcagagcgg agaaagcatt tgtttgtaca agatccgcag    600

acgtgtaaat gttcctgcaa aaacacagac tcgcgttgca aggcgaggca gcttgagtta    660

aacgaacgta cttgcagatg tgacaagccg aggcggtga                           699
```

<210> SEQ ID NO 195
<211> LENGTH: 19
<212> TYPE: DNA
<213> ORGANISM: Homo sapiens
<220> FEATURE:
<223> OTHER INFORMATION: Human TGF-beta isoform 1 shRNA target 1

<400> SEQUENCE: 195

```
gaaacccaca acgaaatct                                                  19
```

<210> SEQ ID NO 196
<211> LENGTH: 19
<212> TYPE: DNA
<213> ORGANISM: Homo sapiens
<220> FEATURE:
<223> OTHER INFORMATION: Human TGF-beta isoform1 shRNA target 2

<400> SEQUENCE: 196
gtacacacag catatatat 19

<210> SEQ ID NO 197
<211> LENGTH: 19
<212> TYPE: DNA
<213> ORGANISM: Homo sapiens
<220> FEATURE:
<223> OTHER INFORMATION: Human TGF-beta isoform1 shRNA target 3

<400> SEQUENCE: 197
ctgctgaggc tcaagttaa 19

<210> SEQ ID NO 198
<211> LENGTH: 19
<212> TYPE: DNA
<213> ORGANISM: Homo sapiens
<220> FEATURE:
<223> OTHER INFORMATION: Human TGF-beta isoform1 shRNA target 4

<400> SEQUENCE: 198
gtggagctgt accagaaat 19

<210> SEQ ID NO 199
<211> LENGTH: 19
<212> TYPE: DNA
<213> ORGANISM: Homo sapiens
<220> FEATURE:
<223> OTHER INFORMATION: Human TGF-beta isoform1 shRNA target 5

<400> SEQUENCE: 199
gactcgccag agtggttat 19

<210> SEQ ID NO 200
<211> LENGTH: 19
<212> TYPE: DNA
<213> ORGANISM: Homo sapiens
<220> FEATURE:
<223> OTHER INFORMATION: Human TGF-beta isoform1 shRNA target 6

<400> SEQUENCE: 200
gagccgtgga ggggaaatt 19

<210> SEQ ID NO 201
<211> LENGTH: 19
<212> TYPE: DNA
<213> ORGANISM: Homo sapiens
<220> FEATURE:
<223> OTHER INFORMATION: Human TGF-beta isoform1 shRNA target 7

<400> SEQUENCE: 201
cctgtgacag cagggataa 19

<210> SEQ ID NO 202
<211> LENGTH: 19
<212> TYPE: DNA
<213> ORGANISM: Homo sapiens
<220> FEATURE:
<223> OTHER INFORMATION: Human TGF-beta isoform1 shRNA target 8

<400> SEQUENCE: 202
gccctggaca ccaactatt 19

<210> SEQ ID NO 203
<211> LENGTH: 19
<212> TYPE: DNA
<213> ORGANISM: Homo sapiens
<220> FEATURE:
<223> OTHER INFORMATION: Human TGF-beta isoform1 shRNA target 9

<400> SEQUENCE: 203
ccctgtacaa ccagcataa 19

<210> SEQ ID NO 204
<211> LENGTH: 19
<212> TYPE: DNA
<213> ORGANISM: Homo sapiens
<220> FEATURE:
<223> OTHER INFORMATION: Human VEGF shRNA target 1

<400> SEQUENCE: 204
gagatcgagt acatcttca 19

<210> SEQ ID NO 205
<211> LENGTH: 19
<212> TYPE: DNA
<213> ORGANISM: Homo sapiens
<220> FEATURE:
<223> OTHER INFORMATION: Human VEGF shRNA target 2

<400> SEQUENCE: 205
gcagattatg cggatcaaa 19

<210> SEQ ID NO 206
<211> LENGTH: 19
<212> TYPE: DNA
<213> ORGANISM: Homo sapiens
<220> FEATURE:
<223> OTHER INFORMATION: Human VEGF shRNA target 3

<400> SEQUENCE: 206
gatagagcaa gacaagaaa 19

<210> SEQ ID NO 207
<211> LENGTH: 19
<212> TYPE: DNA
<213> ORGANISM: Homo sapiens
<220> FEATURE:
<223> OTHER INFORMATION: Human VEGF shRNA target 4

<400> SEQUENCE: 207
ggagaaagca tttgtttgt 19

<210> SEQ ID NO 208
<211> LENGTH: 19
<212> TYPE: DNA
<213> ORGANISM: Homo sapiens
<220> FEATURE:
<223> OTHER INFORMATION: Human VEGF shRNA target 5

<400> SEQUENCE: 208
gatccgcaga cgtgtaaat 19

<210> SEQ ID NO 209

<211> LENGTH: 19
<212> TYPE: DNA
<213> ORGANISM: Homo sapiens
<220> FEATURE:
<223> OTHER INFORMATION: Human VEGF shRNA target 6

<400> SEQUENCE: 209
gcgaggcagc ttgagttaa 19

<210> SEQ ID NO 210
<211> LENGTH: 3888
<212> TYPE: DNA
<213> ORGANISM: Artificial Sequence
<220> FEATURE:
<223> OTHER INFORMATION: ARI-134

<400> SEQUENCE: 210
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga gaattggtac catatttgca tgtcgctatg 720
tgttctggga aatcaccata aacgtgaaat gtctttggat ttgggaatct tataagttct 780
gtatgagacc actccctagg ccacactgta tggactattc tagagatagt ccatacagtg 840
tggctttttt cgacagatct ggcgcgccat agtggccagc ggccgcaggt aagccagccc 900
aggcctcgcc ctccagctca aggcgggaca ggtgccctag agtagcctgc atccagggac 960
aggccccagc cgggtgctga cacgtccacc tccatctctt cctcaggtct gcccgggtgg 1020
catccctgtg acccctcccc agtgcctctc ctggccctgg aagttgccac tccagtgccc 1080
accagccttg tcctaataaa attaagttgc atcattttgt ctgactaggt gtccttctat 1140
aatattatgg ggtggagggg ggtggtatgg agcaaggggc ccaagttaac ttgtttattg 1200
cagcttataa tggttacaaa taaagcaata gcatcacaaa tttcacaaat aaagcatttt 1260
tttcactgca ttctagttgt ggtttgtcca aactcatcaa tgtatcttat catgtctgga 1320
tccaaggtcg ggcaggaaga gggcctattt cccatgattc cttcatattt gcatatacga 1380
tacaaggctg ttagagagat aattagaatt aatttgactg taaacacaaa gatattagta 1440
caaaatacgt gacgtagaaa gtaataattt cttgggtagt ttgcagtttt aaaattatgt 1500
tttaaaatgg actatcatat gcttaccgta acttgaaagt atttcgattt cttggcttta 1560
tatatcttgt ggaaaggacg aaactaggcc gactacaagc gaattatcta gagtaattcg 1620
cttgtagtcg gctttttttcg agtagctaga gaattcatgg taatagcgat gactaatacg 1680
tagatgtact gccaagtagg aaagtcccat aaggtcatgt actgggcata atgccaggcg 1740
ggccatttac cgtcattgac gtcaataggg ggcgtacttg gcatatgata cacttgatgt 1800

```
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctctttttcc gaaggtaact   3360
ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
agggagcttc caggggggaaa cgcctggtat ctttatagtc ctgtcgggtt tcgccacctc   3780
tgacttgagc gtcgattttt gtgatgctcg tcaggggggc ggagcctatg gaaaaacgcc   3840
agcaacgcgg cctttttacg gttcctggcc ttttgctggc cttttgct                3888
```

<210> SEQ ID NO 211
<211> LENGTH: 3888
<212> TYPE: DNA
<213> ORGANISM: Artificial Sequence
<220> FEATURE:
<223> OTHER INFORMATION: ARI-135

<400> SEQUENCE: 211

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg agctggctcc tggtgaattc tagagattca ccaggagcca    840
gctctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gcccgggtgg   1020
catccctgtg accccctccc agtgcctctc ctggccctgg aagttgccac tccagtgccc   1080
accagccttg tcctaataaa attaagttgc atcattttgt ctgactaggt gtccttctat   1140
aatattatgg ggtggagggg ggtggtatgg agcaaggggc ccaagttaac ttgtttattg   1200
cagcttataa tggttacaaa taaagcaata gcatcacaaa tttcacaaat aaagcatttt   1260
tttcactgca ttctagttgt ggtttgtcca aactcatcaa tgtatcttat catgtctgga   1320
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggcc gactacaagc gaattatcta gagtaattcg   1620
cttgtagtcg gctttttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
```

```
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
tcacttgata accttatttt tgacgagggg aaattaatag gttgtattga tgttggacga   2940
gtcggaatcg cagaccgata ccaggatctt gccatcctat ggaactgcct cggtgagttt   3000
tctccttcat tacagaaacg gctttttcaa aaatatggta ttgataatcc tgatatgaat   3060
aaattgcagt ttcatttgat gctcgatgag tttttctaat cagaattggt taattggttg   3120
taacactggc agagcattac gctgacttga cgggacggcg caagctcatg accaaaatcc   3180
cttaacgtga gttacgcgtc gttccactga gcgtcagacc ccgtagaaaa gatcaaagga   3240
tcttcttgag atcctttttt tctgcgcgta atctgctgct tgcaaacaaa aaaaccaccg   3300
ctaccagcgg tggtttgttt gccggatcaa gagctaccaa ctctttttcc gaaggtaact   3360
ggcttcagca gagcgcagat accaaatact gtccttctag tgtagccgta gttaggccac   3420
cacttcaaga actctgtagc accgcctaca tacctcgctc tgctaatcct gttaccagtg   3480
gctgctgcca gtggcgataa gtcgtgtctt accgggttgg actcaagacg atagttaccg   3540
gataaggcgc agcggtcggg ctgaacgggg ggttcgtgca cacagcccag cttggagcga   3600
acgacctaca ccgaactgag atacctacag cgtgagcatt gagaaagcgc cacgcttccc   3660
gaagggagaa aggcggacag gtatccggta agcggcaggg tcggaacagg agagcgcacg   3720
agggagcttc caggggggaaa cgcctggtat ctttatagtc ctgtcgggtt tcgccacctc   3780
tgacttgagc gtcgattttt gtgatgctcg tcaggggggc ggagcctatg gaaaaacgcc   3840
agcaacgcgg cctttttacg gttcctggcc ttttgctggc cttttgct                3888
```

<210> SEQ ID NO 212
<211> LENGTH: 3888
<212> TYPE: DNA
<213> ORGANISM: Artificial Sequence
<220> FEATURE:
<223> OTHER INFORMATION: ARI-136

<400> SEQUENCE: 212

```
ctttcctgcg ttatcccctg attctgtgga taaccgtatt accgcctttg agtgagctga     60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
```

-continued

```
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga gaattggtac catatttgca tgtcgctatg    720
tgttctggga aatcaccata aacgtgaaat gtctttggat ttgggaatct tataagttct    780
gtatgagacc actccctagg cagctggaat tctttctatc tagagtagaa agaattccag    840
ctgctttttt cgacagatct ggcgcgccat agtggccagc ggccgcaggt aagccagccc    900
aggcctcgcc ctccagctca aggcgggaca ggtgccctag agtagcctgc atccagggac    960
aggccccagc cgggtgctga cacgtccacc tccatctctt cctcaggtct gcccgggtgg   1020
catccctgtg accccctcccc agtgcctctc ctggccctgg aagttgccac tccagtgccc   1080
accagccttg tcctaataaa attaagttgc atcattttgt ctgactaggt gtccttctat   1140
aatattatgg ggtggagggg ggtggtatgg agcaaggggc ccaagttaac ttgtttattg   1200
cagcttataa tggttacaaa taaagcaata gcatcacaaa tttcacaaat aaagcatttt   1260
tttcactgca ttctagttgt ggtttgtcca aactcatcaa tgtatcttat catgtctgga   1320
tccaaggtcg ggcaggaaga gggcctattt cccatgattc cttcatattt gcatatacga   1380
tacaaggctg ttagagagat aattagaatt aatttgactg taaacacaaa gatattagta   1440
caaaatacgt gacgtagaaa gtaataattt cttgggtagt ttgcagtttt aaaattatgt   1500
tttaaaatgg actatcatat gcttaccgta acttgaaagt atttcgattt cttggcttta   1560
tatatcttgt ggaaaggacg aaactaggcc gactacaagc gaattatcta gagtaattcg   1620
cttgtagtcg gctttttcg agtagctaga gaattcatgg taatagcgat gactaatacg   1680
tagatgtact gccaagtagg aaagtcccat aaggtcatgt actgggcata atgccaggcg   1740
ggccatttac cgtcattgac gtcaataggg ggcgtacttg gcatatgata cacttgatgt   1800
actgccaagt gggcagttta ccgtaaatag tccacccatt gacgtcaatg gaaagtccct   1860
attggcgtta ctatgggaac atacgtcatt attgacgtca atgggcgggg gtcgttgggc   1920
ggtcagccag gcgggccatt taccgtaagt tatgtaacgc ggaactccat atatgggcta   1980
tgaactaatg accccgtaat tgattactat taataactag acccagcttt cttgtacaaa   2040
gttggcatta taagaaagca ttgcttatca atttgttgca acgaacaggt cactatcagt   2100
caaaataaaa tcattatttg ccatccagct gatatcccct atagtgagtc gtattacatg   2160
gtcatagctg tttcctggca gctctggccc gtgtctcaaa atctctgatg ttacattgca   2220
caagataaaa atatatcatc atgaacaata aaactgtctg cttacataaa cagtaataca   2280
aggggtgtta tgagccatat tcaacgggaa acgtcgaggc cgcgattaaa ttccaacatg   2340
gatgctgatt tatatgggta taaatgggct cgcgataatg tcgggcaatc aggtgcgaca   2400
atctatcgct tgtatgggaa gcccgatgcg ccagagttgt ttctgaaaca tggcaaaggt   2460
agcgttgcca atgatgttac agatgagatg gtcagactaa actggctgac ggaatttatg   2520
cctcttccga ccatcaagca ttttatccgt actcctgatg atgcatggtt actcaccact   2580
gcgatccccg gaaaaacagc attccaggta ttagaagaat atcctgattc aggtgaaaat   2640
attgttgatg cgctggcagt gttcctgcgc cggttgcatt cgattcctgt ttgtaattgt   2700
ccttttaaca gcgatcgcgt atttcgtctc gctcaggcgc aatcacgaat gaataacggt   2760
ttggttgatg cgagtgattt tgatgacgag cgtaatggct ggcctgttga acaagtctgg   2820
aaagaaatgc ataaactttt gccattctca ccggattcag tcgtcactca tggtgatttc   2880
```

tcacttgata accttatttt tgacgagggg aaattaatag gttgtattga tgttggacga 2940
gtcggaatcg cagaccgata ccaggatctt gccatcctat ggaactgcct cggtgagttt 3000
tctccttcat tacagaaacg gctttttcaa aaatatggta ttgataatcc tgatatgaat 3060
aaattgcagt ttcatttgat gctcgatgag tttttctaat cagaattggt taattggttg 3120
taacactggc agagcattac gctgacttga cgggacggcg caagctcatg accaaaatcc 3180
cttaacgtga gttacgcgtc gttccactga gcgtcagacc ccgtagaaaa gatcaaagga 3240
tcttcttgag atcctttttt tctgcgcgta atctgctgct tgcaaacaaa aaaaccaccg 3300
ctaccagcgg tggtttgttt gccggatcaa gagctaccaa ctctttttcc gaaggtaact 3360
ggcttcagca gagcgcagat accaaatact gtccttctag tgtagccgta gttaggccac 3420
cacttcaaga actctgtagc accgcctaca tacctcgctc tgctaatcct gttaccagtg 3480
gctgctgcca gtggcgataa gtcgtgtctt accgggttgg actcaagacg atagttaccg 3540
gataaggcgc agcggtcggg ctgaacgggg ggttcgtgca cacagcccag cttggagcga 3600
acgacctaca ccgaactgag atacctacag cgtgagcatt gagaaagcgc cacgcttccc 3660
gaagggagaa aggcggacag gtatccggta agcggcaggg tcggaacagg agagcgcacg 3720
agggagcttc cagggggaaa cgcctggtat ctttatagtc ctgtcgggtt tcgccacctc 3780
tgacttgagc gtcgattttt gtgatgctcg tcaggggggc ggagcctatg gaaaaacgcc 3840
agcaacgcgg cctttttacg gttcctggcc ttttgctggc cttttgct 3888

<210> SEQ ID NO 213
<211> LENGTH: 3890
<212> TYPE: DNA
<213> ORGANISM: Artificial Sequence
<220> FEATURE:
<223> OTHER INFORMATION: ARI-137

<400> SEQUENCE: 213
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga gaattggtac catatttgca tgtcgctatg 720
tgttctggga aatcaccata aacgtgaaat gtctttggat ttgggaatct tataagttct 780
gtatgagacc actccctagg atgtgacctt ctacaagatt ctagagatct tgtagaaggt 840
cacatctttt ttcgacagat ctggcgcgcc atagtggcca gcggccgcag gtaagccagc 900
ccaggcctcg ccctccagct caaggcggga caggtgccct agagtagcct gcatccaggg 960
acaggcccca gccgggtgct gacacgtcca cctccatctc ttcctcaggt ctgcccgggt 1020

-continued ggcatccctg tgacccctcc ccagtgcctc tcctggccct ggaagttgcc actccagtgc 1080
ccaccagcct tgtcctaata aaattaagtt gcatcatttt gtctgactag gtgtccttct 1140
ataatattat ggggtggagg ggggtggtat ggagcaaggg gcccaagtta acttgtttat 1200
tgcagcttat aatggttaca aataaagcaa tagcatcaca aatttcacaa ataaagcatt 1260
tttttcactg cattctagtt gtggtttgtc caaactcatc aatgtatctt atcatgtctg 1320
gatccaaggt cgggcaggaa gagggcctat ttcccatgat tccttcatat ttgcatatac 1380
gatacaaggc tgttagagag ataattagaa ttaatttgac tgtaaacaca aagatattag 1440
tacaaaatac gtgacgtaga aagtaataat ttcttgggta gtttgcagtt ttaaaattat 1500
gttttaaaat ggactatcat atgcttaccg taacttgaaa gtatttcgat ttcttggctt 1560
tatatatctt gtggaaagga cgaaactagg ccgactacaa gcgaattatc tagagtaatt 1620
cgcttgtagt cggctttttt cgagtagcta gagaattcat ggtaatagcg atgactaata 1680
cgtagatgta ctgccaagta ggaaagtccc ataaggtcat gtactgggca taatgccagg 1740
cgggccattt accgtcattg acgtcaatag ggggcgtact tggcatatga tacacttgat 1800
gtactgccaa gtgggcagtt taccgtaaat agtccaccca ttgacgtcaa tggaaagtcc 1860
ctattggcgt tactatggga acatacgtca ttattgacgt caatgggcgg gggtcgttgg 1920
gcggtcagcc aggcgggcca tttaccgtaa gttatgtaac gcggaactcc atatatgggc 1980
tatgaactaa tgaccccgta attgattact attaataact agacccagct ttcttgtaca 2040
aagttggcat tataagaaag cattgcttat caatttgttg caacgaacag gtcactatca 2100
gtcaaaataa aatcattatt tgccatccag ctgatatccc ctatagtgag tcgtattaca 2160
tggtcatagc tgtttcctgg cagctctggc ccgtgtctca aaatctctga tgttacattg 2220
cacaagataa aaatatatca tcatgaacaa taaaactgtc tgcttacata aacagtaata 2280
caaggggtgt tatgagccat attcaacggg aaacgtcgag gccgcgatta aattccaaca 2340
tggatgctga tttatatggg tataaatggg ctcgcgataa tgtcgggcaa tcaggtgcga 2400
caatctatcg cttgtatggg aagcccgatg cgccagagtt gtttctgaaa catggcaaag 2460
gtagcgttgc caatgatgtt acagatgaga tggtcagact aaactggctg acggaattta 2520
tgcctcttcc gaccatcaag cattttatcc gtactcctga tgatgcatgg ttactcacca 2580
ctgcgatccc cggaaaaaca gcattccagg tattagaaga atatcctgat tcaggtgaaa 2640
atattgttga tgcgctggca gtgttcctgc gccggttgca ttcgattcct gtttgtaatt 2700
gtccttttaa cagcgatcgc gtatttcgtc tcgctcaggc gcaatcacga atgaataacg 2760
gtttggttga tgcgagtgat tttgatgacg agcgtaatgg ctggcctgtt gaacaagtct 2820
ggaaagaaat gcataaactt ttgccattct caccggattc agtcgtcact catggtgatt 2880
tctcacttga taaccttatt tttgacgagg ggaaattaat aggttgtatt gatgttggac 2940
gagtcggaat cgcagaccga taccaggatc ttgccatcct atggaactgc ctcggtgagt 3000
tttctccttc attacagaaa cggctttttc aaaaatatgg tattgataat cctgatatga 3060
ataaattgca gtttcatttg atgctcgatg agtttttcta atcagaattg gttaattggt 3120
tgtaacactg gcagagcatt acgctgactt gacgggacgg cgcaagctca tgaccaaaat 3180
cccttaacgt gagttacgcg tcgttccact gagcgtcaga ccccgtagaa aagatcaaag 3240
gatcttcttg agatcctttt tttctgcgcg taatctgctg cttgcaaaca aaaaaaccac 3300
cgctaccagc ggtggtttgt ttgccggatc aagagctacc aactcttttt ccgaaggtaa 3360
ctggcttcag cagagcgcag ataccaaata ctgtccttct agtgtagccg tagttaggcc 3420

-continued

```
accacttcaa gaactctgta gcaccgccta catacctcgc tctgctaatc ctgttaccag   3480

tggctgctgc cagtggcgat aagtcgtgtc ttaccgggtt ggactcaaga cgatagttac   3540

cggataaggc gcagcggtcg ggctgaacgg ggggttcgtg cacacagccc agcttggagc   3600

gaacgaccta caccgaactg agatacctac agcgtgagca ttgagaaagc gccacgcttc   3660

ccgaagggag aaaggcggac aggtatccgg taagcggcag ggtcggaaca ggagagcgca   3720

cgagggagct tccaggggga aacgcctggt atctttatag tcctgtcggg tttcgccacc   3780

tctgacttga gcgtcgattt ttgtgatgct cgtcaggggg gcggagccta tggaaaaacg   3840

ccagcaacgc ggccttttta cggttcctgg ccttttgctg gccttttgct              3890
```

<210> SEQ ID NO 214
<211> LENGTH: 3379
<212> TYPE: DNA
<213> ORGANISM: Artificial Sequence
<220> FEATURE:
<221> NAME/KEY: misc_feature
<222> LOCATION: (1018)...(1038)
<223> OTHER INFORMATION: n may be any nucleotide
<220> FEATURE:
<221> NAME/KEY: misc_feature
<222> LOCATION: (1060)...(1080)
<223> OTHER INFORMATION: n may be any nucleotide
<220> FEATURE:
<221> NAME/KEY: source
<222> LOCATION: (1)...(3379)
<223> OTHER INFORMATION: ARI-205

<400> SEQUENCE: 214

```
ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480

gcagttccct actctcgcgt taacgctagc atggatgttt tcccagtcac gacgttgtaa    540

aacgacggcc agtcttaagc tcgggcccca aataatgatt ttattttgac tgatagtgac    600

ctgttcgttg caacaaattg atgagcaatg cttttttata atgccaactt tgtacaaaaa    660

agcaggcttt aaaggaacca attcagtcga ctggatccaa ggtcgggcag gaagagggcc    720

tatttcccat gattccttca tatttgcata tacgatacaa ggctgttaga gagataatta    780

gaattaattt gactgtaaac acaaagatat tagtacaaaa tacgtgacgt agaaagtaat    840

aatttcttgg gtagtttgca gttttaaaat tatgttttaa aatggactat catatgctta    900

ccgtaacttg aaagtatttc gatttcttgg ctttatatat cttgtggaaa ggacgaaact    960

agtccggatc aacgccctag gtttatgttt ggatgaactg acatacgcgt atccgtcnnn   1020

nnnnnnnnnn nnnnnnnngt agtgaaatat atattaaacn nnnnnnnnnn nnnnnnnnnn   1080

tacggtaacg cggaattcgc aactatttta tcaatttttt gcgtcgactc gagtagctag   1140

agaattcatg gtaatagcga tgactaatac gtagatgtac tgccaagtag gaaagtccca   1200

taaggtcatg tactgggcat aatgccaggc gggccattta ccgtcattga cgtcaatagg   1260
```

-continued

```
gggcgtactt ggcatatgat acacttgatg tactgccaag tgggcagttt accgtaaata   1320
gtccacccat tgacgtcaat ggaaagtccc tattggcgtt actatgggaa catacgtcat   1380
tattgacgtc aatgggcggg ggtcgttggg cggtcagcca ggcgggccat ttaccgtaag   1440
ttatgtaacg cggaactcca tatatgggct atgaactaat gaccccgtaa ttgattacta   1500
ttaataacta gacccagctt tcttgtacaa agttggcatt ataagaaagc attgcttatc   1560
aatttgttgc aacgaacagg tcactatcag tcaaaataaa atcattattt gccatccagc   1620
tgatatcccc tatagtgagt cgtattacat ggtcatagct gtttcctggc agctctggcc   1680
cgtgtctcaa aatctctgat gttacattgc acaagataaa aatatatcat catgaacaat   1740
aaaactgtct gcttacataa acagtaatac aaggggtgtt atgagccata ttcaacggga   1800
aacgtcgagg ccgcgattaa attccaacat ggatgctgat ttatatgggt ataaatgggc   1860
tcgcgataat gtcgggcaat caggtgcgac aatctatcgc ttgtatggga agcccgatgc   1920
gccagagttg tttctgaaac atggcaaagg tagcgttgcc aatgatgtta cagatgagat   1980
ggtcagacta aactggctga cggaatttat gcctcttccg accatcaagc attttatccg   2040
tactcctgat gatgcatggt tactcaccac tgcgatcccc ggaaaaacag cattccaggt   2100
attagaagaa tatcctgatt caggtgaaaa tattgttgat gcgctggcag tgttcctgcg   2160
ccggttgcat tcgattcctg tttgtaattg tccttttaac agcgatcgcg tatttcgtct   2220
cgctcaggcg caatcacgaa tgaataacgg tttggttgat gcgagtgatt ttgatgacga   2280
gcgtaatggc tggcctgttg aacaagtctg gaaagaaatg cataaacttt tgccattctc   2340
accggattca gtcgtcactc atggtgattt ctcacttgat aaccttattt ttgacgaggg   2400
gaaattaata ggttgtattg atgttggacg agtcggaatc gcagaccgat accaggatct   2460
tgccatccta tggaactgcc tcggtgagtt ttctccttca ttacagaaac ggctttttca   2520
aaaatatggt attgataatc ctgatatgaa taaattgcag tttcatttga tgctcgatga   2580
gtttttctaa tcagaattgg ttaattggtt gtaacactgg cagagcatta cgctgacttg   2640
acgggacggc gcaagctcat gaccaaaatc ccttaacgtg agttacgcgt cgttccactg   2700
agcgtcagac cccgtagaaa agatcaaagg atcttcttga gatccttttt ttctgcgcgt   2760
aatctgctgc ttgcaaacaa aaaaaccacc gctaccagcg gtggtttgtt tgccggatca   2820
agagctacca actctttttc cgaaggtaac tggcttcagc agagcgcaga taccaaatac   2880
tgtccttcta gtgtagccgt agttaggcca ccacttcaag aactctgtag caccgcctac   2940
atacctcgct ctgctaatcc tgttaccagt ggctgctgcc agtggcgata agtcgtgtct   3000
taccgggttg gactcaagac gatagttacc ggataaggcg cagcggtcgg gctgaacggg   3060
gggttcgtgc acacagccca gcttggagcg aacgacctac accgaactga gatacctaca   3120
gcgtgagcat tgagaaagcg ccacgcttcc cgaagggaga aaggcggaca ggtatccggt   3180
aagcggcagg gtcggaacag gagagcgcac gagggagctt ccagggggaa acgcctggta   3240
tctttatagt cctgtcgggt ttcgccacct ctgacttgag cgtcgatttt tgtgatgctc   3300
gtcagggggg cggagcctat ggaaaaacgc cagcaacgcg gcctttttac ggttcctggc   3360
cttttgctgg ccttttgct                                                3379
```

<210> SEQ ID NO 215
<211> LENGTH: 4744
<212> TYPE: DNA
<213> ORGANISM: Artificial Sequence
<220> FEATURE:
<221> NAME/KEY: misc_feature
<222> LOCATION: (3377)...(3398)
<223> OTHER INFORMATION: n may be any nucleotide
<220> FEATURE:
<221> NAME/KEY: misc_feature
<222> LOCATION: (3418)...(3439)
<223> OTHER INFORMATION: n may be any nucleotide
<220> FEATURE:
<221> NAME/KEY: source
<222> LOCATION: (1)...(4744)
<223> OTHER INFORMATION: ARI-206

<400> SEQUENCE: 215
aacatgtgag caaaaggcca gcaaaaggcc aggaaccgta aaaaggccgc gttgctggcg 60
tttttccata ggctccgccc ccctgacgag catcacaaaa atcgacgctc aagtcagagg 120
tggcgaaacc cgacaggact ataaagatac caggcgtttc cccctggaag ctccctcgtg 180
cgctctcctg ttccgaccct gccgcttacc ggatacctgt ccgcctttct cccttcggga 240
agcgtggcgc tttctcaatg ctcacgctgt aggtatctca gttcggtgta ggtcgttcgc 300
tccaagctgg gctgtgtgca cgaacccccc gttcagcccg accgctgcgc cttatccggt 360
aactatcgtc ttgagtccaa cccggtaaga cacgacttat cgccactggc agcagccact 420
ggtaacagga ttagcagagc gaggtatgta ggcggtgcta cagagttctt gaagtggtgg 480
cctaactacg gctacactag aaggacagta tttggtatct gcgctctgct gaagccagtt 540
accttcggaa aaagagttgg tagctcttga tccggcaaac aaaccaccgc tggtagcggt 600
ggtttttttg tttgcaagca gcagattacg cgcagaaaaa aaggatctca agaagatcct 660
ttgatctttt ctacggggtc tgacgctcag tggaacgacg cgtaactcac gttaagggat 720
tttggtcatg agcttgcgcc gtcccgtcaa gtcagcgtaa tgctctgcca gtgttacaac 780
caattaacca attctgatta gaaaaactca tcgagcatca aatgaaactg caatttattc 840
atatcaggat tatcaatacc atatttttga aaaagccgtt tctgtaatga aggagaaaac 900
tcaccgaggc agttccatag gatggcaaga tcctggtatc ggtctgcgat tccgactcgt 960
ccaacatcaa tacaacctat taatttcccc tcgtcaaaaa taaggttatc aagtgagaaa 1020
tcaccatgag tgacgactga atccggtgag aatggcaaaa gtttatgcat ttctttccag 1080
acttgttcaa caggccagcc attacgctcg tcatcaaaat cactcgcatc aaccaaaccg 1140
ttattcattc gtgattgcgc ctgagcgaga cgaaatacgc gatcgctgtt aaaaggacaa 1200
ttacaaacag gaatcgaatg caaccggcgc aggaacactg ccagcgcatc aacaatattt 1260
tcacctgaat caggatattc ttctaatacc tggaatgctg tttttccggg gatcgcagtg 1320
gtgagtaacc atgcatcatc aggagtacgg ataaaatgct tgatggtcgg aagaggcata 1380
aattccgtca gccagtttag tctgaccatc tcatctgtaa catcattggc aacgctacct 1440
ttgccatgtt tcagaaacaa ctctggcgca tcgggcttcc catacaagcg atagattgtc 1500
gcacctgatt gcccgacatt atcgcgagcc catttatacc catataaatc agcatccatg 1560
ttggaattta atcgcggcct cgacgtttcc cgttgaatat ggctcataac accccttgta 1620
ttactgttta tgtaagcaga cagttttatt gttcatgatg atatattttt atcttgtgca 1680
atgtaacatc agagattttg agacacgggc cagagctgcc aggaaacagc tatgaccatg 1740
taatacgact cactataggg gatatcagct ggatggcaaa taatgatttt attttgactg 1800
atagtgacct gttcgttgca acaaattgat aagcaatgct ttcttataat gccaactttg 1860
tacaagaaag ctgggtctag ttattaatag taatcaatta cggggtcatt agttcatagc 1920
ccatatatgg agttccgcgt tacataactt acggtaaatg gcccgcctgg ctgaccgccc 1980

-continued

```
aacgaccccc gcccattgac gtcaataatg acgtatgttc ccatagtaac gccaataggg   2040
actttccatt gacgtcaatg ggtggactat ttacggtaaa ctgcccactt ggcagtacat   2100
caagtgtatc atatgccaag tacgccccct attgacgtca atgacggtaa atggcccgcc   2160
tggcattatg cccagtacat gaccttatgg gactttccta cttggcagta catctacgta   2220
ttagtcatcg ctattaccat ggtgatgcgg ttttggcagt acatcaatgg gcgtggatag   2280
cggtttgact cacggggatt tccaagtctc caccccattg acgtcaatgg gagtttgttt   2340
tggcaccaaa atcaacggga ctttccaaaa tgtcgtaaca actccgcccc attgacgcaa   2400
atgggcggta ggcgtgtacg gtgggaggtc tatataagca gagctctctg gctaactaga   2460
gaacccactg cttactggct tatcgaaatt aatacgactc actataggga gacccaagct   2520
tagatctgtt tccggtcgcc accatgagcg agctgatcaa ggagaacatg cacatgaagc   2580
tgtacatgga gggcaccgtg aacaaccacc acttcaagtg cacatccgag ggcgaaggca   2640
agccctacga gggcacccag accatgaaga tcaaggtggt cgagggcggc cctctcccct   2700
tcgccttcga catcctggct accagcttca tgtacggcag caaagccttc atcaaccaca   2760
cccagggcat ccccgacttc tttaagcagt ccttccctga gggcttcaca tgggagagaa   2820
tcaccacata cgaagacggg ggcgtgctga ccgctaccca ggacaccagc ttccagaacg   2880
gctgcatcat ctacaacgtc aagatcaacg ggtgaactt cccatccaac ggccctgtga    2940
tgcagaagaa aacacgcggc tgggaggcca acaccgagat gctgtacccc gctgacggcg   3000
gcctgagagg ccacagccag atggccctga agctcgtggg cgggggctac ctgcactgct   3060
ccttcaagac cacatacaga tccaagaaac ccgctaagaa cctcaagatg cccggcttcc   3120
acttcgtgga ccacagactg gaaagaatca aggaggccga caaagagacc tacgtcgagc   3180
agcacgagat ggctgtggcc aagtactgcg acctccctag caaactgggg cacagataat   3240
cgatagtttg tttgaatgag gcttcagtac tttacagaat cgttgcctgc acatcttgga   3300
aacacttgct gggattactt cttcaggtta acccaacaga aggctcgaga aggtatattg   3360
ctgttgacag tgagcgnnnn nnnnnnnnnn nnnnnnnnta gtgaagccac agatgtannn   3420
nnnnnnnnnn nnnnnnnnnt gcctactgcc tcggaattca aggggctact ttaggagcaa   3480
ttatcttgtt tactaaaact gaataccttg ctatctcttt gatacatttt tacaaagctg   3540
aattaaaatg gtataaatta aatcactttt ttcaattctc tagaggtacc gcatgcgtac   3600
gtggccagcg gccgcaggta agccagccca ggcctcgccc tccagctcaa ggcgggacag   3660
gtgccctaga gtagcctgca tccagggaca ggccccagcc gggtgctgac acgtccacct   3720
ccatctcttc ctcaggtctg cccgggtggc atccctgtga cccctcccca gtgcctctcc   3780
tggccctgga agttgccact ccagtgccca ccagccttgt cctaataaaa ttaagttgca   3840
tcattttgtc tgactaggtg tccttctata atattatggg gtggaggggg gtggtatgga   3900
gcaaggggcc caagttaact tgtttattgc agcttataat ggttacaaat aaagcaatag   3960
catcacaaat ttcacaaata aagcattttt ttcactgcat tctagttgtg gtttgtccaa   4020
actcatcaat gtatcttatc atgtctggat ccagtcgact gaattggttc ctttaaagcc   4080
tgcttttttg tacaaagttg gcattataaa aaagcattgc tcatcaattt gttgcaacga   4140
acaggtcact atcagtcaaa ataaaatcat tatttggggc ccgagcttaa gactggccgt   4200
cgttttacaa cgtcgtgact gggaaaacat ccatgctagc gttaacgcga gagtagggaa   4260
ctgccaggca tcaaataaaa cgaaaggctc agtcggaaga ctgggccttt cgttttatct   4320
gttgtttgtc ggtgaacgct ctcctgagta ggacaaatcc gccgggagcg gatttgaacg   4380
```

ttgtgaagca acggcccgga gggtggcggg caggacgccc gccataaact gccaggcatc 4440
aaactaagca gaaggccatc ctgacggatg gcctttttgc gtttctacaa actcttcctg 4500
gctagcggta cgcgtattaa ttgcgttgcg ctcactgccc gctttccagt cgggaaacct 4560
gtcgtgccag ctgcattaat gaatcggcca acgcgcgggg agaggcggtt tgcgtattgg 4620
gcgctcttcc gcttcctcgc tcactgactc gctgcgctcg gtcgttcggc tgcggcgagc 4680
ggtatcagct cactcaaagg cggtaatacg gttatccaca gaatcagggg ataacgcagg 4740
aaag 4744

<210> SEQ ID NO 216
<211> LENGTH: 3377
<212> TYPE: DNA
<213> ORGANISM: Artificial Sequence
<220> FEATURE:
<221> NAME/KEY: misc_feature
<222> LOCATION: (1018)...(1036)
<223> OTHER INFORMATION: n may be any nucleotide
<220> FEATURE:
<221> NAME/KEY: misc_feature
<222> LOCATION: (1058)...(1078)
<223> OTHER INFORMATION: n may be any nucleotide
<220> FEATURE:
<221> NAME/KEY: source
<222> LOCATION: (1)...(3377)
<223> OTHER INFORMATION: ARI-207

<400> SEQUENCE: 216
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggcttt aaaggaacca attcagtcga ctggatccaa ggtcgggcag gaagagggcc 720
tatttcccat gattccttca tatttgcata tacgatacaa ggctgttaga gagataatta 780
gaattaattt gactgtaaac acaaagatat tagtacaaaa tacgtgacgt agaaagtaat 840
aatttcttgg gtagtttgca gttttaaaat tatgttttaa aatggactat catatgctta 900
ccgtaacttg aaagtatttc gatttcttgg ctttatatat cttgtggaaa ggacgaaact 960
agtccggatc aacgccctag gtttatgttt ggatgaactg acatacgcgt atccgtcnnn 1020
nnnnnnnnnn nnnnnngtag tgaaatatat attaaacnnn nnnnnnnnnn nnnnnnnnta 1080
cggtaacgcg gaattcgcaa ctattttatc aattttttgc gtcgactcga gtagctagag 1140
aattcatggt aatagcgatg actaatacgt agatgtactg ccaagtagga aagtcccata 1200
aggtcatgta ctgggcataa tgccaggcgg gccatttacc gtcattgacg tcaatagggg 1260
gcgtacttgg catatgatac acttgatgta ctgccaagtg ggcagtttac cgtaaatagt 1320

-continued

```
ccacccattg acgtcaatgg aaagtcccta ttggcgttac tatgggaaca tacgtcatta   1380
ttgacgtcaa tgggcggggg tcgttgggcg gtcagccagg cgggccattt accgtaagtt   1440
atgtaacgcg gaactccata tatgggctat gaactaatga ccccgtaatt gattactatt   1500
aataactaga cccagctttc ttgtacaaag ttggcattat aagaaagcat tgcttatcaa   1560
tttgttgcaa cgaacaggtc actatcagtc aaaataaaat cattatttgc catccagctg   1620
atatccccta tagtgagtcg tattacatgg tcatagctgt ttcctggcag ctctggcccg   1680
tgtctcaaaa tctctgatgt tacattgcac aagataaaaa tatatcatca tgaacaataa   1740
aactgtctgc ttacataaac agtaatacaa ggggtgttat gagccatatt caacgggaaa   1800
cgtcgaggcc gcgattaaat tccaacatgg atgctgattt atatgggtat aaatgggctc   1860
gcgataatgt cgggcaatca ggtgcgacaa tctatcgctt gtatgggaag cccgatgcgc   1920
cagagttgtt tctgaaacat ggcaaaggta gcgttgccaa tgatgttaca gatgagatgg   1980
tcagactaaa ctggctgacg gaatttatgc ctcttccgac catcaagcat tttatccgta   2040
ctcctgatga tgcatggtta ctcaccactg cgatccccgg aaaaacagca ttccaggtat   2100
tagaagaata tcctgattca ggtgaaaata ttgttgatgc gctggcagtg ttcctgcgcc   2160
ggttgcattc gattcctgtt tgtaattgtc cttttaacag cgatcgcgta tttcgtctcg   2220
ctcaggcgca atcacgaatg aataacggtt tggttgatgc gagtgatttt gatgacgagc   2280
gtaatggctg gcctgttgaa caagtctgga aagaaatgca taaacttttg ccattctcac   2340
cggattcagt cgtcactcat ggtgatttct cacttgataa ccttattttt gacgagggga   2400
aattaatagg ttgtattgat gttggacgag tcggaatcgc agaccgatac caggatcttg   2460
ccatcctatg gaactgcctc ggtgagtttt ctccttcatt acagaaacgg ctttttcaaa   2520
aatatggtat tgataatcct gatatgaata aattgcagtt tcatttgatg ctcgatgagt   2580
ttttctaatc agaattggtt aattggttgt aacactggca gagcattacg ctgacttgac   2640
gggacggcgc aagctcatga ccaaaatccc ttaacgtgag ttacgcgtcg ttccactgag   2700
cgtcagaccc cgtagaaaag atcaaaggat cttcttgaga tccttttttt ctgcgcgtaa   2760
tctgctgctt gcaaacaaaa aaaccaccgc taccagcggt ggtttgtttg ccggatcaag   2820
agctaccaac tctttttccg aaggtaactg gcttcagcag agcgcagata ccaaatactg   2880
tccttctagt gtagccgtag ttaggccacc acttcaagaa ctctgtagca ccgcctacat   2940
acctcgctct gctaatcctg ttaccagtgg ctgctgccag tggcgataag tcgtgtctta   3000
ccgggttgga ctcaagacga tagttaccgg ataaggcgca gcggtcgggc tgaacggggg   3060
gttcgtgcac acagcccagc ttggagcgaa cgacctacac cgaactgaga tacctacagc   3120
gtgagcattg agaaagcgcc acgcttcccg aagggagaaa ggcggacagg tatccggtaa   3180
gcggcagggt cggaacagga gagcgcacga gggagcttcc agggggaaac gcctggtatc   3240
tttatagtcc tgtcgggttt cgccacctct gacttgagcg tcgatttttg tgatgctcgt   3300
caggggggcg gagcctatgg aaaaacgcca gcaacgcggc ctttttacgg ttcctggcct   3360
tttgctggcc ttttgct                                                  3377
```

<210> SEQ ID NO 217
<211> LENGTH: 4738
<212> TYPE: DNA
<213> ORGANISM: Artificial Sequence
<220> FEATURE:
<221> NAME/KEY: misc_feature
<222> LOCATION: (3377)...(3395)
<223> OTHER INFORMATION: n may be any nucleotide

```
<220> FEATURE:
<221> NAME/KEY: misc_feature
<222> LOCATION: (3415)...(3433)
<223> OTHER INFORMATION: n may be any nucleotide
<220> FEATURE:
<221> NAME/KEY: source
<222> LOCATION: (1)...(4738)
<223> OTHER INFORMATION: ARI-208

<400> SEQUENCE: 217

aacatgtgag caaaaggcca gcaaaaggcc aggaaccgta aaaaggccgc gttgctggcg     60
tttttccata ggctccgccc ccctgacgag catcacaaaa atcgacgctc aagtcagagg    120
tggcgaaacc cgacaggact ataaagatac caggcgtttc cccctggaag ctccctcgtg    180
cgctctcctg ttccgaccct gccgcttacc ggatacctgt ccgcctttct cccttcggga    240
agcgtggcgc tttctcaatg ctcacgctgt aggtatctca gttcggtgta ggtcgttcgc    300
tccaagctgg gctgtgtgca cgaacccccc gttcagcccg accgctgcgc cttatccggt    360
aactatcgtc ttgagtccaa cccggtaaga cacgacttat cgccactggc agcagccact    420
ggtaacagga ttagcagagc gaggtatgta ggcggtgcta cagagttctt gaagtggtgg    480
cctaactacg gctacactag aaggacagta tttggtatct gcgctctgct gaagccagtt    540
accttcggaa aaagagttgg tagctcttga tccggcaaac aaaccaccgc tggtagcggt    600
ggtttttttg tttgcaagca gcagattacg cgcagaaaaa aaggatctca agaagatcct    660
ttgatctttt ctacggggtc tgacgctcag tggaacgacg cgtaactcac gttaagggat    720
tttggtcatg agcttgcgcc gtcccgtcaa gtcagcgtaa tgctctgcca gtgttacaac    780
caattaacca attctgatta gaaaaactca tcgagcatca aatgaaactg caatttattc    840
atatcaggat tatcaatacc atatttttga aaaagccgtt tctgtaatga aggagaaaac    900
tcaccgaggc agttccatag gatggcaaga tcctggtatc ggtctgcgat tccgactcgt    960
ccaacatcaa tacaacctat taatttcccc tcgtcaaaaa taaggttatc aagtgagaaa   1020
tcaccatgag tgacgactga atccggtgag aatggcaaaa gtttatgcat ttctttccag   1080
acttgttcaa caggccagcc attacgctcg tcatcaaaat cactcgcatc aaccaaaccg   1140
ttattcattc gtgattgcgc ctgagcgaga cgaaatacgc gatcgctgtt aaaaggacaa   1200
ttacaaacag gaatcgaatg caaccggcgc aggaacactg ccagcgcatc aacaatattt   1260
tcacctgaat caggatattc ttctaatacc tggaatgctg tttttccggg gatcgcagtg   1320
gtgagtaacc atgcatcatc aggagtacgg ataaaatgct tgatggtcgg aagaggcata   1380
aattccgtca gccagtttag tctgaccatc tcatctgtaa catcattggc aacgctacct   1440
ttgccatgtt tcagaaacaa ctctggcgca tcgggcttcc catacaagcg atagattgtc   1500
gcacctgatt gcccgacatt atcgcgagcc catttatacc catataaatc agcatccatg   1560
ttggaattta atcgcggcct cgacgtttcc cgttgaatat ggctcataac accccttgta   1620
ttactgttta tgtaagcaga cagttttatt gttcatgatg atatattttt atcttgtgca   1680
atgtaacatc agagattttg agacacgggc cagagctgcc aggaaacagc tatgaccatg   1740
taatacgact cactataggg gatatcagct ggatggcaaa taatgatttt attttgactg   1800
atagtgacct gttcgttgca acaaattgat aagcaatgct ttcttataat gccaactttg   1860
tacaagaaag ctgggtctag ttattaatag taatcaatta cggggtcatt agttcatagc   1920
ccatatatgg agttccgcgt tacataactt acggtaaatg gcccgcctgg ctgaccgccc   1980
aacgaccccc gcccattgac gtcaataatg acgtatgttc ccatagtaac gccaataggg   2040
```

```
actttccatt gacgtcaatg ggtggactat ttacggtaaa ctgcccactt ggcagtacat   2100
caagtgtatc atatgccaag tacgccccct attgacgtca atgacggtaa atggcccgcc   2160
tggcattatg cccagtacat gaccttatgg gactttccta cttggcagta catctacgta   2220
ttagtcatcg ctattaccat ggtgatgcgg ttttggcagt acatcaatgg gcgtggatag   2280
cggtttgact cacggggatt tccaagtctc caccccattg acgtcaatgg gagtttgttt   2340
tggcaccaaa atcaacggga ctttccaaaa tgtcgtaaca actccgcccc attgacgcaa   2400
atgggcggta ggcgtgtacg gtgggaggtc tatataagca gagctctctg gctaactaga   2460
gaacccactg cttactggct tatcgaaatt aatacgactc actataggga gacccaagct   2520
tagatctgtt tccggtcgcc accatgagcg agctgatcaa ggagaacatg cacatgaagc   2580
tgtacatgga gggcaccgtg aacaaccacc acttcaagtg cacatccgag ggcgaaggca   2640
agccctacga gggcacccag accatgaaga tcaaggtggt cgagggcggc cctctcccct   2700
tcgccttcga catcctggct accagcttca tgtacggcag caaagccttc atcaaccaca   2760
cccagggcat ccccgacttc tttaagcagt ccttccctga gggcttcaca tgggagagaa   2820
tcaccacata cgaagacggg ggcgtgctga ccgctaccca ggacaccagc ttccagaacg   2880
gctgcatcat ctacaacgtc aagatcaacg gggtgaactt cccatccaac ggccctgtga   2940
tgcagaagaa aacacgcggc tgggaggcca acaccgagat gctgtacccc gctgacggcg   3000
gcctgagagg ccacagccag atggccctga agctcgtggg cgggggctac ctgcactgct   3060
ccttcaagac cacatacaga tccaagaaac ccgctaagaa cctcaagatg cccggcttcc   3120
acttcgtgga ccacagactg gaaagaatca aggaggccga caaagagacc tacgtcgagc   3180
agcacgagat ggctgtggcc aagtactgcg acctccctag caaactgggg cacagataat   3240
cgatagtttg tttgaatgag gcttcagtac tttacagaat cgttgcctgc acatcttgga   3300
aacacttgct gggattactt cttcaggtta acccaacaga aggctcgaga aggtatattg   3360
ctgttgacag tgagcgnnnn nnnnnnnnnn nnnnntagtg aagccacaga tgtannnnnn   3420
nnnnnnnnnn nnntgcctac tgcctcggaa ttcaaggggc tactttagga gcaattatct   3480
tgtttactaa aactgaatac cttgctatct ctttgataca tttttacaaa gctgaattaa   3540
aatggtataa attaaatcac tttttttcaat tctctagagg taccgcatgc gtacgtggcc   3600
agcggccgca ggtaagccag cccaggcctc gccctccagc tcaaggcggg acaggtgccc   3660
tagagtagcc tgcatccagg gacaggcccc agccgggtgc tgacacgtcc acctccatct   3720
cttcctcagg tctgcccggg tggcatccct gtgacccctc cccagtgcct ctcctggccc   3780
tggaagttgc cactccagtg cccaccagcc ttgtcctaat aaaattaagt tgcatcattt   3840
tgtctgacta ggtgtccttc tataatatta tggggtggag gggggtggta tggagcaagg   3900
ggcccaagtt aacttgttta ttgcagctta taatggttac aaataaagca atagcatcac   3960
aaatttcaca aataaagcat ttttttcact gcattctagt tgtggtttgt ccaaactcat   4020
caatgtatct tatcatgtct ggatccagtc gactgaattg gttcctttaa agcctgcttt   4080
tttgtacaaa gttggcatta taaaaaagca ttgctcatca atttgttgca acgaacaggt   4140
cactatcagt caaaataaaa tcattatttg gggcccgagc ttaagactgg ccgtcgtttt   4200
acaacgtcgt gactgggaaa acatccatgc tagcgttaac gcgagagtag ggaactgcca   4260
ggcatcaaat aaaacgaaag gctcagtcgg aagactgggc ctttcgtttt atctgttgtt   4320
tgtcggtgaa cgctctcctg agtaggacaa atccgccggg agcggatttg aacgttgtga   4380
agcaacggcc cggagggtgg cgggcaggac gcccgccata aactgccagg catcaaacta   4440
```

agcagaaggc catcctgacg gatggccttt ttgcgtttct acaaactctt cctggctagc 4500
ggtacgcgta ttaattgcgt tgcgctcact gcccgctttc cagtcgggaa acctgtcgtg 4560
ccagctgcat taatgaatcg gccaacgcgc ggggagaggc ggtttgcgta ttgggcgctc 4620
ttccgcttcc tcgctcactg actcgctgcg ctcggtcgtt cggctgcggc gagcggtatc 4680
agctcactca aaggcggtaa tacggttatc cacagaatca ggggataacg caggaaag 4738

<210> SEQ ID NO 218
<211> LENGTH: 6329
<212> TYPE: DNA
<213> ORGANISM: Artificial Sequence
<220> FEATURE:
<223> OTHER INFORMATION: pKD46

<400> SEQUENCE: 218
catcgattta ttatgacaac ttgacggcta catcattcac tttttcttca caaccggcac 60
ggaactcgct cgggctggcc ccggtgcatt ttttaaatac ccgcgagaaa tagagttgat 120
cgtcaaaacc aacattgcga ccgacggtgg cgataggcat ccgggtggtg ctcaaaagca 180
gcttcgcctg gctgatacgt tggtcctcgc gccagcttaa gacgctaatc cctaactgct 240
ggcggaaaag atgtgacaga cgcgacggcg acaagcaaac atgctgtgcg acgctggcga 300
tatcaaaatt gctgtctgcc aggtgatcgc tgatgtactg acaagcctcg cgtacccgat 360
tatccatcgg tggatggagc gactcgttaa tcgcttccat gcgccgcagt aacaattgct 420
caagcagatt tatcgccagc agctccgaat agcgcccttc cccttgcccg gcgttaatga 480
tttgcccaaa caggtcgctg aaatgcggct ggtgcgcttc atccgggcga aagaaccccg 540
tattggcaaa tattgacggc cagttaagcc attcatgcca gtaggcgcgc ggacgaaagt 600
aaacccactg gtgataccat tcgcgagcct ccggatgacg accgtagtga tgaatctctc 660
ctggcgggaa cagcaaaata tcacccggtc ggcaaacaaa ttctcgtccc tgatttttca 720 ccacccccctg accgcgaatg gtgagattga gaatataacc tttcattccc agcggtcggt 780
cgataaaaaa atcgagataa ccgttggcct caatcggcgt taaacccgcc accagatggg 840
cattaaacga gtatcccggc agcaggggat cattttgcgc ttcagccata cttttcatac 900
tcccgccatt cagagaagaa accaattgtc catattgcat cagacattgc cgtcactgcg 960
tcttttactg gctcttctcg ctaaccaaac cggtaacccc gcttattaaa agcattctgt 1020
aacaaagcgg gaccaaagcc atgacaaaaa cgcgtaacaa aagtgtctat aatcacggca 1080
gaaaagtcca cattgattat ttgcacggcg tcacactttg ctatgccata gcatttttat 1140
ccataagatt agcggatcct acctgacgct ttttatcgca actctctact gtttctccat 1200
acccgttttt ttgggaattc gagctctaag gaggttataa aaaatggata ttaatactga 1260
aactgagatc aagcaaaagc attcactaac cccctttcct gttttcctaa tcagcccggc 1320
atttcgcggg cgatattttc acagctattt caggagttca gccatgaacg cttattacat 1380
tcaggatcgt cttgaggctc agagctgggc gcgtcactac cagcagctcg cccgtgaaga 1440
gaaagaggca gaactggcag acgacatgga aaaaggcctg ccccagcacc tgtttgaatc 1500
gctatgcatc gatcatttgc aacgccacgg ggccagcaaa aaatccatta cccgtgcgtt 1560
tgatgacgat gttgagtttc aggagcgcat ggcagaacac atccggtaca tggttgaaac 1620
cattgctcac caccaggttg atattgattc agaggtataa aacgaatgag tactgcactc 1680
gcaacgctgg ctgggaagct ggctgaacgt gtcggcatgg attctgtcga cccacaggaa 1740

-continued

```
ctgatcacca ctcttcgcca gacggcattt aaaggtgatg ccagcgatgc gcagttcatc   1800

gcattactga tcgttgccaa ccagtacggc cttaatccgt ggacgaaaga aatttacgcc   1860

tttcctgata agcagaatgg catcgttccg gtggtgggcg ttgatggctg gtcccgcatc   1920

atcaatgaaa accagcagtt tgatggcatg gactttgagc aggacaatga atcctgtaca   1980

tgccggattt accgcaagga ccgtaatcat ccgatctgcg ttaccgaatg gatggatgaa   2040

tgccgccgcg aaccattcaa aactcgcgaa ggcagagaaa tcacggggcc gtggcagtcg   2100

catcccaaac ggatgttacg tcataaagcc atgattcagt gtgcccgtct ggccttcgga   2160

tttgctggta tctatgacaa ggatgaagcc gagcgcattg tcgaaaatac tgcatacact   2220

gcagaacgtc agccggaacg cgacatcact ccggttaacg atgaaaccat gcaggagatt   2280

aacactctgc tgatcgccct ggataaaaca tgggatgacg acttattgcc gctctgttcc   2340

cagatatttc gccgcgacat tcgtgcatcg tcagaactga cacaggccga agcagtaaaa   2400

gctcttggat tcctgaaaca gaaagccgca gagcagaagg tggcagcatg acaccggaca   2460

ttatcctgca gcgtaccggg atcgatgtga gagctgtcga acagggggat gatgcgtggc   2520

acaaattacg gctcggcgtc atcaccgctt cagaagttca caacgtgata gcaaaacccc   2580

gctccggaaa gaagtggcct gacatgaaaa tgtcctactt ccacaccctg cttgctgagg   2640

tttgcaccgg tgtggctccg gaagttaacg ctaaagcact ggcctgggga aaacagtacg   2700

agaacgacgc cagaaccctg tttgaattca cttccggcgt gaatgttact gaatccccga   2760

tcatctatcg cgacgaaagt atgcgtaccg cctgctctcc cgatggttta tgcagtgacg   2820

gcaacggcct tgaactgaaa tgcccgttta cctcccggga tttcatgaag ttccggctcg   2880

gtggtttcga ggccataaag tcagcttaca tggcccaggt gcagtacagc atgtgggtga   2940

cgcgaaaaaa tgcctggtac tttgccaact atgacccgcg tatgaagcgt gaaggcctgc   3000

attatgtcgt gattgagcgg gatgaaaagt acatggcgag ttttgacgag atcgtgccgg   3060

agttcatcga aaaaatggac gaggcactgg ctgaaattgg ttttgtattt ggggagcaat   3120

ggcgatgacg catcctcacg ataatatccg ggtaggcgca atcactttcg tctactccgt   3180

tacaaagcga ggctgggtat ttcccggcct ttctgttatc cgaaatccac tgaaagcaca   3240

gcggctggct gaggagataa ataataaacg aggggctgta tgcacaaagc atcttctgtt   3300

gagttaagaa cgagtatcga gatggcacat agccttgctc aaattggaat caggtttgtg   3360

ccaataccag tagaaacaga cgaagaatcc atgggtatgg acagttttcc ctttgatatg   3420

taacggtgaa cagttgttct acttttgttt gttagtcttg atgcttcact gatagataca   3480

agagccataa gaacctcaga tccttccgta tttagccagt atgttctcta gtgtggttcg   3540

ttgtttttgc gtgagccatg agaacgaacc attgagatca tacttacttt gcatgtcact   3600

caaaaatttt gcctcaaaac tggtgagctg aatttttgca gttaaagcat cgtgtagtgt   3660

ttttcttagt ccgttacgta ggtaggaatc tgatgtaatg gttgttggta ttttgtcacc   3720

attcattttt atctggttgt tctcaagttc ggttacgaga tccatttgtc tatctagttc   3780

aacttggaaa atcaacgtat cagtcgggcg gcctcgctta tcaaccacca atttcatatt   3840

gctgtaagtg tttaaatctt tacttattgg tttcaaaacc cattggttaa gccttttaaa   3900

ctcatggtag ttattttcaa gcattaacat gaacttaaat tcatcaaggc taatctctat   3960

atttgccttg tgagttttct tttgtgttag ttcttttaat aaccactcat aaatcctcat   4020

agagtatttg ttttcaaaag acttaacatg ttccagatta tattttatga atttttttaa   4080

ctggaaaaga taaggcaata tctcttcact aaaaactaat tctaattttt cgcttgagaa   4140
```

-continued

```
cttggcatag tttgtccact ggaaaatctc aaagccttta accaaaggat tcctgatttc   4200
cacagttctc gtcatcagct ctctggttgc tttagctaat acaccataag cattttccct   4260
actgatgttc atcatctgag cgtattggtt ataagtgaac gataccgtcc gttctttcct   4320
tgtagggttt tcaatcgtgg ggttgagtag tgccacacag cataaaatta gcttggtttc   4380
atgctccgtt aagtcatagc gactaatcgc tagttcattt gctttgaaaa caactaattc   4440
agacatacat ctcaattggt ctaggtgatt ttaatcacta taccaattga gatgggctag   4500
tcaatgataa ttactagtcc ttttcctttg agttgtgggt atctgtaaat tctgctagac   4560
ctttgctgga aaacttgtaa attctgctag accctctgta aattccgcta gacctttgtg   4620
tgtttttttt gtttatattc aagtggttat aatttataga ataaagaaag aataaaaaaa   4680
gataaaaaga atagatccca gccctgtgta taactcacta ctttagtcag ttccgcagta   4740
ttacaaaagg atgtcgcaaa cgctgtttgc tcctctacaa aacagacctt aaaaccctaa   4800
aggcttaagt agcaccctcg caagctcggt tgcggccgca atcgggcaaa tcgctgaata   4860
ttccttttgt ctccgaccat caggcacctg agtcgctgtc tttttcgtga cattcagttc   4920
gctgcgctca cggctctggc agtgaatggg ggtaaatggc actacaggcg ccttttatgg   4980
attcatgcaa ggaaactacc cataatacaa gaaaagcccg tcacgggctt ctcagggcgt   5040
tttatggcgg gtctgctatg tggtgctatc tgactttttg ctgttcagca gttcctgccc   5100
tctgattttc cagtctgacc acttcggatt atcccgtgac aggtcattca gactggctaa   5160
tgcacccagt aaggcagcgg tatcatcaac ggggtctgac gctcagtgga acgaaaactc   5220
acgttaaggg attttggtca tgagattatc aaaaaggatc ttcacctaga tccttttaaa   5280
ttaaaaatga agttttaaat caatctaaag tatatatgag taaacttggt ctgacagtta   5340
ccaatgctta atcagtgagg cacctatctc agcgatctgt ctatttcgtt catccatagt   5400
tgcctgactc cccgtcgtgt agataactac gatacgggag ggcttaccat ctggccccag   5460
tgctgcaatg ataccgcgag acccacgctc accggctcca gatttatcag caataaacca   5520
gccagccgga agggccgagc gcagaagtgg tcctgcaact ttatccgcct ccatccagtc   5580
tattaattgt tgccgggaag ctagagtaag tagttcgcca gttaatagtt tgcgcaacgt   5640
tgttgccatt gctacaggca tcgtggtgtc acgctcgtcg tttggtatgg cttcattcag   5700
ctccggttcc caacgatcaa ggcgagttac atgatccccc atgttgtgca aaaaagcggt   5760
tagctccttc ggtcctccga tcgttgtcag aagtaagttg gccgcagtgt tatcactcat   5820
ggttatggca gcactgcata attctcttac tgtcatgcca tccgtaagat gcttttctgt   5880
gactggtgag tactcaacca agtcattctg agaatagtgt atgcggcgac cgagttgctc   5940
ttgcccggcg tcaatacggg ataataccgc gccacatagc agaactttaa aagtgctcat   6000
cattggaaaa cgttcttcgg ggcgaaaact ctcaaggatc ttaccgctgt tgagatccag   6060
ttcgatgtaa cccactcgtg cacccaactg atcttcagca tcttttactt tcaccagcgt   6120
ttctgggtga gcaaaaacag gaaggcaaaa tgccgcaaaa aagggaataa gggcgacacg   6180
gaaatgttga atactcatac tcttcctttt tcaatattat tgaagcattt atcagggtta   6240
ttgtctcatg agcggataca tatttgaatg tatttagaaa aataaacaaa taggggttcc   6300
gcgcacattt ccccgaaaag tgccacctg                                     6329
```

<210> SEQ ID NO 219
<211> LENGTH: 22
<212> TYPE: DNA

<213> ORGANISM: Artificial Sequence
<220> FEATURE:
<223> OTHER INFORMATION: asd-1 primer

<400> SEQUENCE: 219
ccttcctaac gcaaattccc tg 22

<210> SEQ ID NO 220
<211> LENGTH: 22
<212> TYPE: DNA
<213> ORGANISM: Artificial Sequence
<220> FEATURE:
<223> OTHER INFORMATION: asd-2 primer

<400> SEQUENCE: 220
ccaatgctct gcttaactcc tg 22

<210> SEQ ID NO 221
<211> LENGTH: 21
<212> TYPE: DNA
<213> ORGANISM: Artificial Sequence
<220> FEATURE:
<223> OTHER INFORMATION: asd-3 primer

<400> SEQUENCE: 221
gcctcgccat gtttcagtac g 21

<210> SEQ ID NO 222
<211> LENGTH: 21
<212> TYPE: DNA
<213> ORGANISM: Artificial Sequence
<220> FEATURE:
<223> OTHER INFORMATION: asd-4 primer

<400> SEQUENCE: 222
ggtctggtgc attccgagta c 21

<210> SEQ ID NO 223
<211> LENGTH: 23
<212> TYPE: DNA
<213> ORGANISM: Artificial Sequence
<220> FEATURE:
<223> OTHER INFORMATION: scFv-3 primer

<400> SEQUENCE: 223
cataatctgg gtccttggtc tgc 23

<210> SEQ ID NO 224
<211> LENGTH: 5728
<212> TYPE: DNA
<213> ORGANISM: Artificial Sequence
<220> FEATURE:
<223> OTHER INFORMATION: pJW168 plasmid

<400> SEQUENCE: 224
ttactaatcg ccatcttcca gcaggcgcac cattgcccct gtttcactat ccaggttacg 60
gatatagttc atgacaatat ttacattggt ccagccacca gcttgcatga tctccggtat 120
tgaaactcca gcgcgggcca tatctcgcgc ggctccgaca cgggcactgt gtccagacca 180
ggccaggtat ctctgaccag agtcatcctt agcgccgtaa atcaatcgat gagttgcttc 240
aaaaatccct tccagggcgc gagttgatag ctggctggtg gcagatggcg cggcaacacc 300 atttttctg acccggcaaa acaggtagtt attcggatca tcagctacac cagagacgga 360
aatccatcgc tcgaccagtt tagttacccc caggctaagt gccttctcta cacctgcggt 420
gctaaccagc gttttcgttc tgccaatatg gattaacatt ctcccaccgt cagtacgtga 480
gatatcttta accctgatcc tggcaatttc ggctatacgt aacagggtgt tataagcaat 540
ccccagaaat gccagattac gtatatcctg gcagcgatcg ctattttcca tgagtgaacg 600
aacctggtcg aaatcagtgc gttcgaacgc tagagcctgt tttgcacgtt caccggcatc 660
aacgttttct tttcggatcc gccgcataac cagtgaaaca gcattgctgt cacttggtcg 720
tggcagcccg gaccgacgat gaagcatgtt tagctggccc aaatgttgct ggatagtttt 780
tactgccaga ccgcgcgcct gaagatatag aagataatcg cgaacatctt caggttctgc 840
gggaaaccat ttccggttat tcaacttgca ccatgccgcc cacgaccggc aaacggacag 900
aagcattttc caggtatgct cagaaaacgc ctggcgatcc ctgaacatgt ccatcaggtt 960
cttgcgaacc tcatcactcg ttgcatcgac cggtaatgca ggcaaatttt ggtgtacggg 1020
cagtaaattg gacatgtcaa cggtacctgc agtctagagt cgaggcctgt ttcctgtgtg 1080
aaattgttat ccgctcacaa ttccacacat tatacgagcc ggaagcataa agtgtaaagc 1140
ctggggtgcc taatgagtga gctgtttcct gtgtgaaatt gttatccgct cacaattcca 1200
cacattatac gagccggaag cataaagtgt aaagcctggg gtgcctaatg agtgagctgc 1260
ctcgcgcgtt tcggtgatga cggtgaaaac ctctgacaca tgcagctccc ggagacggtc 1320
acagcttgtc tgtaagcgga tgccgggagc agacaagccc gtcagggcgc gtcagcgggt 1380
gttggcgggt gtcggggcgc agccatgacc cagtcacgta gcgatagacg gagtgtatcc 1440
gacaccatcg aatggtgcaa aacctttcgc ggtatggcat gatagcgccc ggaagagagt 1500
caattcaggg tggtgaatgt gaaaccagta acgttatacg atgtcgcaga gtatgccggt 1560
gtctcttatc agaccgtttc ccgcgtggtg aaccaggcca gccacgtttc tgcgaaaacg 1620
cgggaaaaag tggaagcggc gatggcggag ctgaattaca ttcccaaccg cgtggcacaa 1680
caactggcgg gcaaacagtc gttgctgatt ggcgttgcca cctccagtct ggccctgcac 1740
gcgccgtcgc aaattgtcgc ggcgattaaa tctcgcgccg atcaactggg tgccagcgtg 1800
gtggtgtcga tggtagaacg aagcggcgtc gaagcctgta aagcggcggt gcacaatctt 1860
ctcgcgcaac gcgtcagtgg gctgatcatt aactatccgc tggatgacca ggatgccatt 1920
gctgtggaag ctgcctgcac taatgttccg gcgttatttc ttgatgtctc tgaccagaca 1980
cccatcaaca gtattatttt ctcccatgaa gacggtacgc gactgggcgt ggagcatctg 2040
gtcgcattgg gtcaccagca aatcgcgctg ttagcgggcc cattaagttc tgtctcggcg 2100
cgtctgcgtc tggctggctg gcataaatat ctcactcgca atcaaattca gccgatagcg 2160
gaacgggaag gcgactggag tgccatgtcc ggttttcaac aaaccatgca aatgctgaat 2220
gagggcatcg ttcccactgc gatgctggtt gccaacgatc agatggcgct gggcgcaatg 2280
cgcgccatta ccgagtccgg gctgcgcgtt ggtgcggata tctcggtagt gggatacgac 2340
gataccgaag acagctcatg ttatatcccg ccgttaacca ccatcaaaca ggattttcgc 2400
ctgctggggc aaaccagcgt ggaccgcttg ctgcaactct ctcagggcca ggcggtgaag 2460
ggcaatcagc tgttgcccgt ctcactggtg aaaagaaaaa ccaccctggc gcccaatacg 2520
caaaccgcct ctccccgcgc gttggccgat tcattaatgc agctggcacg acaggtttcc 2580
cgactggaaa gcgggcagtg agcgcaacgc aatcaatgtg agttagctca ctcattaggc 2640
accccaggct ttacacttta tgcttccgac catactggct taactatgcg gcatcagagc 2700
agattgtact gagagtgcac catcgatgca ggtggcactt ttcggggaaa tgtgcgcgga 2760

-continued

```
accccctattt gtttattttt ctaaatacat tcaaatatgt atccgctcat gagacaataa   2820
ccctgataaa tgcttcaata atattgaaaa aggaagagta tgagtattca acatttccgt   2880
gtcgccctta ttcccttttt tgcggcattt tgccttcctg tttttgctca cccagaaacg   2940
ctggtgaaag taaaagatgc tgaagatcag ttgggtgcac gagtgggtta catcgaactg   3000
gatctcaaca gcggtaagat ccttgagagt tttcgccccg aagaacgttt tccaatgatg   3060
agcactttta aagttctgct atgtggcgcg gtattatccc gtattgacgc cgggcaagag   3120
caactcggtc gccgcataca ctattctcag aatgacttgg ttgagtactc accagtcaca   3180
gaaaagcatc ttacggatgg catgacagta agagaattat gcagtgctgc cataaccatg   3240
agtgataaca ctgcggccaa cttacttctg acaacgatcg gaggaccgaa ggagctaacc   3300
gcttttttgc acaacatggg ggatcatgta actcgccttg atcgttggga accggagctg   3360
aatgaagcca taccaaacga cgagcgtgac accacgatgc ctgtagcaat ggcaacaacg   3420
ttgcgcaaac tattaactgg cgaactactt actctagctt cccggcaaca attaatagac   3480
tggatggagg cggataaagt tgcaggacca cttctgcgct cggcccttcc ggctggctgg   3540
tttattgctg ataaatctgg agccggtgag cgtgggtctc gcggtatcat tgcagcactg   3600
gggccagatg gtaagccctc ccgtatcgta gttatctaca cgacggggag tcaggcaact   3660
atggatgaac gaaatagaca gatcgctgag ataggtgcct cactgattaa gcattggtaa   3720
ctgtcagacc aagtttactc atatatactt tagattgatt taaaacttca tttttaattt   3780
aaaaggatct aggtgaagat cctttttgat aatctcatga ccaaaatccc ttaacgtgag   3840
ttttcgttcc actgagcgtc agaccccgtt gatgataccg ctgccttact gggtgcatta   3900
gccagtctga atgacctgtc acgggataat ccgaagtggt cagactggaa aatcagaggg   3960
caggaactgc tgaacagcaa aaagtcagat agcaccacat agcagacccg ccataaaacg   4020
ccctgagaag cccgtgacgg gcttttcttg tattatgggt agtttccttg catgaatcca   4080
taaaaggcgc ctgtagtgcc atttaccccc attcactgcc agagccgtga gcgcagcgaa   4140
ctgaatgtca cgaaaaagac agcgactcag gtgcctgatg gtcggagaca aaaggaatat   4200
tcagcgattt gcccgattgc ggccgcaacc gagcttgcga gggtgctact taagccttta   4260
gggttttaag gtctgttttg tagaggagca aacagcgttt gcgacatcct tttgtaatac   4320
tgcggaactg actaaagtag tgagttatac acagggctgg gatctattct ttttatcttt   4380
ttttattctt tctttattct ataaattata accacttgaa tataaacaaa aaaaacacac   4440
aaaggtctag cggaatttac agagggtcta gcagaattta caagttttcc agcaaaggtc   4500
tagcagaatt tacagatacc cacaactcaa aggaaaagga ctagtaatta tcattgacta   4560
gcccatctca attggtatag tgattaaaat cacctagacc aattgagatg tatgtctgaa   4620
ttagttgttt tcaaagcaaa tgaactagcg attagtcgct atgacttaac ggagcatgaa   4680
accaagctaa ttttatgctg tgtggcacta ctcaacccca cgattgaaaa ccctacaagg   4740
aaagaacgga cggtatcgtt cacttataac caatacgttc agatgatgaa catcagtagg   4800
gaaaatgctt atggtgtatt agctaaagca accagagagc tgatgacgag aactgtggaa   4860
atcaggaatc ctttggttaa aggctttgag attttccagt ggacaaacta tgccaagttc   4920
tcaagcgaaa aattagaatt agtttttagt gaagagatat tgccttatct tttccagtta   4980
aaaaaattca taaaatataa tctggaacat gttaagtctt ttgaaaacaa atactctatg   5040
aggatttatg agtggttatt aaaagaacta acacaaaaga aaactcacaa ggcaaatata   5100
gagattagcc ttgatgaatt taagttcatg ttaatgcttg aaaataacta ccatgagttt   5160
```

-continued aaaaggctta accaatgggt tttgaaacca ataagtaaag atttaaacac ttacagcaat 5220
atgaaattgg tggttgataa gcgaggccgc ccgactgata cgttgatttt ccaagttgaa 5280
ctagatagac aaatggatct cgtaaccgaa cttgagaaca accagataaa aatgaatggt 5340
gacaaaatac caacaaccat tacatcagat tcctacctac ataacggact aagaaaaaca 5400
ctacacgatg ctttaactgc aaaaaattcag ctcaccagtt ttgaggcaaa atttttgagt 5460
gacatgcaaa gtaagyatga tctcaatggt tcgttctcat ggctcacgca aaaacaacga 5520
accacactag agaacatact ggctaaatac ggaaggatct gaggttctta tggctcttgt 5580
atctatcagt gaagcatcaa gactaacaaa caaaagtaga acaactgttc accgttacat 5640
atcaaaggga aaactgtcca tacccatggg ctagctgatc agccagtgcc aagcttgctc 5700
aatcaatcac cggatccccc gggaattc 5728

<210> SEQ ID NO 225
<211> LENGTH: 3736
<212> TYPE: DNA
<213> ORGANISM: Artificial Sequence
<220> FEATURE:
<223> OTHER INFORMATION: pATIU6 plasmid

<400> SEQUENCE: 225
gcgcccaata cgcaaaccgc ctctccccgc gcgttggccg attcattaat gcagctggca 60
cgacaggttt cccgactgga aagcgggcag tgagcgcaac gcaatggatc caaggtcggg 120
caggaagagg gcctatttcc catgattcct tcatatttgc atatacgata caaggctgtt 180
agagagataa ttagaattaa tttgactgta aacacaaaga tattagtaca aaatacgtga 240
cgtagaaagt aataatttct tgggtagttt gcagttttaa aattatgttt taaaatggac 300
tatcatatgc ttaccgtaac ttgaaagtat ttcgatttct tggctttata tatcttgtgg 360
aaaggacgaa actagttttt tctcgagtag ctagagaatt cttaagccag ccccgacacc 420
cgccaacacc cgctgacgcg ccctgacggg cttgtctgct cccggcatcc gcttacagac 480
aagctgtgac cgtctccggg agctgcatgt gtcagaggtt ttcaccgtca tcaccgaaac 540
gcgcgagacg aaagggcctc gtgatacgcc tatttttata ggttaatgtc atgataataa 600
tggtttctta gacgtcaggt ggcacttttc ggggaaatgt gaagcttcgc ggaaccccta 660
tttgtttatt tttctaaata cattcaaata tgtatccgct catgagacaa taaccctgat 720
aaatgcttca ataatattga aaaaggaaga gtatgagtat tcaacatttc cgtgtcgccc 780
ttattccctt ttttgcggca ttttgccttc ctgtttttgc tcacccagaa acgctggtga 840
aagtaaaaga tgctgaagat cagttgggtg cacgagtggg ttacatcgaa ctggatctca 900
acagcggtaa gatccttgag agttttcgcc ccgaagaacg ttttccaatg atgagcactt 960
ttaaagttct gctatgtggc gcggtattat cccgtattga cgccgggcaa gagcaactcg 1020
gtcgccgcat acactattct cagaatgact tggttgagta ctcaccagtc acagaaaagc 1080
atcttacgga tggcatgaca gtaagagaat tatgcagtgc tgccataacc atgagtgata 1140
acactgcggc caacttactt ctgacaacga tcggaggacc gaaggagcta accgcttttt 1200
tgcacaacat gggggatcat gtaactcgcc ttgatcgttg ggaaccggag ctgaatgaag 1260
ccataccaaa cgacgagcgt gacaccacga tgcctgtagc aatggcaaca acgttgcgca 1320
aactattaac tggcgaacta cttactctag cttcccggca acaattaata gactggatgg 1380
aggcggataa agttgcagga ccacttctgc gctcggccct tccggctggc tggtttattg 1440

```
ctgataaatc tggagccggt gagcgtgggt ctcgcggtat cattgcagca ctggggccag   1500
atggtaagcc ctcccgtatc gtagttatct acacgacggg gagtcaggca actatggatg   1560
aacgaaatag acagatcgct gagataggtg cctcactgat taagcattgg taaaagcttc   1620
tgtcagacca agtttactca tatatacttt agattgattt aaaacttcat ttttaattta   1680
aaaggatcta ggtgaagatc ctttatggtg aaggatgcgc cacaggatac tggcgcgcat   1740
acacagcaca tctctttgca ggaaaaaaac gctatgaaaa atgttggttt tatcggctgg   1800
cgcggaatgg tcggctctgt tctcatgcaa cgcatggtag aggagcgcga tttcgacgct   1860
attcgccctg ttttcttttc tacctcccag tttggacagg cggcgcccac cttcggcgac   1920
acctccaccg gcacgctaca ggacgctttt gatctggatg cgctaaaagc gctcgatatc   1980
atcgtgacct gccagggcgg cgattatacc aacgaaattt atccaaagct gcgcgaaagc   2040
ggatggcagg gttactggat tgatgcggct tctacgctgc gcatgaaaga tgatgccatt   2100
attattctcg acccggtcaa ccaggacgtg attaccgacg gcctgaacaa tggcgtgaag   2160
acctttgtgg gcggtaactg taccgttagc ctgatgttga tgtcgctggg cggtctcttt   2220
gcccataatc tcgttgactg ggtatccgtc gcgacctatc aggccgcctc cggcggcggc   2280
gcgcgccata tgcgcgagct gttaacccag atgggtcagt tgtatggcca tgtcgccgat   2340
gaactggcga cgccgtcttc cgcaattctt gatattgaac gcaaagttac ggcattgacc   2400
cgcagcggcg agctgccggt tgataacttt ggcgtaccgc tggcgggaag cctgatcccc   2460
tggatcgaca aacagctcga taacggccag agccgcgaag agtggaaagg ccaggcggaa   2520
accaacaaga ttctcaatac tgcctctgtg attccggttg atggtttgtg tgtgcgcgtc   2580
ggcgcgctgc gctgtcacag ccaggcgttc accatcaagc tgaaaaaaga ggtatccatt   2640
ccgacggtgg aagaactgct ggcggcacat aatccgtggg cgaaagtggt gccgaacgat   2700
cgtgatatca ctatgcgcga attaaccccg gcggcggtga ccggcacgtt gactacgccg   2760
gttggtcgtc tgcgtaagct gaacatgggg ccagagttct tgtcggcgtt taccgtaggc   2820
gaccagttgt tatggggcgc cgccgagccg ctgcgtcgaa tgctgcgcca gttggcgtag   2880
ttgataatct catgaccaaa atcccttaac gtgagttttc gttccactga gcgtcagacc   2940
ccgtagaaaa gatcaaagga tcttcttgag atcctttttt tctgcgcgta atctgctgct   3000
tgcaaacaaa aaaaccaccg ctaccagcgg tggtttgttt gccggatcaa gagctaccaa   3060
ctctttttcc gaaggtaact ggcttcagca gagcgcagat accaaatact gttcttctag   3120
tgtagccgta gttaggccac cacttcaaga actctgtagc accgcctaca tacctcgctc   3180
tgctaatcct gttaccagtg gctgctgcca gtggcgataa gtcgtgtctt accgggttgg   3240
actcaagacg atagttaccg gataaggcgc agcggtcggg ctgaacgggg ggttcgtgca   3300
cacagcccag cttggagcga acgacctaca ccgaactgag atacctacag cgtgagctat   3360
gagaaagcgc cacgcttccc gaagggagaa aggcggacag gtatccggta agcggcaggg   3420
tcggaacagg agagcgcacg agggagcttc cagggggaaa cgcctggtat ctttatagtc   3480
ctgtcgggtt tcgccacctc tgacttgagc gtcgattttt gtgatgctcg tcaggggggc   3540
ggagcctatg gaaaaacgcc agcaacgcgg cctttttacg gttcctggcc ttttgctggc   3600
cttttgctca catgttcttt cctgcgttat cccctgattc tgtggataac cgtattaccg   3660
cctttgagtg agctgatacc gctcgccgca gccgaacgac cgagcgcagc gagtcagtga   3720
gcgaggaagc ggaaga                                                   3736
```

<210> SEQ ID NO 226
<211> LENGTH: 26
<212> TYPE: DNA
<213> ORGANISM: Artificial Sequence
<220> FEATURE:
<223> OTHER INFORMATION: APR-001 Kan PrimerF

<400> SEQUENCE: 226
aaaaaagctt gcagctctgg cccgtg 26

<210> SEQ ID NO 227
<211> LENGTH: 38
<212> TYPE: DNA
<213> ORGANISM: Artificial Sequence
<220> FEATURE:
<223> OTHER INFORMATION: APR-002 Kan PrimerR

<400> SEQUENCE: 227
aaaaaagctt ttagaaaaac tcatcgagca tcaaatga 38

<210> SEQ ID NO 228
<211> LENGTH: 28
<212> TYPE: DNA
<213> ORGANISM: Artificial Sequence
<220> FEATURE:
<223> OTHER INFORMATION: APR-003 pATI ori T148CF

<400> SEQUENCE: 228
acactagaag gacagtattt ggtatctg 28

<210> SEQ ID NO 229
<211> LENGTH: 18
<212> TYPE: DNA
<213> ORGANISM: Artificial Sequence
<220> FEATURE:
<223> OTHER INFORMATION: APR-004 pATI ori T148CR

<400> SEQUENCE: 229
agccgtagtt aggccacc 18

<210> SEQ ID NO 230
<211> LENGTH: 3203
<212> TYPE: DNA
<213> ORGANISM: Artificial Sequence
<220> FEATURE:
<223> OTHER INFORMATION: pSL0147 plasmid

<400> SEQUENCE: 230
gacgaaaggg cctcgtgata cgcctatttt tataggttaa tgtcatgata ataatggttt 60
cttagacgtc aggtggcact tttcggggaa atgtgcgcgg aacccctatt tgtttatttt 120
tctaaataca ttcaaatatg tatccgctca tgagacaata accctgataa atgcttcaat 180
aatattgaaa aaggaagagt atgagtattc aacatttccg tgtcgccctt attccctttt 240
ttgcggcatt ttgccttcct gtttttgctc acccagaaac gctggtgaaa gtaaaagatg 300
ctgaagatca gttgggtgca cgagtgggtt acatcgaact ggatctcaac agcggtaaga 360
tccttgagag ttttcgcccc gaagaacgtt ttccaatgat gagcactttt aaagttctgc 420
tatgtggcgc ggtattatcc cgtattgacg ccgggcaaga gcaactcggt cgccgcatac 480
actattctca gaatgacttg gttgagtact caccagtcac agaaaagcat cttacggatg 540
gcatgacagt aagagaatta tgcagtgctg ccataaccat gagtgataac actgcggcca 600
acttacttct gacaacgatc ggaggaccga aggagctaac cgcttttttg cacaacatgg 660

-continued

```
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctc ggcgcgccat tgggatggaa cgcgttatcg gcaatctgga   2280
ggcaaagttt aatgataatt ttgcaaaaat aatgcgcgga ataatgatgc ataaagcggc   2340
tatttcgccg cctaagaaaa agatcggggg aagtgaaaaa ttttctaaag ttcgaaattc   2400
aggtgccgat acaagggtta cggtgagaaa ccgtgggcaa cagcccaata acatcaagtt   2460
gtaattgata aggaaaagat catgggctag cctcaataag cttcttgcct ttctgcagac   2520
caaggaccca gattatgttg cagcaggccg gtacctccgt tctggcgcag gcgaaccagg   2580
ttccgcaaaa cgtcctctct ttactgcgtt aatccggcga ttgattcacc gacacgtggt   2640
acacaatcaa ggcagcgaaa gctgcctttt ttaattccgg agcctgtgta atgaaagaaa   2700
tcaccgtcac tgaacctgcc tttgtcaccc gcttttcctg ttctggctcg gcctgtcgcg   2760
accactgttg taagggctgg aaagttccat cccaatacgc gtcaattcac tggccgtcgt   2820
tttacaacgt cgtgactggg aaaaccctgg cgttacccaa cttaatcgcc ttgcagcaca   2880
tccccctttc gccagctggc gtaatagcga agaggcccgc accgatcgcc cttcccaaca   2940
gttgcgcagc ctgaatggcg aatggcgcct gatgcggtat tttctcctta cgcatctgtg   3000
cggtatttca caccgcatat ggtgcactct cagtacaatc tgctctgatg ccgcatagtt   3060
```

```
aagccagccc cgacacccgc caacacccgc tgacgcgccc tgacgggctt gtctgctccc   3120

ggcatccgct tacagacaag ctgtgaccgt ctccgggagc tgcatgtgtc agaggttttc   3180

accgtcatca ccgaaacgcg cga                                           3203
```

<210> SEQ ID NO 231
<211> LENGTH: 3196
<212> TYPE: DNA
<213> ORGANISM: Artificial Sequence
<220> FEATURE:
<223> OTHER INFORMATION: pSL0148 plasmid

<400> SEQUENCE: 231

```
gacgaaaggg cctcgtgata cgcctatttt tataggttaa tgtcatgata ataatggttt     60

cttagacgtc aggtggcact tttcggggaa atgtgcgcgg aacccctatt tgtttatttt    120

tctaaataca ttcaaatatg tatccgctca tgagacaata accctgataa atgcttcaat    180

aatattgaaa aaggaagagt atgagtattc aacatttccg tgtcgccctt attccctttt    240

ttgcggcatt ttgccttcct gtttttgctc acccagaaac gctggtgaaa gtaaaagatg    300

ctgaagatca gttgggtgca cgagtgggtt acatcgaact ggatctcaac agcggtaaga    360

tccttgagag ttttcgcccc gaagaacgtt ttccaatgat gagcactttt aaagttctgc    420

tatgtggcgc ggtattatcc cgtattgacg ccgggcaaga gcaactcggt cgccgcatac    480

actattctca gaatgacttg gttgagtact caccagtcac agaaaagcat cttacggatg    540

gcatgacagt aagagaatta tgcagtgctg ccataaccat gagtgataac actgcggcca    600

acttacttct gacaacgatc ggaggaccga aggagctaac cgcttttttg cacaacatgg    660

gggatcatgt aactcgcctt gatcgttggg aaccggagct gaatgaagcc ataccaaacg    720

acgagcgtga caccacgatg cctgtagcaa tggcaacaac gttgcgcaaa ctattaactg    780

gcgaactact tactctagct tcccggcaac aattaataga ctggatggag gcggataaag    840

ttgcaggacc acttctgcgc tcggcccttc cggctggctg gtttattgct gataaatctg    900

gagccggtga gcgtgggtct cgcggtatca ttgcagcact ggggccagat ggtaagccct    960

cccgtatcgt agttatctac acgacgggga gtcaggcaac tatggatgaa cgaaatagac   1020

agatcgctga gataggtgcc tcactgatta agcattggta actgtcagac caagtttact   1080

catatatact ttagattgat ttaaaacttc atttttaatt taaaaggatc taggtgaaga   1140

tcctttttga taatctcatg accaaaatcc cttaacgtga gttttcgttc cactgagcgt   1200

cagaccccgt agaaaagatc aaaggatctt cttgagatcc tttttttctg cgcgtaatct   1260

gctgcttgca aacaaaaaaa ccaccgctac cagcggtggt ttgtttgccg gatcaagagc   1320

taccaactct ttttccgaag gtaactggct tcagcagagc gcagatacca aatactgttc   1380

ttctagtgta gccgtagtta ggccaccact tcaagaactc tgtagcaccg cctacatacc   1440

tcgctctgct aatcctgtta ccagtggctg ctgccagtgg cgataagtcg tgtcttaccg   1500

ggttggactc aagacgatag ttaccggata aggcgcagcg gtcgggctga acggggggtt   1560

cgtgcacaca gcccagcttg gagcgaacga cctacaccga actgagatac ctacagcgtg   1620

agctatgaga aagcgccacg cttcccgaag ggagaaaggc ggacaggtat ccggtaagcg   1680

gcagggtcgg aacaggagag cgcacgaggg agcttccagg gggaaacgcc tggtatcttt   1740

atagtcctgt cgggtttcgc cacctctgac ttgagcgtcg atttttgtga tgctcgtcag   1800

gggggcggag cctatggaaa aacgccagca acgcggcctt tttacggttc ctggcctttt   1860
```

```
gctggccttt tgctcacatg ttctttcctg cgttatcccc tgattctgtg gataaccgta   1920

ttaccgcctt tgagtgagct gataccgctc gccgcagccg aacgaccgag cgcagcgagt   1980

cagtgagcga ggaagcggaa gagcgcccaa tacgcaaacc gcctctcccc gcgcgttggc   2040

cgattcatta atgcagctgg cacgacaggt ttcccgactg gaaagcgggc agtgagcgca   2100

acgcaattaa tgtgagttag ctcactcatt aggcacccca ggctttacac tttatgcttc   2160

cggctcgtat gttgtgtgga attgtgagcg gataacaatt tcacacagga aacagctatg   2220

accatgatta cgccaagctc ggcgcgccat tgggatggaa cttccagacg acaagagtat   2280

cgcctttatt tacatacttt aacgctcgtt tcaggccggg gcggtttgca atcttgccac   2340

tgatacggtc ctcaaaaatg cggtcacaat ttgcactagt aagcgcatta cgctgtaaat   2400

cgatattttg gtcaattgtt gacacccgaa tatacccaat agtagccatg attttctcct   2460

ttacatcaga taaggaagaa ttttagtcgc ttttctcatg gaggattgct gctagcctca   2520

ataagcttct tgcctttctg cagaccaagg acccagatta tgtatggaat gtatggctgt   2580

aaatgatatt tcctacgggc gagaagctga aatatggccg cgggattatt ctatgcttgc   2640

tcgtcgagtt caatttctac gttttaatga tatccctgtt cgattggtga gtaataatgc   2700

ccggataatc acaggctaca ttgcgaagtt taatccgaag gaaaatttga ttctggcttc   2760

ggataaacct aaaggagttc catcccaata cgcgtcaatt cactggccgt cgttttacaa   2820

cgtcgtgact gggaaaaccc tggcgttacc caacttaatc gccttgcagc acatccccct   2880

ttcgccagct ggcgtaatag cgaagaggcc cgcaccgatc gcccttccca acagttgcgc   2940

agcctgaatg gcgaatggcg cctgatgcgg tattttctcc ttacgcatct gtgcggtatt   3000

tcacaccgca tatggtgcac tctcagtaca atctgctctg atgccgcata gttaagccag   3060

ccccgacacc cgccaacacc cgctgacgcg ccctgacggg cttgtctgct cccggcatcc   3120

gcttacagac aagctgtgac cgtctccggg agctgcatgt gtcagaggtt ttcaccgtca   3180

tcaccgaaac gcgcga                                                    3196
```

<210> SEQ ID NO 232
<211> LENGTH: 21
<212> TYPE: DNA
<213> ORGANISM: Artificial Sequence
<220> FEATURE:
<223> OTHER INFORMATION: flic-1 primer

<400> SEQUENCE: 232

```
cgttatcggc aatctggagg c                                               21
```

<210> SEQ ID NO 233
<211> LENGTH: 21
<212> TYPE: DNA
<213> ORGANISM: Artificial Sequence
<220> FEATURE:
<223> OTHER INFORMATION: flic-2 primer

<400> SEQUENCE: 233

```
ccagccctta caacagtggt c                                               21
```

<210> SEQ ID NO 234
<211> LENGTH: 24
<212> TYPE: DNA
<213> ORGANISM: Artificial Sequence
<220> FEATURE:
<223> OTHER INFORMATION: flic-3 primer

<400> SEQUENCE: 234
gtctgtcaac aactggtcta acgg 24

<210> SEQ ID NO 235
<211> LENGTH: 23
<212> TYPE: DNA
<213> ORGANISM: Artificial Sequence
<220> FEATURE:
<223> OTHER INFORMATION: flic-4 primer

<400> SEQUENCE: 235
agacggtcct catccagata agg 23

<210> SEQ ID NO 236
<211> LENGTH: 22
<212> TYPE: DNA
<213> ORGANISM: Artificial Sequence
<220> FEATURE:
<223> OTHER INFORMATION: fljb-1 primer sequence

<400> SEQUENCE: 236
ttccagacga caagagtatc gc 22

<210> SEQ ID NO 237
<211> LENGTH: 27
<212> TYPE: DNA
<213> ORGANISM: Artificial Sequence
<220> FEATURE:
<223> OTHER INFORMATION: fljb-2 primer

<400> SEQUENCE: 237
cctttaggtt tatccgaagc cagaatc 27

<210> SEQ ID NO 238
<211> LENGTH: 20
<212> TYPE: DNA
<213> ORGANISM: Artificial Sequence
<220> FEATURE:
<223> OTHER INFORMATION: fljb-3 primer

<400> SEQUENCE: 238
caccaggttt ttcacgctgc 20

<210> SEQ ID NO 239
<211> LENGTH: 20
<212> TYPE: DNA
<213> ORGANISM: Artificial Sequence
<220> FEATURE:
<223> OTHER INFORMATION: fljb-4 primer

<400> SEQUENCE: 239
acacgcattt acgcctgtcg 20

<210> SEQ ID NO 240
<211> LENGTH: 1518
<212> TYPE: DNA
<213> ORGANISM: Artificial Sequence
<220> FEATURE:
<223> OTHER INFORMATION: cytoLLO ORF

<400> SEQUENCE: 240
atgaaagacg cctccgcgtt taacaaggag aactccatca gctccatggc cccgcccgct 60
tccccgccgg cgagccctaa aaccccgatc gagaaaaagc acgccgacga gattgacaaa 120
tatattcaag gtttagacta caataagaac aacgtgctgg tgtatcacgg cgatgcggtg 180

```
accaatgttc cgccgcgcaa gggctacaaa gatggtaacg aatatatcgt ggttgagaaa    240

aagaaaaaaa gcatcaacca gaacaacgcc gatatccaag ttgtgaacgc catcagctct    300

ttaacctatc cgggcgcgct ggtgaaagcc aacagcgaac tggtggaaaa ccagcccgat    360

gtgctgccgg tgaaacgcga ttctttaacg ctgagcattg atttaccggg catgacgaac    420

caagataaca aaatcgtggt gaagaacgcg accaagtcca acgtgaacaa cgcggtgaac    480

acgctggtgg aacgctggaa cgaaaaatac gcccaagctt acccgaacgt gagcgcgaag    540

attgactacg acgacgaaat ggcctacagc gagagccagc tgatcgcgaa attcggcacc    600

gcgttcaaag cggtgaacaa ctctttaaac gtgaactttg gcgcgatcag cgaaggcaaa    660

atgcaagaag aggtgatcag ctttaaacaa atctattata acgtgaatgt taacgagccg    720

acgcgtccga gccgcttttt cggcaaagcg gtgacgaagg aacagctgca agcgcttggc    780

gtgaacgcgg aaaaccctcc ggcctatatt tccagcgtgg cgtatggccg ccaagtttat    840

ctgaagctga gcacgaacag ccacagcacc aaagttaagg cggcctttga tgcggcggtg    900

agcggcaaaa gcgttagcgg cgacgttgag ctgacgaaca tcatcaagaa cagctccttt    960

aaagcggtga tctatggcgg tagcgcgaaa gacgaagtgc agatcatcga cggcaattta   1020

ggtgatctgc gcgatatttt aaaaaagggc gccaccttca accgtgagac gcccggtgtg   1080

ccgatcgcct acaccaccaa ctttttaaag gataacgagc tggccgtgat caaaaacaat   1140

tccgaatata tcgaaaccac gagcaaggcg tataccgatg gcaagatcaa cattgaccac   1200

agcggtggct atgtggcgca gttcaacatc agctgggatg aagtgaacta tgatccggag   1260

ggcaacgaga tcgtgcagca caagaactgg tccgagaaca acaaatccaa gctggcgcat   1320

ttcaccagca gcatctatct gccgggcaac gcgcgcaaca ttaatgtgta cgcgaaagag   1380

tgcacgggtc ttgcgtggga atggtggcgc accgtgatcg atgatcgcaa tttaccgctg   1440

gtgaaaaacc gcaacatctc catctggggc accactttat acccgaaata ttccaacaaa   1500

gttgataacc ctattgag                                                 1518
```

<210> SEQ ID NO 241
<211> LENGTH: 45
<212> TYPE: DNA
<213> ORGANISM: Artificial Sequence
<220> FEATURE:
<223> OTHER INFORMATION: LLO promoter

<400> SEQUENCE: 241

```
attatgtctt gacatgtagt gagtgggctg gtataatgca gcaag                     45
```

<210> SEQ ID NO 242
<211> LENGTH: 1176
<212> TYPE: DNA
<213> ORGANISM: Artificial Sequence
<220> FEATURE:
<223> OTHER INFORMATION: Asd Gene ORF

<400> SEQUENCE: 242

```
ctacgccaac tggcgcagca ttcgacgcag cggctcggcg gcgccccata acaactggtc     60

gcctacggta aacgccgaca agaactctgg ccccatgttc agcttacgca gacgaccaac    120

cggcgtagtc aacgtgccgg tcaccgccgc cggggttaat tcgcgcatag tgatatcacg    180

atcgttcggc accactttcg cccacggatt atgtgccgcc agcagttctt ccaccgtcgg    240

aatggatacc tctttttca gcttgatggt gaacgcctgg ctgtgacagc gcagcgcgcc     300

gacgcgcaca cacaaaccat caaccggaat cacagaggca gtattgagaa tcttgttggt    360
```

ttccgcctgg cctttccact cttcgcggct ctggccgtta tcgagctgtt tgtcgatcca 420
ggggatcagg cttcccgcca gcggtacgcc aaagttatca accggcagct cgccgctgcg 480
ggtcaatgcc gtaactttgc gttcaatatc aagaattgcg gaagacggcg tcgccagttc 540
atcggcgaca tggccataca actgacccat ctgggttaac agctcgcgca tatggcgcgc 600
gccgccgccg gaggcggcct gataggtcgc gacggatacc cagtcaacga gattatgggc 660
aaagagaccg cccagcgaca tcaacatcag gctaacggta cagttaccgc ccacaaaggt 720
cttcacgcca ttgttcaggc cgtcggtaat cacgtcctgg ttgaccgggt cgagaataat 780
aatggcatca tctttcatgc gcagcgtaga agccgcatca atccagtaac cctgccatcc 840
gctttcgcgc agctttggat aaatttcgtt ggtataatcg ccgccctggc aggtcacgat 900
gatatcgagc gcttttagcg catccagatc aaaagcgtcc tgtagcgtgc cggtggaggt 960
gtcgccgaag gtgggcgccg cctgtccaaa ctgggaggta gaaaagaaaa cagggcgaat 1020
agcgtcgaaa tcgcgctcct ctaccatgcg ttgcatgaga acagagccga ccattccgcg 1080
ccagccgata aaaccaacat ttttcatagc gttttttttcc tgcaaagaga tgtgctgtgt 1140
atgcgcgcca gtatcctgtg gcgcatcctt caccat 1176

<210> SEQ ID NO 243
<211> LENGTH: 589
<212> TYPE: DNA
<213> ORGANISM: Artificial Sequence
<220> FEATURE:
<223> OTHER INFORMATION: pBR322 Origin

<400> SEQUENCE: 243
ttgagatcct ttttttctgc gcgtaatctg ctgcttgcaa acaaaaaaac caccgctacc 60
agcggtggtt tgtttgccgg atcaagagct accaactctt tttccgaagg taactggctt 120
cagcagagcg cagataccaa atactgtcct tctagtgtag ccgtagttag gccaccactt 180
caagaactct gtagcaccgc ctacatacct cgctctgcta atcctgttac cagtggctgc 240
tgccagtggc gataagtcgt gtcttaccgg gttggactca agacgatagt taccggataa 300
ggcgcagcgg tcgggctgaa cggggggttc gtgcacacag cccagcttgg agcgaacgac 360
ctacaccgaa ctgagatacc tacagcgtga gctatgagaa agcgccacgc ttcccgaagg 420
gagaaaggcg gacaggtatc cggtaagcgg cagggtcgga acaggagagc gcacgaggga 480
gcttccaggg ggaaacgcct ggtatcttta tagtcctgtc gggtttcgcc acctctgact 540
tgagcgtcga tttttgtgat gctcgtcagg ggggcggagc ctatggaaa 589

<210> SEQ ID NO 244
<211> LENGTH: 3269
<212> TYPE: DNA
<213> ORGANISM: Artificial Sequence
<220> FEATURE:
<223> OTHER INFORMATION: pEQU6 shSCR

<400> SEQUENCE: 244
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300

```
gtttgatgcc tggcagttta tggcgggcgt cctgcccgcc accctccggg ccgttgcttc    360
acaacgttca aatccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggcttt aaaggaacca attcagtcga ctggatccaa ggtcgggcag gaagagggcc    720
tatttcccat gattccttca tatttgcata tacgatacaa ggctgttaga gagataatta    780
gaattaattt gactgtaaac acaaagatat tagtacaaaa tacgtgacgt agaaagtaat    840
aatttcttgg gtagtttgca gttttaaaat tatgttttaa aatggactat catatgctta    900
ccgtaacttg aaagtatttc gatttcttgg ctttatatat cttgtggaaa ggacgaaact    960
agcaacaaga tgaagagcac caattctaga gattggtgct cttcatcttg ttgtttttc    1020
gagtagctag agaattcatg gtaatagcga tgactaatac gtagatgtac tgccaagtag   1080
gaaagtccca taaggtcatg tactgggcat aatgccaggc gggccattta ccgtcattga   1140
cgtcaatagg gggcgtactt ggcatatgat acacttgatg tactgccaag tgggcagttt   1200
accgtaaata gtccacccat tgacgtcaat ggaaagtccc tattggcgtt actatgggaa   1260
catacgtcat tattgacgtc aatgggcggg ggtcgttggg cggtcagcca ggcgggccat   1320
ttaccgtaag ttatgtaacg cggaactcca tatatgggct atgaactaat gaccccgtaa   1380
ttgattacta ttaataacta gacccagctt tcttgtacaa agttggcatt ataagaaagc   1440
attgcttatc aatttgttgc aacgaacagg tcactatcag tcaaaataaa atcattattt   1500
gccatccagc tgatatcccc tatagtgagt cgtattacat ggtcatagct gtttcctggc   1560
agctctggcc cgtgtctcaa aatctctgat gttacattgc acaagataaa aatatatcat   1620
catgaacaat aaaactgtct gcttacataa acagtaatac aaggggtgtt atgagccata   1680
ttcaacggga aacgtcgagg ccgcgattaa attccaacat ggatgctgat ttatatgggt   1740
ataaatgggc tcgcgataat gtcgggcaat caggtgcgac aatctatcgc ttgtatggga   1800
agcccgatgc gccagagttg tttctgaaac atggcaaagg tagcgttgcc aatgatgtta   1860
cagatgagat ggtcagacta aactggctga cggaatttat gcctcttccg accatcaagc   1920
attttatccg tactcctgat gatgcatggt tactcaccac tgcgatcccc ggaaaaacag   1980
cattccaggt attagaagaa tatcctgatt caggtgaaaa tattgttgat gcgctggcag   2040
tgttcctgcg ccggttgcat tcgattcctg tttgtaattg tccttttaac agcgatcgcg   2100
tatttcgtct cgctcaggcg caatcacgaa tgaataacgg tttggttgat gcgagtgatt   2160
ttgatgacga gcgtaatggc tggcctgttg aacaagtctg gaaagaaatg cataaacttt   2220
tgccattctc accggattca gtcgtcactc atggtgattt ctcacttgat aaccttattt   2280
ttgacgaggg gaaattaata ggttgtattg atgttggacg agtcggaatc gcagaccgat   2340
accaggatct tgccatccta tggaactgcc tcggtgagtt ttctccttca ttacagaaac   2400
ggctttttca aaaatatggt attgataatc ctgatatgaa taaattgcag tttcatttga   2460
tgctcgatga gtttttctaa tcagaattgg ttaattggtt gtaacactgg cagagcatta   2520
cgctgacttg acgggacggc gcaagctcat gaccaaaatc ccttaacgtg agttacgcgt   2580
cgttccactg agcgtcagac cccgtagaaa agatcaaagg atcttcttga gatccttttt   2640
ttctgcgcgt aatctgctgc ttgcaaacaa aaaaaccacc gctaccagcg gtggtttgtt   2700
```

tgccggatca agagctacca actctttttc cgaaggtaac tggcttcagc agagcgcaga 2760
taccaaatac tgtccttcta gtgtagccgt agttaggcca ccacttcaag aactctgtag 2820
caccgcctac atacctcgct ctgctaatcc tgttaccagt ggctgctgcc agtggcgata 2880
agtcgtgtct taccgggttg gactcaagac gatagttacc ggataaggcg cagcggtcgg 2940
gctgaacggg gggttcgtgc acacagccca gcttggagcg aacgacctac accgaactga 3000
gatacctaca gcgtgagcat tgagaaagcg ccacgcttcc cgaagggaga aaggcggaca 3060
ggtatccggt aagcggcagg gtcggaacag gagagcgcac gagggagctt ccagggggaa 3120
acgcctggta tctttatagt cctgtcgggt ttcgccacct ctgacttgag cgtcgatttt 3180
tgtgatgctc gtcagggggg cggagcctat ggaaaaacgc cagcaacgcg gcctttttac 3240
ggttcctggc cttttgctgg ccttttgct 3269

<210> SEQ ID NO 245
<211> LENGTH: 4642
<212> TYPE: DNA
<213> ORGANISM: Artificial Sequence
<220> FEATURE:
<223> OTHER INFORMATION: pATI2.0 U6-H1 Plasmid

<400> SEQUENCE: 245
accggtctgt ggaatgtgtg tcagttaggg tgtggaaagt ccccaggctc cccagcaggc 60
agaagtatgc aaagcatgca tctcaattag tcagcaacca accggtcttg cacctcagca 120
aaaggccatc cgtcaggatg gccttctgct tagtttgatg cctggcagtt tatggcgggc 180
gtcctgcccg ccaccctccg ggccgttgct tcacaacgtt caaatccgct cccggcggat 240
ttgtcctact caggagagcg ttcaccgaca aacaacagat aaaacgaaag gcccagtctt 300
ccgactgagc ctttcgtttt atttgggccg gccatgcctg gcagttccct actctcgcgt 360
taacgctagc atggatgttt tcccagtcac gacgttctta agctcgggcc cttaaaggaa 420
ccaattcagt cgagaattac tagtggtacc atatttgcat gtcgctatgt gttctgggaa 480
atcaccataa acgtgaaatg tctttggatt tgggaatctt ataagttctg tatgagacca 540
ctccctaggt ttttgtcgac agatctggcg cgccgactac caaaatgact tcggatatga 600
ccattatggt gcccgacttc gtaatttacg cgtacccatt tggatgacgg tgcgtccatg 660
tttgttctgc atgcctgaga tagtaaggcc gacccccaac aatccacaag gccacgattg 720
acacatgagg ttcctttttt aaacctgaac ctttagttca cacaggtggc tgcgccgccg 780
tgaatggtgg cagtagttac ttctaatcaa gctcaatccc tcggctctga agaggacata 840
gtagacctca tctggtcttt cgactacggg ggtaacaga tgtcggtggt ataacaatcc 900
tccacgagat catttcacgt aagcatgact tttacaccta tcggaatcat ataactgtta 960
ggcaatggtt tatgattggg cgacagacgt cagatcggcg aacctttacg tagccccccg 1020
ttcatctaga caggaagagg gcctatttcc catgattcct tcatatttgc atatacgata 1080
caaggctgtt agagagataa ttagaattaa tttgactgta aacacaaaga tattagtaca 1140
aaatacgtga cgtagaaagt aataatttct tgggtagttt gcagttttaa aattatgttt 1200
taaaatggac tatcatatgc ttaccgtaac ttgaaagtat ttcgatttct tggctttata 1260
tatcttgtgg aaaggacgaa acttgttttt tctcgagtag ctagagaatt cgtcgacgga 1320
actccatata tgggctatga actaatgacc ccgtaattga ttactattaa taactagcca 1380
tccagctgat atccgccggc gctgcagcta cgccaactgg cgcagcattc gacgcagcgg 1440
ctcggcggcg ccccataaca actggtcgcc tacggtaaac gccgacaaga actctggccc 1500
catgttcagc ttacgcagac gaccaaccgg cgtagtcaac gtgccggtca ccgccgccgg 1560
ggttaattcg cgcatagtga tatcacgatc gttcggcacc actttcgccc acggattatg 1620
tgccgccagc agttcttcca ccgtcggaat ggatacctct tttttcagct tgatggtgaa 1680
cgcctggctg tgacagcgca gcgcgccgac gcgcacacac aaaccatcaa ccggaatcac 1740
agaggcagta ttgagaatct tgttggtttc cgcctggcct ttccactctt cgcggctctg 1800
gccgttatcg agctgtttgt cgatccaggg gatcaggctt cccgccagcg gtacgccaaa 1860
gttatcaacc ggcagctcgc cgctgcgggt caatgccgta actttgcgtt caatatcaag 1920
aattgcggaa gacggcgtcg ccagttcatc ggcgacatgg ccatacaact gacccatctg 1980
ggttaacagc tcgcgcatat ggcgcgcgcc gccgccggag gcggcctgat aggtcgcgac 2040
ggatacccag tcaacgagat tatgggcaaa gagaccgccc agcgacatca acatcaggct 2100
aacggtacag ttaccgccca caaaggtctt cacgccattg ttcaggccgt cggtaatcac 2160
gtcctggttg accgggtcga gaataataat ggcatcatct ttcatgcgca gcgtagaagc 2220
cgcatcaatc cagtaaccct gccatccgct ttcgcgcagc tttggataaa tttcgttggt 2280
ataatcgccg ccctggcagg tcacgatgat atcgagcgct tttagcgcat ccagatcaaa 2340
agcgtcctgt agcgtgccgg tggaggtgtc gccgaaggtg ggcgccgcct gtccaaactg 2400
ggaggtagaa aagaaaacag ggcgaatagc gtcgaaatcg cgctcctcta ccatgcgttg 2460
catgagaaca gagccgacca ttccgcgcca gccgataaaa ccaacatttt tcatagcgtt 2520
tttttcctgc aaagagatgt gctgtgtatg cgcgccagta tcctgtggcg catccttcac 2580
cataaaggat cttcacctag atccttttaa attaaaaatg aagttttaaa tcaatctaaa 2640
gtatatatga gtaaacttgg tctgacagtc tgcaggatat cccatgggca ttggcgcaga 2700
aaaaaatgcc tgatgcgacg ctgcgcgtct tatactccca catatgccag attcagcaac 2760
ggatacggct tccccaactt gcccacttcc atacgtgtcc tccttaccag aaatttatcc 2820
ttaaccatgg aagctttgca gctctggccc gtgtctcaaa atctctgatg ttacattgca 2880
caagataaaa atatatcatc atgaacaata aaactgtctg cttacataaa cagtaataca 2940
aggggtgtta tgagccatat tcaacgggaa acgtcgaggc cgcgattaaa ttccaacatg 3000
gatgctgatt tatatgggta taaatgggct cgcgataatg tcgggcaatc aggtgcgaca 3060
atctatcgct tgtatgggaa gcccgatgcg ccagagttgt ttctgaaaca tggcaaaggt 3120
agcgttgcca atgatgttac agatgagatg gtcagactaa actggctgac ggaatttatg 3180
cctcttccga ccatcaagca ttttatccgt actcctgatg atgcatggtt actcaccact 3240
gcgatccccg gaaaaacagc attccaggta ttagaagaat atcctgattc aggtgaaaat 3300
attgttgatg cgctggcagt gttcctgcgc cggttgcatt cgattcctgt ttgtaattgt 3360
ccttttaaca gcgatcgcgt atttcgtctc gctcaggcgc aatcacgaat gaataacggt 3420
ttggttgatg cgagtgattt tgatgacgag cgtaatggct ggcctgttga acaagtctgg 3480
aaagaaatgc ataaactttt gccattctca ccggattcag tcgtcactca tggtgatttc 3540
tcacttgata accttatttt tgacgagggg aaattaatag gttgtattga tgttggacga 3600
gtcggaatcg cagaccgata ccaggatctt gccatcctat ggaactgcct cggtgagttt 3660
tctccttcat tacagaaacg gctttttcaa aaatatggta ttgataatcc tgatatgaat 3720
aaattgcagt ttcatttgat gctcgatgag tttttctaaa gctttcagaa ttggttaatt 3780
ggttgtaaca ctggcagagc attacgctga cttgacggga cggcgcaagc tcatggatcc 3840

```
caattggcgg ccgcttaatt aaacatgtga gctcgatgta cattcgaagg accccaaaat   3900

cccttaacgt gagttacgcg tcgttccact gagcgtcaga ccccgtagaa aagatcaaag   3960

gatcttcatc gatttgagat ccttttttc tgcgcgtaat ctgctgcttg caaacaaaaa   4020

aaccaccgct accagcggtg gtttgtttgc cggatcaaga gctaccaact ctttttccga   4080

aggtaactgg cttcagcaga gcgcagatac caaatactgt ccttctagtg tagccgtagt   4140

taggccacca cttcaagaac tctgtagcac cgcctacata cctcgctctg ctaatcctgt   4200

taccagtggc tgctgccagt ggcgataagt cgtgtcttac cgggttggac tcaagacgat   4260

agttaccgga taaggcgcag cggtcgggct gaacgggggg ttcgtgcaca cagcccagct   4320

tggagcgaac gacctacacc gaactgagat acctacagcg tgagctatga gaaagcgcca   4380

cgcttcccga agggagaaag gcggacaggt atccggtaag cggcagggtc ggaacaggag   4440

agcgcacgag ggagcttcca gggggaaacg cctggtatct ttatagtcct gtcgggtttc   4500

gccacctctg acttgagcgt cgatttttgt gatgctcgtc aggggggcgg agcctatgga   4560

aaatcgattc cggaaacgcc aggctcttcc aacgcggcct ttttacggtt gaagagccct   4620

ggccttttgc tggccttttg ct                                             4642
```

<210> SEQ ID NO 246
<211> LENGTH: 1261
<212> TYPE: DNA
<213> ORGANISM: Artificial Sequence
<220> FEATURE:
<223> OTHER INFORMATION: ASD gene orf + 85 bp upstream

<400> SEQUENCE: 246

```
ctgtcagacc aagtttactc atatatactt tagattgatt taaaacttca tttttaattt     60

aaaaggatct aggtgaagat cctttatggt gaaggatgcg ccacaggata ctggcgcgca    120

tacacagcac atctctttgc aggaaaaaaa cgctatgaaa aatgttggtt ttatcggctg    180

gcgcggaatg gtcggctctg ttctcatgca acgcatggta gaggagcgcg atttcgacgc    240

tattcgccct gttttctttt ctacctccca gtttggacag gcggcgccca ccttcggcga    300

cacctccacc ggcacgctac aggacgcttt tgatctggat gcgctaaaag cgctcgatat    360

catcgtgacc tgccagggcg gcgattatac caacgaaatt tatccaaagc tgcgcgaaag    420

cggatggcag ggttactgga ttgatgcggc ttctacgctg cgcatgaaag atgatgccat    480

tattattctc gacccggtca accaggacgt gattaccgac ggcctgaaca atggcgtgaa    540

gacctttgtg ggcggtaact gtaccgttag cctgatgttg atgtcgctgg gcggtctctt    600

tgcccataat ctcgttgact gggtatccgt cgcgacctat caggccgcct ccggcggcgg    660

cgcgcgccat atgcgcgagc tgttaaccca gatgggtcag ttgtatggcc atgtcgccga    720

tgaactggcg acgccgtctt ccgcaattct tgatattgaa cgcaaagtta cggcattgac    780

ccgcagcggc gagctgccgg ttgataactt tggcgtaccg ctggcgggaa gcctgatccc    840

ctggatcgac aaacagctcg ataacggcca gagccgcgaa gagtggaaag gccaggcgga    900

aaccaacaag attctcaata ctgcctctgt gattccggtt gatggtttgt gtgtgcgcgt    960

cggcgcgctg cgctgtcaca gccaggcgtt caccatcaag ctgaaaaaag aggtatccat   1020

tccgacggtg gaagaactgc tggcggcaca taatccgtgg gcgaaagtgg tgccgaacga   1080

tcgtgatatc actatgcgcg aattaacccc ggcggcggtg accggcacgt tgactacgcc   1140

ggttggtcgt ctgcgtaagc tgaacatggg gccagagttc ttgtcggcgt ttaccgtagg   1200
```

cgaccagttg ttatggggcg ccgccgagcc gctgcgtcga atgctgcgcc agttggcgta 1260
g 1261

<210> SEQ ID NO 247
<211> LENGTH: 4112
<212> TYPE: DNA
<213> ORGANISM: Artificial Sequence
<220> FEATURE:
<223> OTHER INFORMATION: pATI2.0 synthetic v26 scramble pBR322ori.dna

<400> SEQUENCE: 247
accggtctgt ggaatgtgtg tcagttaggg tgtggaaagt ccccaggctc cccagcaggc 60
agaagtatgc aaagcatgca tctcaattag tcagcaacca accggtcttg cacctcagca 120
aaaggccatc cgtcaggatg gccttctgct tagtttgatg cctggcagtt tatggcgggc 180
gtcctgcccg ccaccctccg ggccgttgct tcacaacgtt caaatccgct cccggcggat 240
ttgtcctact caggagagcg ttcaccgaca aacaacagat aaaacgaaag gcccagtctt 300
ccgactgagc ctttcgtttt atttgggccg gccatgcctg gcagttccct actctcgcgt 360
taacgctagc atggatgttt tcccagtcac gacgttctta agctcgggcc cttaaaggaa 420
ccaattcagt cgagaattac tagtggtacc caggaagagg gcctatttcc catgattcct 480
tcatatttgc atatacgata caaggctgtt agagagataa ttagaattaa tttgactgta 540
aacacaaaga tattagtaca aaatacgtga cgtagaaagt aataatttct tgggtagttt 600
gcagttttaa aattatgttt taaaatggac tatcatatgc ttaccgtaac ttgaaagtat 660
ttcgatttct tggctttata tatcttgtgg aaaggacgaa actagcaaca agatgaagag 720
caccaattct agagattggt gctcttcatc ttgttgtttt tctcgagtag ctagagaatt 780
cgtcgacgga actccatata tgggctatga actaatgacc ccgtaattga ttactattaa 840
taactagcca tccagctgat atccgccggc gctgcagcta cgccaactgg cgcagcattc 900
gacgcagcgg ctcggcggcg ccccataaca actggtcgcc tacggtaaac gccgacaaga 960
actctggccc catgttcagc ttacgcagac gaccaaccgg cgtagtcaac gtgccggtca 1020
ccgccgccgg ggttaattcg cgcatagtga tatcacgatc gttcggcacc actttcgccc 1080
acggattatg tgccgccagc agttcttcca ccgtcggaat ggatacctct tttttcagct 1140
tgatggtgaa cgcctggctg tgacagcgca gcgcgccgac gcgcacacac aaaccatcaa 1200
ccggaatcac agaggcagta ttgagaatct tgttggtttc cgcctggcct ttccactctt 1260
cgcggctctg gccgttatcg agctgtttgt cgatccaggg gatcaggctt cccgccagcg 1320
gtacgccaaa gttatcaacc ggcagctcgc cgctgcgggt caatgccgta actttgcgtt 1380
caatatcaag aattgcggaa gacggcgtcg ccagttcatc ggcgacatgg ccatacaact 1440
gacccatctg ggttaacagc tcgcgcatat ggcgcgcgcc gccgccggag gcggcctgat 1500
aggtcgcgac ggatacccag tcaacgagat tatgggcaaa gagaccgccc agcgacatca 1560
acatcaggct aacggtacag ttaccgccca caaaggtctt cacgccattg ttcaggccgt 1620
cggtaatcac gtcctggttg accgggtcga gaataataat ggcatcatct ttcatgcgca 1680
gcgtagaagc cgcatcaatc cagtaaccct gccatccgct ttcgcgcagc tttggataaa 1740
tttcgttggt ataatcgccg ccctggcagg tcacgatgat atcgagcgct tttagcgcat 1800
ccagatcaaa agcgtcctgt agcgtgccgg tggaggtgtc gccgaaggtg ggcgccgcct 1860
gtccaaactg ggaggtagaa aagaaaacag ggcgaatagc gtcgaaatcg cgctcctcta 1920
ccatgcgttg catgagaaca gagccgacca ttccgcgcca gccgataaaa ccaacatttt 1980

```
tcatagcgtt tttttcctgc aaagagatgt gctgtgtatg cgcgccagta tcctgtggcg   2040
catccttcac cataaaggat cttcacctag atccttttaa attaaaaatg aagttttaaa   2100
tcaatctaaa gtatatatga gtaaacttgg tctgacagtc tgcaggatat cccatgggca   2160
ttggcgcaga aaaaaatgcc tgatgcgacg ctgcgcgtct tatactccca catatgccag   2220
attcagcaac ggatacggct tccccaactt gcccacttcc atacgtgtcc tccttaccag   2280
aaatttatcc ttaaccatgg aagctttgca gctctggccc gtgtctcaaa atctctgatg   2340
ttacattgca caagataaaa atatatcatc atgaacaata aaactgtctg cttacataaa   2400
cagtaataca aggggtgtta tgagccatat tcaacgggaa acgtcgaggc cgcgattaaa   2460
ttccaacatg gatgctgatt tatatgggta taaatgggct cgcgataatg tcgggcaatc   2520
aggtgcgaca atctatcgct tgtatgggaa gcccgatgcg ccagagttgt ttctgaaaca   2580
tggcaaaggt agcgttgcca atgatgttac agatgagatg gtcagactaa actggctgac   2640
ggaatttatg cctcttccga ccatcaagca ttttatccgt actcctgatg atgcatggtt   2700
actcaccact gcgatccccg gaaaaacagc attccaggta ttagaagaat atcctgattc   2760
aggtgaaaat attgttgatg cgctggcagt gttcctgcgc cggttgcatt cgattcctgt   2820
ttgtaattgt ccttttaaca gcgatcgcgt atttcgtctc gctcaggcgc aatcacgaat   2880
gaataacggt ttggttgatg cgagtgattt tgatgacgag cgtaatggct ggcctgttga   2940
acaagtctgg aaagaaatgc ataaactttt gccattctca ccggattcag tcgtcactca   3000
tggtgatttc tcacttgata accttatttt tgacgagggg aaattaatag gttgtattga   3060
tgttggacga gtcggaatcg cagaccgata ccaggatctt gccatcctat ggaactgcct   3120
cggtgagttt tctccttcat tacagaaacg gctttttcaa aaatatggta ttgataatcc   3180
tgatatgaat aaattgcagt ttcatttgat gctcgatgag tttttctaaa gctttcagaa   3240
ttggttaatt ggttgtaaca ctggcagagc attacgctga cttgacggga cggcgcaagc   3300
tcatggatcc caattggcgg ccgcttaatt aaacatgtga gctcgatgta cattcgaagg   3360
accccaaaat cccttaacgt gagttacgcg tcgttccact gagcgtcaga ccccgtagaa   3420
aagatcaaag gatcttcatc gatttgagat cctttttttc tgcgcgtaat ctgctgcttg   3480
caaacaaaaa aaccaccgct accagcggtg gtttgtttgc cggatcaaga gctaccaact   3540
ctttttccga aggtaactgg cttcagcaga gcgcagatac caaatactgt ccttctagtg   3600
tagccgtagt taggccacca cttcaagaac tctgtagcac cgcctacata cctcgctctg   3660
ctaatcctgt taccagtggc tgctgccagt ggcgataagt cgtgtcttac cgggttggac   3720
tcaagacgat agttaccgga taaggcgcag cggtcgggct gaacgggggg ttcgtgcaca   3780
cagcccagct tggagcgaac gacctacacc gaactgagat acctacagcg tgagctatga   3840
gaaagcgcca cgcttcccga agggagaaag gcggacaggt atccggtaag cggcagggtc   3900
ggaacaggag agcgcacgag ggagcttcca gggggaaacg cctggtatct ttatagtcct   3960
gtcgggtttc gccacctctg acttgagcgt cgatttttgt gatgctcgtc aggggggcgg   4020
agcctatgga aaatcgattc cggaaacgcc aggctcttcc aacgcggcct ttttacggtt   4080
gaagagccct ggccttttgc tggccttttg ct                                 4112
```

<210> SEQ ID NO 248
<211> LENGTH: 165
<212> TYPE: DNA
<213> ORGANISM: Artificial Sequence
<220> FEATURE:

<223> OTHER INFORMATION: miR-16-2

<400> SEQUENCE: 248
ccggatcaac gccctaggtt tatgtttgga tgaactgaca tacttgttcc actctagcag 60
cacgtaaata ttggcgtagt gaaatatata ttaaacacca atattactgt gctgctttag 120
tgtgacaggg atacagcaac tattttatca attgtttgcg tcgac 165

<210> SEQ ID NO 249
<211> LENGTH: 165
<212> TYPE: DNA
<213> ORGANISM: Artificial Sequence
<220> FEATURE:
<221> NAME/KEY: misc_feature
<222> LOCATION: (55)...(75)
<223> OTHER INFORMATION: n may be any nucleotide
<220> FEATURE:
<221> NAME/KEY: misc_feature
<222> LOCATION: (97)...(117)
<223> OTHER INFORMATION: n may be any nucleotide
<220> FEATURE:
<221> NAME/KEY: source
<222> LOCATION: (1)...(165)
<223> OTHER INFORMATION: microRNA backbone where Ns represent inserted anti-sense and sense microRNAs

<400> SEQUENCE: 249
ccggatcaac gccctaggtt tatgtttgga tgaactgaca tacgcgtatc cgtcnnnnnn 60
nnnnnnnnnn nnnnngtagt gaaatatata ttaaacnnnn nnnnnnnnnn nnnnnnntac 120
ggtaacgcgg aattcgcaac tattttatca attttttgcg tcgac 165

<210> SEQ ID NO 250
<211> LENGTH: 708
<212> TYPE: DNA
<213> ORGANISM: Salmonella typhimurium
<220> FEATURE:
<223> OTHER INFORMATION: endA

<400> SEQUENCE: 250
atgtaccgta atttctcttt tgccgctgtg ttgctggccg cagcgttttc aggccaggcc 60
ctggccgatg gcattaacaa tttttctcag gccaaagcgg cgagcgtcaa agtcaatgct 120
gacgcgcccg gcagctttta ctgcgggtgc caaatccgct ggcagggtaa aaaaggcgtc 180
gtagacctgg agtcctgcgg ctataaggtg cgtaaaaacg agaatcgcgc cagacgcatt 240
gagtgggagc acgttgtccc cgcctggcaa ttcggtcatc agcgccagtg ctggcaggac 300
ggcgggcgaa aaaactgcgc taaagacccg gtctaccgca aaatggaaag cgatatgcat 360
aacctgcaac ccgcgattgg cgaagtgaat ggcgatcgcg gcaactttat gtatagccag 420
tggaacggcg gcgaaggtca gtacgggcag tgcgccatga aagtagattt caaagcgaag 480
ctcgccgagc cgcccgcccg cgcccgtggc gcaatcgccc gcacttattt ttatatgcgc 540
gaccaatacc aactgaaact ttcccgccaa caaacgcagc tttttaacgt ctgggataag 600
cagtaccccg ttaccgcctg ggagtgcgag cgcgatgcgc gtatcgcgaa ggtccagggt 660
aatcataatc cctatgtgca acgcgcttgc caggcgcgaa agagctaa 708

<210> SEQ ID NO 251
<211> LENGTH: 235
<212> TYPE: PRT
<213> ORGANISM: Salmonella typhimurium
<220> FEATURE:
<223> OTHER INFORMATION: endA

<400> SEQUENCE: 251

```
Met Tyr Arg Asn Phe Ser Phe Ala Ala Ala Leu Leu Ala Ala Ala Phe
1               5                   10                  15

Ser Gly Gln Ala Leu Ala Asp Gly Ile Asn Asn Phe Ser Gln Ala Lys
            20                  25                  30

Ala Ala Ser Val Lys Val Asn Ala Asp Ala Pro Gly Ser Phe Tyr Cys
        35                  40                  45

Gly Cys Gln Ile Arg Trp Gln Gly Lys Lys Gly Val Val Asp Leu Glu
    50                  55                  60

Ser Cys Gly Tyr Lys Val Arg Lys Asn Glu Asn Arg Ala Arg Arg Ile
65                  70                  75                  80

Glu Trp Glu His Val Val Pro Ala Trp Gln Phe Gly His Gln Arg Gln
                85                  90                  95

Cys Trp Gln Asp Gly Gly Arg Lys Asn Cys Ala Lys Asp Pro Val Tyr
            100                 105                 110

Arg Lys Met Glu Ser Asp Met His Asn Leu Gln Pro Ala Ile Gly Glu
        115                 120                 125

Val Asn Gly Asp Arg Gly Asn Phe Met Tyr Ser Gln Trp Asn Gly Gly
    130                 135                 140

Glu Gly Gln Tyr Gly Gln Cys Ala Met Lys Val Asp Phe Lys Ala Lys
145                 150                 155                 160

Ile Ala Glu Pro Pro Ala Arg Ala Arg Gly Ala Ile Ala Arg Ile Tyr
                165                 170                 175

Phe Tyr Met Arg Asp Gln Tyr Gln Leu Lys Leu Ser Arg Gln Gln Thr
            180                 185                 190

Gln Leu Phe Asn Val Trp Asp Lys Gln Tyr Pro Val Thr Ala Trp Glu
        195                 200                 205

Cys Glu Arg Asp Ala Arg Ile Ala Lys Val Gln Gly Asn His Asn Pro
    210                 215                 220

Tyr Val Gln Arg Ala Cys Gln Ala Arg Lys Ser
225                 230                 235
```

<210> SEQ ID NO 252
<211> LENGTH: 78
<212> TYPE: DNA
<213> ORGANISM: Homo sapiens
<220> FEATURE:
<223> OTHER INFORMATION: microRNA-103a1 (miR-103a1)

<400> SEQUENCE: 252

```
tactgccctc ggcttcttta cagtgctgcc ttgttgcata tggatcaagc agcattgtac     60

agggctatga aggcattg                                                   78
```

<210> SEQ ID NO 253
<211> LENGTH: 71
<212> TYPE: DNA
<213> ORGANISM: Homo sapiens
<220> FEATURE:
<223> OTHER INFORMATION: microRNA-30a (miR-30a)

<400> SEQUENCE: 253

```
gcgactgtaa acatcctcga ctggaagctg tgaagccaca gatgggcttt cagtcggatg     60

tttgcagctg c                                                          71
```

<210> SEQ ID NO 254
<211> LENGTH: 615
<212> TYPE: DNA

<213> ORGANISM: Artificial Sequence
<220> FEATURE:
<223> OTHER INFORMATION: pMB1 origin of replication

<400> SEQUENCE: 254
aaaggatctt cttgagatcc tttttttctg cgcgtaatct gctgcttgca aacaaaaaaa 60
ccaccgctac cagcggtggt ttgtttgccg gatcaagagc taccaactct ttttccgaag 120
gtaactggct tcagcagagc gcagatacca aatactgttc ttctagtgta gccgtagtta 180
ggccaccact tcaagaactc tgtagcaccg cctacatacc tcgctctgct aatcctgtta 240
ccagtggctg ctgccagtgg cgataagtcg tgtcttaccg ggttggactc aagacgatag 300
ttaccggata aggcgcagcg gtcgggctga acggggggtt cgtgcacaca gcccagcttg 360
gagcgaacga cctacaccga actgagatac ctacagcgtg agctatgaga aagcgccacg 420
cttcccgaag ggagaaaggc ggacaggtat ccggtaagcg gcagggtcgg aacaggagag 480
cgcacgaggg agcttccagg gggaaacgcc tggtatcttt atagtcctgt cgggtttcgc 540
cacctctgac ttgagcgtcg atttttgtga tgctcgtcag gggggcggag cctatggaaa 600
aacgccagca acgcg 615

<210> SEQ ID NO 255
<211> LENGTH: 913
<212> TYPE: DNA
<213> ORGANISM: Artificial Sequence
<220> FEATURE:
<223> OTHER INFORMATION: p15A origin of replication

<400> SEQUENCE: 255
gcgctagcgg agtgtatact ggcttactat gttggcactg atgagggtgt cagtgaagtg 60
cttcatgtgg caggagaaaa aaggctgcac cggtgcgtca gcagaatatg tgatacagga 120
tatattccgc ttcctcgctc actgactcgc tacgctcggt cgttcgactg cggcgagcgg 180
aaatggctta cgaacggggc ggagatttcc tggaagatgc caggaagata cttaacaggg 240
aagtgagagg gccgcggcaa agccgttttt ccataggctc cgcccccctg acaagcatca 300
cgaaatctga cgctcaaatc agtggtggcg aaacccgaca ggactataaa gataccaggc 360
gtttccccct ggcggctccc tcgtgcgctc tcctgttcct gcctttcggt ttaccggtgt 420
cattccgctg ttatggccgc gtttgtctca ttccacgcct gacactcagt tccgggtagg 480
cagttcgctc caagctggac tgtatgcacg aaccccccgt tcagtccgac cgctgcgcct 540
tatccggtaa ctatcgtctt gagtccaacc cggaaagaca tgcaaaagca ccactggcag 600
cagccactgg taattgattt agaggagtta gtcttgaagt catgcgccgg ttaaggctaa 660
actgaaagga caagttttgg tgactgcgct cctccaagcc agttacctcg gttcaaagag 720
ttggtagctc agagaacctt cgaaaaaccg ccctgcaagg cggttttttc gttttcagag 780
caagagatta cgcgcagacc aaaacgatct caagaagatc atcttattaa tcagataaaa 840
tatttctaga tttcagtgca atttatctct tcaaatgtag cacctgaagt cagccccata 900
cgatataagt tgt 913

<210> SEQ ID NO 256
<211> LENGTH: 223
<212> TYPE: DNA
<213> ORGANISM: Artificial Sequence
<220> FEATURE:
<223> OTHER INFORMATION: pSC101 origin of replication

<400> SEQUENCE: 256
gagttataca cagggctggg atctattctt tttatctttt tttattcttt ctttattcta 60
taaattataa ccacttgaat ataaacaaaa aaaacacaca aaggtctagc ggaatttaca 120
gagggtctag cagaatttac aagttttcca gcaaaggtct agcagaattt acagataccc 180
acaactcaaa ggaaaaggac tagtaattat cattgactag ccc 223

<210> SEQ ID NO 257
<211> LENGTH: 602
<212> TYPE: DNA
<213> ORGANISM: E. coli
<220> FEATURE:
<223> OTHER INFORMATION: ColE1 origin of replication

<400> SEQUENCE: 257
aggatcttct tgagatcctt tttttctgcg cgtaatctgc tgcttgcaaa caaaaaaacc 60
accgctacca acggtggttt gtttgccgga tcaagagcta ccaactcttt ttccgaaggt 120
aactggcttc agcagagcgc agataccaaa tactgtcctt ctagtgtagc cgtagtcggg 180
ccactacttc aagaactctg tagcaccgtt tgtgccatca tcgctctgct aatccggtta 240
ccagtggctg ctgccagtgg cgttaaggcg tgccttaccg ggttggactc aagacgatag 300
ttaccggata aggcgcagcg gtcgggctga acggggggtt cgtgcacaca gcccagcttg 360
gagcgaacga cctacaccga actgagatac caacagcgtg agctatgaga aagcgccacg 420
cttcccgaag ggagaaaggc ggacaggtat ccggtaagcg gcagggtcgg aacaggagag 480
cgcacgaggg agcttccagg gggaaacgcc tggtatcttt atagtcctgt cgggtttcgc 540
cacctctgac ttgagcgtct atttttgtga tgctcgtcag gggggcggag cctatggaaa 600
aa 602

<210> SEQ ID NO 258
<211> LENGTH: 201
<212> TYPE: DNA
<213> ORGANISM: Pseudomonas syringae
<220> FEATURE:
<223> OTHER INFORMATION: pPS10 origin of replication

<400> SEQUENCE: 258
acctgaccgg cgcggaagcg ctcttgatct ttttttcttg tttttacttg ttgttccttg 60
ttttcgtaat tttaactata tgatttataa gaaaaaaaag ggtttaaagg ggacagattc 120
agggtttaaa ggggacagat tcagggttta aaggggacag attcagggtt taaaggggac 180
agattcaggc tgatatccac a 201

<210> SEQ ID NO 259
<211> LENGTH: 617
<212> TYPE: DNA
<213> ORGANISM: E. coli
<220> FEATURE:
<223> OTHER INFORMATION: RK2 origin of replication

<400> SEQUENCE: 259
ccgggctggt tgccctcgcc gctgggctgg cggccgtcta tggccctgca aacgcgccag 60
aaacgccgtc gaagccgtgt gcgagacacc gcggccgccg gcgttgtgga taccacgcgg 120
aaaacttggc cctcactgac agatgagggg cggacgttga cacttgaggg gccgactcac 180
ccggcgcggc gttgacagat gaggggcagg ctcgatttcg gccggcgacg tggagctggc 240
cagcctcgca aatcggcgaa aacgcctgat tttacgcgag tttcccacag atgatgtgga 300

-continued caagcctggg gataagtgcc ctgcggtatt gacacttgag ggcgcgact actgacagat 360 gaggggcgcg atccttgaca cttgaggggc agagtgatga cagatgaggg gcgcacctat 420
tgacatttga ggggctgtcc acaggcagaa aatccagcat ttgcaagggt ttccgcccgt 480
ttttcggcca ccgctaacct gtcttttaac ctgcttttaa accaatattt ataaaccttg 540
tttttaacca gggctgcgcc ctggcgcgtg accgcgcacg ccgaaggggg gtgccccccc 600
ttctcgaacc ctcccgg 617

<210> SEQ ID NO 260
<211> LENGTH: 639
<212> TYPE: DNA
<213> ORGANISM: E. coli
<220> FEATURE:
<223> OTHER INFORMATION: R6K alpha origin of replication

<400> SEQUENCE: 260
tcttacttct ttgcgtagct gttaaataca gcgttgtttt gataaaatca tcattatcat 60
cgataatgct ttcttcaatt tttttatcct tactctttaa taaagcactt gctaataact 120
tcataccttt tgcaactgtc aaatttggtt catcagggta aatgctttta aggcatacta 180
acaaataatc atggtcttca tcttcaactc taaactgaat ttttttcatc ataactccca 240
acaagaaccg actgtaggtc accgggcaaa cgctgaaaaa taacgtcgaa tgacgtcatt 300
ttgcggcgtt tgccctatcc tgcatcgcag tagaaaatgc cacaactgaa attgtgcttc 360
agtatgtaca gaaatgcaaa atctgaggga tttcgtagct gaaagatcgc cagtcttcga 420
ccgtaaggat aggagttgct gtaagacctg tgcggggcgt tcgcttcgcg aacgggtctg 480
gcagggggca caagcgctgt gctgtgatat atgcaaaaga agccacccac gaacgggagg 540
gcttcggcga atcgactata gtgatctatt tacccggctg attgtcgcct tctagccctc 600
gcgggcatca tgcaaccagt gcctgaattt agttatatg 639

<210> SEQ ID NO 261
<211> LENGTH: 1027
<212> TYPE: DNA
<213> ORGANISM: E. coli
<220> FEATURE:
<223> OTHER INFORMATION: R6K beta origin of replication

<400> SEQUENCE: 261
tgaagctttt tttatgaatt tatctgaagc tgatgcagct tttctcaagg tatttgatga 60
aaccgtacct cccaaaaaag ctaaggggtg atatatggct aaaatttacg atttccctca 120
aggagccgaa cgccgcagga tgcaccgcaa aatccagtgg aacaacgctg taaaattatc 180
taaaaatggc tggagtaagc cagaggttaa acgctggtct tttttagcat tcatctcaac 240
tggctggtat tactttcgcc tttcggtagc agtcattttc catatcatta ctatttgtgg 300
tttagctgtg ctcgcggcgt taagcaatac gatattctgg attggtggcg cgatatgtct 360
tgtaacctgg tatacaaatg accatcaaat ttggagtact aacaatctta ctatccctat 420
tgttttcgga ctttgggtgt taagtttagt agctgcacca ctcatagatt ttttcagtca 480
aaaattgccc ttttatcgtc ttcttgtgcc tgatgcgaag cgtgaggaag tgggcgaaga 540
tgattcttaa agccctgccc tgtacggctt taacgccttc tcgcggtaga tctatggatg 600
ttgagaatgt agtatggtta tactgcgatg caggataggg caaacgccgt aaaatgacgt 660
ctttgacgtt atttttcagc gcttgcccgg tgacctacag tcggtgcttg ttgggagatt 720
ttatgaagtt tactagtaaa ggattttatc agtgataaat atgcaaaggc tattaacatt 780

-continued ttaaatgata accttaaaga aaactactat gtttttttatg gtgtaaggtt aagtgaaatt 840
ctttttcctg caagtgatta tggtacagat gattttttta aggagtttga ggaaataaac 900
aacgttacct tgcctttagt tgtttttgaa ataaatgaac gtgaacctgt gattgtaatt 960
ggttttgatg aaataaatcc tgcgattctt atagagaaat ccggtataaa ggttttagta 1020
atcggac 1027

<210> SEQ ID NO 262
<211> LENGTH: 442
<212> TYPE: DNA
<213> ORGANISM: E. coli
<220> FEATURE:
<223> OTHER INFORMATION: R6K gamma origin of replication

<400> SEQUENCE: 262
gatcgctagt ttgttttgac tccatccatt agggcttcta aaacgccttc taaggccatg 60
tcagccgtta agtgttcctg tgtcactgaa aattgctttg agaggctcta agggcttctc 120
agtgcgttac atccctggct tgttgtccac aaccgttaaa ccttaaaagc tttaaaagcc 180
ttatatattc ttttttttct tataaaactt aaaaccttag aggctattta agttgctgat 240
ttatattaat tttattgttc aaacatgaga gcttagtacg tgaaacatga gagcttagta 300
cgttagccat gagagcttag tacgttagcc atgagggttt agttcgttaa acatgagagc 360
ttagtacgtt aaacatgaga gcttagtacg tgaaacatga gagcttagta cgtactatca 420
acaggttgaa ctgctgatct tc 442

<210> SEQ ID NO 263
<211> LENGTH: 242
<212> TYPE: DNA
<213> ORGANISM: Enterobacteria phage P1
<220> FEATURE:
<223> OTHER INFORMATION: P1 origin of plasmid replication oriR

<400> SEQUENCE: 263
tttcccgtca acacacatcc tatatcccgc cagcacacat tagcaacccg tcagcacaca 60
tttttatccc tccagcacac atcgttttcc ctccagcaca catcgcgata cacttctaag 120
ccagacgtgg cgcggcctgc aacgatcagg gatctatatg gatctaattg ggatctgtat 180
ggacctgatt attggatcta tccagtggat aatgtggata agtgaaaaac cggccaacgt 240
ag 242

<210> SEQ ID NO 264
<211> LENGTH: 792
<212> TYPE: DNA
<213> ORGANISM: Artificial Sequence
<220> FEATURE:
<223> OTHER INFORMATION: R1 origin of replication

<400> SEQUENCE: 264
ttatccacat ttaactgcaa gggacttccc cataaggtta caaccgttca tgtcataaag 60
cgccagccgc cagtcttaca gggtgcaatg tatcttttaa acacctgttt atatctcctt 120
taaactactt aattacattc atttaaaaag aaaacctatt cactgcctgt cctgtggaca 180
gacagatatg cacctcccac cgcaagcggc gggccccgac cggagccact ttagttacaa 240
cacacaaaaa caacctccag aaaaaccccg gtccagcgca gaaccgaaac cacaaagccc 300
ctccctcata actgaaaagc ggccccgccc cggcccaaag ggccggaaca gagtcgcttt 360

-continued

```
taattatgaa tgttgtaact acatcttcat cgctgtcagt cttctcgctg gaagttctca    420

gtacacgctc gtaagcggcc ctcacggccc gctaacgcgg agatacgccc cgacttcggg    480

taaaccctcg tcgggaccac tccgaccgcg cacagaagct ctctcatggc tgaaagcggg    540

tatggtctgg cagggctggg gatgggtaag gtgaaatcta tcaatcagta ccggcttacg    600

ccgggcttcg gcggttttac tcctgtatca tatgaaacaa cagagtgccg ccttccatgc    660

cgctgatgcg gcatatcctg gtaacgatat ctgaattgtt atacatgtgt atatacgtgg    720

taatgacaaa aataggacaa gttaaaaatt tacaggcgat gcaatgattc aaacacgtaa    780

tcaatatctg ca                                                         792


<210> SEQ ID NO 265
<211> LENGTH: 2920
<212> TYPE: DNA
<213> ORGANISM: Artificial Sequence
<220> FEATURE:
<223> OTHER INFORMATION: pWSK origin of replication

<400> SEQUENCE: 265

ccgatgccct tgagagcctt caacccagtc agctccttcc ggtgggcgcg gggcatgact     60

atcgtcgccg cacttatgac tgtcttcttt atcatgcaac tcgtaggaca gggtgccggc    120

agcgctctgg gtcattttcg gcgaggaccg ctttcgctgg agcgcgacga tgatcggcct    180

gtcgcttgcg gtattcggaa tcttgcacgc cctcgctcaa gccttcgtca ctggtcccgc    240

caccaaacgt ttcggcgaga agcaggccat tatcgccggc atggcggccg acgcgctggg    300

ctacgtcttg ctggcgttcg cgacgcgagg ctggatggcc ttccccatta tgattcttct    360

cgcttccggc ggcatcggga tgcccgcgtt gcaggccatg ctgtccaggc aggtagatga    420

cgaccatcag ggacagcttc aaggatcgct cgcggctctt accagcctaa cttcgatcat    480

tggaccgctg atcgtcacgg cgatttatgc cgcctcggcg agcacatgga acgggttggc    540

atggattgta ggcgccgccc tataccttgt ctgcctcccc gcgttgcgtc gcggtgcatg    600

gagccgggcc acctcgacct gaatggaagc cggcggcacc tcgctaacgg attcaccact    660

ccgcagaccc gccataaaac gccctgagaa gcccgtgacg ggcttttctt gtattatggg    720

tagtttcctt gcatgaatcc ataaaaggcg cctgtagtgc catttacccc cattcactgc    780

cagagccgtg agcgcagcga actgaatgtc acgaaaaaga cagcgactca ggtgcctgat    840

ggtcggagac aaaaggaata ttcagcgatt tgcccgagct tgcgagggtg ctacttaagc    900

ctttagggtt ttaaggtctg ttttgtagag gagcaaacag cgtttgcgac atccttttgt    960

aatactgcgg aactgactaa agtagtgagt tatacacagg gctgggatct attcttttta   1020

tcttttttta ttctttcttt attctataaa ttataaccac ttgaatataa acaaaaaaaa   1080

cacacaaagg tctagcggaa tttacagagg gtctagcaga atttacaagt tttccagcaa   1140

aggtctagca gaatttacag atacccacaa ctcaaaggaa aaggactagt aattatcatt   1200

gactagccca tctcaattgg tatagtgatt aaaatcacct agaccaattg agatgtatgt   1260

ctgaattagt tgttttcaaa gcaaatgaac tagcgattag tcgctatgac ttaacggagc   1320

atgaaaccaa gctaatttta tgctgtgtgg cactactcaa ccccacgatt gaaaacccta   1380

caaggaaaga acggacggta tcgttcactt ataaccaata cgctcagatg atgaacatca   1440

gtagggaaaa tgcttatggt gtattagcta aagcaaccag agagctgatg acgagaactg   1500

tggaaatcag gaatcctttg gttaaaggct ttgagatttt ccagtggaca aactatgcca   1560

agttctcaag cgaaaaatta gaattagttt ttagtgaaga gatattgcct tatctttttc   1620
```

agttaaaaaa attcataaaa tataatctgg aacatgttaa gtcttttgaa aacaaatact 1680
ctatgaggat ttatgagtgg ttattaaaag aactaacaca aaagaaaact cacaaggcaa 1740
atatagagat tagccttgat gaatttaagt tcatgttaat gcttgaaaat aactaccatg 1800
agtttaaaag gcttaaccaa tgggttttga aaccaataag taaagattta aacacttaca 1860
gcaatatgaa attggtggtt gataagcgag gccgcccgac tgatacgttg attttccaag 1920
ttgaactaga tagacaaatg gatctcgtaa ccgaacttga gaacaaccag ataaaaatga 1980
atggtgacaa aataccaaca accattacat cagattccta cctacataac ggactaagaa 2040
aaacactaca cgatgcttta actgcaaaaa ttcagctcac cagttttgag gcaaaatttt 2100
tgagtgacat gcaaagtaag tatgatctca atggttcgtt ctcatggctc acgcaaaaac 2160
aacgaaccac actagagaac atactggcta aatacggaag gatctgaggt tcttatggct 2220
cttgtatcta tcagtgaagc atcaagacta acaaacaaaa gtagaacaac tgttcaccgt 2280
tacatatcaa agggaaaact gtccatatgc acagatgaaa acggtgtaaa aaagatagat 2340
acatcagagc ttttacgagt ttttggtgca ttcaaagctg ttcaccatga acagatcgac 2400
aatgtaacag atgaacagca tgtaacacct aatagaacag gtgaaaccag taaaacaaag 2460
caactagaac atgaaattga acacctgaga caacttgtta cagctcaaca gtcacacata 2520
gacagcctga aacaggcgat gctgcttatc gaatcaaagc tgccgacaac acgggagcca 2580
gtgacgcctc ccgtggggaa aaaatcatgg caattctgga agaaatagcg ctttcagccg 2640
gcaaaccggc tgaagccgga tctgcgattc tgataacaaa ctagcaacac cagaacagcc 2700
cgtttgcggg cagcaaaacc cgtacttttg gacgttccgg cggttttttg tggcgagtgg 2760
tgttcgggcg gtgcgcgcaa gatccattat gttaaacggg cgagtttaca tctcaaaacc 2820
gcccgcttaa caccatcaga aatcctcagc gcgattttaa gcaccaaccc ccccccgtaa 2880
cacccaaatc catactgaaa gtggctttgt tgaataaatc 2920

<210> SEQ ID NO 266
<211> LENGTH: 37
<212> TYPE: DNA
<213> ORGANISM: E. coli
<220> FEATURE:
<223> OTHER INFORMATION: ColE2 origin of replication

<400> SEQUENCE: 266
aaaatgagac cagataagcc ttatcagata acagcgc 37

<210> SEQ ID NO 267
<211> LENGTH: 668
<212> TYPE: DNA
<213> ORGANISM: Artificial Sequence
<220> FEATURE:
<223> OTHER INFORMATION: pUC origin of replication

<400> SEQUENCE: 267
tgagcaaaag gccagcaaaa ggccaggaac cgtaaaaagg ccgcgttgct ggcgtttttc 60
cataggctcc gcccccctga cgagcatcac aaaaatcgac gctcaagtca gaggtggcga 120
aacccgacag gactataaag ataccaggcg tttccccctg gaagctccct cgtgcgctct 180
cctgttccga ccctgccgct taccggatac ctgtccgcct ttctcccttc gggaagcgtg 240
gcgctttctc atagctcacg ctgtaggtat ctcagttcgg tgtaggtcgt tcgctccaag 300
ctgggctgtg tgcacgaacc ccccgttcag cccgaccgct gcgccttatc cggtaactat 360

-continued

```
cgtcttgagt ccaacccggt aagacacgac ttatcgccac tggcagcagc cactggtaac    420

aggattagca gagcgaggta tgtaggcggt gctacagagt tcttgaagtg gtggcctaac    480

tacggctaca ctagaagaac agtatttggt atctgcgctc tgctgaagcc agttaccttc    540

ggaaaaagag ttggtagctc ttgatccggc aaacaaacca ccgctggtag cggtggtttt    600

tttgtttgca agcagcagat tacgcgcaga aaaaaaggat ctcaagaaga tcctttgatc    660

ttttctac                                                             668
```

<210> SEQ ID NO 268
<211> LENGTH: 457
<212> TYPE: DNA
<213> ORGANISM: Bacteriophage F1
<220> FEATURE:
<223> OTHER INFORMATION: F1 origin of replication

<400> SEQUENCE: 268

```
gacgcgccct gtagcggcgc attaagcgcg gcgggtgtgg tggttacgcg cagcgtgacc     60

gctacacttg ccagcgccct agcgcccgct cctttcgctt tcttcccttc ctttctcgcc    120

acgttcgccg gctttccccg tcaagctcta aatcgggggc tccctttagg gttccgattt    180

agtgctttac ggcacctcga ccccaaaaaa cttgattagg gtgatggttc acgtagtggg    240

ccatcgccct gatagacggt ttttcgccct ttgacgttgg agtccacgtt ctttaatagt    300

ggactcttgt tccaaactgg aacaacactc aaccctatct cggtctattc ttttgattta    360

taagggattt tgccgatttc ggcctattgg ttaaaaaatg agctgattta acaaaaattt    420

aacgcgaatt ttaacaaaat attaacgctt acaattt                             457
```

<210> SEQ ID NO 269
<211> LENGTH: 534
<212> TYPE: DNA
<213> ORGANISM: Homo sapiens
<220> FEATURE:
<223> OTHER INFORMATION: IL-7

<400> SEQUENCE: 269

```
atgttccatg tttcttttag gtatatcttt ggacttcctc ccctgatcct tgttctgttg     60

ccagtagcat catctgattg tgatattgaa ggtaaagatg gcaaacaata tgagagtgtt    120

ctaatggtca gcatcgatca attattggac agcatgaaag aaattggtag caattgcctg    180

aataatgaat ttaacttttt taaaagacat atctgtgatg ctaataagga aggtatgttt    240

ttattccgtg ctgctcgcaa gttgaggcaa tttcttaaaa tgaatagcac tggtgatttt    300

gatctccact tattaaaagt ttcagaaggc acaacaatac tgttgaactg cactggccag    360

gttaaaggaa gaaaaccagc tgccctgggt gaagcccaac caacaaagag tttggaagaa    420

aataaatctt taaaggaaca gaaaaaactg aatgacttgt gtttcctaaa gagactatta    480

caagagataa aaacttgttg gaataaaatt ttgatgggca ctaaagaaca ctga          534
```

<210> SEQ ID NO 270
<211> LENGTH: 987
<212> TYPE: DNA
<213> ORGANISM: Homo sapiens
<220> FEATURE:
<223> OTHER INFORMATION: IL12B

<400> SEQUENCE: 270

```
atgtgtcacc agcagttggt catctcttgg ttttccctgg tttttctggc atctcccctc     60

gtggccatat gggaactgaa gaaagatgtt tatgtcgtag aattggattg gtatccggat    120
```

```
gcccctggag aaatggtggt cctcacctgt gacacccctg aagaagatgg tatcacctgg    180

accttggacc agagcagtga ggtcttaggc tctggcaaaa ccctgaccat ccaagtcaaa    240

gagtttggag atgctggcca gtacacctgt cacaaaggag gcgaggttct aagccattcg    300

ctcctgctgc ttcacaaaaa ggaagatgga atttggtcca ctgatatttt aaaggaccag    360

aaagaaccca aaaataagac ctttctaaga tgcgaggcca agaattattc tggacgtttc    420

acctgctggt ggctgacgac aatcagtact gatttgacat tcagtgtcaa aagcagcaga    480

ggctcttctg acccccaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gaaaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840

agcaagagag aaaagaaaga tagagtcttc acggacaaga cctcagccac ggtcatctgc    900

cgcaaaaatg ccagcattag cgtgcgggcc caggaccgct actatagctc atcttggagc    960

gaatgggcat ctgtgccctg cagttag                                        987
```

```
<210> SEQ ID NO 271
<211> LENGTH: 762
<212> TYPE: DNA
<213> ORGANISM: Homo sapiens
<220> FEATURE:
<223> OTHER INFORMATION: IL12A

<400> SEQUENCE: 271

atgtggcccc ctgggtcagc ctcccagcca ccgccctcac ctgccgcggc cacaggtctg     60

catccagcgg ctcgccctgt gtccctgcag tgccggctca gcatgtgtcc agcgcgcagc    120

ctcctccttg tggctaccct ggtcctcctg gaccacctca gtttggccag aaacctcccc    180

gtggccactc cagacccagg aatgttccca tgccttcacc actcccaaaa cctgctgagg    240

gccgtcagca acatgctcca gaaggccaga caaactctag aattttaccc ttgcacttct    300

gaagagattg atcatgaaga tatcacaaaa gataaaacca gcacagtgga ggcctgttta    360

ccattggaat taaccaagaa tgagagttgc ctaaattcca gagagacctc tttcataact    420

aatgggagtt gcctggcctc cagaaagacc tcttttatga tggccctgtg ccttagtagt    480

atttatgaag acttgaagat gtaccaggtg gagttcaaga ccatgaatgc aaagcttctg    540

atggatccta agaggcagat ctttctagat caaaacatgc tggcagttat tgatgagctg    600

atgcaggccc tgaatttcaa cagtgagact gtgccacaaa aatcctccct tgaagaaccg    660

gatttttata aaactaaaat caagctctgc atacttcttc atgctttcag aattcgggca    720

gtgactattg atagagtgat gagctatctg aatgcttcct aa                       762
```

```
<210> SEQ ID NO 272
<211> LENGTH: 489
<212> TYPE: DNA
<213> ORGANISM: Homo sapiens
<220> FEATURE:
<223> OTHER INFORMATION: IL-15

<400> SEQUENCE: 272

atgagaattt cgaaaccaca tttgagaagt atttccatcc agtgctactt gtgtttactt     60
```

-continued

```
ctaaacagtc attttctaac tgaagctggc attcatgtct tcattttggg ctgtttcagt    120

gcagggcttc ctaaaacaga agccaactgg gtgaatgtaa taagtgattt gaaaaaaatt    180

gaagatctta ttcaatctat gcatattgat gctactttat atacggaaag tgatgttcac    240

cccagttgca aagtaacagc aatgaagtgc tttctcttgg agttacaagt tatttcactt    300

gagtccggag atgcaagtat tcatgataca gtagaaaatc tgatcatcct agcaaacaac    360

agtttgtctt ctaatgggaa tgtaacagaa tctggatgca aagaatgtga ggaactggag    420

gaaaaaaata ttaaagaatt tttgcagagt tttgtacata ttgtccaaat gttcatcaac    480

acttcttga                                                             489
```

<210> SEQ ID NO 273
<211> LENGTH: 804
<212> TYPE: DNA
<213> ORGANISM: Homo sapiens
<220> FEATURE:
<223> OTHER INFORMATION: IL15RA

<400> SEQUENCE: 273

```
atggccccgc ggcgggcgcg cggctgccgg accctcggtc tcccggcgct gctactgctg     60

ctgctgctcc ggccgccggc gacgcggggc atcacgtgcc ctccccccat gtccgtggaa    120

cacgcagaca tctgggtcaa gagctacagc ttgtactcca gggagcggta catttgtaac    180

tctggtttca agcgtaaagc cggcacgtcc agcctgacgg agtgcgtgtt gaacaaggcc    240

acgaatgtcg cccactggac aacccccagt ctcaaatgca ttagagaccc tgccctggtt    300

caccaaaggc cagcgccacc ctccacagta acgacggcag gggtgacccc acagccagag    360

agcctctccc cttctggaaa agagcccgca gcttcatctc ccagctcaaa caacacagcg    420

gccacaacag cagctattgt cccgggctcc cagctgatgc cttcaaaatc accttccaca    480

ggaaccacag agataagcag tcatgagtcc tcccacggca ccccctctca gacaacagcc    540

aagaactggg aactcacagc atccgcctcc caccagccgc caggtgtgta tccacagggc    600

cacagcgaca ccactgtggc tatctccacg tccactgtcc tgctgtgtgg gctgagcgct    660

gtgtctctcc tggcatgcta cctcaagtca aggcaaactc ccccgctggc cagcgttgaa    720

atggaagcca tggaggctct gccggtgact tgggggacca gcagcagaga tgaagacttg    780

gaaaactgct ctcaccacct atga                                            804
```

<210> SEQ ID NO 274
<211> LENGTH: 378
<212> TYPE: DNA
<213> ORGANISM: Homo sapiens
<220> FEATURE:
<223> OTHER INFORMATION: CXCL9

<400> SEQUENCE: 274

```
atgaagaaaa gtggtgttct ttttcctcttg ggcatcatct tgctggttct gattggagtg     60

caaggaaccc cagtagtgag aaagggtcgc tgttcctgca tcagcaccaa ccaagggact    120

atccacctac aatccttgaa agaccttaaa caatttgccc caagcccttc ctgcgagaaa    180

attgaaatca ttgctacact gaagaatgga gttcaaacat gtctaaaccc agattcagca    240

gatgtgaagg aactgattaa aaagtgggag aaacaggtca gccaaaagaa aaagcaaaag    300

aatgggaaaa aacatcaaaa aaagaaagtt ctgaaagttc gaaaatctca acgttctcgt    360

caaaagaaga ctacataa                                                   378
```

<210> SEQ ID NO 275
<211> LENGTH: 297
<212> TYPE: DNA
<213> ORGANISM: Homo sapiens
<220> FEATURE:
<223> OTHER INFORMATION: CXCL10

<400> SEQUENCE: 275
atgaatcaaa ctgccattct gatttgctgc cttatctttc tgactctaag tggcattcaa 60
ggagtacctc tctctagaac tgtacgctgt acctgcatca gcattagtaa tcaacctgtt 120
aatccaaggt ctttagaaaa acttgaaatt attcctgcaa gccaattttg tccacgtgtt 180
gagatcattg ctacaatgaa aaagaagggt gagaagagat gtctgaatcc agaatcgaag 240
gccatcaaga atttactgaa agcagttagc aaggaaaggt ctaaaagatc tccttaa 297

<210> SEQ ID NO 276
<211> LENGTH: 285
<212> TYPE: DNA
<213> ORGANISM: Homo sapiens
<220> FEATURE:
<223> OTHER INFORMATION: CXCL11

<400> SEQUENCE: 276
atgagtgtga agggcatggc tatagccttg gctgtgatat tgtgtgctac agttgttcaa 60
ggcttcccca tgttcaaaag aggacgctgt ctttgcatag gccctggggt aaaagcagtg 120
aaagtggcag atattgagaa agcctccata atgtacccaa gtaacaactg tgacaaaata 180
gaagtgatta ttaccctgaa agaaaataaa ggacaacgat gcctaaatcc caaatcgaag 240
caagcaaggc ttataatcaa aaaagttgaa agaaagaatt tttaa 285

<210> SEQ ID NO 277
<211> LENGTH: 465
<212> TYPE: DNA
<213> ORGANISM: Homo sapiens
<220> FEATURE:
<223> OTHER INFORMATION: CCL5

<400> SEQUENCE: 277
atgaaggtct ccgcggcagc cctcgctgtc atcctcattg ctactgccct ctgcgctcct 60
gcatctgcct ccccatattc ctcggacacc acaccctgct gctttgccta cattgcccgc 120
ccactgcccc gtgcccacat caaggagtat ttctacacca gtggcaagtg ctccaaccca 180
gcagtcgtcc acaggtcaag gatgccaaag agagagggac agcaagtctg gcaggatttc 240
ctgtatgact cccggctgaa caagggcaag ctttgtcacc cgaaagaacc gccaagtgtg 300
tgccaaccca gagaagaaat gggttcggga gtacatcaac tctttggaga tgagctagga 360
tggagagtcc ttgaacctga acttacacaa atttgcctgt ttctgcttgc tcttgtccta 420
gcttgggagg cttcccctca ctatcctacc ccacccgctc cttga 465

<210> SEQ ID NO 278
<211> LENGTH: 765
<212> TYPE: DNA
<213> ORGANISM: Homo sapiens
<220> FEATURE:
<223> OTHER INFORMATION: 4-1BB Ligand

<400> SEQUENCE: 278
atggaatacg cctctgacgc ttcactggac cccgaagccc cgtggcctcc cgcgccccgc 60
gctcgcgcct gccgcgtact gccttgggcc ctggtcgcgg ggctgctgct gctgctgctg 120

```
ctcgctgccg cctgcgccgt cttcctcgcc tgcccctggg ccgtgtccgg ggctcgcgcc    180

tcgcccggct ccgcggccag cccgagactc cgcgagggtc ccgagctttc gcccgacgat    240

cccgccggcc tcttggacct gcggcagggc atgtttgcgc agctggtggc ccaaaatgtt    300

ctgctgatcg atgggcccct gagctggtac agtgacccag gcctggcagg cgtgtccctg    360

acggggggcc tgagctacaa agaggacacg aaggagctgg tggtggccaa ggctggagtc    420

tactatgtct tctttcaact agagctgcgg cgcgtggtgg ccggcgaggg ctcaggctcc    480

gtttcacttg cgctgcacct gcagccactg cgctctgctg ctggggccgc cgccctggct    540

ttgaccgtgg acctgccacc cgcctcctcc gaggctcgga actcggcctt cggtttccag    600

ggccgcttgc tgcacctgag tgccggccag cgcctgggcg tccatcttca cactgaggcc    660

agggcacgcc atgcctggca gcttacccag ggcgccacag tcttgggact cttccgggtg    720

acccccgaaa tcccagccgg actcccttca ccgaggtcgg aataa                    765
```

```
<210> SEQ ID NO 279
<211> LENGTH: 1368
<212> TYPE: DNA
<213> ORGANISM: Homo sapiens
<220> FEATURE:
<223> OTHER INFORMATION: TNFRSF1A

<400> SEQUENCE: 279

atgggcctct ccaccgtgcc tgacctgctg ctgccactgg tgctcctgga gctgttggtg     60

ggaatatacc cctcaggggt tattggactg gtccctcacc taggggacag ggagaagaga    120

gatagtgtgt gtccccaagg aaaatatatc caccctcaaa ataattcgat ttgctgtacc    180

aagtgccaca aaggaaccta cttgtacaat gactgtccag gcccggggca ggatacggac    240

tgcagggagt gtgagagcgg ctccttcacc gcttcagaaa accacctcag acactgcctc    300

agctgctcca aatgccgaaa ggaaatgggt caggtggaga tctcttcttg cacagtggac    360

cgggacaccg tgtgtggctg caggaagaac cagtaccggc attattggag tgaaaacctt    420

ttccagtgct tcaattgcag cctctgcctc aatgggaccg tgcacctctc ctgccaggag    480

aaacagaaca ccgtgtgcac ctgccatgca ggtttctttc taagagaaaa cgagtgtgtc    540

tcctgtagta actgtaagaa aagcctggag tgcacgaagt tgtgcctacc ccagattgag    600

aatgttaagg gcactgagga ctcaggcacc acagtgctgt tgcccctggt cattttcttt    660

ggtctttgcc ttttatccct cctcttcatt ggtttaatgt atcgctacca acggtggaag    720

tccaagctct actccattgt ttgtgggaaa tcgacacctg aaaaagaggg ggagcttgaa    780

ggaactacta ctaagcccct ggccccaaac ccaagcttca gtcccactcc aggcttcacc    840

cccaccctgg gcttcagtcc cgtgcccagt tccaccttca cctccagctc cacctatacc    900

cccggtgact gtcccaactt tgcggctccc cgcagagagg tggcaccacc ctatcagggg    960

gctgacccca tccttgcgac agccctcgcc tccgacccca tccccaaccc ccttcagaag   1020

tgggaggaca gcgcccacaa gccacagagc ctagacactg atgaccccgc gacgctgtac   1080

gccgtggtgg agaacgtgcc cccgttgcgc tggaaggaat tcgtgcggcg cctagggctg   1140

agcgaccacg agatcgatcg gctggagctg cagaacgggc gctgcctgcg cgaggcgcaa   1200

tacagcatgc tggcgacctg gaggcggcgc acgccgcggc gcgaggccac gctggagctg   1260

ctgggacgcg tgctccgcga catggacctg ctgggctgcc tggaggacat cgaggaggcg   1320

ctttgcggcc ccgccgccct cccgcccgcg cccagtcttc tcagatga                1368
```

<210> SEQ ID NO 280
<211> LENGTH: 1386
<212> TYPE: DNA
<213> ORGANISM: Homo sapiens
<220> FEATURE:
<223> OTHER INFORMATION: TNFRSF1B

<400> SEQUENCE: 280
atggcgcccg tcgccgtctg ggccgcgctg gccgtcggac tggagctctg ggctgcggcg 60
cacgccttgc ccgcccaggt ggcatttaca ccctacgccc cggagcccgg gagcacatgc 120
cggctcagag aatactatga ccagacagct cagatgtgct gcagcaaatg ctcgccgggc 180
caacatgcaa aagtcttctg taccaagacc tcggacaccg tgtgtgactc ctgtgaggac 240
agcacataca cccagctctg gaactgggtt cccgagtgct tgagctgtgg ctcccgctgt 300
agctctgacc aggtggaaac tcaagcctgc actcgggaac agaaccgcat ctgcacctgc 360
aggcccggct ggtactgcgc gctgagcaag caggaggggt gccggctgtg cgcgccgctg 420
cgcaagtgcc gcccgggctt cggcgtggcc agaccaggaa ctgaaacatc agacgtggtg 480
tgcaagccct gtgccccggg gacgttctcc aacacgactt catccacgga tatttgcagg 540
ccccaccaga tctgtaacgt ggtggccatc cctgggaatg caagcatgga tgcagtctgc 600
acgtccacgt cccccacccg gagtatggcc ccaggggcag tacacttacc ccagccagtg 660
tccacacgat cccaacacac gcagccaact ccagaaccca gcactgctcc aagcacctcc 720
ttcctgctcc caatgggccc cagccccccca gctgaaggga gcactggcga cttcgctctt 780
ccagttggac tgattgtggg tgtgacagcc ttgggtctac taataatagg agtggtgaac 840
tgtgtcatca tgacccaggt gaaaaagaag cccttgtgcc tgcagagaga agccaaggtg 900
cctcacttgc ctgccgataa ggcccggggt acacagggcc ccgagcagca gcacctgctg 960
atcacagcgc cgagctccag cagcagctcc ctggagagct cggccagtgc gttggacaga 1020
agggcgccca ctcggaacca gccacaggca ccaggcgtgg aggccagtgg ggccggggag 1080
gcccgggcca gcaccgggag ctcagattct tcccctggtg gccatgggac ccaggtcaat 1140
gtcacctgca tcgtgaacgt ctgtagcagc tctgaccaca gctcacagtg ctcctcccaa 1200
gccagctcca caatgggaga cacagattcc agcccctcgg agtccccgaa ggacgagcag 1260
gtccccttct ccaaggagga atgtgccttt cggtcacagc tggagacgcc agagaccctg 1320
ctggggagca ccgaagagaa gcccctgccc cttggagtgc ctgatgctgg gatgaagccc 1380
agttaa 1386

<210> SEQ ID NO 281
<211> LENGTH: 1308
<212> TYPE: DNA
<213> ORGANISM: Homo sapiens
<220> FEATURE:
<223> OTHER INFORMATION: LTBR

<400> SEQUENCE: 281
atgctcctgc cttgggccac ctctgccccc ggcctggcct gggggcctct ggtgctgggc 60
ctcttcgggc tcctggcagc atcgcagccc caggcggtgc ctccatatgc gtcggagaac 120
cagacctgca gggaccagga aaaggaatac tatgagcccc agcaccgcat ctgctgctcc 180
cgctgcccgc caggcaccta tgtctcagct aaatgtagcc gcatccggga cacagtttgt 240
gccacatgtg ccgagaattc ctacaacgag cactggaact acctgaccat ctgccagctg 300
tgccgcccct gtgacccagt gatgggcctc gaggagattg ccccctgcac aagcaaacgg 360

```
aagacccagt gccgctgcca gccgggaatg ttctgtgctg cctgggccct cgagtgtaca     420
cactgcgagc tactttctga ctgcccgcct ggcactgaag ccgagctcaa agatgaagtt     480
gggaagggta acaaccactg cgtcccctgc aaggccgggc acttccagaa tacctcctcc     540
cccagcgccc gctgccagcc ccacaccagg tgtgagaacc aaggtctggt ggaggcagct     600
ccaggcactg cccagtccga cacaacctgc aaaaatccat tagagccact gcccccagag     660
atgtcaggaa ccatgctgat gctggccgtt ctgctgccac tggccttctt tctgctcctt     720
gccaccgtct tctcctgcat ctggaagagc cacccttctc tctgcaggaa actgggatcg     780
ctgctcaaga ggcgtccgca gggagaggga cccaatcctg tagctggaag ctgggagcct     840
ccgaaggccc atccatactt ccctgacttg gtacagccac tgctacccat ttctggagat     900
gtttccccag tatccactgg gctccccgca gccccagttt tggaggcagg ggtgccgcaa     960
cagcagagtc ctctggacct gaccagggag ccgcagttgg aacccgggga gcagagccag    1020
gtggcccacg gtaccaatgg cattcatgtc accggcgggt ctatgactat cactggcaac    1080
atctacatct acaatggacc agtactgggg ggaccaccgg gtcctggaga cctcccagct    1140
acccccgaac ctccataccc cattcccgaa gagggggacc ctggccctcc cgggctctct    1200
acaccccacc aggaagatgg caaggcttgg cacctagcgg agacagagca ctgtggtgcc    1260
acaccctcta acaggggccc aaggaaccaa tttatcaccc atgactga                1308
```

<210> SEQ ID NO 282
<211> LENGTH: 1008
<212> TYPE: DNA
<213> ORGANISM: Homo sapiens
<220> FEATURE:
<223> OTHER INFORMATION: FAS

<400> SEQUENCE: 282

```
atgctgggca tctggaccct cctacctctg gttcttacgt ctgttgctag attatcgtcc      60
aaaagtgtta atgcccaagt gactgacatc aactccaagg gattggaatt gaggaagact     120
gttactacag ttgagactca gaacttggaa ggcctgcatc atgatggcca attctgccat     180
aagccctgtc ctccaggtga aaggaaagct agggactgca cagtcaatgg ggatgaacca     240
gactgcgtgc cctgccaaga agggaaggag tacacagaca aagcccattt ttcttccaaa     300
tgcagaagat gtagattgtg tgatgaagga catggcttag aagtggaaat aaactgcacc     360
cggacccaga ataccaagtg cagatgtaaa ccaaactttt tttgtaactc tactgtatgt     420
gaacactgtg acccttgcac caaatgtgaa catggaatca tcaaggaatg cacactcacc     480
agcaacacca agtgcaaaga ggaaggatcc agatctaact tggggtggct ttgtcttctt     540
cttttgccaa ttccactaat tgtttgggtg aagagaaagg aagtacagaa aacatgcaga     600
aagcacagaa aggaaaacca aggttctcat gaatctccaa ctttaaatcc tgaaacagtg     660
gcaataaatt tatctgatgt tgacttgagt aaatatatca ccactattgc tggagtcatg     720
acactaagtc aagttaaagg ctttgttcga aagaatggtg tcaatgaagc caaaatagat     780
gagatcaaga atgacaatgt ccaagacaca gcagaacaga aagttcaact gcttcgtaat     840
tggcatcaac ttcatggaaa gaaagaagcg tatgacacat tgattaaaga tctcaaaaaa     900
gccaatcttt gtactcttgc agagaaaatt cagactatca tcctcaagga cattactagt     960
gactcagaaa attcaaactt cagaaatgaa atccaaagct tggtctag                1008
```

<210> SEQ ID NO 283
<211> LENGTH: 903

<212> TYPE: DNA
<213> ORGANISM: Homo sapiens
<220> FEATURE:
<223> OTHER INFORMATION: TNFRSF6B

<400> SEQUENCE: 283
atgagggcgc tggaggggcc aggcctgtcg ctgctgtgcc tggtgttggc gctgcctgcc 60
ctgctgccgg tgccggctgt acgcggagtg gcagaaacac ccacctaccc ctggcgggac 120
gcagagacag gggagcggct ggtgtgcgcc cagtgccccc caggcacctt tgtgcagcgg 180
ccgtgccgcc gagacagccc cacgacgtgt ggcccgtgtc caccgcgcca ctacacgcag 240
ttctggaact acctagagcg ctgccgctac tgcaacgtcc tctgcgggga gcgtgaggag 300
gaggcacggg cttgccacgc cacccacaac cgtgcctgcc gctgccgcac cggcttcttc 360
gcgcacgctg gtttctgctt ggagcacgca tcgtgtccac ctggtgccgg cgtgattgcc 420
ccgggcaccc ccagccagaa cacgcagtgc cagccgtgcc ccccaggcac cttctcagcc 480
agcagctcca gctcagagca gtgccagccc caccgcaact gcacggccct gggcctggcc 540
ctcaatgtgc caggctcttc ctcccatgac accctgtgca ccagctgcac tggcttcccc 600
ctcagcacca gggtaccagg agctgaggag tgtgagcgtg ccgtcatcga ctttgtggct 660
ttccaggaca tctccatcaa gaggctgcag cggctgctgc aggccctcga ggccccggag 720
ggctggggtc cgacaccaag ggcgggccgc gcggccttgc agctgaagct gcgtcggcgg 780
ctcacggagc tcctgggggc gcaggacggg gcgctgctgg tgcggctgct gcaggcgctg 840
cgcgtggcca ggatgcccgg gctggagcgg agcgtccgtg agcgcttcct ccctgtgcac 900
tga 903

<210> SEQ ID NO 284
<211> LENGTH: 783
<212> TYPE: DNA
<213> ORGANISM: Homo sapiens
<220> FEATURE:
<223> OTHER INFORMATION: CD27

<400> SEQUENCE: 284
atggcacggc cacatccctg gtggctgtgc gttctgggga ccctggtggg gctctcagct 60
actccagccc ccaagagctg cccagagagg cactactggg ctcagggaaa gctgtgctgc 120
cagatgtgtg agccaggaac attcctcgtg aaggactgtg accagcatag aaaggctgct 180
cagtgtgatc cttgcatacc gggggtctcc ttctctcctg accaccacac ccggccccac 240
tgtgagagct gtcggcactg taactctggt cttctcgttc gcaactgcac catcactgcc 300
aatgctgagt gtgcctgtcg caatggctgg cagtgcaggg acaaggagtg caccgagtgt 360
gatcctcttc caaacccttc gctgaccgct cggtcgtctc aggccctgag cccacaccct 420
cagcccaccc acttacctta tgtcagtgag atgctggagg ccaggacagc tgggcacatg 480
cagactctgg ctgacttcag gcagctgcct gcccggactc tctctaccca ctggccaccc 540
caaagatccc tgtgcagctc cgattttatt cgcatccttg tgatcttctc tggaatgttc 600
cttgttttca ccctggccgg ggccctgttc ctccatcaac gaaggaaata tagatcaaac 660
aaaggagaaa gtcctgtgga gcctgcagag ccttgtcgtt acagctgccc cagggaggag 720
gagggcagca ccatccccat ccaggaggat taccgaaaac cggagcctgc ctgctccccc 780
tga 783

<210> SEQ ID NO 285

<211> LENGTH: 1788
<212> TYPE: DNA
<213> ORGANISM: Homo sapiens
<220> FEATURE:
<223> OTHER INFORMATION: TNFRSF8

<400> SEQUENCE: 285
atgcgcgtcc tcctcgccgc gctgggactg ctgttcctgg gggcgctacg agccttccca 60
caggatcgac ccttcgagga cacctgtcat ggaaacccca gccactacta tgacaaggct 120
gtcaggaggt gctgttaccg ctgccccatg ggctgttcc cgacacagca gtgcccacag 180
aggcctactg actgcaggaa gcagtgtgag cctgactact acctggatga ggccgaccgc 240
tgtacagcct gcgtgacttg ttctcgagac gacctcgtgg agaagacgcc gtgtgcatgg 300
aactcctccc gtgtctgcga atgtcgaccc ggcatgttct gttccacgtc tgccgtcaac 360
tcctgtgccc gctgcttctt ccattctgtc tgtccggcag ggatgattgt caagttccca 420
ggcacggcgc agaagaacac ggtctgtgag ccggcttccc caggggtcag ccctgcctgt 480
gccagcccag agaactgcaa ggaaccctcc agtggcacca tcccccaggc caagcccacc 540
ccggtgtccc cagcaacctc cagtgccagc accatgcctg taagaggggg cacccgcctc 600
gcccaggaag ctgcttctaa actgacgagg gctcccgact ctccctcctc tgtgggaagg 660
cctagttcag atccaggtct gtccccaaca cagccatgcc cagaggggtc tggtgattgc 720
agaaagcagt gtgagcccga ctactacctg gacgaggccg gccgctgcac ggcctgcgtg 780
agctgttctc gagatgacct tgtggagaag acgccatgtg catggaactc ctcccgcacc 840
tgcgaatgtc gacctggcat gatctgtgcc acatcagcca ccaactcctg tgcccgctgt 900
gtcccctacc caatctgtgc agcagagacg gtcaccaagc cccaggatat ggctgagaag 960
gacaccacct ttgaggcgcc acccctgggg acccagccgg actgcaaccc caccccagag 1020
aatggcgagg cgcctgccag caccagcccc actcagagct tgctggtgga ctcccaggcc 1080
agtaagacgc tgcccatccc aaccagcgct cccgtcgctc tctcctccac ggggaagccc 1140
gttctggatg cagggccagt gctcttctgg gtgatcctgg tgttggttgt ggtggtcggc 1200
tccagcgcct tcctcctgtg ccaccggagg gcctgcagga agcgaattcg gcagaagctc 1260
cacctgtgct acccggtcca gacctcccag cccaagctag agcttgtgga ttccagaccc 1320
aggaggagct caacgcagct gaggagtggt gcgtcggtga cagaacccgt cgcggaagag 1380
cgagggttaa tgagccagcc actgatggag acctgccaca gcgtgggggc agcctacctg 1440
gagagcctgc cgctgcagga tgccagcccg gccgggggcc cctcgtcccc cagggacctt 1500
cctgagcccc gggtgtccac ggagcacacc aataacaaga ttgagaaaat ctacatcatg 1560
aaggctgaca ccgtgatcgt ggggaccgtg aaggctgagc tgccggaggg ccggggcctg 1620
gcggggccag cagagcccga gttggaggag gagctggagg cggaccatac cccccactac 1680
cccgagcagg agacagaacc gcctctgggc agctgcagcg atgtcatgct ctcagtggaa 1740
gaggaaggga aagaagaccc cttgcccaca gctgcctctg gaaagtga 1788

<210> SEQ ID NO 286
<211> LENGTH: 1407
<212> TYPE: DNA
<213> ORGANISM: Homo sapiens
<220> FEATURE:
<223> OTHER INFORMATION: TNFRSF10A

<400> SEQUENCE: 286
atggcgccac caccagctag agtacatcta ggtgcgttcc tggcagtgac tccgaatccc 60

```
gggagcgcag cgagtgggac agaggcagcc gcggccacac ccagcaaagt gtggggctct    120
tccgcgggga ggattgaacc acgaggcggg ggccgaggag cgctccctac ctccatggga    180
cagcacggac ccagtgcccg ggcccgggca gggcgcgccc caggacccag gccggcgcgg    240
gaagccagcc ctcggctccg ggtccacaag accttcaagt ttgtcgtcgt cggggtcctg    300
ctgcaggtcg tacctagctc agctgcaacc atcaaacttc atgatcaatc aattggcaca    360
cagcaatggg aacatagccc tttgggagag ttgtgtccac caggatctca tagatcagaa    420
catcctggag cctgtaaccg gtgcacagag ggtgtgggtt acaccaatgc ttccaacaat    480
ttgtttgctt gcctcccatg tacagcttgt aaatcagatg aagaagagag aagtccctgc    540
accacgacca ggaacacagc atgtcagtgc aaaccaggaa ctttccggaa tgacaattct    600
gctgagatgt gccggaagtg cagcagaggg tgccccagag ggatggtcaa ggtcaaggat    660
tgtacgccct ggagtgacat cgagtgtgtc cacaaagaat caggcaatgg acataatata    720
tgggtgattt tggttgtgac tttggttgtt ccgttgctgt tggtggctgt gctgattgtc    780
tgttgttgca tcggctcagg ttgtggaggg gaccccaagt gcatggacag ggtgtgtttc    840
tggcgcttgg gtctcctacg agggcctggg gctgaggaca atgctcacaa cgagattctg    900
agcaacgcag actcgctgtc cactttcgtc tctgagcagc aaatggaaag ccaggagccg    960
gcagatttga caggtgtcac tgtacagtcc ccaggggagg cacagtgtct gctgggaccg   1020
gcagaagctg aagggtctca gaggaggagg ctgctggttc cagcaaatgg tgctgacccc   1080
actgagactc tgatgctgtt ctttgacaag tttgcaaaca tcgtgccctt tgactcctgg   1140
gaccagctca tgaggcagct ggacctcacg aaaaatgaga tcgatgtggt cagagctggt   1200
acagcaggcc caggggatgc cttgtatgca atgctgatga aatgggtcaa caaaactgga   1260
cggaacgcct cgatccacac cctgctggat gccttggaga ggatggaaga gagacatgca   1320
agagagaaga ttcaggacct cttggtggac tctggaaagt tcatctactt agaagatggc   1380
acaggctctg ccgtgtcctt ggagtga                                       1407
```

<210> SEQ ID NO 287
<211> LENGTH: 1323
<212> TYPE: DNA
<213> ORGANISM: Homo sapiens
<220> FEATURE:
<223> OTHER INFORMATION: TNFRSF10B

<400> SEQUENCE: 287

```
atggaacaac ggggacagaa cgccccggcc gcttcggggg cccggaaaag gcacggccca     60
ggacccaggg aggcgcgggg agccaggcct gggccccggg tccccaagac ccttgtgctc    120
gttgtcgccg cggtcctgct gttggtctca gctgagtctg ctctgatcac ccaacaagac    180
ctagctcccc agcagagagc ggccccacaa caaaagaggt ccagcccctc agagggattg    240
tgtccacctg gacaccatat ctcagaagac ggtagagatt gcatctcctg caaatatgga    300
caggactata gcactcactg gaatgacctc cttttctgct tgcgctgcac caggtgtgat    360
tcaggtgaag tggagctaag tccctgcacc acgaccagaa acacagtgtg tcagtgcgaa    420
gaaggcacct tccgggaaga agattctcct gagatgtgcc ggaagtgccg cacagggtgt    480
cccagaggga tggtcaaggt cggtgattgt acaccctgga gtgacatcga atgtgtccac    540
aaagaatcag gtacaaagca cagtggggaa gtcccagctg tggaggagac ggtgacctcc    600
agcccaggga ctcctgcctc tccctgttct ctctcaggca tcatcatagg agtcacagtt    660
```

gcagccgtag tcttgattgt ggctgtgttt gtttgcaagt ctttactgtg gaagaaagtc 720
cttccttacc tgaaaggcat ctgctcaggt ggtggtgggg accctgagcg tgtggacaga 780
agctcacaac gacctggggc tgaggacaat gtcctcaatg agatcgtgag tatcttgcag 840
cccacccagg tccctgagca ggaaatggaa gtccaggagc cagcagagcc aacaggtgtc 900
aacatgttgt cccccgggga gtcagagcat ctgctggaac cggcagaagc tgaaaggtct 960
cagaggagga ggctgctggt tccagcaaat gaaggtgatc ccactgagac tctgagacag 1020
tgcttcgatg actttgcaga cttggtgccc tttgactcct gggagccgct catgaggaag 1080
ttgggcctca tggacaatga gataaaggtg gctaaagctg aggcagcggg ccacagggac 1140
accttgtaca cgatgctgat aaagtgggtc aacaaaaccg ggcgagatgc ctctgtccac 1200
accctgctgg atgccttgga gacgctggga gagagacttg ccaagcagaa gattgaggac 1260
cacttgttga gctctggaaa gttcatgtat ctagaaggta atgcagactc tgccatgtcc 1320
taa 1323

<210> SEQ ID NO 288
<211> LENGTH: 780
<212> TYPE: DNA
<213> ORGANISM: Homo sapiens
<220> FEATURE:
<223> OTHER INFORMATION: TNFRSF10C

<400> SEQUENCE: 288
atggcccgga tccccaagac cctaaagttc gtcgtcgtca tcgtcgcggt cctgctgcca 60
gtcctagctt actctgccac cactgcccgg caggaggaag ttccccagca gacagtggcc 120
ccacagcaac agaggcacag cttcaagggg gaggagtgtc cagcaggatc tcatagatca 180
gaacatactg gagcctgtaa cccgtgcaca gagggtgtgg attacaccaa cgcttccaac 240
aatgaacctt cttgcttccc atgtacagtt tgtaaatcag atcaaaaaca taaaagttcc 300
tgcaccatga ccagagacac agtgtgtcag tgtaaagaag gcaccttccg gaatgaaaac 360
tccccagaga tgtgccggaa gtgtagcagg tgccctagtg ggaagtcca agtcagtaat 420 tgtacgtcct gggatgatat ccagtgtgtt gaagaatttg gtgccaatgc cactgtggaa 480
accccagctg ctgaagagac aatgaacacc agcccgggga ctcctgcccc agctgctgaa 540
gagacaatga acaccagccc agggactcct gccccagctg ctgaagagac aatgaccacc 600
agcccgggga ctcctgcccc agctgctgaa gagacaatga ccaccagccc ggggactcct 660
gccccagctg ctgaagagac aatgaccacc agcccgggga ctcctgcctc ttctcattac 720
ctctcatgca ccatcgtagg gatcatagtt ctaattgtgc ttctgattgt gtttgtttga 780

<210> SEQ ID NO 289
<211> LENGTH: 1161
<212> TYPE: DNA
<213> ORGANISM: Homo sapiens
<220> FEATURE:
<223> OTHER INFORMATION: TNFRSF10D

<400> SEQUENCE: 289
atgggacttt ggggacaaag cgtcccgacc gcctcgagcg ctcgagcagg gcgctatcca 60
ggagccagga cagcgtcggg aaccagacca tggctcctgg accccaagat ccttaagttc 120
gtcgtcttca tcgtcgcggt tctgctgccg gtccgggttg actctgccac catcccccgg 180
caggacgaag ttccccagca gacagtggcc ccacagcaac agaggcgcag cctcaaggag 240
gaggagtgtc cagcaggatc tcatagatca gaatatactg gagcctgtaa cccgtgcaca 300
gagggtgtgg attacaccat tgcttccaac aatttgcctt cttgcctgct atgtacagtt 360
tgtaaatcag gtcaaacaaa taaaagttcc tgtaccacga ccagagacac cgtgtgtcag 420
tgtgaaaaag gaagcttcca ggataaaaac tcccctgaga tgtgccggac gtgtagaaca 480
gggtgtccca gagggatggt caaggtcagt aattgtacgc cccggagtga catcaagtgc 540
aaaaatgaat cagctgccag ttccactggg aaaaccccag cagcggagga gacagtgacc 600
accatcctgg ggatgcttgc ctctccctat cactacctta tcatcatagt ggttttagtc 660
atcattttag ctgtggttgt ggttggcttt tcatgtcgga agaaattcat ttcttacctc 720
aaaggcatct gctcaggtgg tggaggaggt cccgaacgtg tgcacagagt cctttttccgg 780 cggcgttcat gtccttcacg agttcctggg gcggaggaca atgcccgcaa cgagaccctg 840
agtaacagat acttgcagcc cacccaggtc tctgagcagg aaatccaagg tcaggagctg 900
gcagagctaa caggtgtgac tgtagagttg ccagaggagc cacagcgtct gctggaacag 960
gcagaagctg aagggtgtca gaggaggagg ctgctggttc cagtgaatga cgctgactcc 1020
gctgacatca gcaccttgct ggatgcctcg gcaacactgg aagaaggaca tgcaaaggaa 1080
acaattcagg accaactggt gggctccgaa aagctctttt atgaagaaga tgaggcaggc 1140
tctgctacgt cctgcctgtg a 1161

<210> SEQ ID NO 290
<211> LENGTH: 1851
<212> TYPE: DNA
<213> ORGANISM: Homo sapiens
<220> FEATURE:
<223> OTHER INFORMATION: TNFRSF11A

<400> SEQUENCE: 290
atggccccgc gcgcccggcg gcgccgcccg ctgttcgcgc tgctgctgct ctgcgcgctg 60
ctcgcccggc tgcaggtggc tttgcagatc gctcctccat gtaccagtga gaagcattat 120
gagcatctgg gacggtgctg taacaaatgt gaaccaggaa agtacatgtc ttctaaatgc 180
actactacct ctgacagtgt atgtctgccc tgtggcccgg atgaatactt ggatagctgg 240
aatgaagaag ataaatgctt gctgcataaa gtttgtgata caggcaaggc cctggtggcc 300
gtggtcgccg gcaacagcac gaccccccgg cgctgcgcgt gcacggctgg gtaccactgg 360
agccaggact gcgagtgctg ccgccgcaac accgagtgcg cgccgggcct gggcgcccag 420
cacccgttgc agctcaacaa ggacacagtg tgcaaacctt gccttgcagg ctacttctct 480
gatgcctttt cctccacgga caaatgcaga ccctggacca actgtacctt ccttggaaag 540
agagtagaac atcatgggac agagaaatcc gatgcggttt gcagttcttc tctgccagct 600
agaaaaccac caaatgaacc ccatgtttac ttgcccggtt taataattct gcttctcttc 660
gcgtctgtgg ccctggtggc tgccatcatc tttggcgttt gctataggaa aaaagggaaa 720
gcactcacag ctaatttgtg gcactggatc aatgaggctt gtggccgcct aagtggagat 780
aaggagtcct caggtgacag ttgtgtcagt acacacacgg caaactttgg tcagcaggga 840
gcatgtgaag gtgtcttact gctgactctg gaggagaaga catttccaga agatatgtgc 900
tacccagatc aaggtggtgt ctgtcagggc acatgtgtag gaggtggtcc ctacgcacaa 960
ggcgaagatg ccaggatgct ctcattggtc agcaagaccg agatagagga agacagcttc 1020
agacagatgc ccacagaaga tgaatacatg gacaggccct cccagcccac agaccagtta 1080
ctgttcctca ctgagcctgg aagcaaatcc acacctcctt tctctgaacc cctggaggtg 1140

-continued

```
ggggagaatg acagtttaag ccagtgcttc acggggacac agagcacagt gggttcagaa   1200

agctgcaact gcactgagcc cctgtgcagg actgattgga ctcccatgtc ctctgaaaac   1260

tacttgcaaa aagaggtgga cagtggccat tgcccgcact gggcagccag ccccagcccc   1320

aactgggcag atgtctgcac aggctgccgg aaccctcctg gggaggactg tgaacccctc   1380

gtgggttccc caaaacgtgg acccttgccc cagtgcgcct atggcatggg ccttcccccct  1440

gaagaagaag ccagcaggac ggaggccaga gaccagcccg aggatggggc tgatgggagg   1500

ctcccaagct cagcgagggc aggtgccggg tctggaagct cccctggtgg ccagtcccct   1560

gcatctggaa atgtgactgg aaacagtaac tccacgttca tctccagcgg gcaggtgatg   1620

aacttcaagg gcgacatcat cgtggtctac gtcagccaga cctcgcagga gggcgcggcg   1680

gcggctgcgg agcccatggg ccgcccggtg caggaggaga ccctggcgcg ccgagactcc   1740

ttcgcgggga acggcccgcg cttcccggac ccgtgcggcg gccccgaggg gctgcgggag   1800

ccggagaagg cctcgaggcc ggtgcaggag caaggcgggg ccaaggcttg a            1851
```

<210> SEQ ID NO 291
<211> LENGTH: 1206
<212> TYPE: DNA
<213> ORGANISM: Homo sapiens
<220> FEATURE:
<223> OTHER INFORMATION: TNFRSF11B

<400> SEQUENCE: 291

```
atgaacaact tgctgtgctg cgcgctcgtg tttctggaca tctccattaa gtggaccacc     60

caggaaacgt ttcctccaaa gtaccttcat tatgacgaag aaacctctca tcagctgttg    120

tgtgacaaat gtcctcctgg tacctaccta aaacaacact gtacagcaaa gtggaagacc    180

gtgtgcgccc cttgccctga ccactactac acagacagct ggcacaccag tgacgagtgt    240

ctatactgca gccccgtgtg caaggagctg cagtacgtca agcaggagtg caatcgcacc    300

cacaaccgcg tgtgcgaatg caaggaaggg cgctaccttg agatagagtt ctgcttgaaa    360

cataggagct gccctcctgg atttggagtg gtgcaagctg gaaccccaga gcgaaataca    420

gtttgcaaaa gatgtccaga tgggttcttc tcaaatgaga cgtcatctaa agcaccctgt    480

agaaaacaca caaattgcag tgtctttggt ctcctgctaa ctcagaaagg aaatgcaaca    540

cacgacaaca tatgttccgg aaacagtgaa tcaactcaaa aatgtggaat agatgttacc    600

ctgtgtgagg aggcattctt caggtttgct gttcctacaa agtttacgcc taactggctt    660

agtgtcttgg tagacaattt gcctggcacc aaagtaaacg cagagagtgt agagaggata    720

aaacggcaac acagctcaca agaacagact ttccagctgc tgaagttatg gaaacatcaa    780

aacaaagacc aagatatagt caagaagatc atccaagata ttgacctctg tgaaaacagc    840

gtgcagcggc acattggaca tgctaacctc accttcgagc agcttcgtag cttgatggaa    900

agcttaccgg gaaagaaagt gggagcagaa gacattgaaa aaacaataaa ggcatgcaaa    960

cccagtgacc agatcctgaa gctgctcagt ttgtggcgaa taaaaaatgg cgaccaagac   1020

accttgaagg gcctaatgca cgcactaaag cactcaaaga cgtaccactt tcccaaaact   1080

gtcactcaga gtctaaagaa gaccatcagg ttccttcaca gcttcacaat gtacaaattg   1140

tatcagaagt tatttttaga aatgataggt aaccaggtcc aatcagtaaa aataagctgc   1200

ttataa                                                              1206
```

<210> SEQ ID NO 292
<211> LENGTH: 390

<212> TYPE: DNA
<213> ORGANISM: Homo sapiens
<220> FEATURE:
<223> OTHER INFORMATION: TNFRSF12A

<400> SEQUENCE: 292
atggctcggg gctcgctgcg ccggttgctg cggctcctcg tgctggggct ctggctggcg 60
ttgctgcgct ccgtggccgg ggagcaagcg ccaggcaccg ccccctgctc ccgcggcagc 120
tcctggagcg cggacctgga caagtgcatg gactgcgcgt cttgcagggc gcgaccgcac 180
agcgacttct gcctgggctg cgctgcagca cctcctgccc ccttccggct gctttggccc 240
atccttgggg gcgctctgag cctgaccttc gtgctggggc tgctttctgg ctttttggtc 300
tggagacgat gccgcaggag agagaagttc accaccccca tagaggagac cggcggagag 360
ggctgcccag ctgtggcgct gatccagtga 390

<210> SEQ ID NO 293
<211> LENGTH: 882
<212> TYPE: DNA
<213> ORGANISM: Homo sapiens
<220> FEATURE:
<223> OTHER INFORMATION: TNFRSF13B

<400> SEQUENCE: 293
atgagtggcc tgggccggag caggcgaggt ggccggagcc gtgtggacca ggaggagcgc 60
tttccacagg gcctgtggac gggggtggct atgagatcct gccccgaaga gcagtactgg 120
gatcctctgc tgggtacctg catgtcctgc aaaaccattt gcaaccatca gagccagcgc 180
acctgtgcag ccttctgcag gtcactcagc tgccgcaagg agcaaggcaa gttctatgac 240
catctcctga gggactgcat cagctgtgcc tccatctgtg gacagcaccc taagcaatgt 300
gcatacttct gtgagaacaa gctcaggagc ccagtgaacc ttccaccaga gctcaggaga 360
cagcggagtg gagaagttga aaacaattca gacaactcgg gaaggtacca aggattggag 420
cacagaggct cagaagcaag tccagctctc ccggggctga agctgagtgc agatcaggtg 480
gccctggtct acagcacgct ggggctctgc ctgtgtgccg tcctctgctg cttcctggtg 540
gcggtggcct gcttcctcaa gaagaggggg gatccctgct cctgccagcc ccgctcaagg 600
ccccgtcaaa gtccggccaa gtcttcccag gatcacgcga tggaagccgg cagccctgtg 660
agcacatccc ccgagccagt ggagacctgc agcttctgct tccctgagtg cagggcgccc 720
acgcaggaga gcgcagtcac gcctgggacc cccgacccca cttgtgctgg aaggtggggg 780
tgccacacca ggaccacagt cctgcagcct tgcccacaca tcccagacag tggccttggc 840
attgtgtgtg tgcctgccca ggagggggc ccaggtgcat aa 882

<210> SEQ ID NO 294
<211> LENGTH: 555
<212> TYPE: DNA
<213> ORGANISM: Homo sapiens
<220> FEATURE:
<223> OTHER INFORMATION: TNFRSF13C

<400> SEQUENCE: 294
atgaggcgag ggccccggag cctgcggggc agggacgcgc cagcccccac gccctgcgtc 60
ccggccgagt gcttcgacct gctggtccgc cactgcgtgg cctgcgggct cctgcgcacg 120
ccgcggccga aaccggccgg ggccagcagc cctgcgccca ggacggcgct gcagccgcag 180
gagtcggtgg gcgcgggggc cggcgaggcg gcgctgcccc tgcccgggct gctctttggc 240

-continued

```
gcccccgcgc tgctgggcct ggcactggtc ctggcgctgg tcctggtggg tctggtgagc    300

tggaggcggc gacagcggcg gcttcgcggc gcgtcctccg cagaggcccc cgacggagac    360

aaggacgccc cagagcccct ggacaaggtc atcattctgt ctccgggaat ctctgatgcc    420

acagctcctg cctggcctcc tcctggggaa gacccaggaa ccacccccacc tggccacagt   480

gtccctgtgc cagccacaga gctgggctcc actgaactgg tgaccaccaa gacggccggc    540

cctgagcaac aatag                                                      555
```

<210> SEQ ID NO 295
<211> LENGTH: 852
<212> TYPE: DNA
<213> ORGANISM: Homo sapiens
<220> FEATURE:
<223> OTHER INFORMATION: TNFRSF14

<400> SEQUENCE: 295

```
atggagcctc ctggagactg gggcctcct ccctggagat ccacccccaa aaccgacgtc      60

ttgaggctgg tgctgtatct caccttcctg ggagcccccct gctacgcccc agctctgccg   120

tcctgcaagg aggacgagta cccagtgggc tccgagtgct gccccaagtg cagtccaggt    180

tatcgtgtga aggaggcctg cggggagctg acgggcacag tgtgtgaacc ctgccctcca    240

ggcacctaca ttgcccacct caatggccta agcaagtgtc tgcagtgcca aatgtgtgac    300

ccagccatgg gcctgcgcgc gagccggaac tgctccagga cagagaacgc cgtgtgtggc    360

tgcagcccag gccacttctg catcgtccag gacggggacc actgcgccgc gtgccgcgct    420

tacgccacct ccagcccggg ccagagggtg cagaagggag gcaccgagag tcaggacacc    480

ctgtgtcaga actgcccccc ggggaccttc tctcccaatg ggaccctgga ggaatgtcag    540

caccagacca agtgcagctg gctggtgacg aaggccggag ctgggaccag cagctcccac    600

tgggtatggt ggtttctctc agggagcctc gtcatcgtca ttgtttgctc cacagttggc    660

ctaatcatat gtgtgaaaag aagaaagcca aggggtgatg tagtcaaggt gatcgtctcc    720

gtccagcgga aaagacagga ggcagaaggt gaggccacag tcattgaggc cctgcaggcc    780

cctccggacg tcaccacggt ggccgtggag gagacaatac cctcattcac ggggaggagc    840

ccaaaccact ga                                                         852
```

<210> SEQ ID NO 296
<211> LENGTH: 1284
<212> TYPE: DNA
<213> ORGANISM: Homo sapiens
<220> FEATURE:
<223> OTHER INFORMATION: NGFR

<400> SEQUENCE: 296

```
atgggggcag gtgccaccgg ccgcgccatg gacgggccgc gcctgctgct gttgctgctt     60

ctgggggtgt cccttggagg tgccaaggag gcatgcccca caggcctgta cacacacagc    120

ggtgagtgct gcaaagcctg caacctgggc gagggtgtgg cccagccttg tggagccaac    180

cagaccgtgt gtgagccctg cctggacagc gtgacgttct ccgacgtggt gagcgcgacc    240

gagccgtgca agccgtgcac cgagtgcgtg gggctccaga gcatgtcggc gccgtgcgtg    300

gaggccgacg acgccgtgtg ccgctgcgcc tacggctact accaggatga gacgactggg    360

cgctgcgagg cgtgccgcgt gtgcgaggcg ggctcgggcc tcgtgttctc ctgccaggac    420

aagcagaaca ccgtgtgcga ggagtgcccc gacggcacgt attccgacga ggccaaccac    480

gtggacccgt gcctgccctg caccgtgtgc gaggacaccg agcgccagct ccgcgagtgc    540
```

```
acacgctggg ccgacgccga gtgcgaggag atccctggcc gttggattac acggtccaca    600

cccccagagg gctcggacag cacagccccc agcacccagg agcctgaggc acctccagaa    660

caagacctca tagccagcac ggtggcaggt gtggtgacca cagtgatggg cagctcccag    720

cccgtggtga cccgaggcac caccgacaac ctcatccctg tctattgctc catcctggct    780

gctgtggttg tgggccttgt ggcctacata gccttcaaga ggtggaacag ctgcaagcag    840

aacaagcaag gagccaacag ccggccagtg aaccagacgc ccccaccaga gggagaaaaa    900

ctccacagcg acagtggcat ctccgtggac agccagagcc tgcatgacca gcagccccac    960

acgcagacag cctcgggcca ggccctcaag ggtgacggag gcctctacag cagcctgccc   1020

ccagccaagc gggaggaggt ggagaagctt ctcaacggct ctgcggggga cacctggcgg   1080

cacctggcgg gcgagctggg ctaccagccc gagcacatag actcctttac ccatgaggcc   1140

tgccccgttc gcgccctgct tgcaagctgg gccacccagg acagcgccac actggacgcc   1200

ctcctggccg ccctgcgccg catccagcga gccgacctcg tggagagtct gtgcagtgag   1260

tccactgcca catccccggt gtga                                          1284
```

<210> SEQ ID NO 297
<211> LENGTH: 555
<212> TYPE: DNA
<213> ORGANISM: Homo sapiens
<220> FEATURE:
<223> OTHER INFORMATION: TNFRSF17

<400> SEQUENCE: 297

```
atgttgcaga tggctgggca gtgctcccaa aatgaatatt ttgacagttt gttgcatgct     60

tgcatacctt gtcaacttcg atgttcttct aatactcctc ctctaacatg tcagcgttat    120

tgtaatgcaa gtgtgaccaa ttcagtgaaa ggaacgaatg cgattctctg gacctgtttg    180

ggactgagct taataatttc tttggcagtt ttcgtgctaa tgtttttgct aaggaagata    240

aactctgaac cattaaagga cgagtttaaa aacacaggat caggtctcct gggcatggct    300

aacattgacc tggaaaagag caggactggt gatgaaatta ttcttccgag aggcctcgag    360

tacacggtgg aagaatgcac ctgtgaagac tgcatcaaga gcaaaccgaa ggtcgactct    420

gaccattgct ttccactccc agctatggag gaaggcgcaa ccattcttgt caccacgaaa    480

acgaatgact attgcaagag cctgccagct gctttgagtg ctacggagat agagaaatca    540

atttctgcta ggtaa                                                     555
```

<210> SEQ ID NO 298
<211> LENGTH: 1254
<212> TYPE: DNA
<213> ORGANISM: Homo sapiens
<220> FEATURE:
<223> OTHER INFORMATION: TNFRSF19

<400> SEQUENCE: 298

```
atggctttaa aagtgctact agaacaagag aaaacgtttt tcactctttt agtattacta     60

ggctatttgt catgtaaagt gacttgtgaa tcaggagact gtagacagca agaattcagg    120

gatcggtctg gaaactgtgt tccctgcaac cagtgtgggc caggcatgga gttgtctaag    180

gaatgtggct tcggctatgg ggaggatgca cagtgtgtga cgtgccggct gcacaggttc    240

aaggaggact ggggcttcca gaaatgcaag ccctgtctgg actgcgcagt ggtgaaccgc    300

tttcagaagg caaattgttc agccaccagt gatgccatct gcggggactg cttgccagga    360
```

-continued

```
ttttatagga agacgaaact tgtcggcttt caagacatgg agtgtgtgcc ttgtggagac    420

cctcctcctc cttacgaacc gcactgtgcc agcaaggtca acctcgtgaa gatcgcgtcc    480

acggcctcca gcccacggga cacggcgctg gctgccgtta tctgcagcgc tctggccacc    540

gtcctgctgg ccctgctcat cctctgtgtc atctattgta agagacagtt tatggagaag    600

aaacccagct ggtctctgcg gtcacaggac attcagtaca acggctctga gctgtcgtgt    660

tttgacagac ctcagctcca cgaatatgcc cacagagcct gctgccagtg ccgccgtgac    720

tcagtgcaga cctgcgggcc ggtgcgcttg ctcccatcca tgtgctgtga ggaggcctgc    780

agccccaacc cggcgactct tggttgtggg gtgcattctg cagccagtct tcaggcaaga    840

aacgcaggcc cagccgggga gatggtgccg actttcttcg gatccctcac gcagtccatc    900

tgtggcgagt tttcagatgc ctggcctctg atgcagaatc ccatgggtgg tgacaacatc    960

tctttttgtg actcttatcc tgaactcact ggagaagaca ttcattctct caatccagaa   1020

cttgaaagct caacgtcttt ggattcaaat agcagtcaag atttggttgg tggggctgtt   1080

ccagtccagt ctcattctga aaactttaca gcagctactg atttatctag atataacaac   1140

acactggtag aatcagcatc aactcaggat gcactaacta tgagaagcca gctagatcag   1200

gagagtggtg ctgtcatcca cccagccact cagacgtccc tccaggaagc ttaa         1254
```

<210> SEQ ID NO 299
<211> LENGTH: 1293
<212> TYPE: DNA
<213> ORGANISM: Homo sapiens
<220> FEATURE:
<223> OTHER INFORMATION: RELT

<400> SEQUENCE: 299

```
atgaagccaa gtctgctgtg ccggcccctg tcctgcttcc ttatgctgct gccctggcct     60

ctcgccaccc tgacatcaac aaccctttgg cagtgcccac ctggggagga gcccgacctg    120

gacccagggc agggcacatt atgcaggccc tgccccccag gcaccttctc agctgcatgg    180

ggctccagcc catgccagcc ccatgcccgt tgcagccttt ggaggaggct ggaggcccag    240

gtgggcatgg caactcgaga tacactctgt ggagactgct ggcctgggtg gtttgggcct    300

tggggggttc cccgcgttcc atgtcaacca tgttcctggg cacctctggg tactcatggc    360

tgtgatgagt gggggcggcg ggcccgacgt ggcgtggagg tggcagcagg ggccagcagc    420

ggtggtgaga cacggcagcc tgggaacggc acccgggcag gtggcccaga ggagacagcc    480

gcccagtacg cggtcatcgc catcgtccct gtcttctgcc tcatggggct gttgggcatc    540

ctggtgtgca acctcctcaa gcggaagggc taccactgca cggcgcacaa ggaggtcggg    600

cccggccctg gaggtggagg cagtggaatc aaccctgcct accggactga ggatgccaat    660

gaggacacca ttggggtcct ggtgcgcttg atcacagaga agaaagagaa tgctgcggcc    720

ctggaggagc tgctgaaaga gtaccacagc aaacagctgg tgcagacgag ccacaggcct    780

gtgtccaagc tgccgccagc gcccccgaac gtgccacaca tctgcccgca ccgccaccat    840

ctccacaccg tgcagggcct ggcctcgctc tctggcccct gctgctcccg ctgtagccag    900

aagaagtggc ccgaggtgct gctgtcccct gaggctgtag ccgccactac tcctgttccc    960

agccttctgc ctaacccgac cagggttccc aaggccgggg ccaaggcagg gcgtcagggc   1020

gagatcacca tcttgtctgt gggcaggttc cgcgtggctc gaattcctga gcagcggaca   1080

agttcaatgg tgtctgaggt gaagaccatc acggaggctg ggccctcgtg gggtgatctc   1140

cctgactccc cacagcctgg cctcccccct gagcagcagg ccctgctagg aagtggcgga   1200
```

agccgtacaa agtggctgaa gcccccagca gagaacaagg ccgaggagaa ccgctatgtg 1260
gtccggctaa gtgagagcaa cctggtcatc tga 1293

<210> SEQ ID NO 300
<211> LENGTH: 1968
<212> TYPE: DNA
<213> ORGANISM: Homo sapiens
<220> FEATURE:
<223> OTHER INFORMATION: TNFRSF21

<400> SEQUENCE: 300
atggggacct ctccgagcag cagcaccgcc ctcgcctcct gcagccgcat cgcccgccga 60
gccacagcca cgatgatcgc gggctccctt ctcctgcttg gattccttag caccaccaca 120
gctcagccag aacagaaggc ctcgaatctc attggcacat accgccatgt tgaccgtgcc 180
accggccagg tgctaacctg tgacaagtgt ccagcaggaa cctatgtctc tgagcattgt 240
accaacacaa gcctgcgcgt ctgcagcagt tgccctgtgg ggacctttac caggcatgag 300
aatggcatag agaaatgcca tgactgtagt cagccatgcc catggccaat gattgagaaa 360
ttaccttgtg ctgccttgac tgaccgagaa tgcacttgcc cacctggcat gttccagtct 420
aacgctacct gtgcccccca tacggtgtgt cctgtgggtt ggggtgtgcg gaagaaaggg 480
acagagactg aggatgtgcg gtgtaagcag tgtgctcggg gtaccttctc agatgtgcct 540
tctagtgtga tgaaatgcaa agcatacaca gactgtctga gtcagaacct ggtggtgatc 600
aagccgggga ccaaggagac agacaacgtc tgtggcacac tcccgtcctt ctccagctcc 660
acctcacctt cccctggcac agccatcttt ccacgccctg agcacatgga aacccatgaa 720
gtcccttcct ccacttatgt tcccaaaggc atgaactcaa cagaatccaa ctcttctgcc 780
tctgttagac caaaggtact gagtagcatc caggaaggga cagtccctga caacacaagc 840
tcagcaaggg ggaaggaaga cgtgaacaag accctcccaa accttcaggt agtcaaccac 900
cagcaaggcc cccaccacag acacatcctg aagctgctgc cgtccatgga ggccactggg 960
ggcgagaagt ccagcacgcc catcaagggc cccaagaggg gacatcctag acagaaccta 1020
cacaagcatt ttgacatcaa tgagcatttg ccctggatga ttgtgctttt cctgctgctg 1080
gtgcttgtgg tgattgtggt gtgcagtatc cggaaaagct cgaggactct gaaaaagggg 1140
ccccggcagg atcccagtgc cattgtggaa aaggcagggc tgaagaaatc catgactcca 1200
acccagaacc gggagaaatg gatctactac tgcaatggcc atggtatcga tatcctgaag 1260
cttgtagcag cccaagtggg aagccagtgg aaagatatct atcagtttct ttgcaatgcc 1320
agtgagaggg aggttgctgc tttctccaat gggtacacag ccgaccacga gcgggcctac 1380
gcagctctgc agcactggac catccggggc cccgaggcca gcctcgccca gctaattagc 1440
gccctgcgcc agcaccggag aaacgatgtt gtggagaaga ttcgtgggct gatggaagac 1500
accacccagc tggaaactga caaactagct ctcccgatga gccccagccc gcttagcccg 1560
agccccatcc ccagccccaa cgcgaaactt gagaattccg ctctcctgac ggtggagcct 1620
tccccacagg acaagaacaa gggcttcttc gtggatgagt cggagcccct tctccgctgt 1680
gactctacat ccagcggctc ctccgcgctg agcaggaacg gttcctttat taccaaagaa 1740
aagaaggaca cagtgttgcg gcaggtacgc ctggacccct gtgacttgca gcctatcttt 1800
gatgacatgc tccactttct aaatcctgag gagctgcggg tgattgaaga gattccccag 1860
gctgaggaca aactagaccg gctattcgaa attattggag tcaagagcca ggaagccagc 1920

-continued cagaccctcc tggactctgt ttatagccat cttcctgacc tgctgtag 1968

<210> SEQ ID NO 301
<211> LENGTH: 1254
<212> TYPE: DNA
<213> ORGANISM: Homo sapiens
<220> FEATURE:
<223> OTHER INFORMATION: TNFRSF25

<400> SEQUENCE: 301
atggagcagc ggccgcgggg ctgcgcggcg gtggcggcgg cgctcctcct ggtgctgctg 60
ggggcccggg cccagggcgg cactcgtagc cccaggtgtg actgtgccgg tgacttccac 120
aagaagattg gtctgttttg ttgcagaggc tgcccagcgg ggcactacct gaaggcccct 180
tgcacggagc cctgcggcaa ctccacctgc cttgtgtgtc cccaagacac cttcttggcc 240
tgggagaacc accataattc tgaatgtgcc cgctgccagg cctgtgatga gcaggcctcc 300
caggtggcgc tggagaactg ttcagcagtg gccgacaccc gctgtggctg taagccaggc 360
tggtttgtgg agtgccaggt cagccaatgt gtcagcagtt caccccttcta ctgccaacca 420 tgcctagact gcggggccct gcaccgccac acacggctac tctgttcccg cagagatact 480
gactgtggga cctgcctgcc tggcttctat gaacatggcg atggctgcgt gtcctgcccc 540
acgagcaccc tggggagctg tccagagcgc tgtgccgctg tctgtggctg gaggcagatg 600
ttctgggtcc aggtgctcct ggctggcctt gtggtccccc tcctgcttgg ggccaccctg 660
acctacacat accgccactg ctggcctcac aagcccctgg ttactgcaga tgaagctggg 720
atggaggctc tgaccccacc accggccacc catctgtcac ccttggacag cgcccacacc 780
cttctagcac ctcctgacag cagtgagaag atctgcaccg tccagttggt gggtaacagc 840
tggacccctg gctaccccga gacccaggag gcgctctgcc cgcaggtgac atggtcctgg 900
gaccagttgc ccagcagagc tcttggcccc gctgctgcgc ccacactctc gccagagtcc 960
ccagccggct cgccagccat gatgctgcag ccgggcccgc agctctacga cgtgatggac 1020
gcggtcccag cgcggcgctg gaaggagttc gtgcgcacgc tggggctgcg cgaggcagag 1080
atcgaagccg tggaggtgga gatcggccgc ttccgagacc agcagtacga gatgctcaag 1140
cgctggcgcc agcagcagcc cgcgggcctc ggagccgttt acgcggccct ggagcgcatg 1200
gggctggacg gctgcgtgga agacttgcgc agccgcctgc agcgcggccc gtga 1254

<210> SEQ ID NO 302
<211> LENGTH: 1347
<212> TYPE: DNA
<213> ORGANISM: Homo sapiens
<220> FEATURE:
<223> OTHER INFORMATION: EDAR

<400> SEQUENCE: 302
atggcccatg tgggggactg cacgcagacg ccctggctcc ccgtcctggt ggtgtctctg 60
atgtgctcag cccgagcgga atactcaaac tgcggtgaga acgagtacta caaccagact 120
acggggctgt gccaggagtg ccccccgtgt gggccgggag aggagcccta cctgtcctgt 180
ggctacggca ccaaagacga ggactacggc tgcgtcccct gcccggcgga gaagttttcc 240
aaaggaggct accagatatg caggcgtcac aaagactgtg agggcttctt ccgggccacc 300
gtgctgacac caggggacat ggagaatgac gctgagtgtg gcccttgcct ccctggctac 360
tacatgctgg agaacagacc gaggaacatc tatggcatgg tctgctactc ctgcctcctg 420
gcacccccca acaccaagga atgtgtggga gccacttcag gagcttctgc caacttccct 480
ggcacctcgg gcagcagcac cctgtctccc ttccagcacg cccacaaaga actctcaggc 540
caaggacacc tggccactgc cctgatcatt gcaatgtcca ccatcttcat catggccatc 600
gccatcgtcc tcatcatcat gttctacatc ctgaagacaa agccctctgc cccagcctgt 660
tgcaccagcc acccggggaa gagcgtggag gcccaagtga gcaaggacga ggagaagaaa 720
gaggccccag acaacgtggt gatgttctcc gagaaggatg aatttgagaa gctgacagca 780
actccagcaa agcccaccaa gagcgagaac gatgcctcat ccgagaatga gcagctgctg 840
agccggagcg tcgacagtga tgaggagccc gcccctgaca agcagggctc cccggagctg 900
tgcctgctgt cgctggttca cctggccagg gagaagtctg ccaccagcaa caagtcagcc 960
gggattcaaa gccggaggaa aaagatcctc gatgtgtatg ccaacgtgtg tggagtcgtg 1020
gaaggtctta gccccacgga gctgccattt gattgcctcg agaagactag ccgaatgctc 1080
agctccacgt acaactctga gaaggctgtt gtgaaaacgt ggcgccacct cgccgagagc 1140
ttcggcctga agagggatga gattgggggc atgacagacg gcatgcaact ctttgaccgc 1200
atcagcacgg caggctacag catccctgag ctactcacaa aactggtgca gattgagcgg 1260
ctggatgctg tggagtcctt gtgtgcagac atactggagt gggcgggggt tgtgccacct 1320
gcctcccagc cacatgctgc atcctga 1347

<210> SEQ ID NO 303
<211> LENGTH: 894
<212> TYPE: DNA
<213> ORGANISM: Homo sapiens
<220> FEATURE:
<223> OTHER INFORMATION: EDA2R

<400> SEQUENCE: 303
atggattgcc aagaaaatga gtactgggac caatggggac ggtgtgtcac ctgccaacgg 60
tgtggtcctg gacaggagct atccaaggat tgtggttatg gagagggtgg agatgcctac 120
tgcacagcct gccctcctcg caggtacaaa agcagctggg gccaccacag atgtcagagt 180
tgcatcacct gtgctgtcat caatcgtgtt cagaaggtca actgcacagc tacctctaat 240
gctgtctgtg gggactgttt gcccaggttc taccgaaaga cacgcattgg aggcctgcag 300
gaccaagagt gcatcccgtg cacgaagcag accccccacct ctgaggttca atgtgccttc 360
cagttgagct tagtggaggc agatacaccc acagtgcccc ctcaggaggc cacacttgtt 420
gcactggtga gcagcctgct agtggtgttt accctggcct tcctggggct cttcttcctc 480
tactgcaagc agttcttcaa cagacattgc cagcgtggag gtttgctgca gtttgaggct 540
gataaaacag caaaggagga atctctcttc cccgtgccac ccagcaagga gaccagtgct 600
gagtcccaag tgagtgagaa catctttcag acccagccac ttaaccctat cctcgaggac 660
gactgcagct cgactagtgg cttccccaca caggagtcct ttaccatggc ctcctgcacc 720
tcagagagcc actcccactg ggtccacagc cccatcgaat gcacagagct ggacctgcaa 780
aagttttcca gctctgcctc ctatactgga gctgagacct tggggggaaa cacagtcgaa 840
agcactggag acaggctgga gctcaatgtg ccctttgaag ttcccagccc ttaa 894

<210> SEQ ID NO 304
<211> LENGTH: 1184
<212> TYPE: DNA
<213> ORGANISM: Artificial Sequence
<220> FEATURE:
<223> OTHER INFORMATION: Elongation factor 1 (EF1) alpha promoter -continued

<400> SEQUENCE: 304

```
cgtgaggctc cggtgcccgt cagtgggcag agcgcacatc gcccacagtc cccgagaagt     60
tgggggggagg ggtcggcaat tgaaccggtg cctagagaag gtggcgcggg gtaaactggg   120
aaagtgatgt cgtgtactgg ctccgccttt ttcccgaggg tgggggagaa ccgtatataa    180
gtgcagtagt cgccgtgaac gttctttttc gcaacgggtt tgccgccaga acacaggtaa    240
gtgccgtgtg tggttcccgc gggcctggcc tctttacggg ttatggccct tgcgtgcctt    300
gaattacttc cacctggctg cagtacgtga ttcttgatcc cgagcttcgg gttggaagtg    360
ggtgggagag ttcgaggcct tgcgcttaag gagccccttc gcctcgtgct tgagttgagg    420
cctggcctgg gcgctggggc cgccgcgtgc gaatctggtg gcaccttcgc gcctgtctcg    480
ctgctttcga taagtctcta gccatttaaa atttttgatg acctgctgcg acgctttttt    540
tctggcaaga tagtcttgta aatgcgggcc aagatctgca cactggtatt tcggtttttg    600
gggccgcggg cggcgacggg gcccgtgcgt cccagcgcac atgttcggcg aggcggggcc    660
tgcgagcgcg gccaccgaga atcggacggg ggtagtctca agctggccgg cctgctctgg    720
tgcctggcct cgcgccgccg tgtatcgccc cgccctgggc ggcaaggctg gcccggtcgg    780
caccagttgc gtgagcggaa agatggccgc ttcccggccc tgctgcaggg agctcaaaat    840
ggaggacgcg gcgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttggggggag gggttttatg   1020
cgatggagtt tccccacact gagtgggtgg agactgaagt taggccagct tggcacttga   1080
tgtaattctc cttggaattt gccctttttg agtttggatc ttggttcatt ctcaagcctc   1140
agacagtggt tcaaagtttt tttcttccat ttcaggtgtc gtga                     1184
```